(12) United States Patent
Kim et al.

(10) Patent No.: US 10,026,905 B2
(45) Date of Patent: Jul. 17, 2018

(54) COMPOUND, ORGANIC ELECTRIC ELEMENT USING THE SAME, AND AN ELECTRONIC DEVICE THEREOF

(71) Applicant: DUK SAN NEOLUX CO., LTD., Cheonan-si, Chungcheongnam-Do (KR)

(72) Inventors: Dongha Kim, Gyeonggi-do (KR); Sunhee Lee, Chungcheongnam-do (KR); Yeonhee Choi, Chungcheongnam-do (KR); Soungyun Mun, Gyeonggi-do (KR); Jungcheol Park, Busan (KR); Yongwook Park, Gyeonggi-do (KR); Heesun Ji, Chungcheongnam-do (KR); Junghwan Park, Seoul (KR); Bumsung Lee, Chungcheongnam-do (KR); Sunpil Hwang, Gyeonggi-do (KR)

(73) Assignee: DUK SAN NEOLUX CO., LTD., Cheonan-si, Chungcheo (KR)

( * ) Notice: Subject to any disclaimer, the term of this patent is extended or adjusted under 35 U.S.C. 154(b) by 892 days.

(21) Appl. No.: 14/362,883

(22) PCT Filed: Jan. 14, 2013

(86) PCT No.: PCT/KR2013/000280
§ 371 (c)(1),
(2) Date: Jun. 4, 2014

(87) PCT Pub. No.: WO2013/109027
PCT Pub. Date: Jul. 25, 2013

(65) Prior Publication Data
US 2014/0374722 A1    Dec. 25, 2014

(30) Foreign Application Priority Data

Jan. 18, 2012  (KR) .................. 10-2012-0005563
Aug. 1, 2012   (KR) .................. 10-2012-0084503
Aug. 2, 2012   (KR) .................. 10-2012-0084945
Aug. 17, 2012  (KR) .................. 10-2012-0090101

(51) Int. Cl.

| H01L 51/00  | (2006.01) |
|---|---|
| C07D 209/08 | (2006.01) |
| C09K 11/06  | (2006.01) |
| C07D 405/10 | (2006.01) |
| C07D 209/82 | (2006.01) |
| H01L 51/50  | (2006.01) |

(52) U.S. Cl.
CPC .......... *H01L 51/006* (2013.01); *C07D 209/08* (2013.01); *C07D 209/82* (2013.01); *C07D 405/10* (2013.01); *C09K 11/06* (2013.01); *H01L 51/0061* (2013.01); *H01L 51/0072* (2013.01); *H01L 51/0052* (2013.01); *H01L 51/0058* (2013.01); *H01L 51/0073* (2013.01); *H01L 51/0074* (2013.01); *H01L 51/0081* (2013.01); *H01L 51/0085* (2013.01); *H01L 51/5012* (2013.01); *H01L 51/5056* (2013.01); *H01L 51/5096* (2013.01); *H01L 2251/308* (2013.01); *Y02E 10/549* (2013.01)

(58) Field of Classification Search
CPC .. C07D 209/08; C07D 209/82; C07D 405/10; C09K 11/06; H01L 2251/308; H01L 51/0052; H01L 51/0058; H01L 51/006; H01L 51/0061; H01L 51/0072; H01L 51/0073; H01L 51/0074; H01L 51/0081; H01L 51/0085; H01L 51/5012; H01L 51/5056; H01L 51/5096; Y02E 10/549
See application file for complete search history.

(56) References Cited

U.S. PATENT DOCUMENTS

| 2008/0014464 A1* | 1/2008 | Kawamura | ............ C09K 11/06 428/690 |
|---|---|---|---|
| 2010/0219404 A1* | 9/2010 | Endo | ..................... H01L 51/006 257/40 |
| 2010/0301318 A1* | 12/2010 | Kuma | .................... B82Y 10/00 257/40 |

FOREIGN PATENT DOCUMENTS

| JP | H10-3105740 A | 11/1998 |
|---|---|---|
| KR | 10-2008-0047209 A | 5/2008 |
| WO | 2007-148660 | * 12/2007 |
| WO | 2007/148660 A1 | * 12/2007 |
| WO | WO2007148660 A1 | 12/2007 |
| WO | WO2008066196 A1 | 6/2008 |
| WO | WO2011102573 A1 | 8/2011 |

OTHER PUBLICATIONS

International Search Report for PCT/KR2013/000280.

* cited by examiner

*Primary Examiner* — Alexander R Pagano
*Assistant Examiner* — Ebenezer Sackey
(74) *Attorney, Agent, or Firm* — Vorys, Sater, Seymour & Pease LLP; Mih Suhn Koh

(57) ABSTRACT

A compound represented by Formula 1. An organic electric element includes a first electrode, a second electrode, and an organic material layer including the compound of Formula 1. The organic material layer include a light emitting layer, a hole transport layer including a compound represented by Formula 2, and an emission-auxiliary layer including the compound represented by Formula 1. When the organic electric element includes the compound in the organic material layer, luminous efficiency, color purity, and life span can be improved.

20 Claims, 1 Drawing Sheet

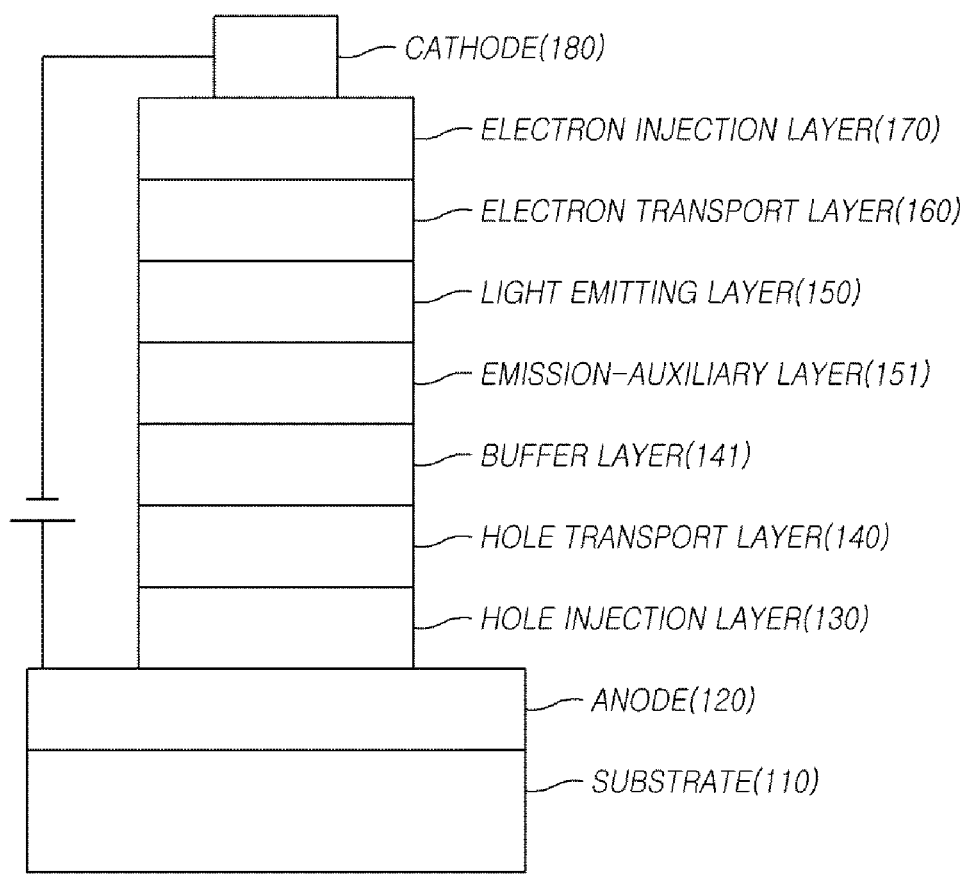

COMPOUND, ORGANIC ELECTRIC ELEMENT USING THE SAME, AND AN ELECTRONIC DEVICE THEREOF

CROSS-REFERENCE TO RELATED APPLICATION

This patent application claims benefit under 35 U.S.C. 119(e), 120, 121, or 365(c), and is a National Stage entry from International Application No. PCT/KR2013/000280, filed Jan. 14, 2013, which claims priority to Korean Patent Application No. 10-2012-0005563, filed on Jan. 18, 2012, Korean Patent Application No. 10-2012-0084503, filed on Aug. 1, 2012, Korean Patent Application No. 10-2012-0084945, filed on Aug. 2, 2012, and Korean Patent Application No. 10-2012-0090101, filed on Aug. 17, 2012, the contents of which are hereby incorporated by reference for all purposes as if fully set forth herein.

BACKGROUND

Technical Field

The present invention relates to an organic electric element including a compound and an electronic device thereof.

Background Art

In general, an organic light emitting phenomenon refers to a phenomenon in which electric energy is converted into light energy by means of an organic material. An organic electric element utilizing the organic light emitting phenomenon usually has a structure including an anode, a cathode, and an organic material layer interposed therebetween. Here, in many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer must be present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton. However, since materials to be used in the hole transport layer must have low HOMO values, they mostly have low T1 values, and on account of this, the exciton formed in the light emitting layer is transferred into the hole transport layer, which causes charge unbalance in the light emitting layer and thus light emission at the light emitting layer-hole transport layer interface. The light emission at the light emitting layer-hole transport layer interface has a problem in that color purity and efficiency are lowered and life span is shortened. Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve the above-mentioned problems occurring in the prior art, an object of the present invention is to provide an organic electric element using a compound, which allows the organic electric element to have high luminous efficiency, low driving voltage, and high heat resistance and to be improved in color purity and life span, and an electronic device including the organic electric element.

In accordance with an aspect of the present invention, there are provided a compound represented by Formula 1 below and an organic electric element, which includes an emission-auxiliary layer containing the compound represented by Formula 1 and a hole transport layer containing a compound represented by Formula 2 below.

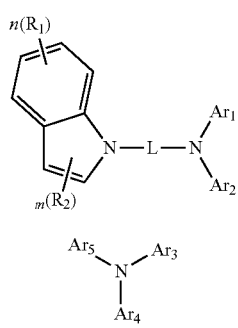

[Formula 1]

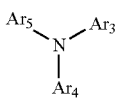

[Formula 2]

In another aspect of the present invention, there is provided an electronic device using an organic electric element containing the compounds represented by Formulas above.

According to embodiments of the present invention, an organic electric element not only has high luminous efficiency, low driving voltage, and high heat resistance, but can also be significantly improved in color purity and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, and iodine.

Unless otherwise stated, the term "alkyl" or "alkyl group" as used herein has, but not limited to, 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxy group" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and examples of the aryl group may include a phenyl group, a biphenyl group, a fluorine group, and a spirofluorene group.

Unless otherwise stated, the term "heteroalkyl" as used herein means alkyl containing one or more heteroatoms.

Unless otherwise stated, the term "heteroaryl group" or "heteroarylene group" as used herein means, but not limited to, a $C_3$ to $C_{60}$ aryl or arylene group containing one or more heteroatoms, includes both monocyclic and polycyclic rings, and may also be formed in conjunction with an adjacent group.

Unless otherwise stated, the term "heterocyclic alkyl" or "heterocyclic group" as used herein contains one or more heteroatoms, has 2 to 60 carbon atoms, includes both monocyclic and polycyclic rings, and may also be formed in conjunction with an adjacent group. Here, the "adjacent group" refers to an immediately adjacent group. Also, the heterocyclic group may mean an alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "saturated or unsaturated ring" means a saturated or unsaturated aliphatic ring, an aromatic ring having 6 to 60 carbon atoms, or a hetero ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_6$ to $C_{20}$ arylthio group, a $C_2$ to $C_{20}$ alkenyl group, a $C_2$ to $C_{20}$ alkynyl group, a $C_3$ to $C_{20}$ cycloalkyl group, a $C_6$ to $C_{60}$ aryl group, a $C_6$ to $C_{20}$ aryl group substituted by deuterium, a $C_8$ to $C_{20}$ arylalkenyl group, a silane group, a boron group, a germanium group, and a $C_5$ to $C_{20}$ heterocyclic group.

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the compound represented by Formulas 1 and 2. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include a protective layer formed on at least one side of the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150.

The organic electric element according to an embodiment of the present invention may be manufactured using a PVD (physical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to an embodiment of the present invention may be formed in various ways, the scope of protection of the present invention is not limited by a method of forming the organic material layer.

According to used materials, the organic electric element according to the present invention may be a top emission type, a bottom emission type, or a dual emission type.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

An organic electric element according to an aspect of the present invention includes an anode, a cathode, and an organic material formed therebetween, and the organic material layer may include an emission-auxiliary layer containing a compound represented by Formula 1 below and a hole transport layer containing a compound represented by Formula 2 below.

Hereinafter, compounds to be applied to an organic electric element according to an aspect of the present invention and an organic electric element containing the compounds will be described.

A compound according to an aspect of the present invention is represented by Formula 1 below.

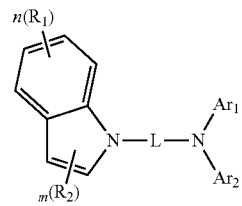

[Formula 1]

The compound represented by Formula 1 above is applied to an emission-auxiliary layer according to an embodiment of the present invention.

A compound according to another aspect of the present invention is represented by Formula 2 below.

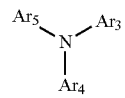

[Formula 2]

In Formula 2 above, $Ar_3$ is

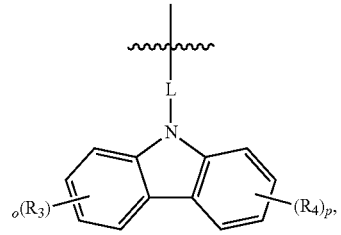

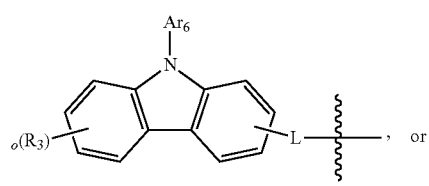, or

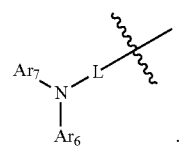

That is, Formula 2 above may be represented by Formula below.

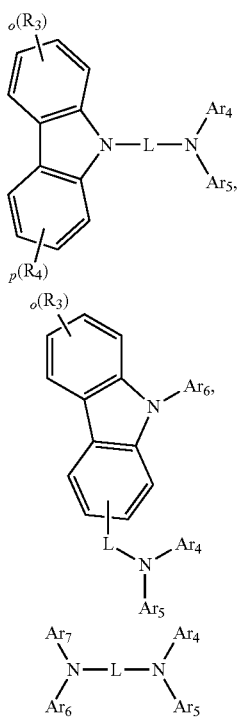

The compound represented by Formula 2 above may be applied to a hole transport layer.

In Formulas 1 and 2 above, n, o, and p are each an integer from 1 to 4; m is an integer of 1 or 2; when m, n, o, and p are each 2 or greater, a plurality of $R_1$s, $R_2$s, $R_3$s, or $R_4$s are the same as or different from each other; and i) $R_1$, $R_2$, $R_3$, and $R_4$ are each independently selected from the group consisting of hydrogen, deuterium, tritium, a halogen group, a $C_6$ to $C_{60}$ aryl group, a $C_1$ to $C_{50}$ alkyl group, a $C_2$ to $C_{40}$ alkenyl group, a $C_6$ to $C_{60}$ arylamine group, a $C_2$ to $C_{60}$ heterocyclic group containing at least one heteroatom selected from O, N, S, Si, and P, a fused ring group of a $C_6$ to $C_{60}$ aromatic ring and a $C_4$ to $C_{60}$ aliphatic ring, an amine group, a nitro group, a nitrile group, an amide group, and a silane group, or ii) at least one pair of two adjacent $R_1$s, two adjacent $R_2$s, two adjacent $R_3$s, and two adjacent $R_4$s are linked together to form aromatic fused ring. Here, $R_1$s, $R_2$s, $R_3$s, and $R_4$s not forming an aromatic ring are as defined in i) above.

Also, in Formulas 1 and 2 above, L is selected from the group consisting of a single bond, a $C_6$ to $C_{60}$ arylene group, a fluorenyl group, a $C_3$ to $C_{60}$ heteroarylene group, and a bivalent aliphatic hydrocarbon group (the arylene group, the fluorenyl group, the heteroarylene group, and the aliphatic hydrocarbon group each may be substituted by one or more substituents selected from the group consisting of hydrogen, deuterium, tritium, nitro, nitrile, halogen, an acetylene group, a $C_7$ to $C_{20}$ arylalkyl group, a $C_8$ to $C_{20}$ arylalkenyl group, a $C_1$ to $C_{50}$ alkyl group, a $C_2$ to $C_{20}$ alkenyl group, a $C_1$ to $C_{20}$ alkoxy group, a $C_6$ to $C_{20}$ aryl group, a $C_2$ to $C_{20}$ heterocyclic group, and an amino group); and $Ar_1$ to $Ar_7$ are each independently selected from the group consisting of a $C_6$ to $C_{60}$ aryl group, a $C_2$ to $C_{60}$ heteroaryl group containing at least one heteroatom selected from O, N, S, Si, and P, a $C_2$ to $C_{20}$ alkenyl group, a fluorenyl group, a $C_1$ to $C_{30}$ alkoxy group, a $C_6$ to $C_{30}$ aryloxy group, a $C_6$ to $C_{60}$ arylamine group, and a $C_1$ to $C_{50}$ alkyl group.

When $R_1$ to $R_4$ and $Ar_1$ to $Ar_7$ are an aryl group, they each may be substituted by one or more substituents selected from the group consisting of hydrogen, deuterium, tritium, a halogen group, a $C_1$ to $C_{60}$ alkyl group, a $C_1$ to $C_{60}$ alkoxy group, a $C_1$ to $C_{60}$ alkylamine group, a $C_6$ to $C_{60}$ arylamine group, a $C_1$ to $C_{60}$ alkylthiophene group, a $C_6$ to $C_{60}$ arylthiophene group, a $C_2$ to $C_{60}$ alkenyl group, a $C_2$ to $C_{60}$ alkynyl group, a $C_3$ to $C_{60}$ cycloalkyl group, a $C_6$ to $C_{60}$ aryl group, a $C_6$ to $C_{60}$ aryl group substituted by deuterium, a $C_8$ to $C_{60}$ arylalkenyl group, a substituted or unsubstituted silane group, a substituted or unsubstituted boron group, a substituted or unsubstituted germanium group, and a substituted or unsubstituted $C_2$ to C60 heterocyclic group (with the proviso that when $Ar_1$ and $Ar_2$ are an aryl group, the above substituent group may further include deuterium, an amino group, a nitrile group, a nitro group, and a phosphineoxide group;

when $R_1$ to $R_4$ and $Ar_1$ to $Ar_7$ are a heterocyclic group, they each may be substituted by one or more substituents selected from the group consisting of hydrogen, deuterium, tritium, a halogen group, a $C_1$ to $C_{60}$ alkyl group, a $C_2$ to $C_{60}$ alkenyl group, a $C_1$ to $C_{60}$ alkoxy group, a $C_1$ to $C_{60}$ alkylamine group, a $C_6$ to $C_{60}$ arylamine group, a $C_1$ to $C_{60}$ alkylthio group, a $C_6$ to $C_{60}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{60}$ heterocyclic group, a $C_2$ to $C_{60}$ alkynyl group, a substituted or unsubstituted silane group, a substituted or unsubstituted boron group, a substituted or unsubstituted germanium group, a nitrile group, and an acetylene group;

when $R_1$ to $R_4$ and $Ar_1$ to $Ar_7$ are an alkyl group, they each may be substituted by one or more substituents selected from the group consisting of hydrogen, deuterium, tritium, a halogen group, a $C_1$ to $C_{20}$alkyl group, a $C_2$ to $C_{20}$alkenyl group, a $C_1$ to $C_{20}$alkoxy group, a $C_6$ to $C_{20}$aryl group, a $C_6$ to $C_{20}$aryl group substituted by deuterium, a $C_7$ to $C_{20}$arylalkyl group, a $C_8$ to $C_{20}$arylalkenyl group, a $C_2$ to $C_{20}$heterocyclic group, a nitrile group, and an acetylene group;

when $R_1$ to $R_4$ and $Ar_1$ to $Ar_7$ are an alkenyl group, they each may be substituted by one or more substituents selected from the group consisting of hydrogen, deuterium, tritium, a halogen group, a $C_1$ to $C_{20}$alkyl group, a $C_2$ to $C_{20}$alkenyl group, a $C_1$ to $C_{20}$alkoxy group, a $C_6$ to $C_{20}$arylamine group, a $C_6$ to $C_{60}$aryl group, a $C_6$ to $C_{20}$aryl group substituted by deuterium, a $C_7$ to $C_{20}$arylalkyl group, a $C_8$ to $C_{20}$arylalkenyl group, a $C_2$ to $C_{20}$heterocyclic group, a nitrile group, and an acetylene group;

when $R_1$ to $R_4$ are an amine group, they each may be substituted by one or more substituents selected from the group consisting of a $C_1$ to $C_{60}$alkyl group, a $C_2$ to $C_{60}$alkenyl group, a $C_6$ to $C_{60}$aryl group, and a $C_8$ to $C_{60}$arylalkyl group;

when $R_1$ to $R_4$ and $Ar_1$ to $Ar_7$ are an alkoxy group, they each may be substituted by one or more substituents selected from the group consisting of hydrogen, deuterium, a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocycloalkyl group, a $C_6$ to $C_{60}$ aryl group, a $C_6$ to $C_{60}$ aryl group substituted by deuterium, and a $C_2$ to $C_{60}$ heteroaryl group;

when $Ar_1$ and $Ar_7$ are a fluorenyl group, they each may be substituted by one or more substituents selected from the group consisting of hydrogen, deuterium, tritium, a halogen group, a $C_2$ to $C_{20}$ alkenyl group, a $C_1$ to $C_{20}$ alkoxy group, a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_1$ to $C_{50}$ alkyl group, a $C_2$ to $C_{20}$ heterocyclic group, a nitrile group, and an acetylene group;

when $Ar_1$ to $Ar_7$ are an aryloxy group, they each may be substituted by one or more substituents selected from the group consisting of hydrogen, deuterium, a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocycloalkyl group, a $C_2$ to $C_{30}$ heterocyclic group, a $C_6$ to $C_{60}$ aryl group, a $C_6$ to $C_{60}$ aryl group substituted by deuterium, and a $C_2$ to $C_{60}$ heteroaryl group; and when $R_1$ to $R_4$ and $Ar_1$ to $Ar_7$ are an arylamine group, they each may be substituted by one or more substituents selected from the group consisting of a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocycloalkyl group, a $C_6$ to $C_{60}$ aryl group, a $C_6$ to $C_{20}$ aryl group substituted by deuterium, and a $C_2$ to $C_{60}$ heteroaryl group.

In Formula 1 above, $Ar_1$ and $Ar_2$ each may be selected from aryl groups or fluorenyl groups below.

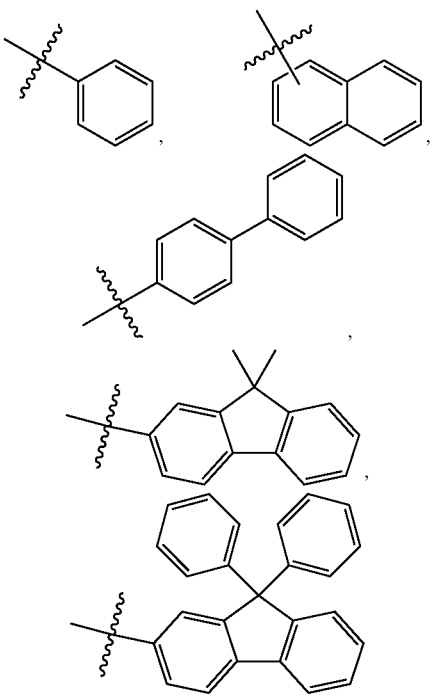

Also, in Formula 1 above, L may be selected from the group consisting of compounds below.

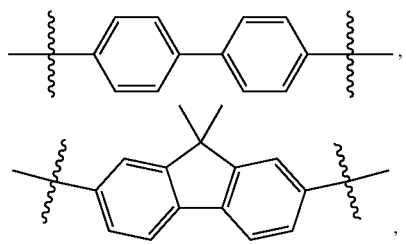

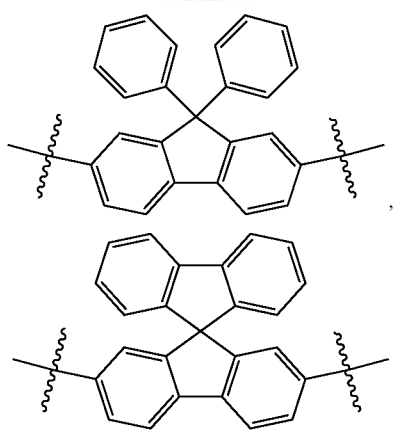

Formula 1 above may be represented by any one of Formulas 3 to 9 and 15 to 18 below. Especially, formulas 6 to 8 correspond to a case where adjacent $R_1$s are linked together to form one or more aromatic hydrocarbons.

[Formula 3]

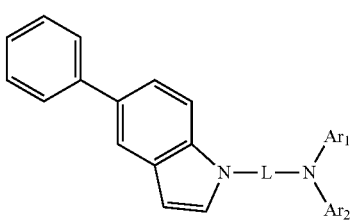

[Formula 4]

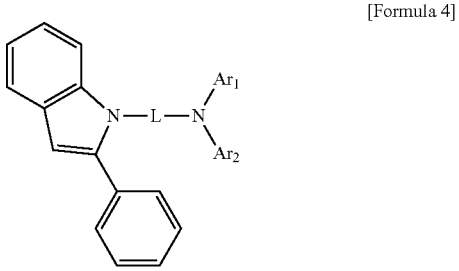

[Formula 5]

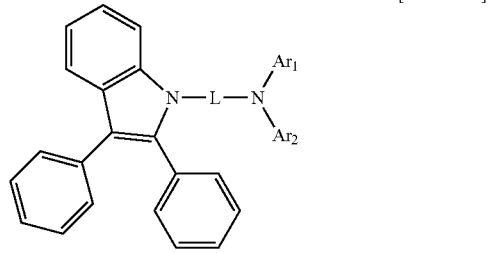

[Formula 6]

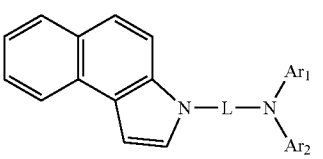

[Formula 7]

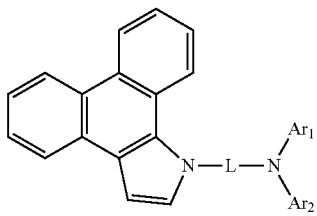

[Formula 8]

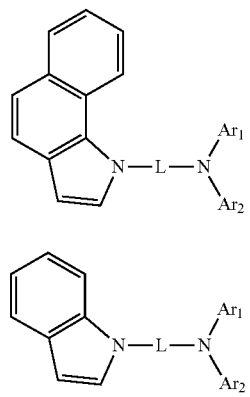

[Formula 9]

[Formula 15]


[Formula 16]

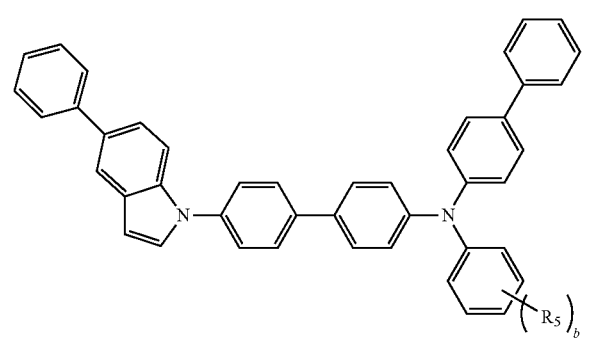

[Formula 17]

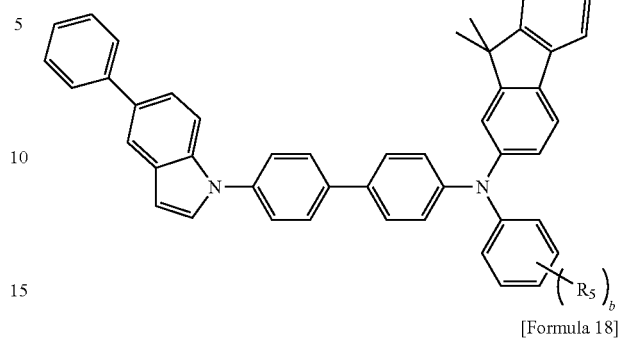

[Formula 18]

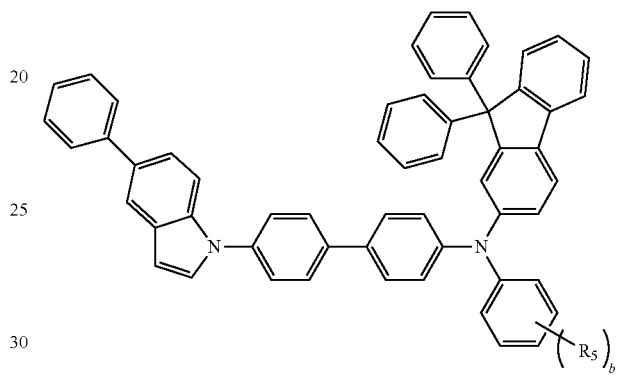

In Formulas 3 to 9 and 15 to 18 above, L, $Ar_1$, and $Ar_2$ are as defined in Formula 1 above.

More specially, Formulas 15 to 18 corresponds to a case where in Formula 1 above, m is an integer of 1 or 2; n is an integer from 1 to 4; when m and/or n are/is 2 or greater, a plurality of $R_1$s or $R_2$s are the same as or different from each other; i) $R_1$ and $R_2$ are each independently selected from the group consisting of hydrogen, deuterium, tritium, a halogen group, a $C_1$ to $C_{50}$ alkyl group, a $C_2$ to $C_{60}$ heterocyclic group containing at least one heteroatom selected from O, N, S, Si, and P, a $C_2$ to $C_{20}$ alkenyl group, a $C_6$ to $C_{60}$ aryl group, and a $C_6$ to $C_{60}$ arylamine group, or ii) two adjacent $R_1$s and two adjacent $R_2$s are each linked together to form at least one ring (wherein, groups not forming a ring are as defined in i) above);

L is a $C_6$ to $C_{60}$ arylene group, a fluorenyl group, a $C_3$ to $C_{60}$ heteroarylene group, or a bivalent aliphatic hydrocarbon group, and the arylene group, the fluorenyl group, the heteroarylene group, and the aliphatic hydrocarbon group each may be substituted by one or more substituents selected from the group consisting of nitro, nitrile, halogen, a $C_1$ to $C_{20}$ alkyl group, a $C_1$ to $C_{20}$ alkoxy group, a $C_6$ to $C_{20}$ aryl group, a $C_2$ to $C_{20}$ heterocyclic group, and an amino group; and $Ar_1$ and $Ar_2$ are each independently selected from the group consisting of a $C_6$ to $C_{60}$ aryl group, a $C_2$ to $C_{60}$ heterocyclic group containing at least one heteroatom selected from O, N, S, Si, and P, a $C_2$ to $C_{20}$ alkenyl group, and a fluorenyl group.

Also, in Formulas 15 to 18, a and b are each an integer from 1 to 5; when a and/or b are/is 2 or greater, a plurality of $R_4$s or $R_5$s are the same as or different from each other; i) $R_4$ and $R_5$ are each independently selected from the group consisting of a $C_6$ to $C_{25}$ aryl group and a $C_2$ to $C_{20}$ alkenyl group, or ii) two adjacent $R_4$s and two adjacent $R_5$s are each linked together to form at least one ring (wherein, groups not forming a ring are as defined in i) above); and when $R_4$ and $R_5$ are an aryl group or an alkenyl group, they each may be substituted by one or more substituents selected from the group consisting of a $C_1$ to $C_4$ alkyl group, a $C_2$ to $C_6$ alkenyl group, and a $C_6$ to $C_{20}$ aryl group.

Formula 2 above may be represented by any one of Formulas 10 to 14 below, all of which correspond to a case where two adjacent $R_3$s or two adjacent $R_4$s are linked together to form one or more aromatic hydrocarbons.

[Formula 10]

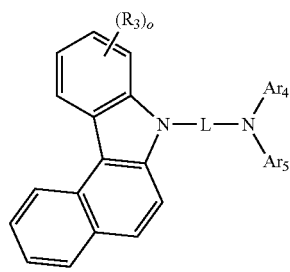

[Formula 11]

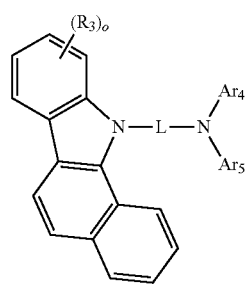

[Formula 12]

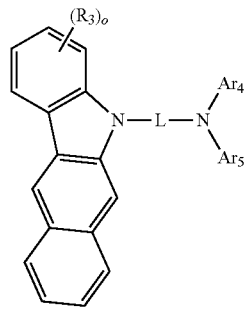

[Formula 13]

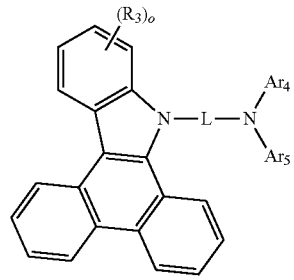

[Formula 14]

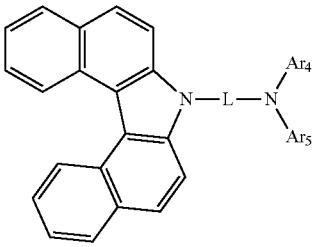

In Formulas 3 to 14 above, L, $Ar_4$, $Ar_5$, $R_3$ and o are as defined in Formula 2 above. More specially, the compound represented by Formula 1 above may be one of compounds 1-1 to 1-150 below, and the compound represented by Formula 2 above may be one of compounds 3-1 to 3-76, 4-1 to 4-108, 5-1 to 5-52, 6-1 to 6-52, 7-1 to 7-64, 8-1 to 8-63, 9-1 to 9-64, and 10-1 to 10-52.

1-1
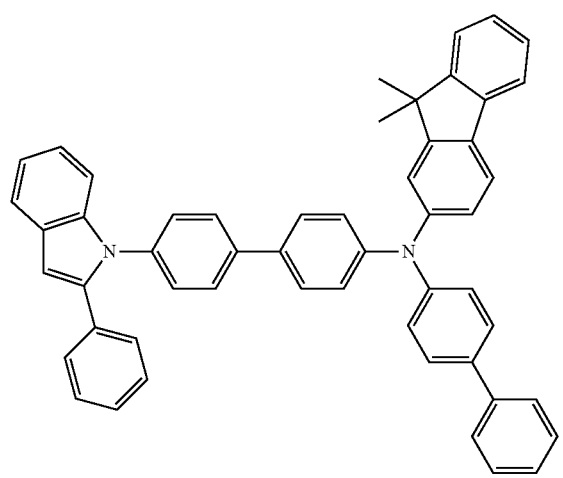
1-2
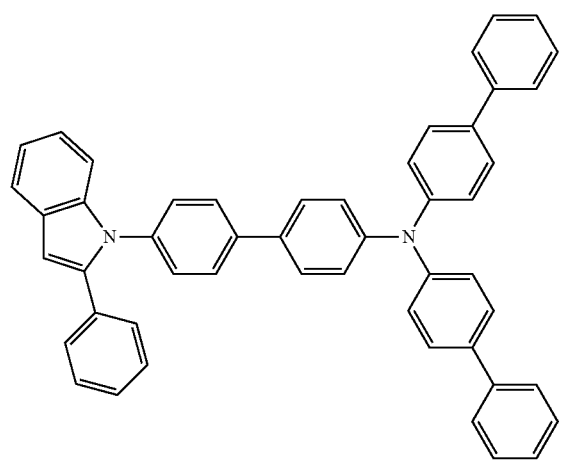
1-3
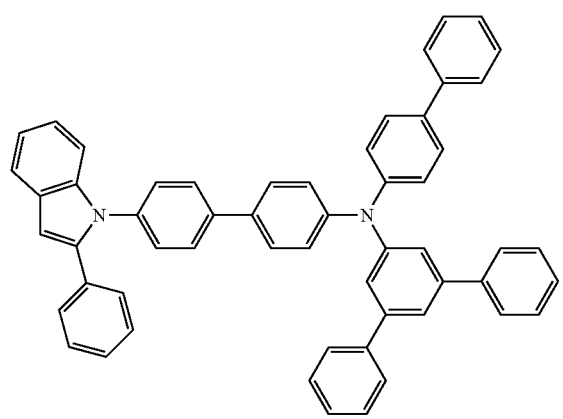
1-4
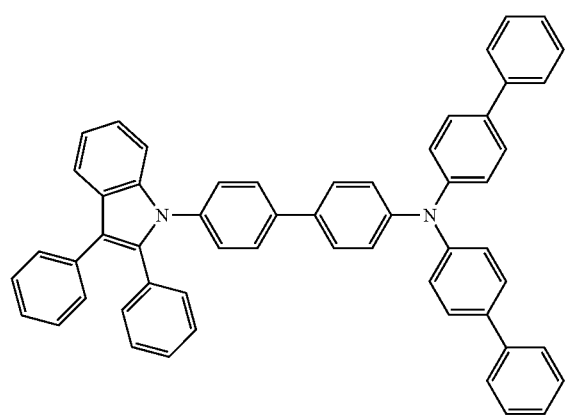
1-5
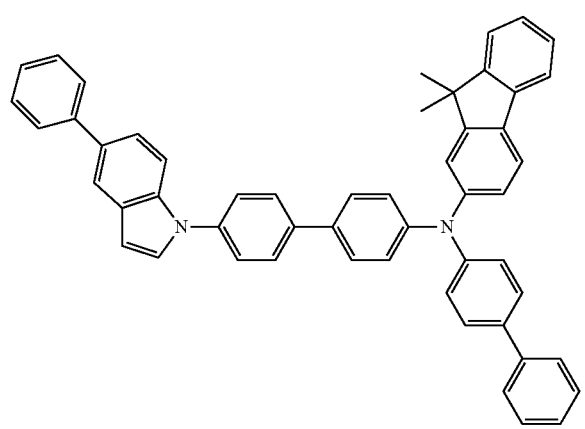
1-6
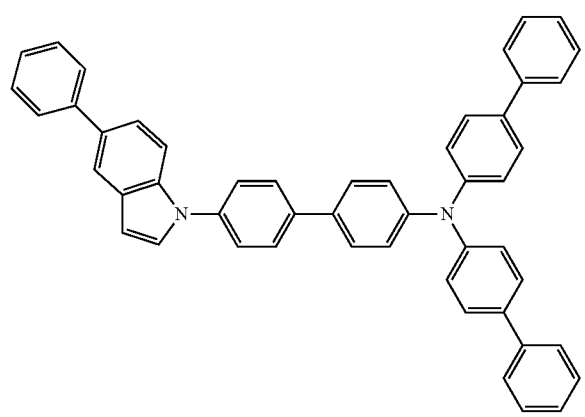

1-7
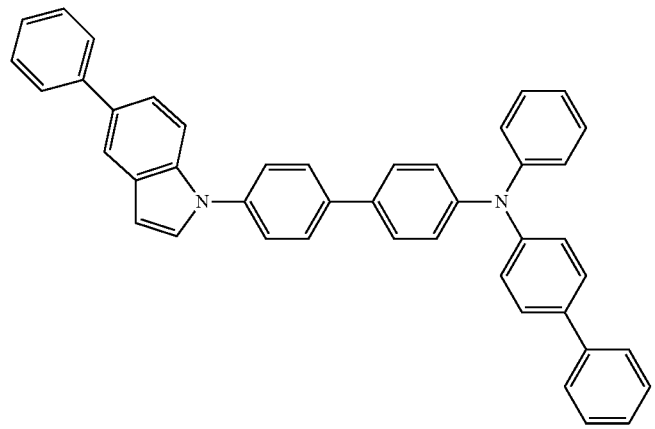
1-8
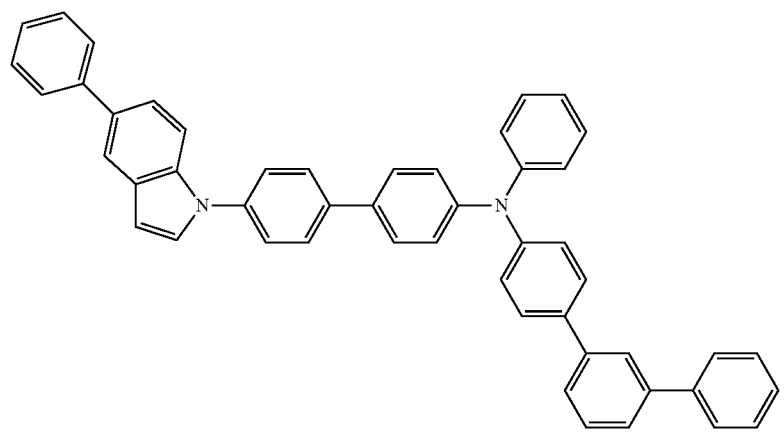
1-9 1-10
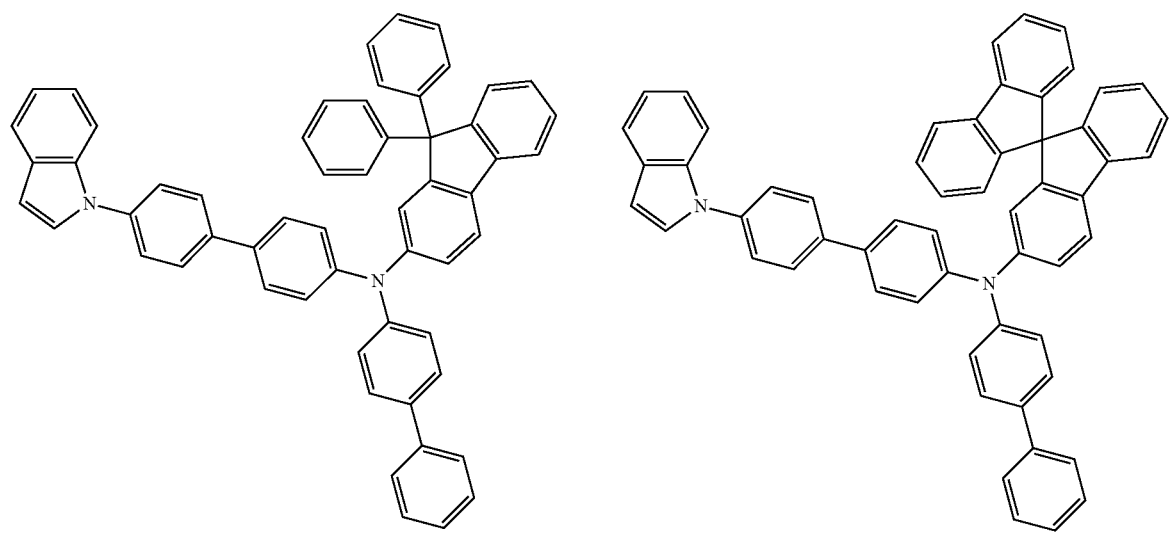

-continued
1-11
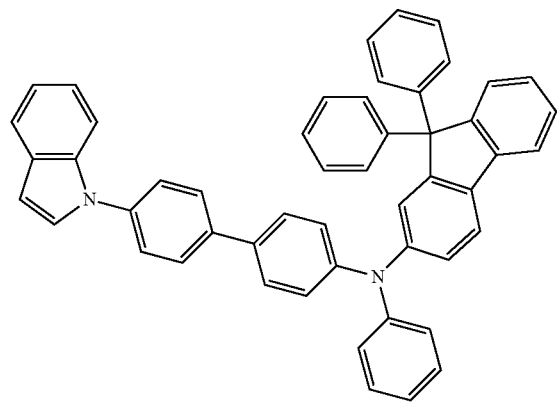
1-12
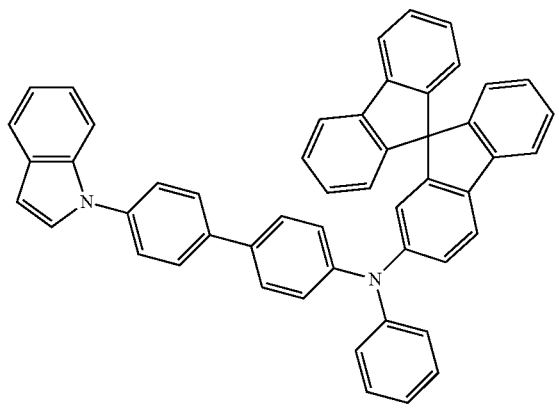
1-13
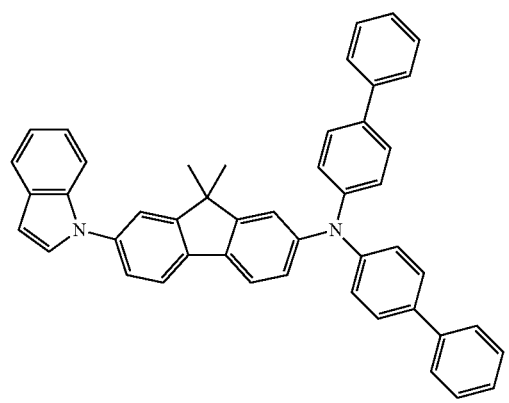
1-14
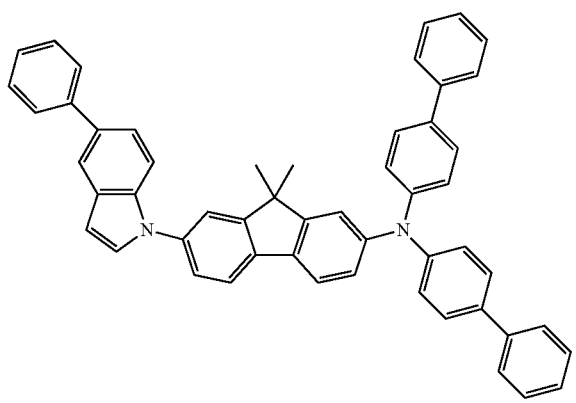
1-15
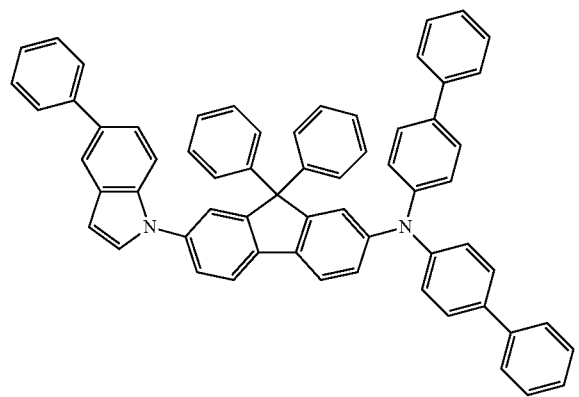
1-16
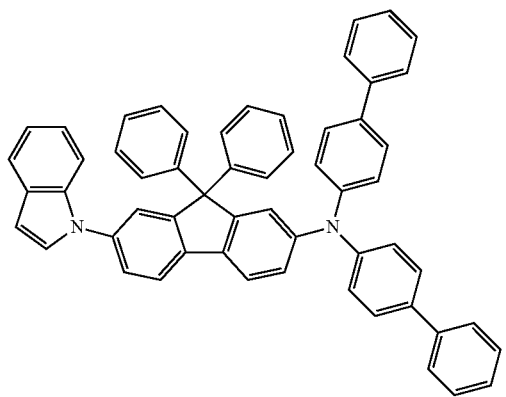
1-17
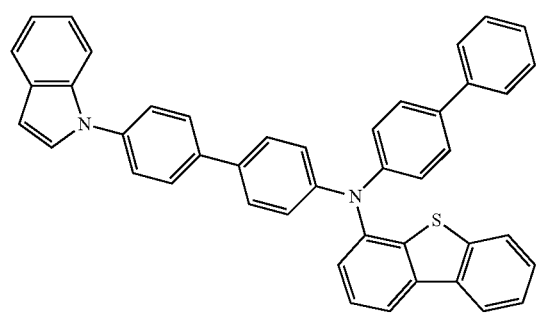
1-18
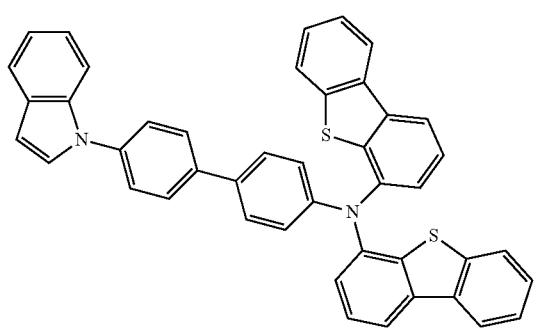

-continued
1-19
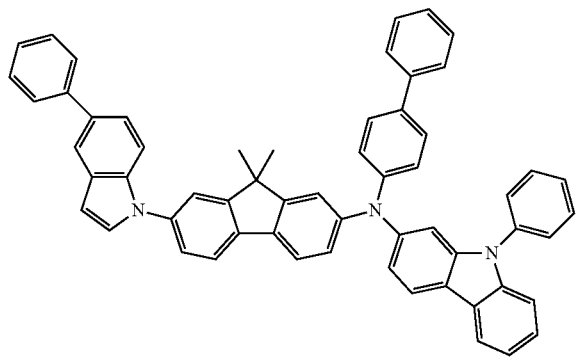
1-20
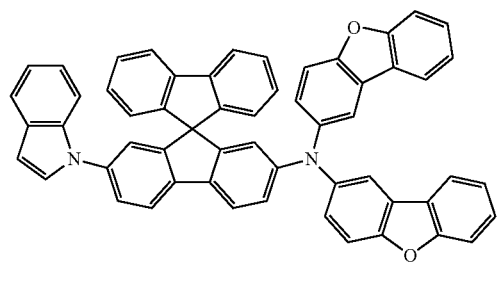
1-21
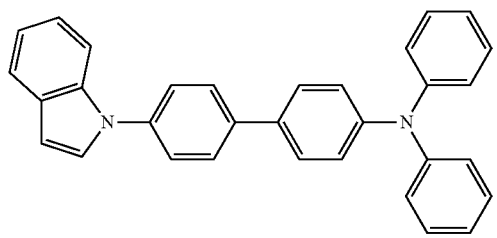
1-22
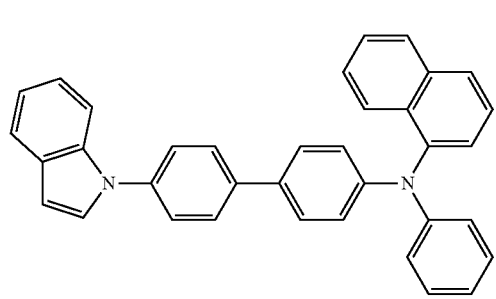
1-23
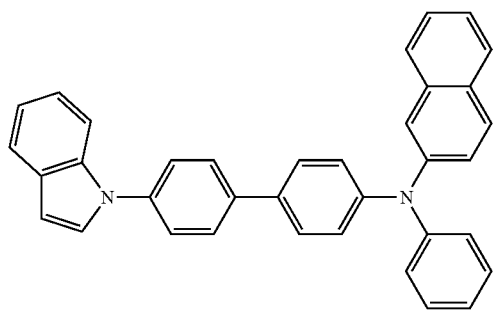
1-24
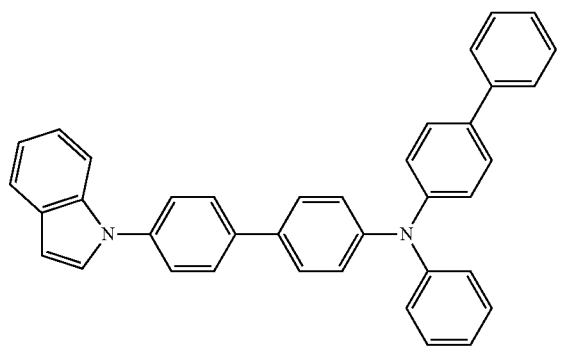
1-25
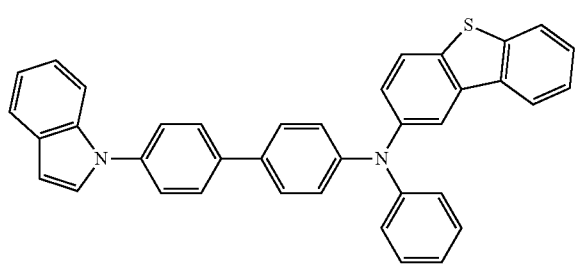
1-26
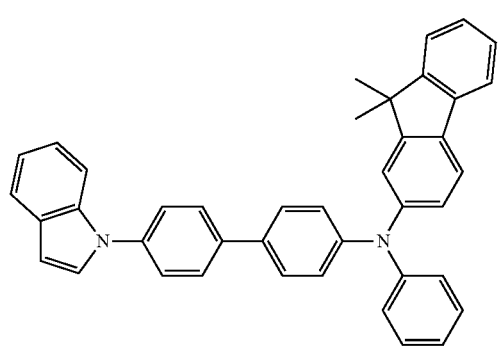

-continued
1-27
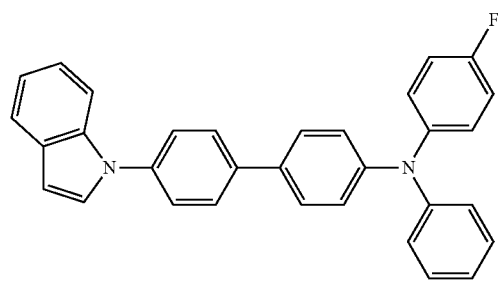
1-28
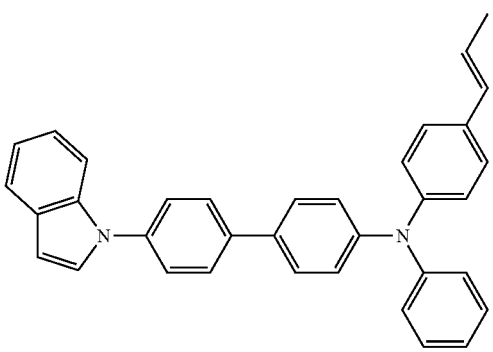
1-29
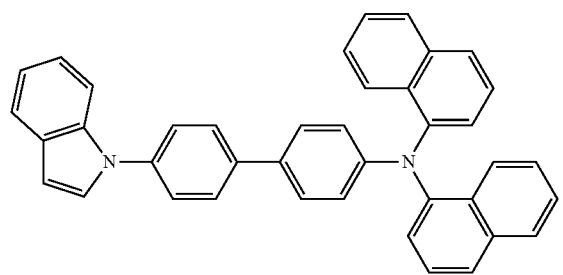
1-30
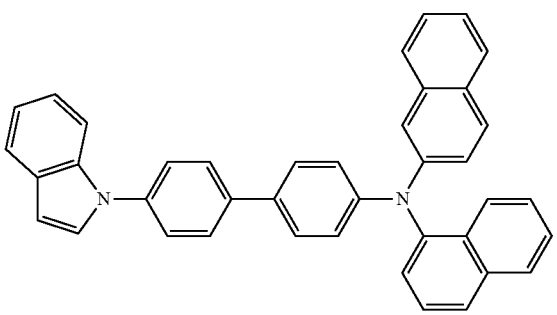
1-31
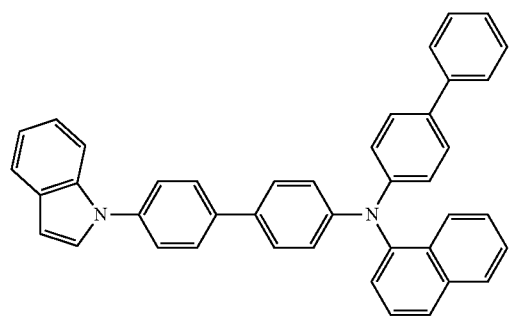
1-32
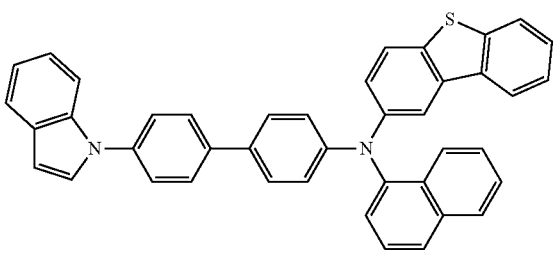
1-33
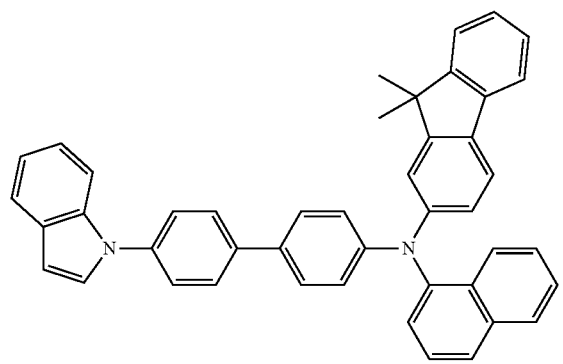
1-34
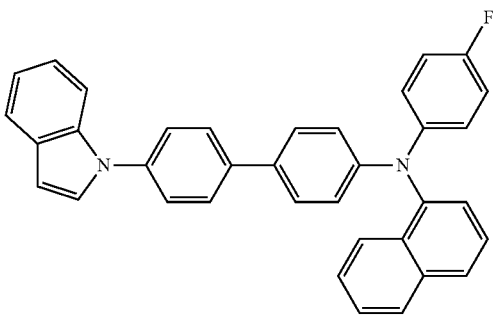

-continued
1-35
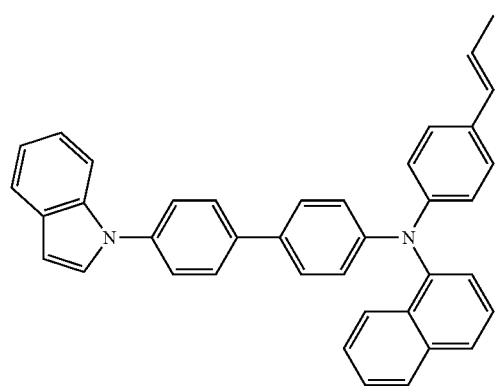
1-36
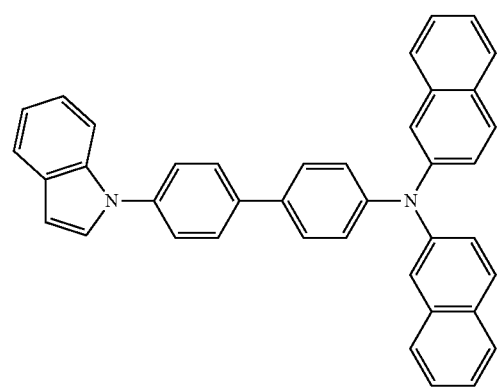
1-37
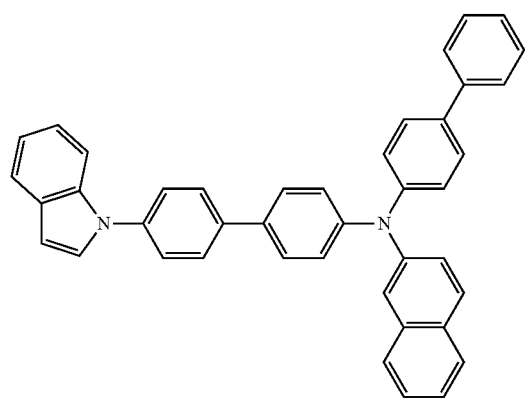
1-38
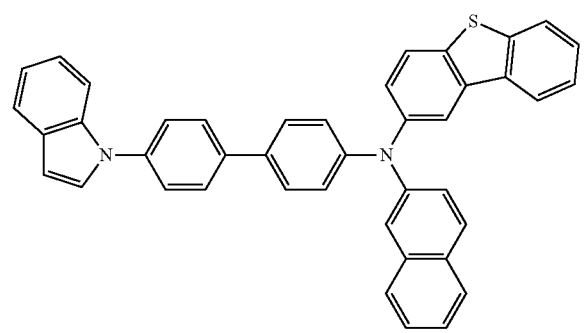
1-39
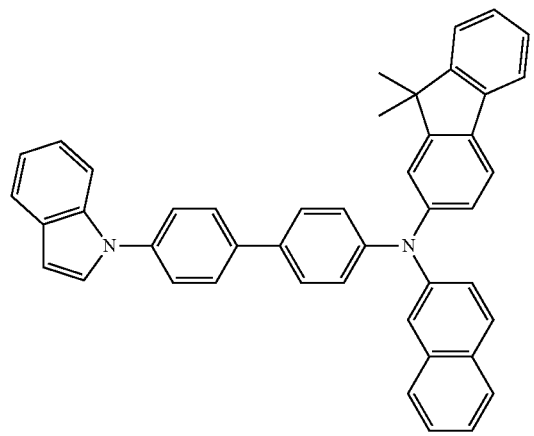
1-40
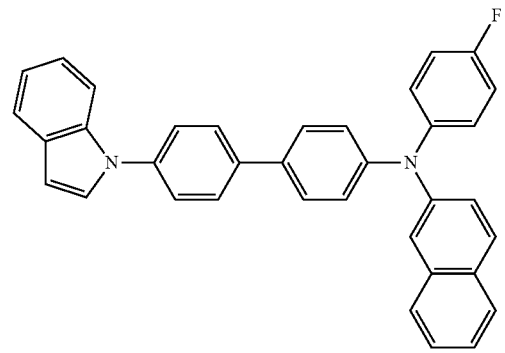

-continued
1-41
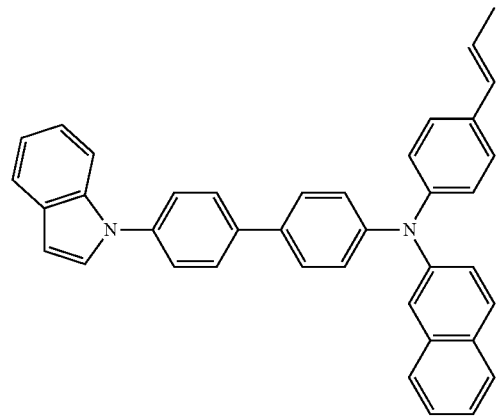
1-42
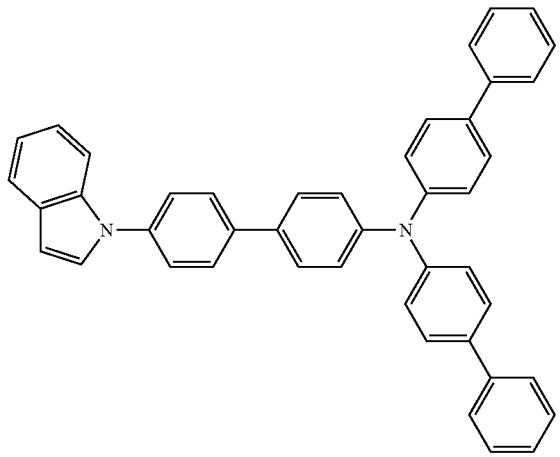
1-43
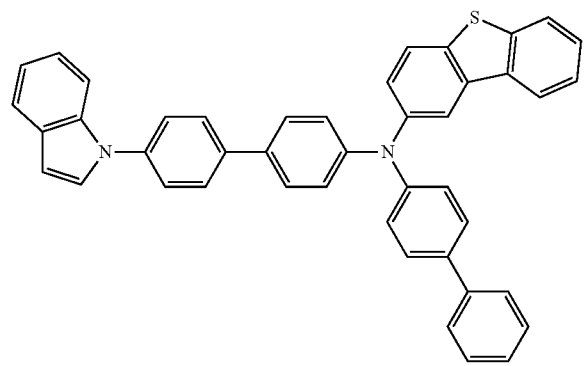
1-44
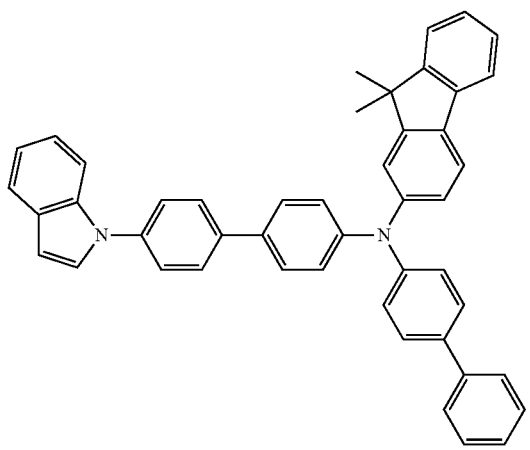
1-45
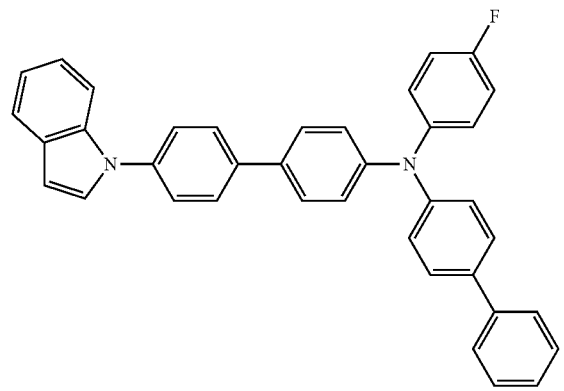
1-46
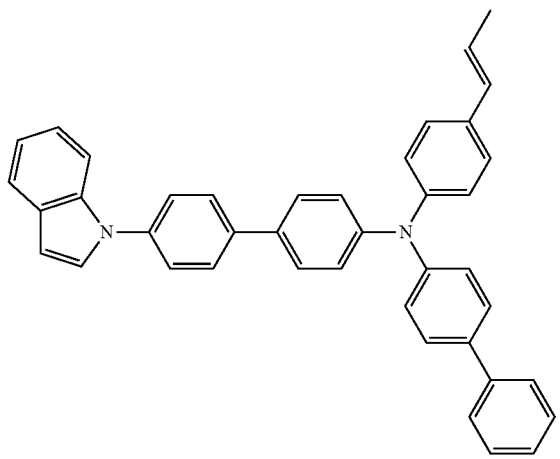

-continued
1-47
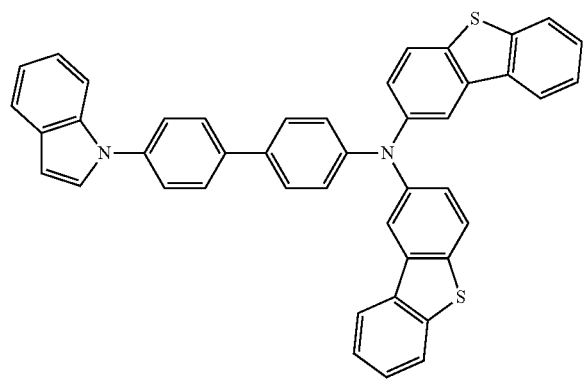
1-48
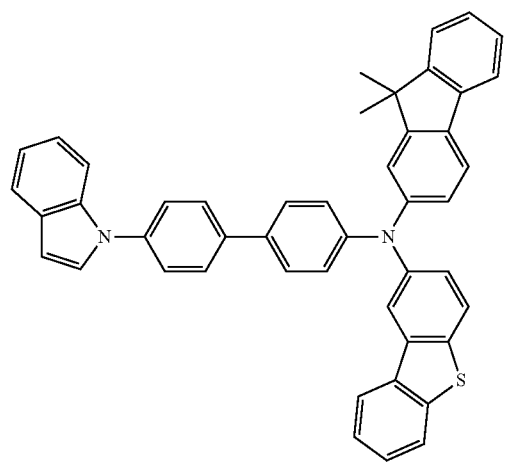
1-49
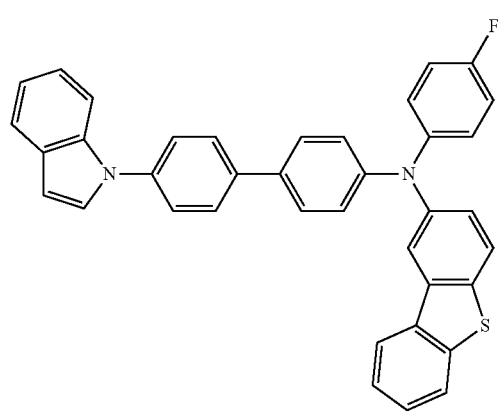
1-50
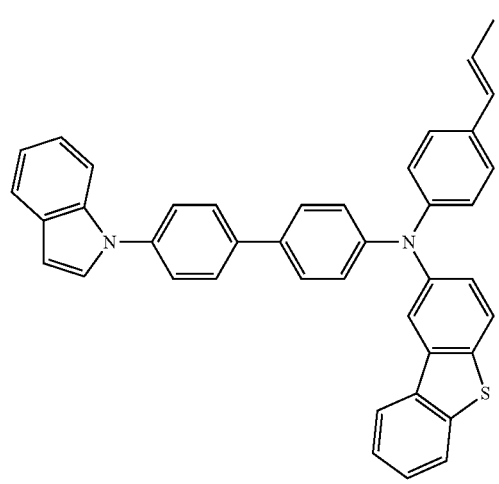
1-51
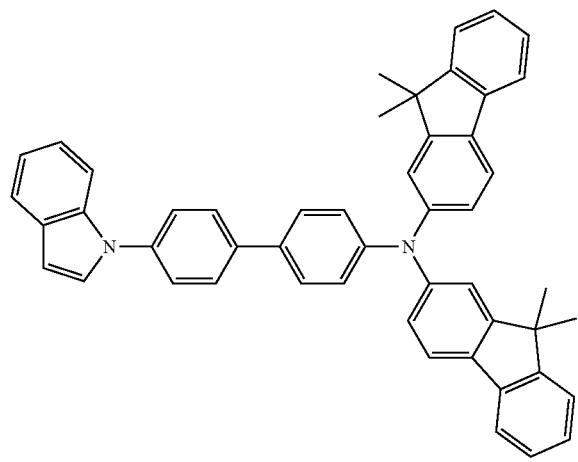
1-52
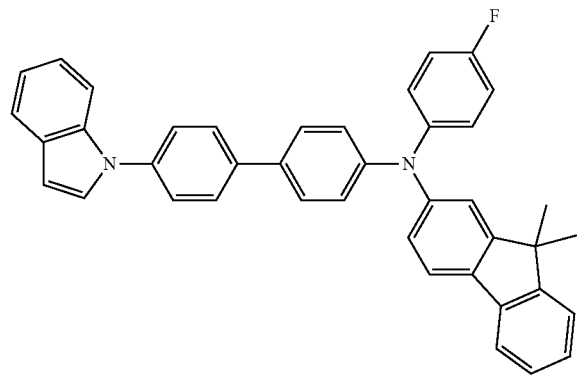

-continued
1-53
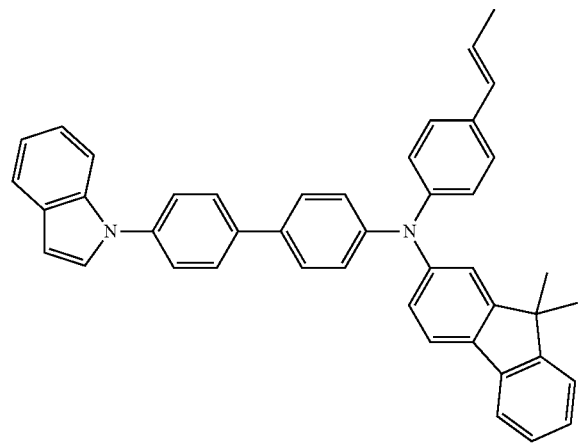
1-54
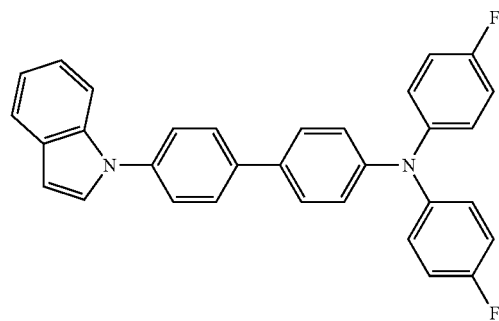
1-55
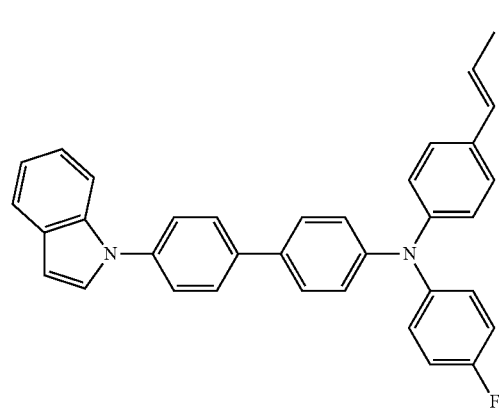
1-56
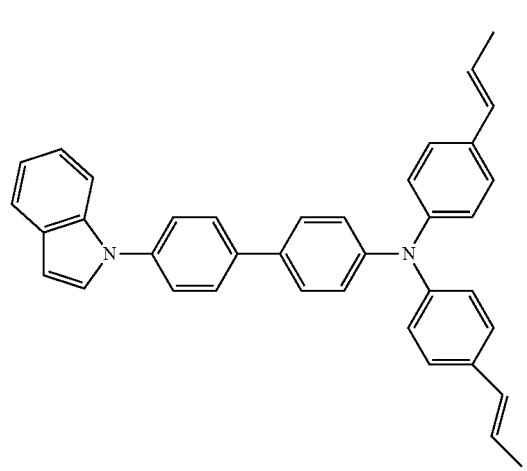
1-57
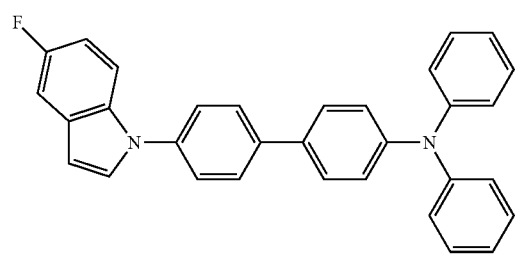
1-58
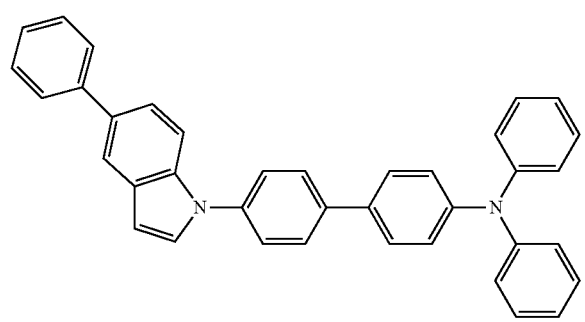
1-59
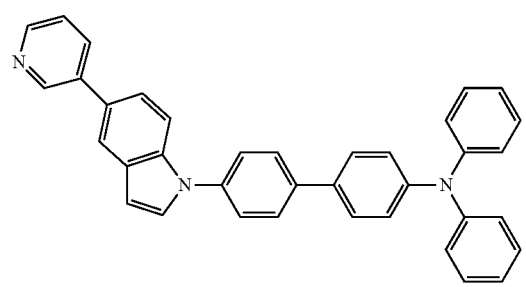
1-60
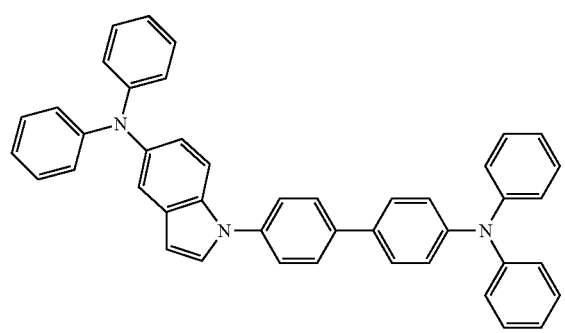

-continued
1-61
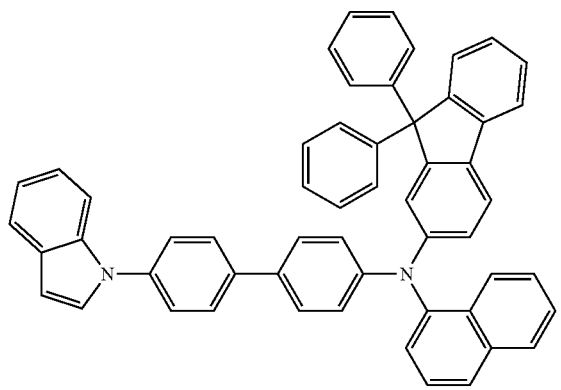
1-62
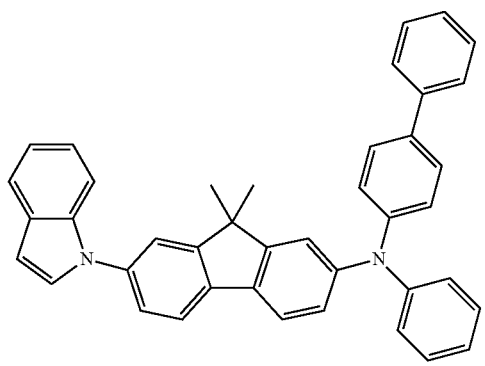
1-63
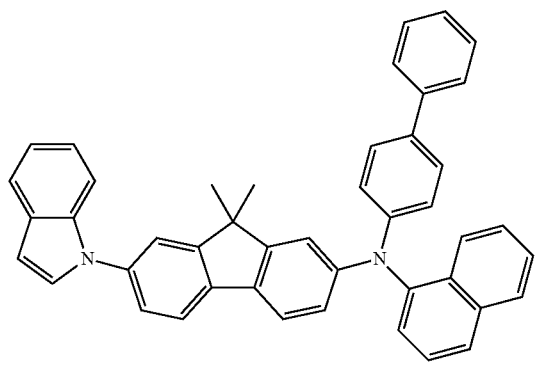
1-64
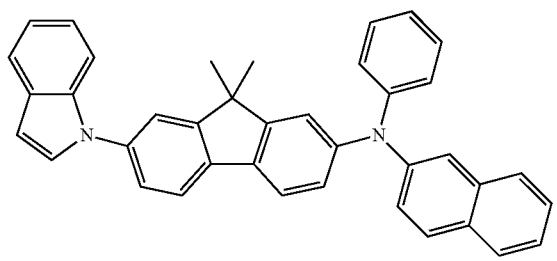
1-65
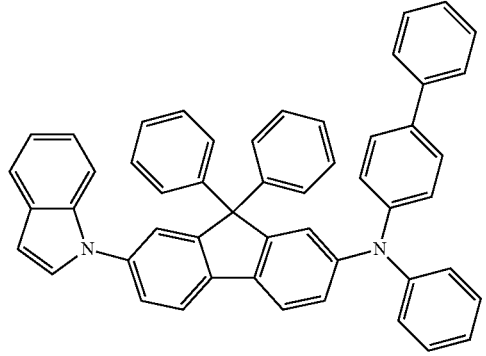
1-66
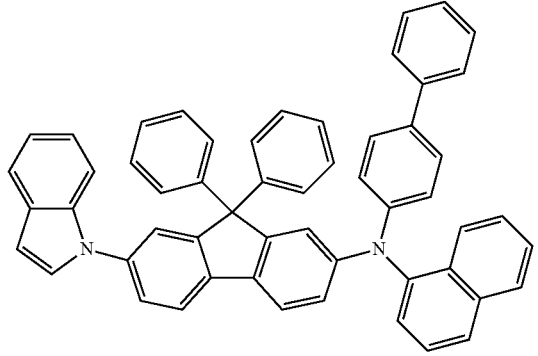
1-67
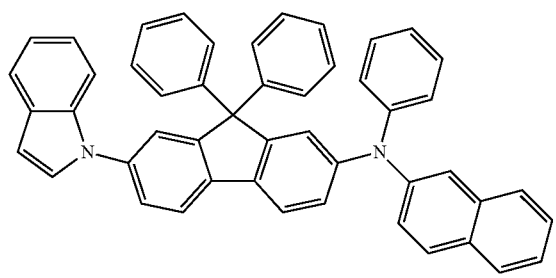
1-68
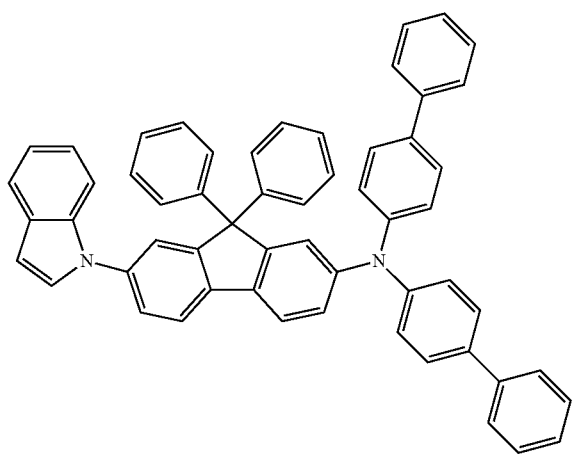

-continued
1-69
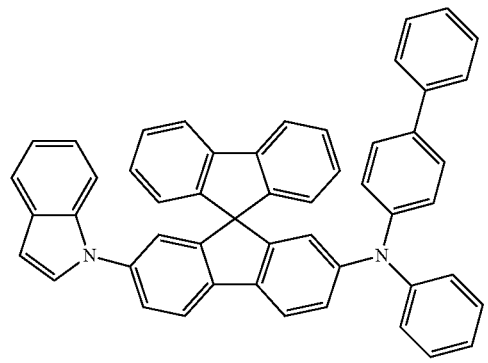
1-70
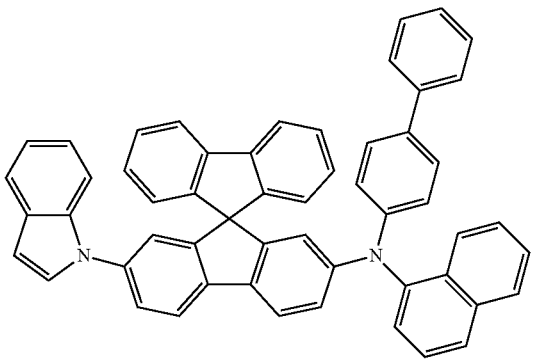
1-71
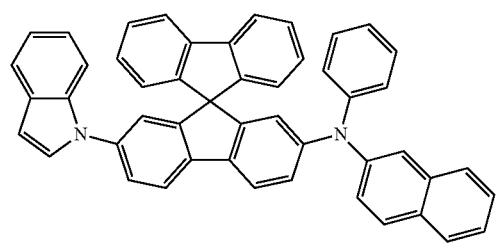
1-72
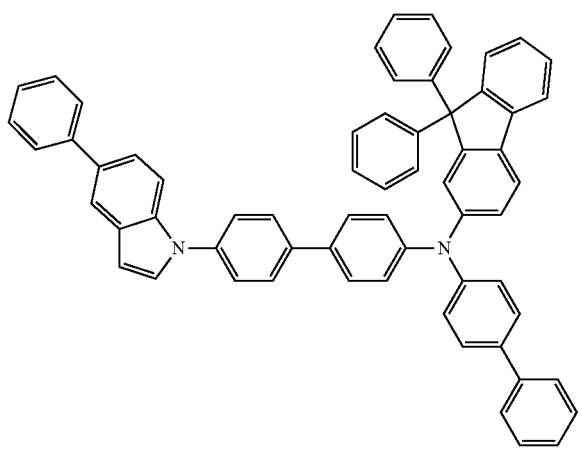
1-73
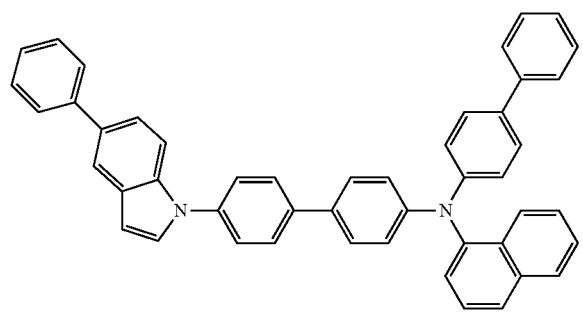
1-74
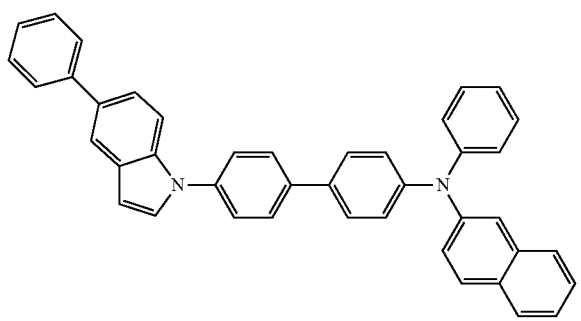
1-75
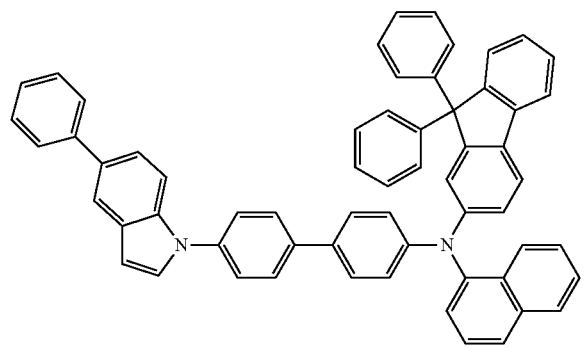
1-76
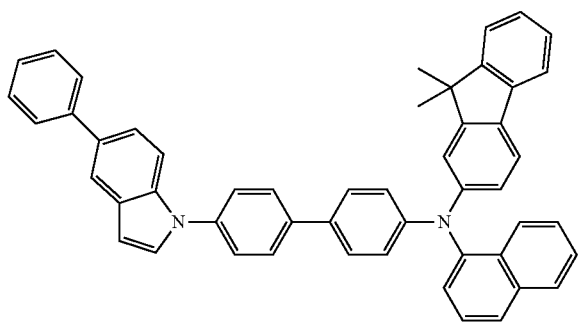

-continued
1-77
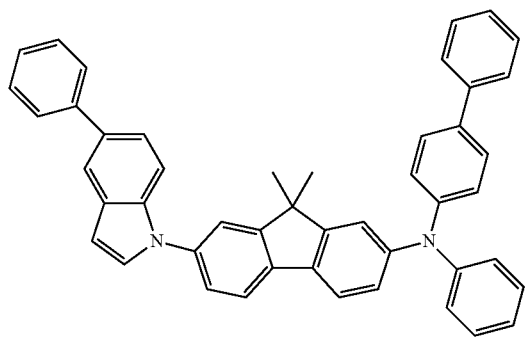
1-78
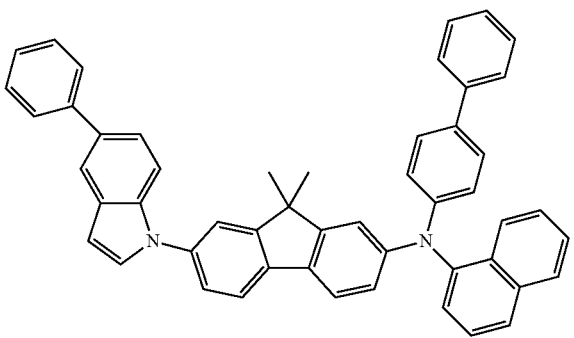
1-79
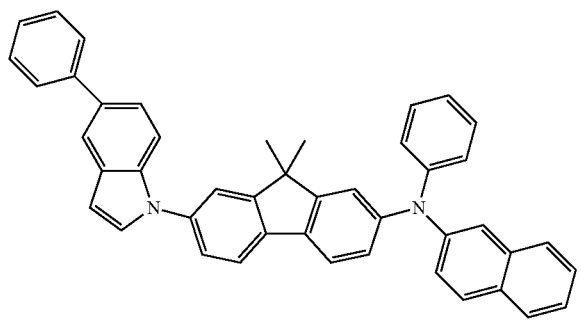
1-80
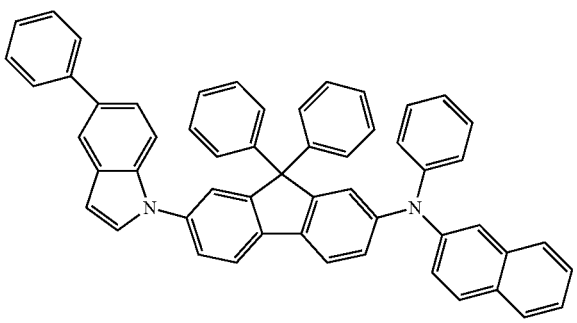
1-81
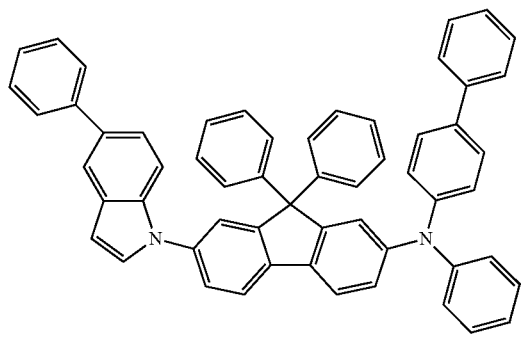
1-82
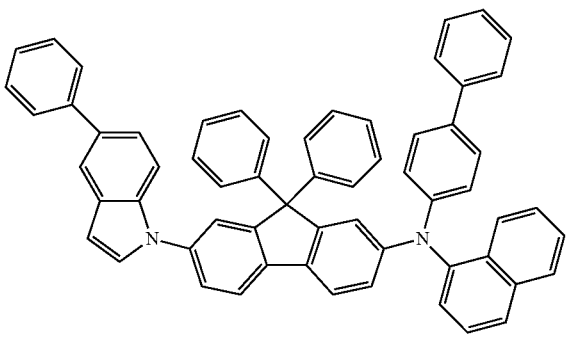
1-83
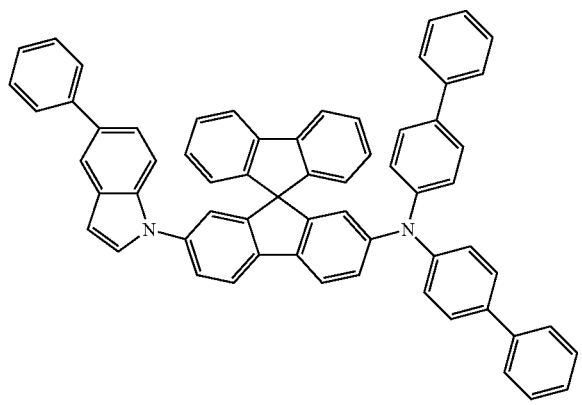
1-84
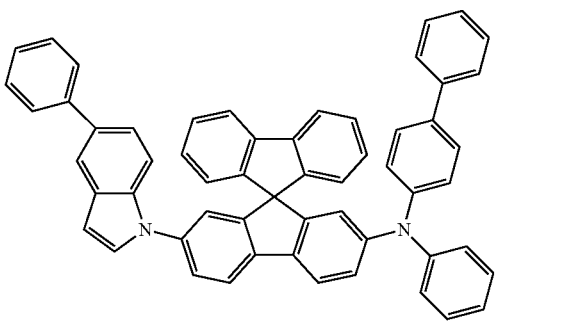

1-85
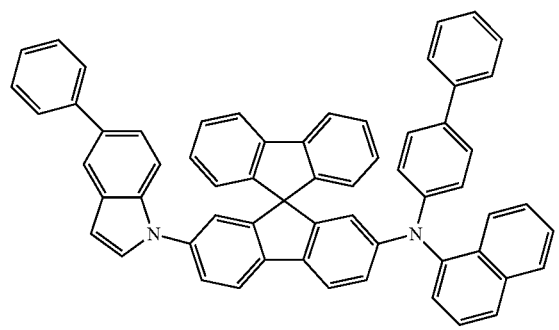
1-86
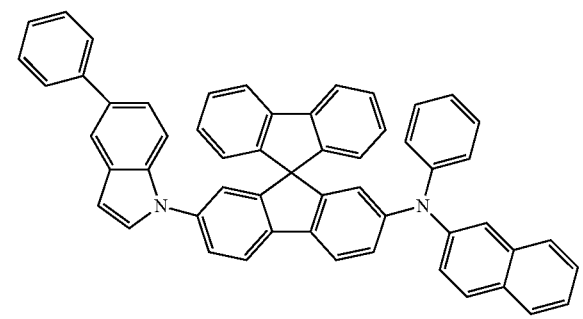
1-87
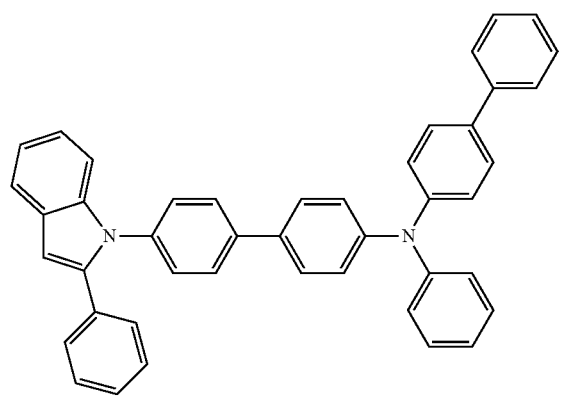
1-88
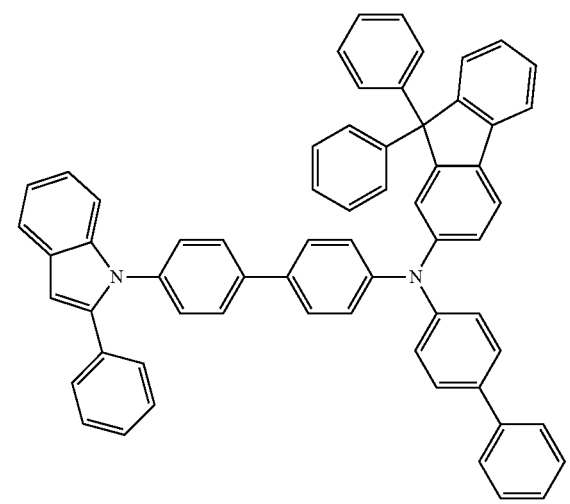
1-89
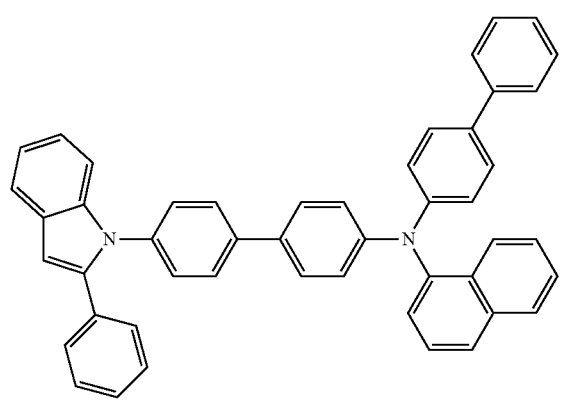
1-90
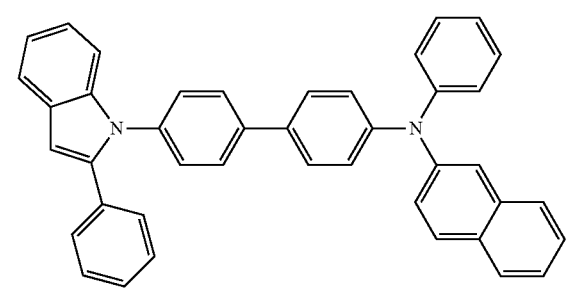

-continued
1-91
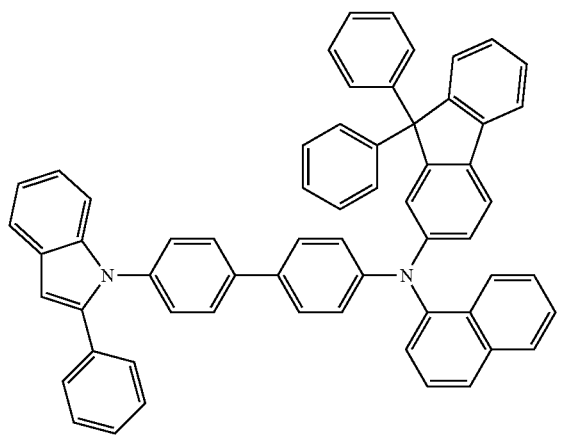
1-92
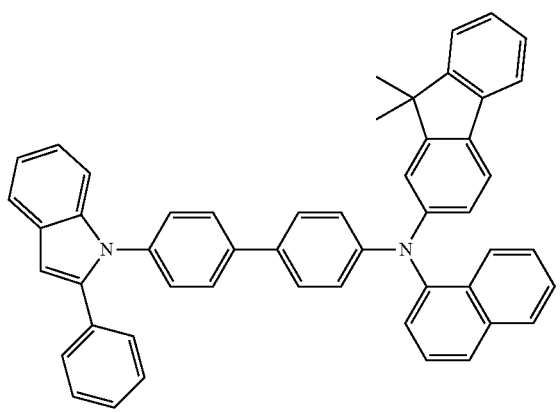
1-93
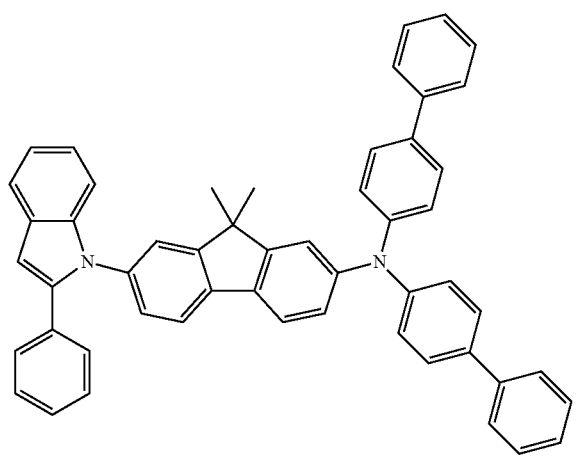
1-94
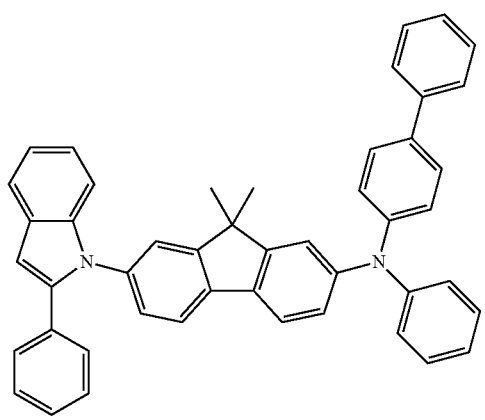
1-95
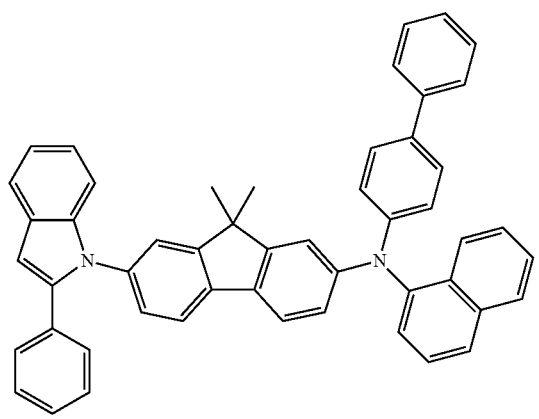
1-96
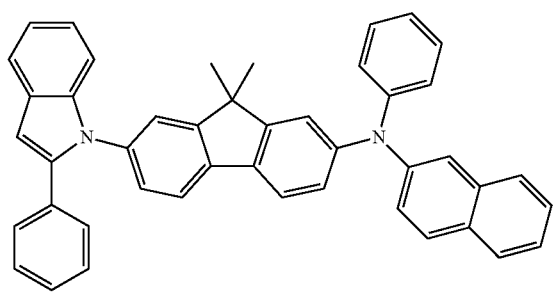

-continued
1-97
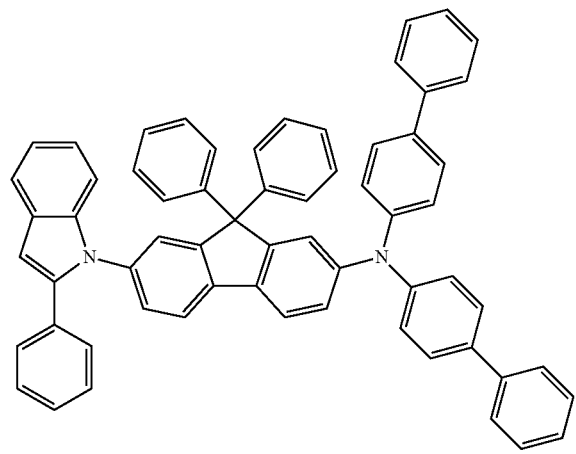
1-98
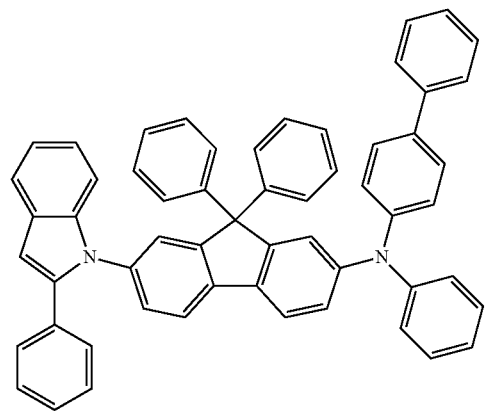
1-99
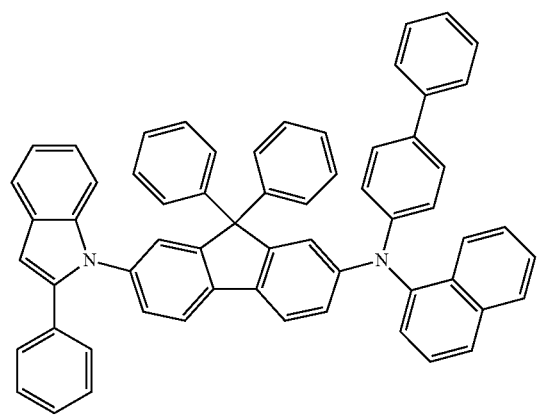
1-100
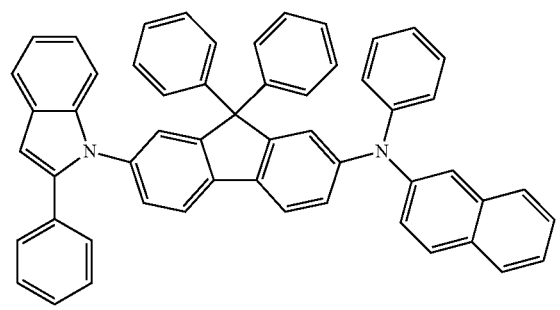
1-101
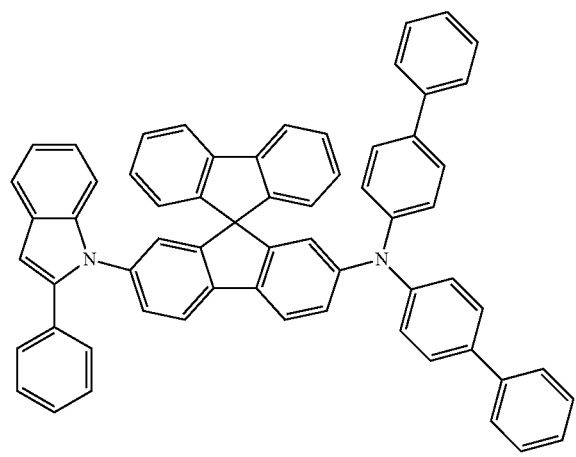
1-102
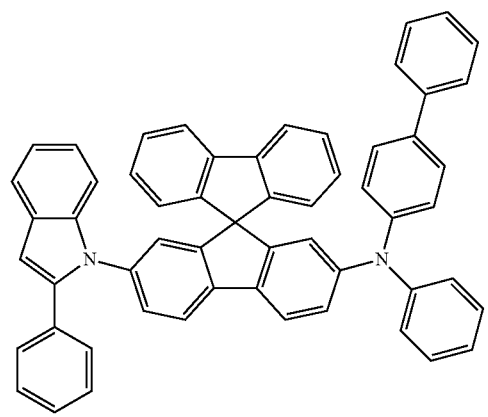

-continued
1-103
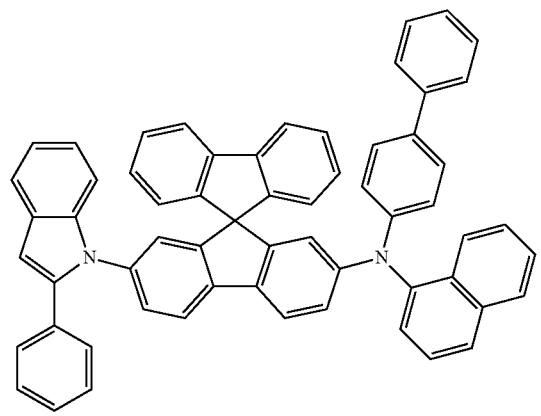
1-104
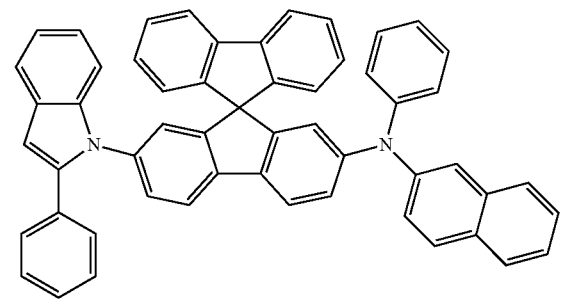
1-105
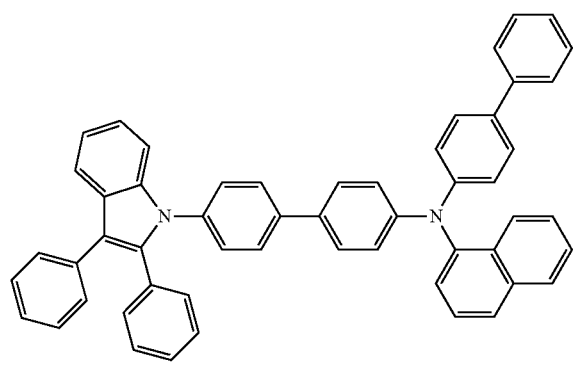
1-106
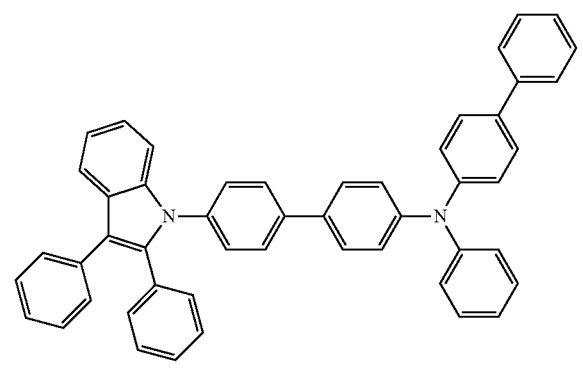
1-107
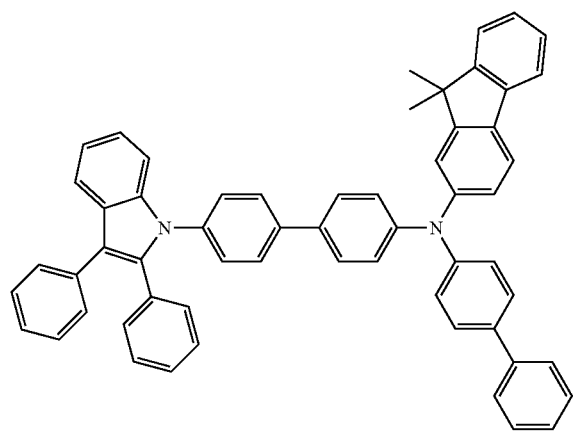
1-108
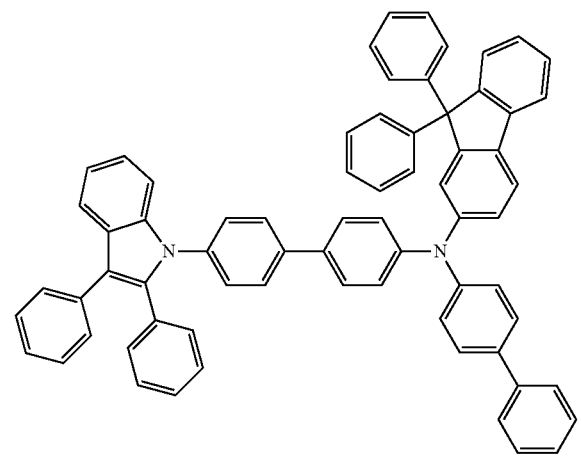

-continued
1-109
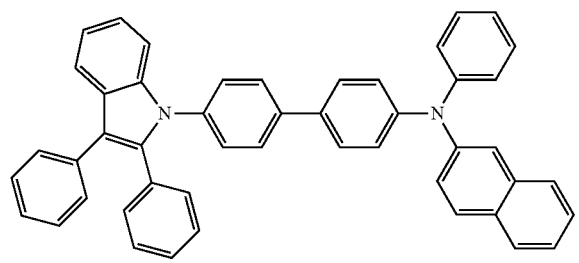
1-110
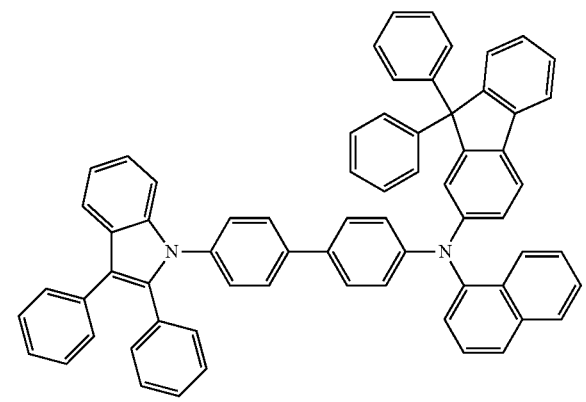
1-111
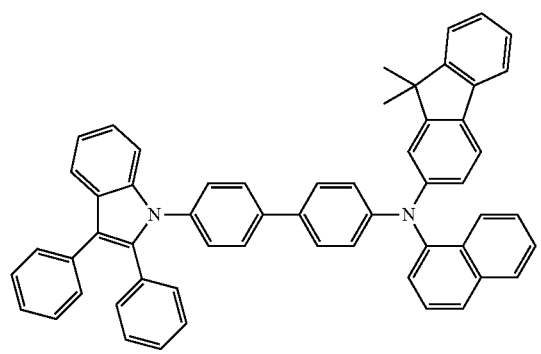
1-112
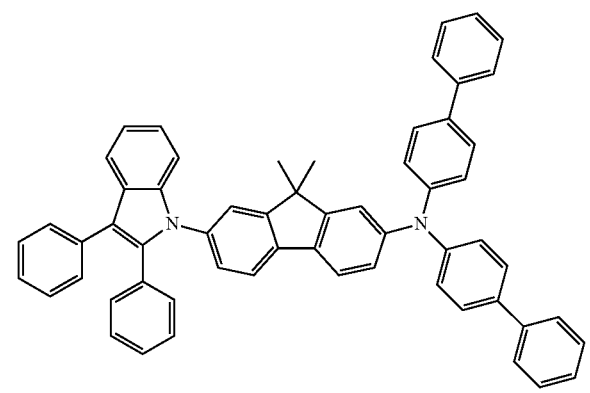
1-113
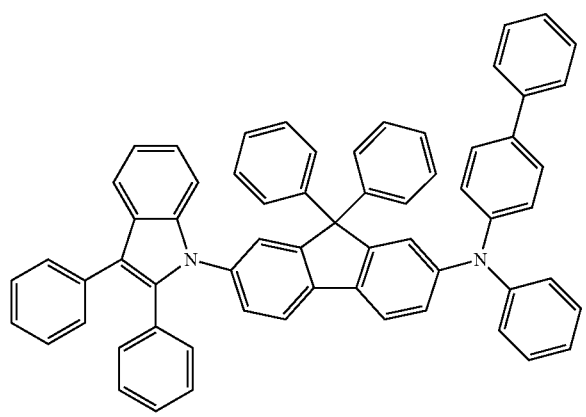
1-114
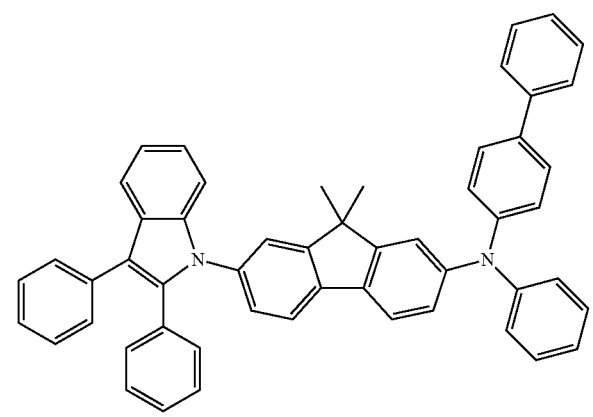
1-115
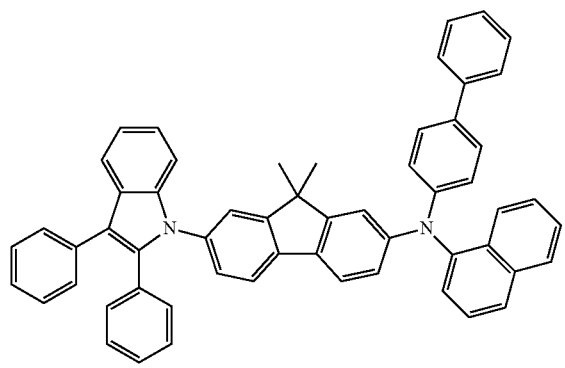
1-116
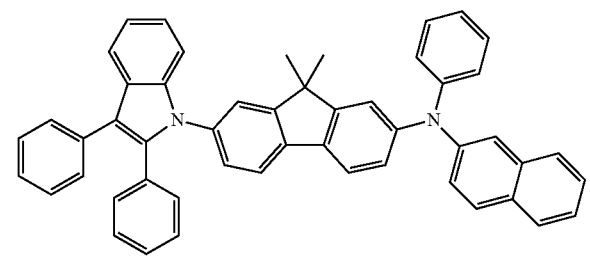

-continued
1-117
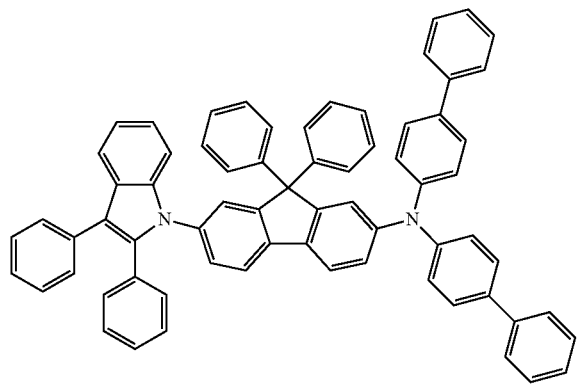
1-118
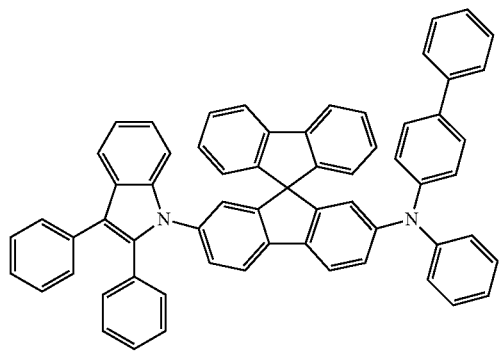
1-119
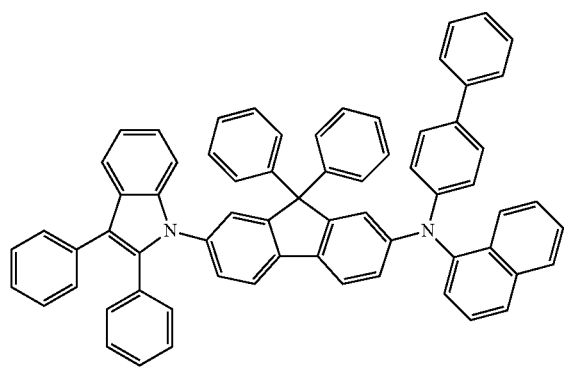
1-120
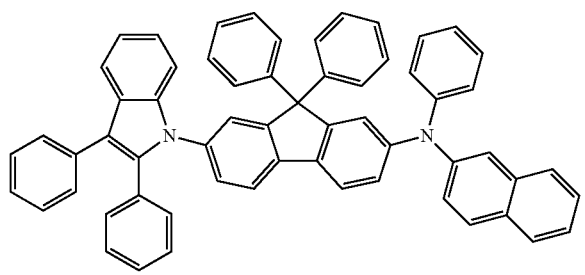
1-121
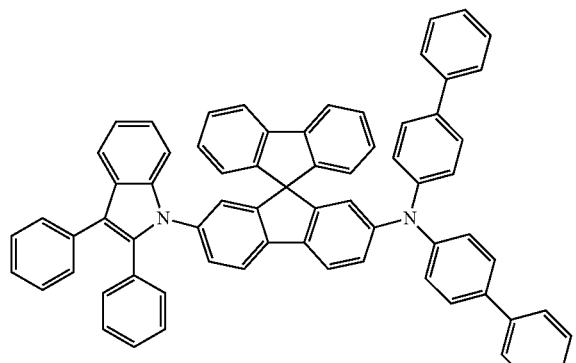
1-122
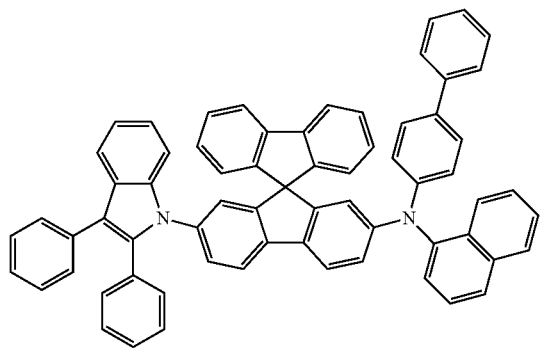
1-123
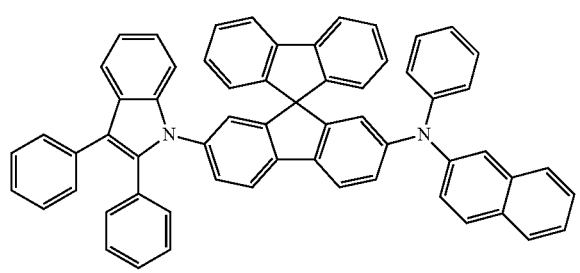
1-124
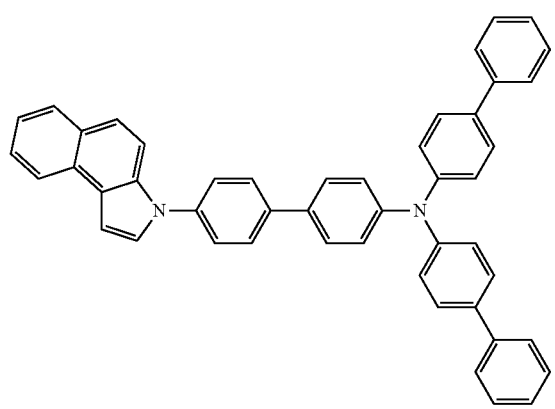

-continued
1-125
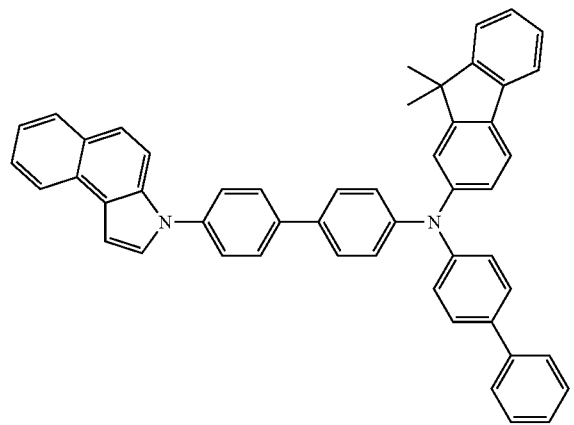
1-126
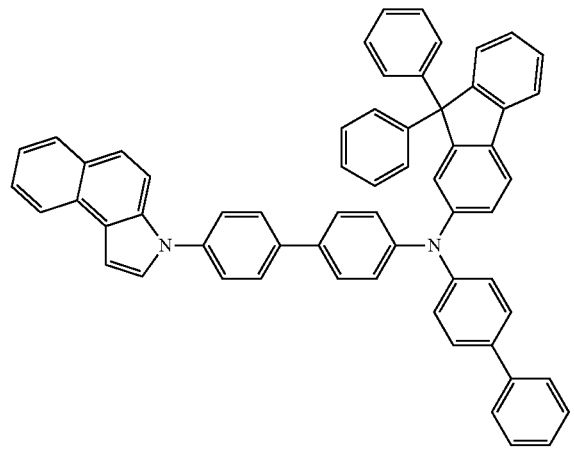
1-127
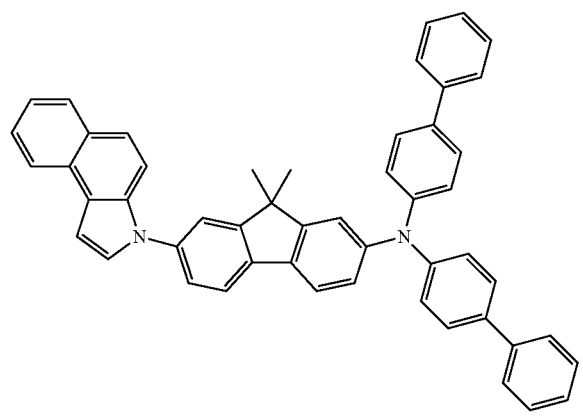
1-128
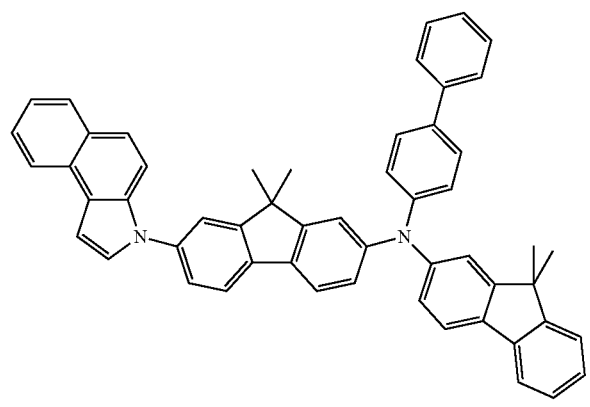
1-129
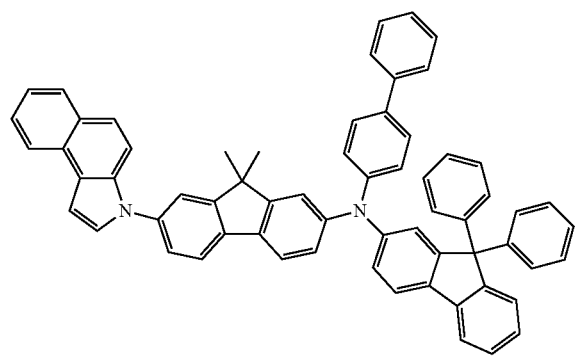
1-130
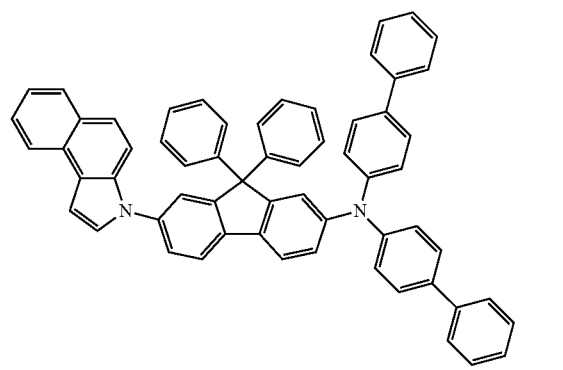

-continued
1-131
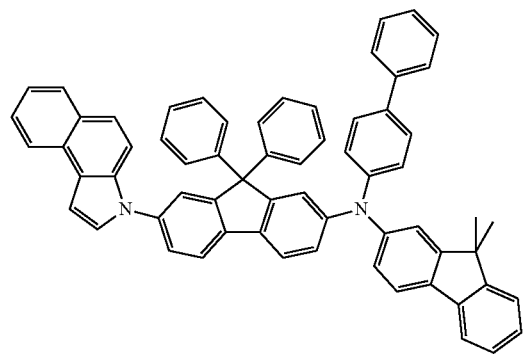
1-132
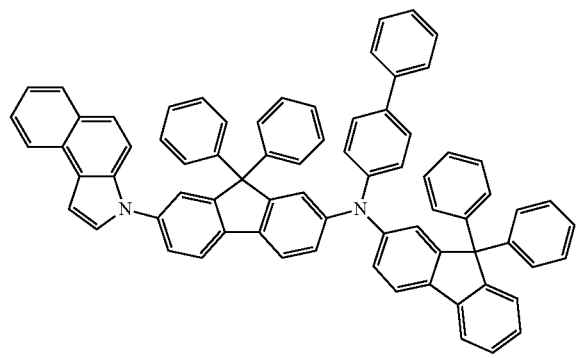
1-133
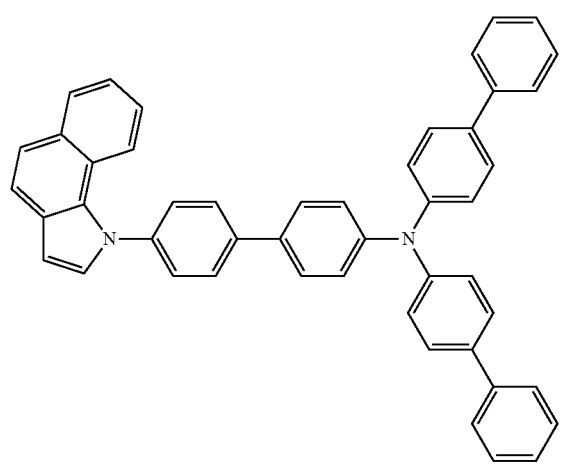
1-134
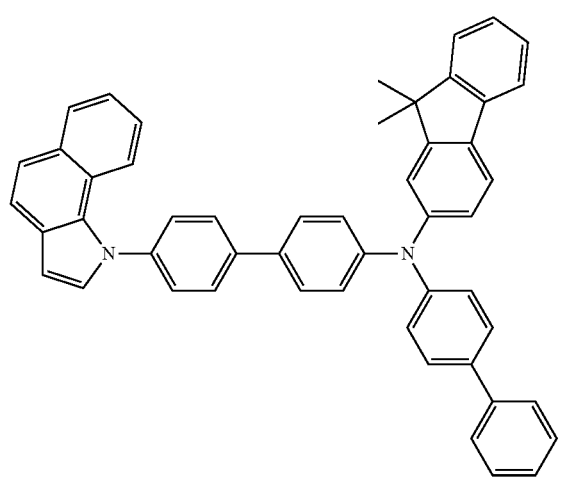
1-135
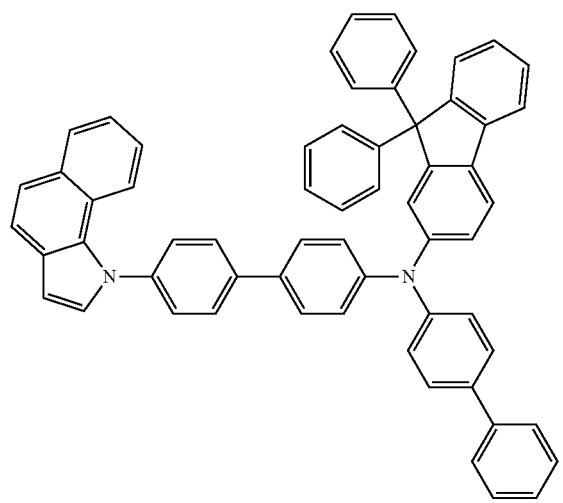
1-136
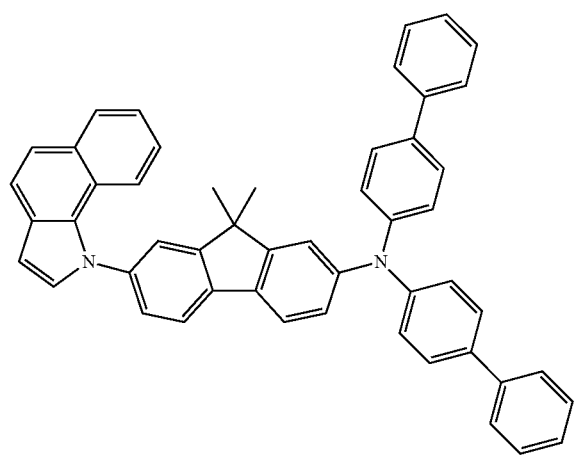

1-137
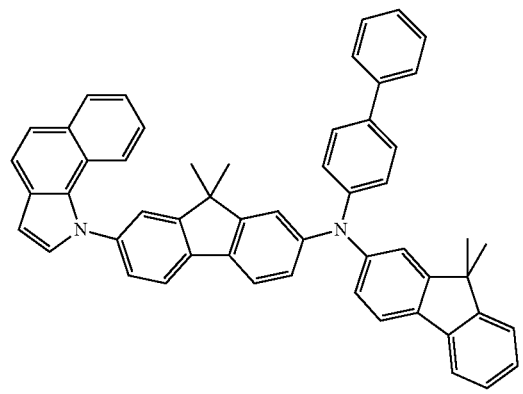
1-138
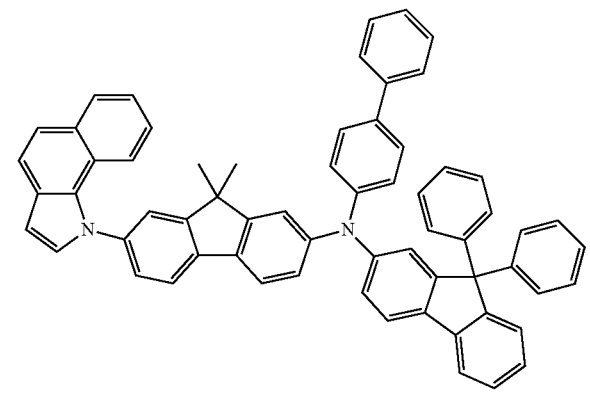
1-139
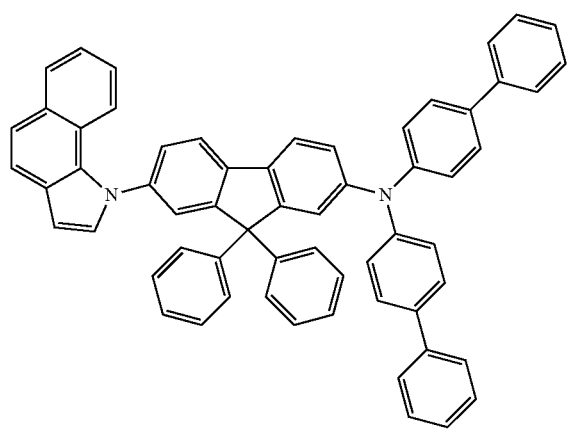
1-140
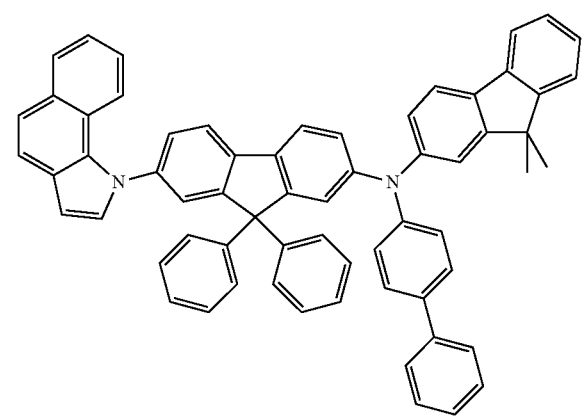
1-141
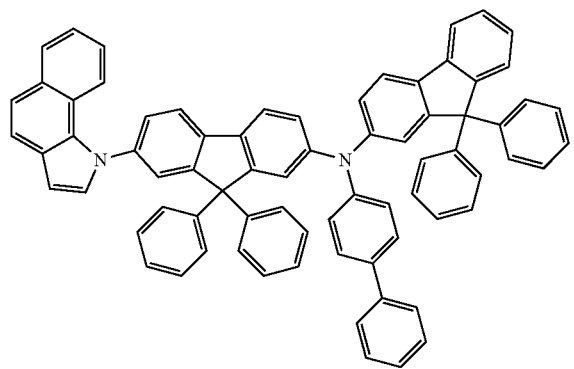
1-142
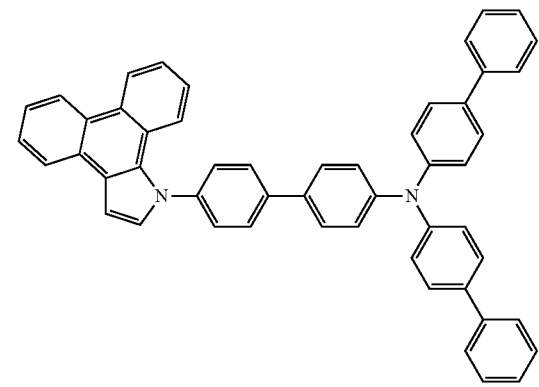

-continued
1-143
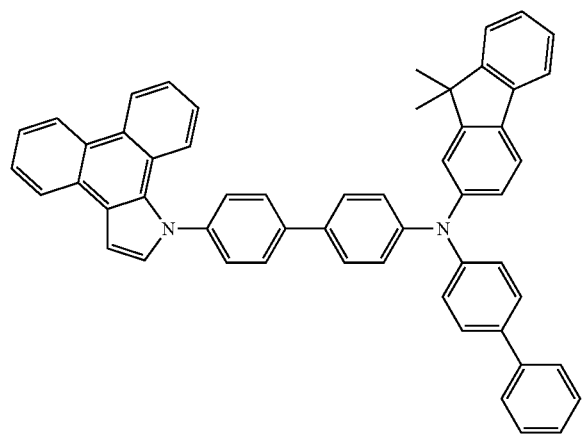
1-144
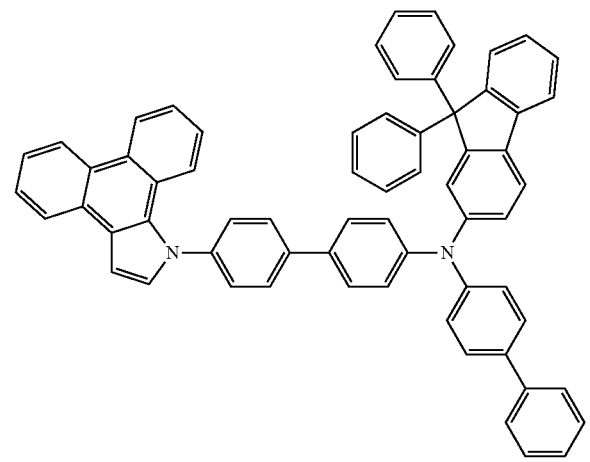
1-145
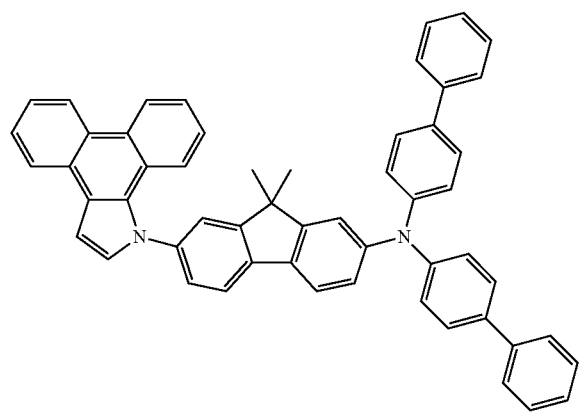
1-146
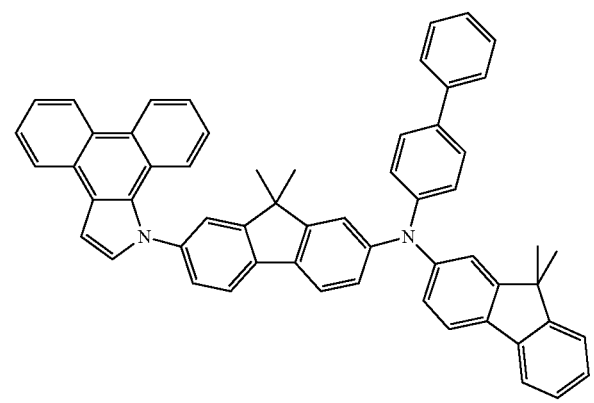
1-147
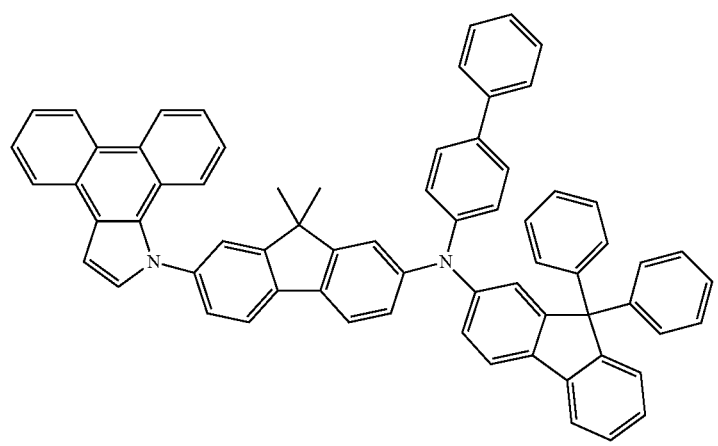

1-148
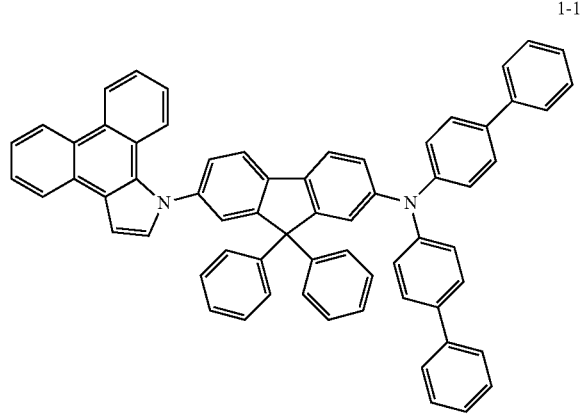
1-149
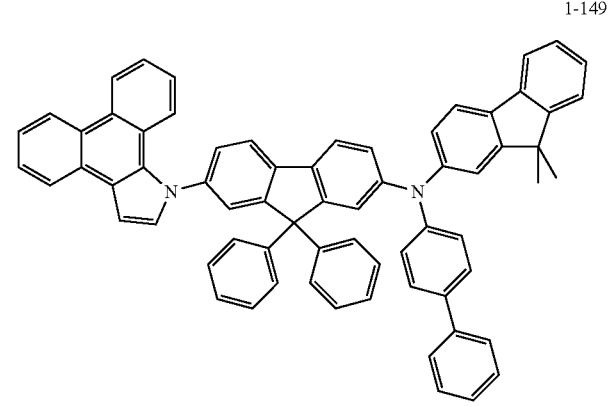
1-150
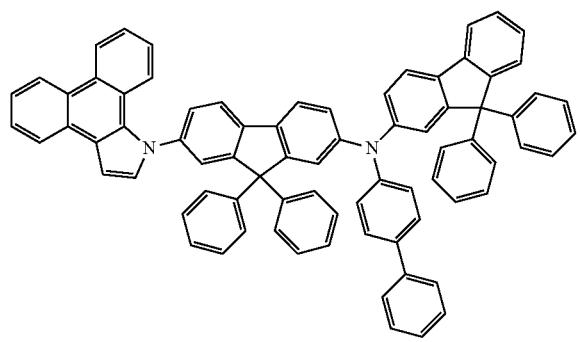
3-1
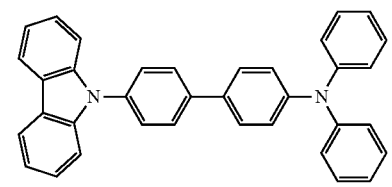
3-2
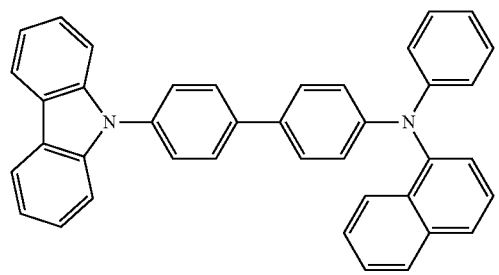
3-3
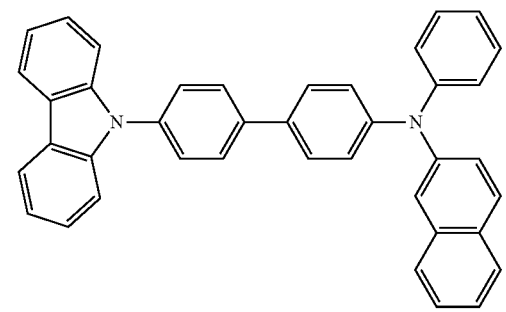
3-4
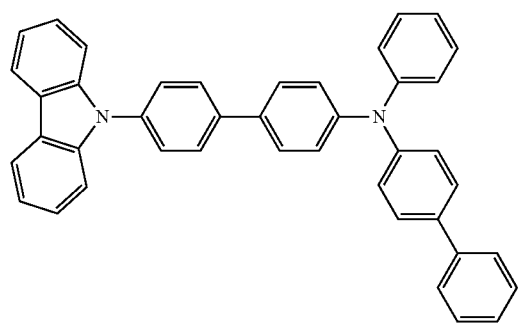
3-5
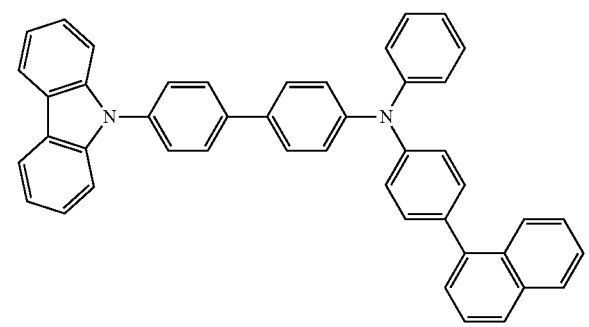

-continued
3-6
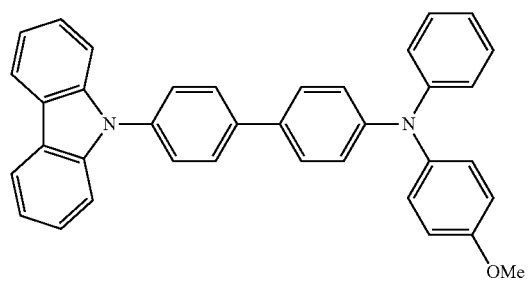
3-7
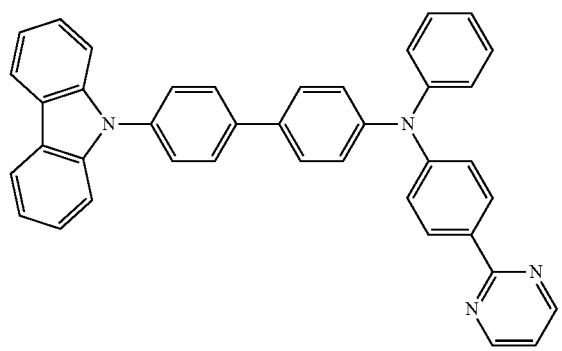
3-8
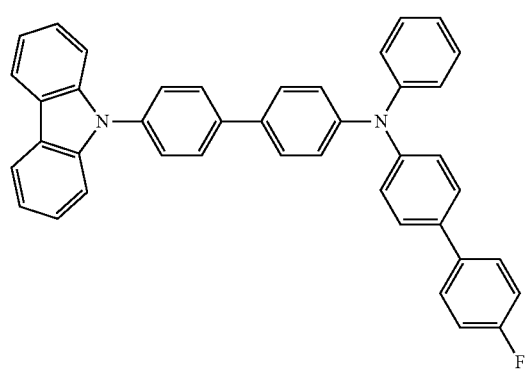
3-9
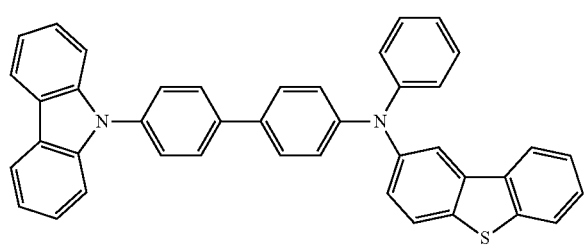
3-10
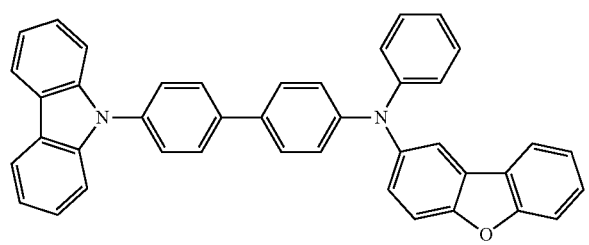
3-11
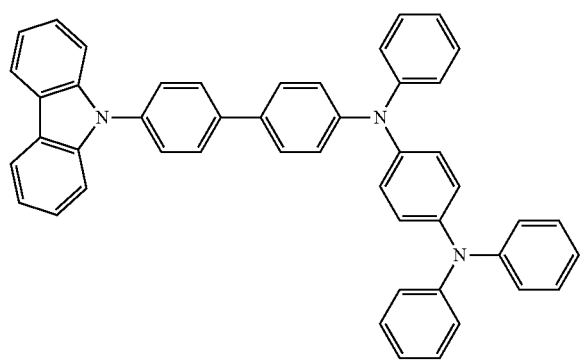
3-12
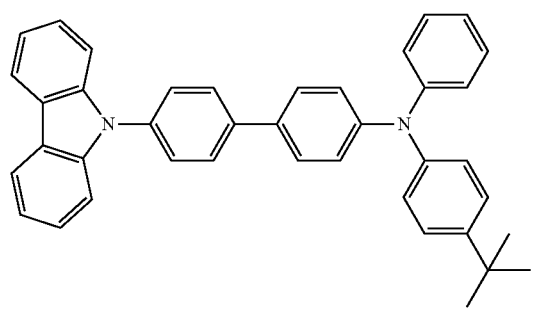
3-13
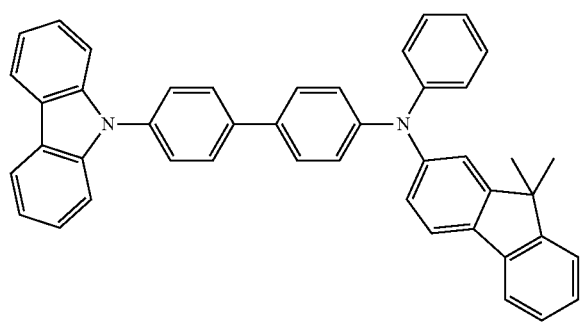

-continued
3-14
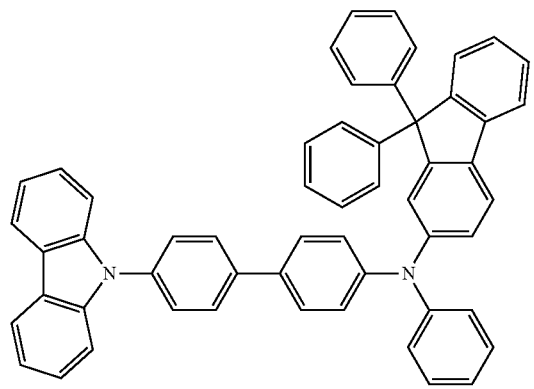
3-15
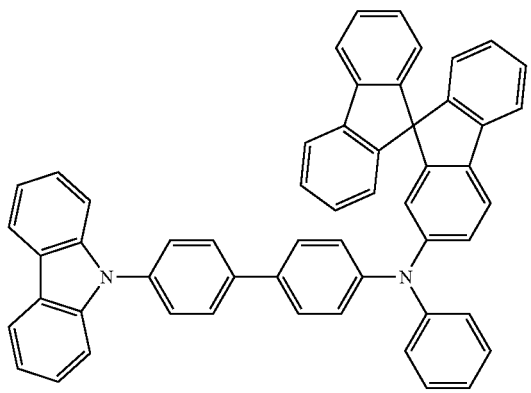
3-16
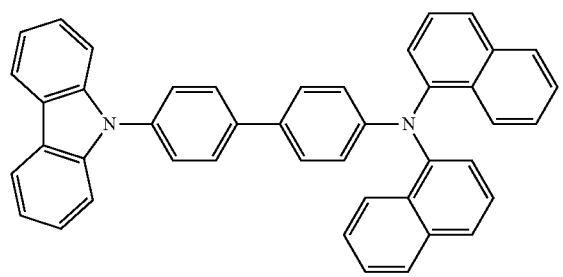
3-17
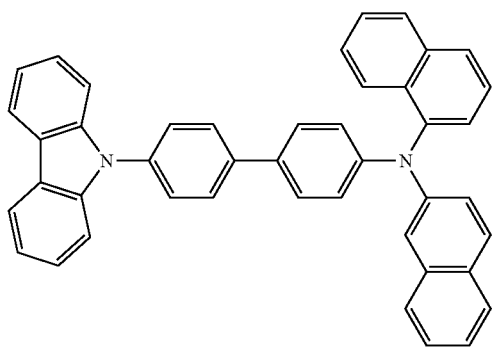
3-18
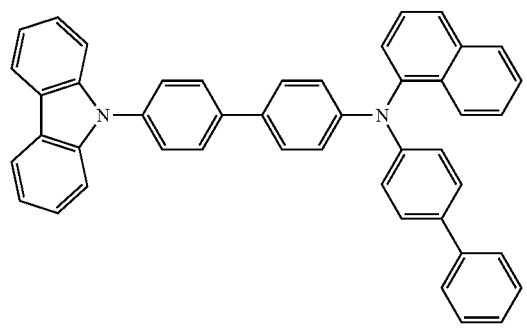
3-19
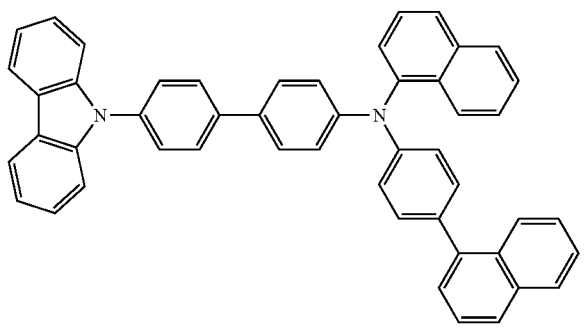
3-20
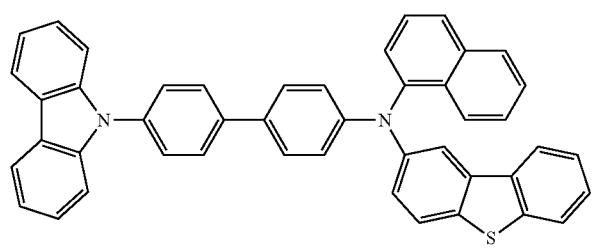
3-21
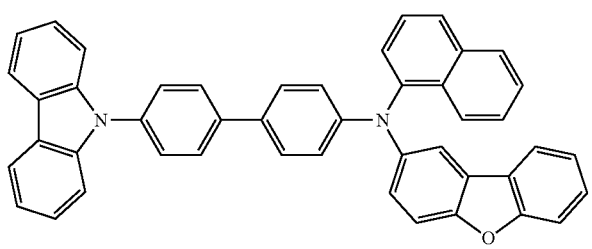

-continued
3-22
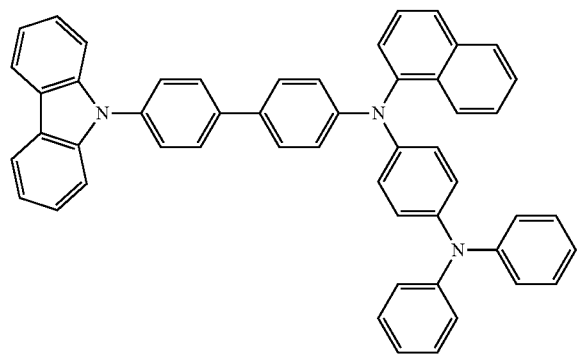
3-23
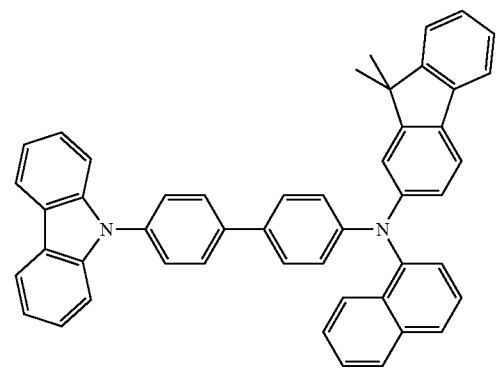
3-24
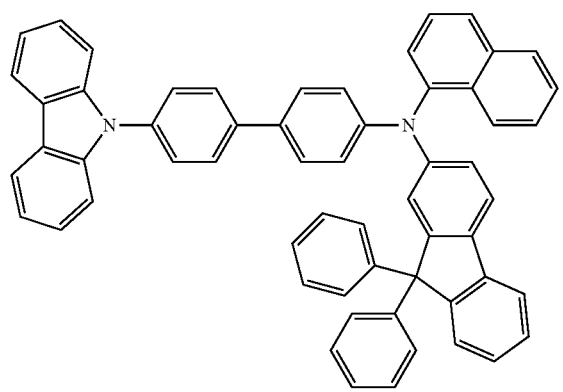
3-25
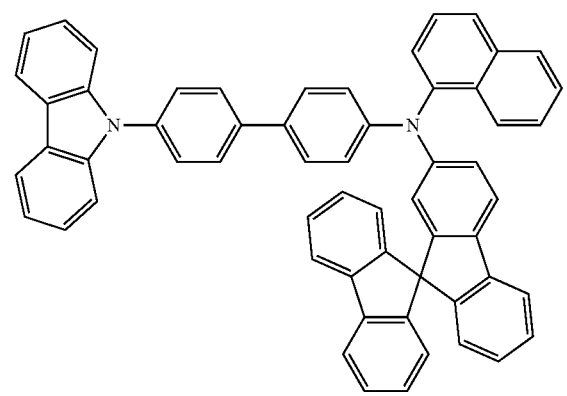
3-26
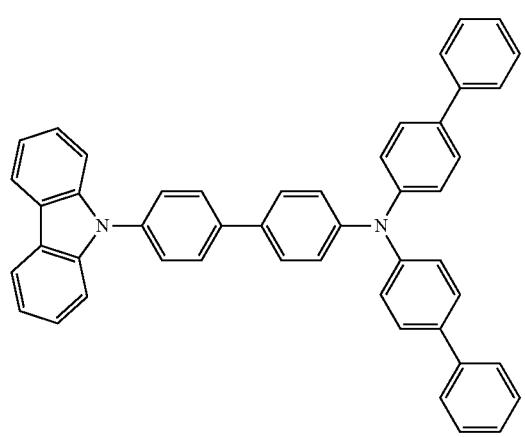
3-27
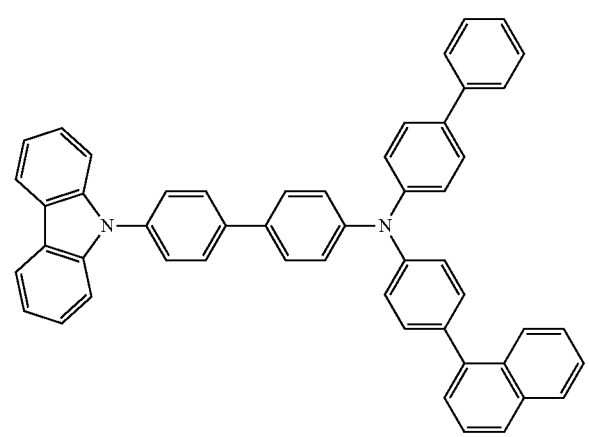

-continued
3-28
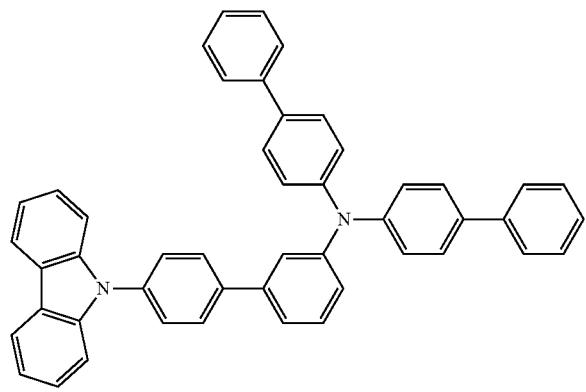
3-29
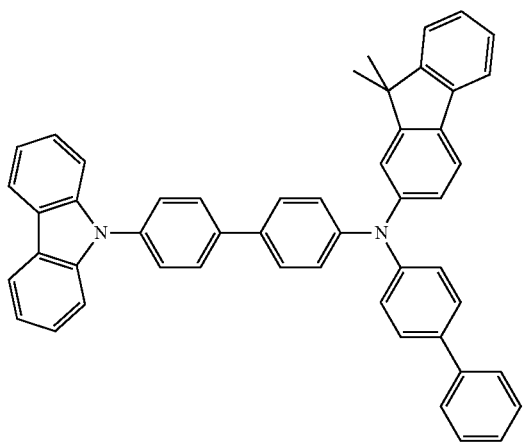
3-30
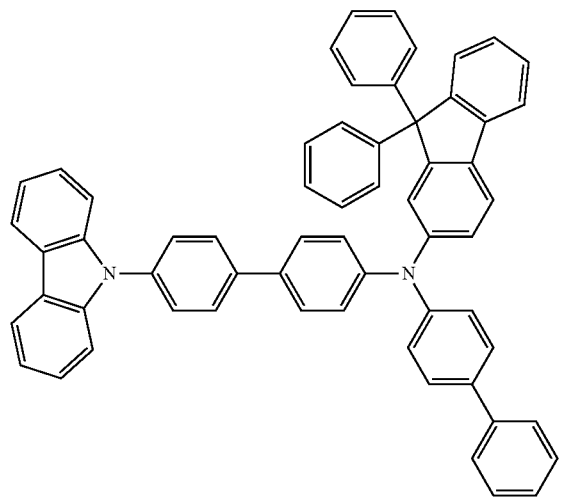
3-31
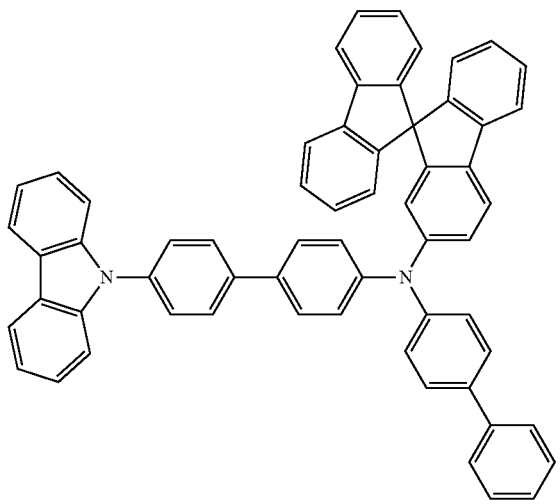
3-32
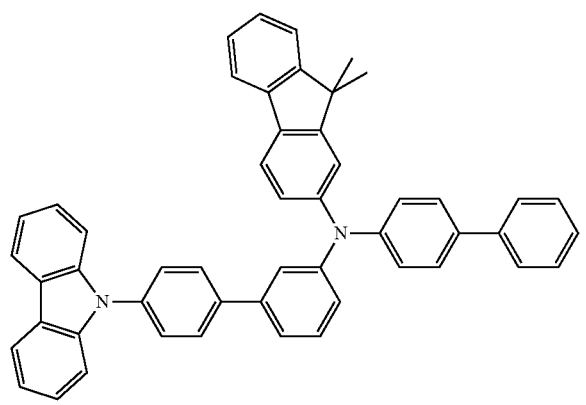
3-33
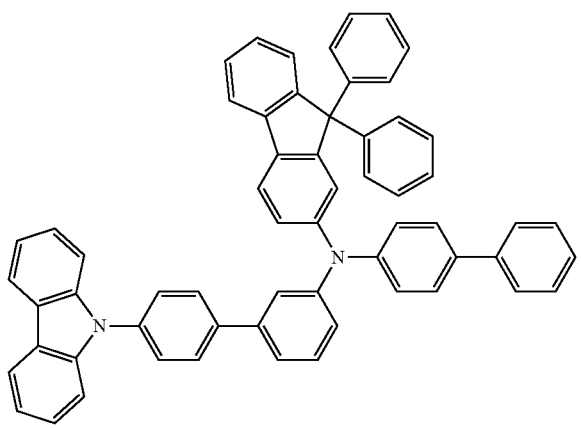

-continued
3-34
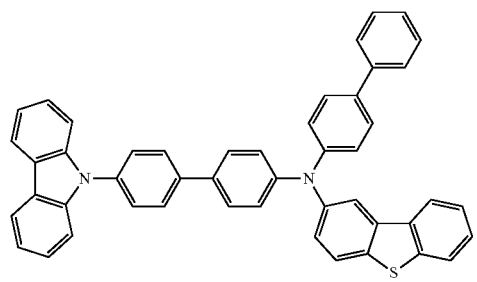
3-35
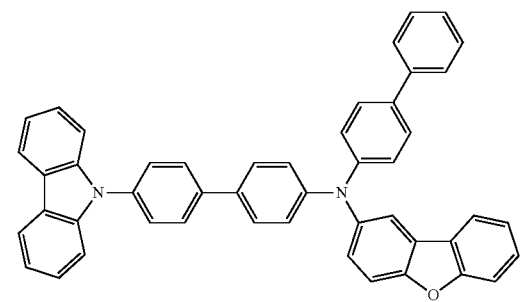
3-36
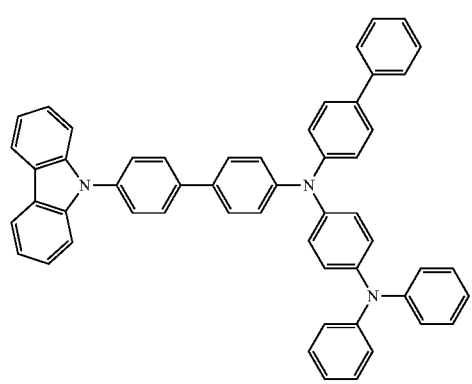
3-37
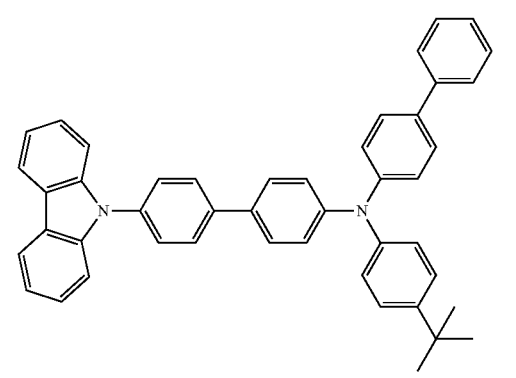
3-38
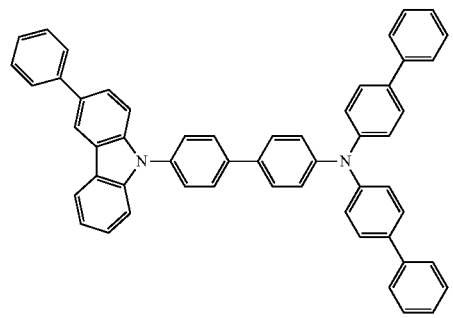
3-39
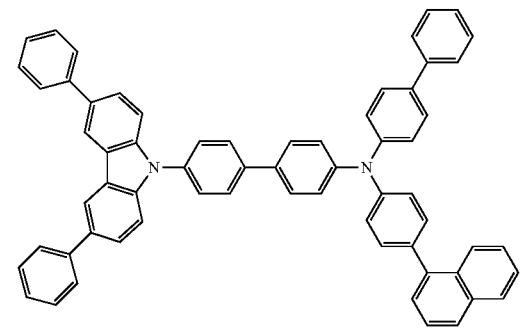
3-40
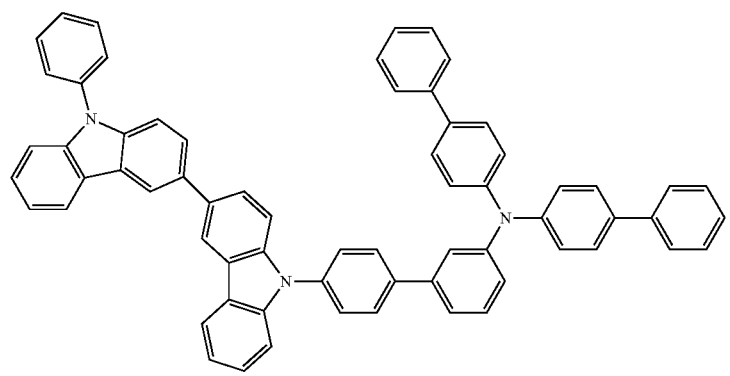

-continued
3-41
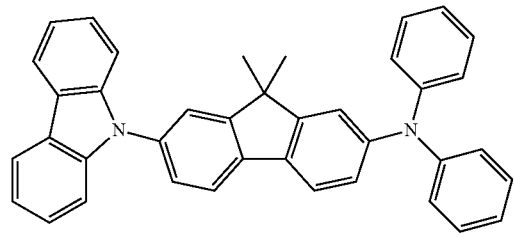
3-42
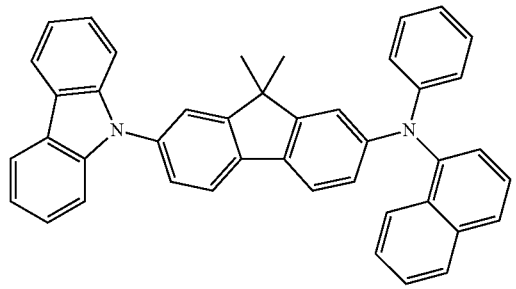
3-43
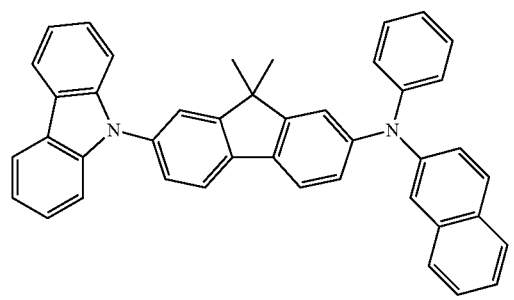
3-44
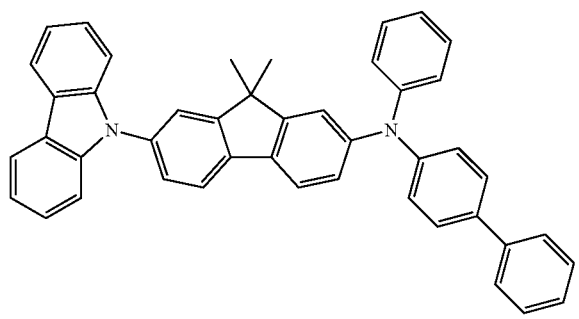
3-45
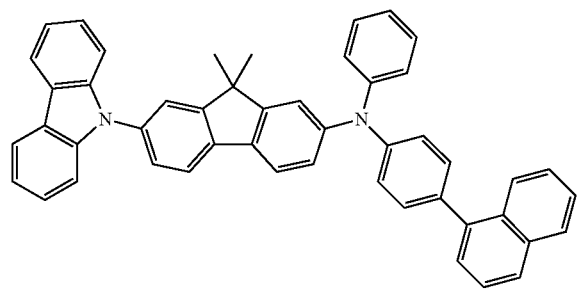
3-46
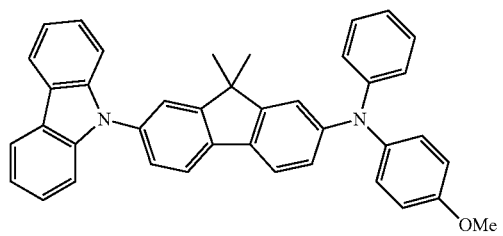
3-47
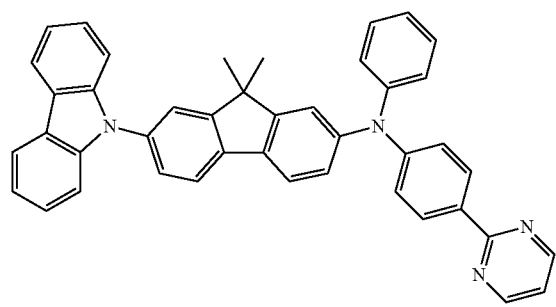
3-48
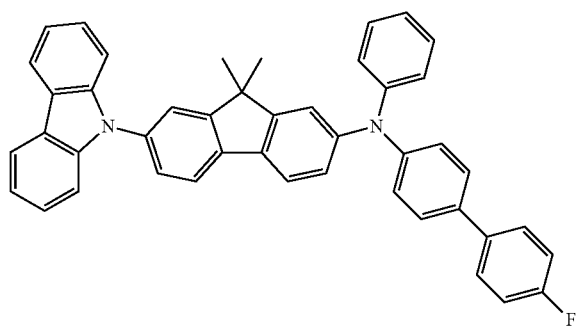
3-49
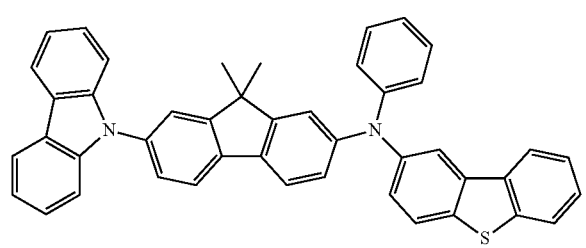
3-50
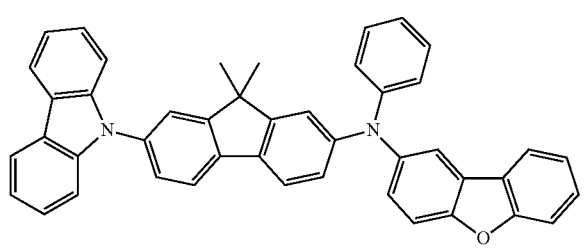

3-51
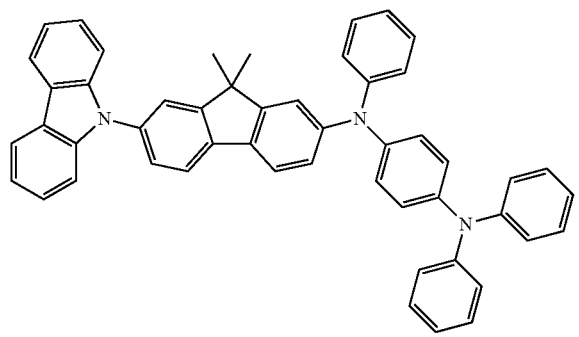
3-52
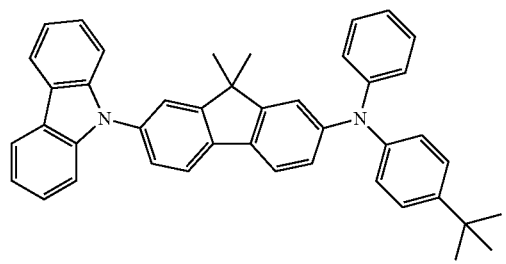
3-53
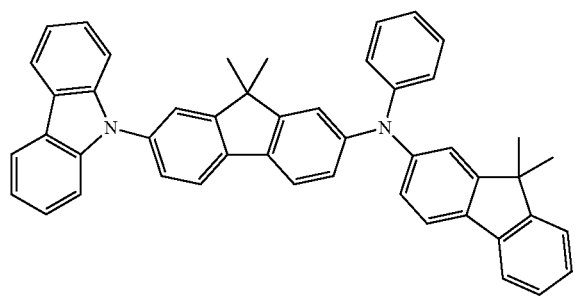
3-54
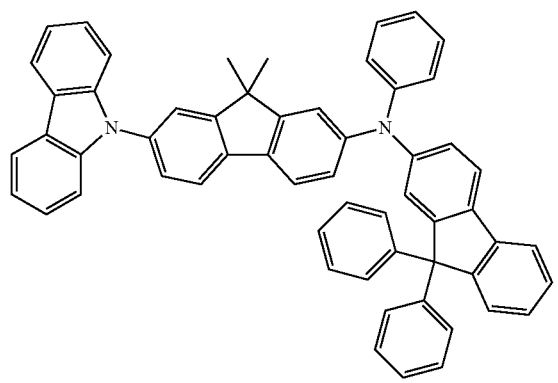
3-55
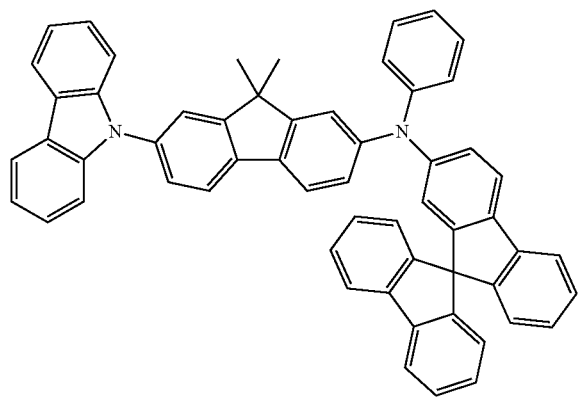
3-56
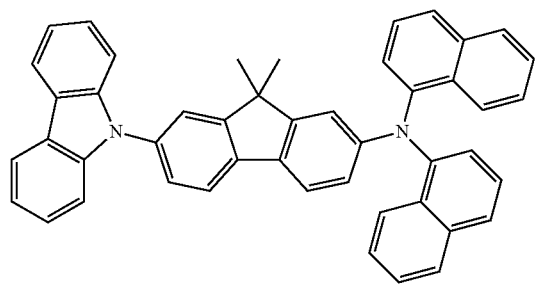
5-57
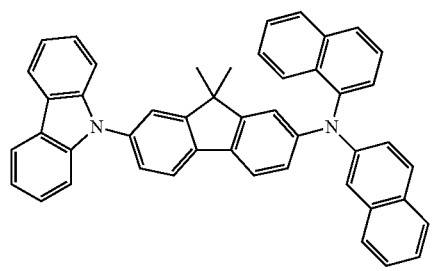
5-58
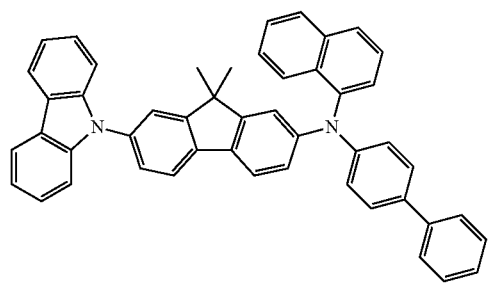

-continued
5-59
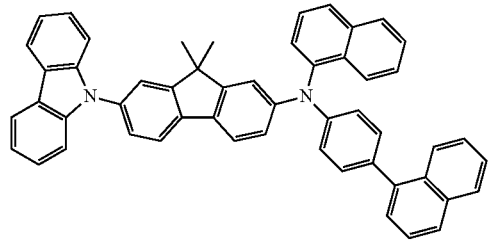
5-60
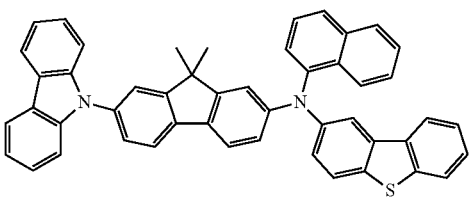
5-61
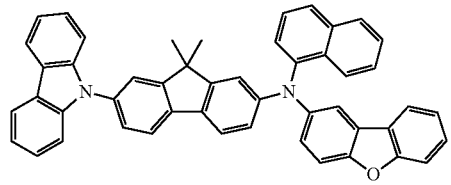
5-62
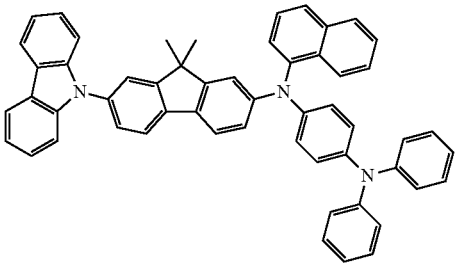
5-63
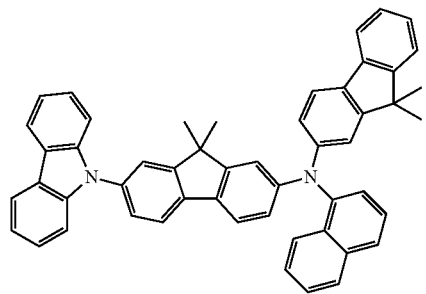
5-64
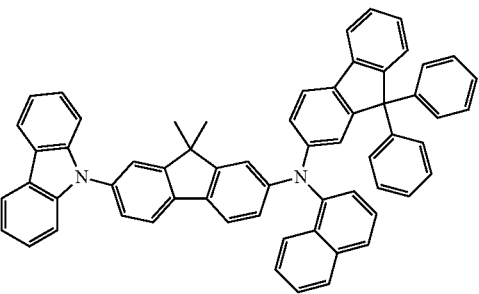
3-65
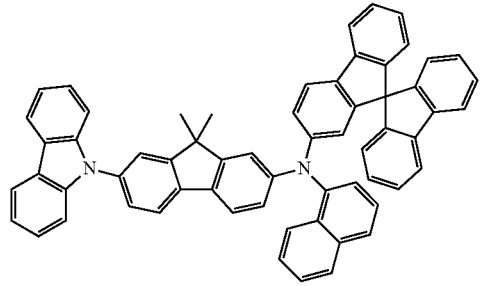
3-66
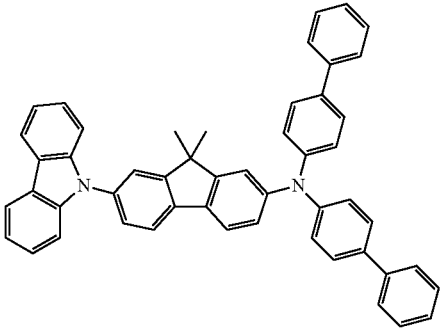
3-67
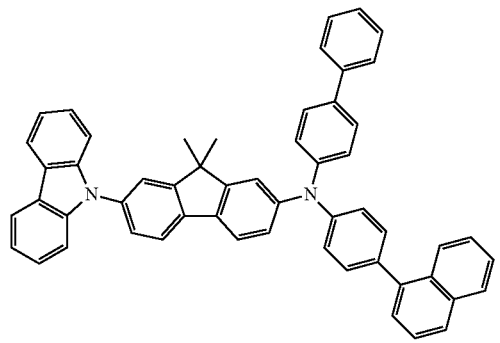
3-68
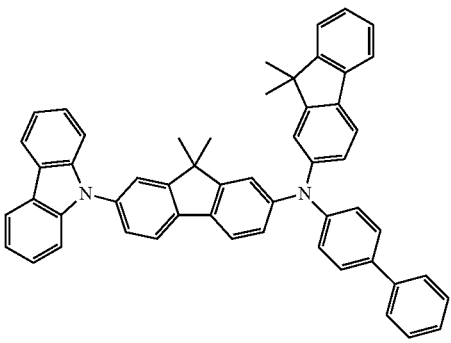

-continued
3-69
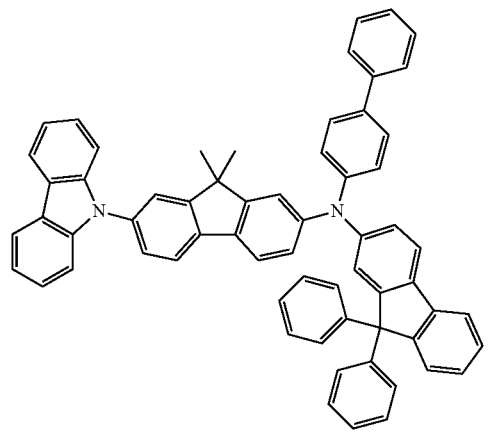
3-70
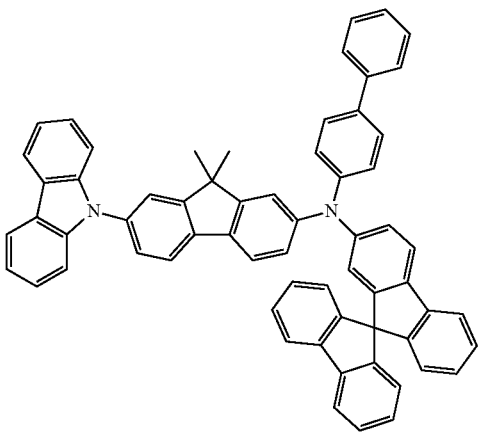
3-71
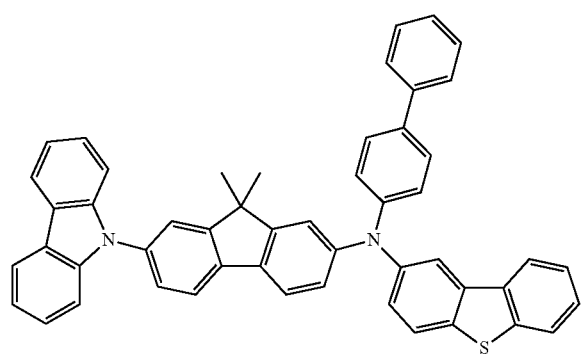
3-72
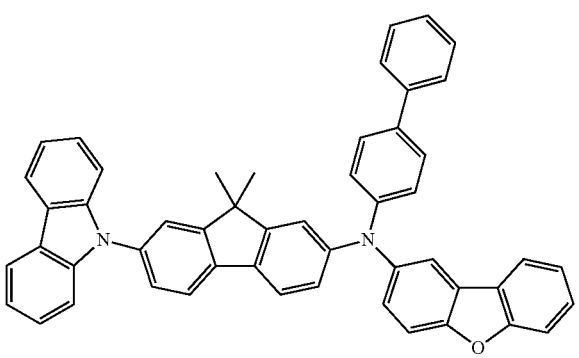
3-73
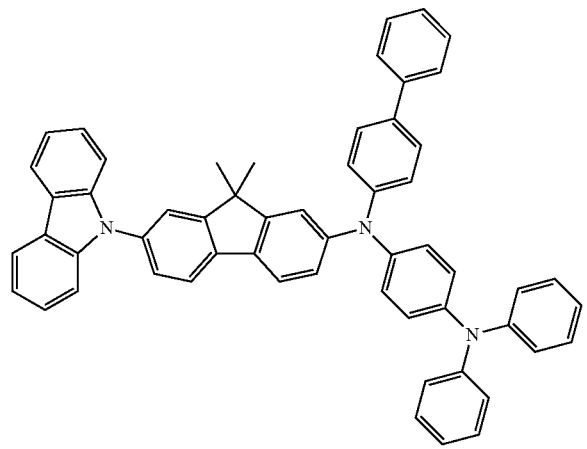
3-74
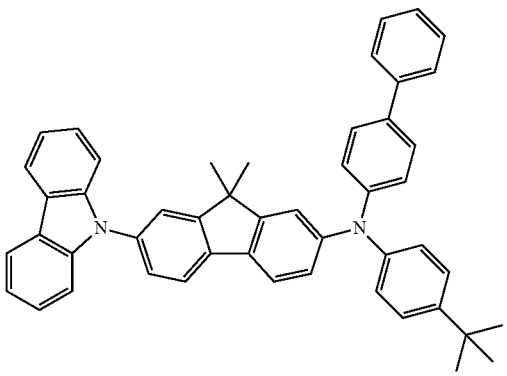
3-75
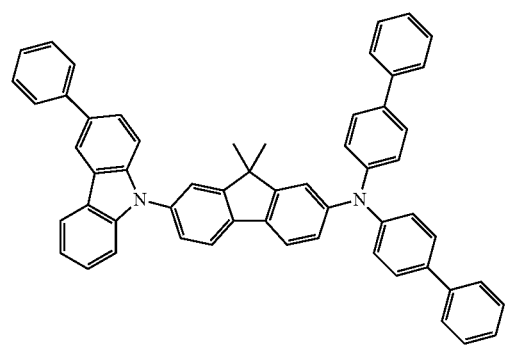
3-76
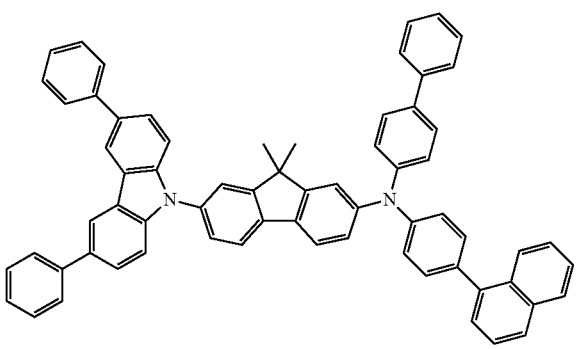

-continued
4-1
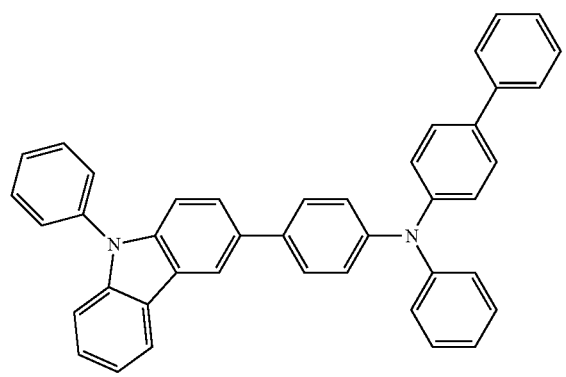
4-2
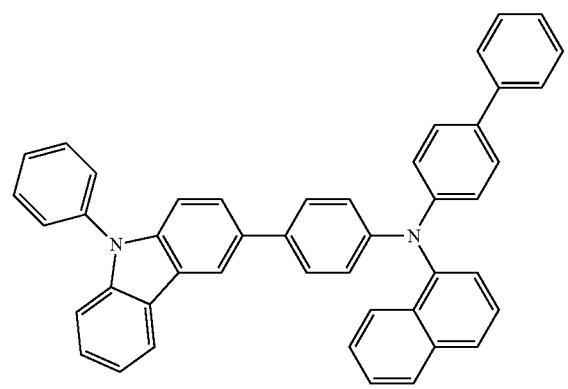
4-3
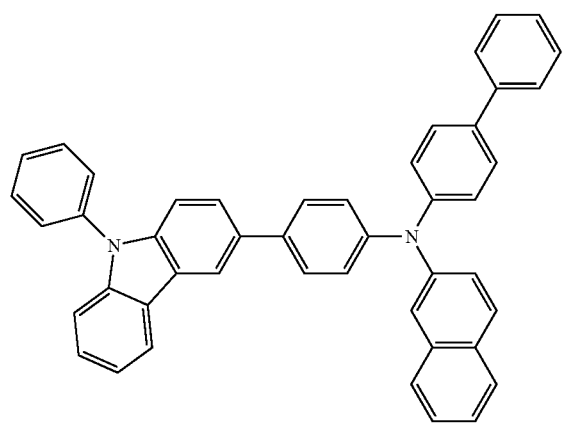
4-4
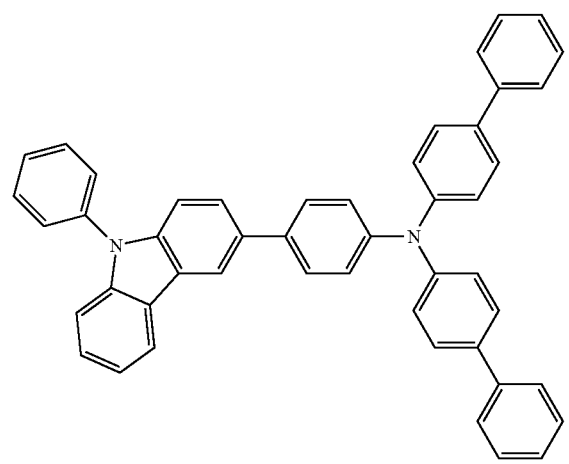
4-5
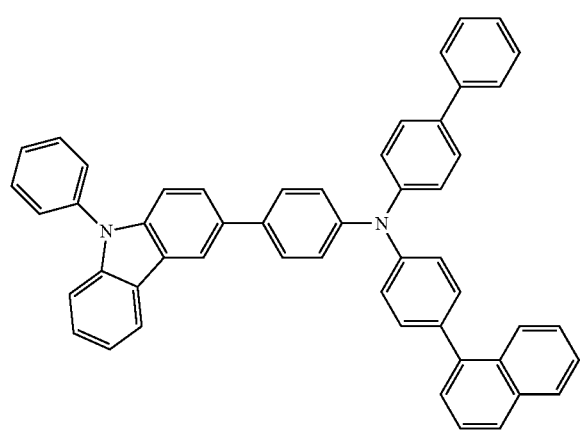
4-6
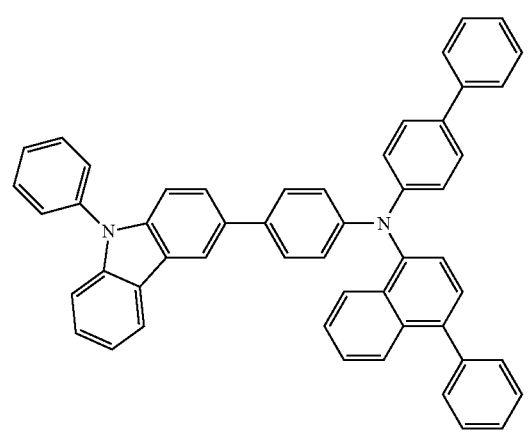

-continued
4-7
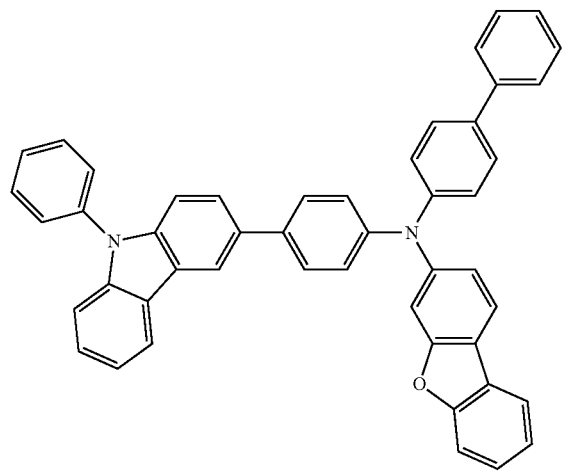
4-8
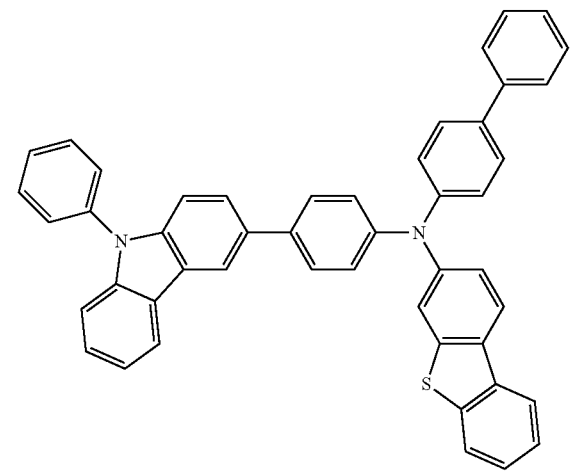
4-9
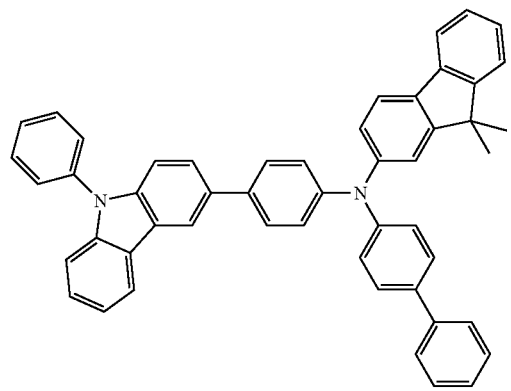
4-10
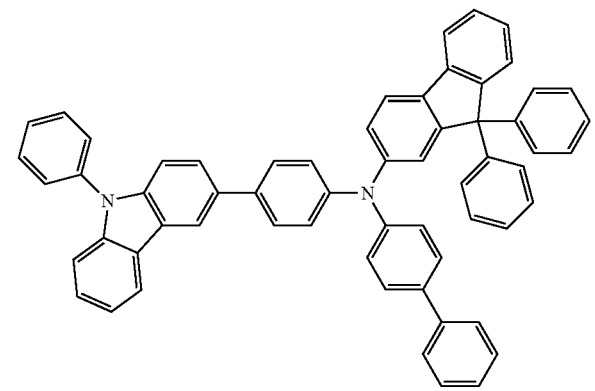
4-11
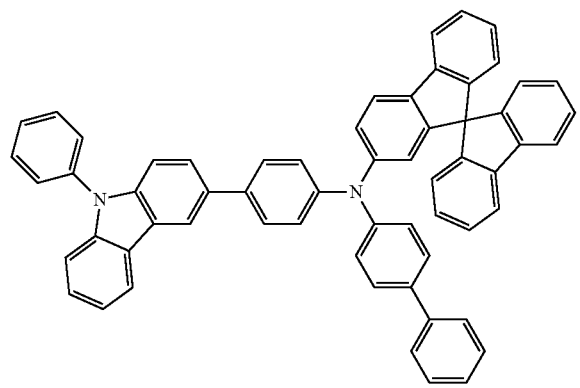
4-12
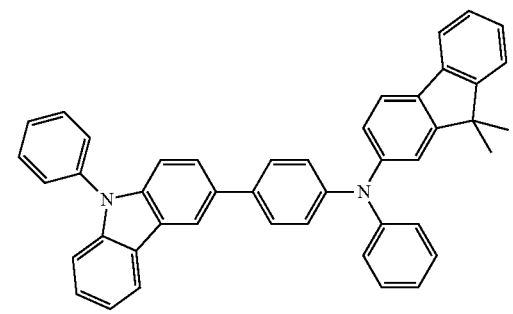
4-13
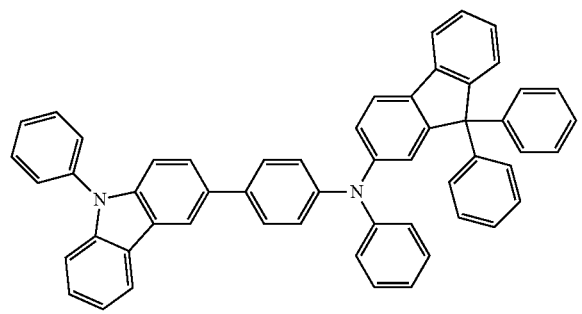
4-14
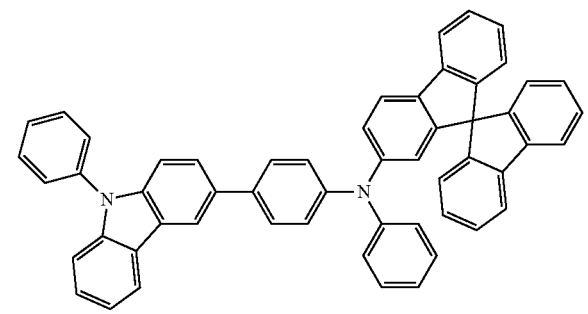

-continued
4-15
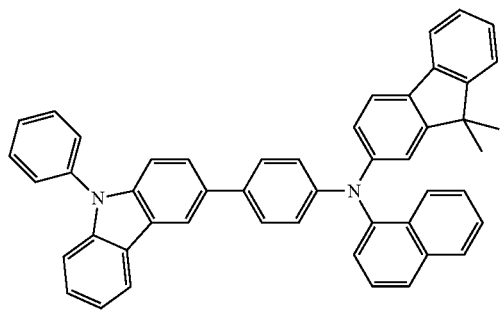
4-16
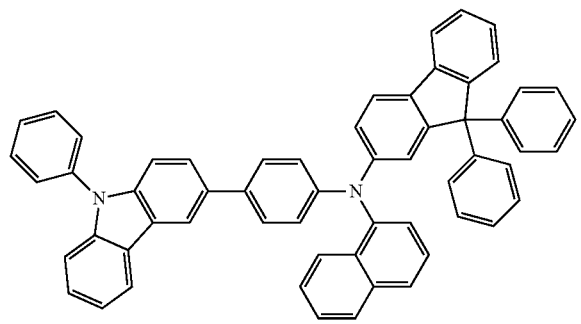
4-17
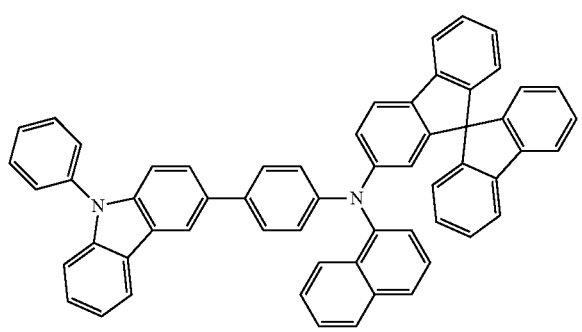
4-18
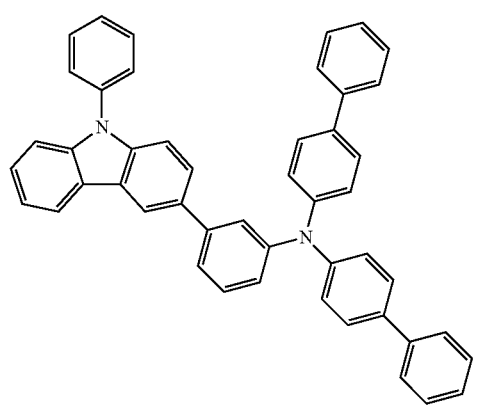
4-19
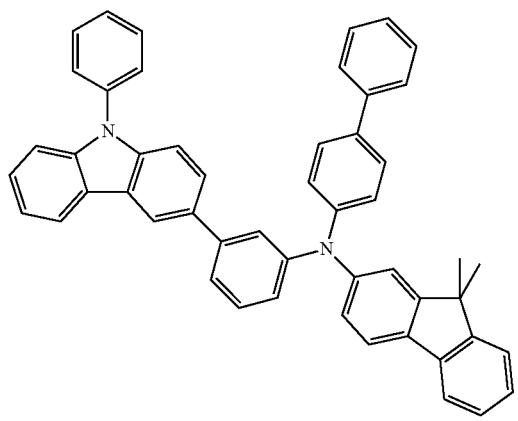
4-20
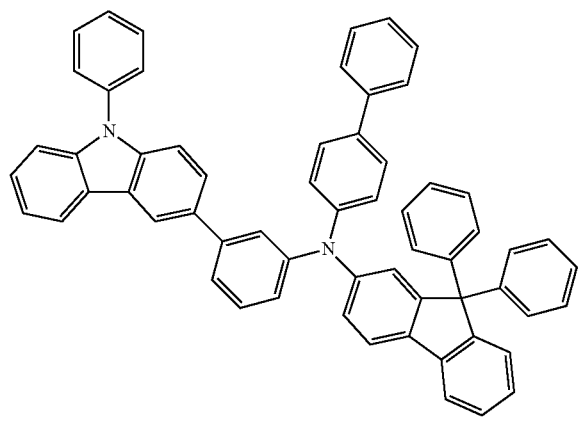
4-21
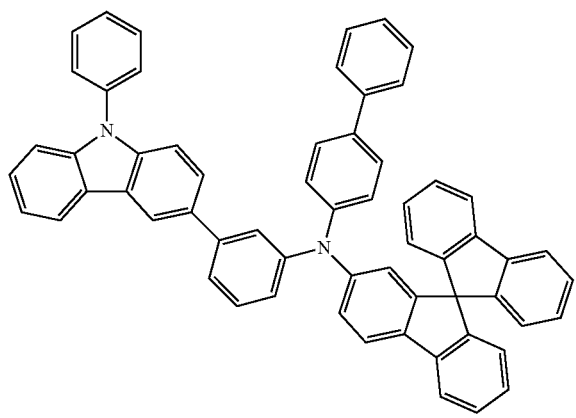
4-22
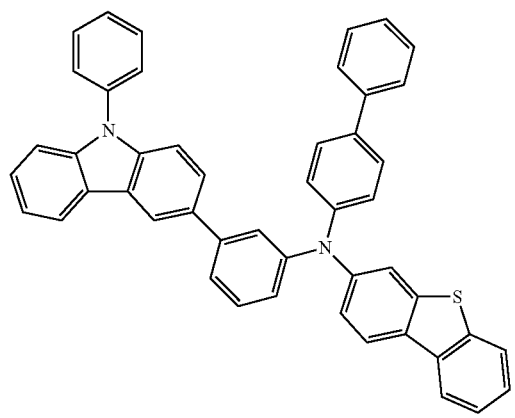

-continued
4-23
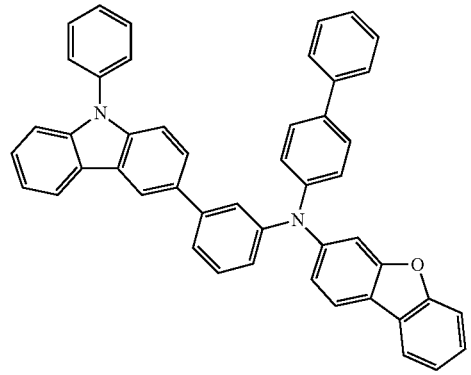
4-24
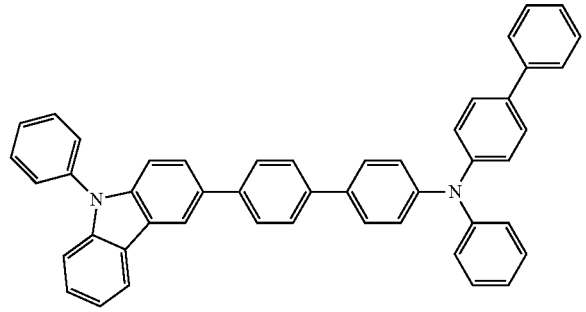
4-25
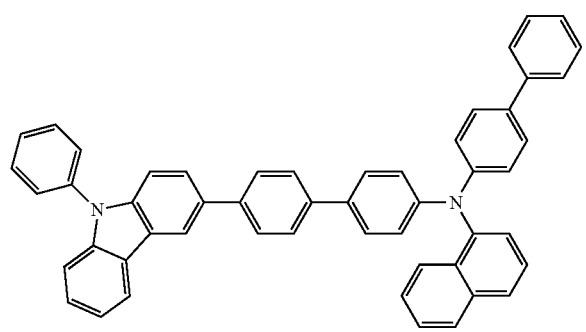
4-26
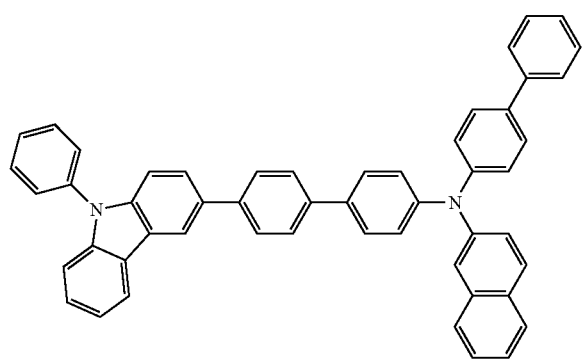
4-27
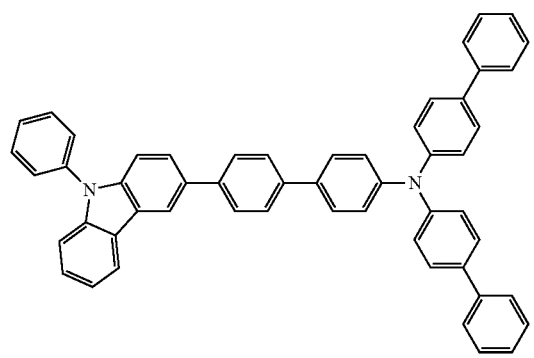
4-28
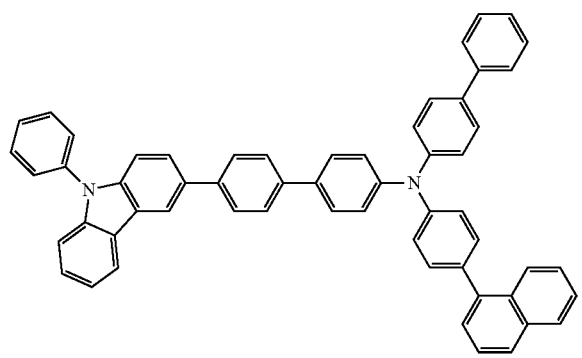
4-29
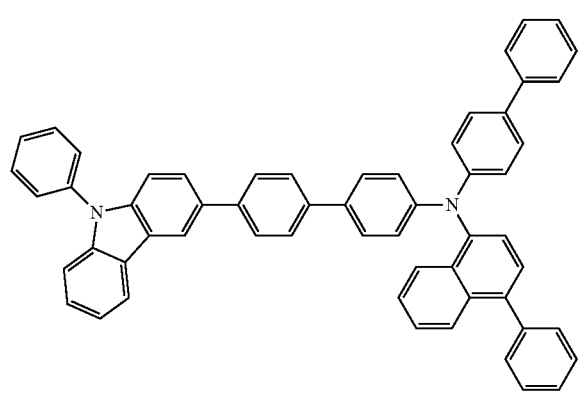
4-30
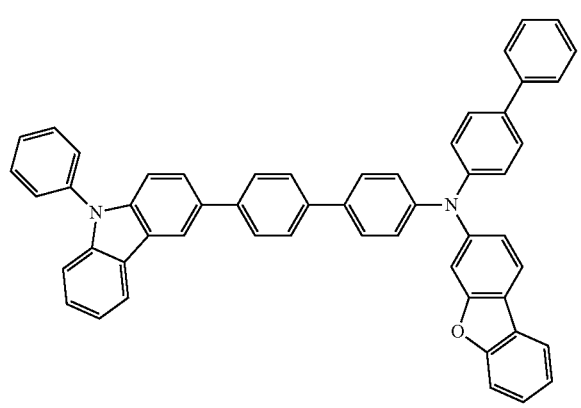

-continued
4-31
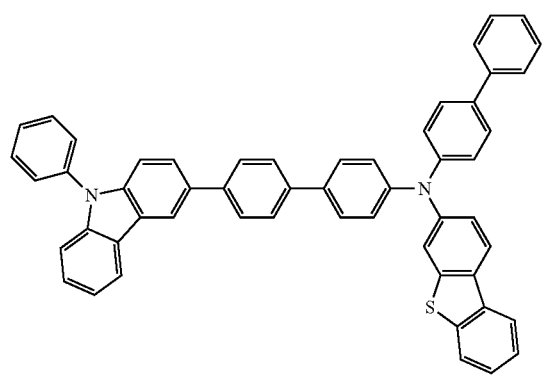
4-32
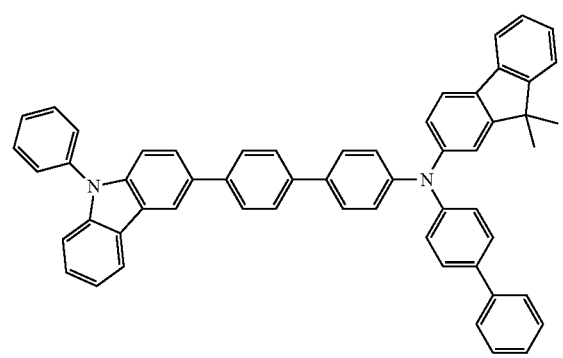
4-33
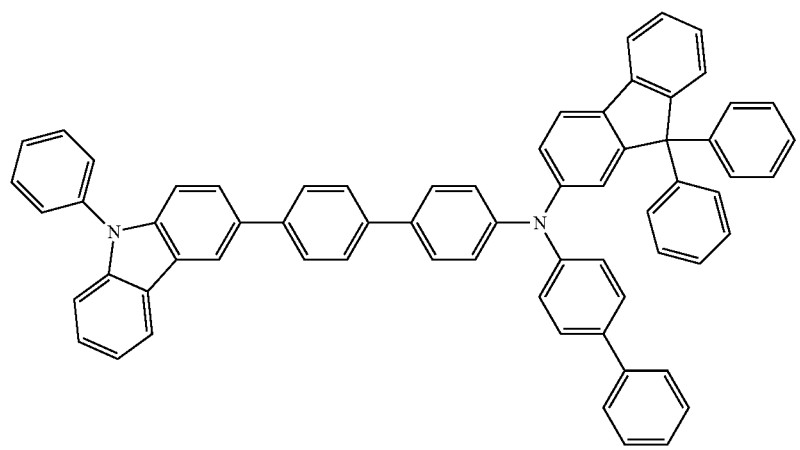
4-34
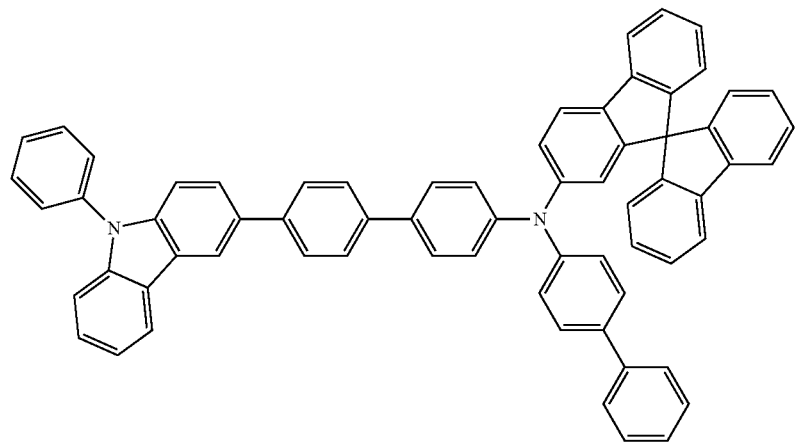
4-35
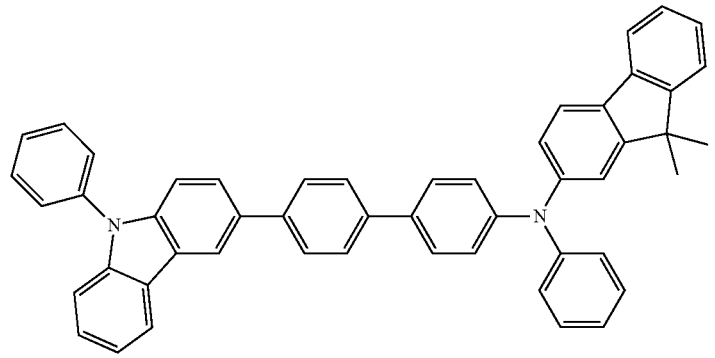

4-36
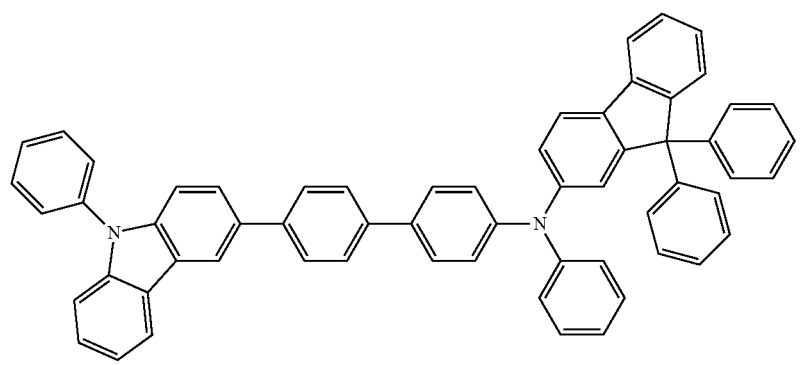
4-37
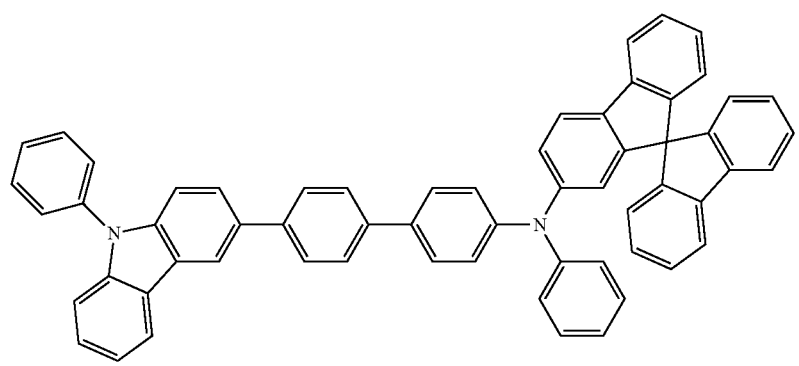
4-38
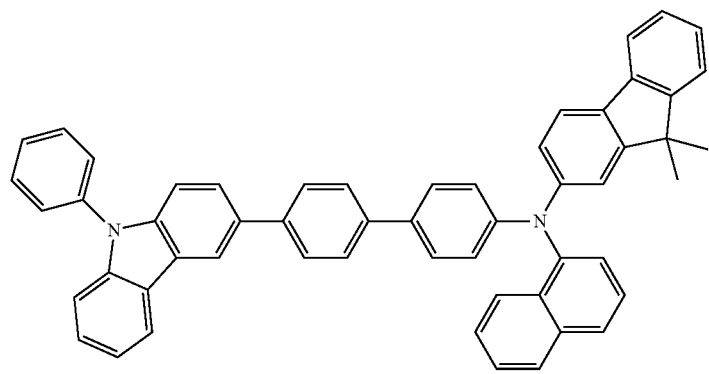
4-39
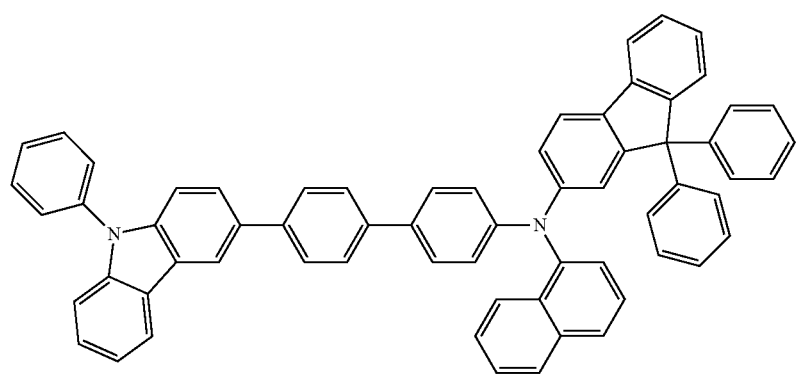

-continued
4-40
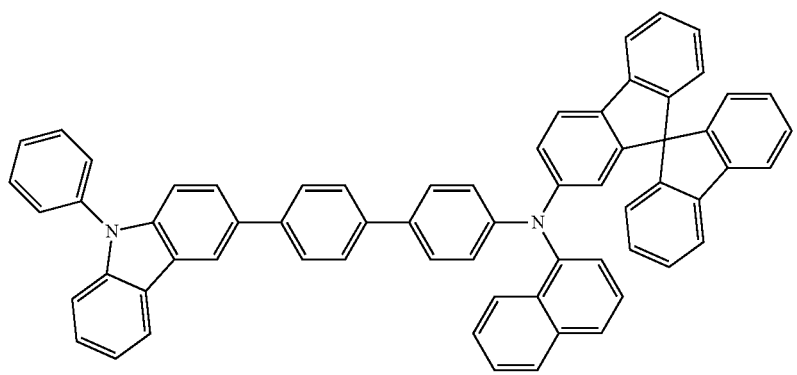
4-41
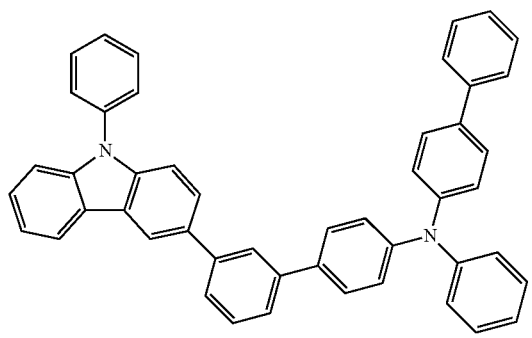
4-42
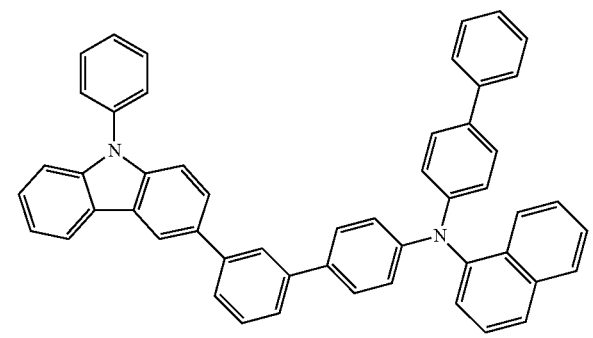
4-43
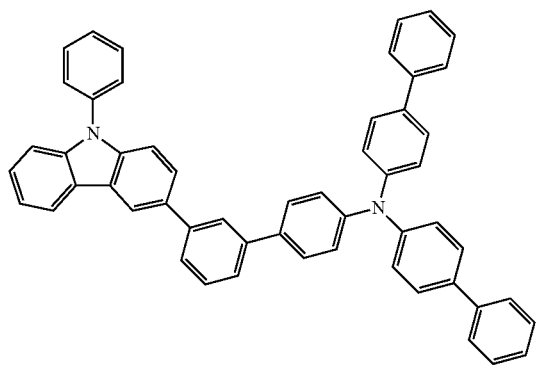
4-44
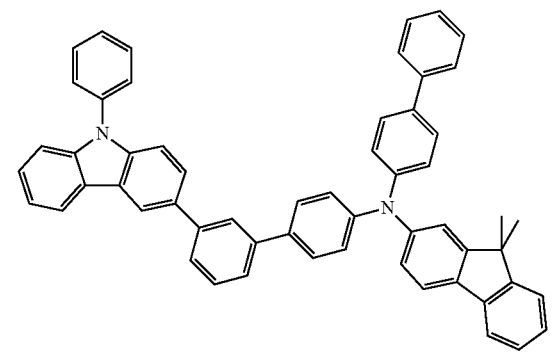
4-45
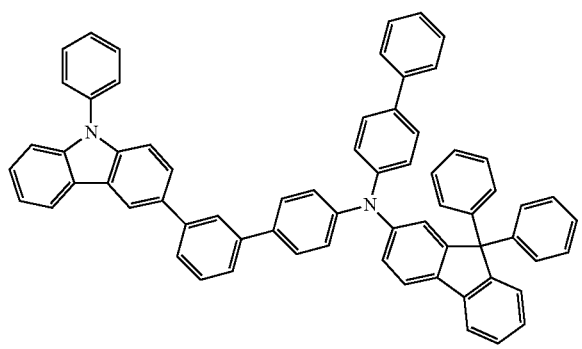
4-46
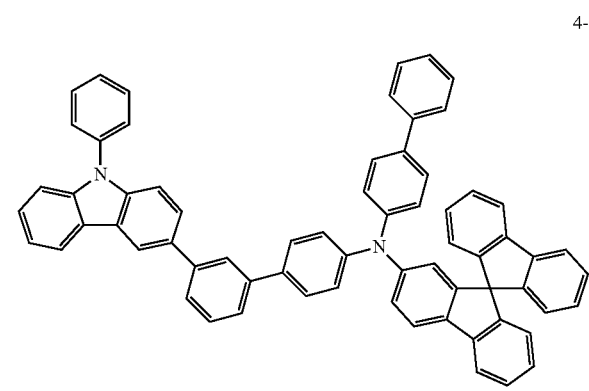

-continued
4-47
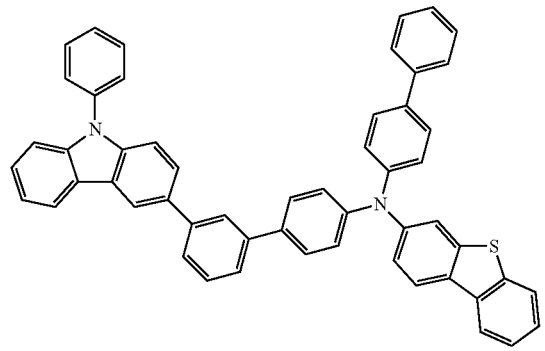
4-48
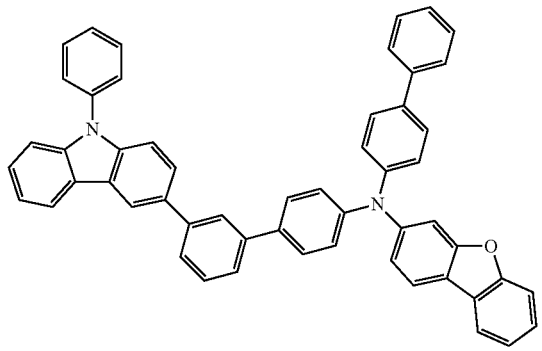
4-49
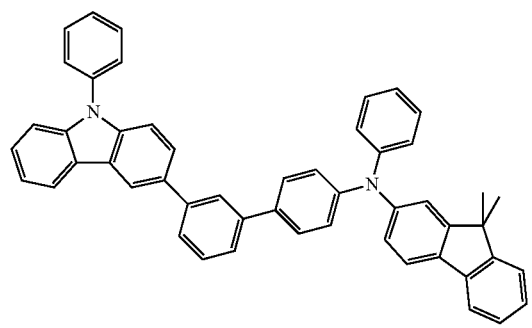
4-50
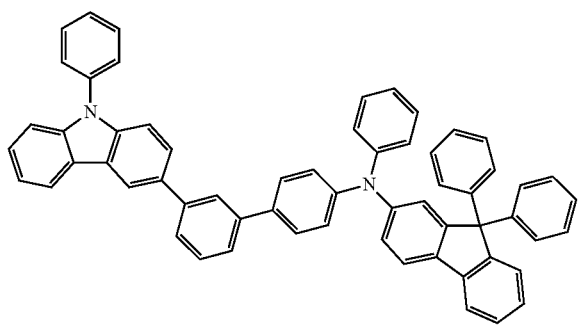
4-51
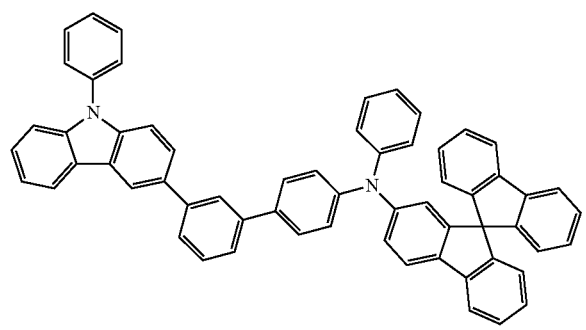
4-52
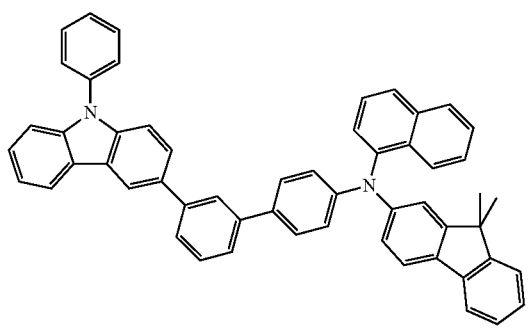
4-53
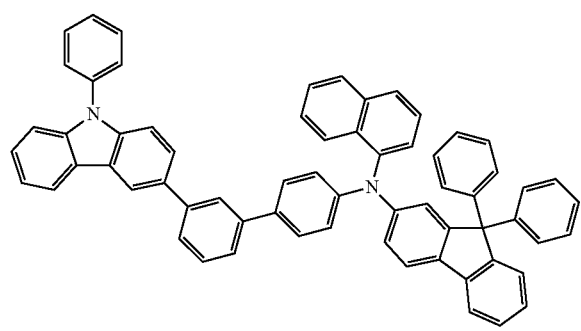
4-54
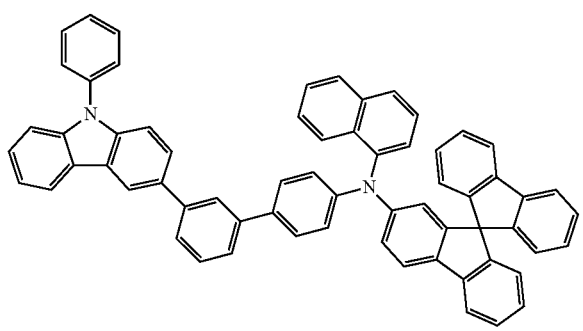

-continued
4-55
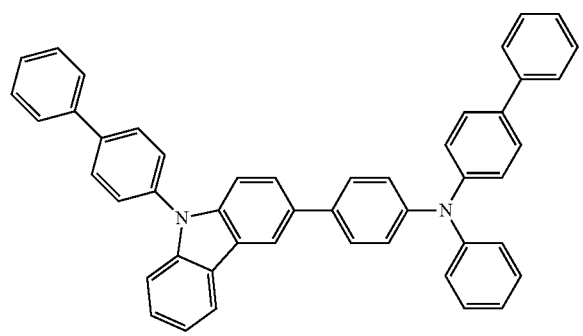
4-56
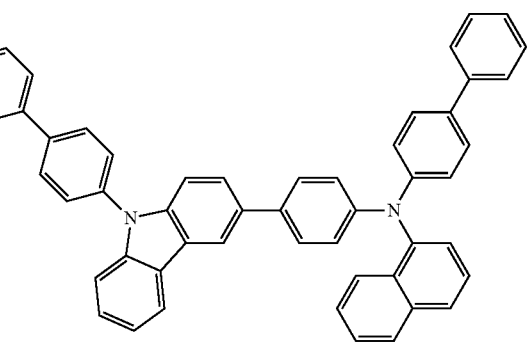
4-57
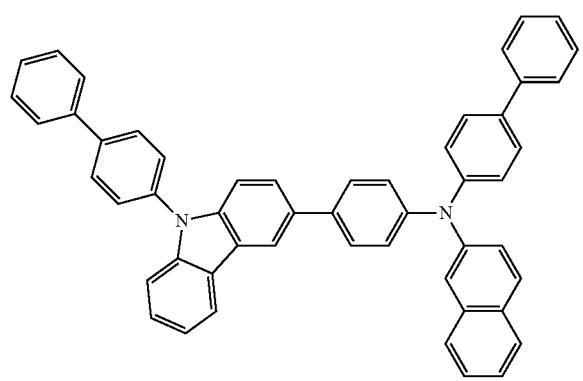
4-58
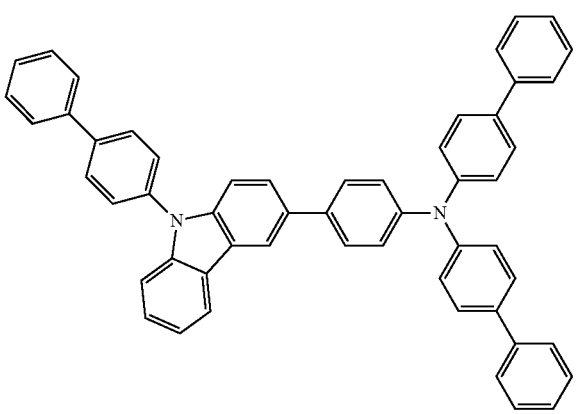
4-59
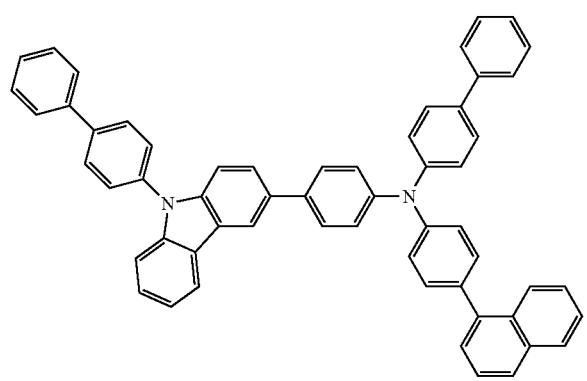
4-60
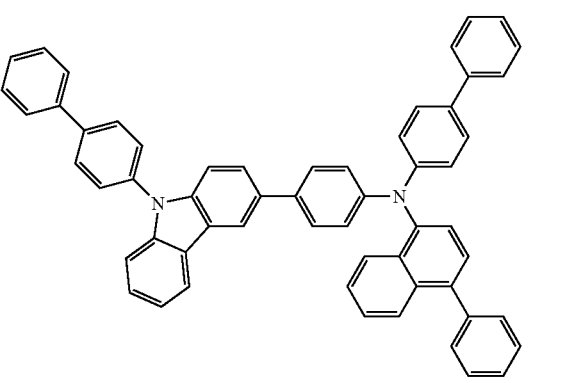
4-61
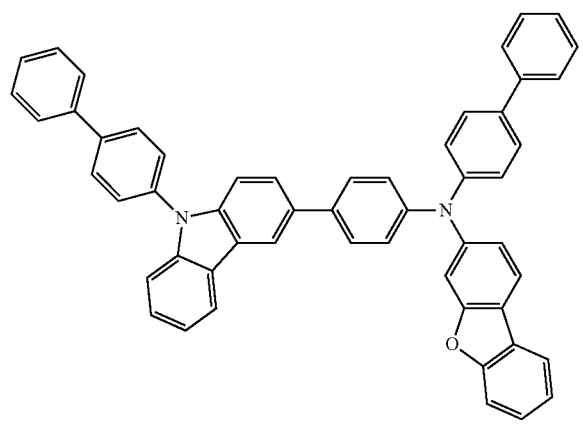
4-62
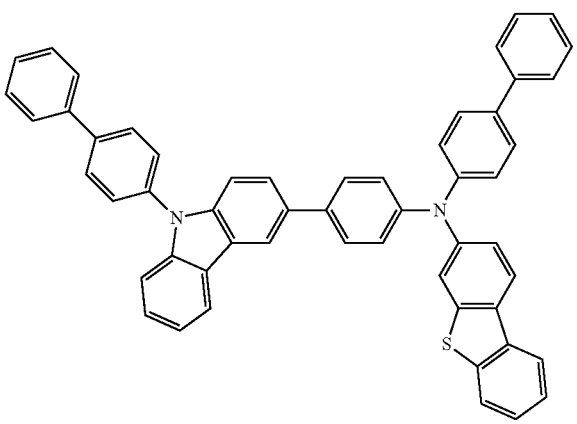

-continued
4-63
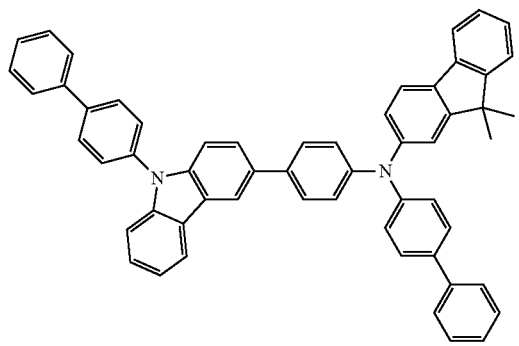
4-64
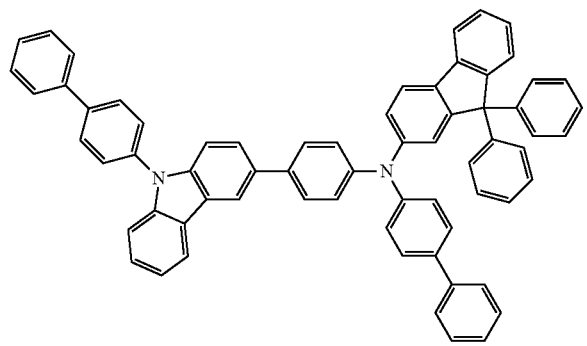
4-65
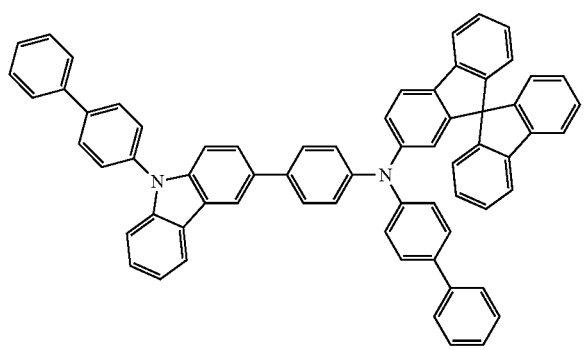
4-66
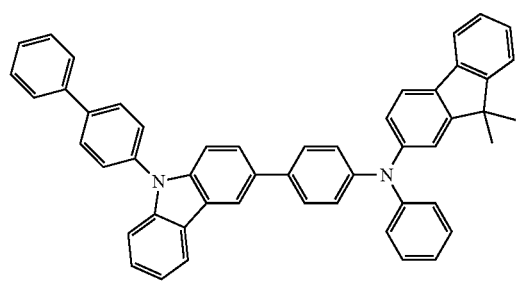
4-67
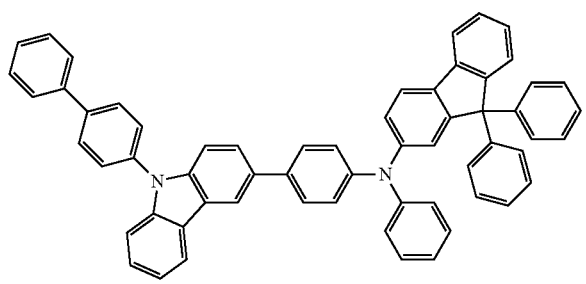
4-68
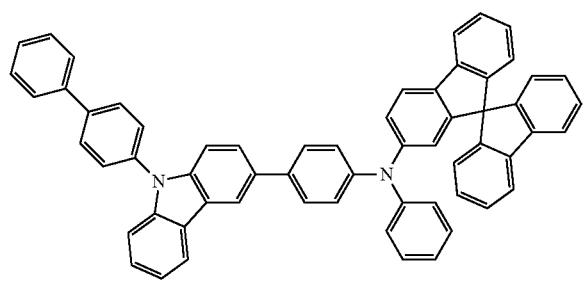
4-69
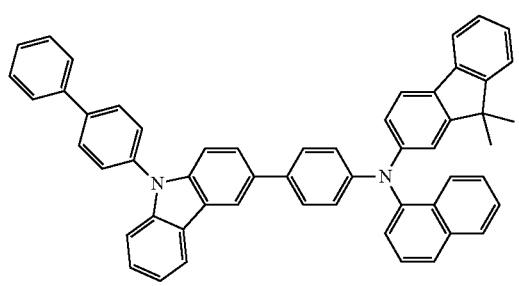
4-70
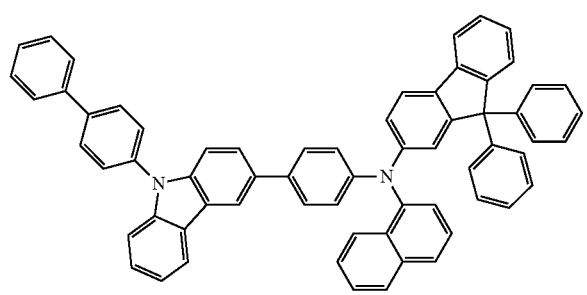

-continued
4-71
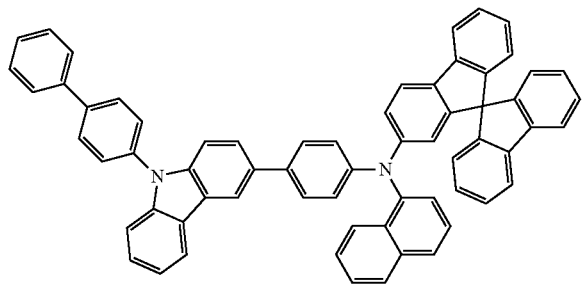
4-72
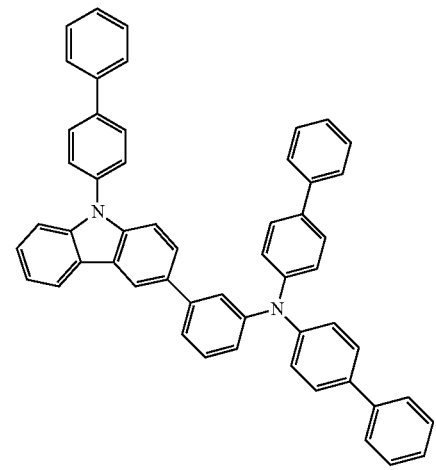
4-73
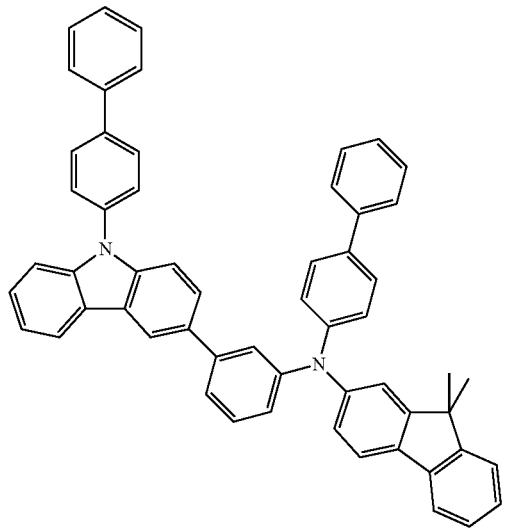
4-74
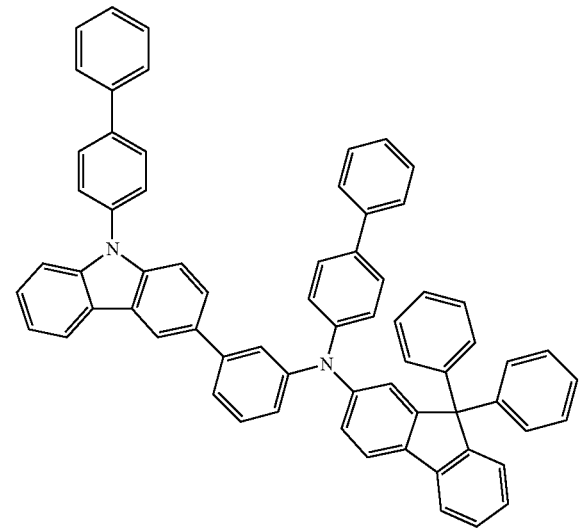
4-75
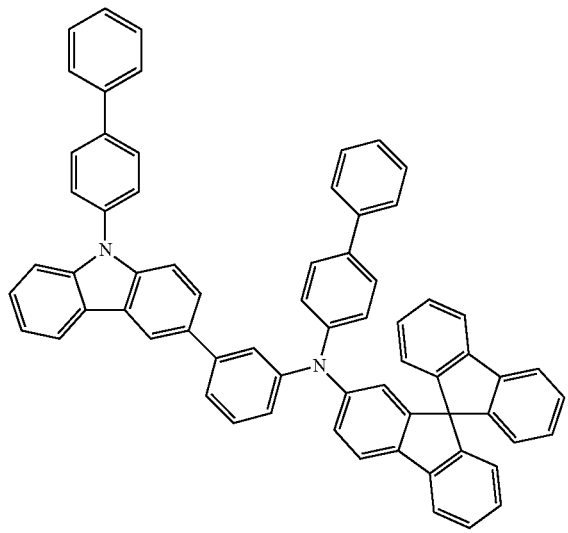
4-76
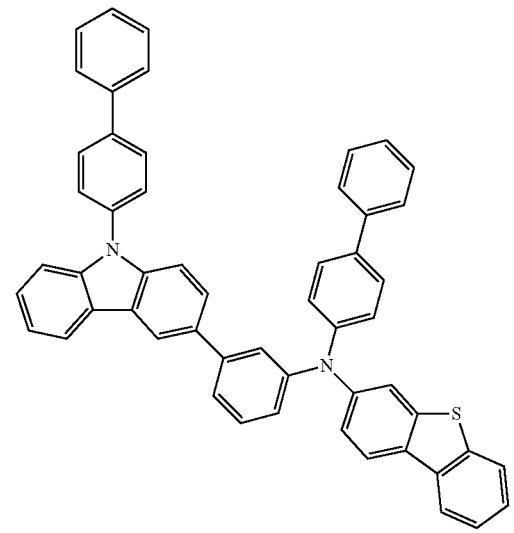

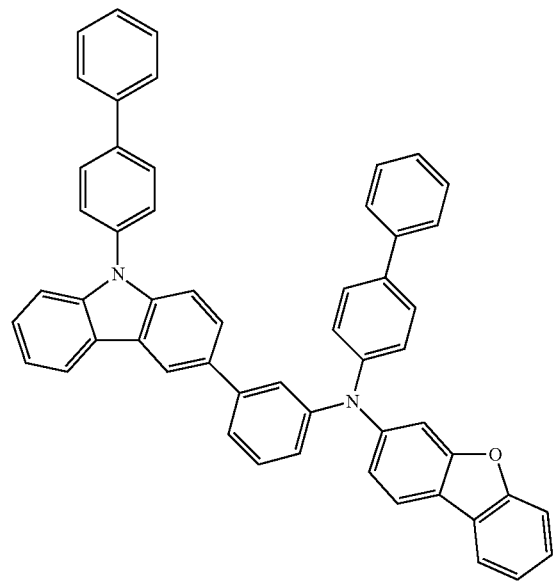
4-77
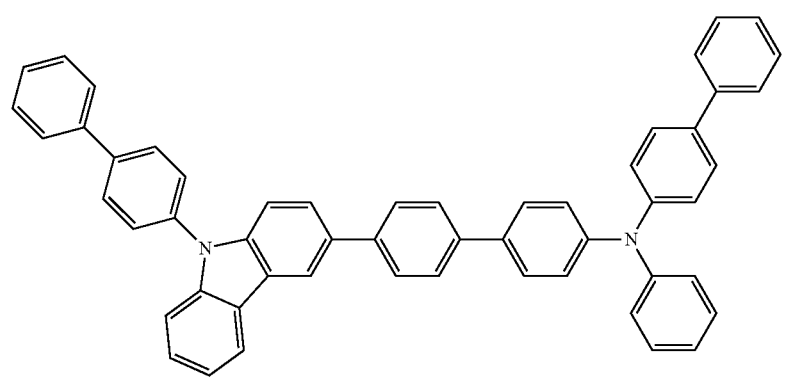
4-78
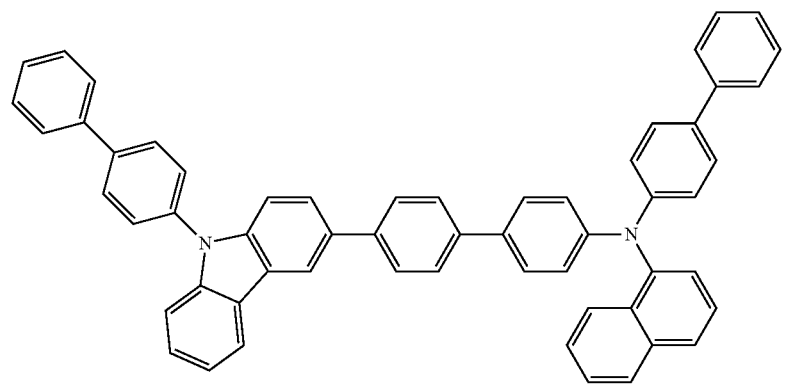
4-79

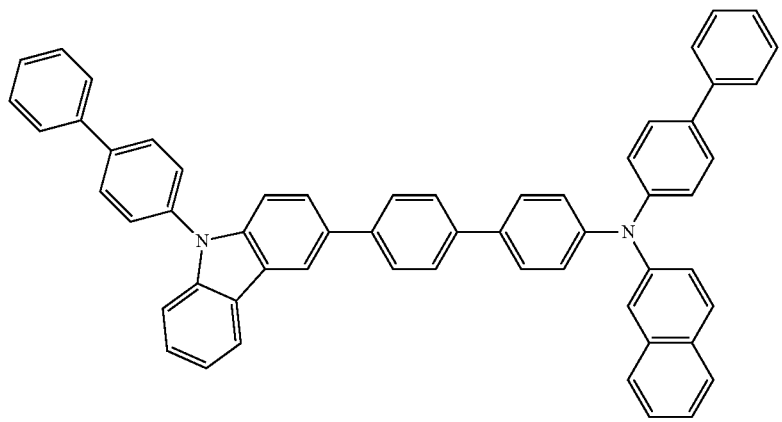
4-80
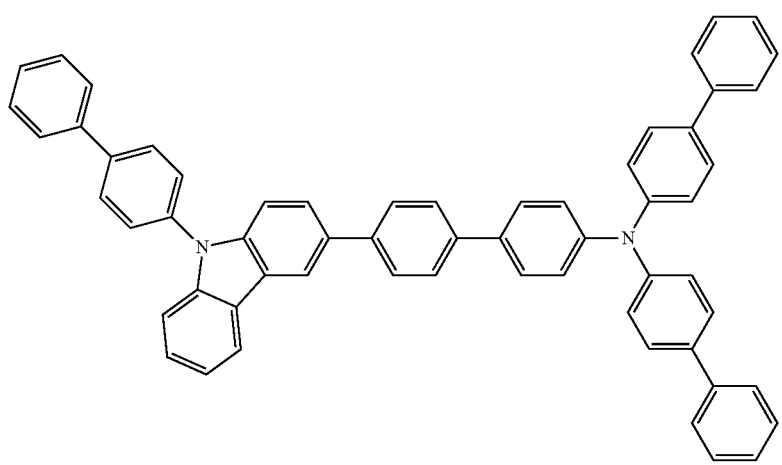
4-81
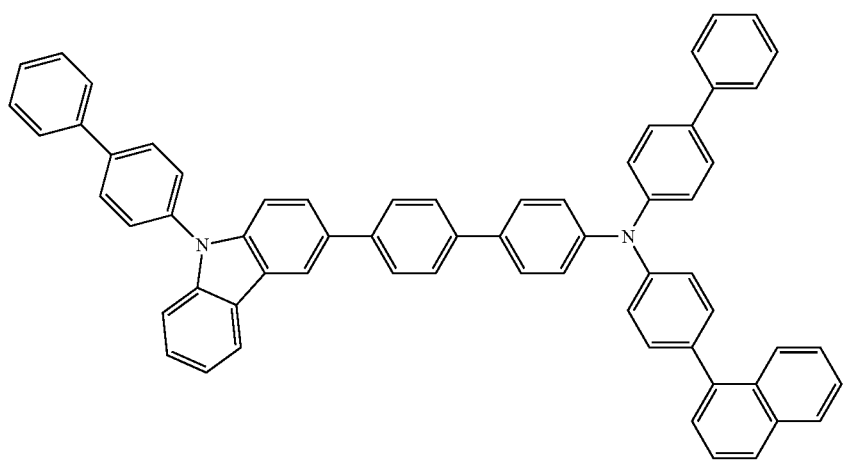
4-82

-continued
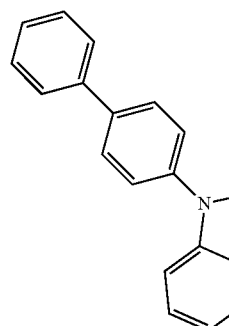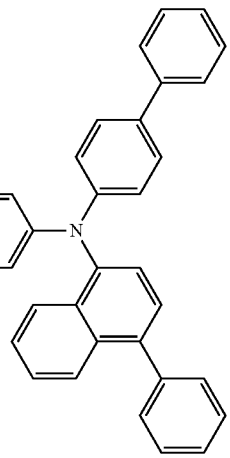
4-83
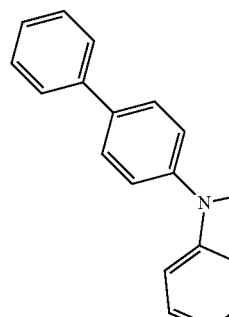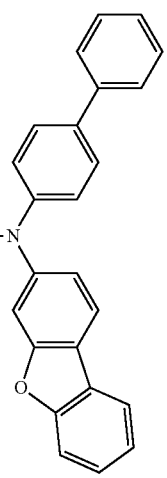
4-84
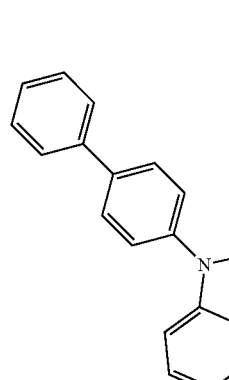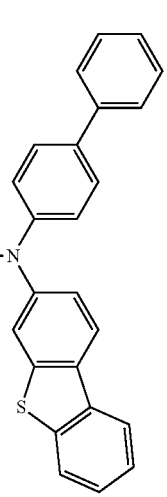
4-85

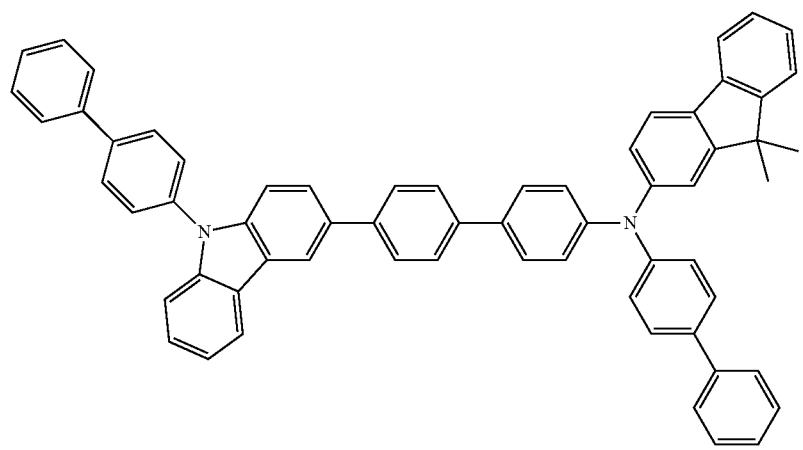
4-86
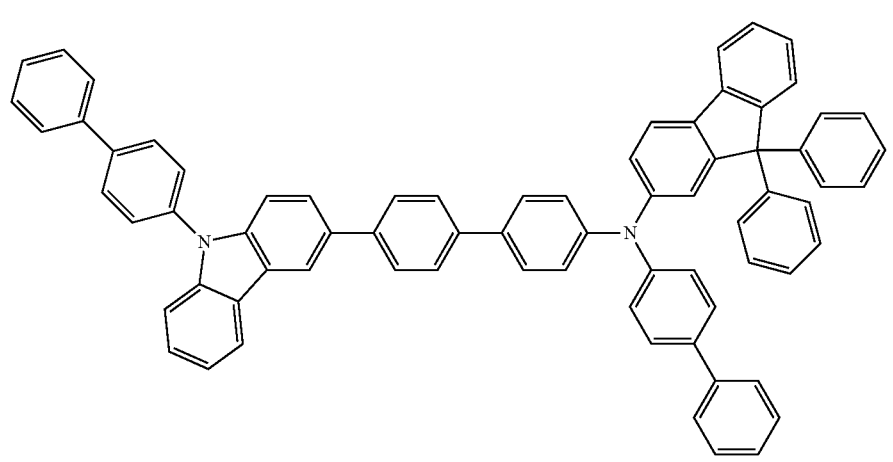
4-87
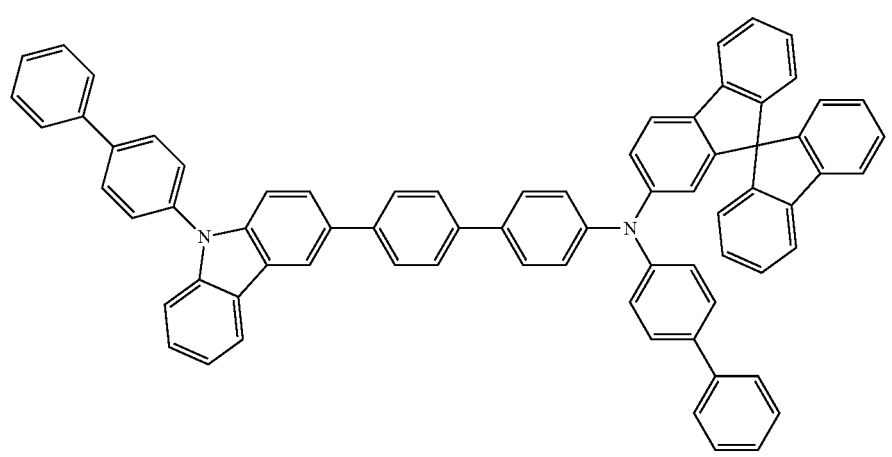
4-88

-continued
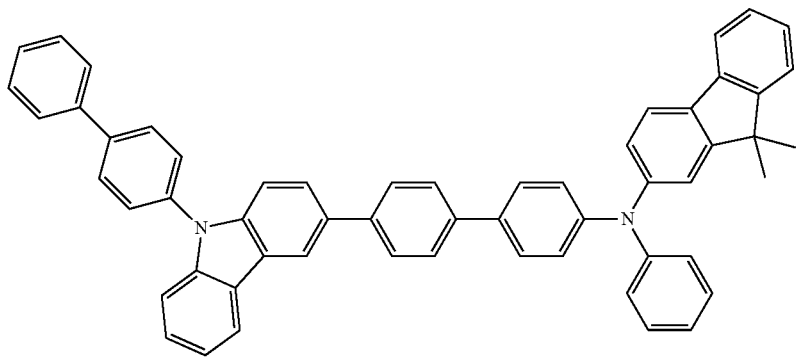
4-89
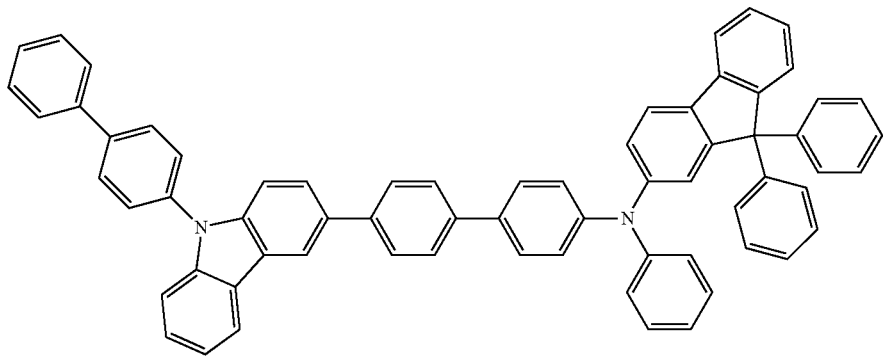
4-90
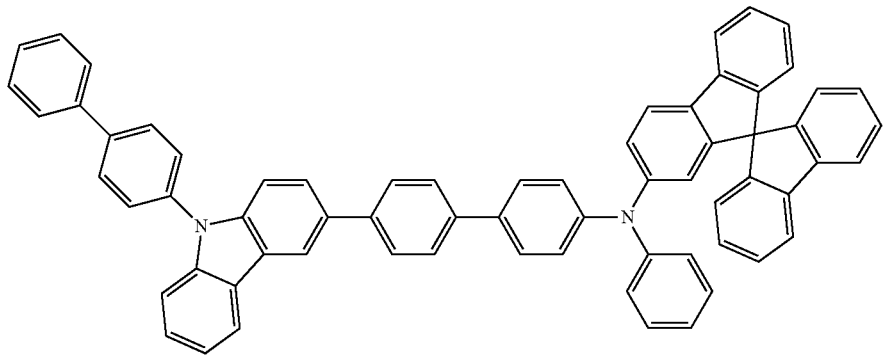
4-91
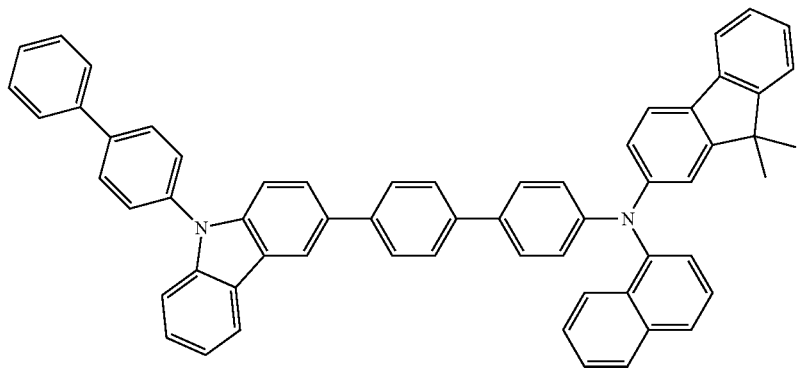
4-92

4-93
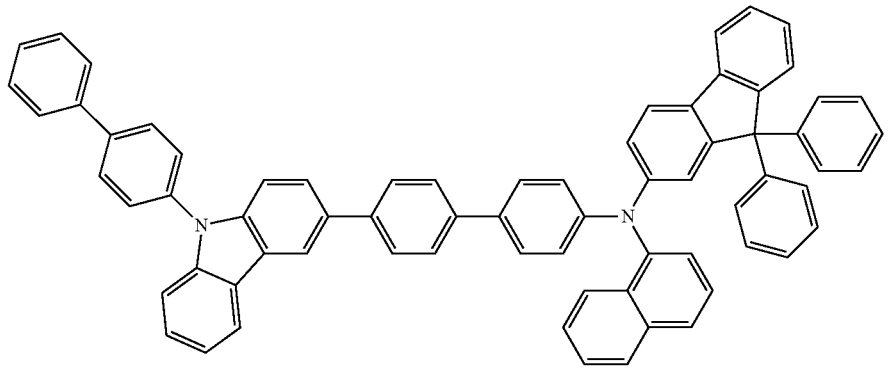
4-94
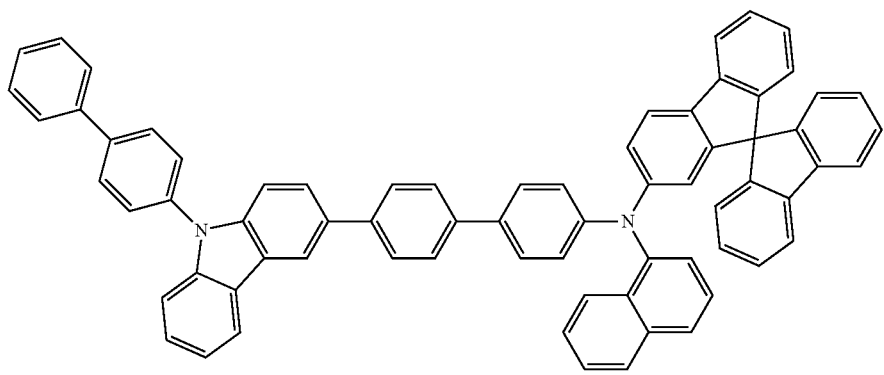
4-95 4-96
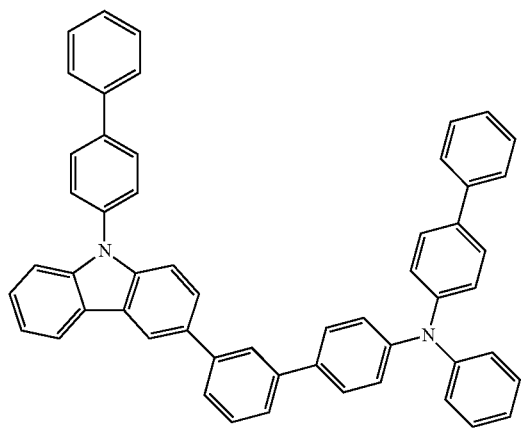

-continued
4-97
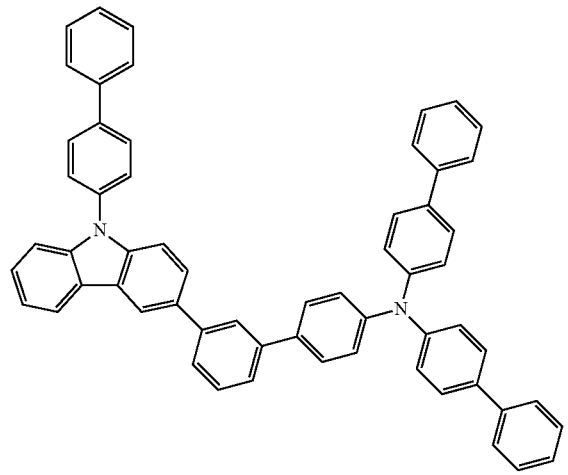
4-98
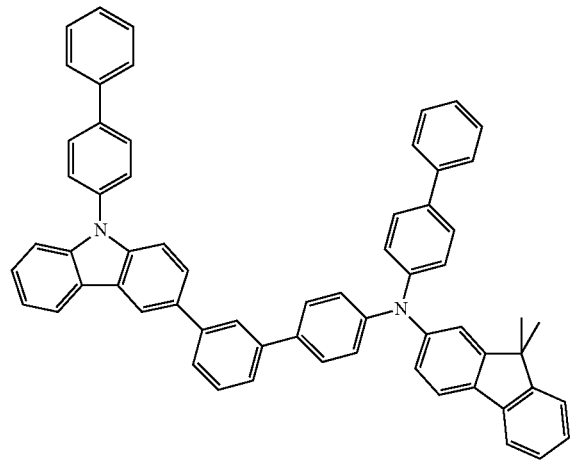
4-99
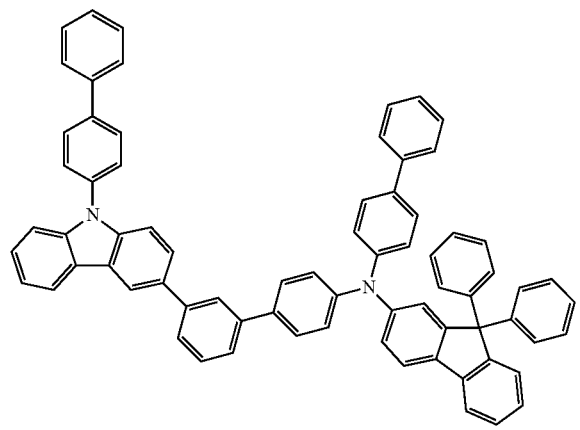
4-100
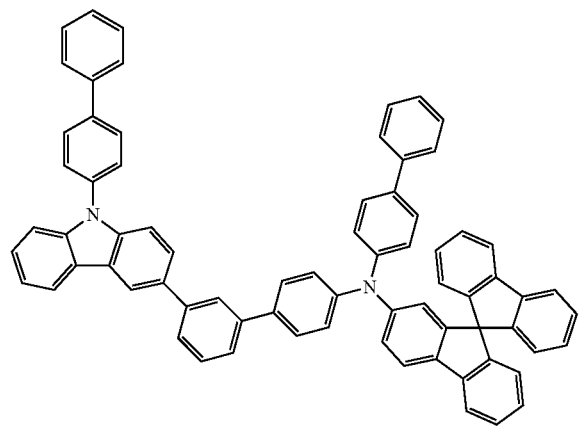
4-101
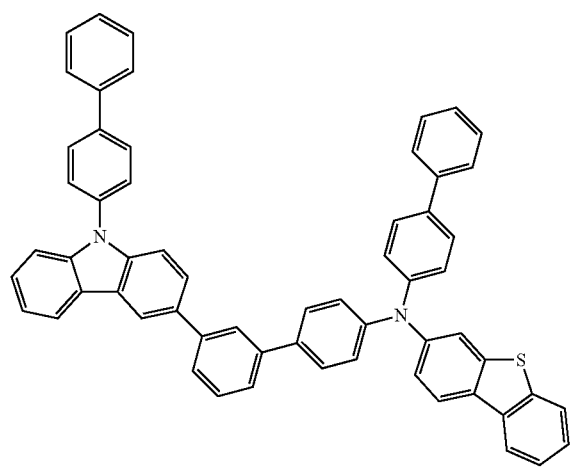
4-102
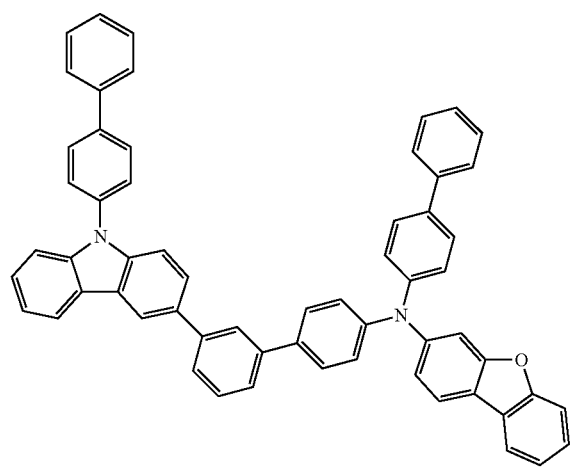

-continued
4-103
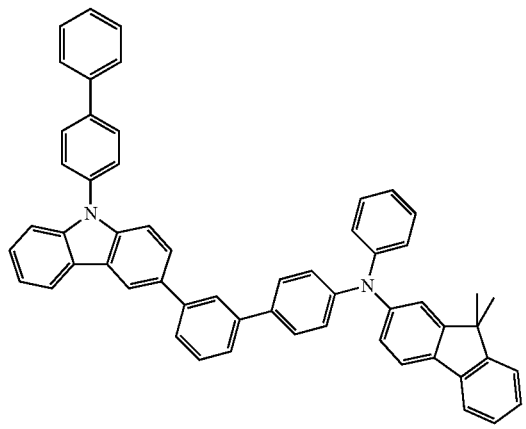
4-104
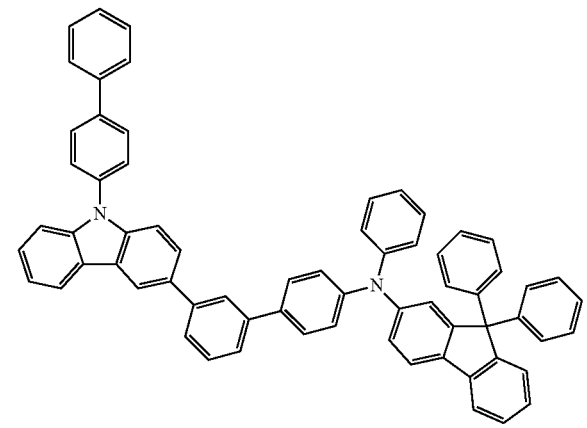
4-105
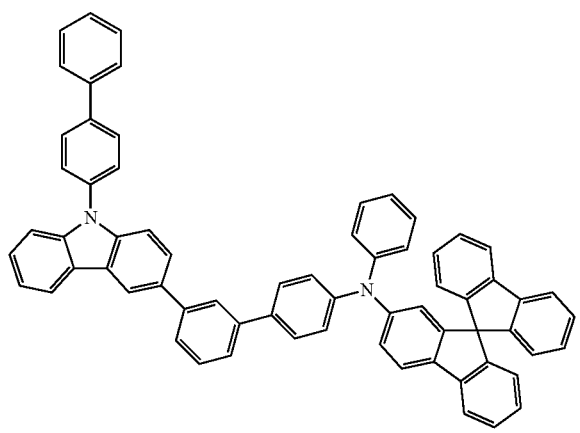
4-106
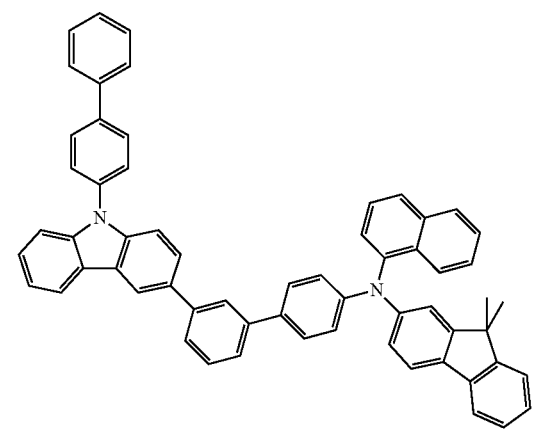
4-107
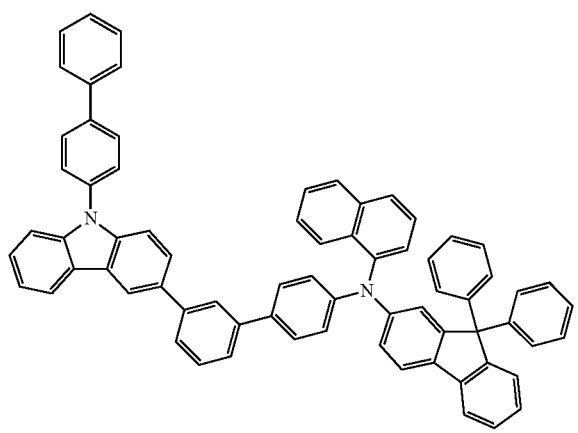
4-108
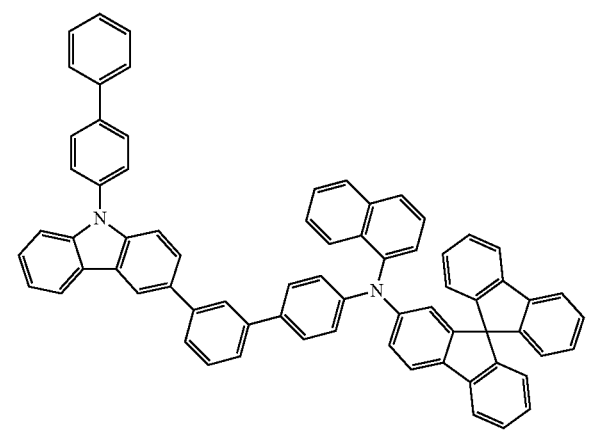
5-1
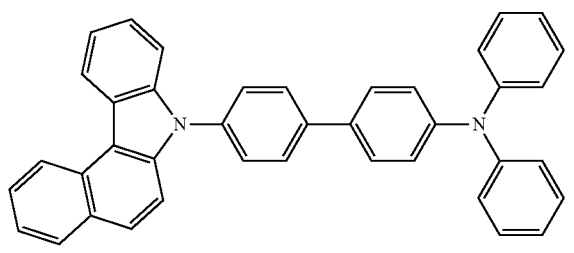
5-2
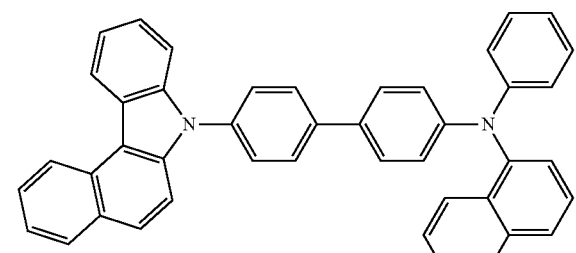

-continued
5-3
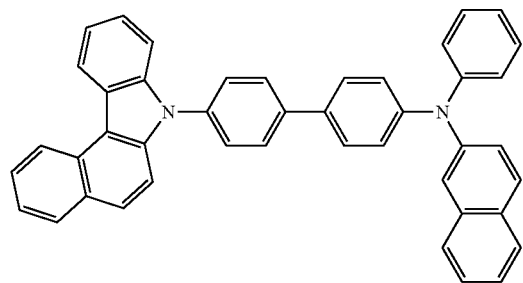
5-4
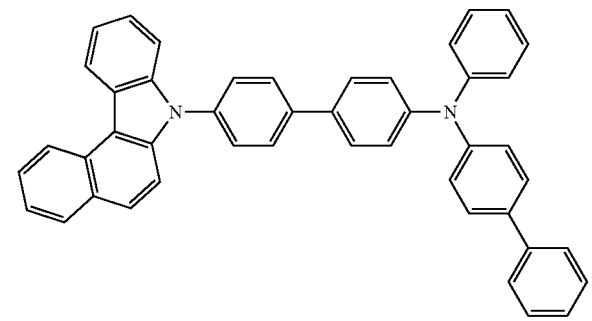
5-5
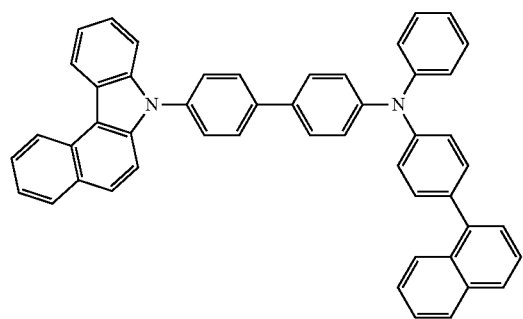
5-6
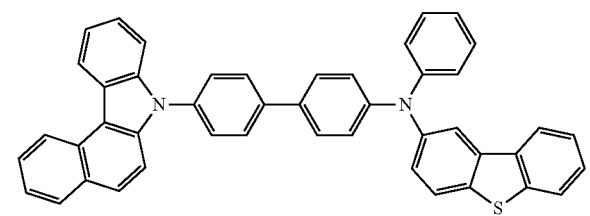
5-7
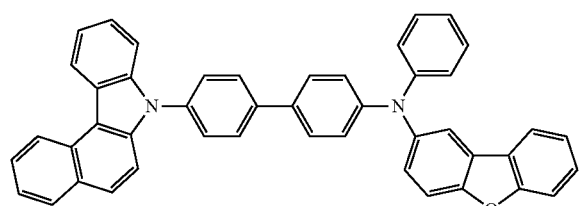
5-8
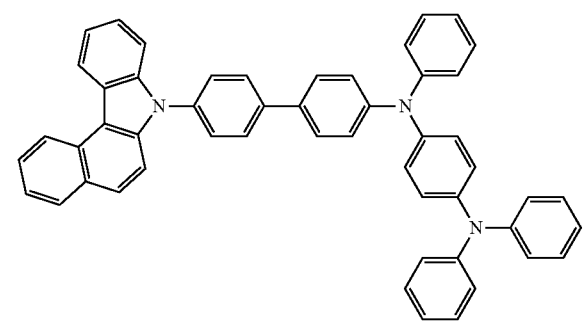
5-9
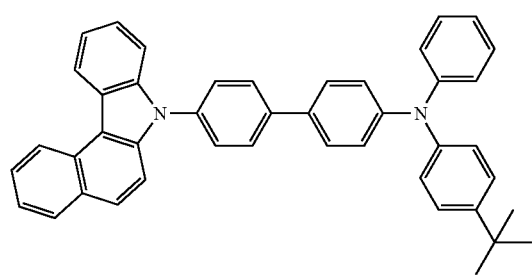
5-10
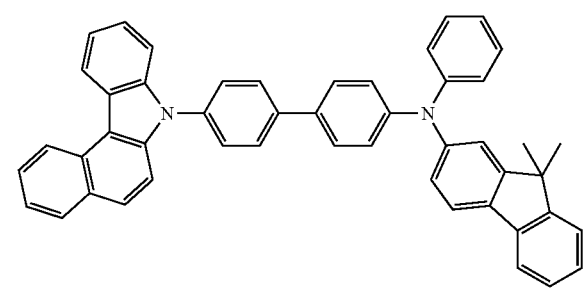

-continued
5-11
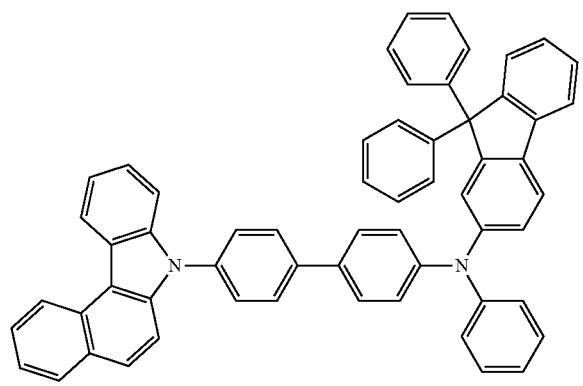
5-12
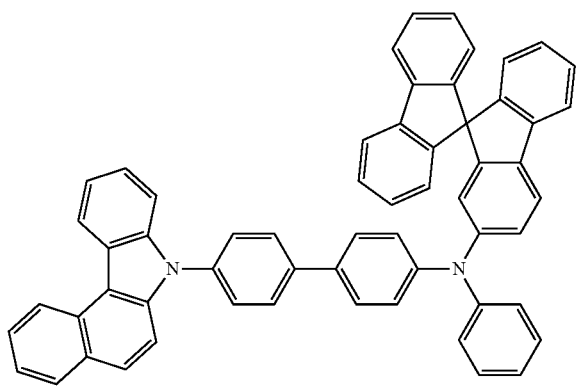
5-13
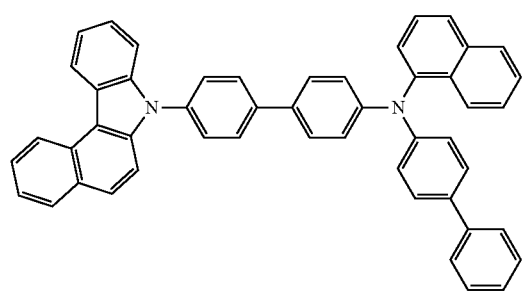
5-14
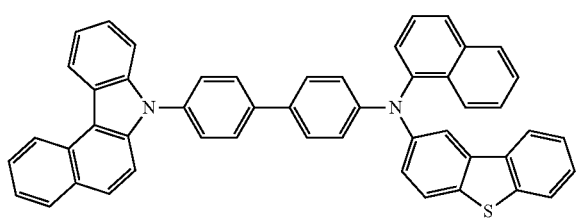
5-15
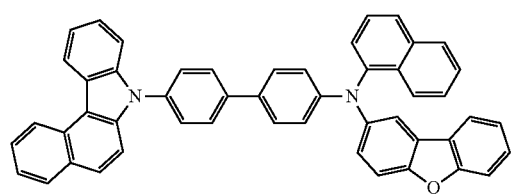
5-16
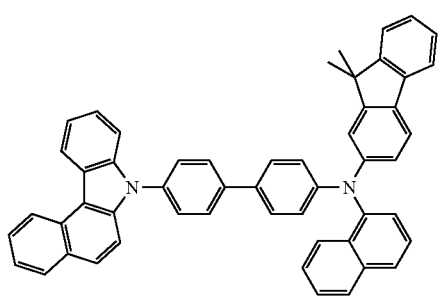
5-17
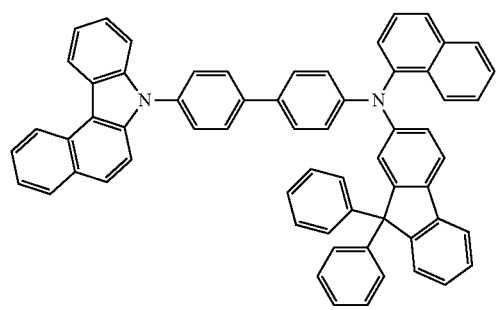
5-18
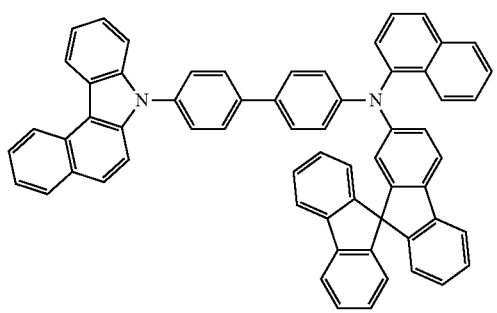

-continued
5-19
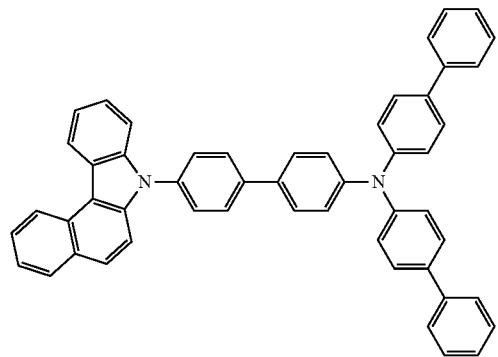
5-20
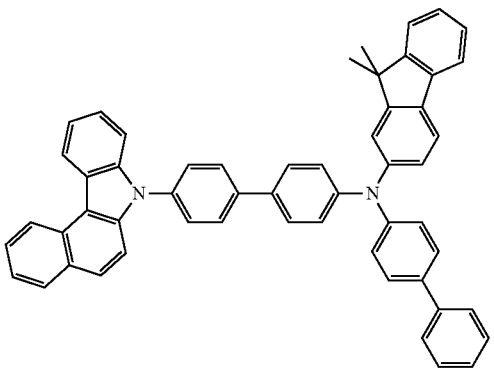
5-21
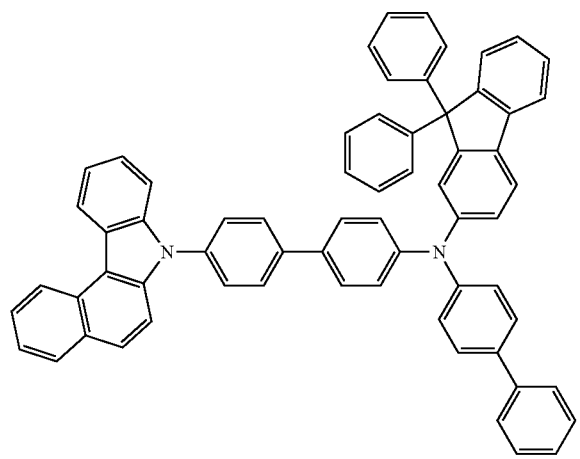
5-22
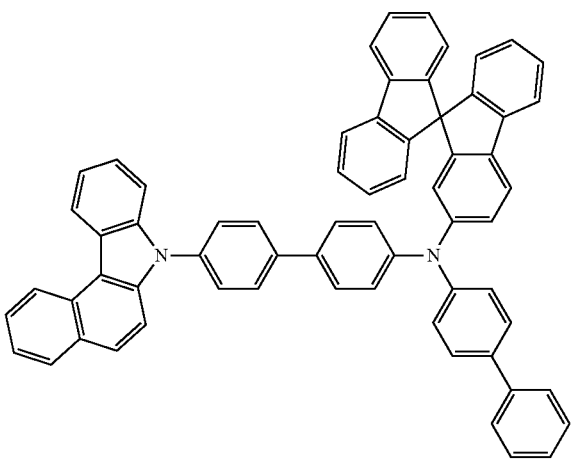
5-23
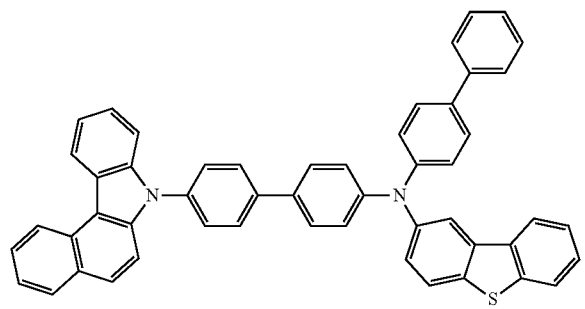
5-24
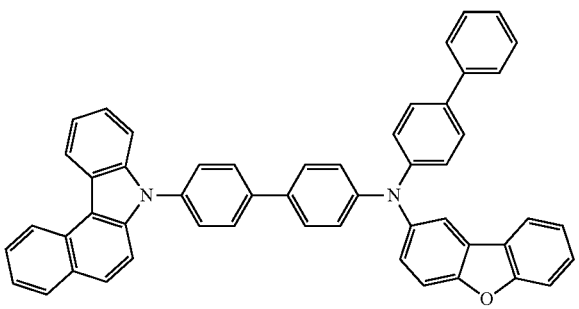
5-25
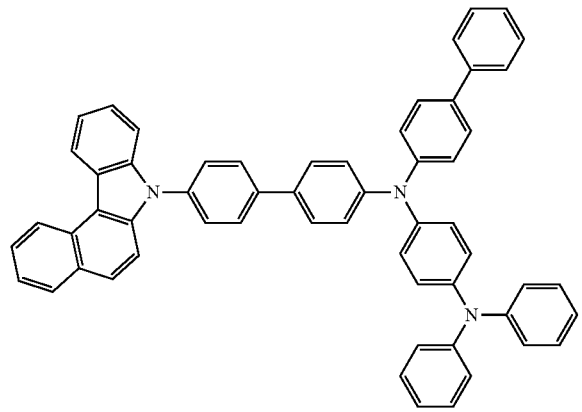
5-26
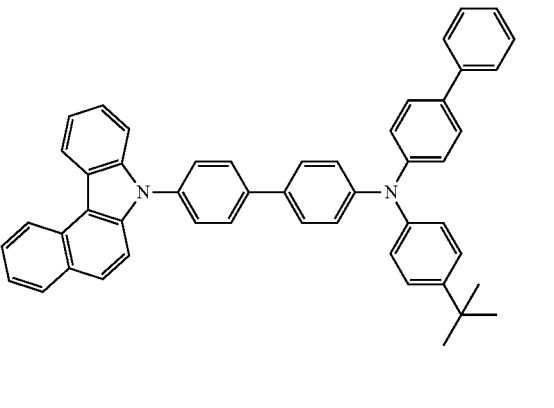

-continued
5-27
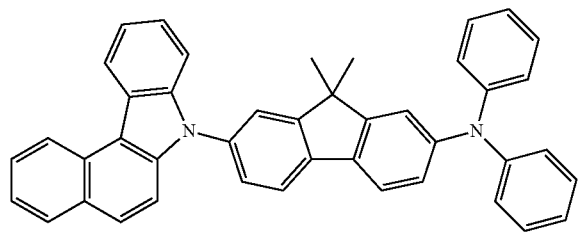
5-28
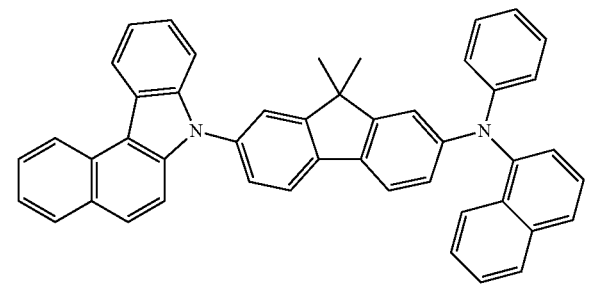
5-29
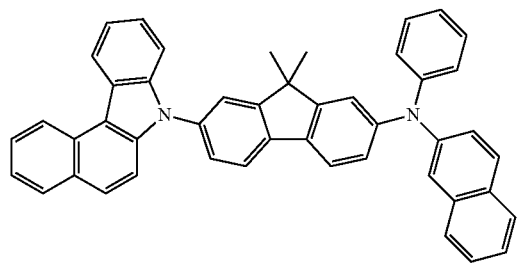
5-30
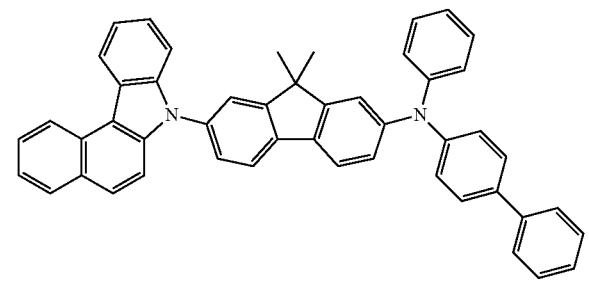
5-31
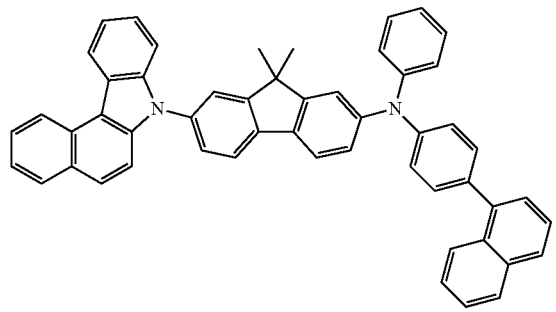
5-32
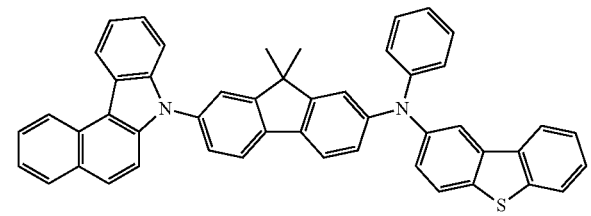
5-33
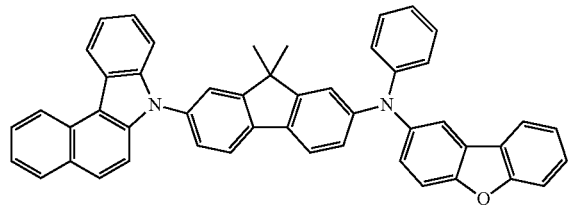
5-34
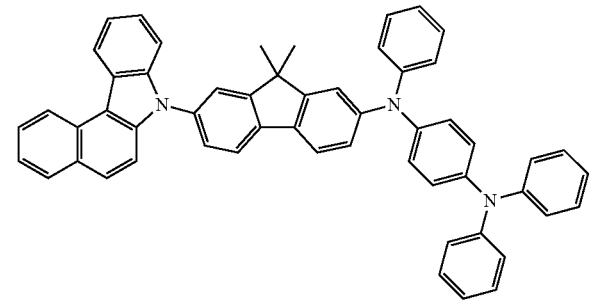
5-35
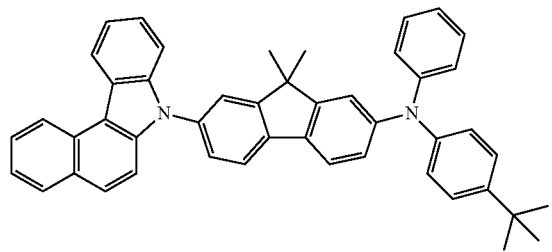
5-36
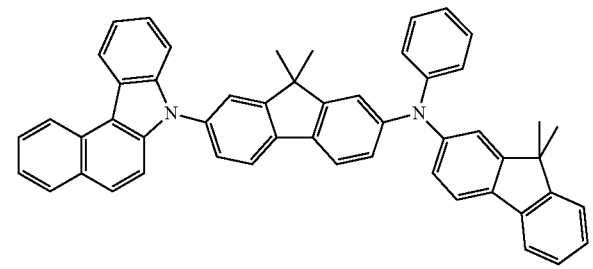

-continued
5-37
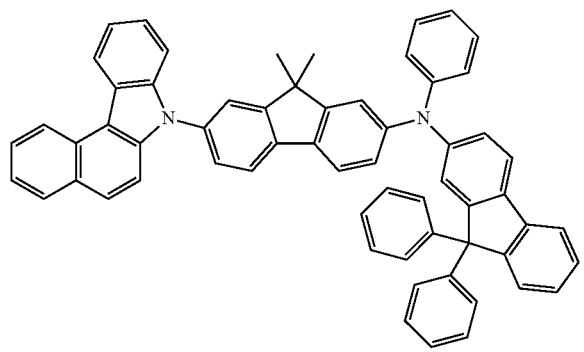
5-38
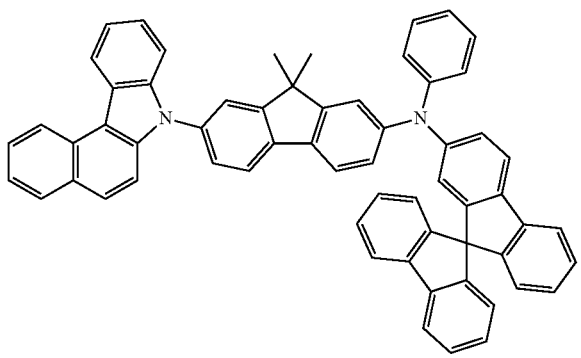
5-39
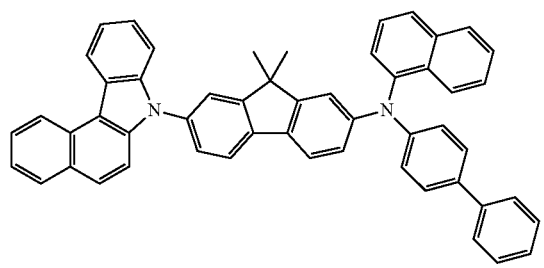
5-40
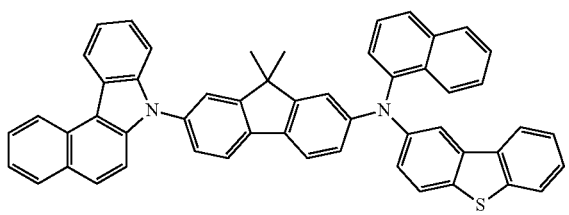
5-41
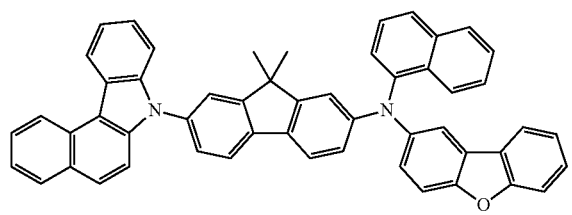
5-42
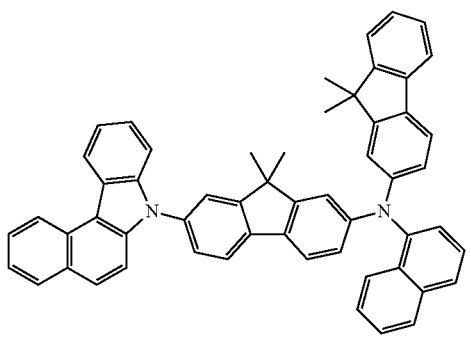
5-43
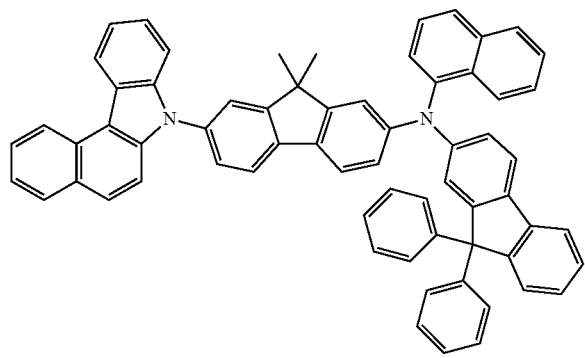
5-44
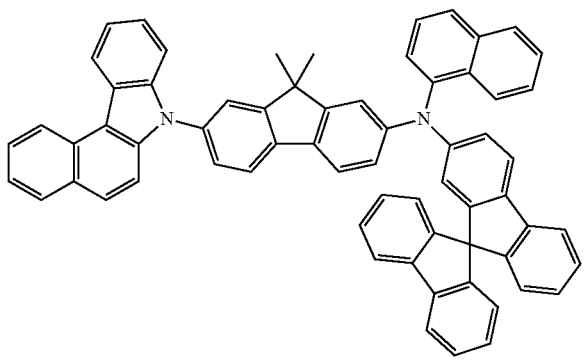

-continued
5-45
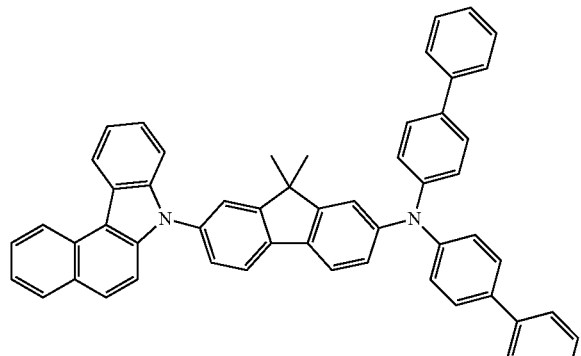
5-46
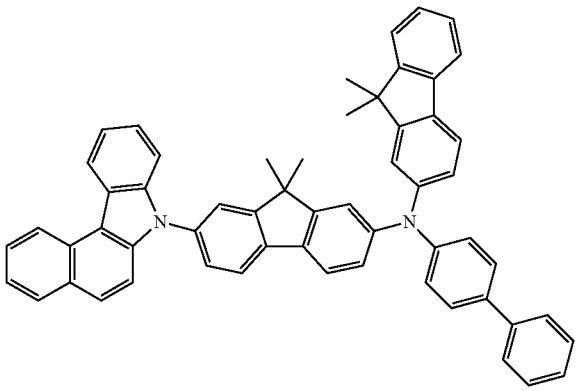
5-47
5-48
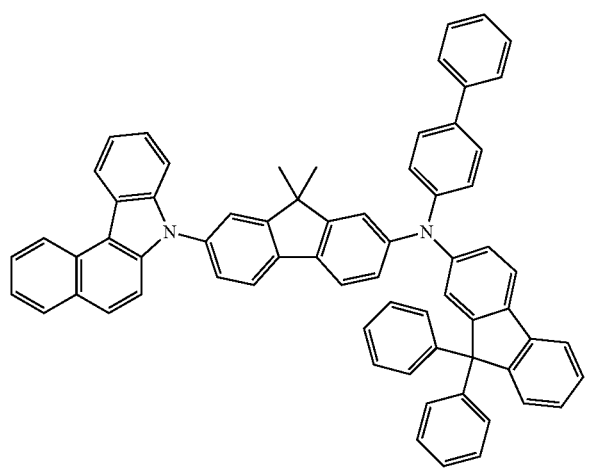
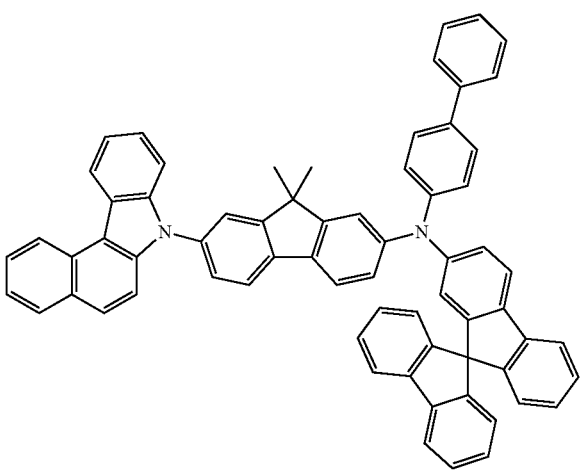
5-49
5-50
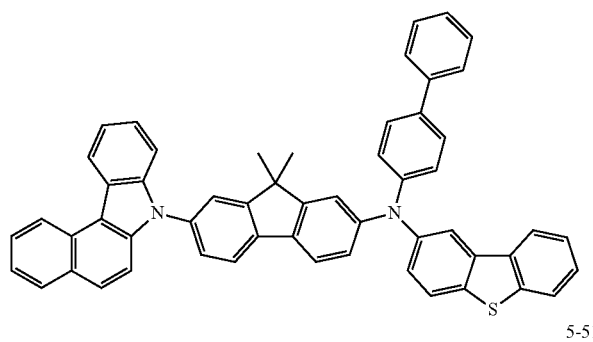
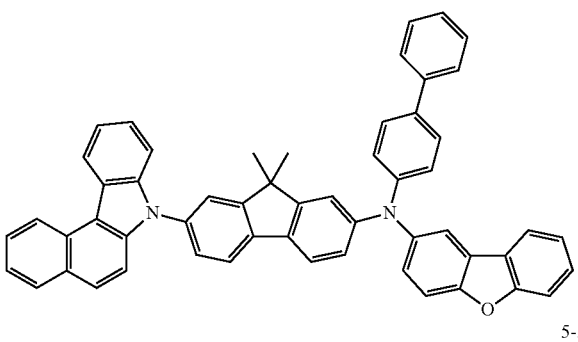
5-51
5-52
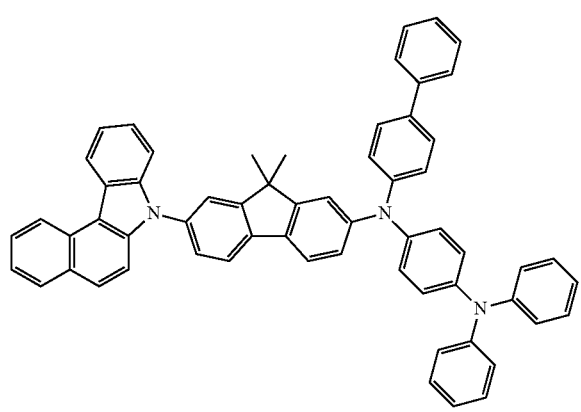

-continued
6-1
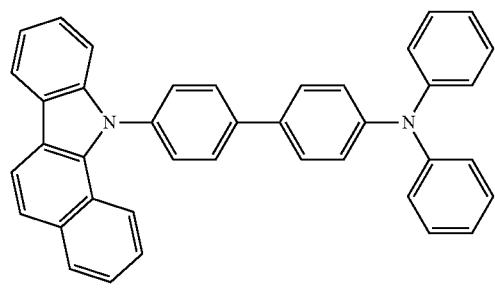
6-2
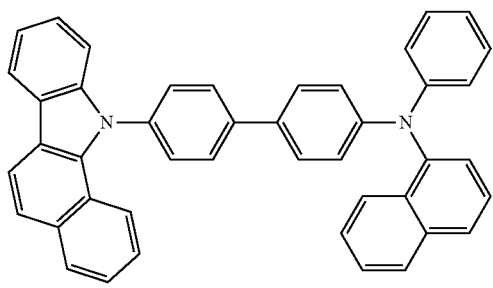
6-3
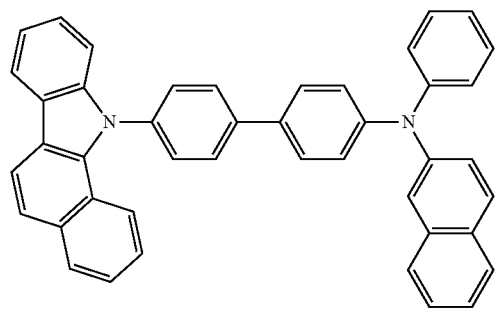
6-4
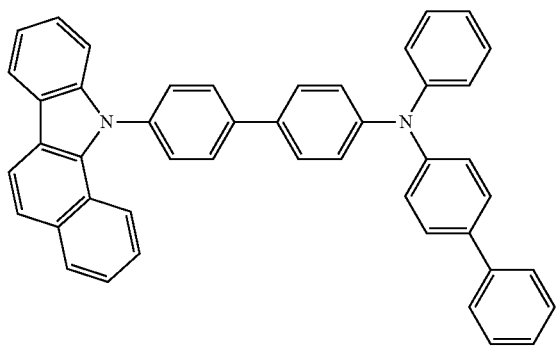
6-5
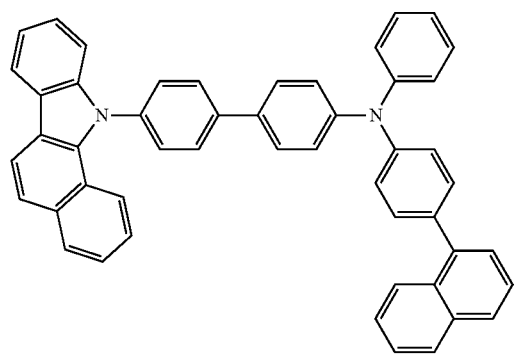
6-6
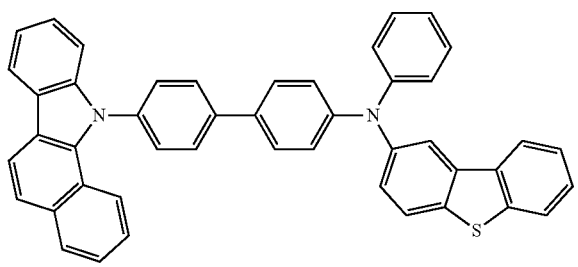
6-7
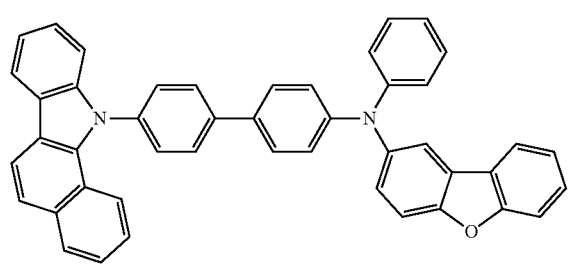
6-8
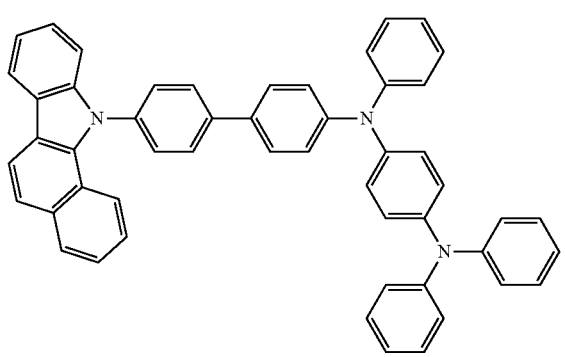

-continued
6-9
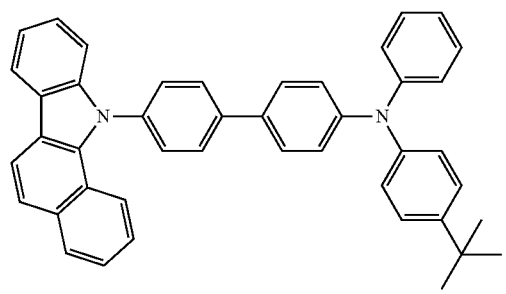
6-10
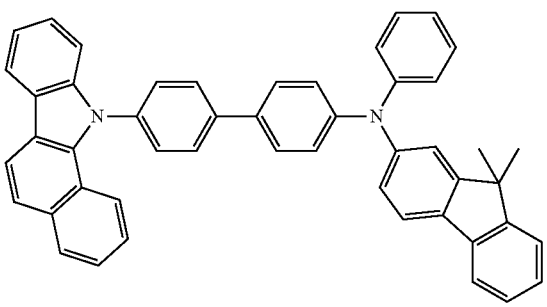
6-11
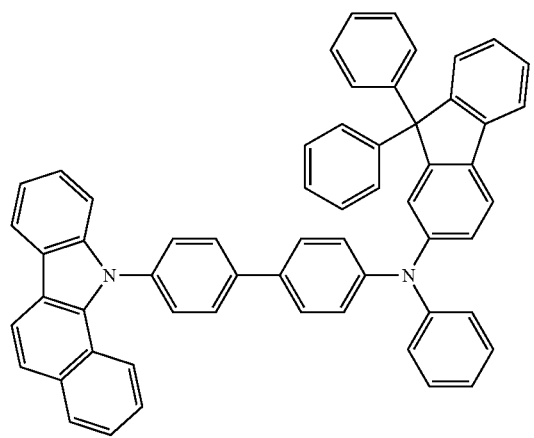
6-12
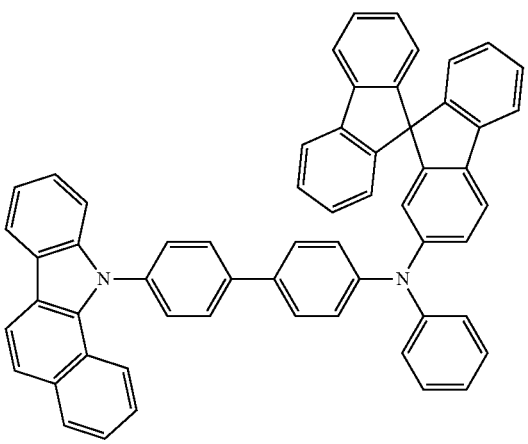
6-13
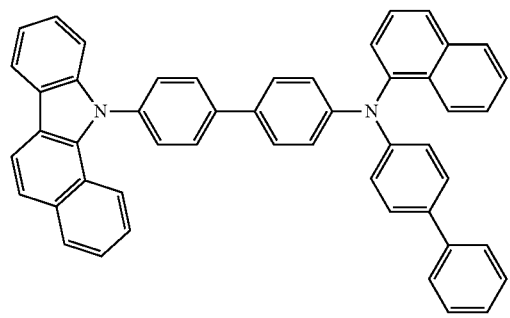
6-14
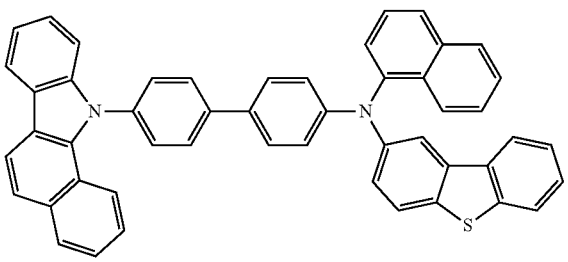
6-15
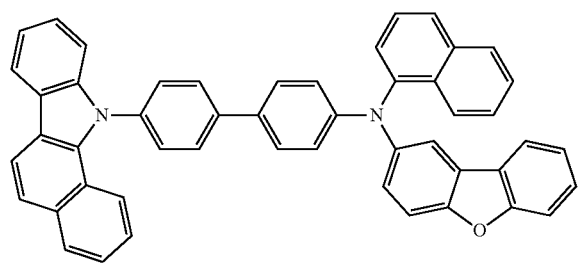
6-16
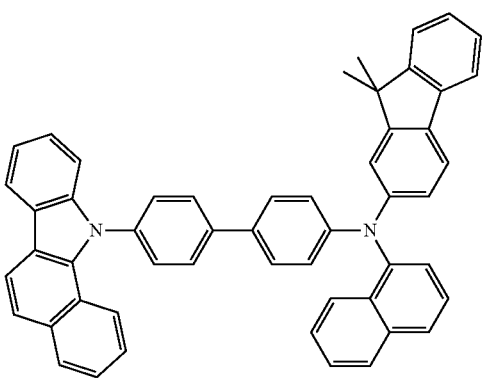

-continued
6-17
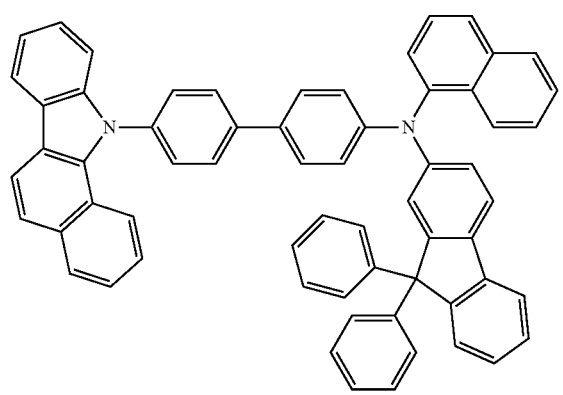
6-18
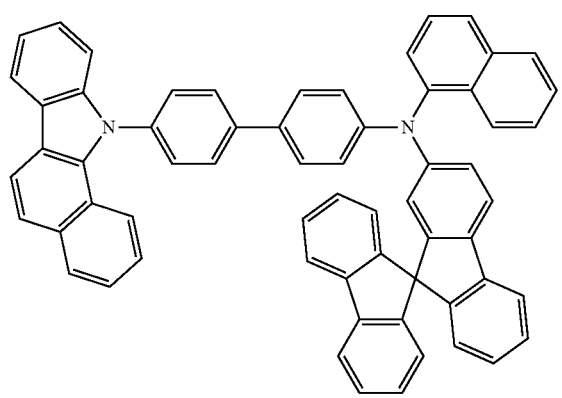
6-19
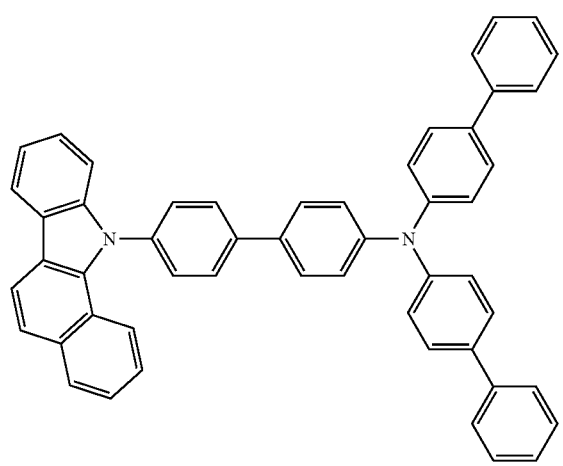
6-20
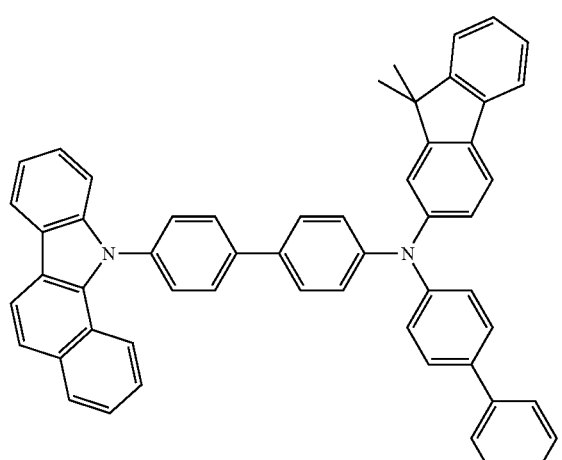
6-21
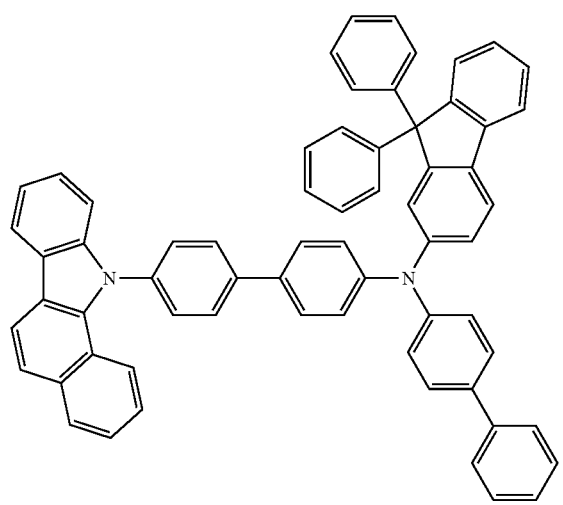
6-22
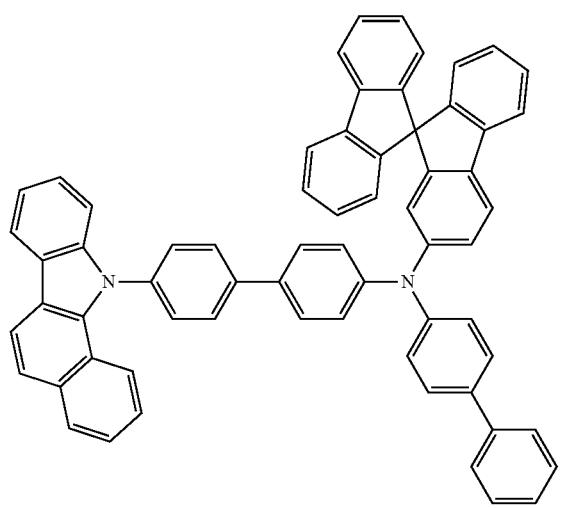

-continued
6-23
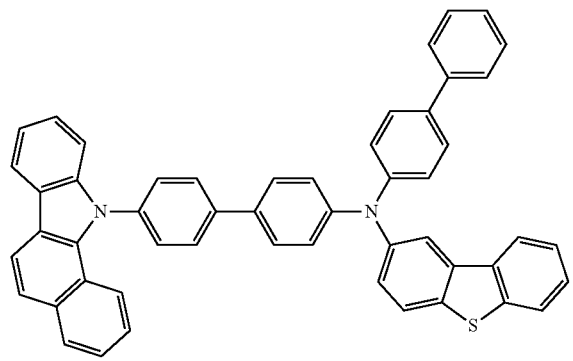
6-24
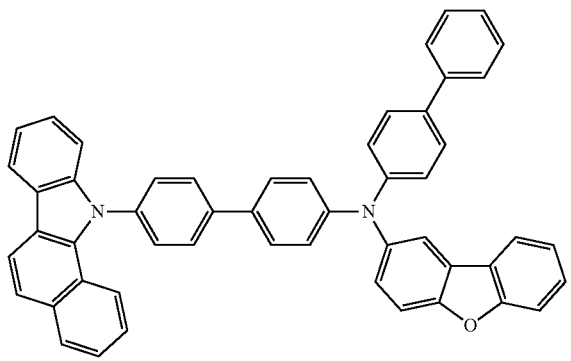
6-25
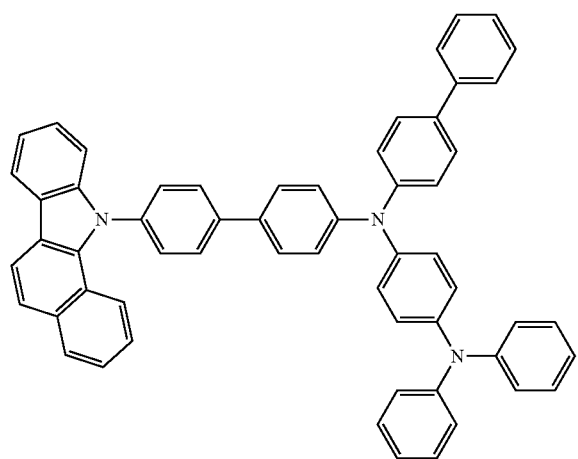
6-26
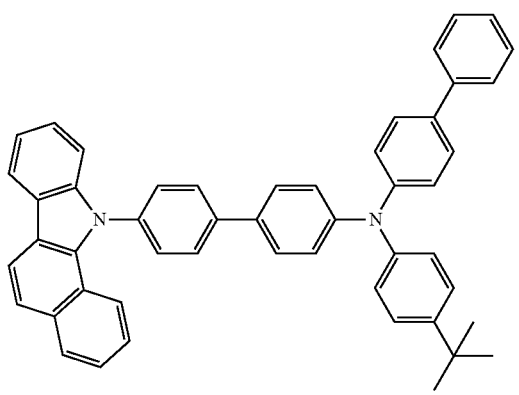
6-27
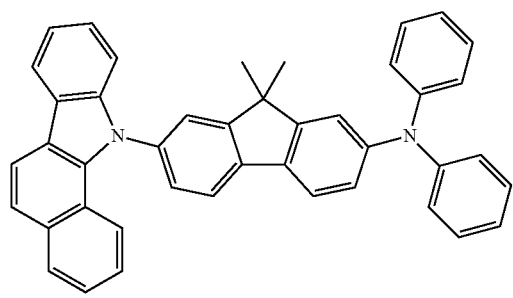
6-28
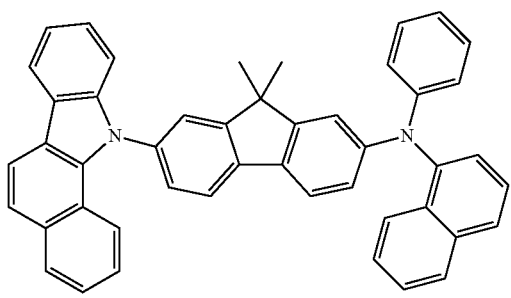
6-29
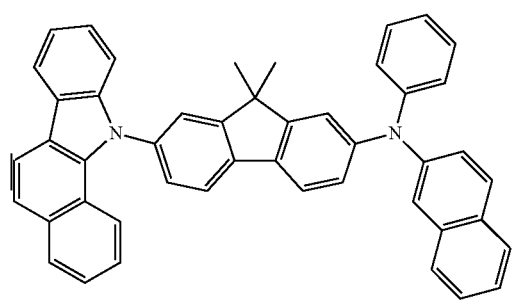
6-30
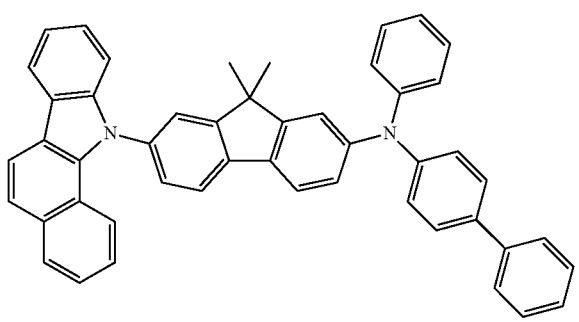

-continued
6-31
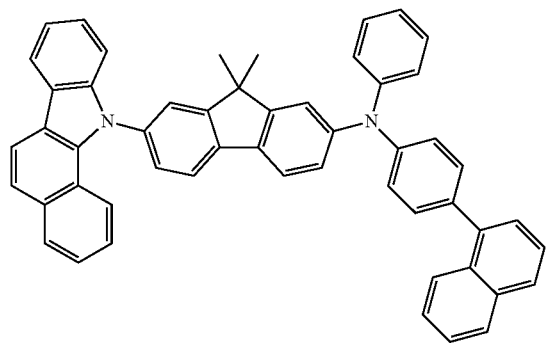
6-32
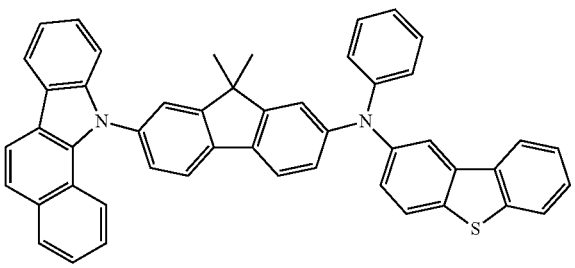
6-33
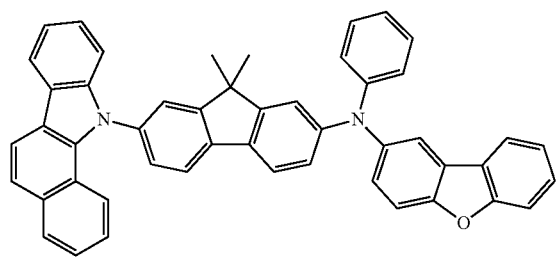
6-34
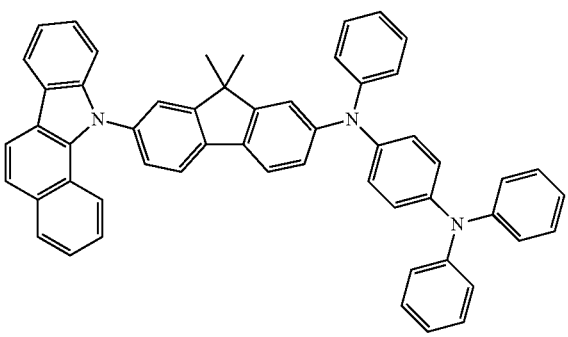
6-35
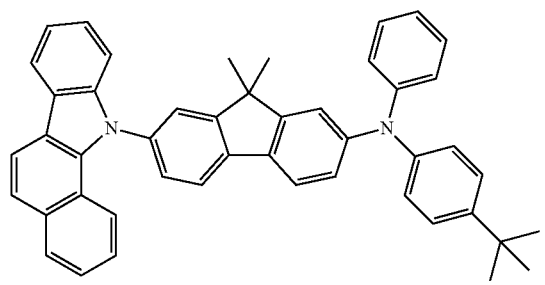
6-36
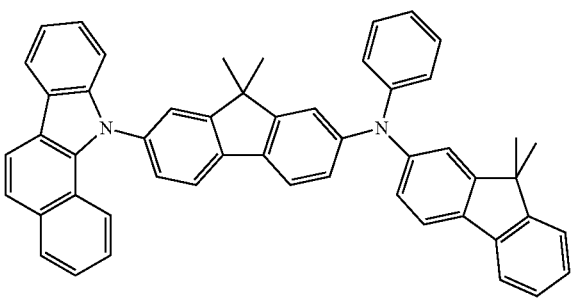
6-37
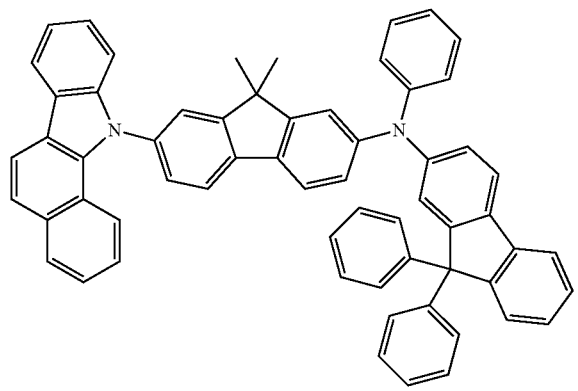
6-38
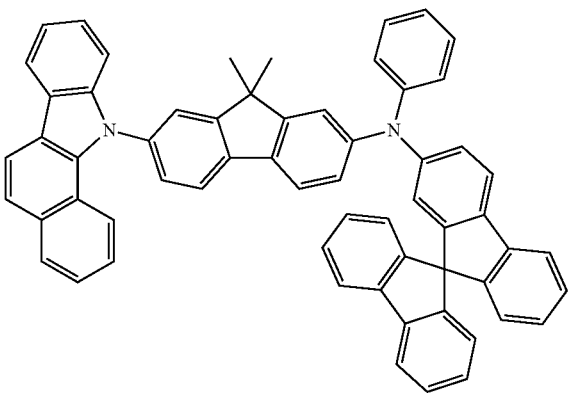

-continued
6-39
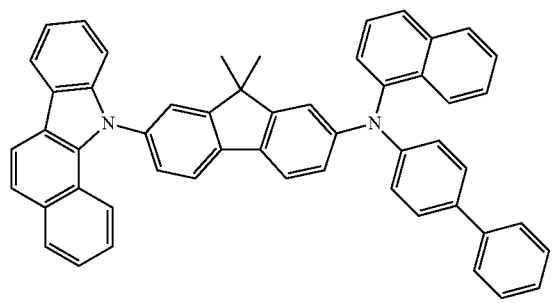
6-40
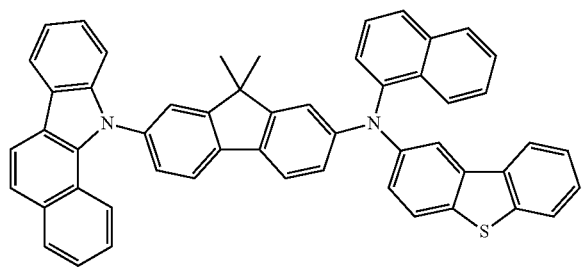
6-41
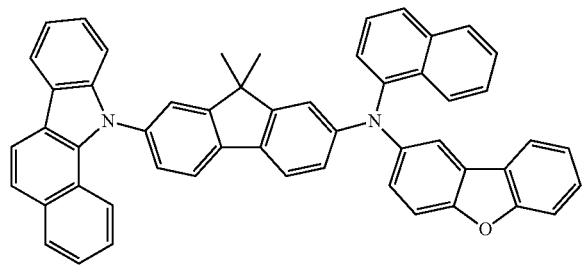
6-42
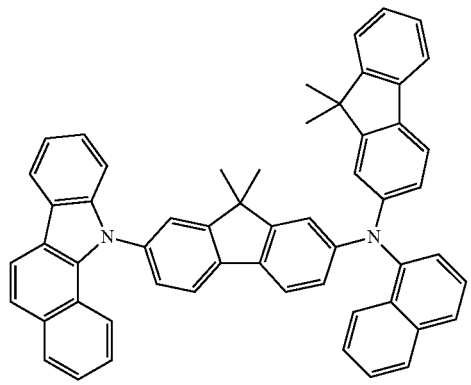
6-43
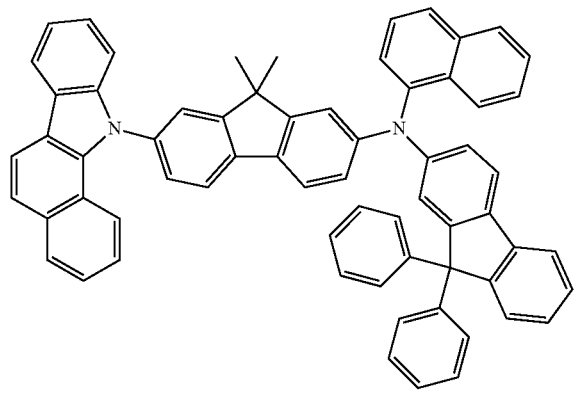
6-44
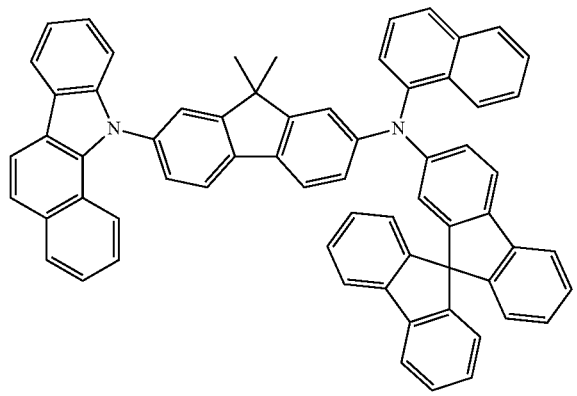
6-45
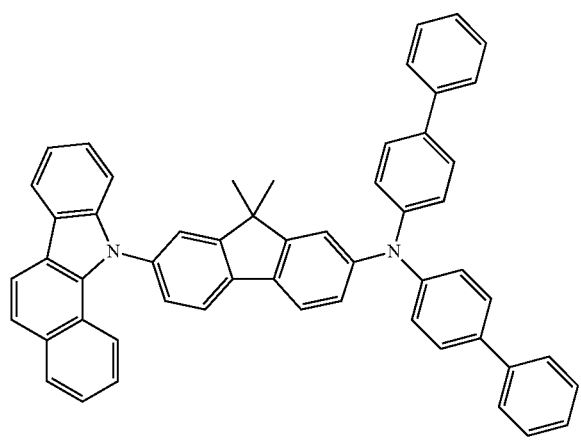
6-46
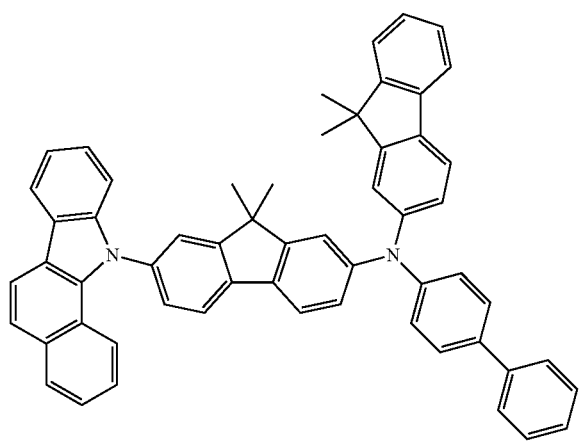

-continued
6-47
6-48
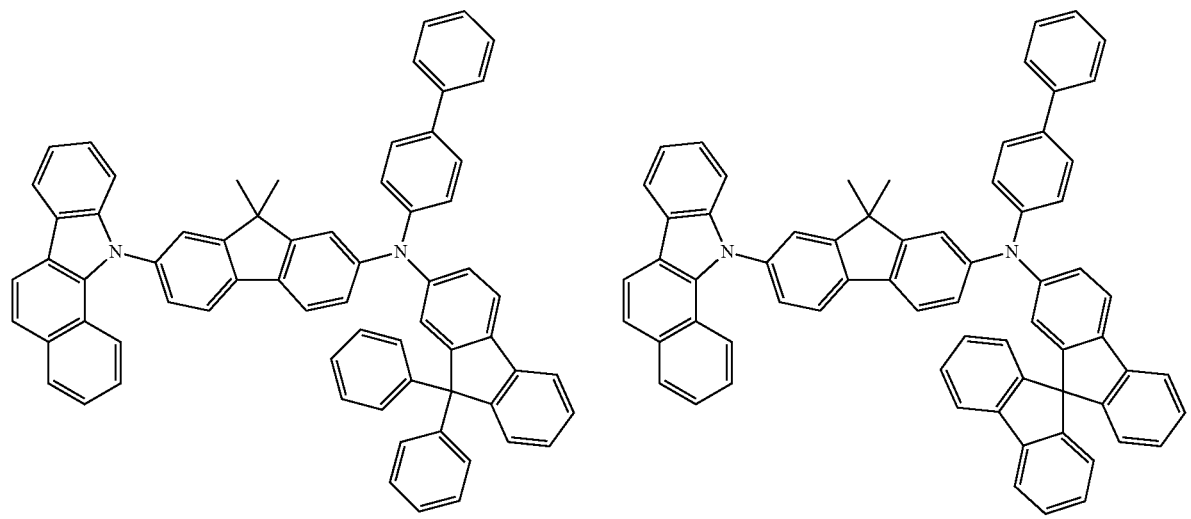
6-49
6-50
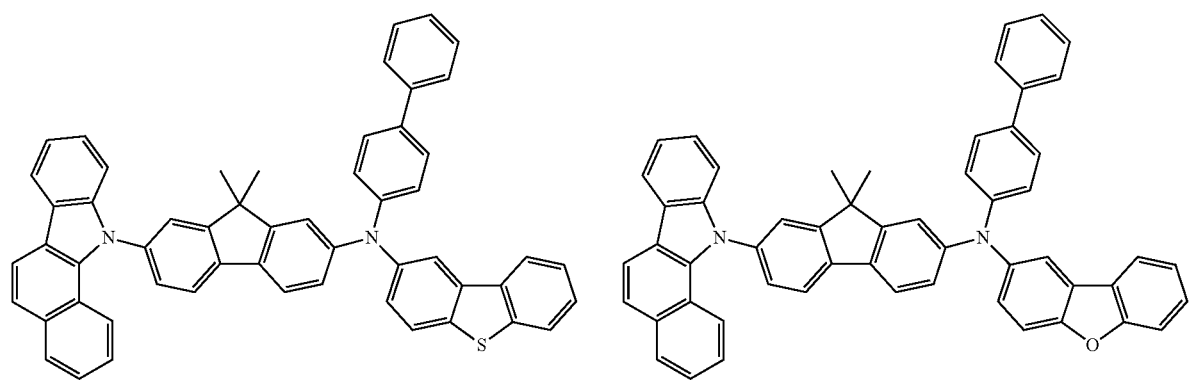
6-51
6-52
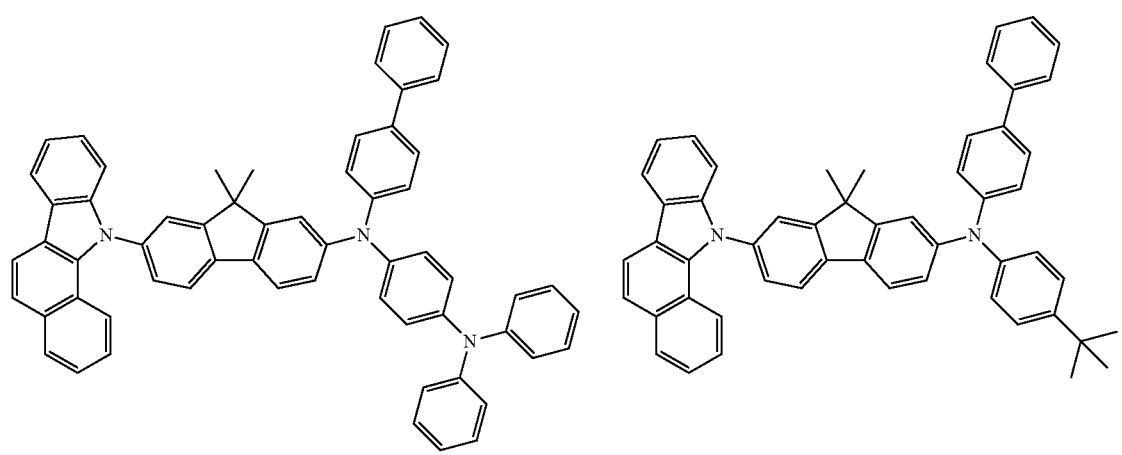

-continued
7-1
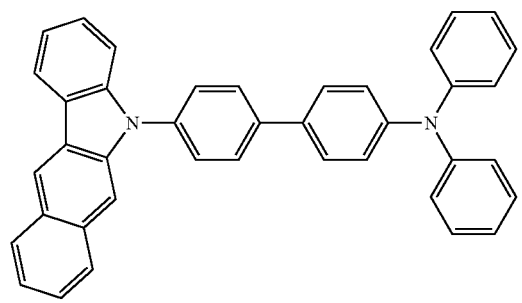
7-2
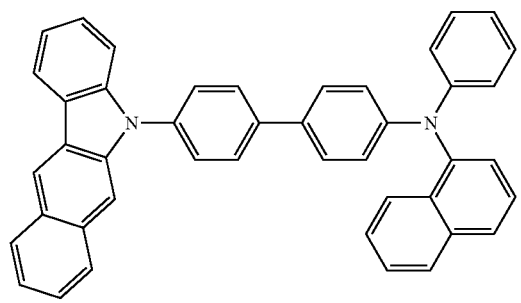
7-3
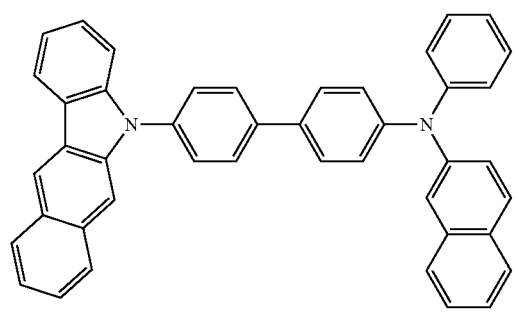
7-4
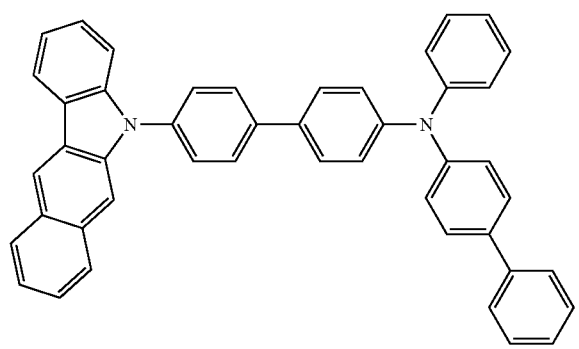
7-5
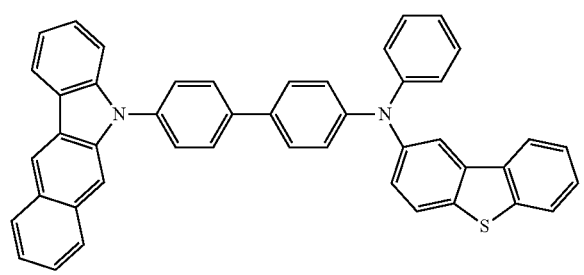
7-6
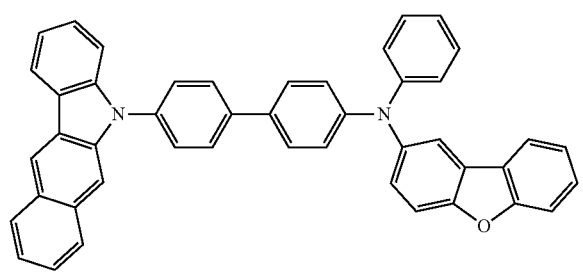
7-7
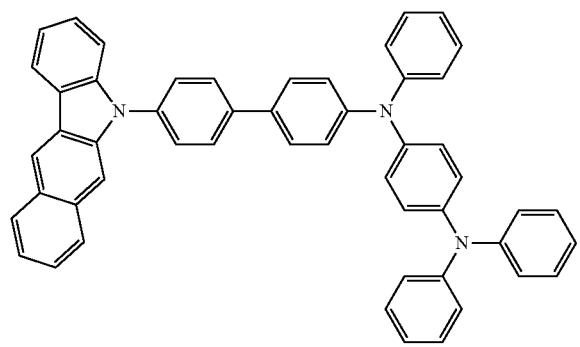
7-8
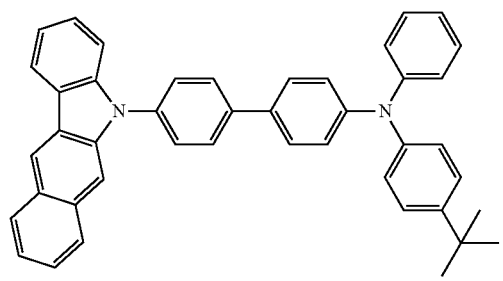

-continued
7-9
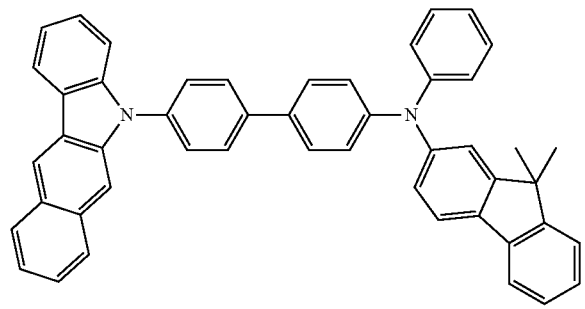
7-10
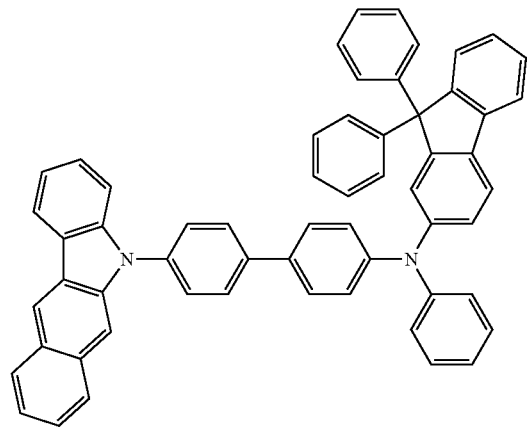
7-11
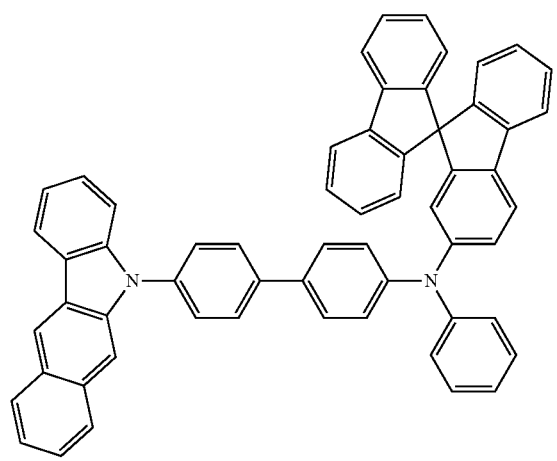
7-12
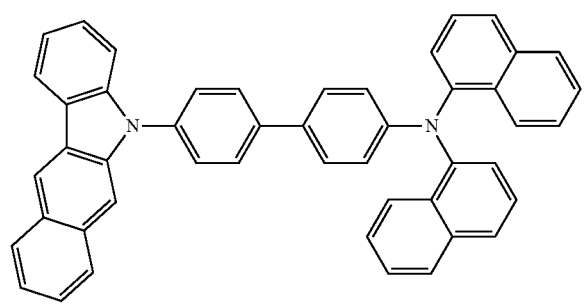
7-13
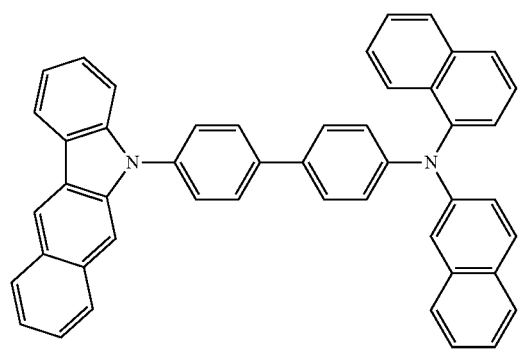
7-14
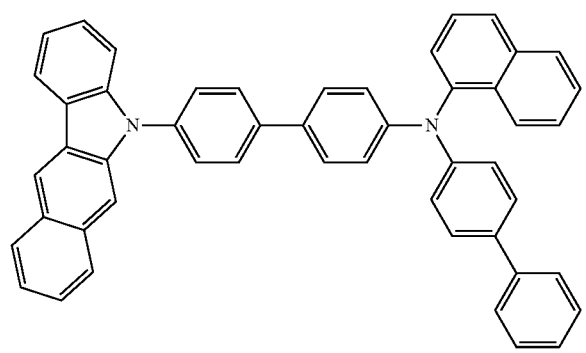
7-15
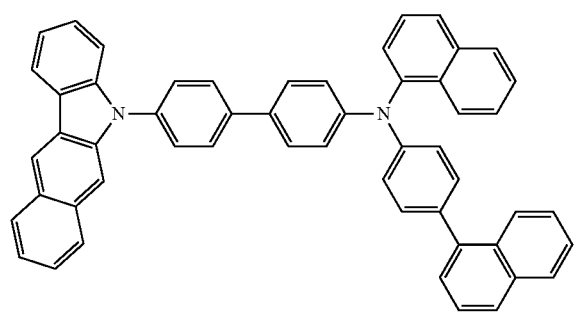
7-16
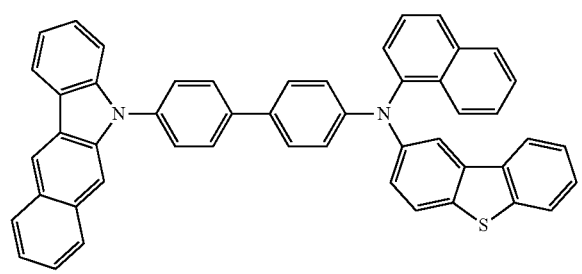

-continued
7-17
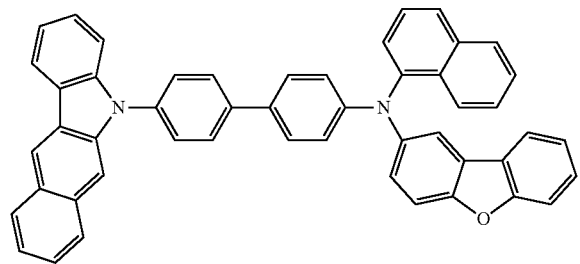
7-18
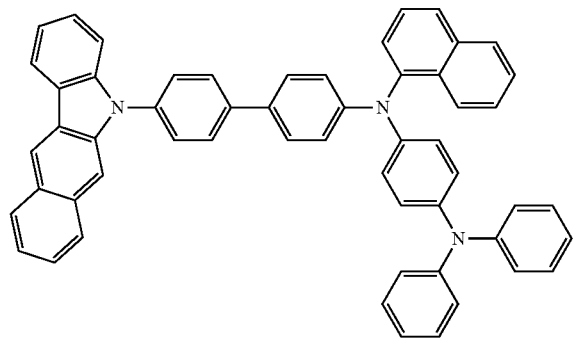
7-19
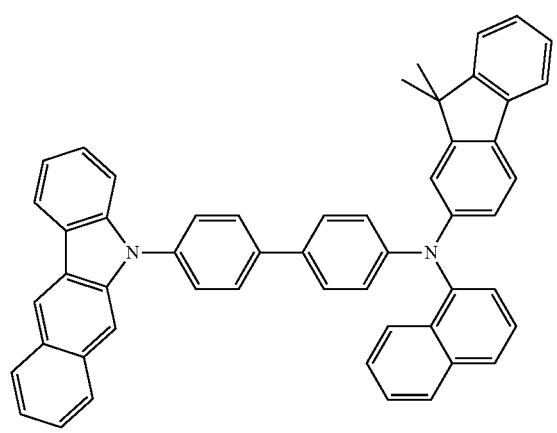
7-20
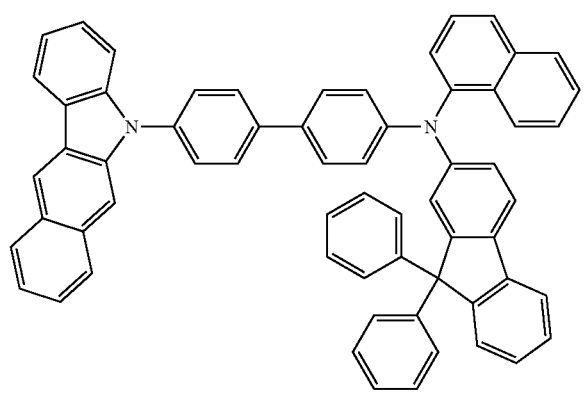
7-21
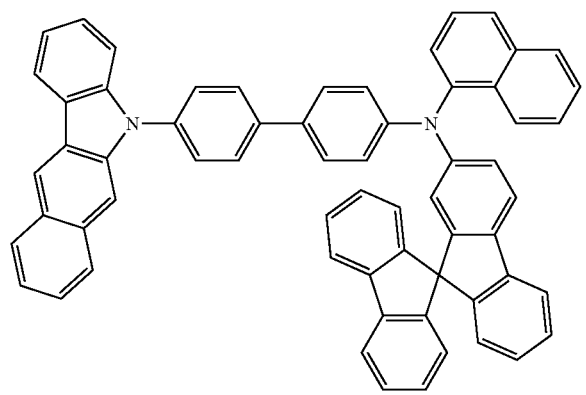
7-22
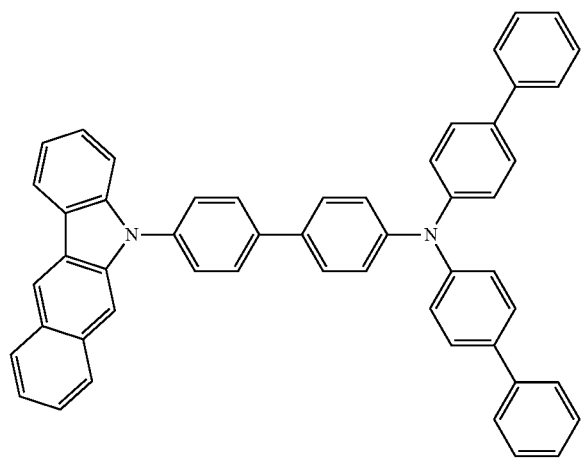

-continued
7-23
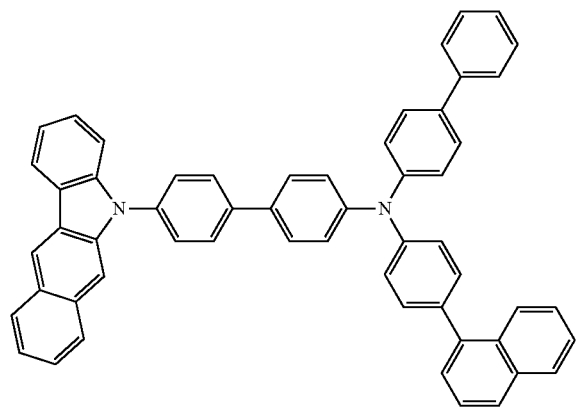
7-24
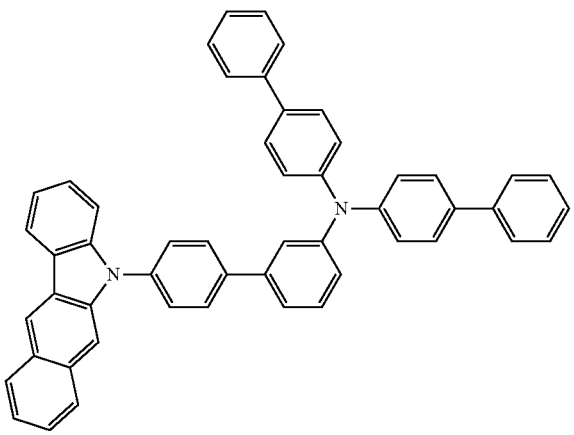
7-25
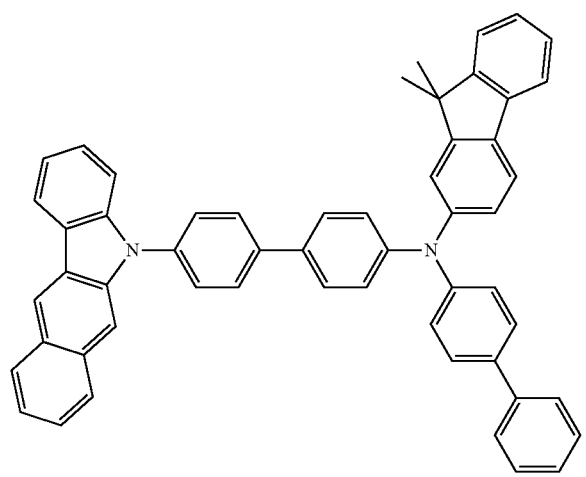
7-26
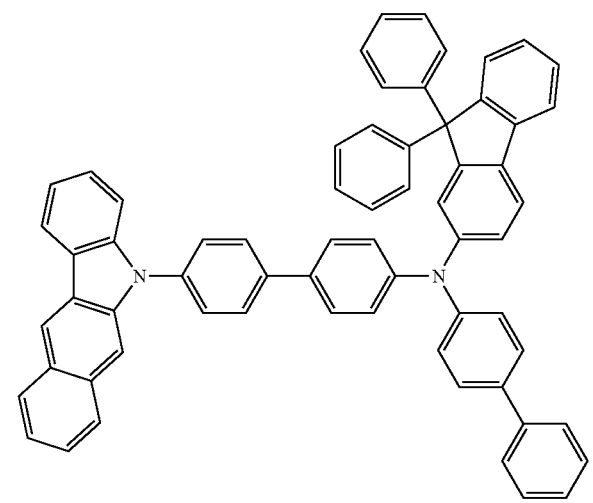
7-27
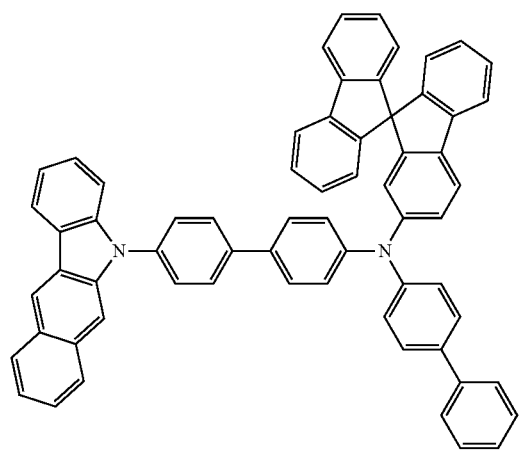
7-28
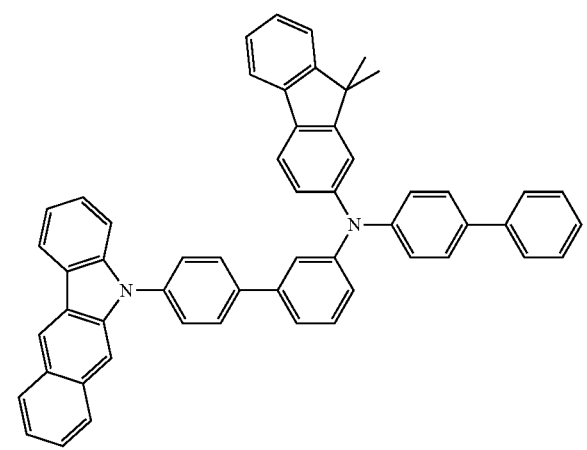

-continued
7-29
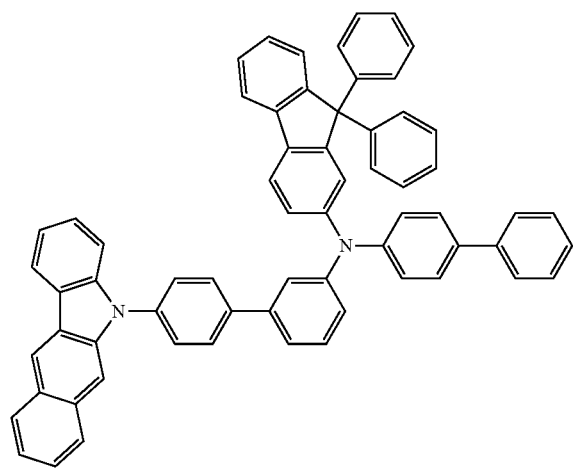
7-30
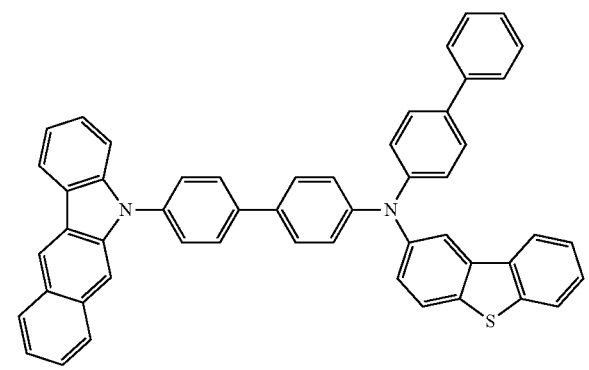
7-31
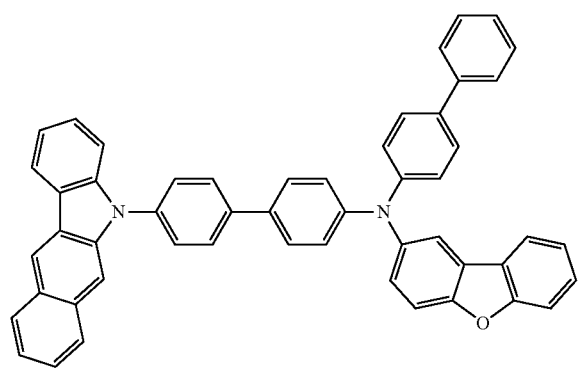
7-32
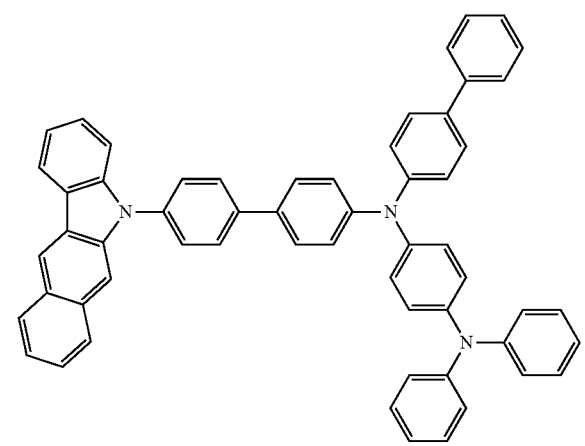
7-33
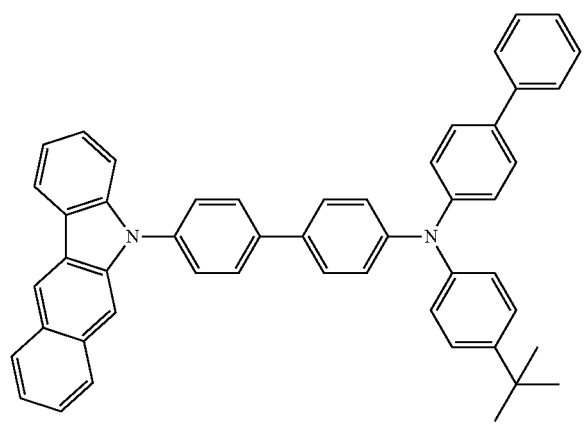

-continued
7-34
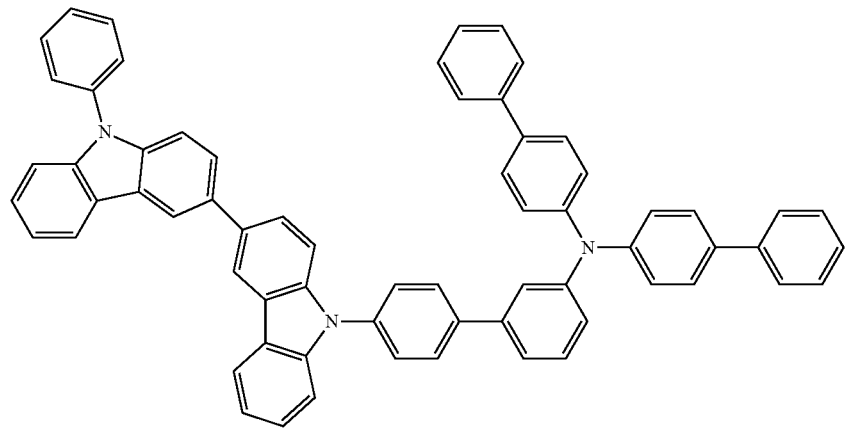
7-35
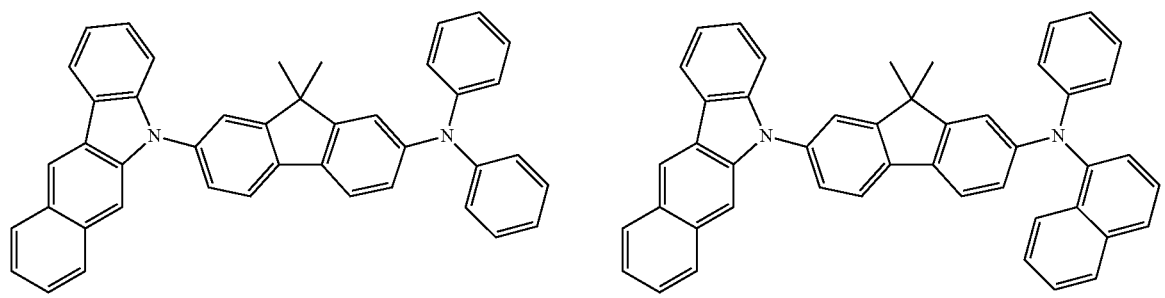
7-36
7-37
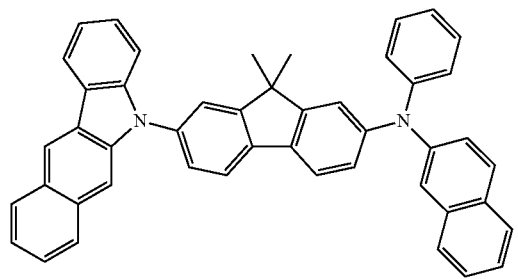
7-38
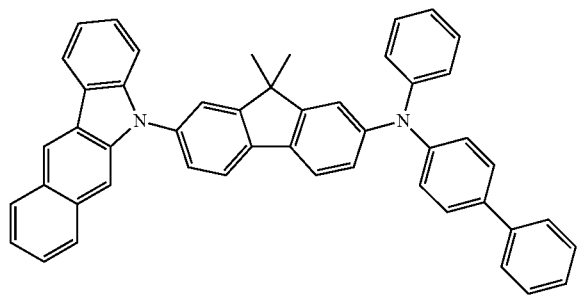
7-39
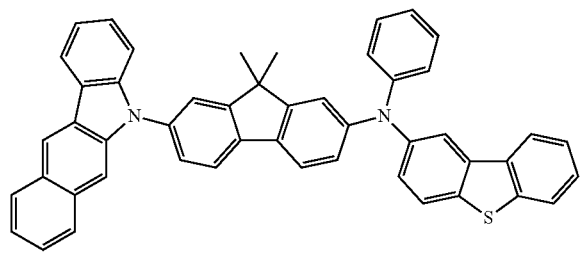
7-40
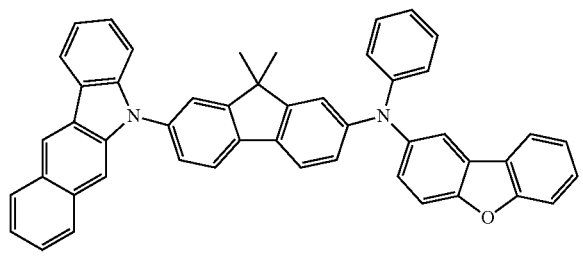

-continued
7-41 7-42
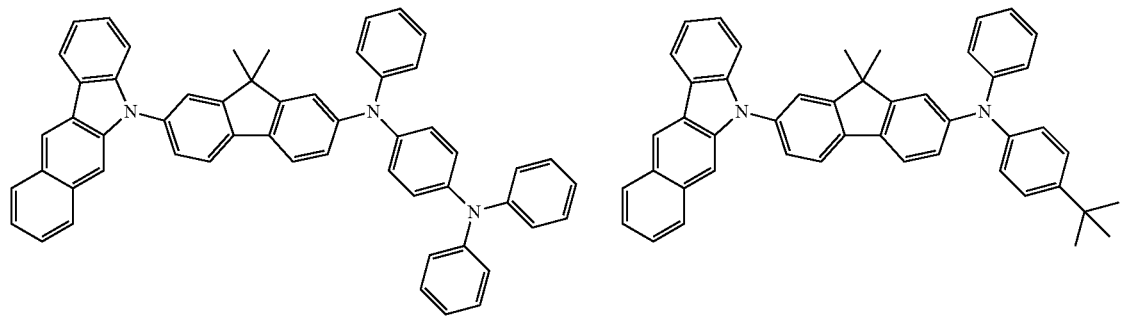
7-43 7-44
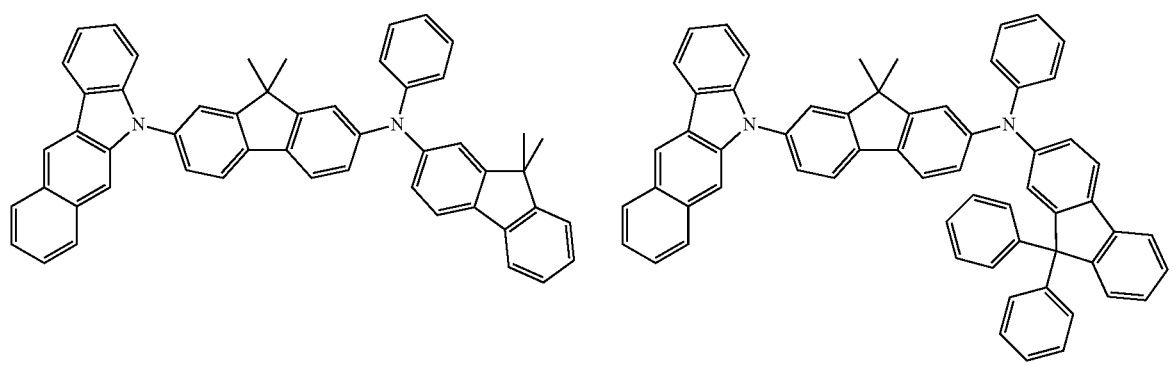
7-45 7-46
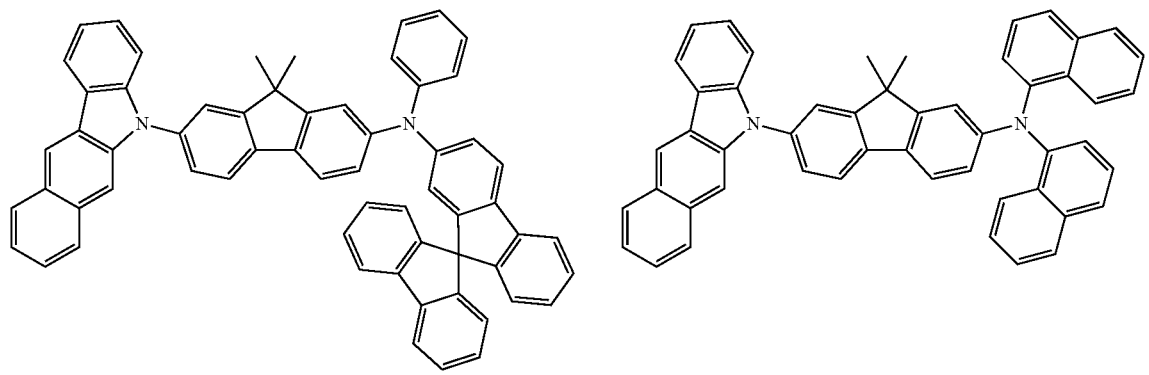
7-47 7-48
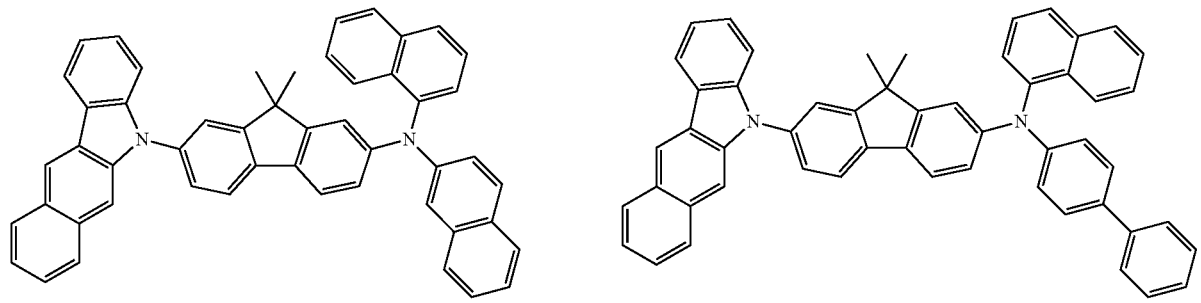

-continued
7-49
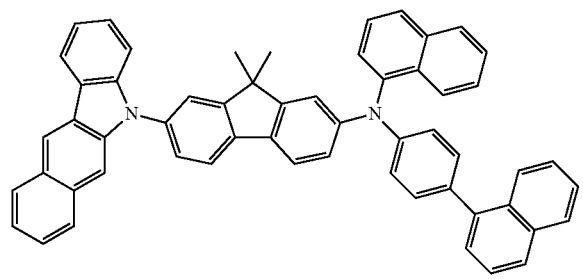
7-50
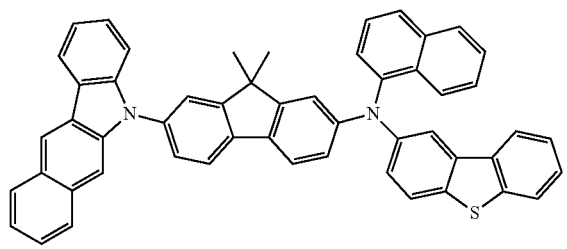
7-51
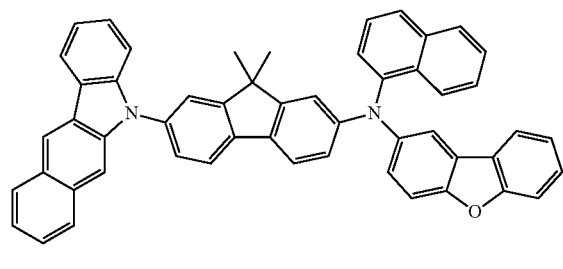
7-52
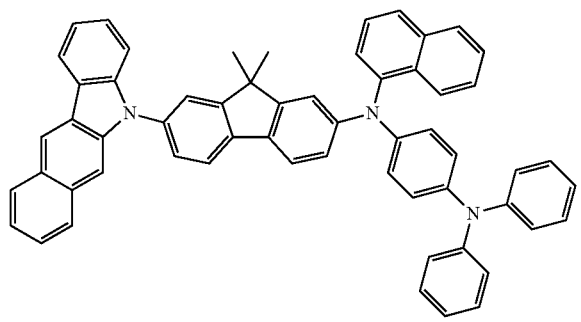
7-53
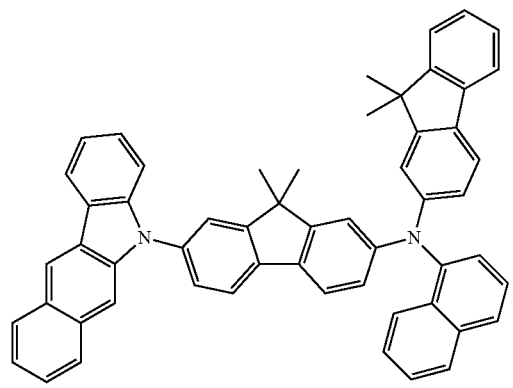
7-54
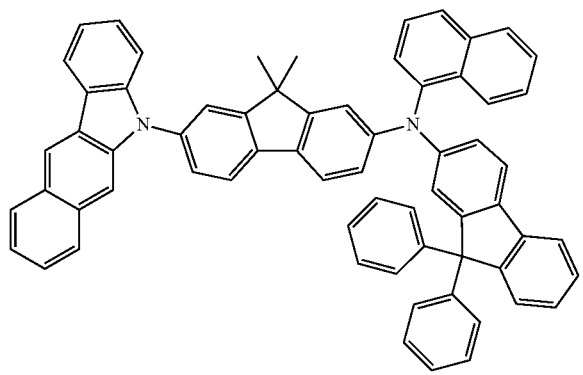
7-55
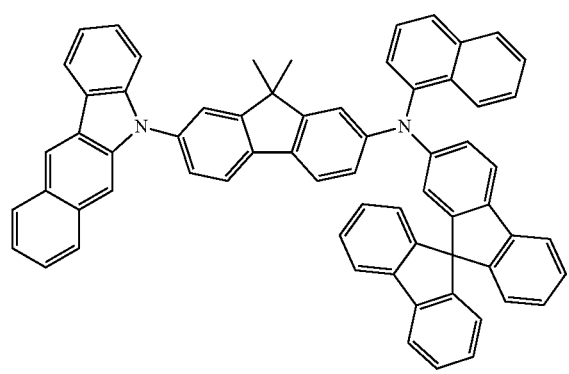
7-56
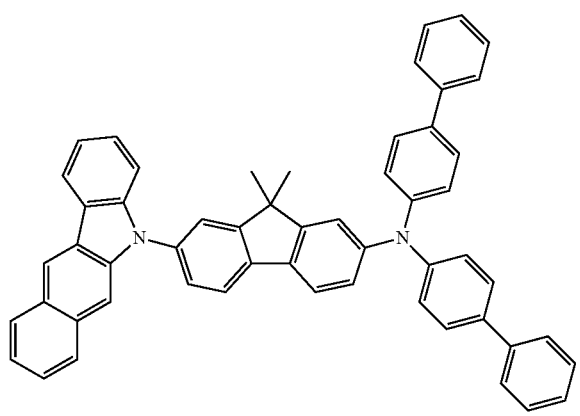

-continued
7-57
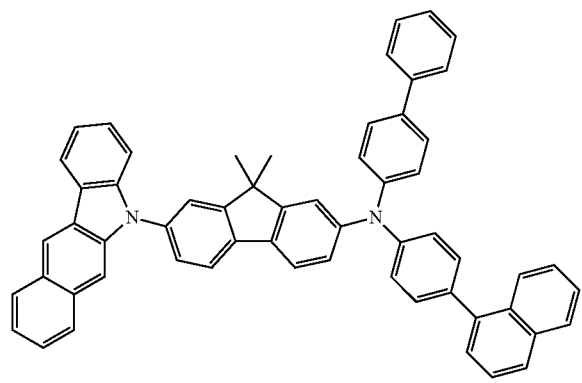
7-58
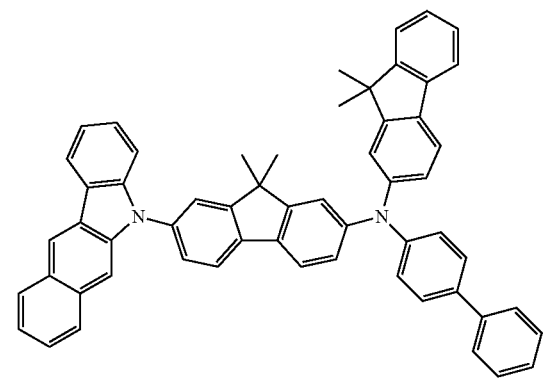
7-59
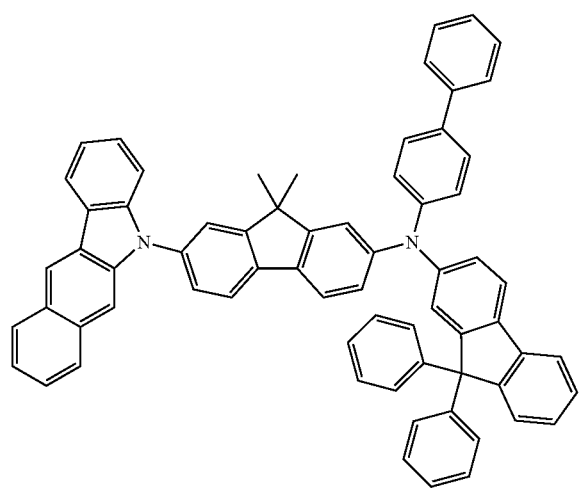
7-60
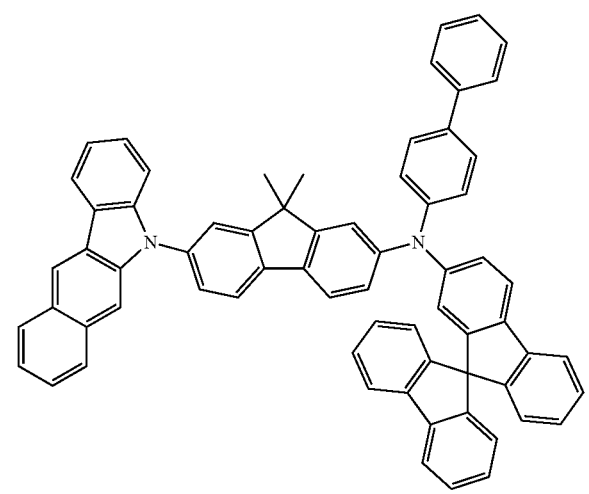
7-61
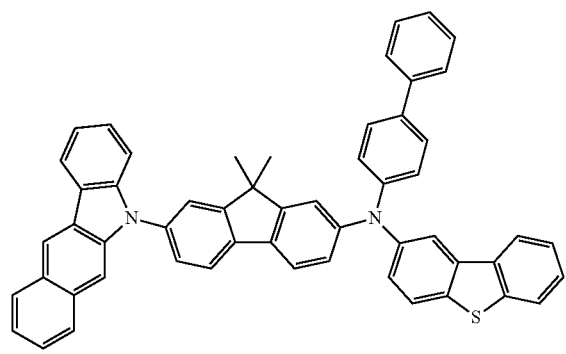
7-62
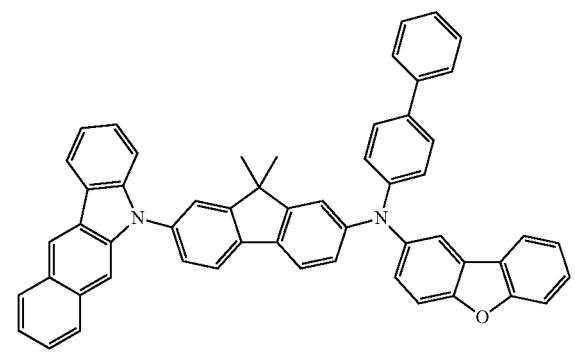

-continued
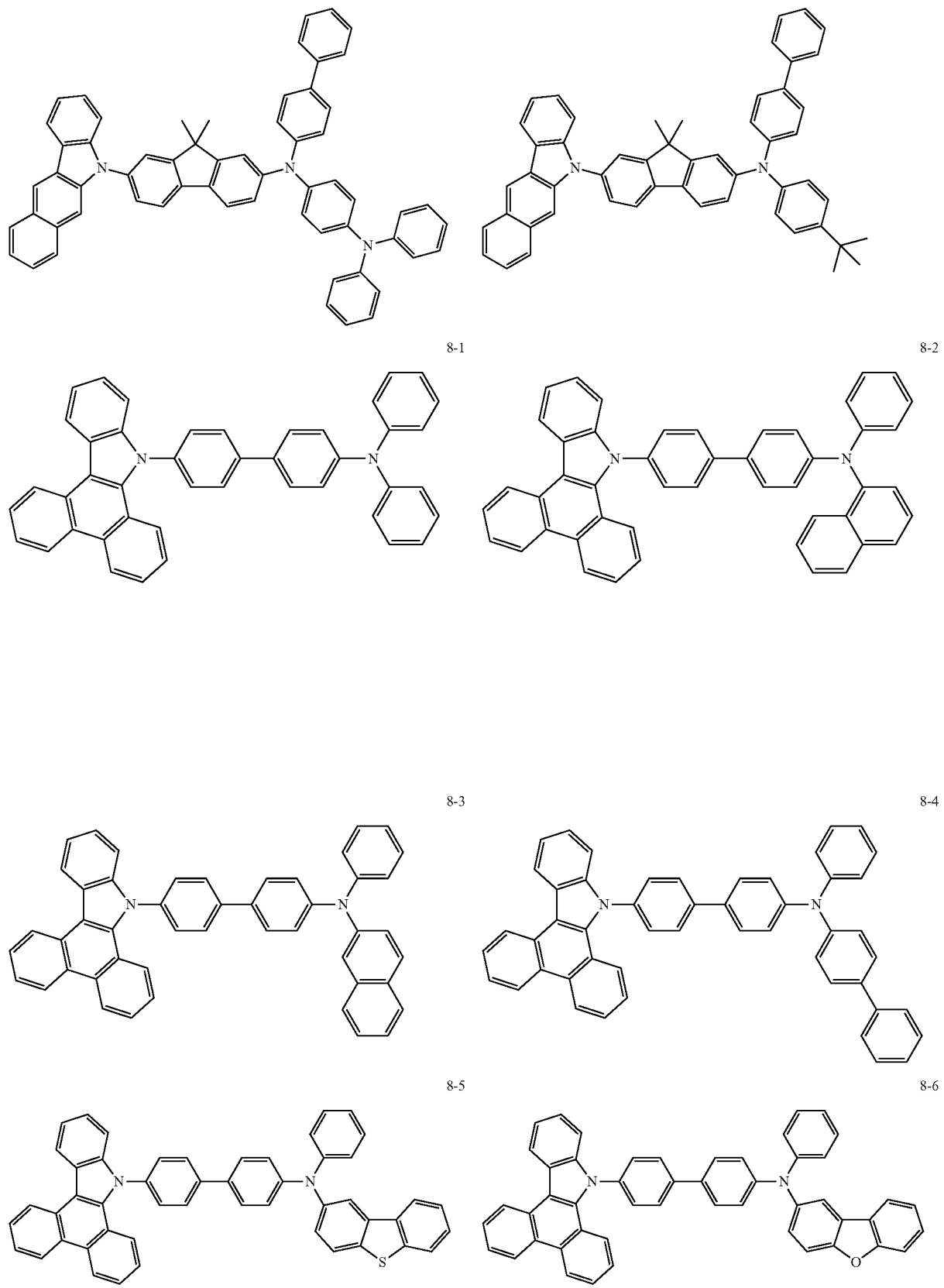

-continued
8-7
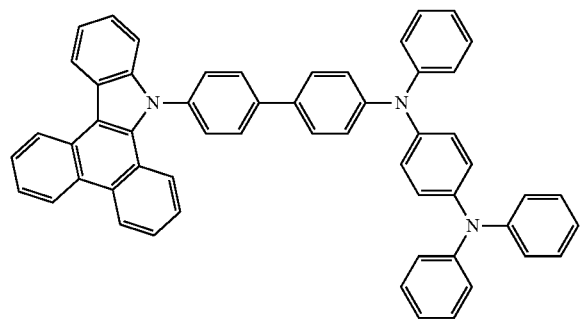
8-8
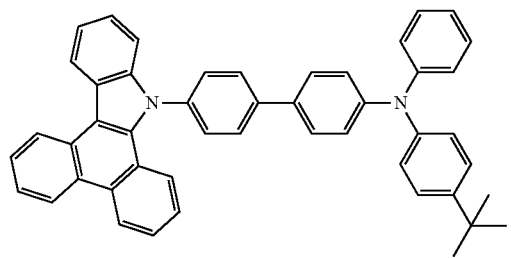
8-9
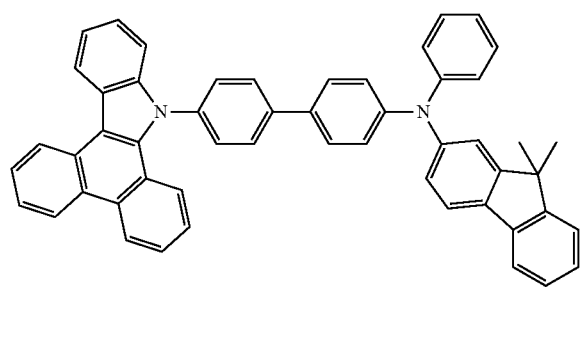
8-10
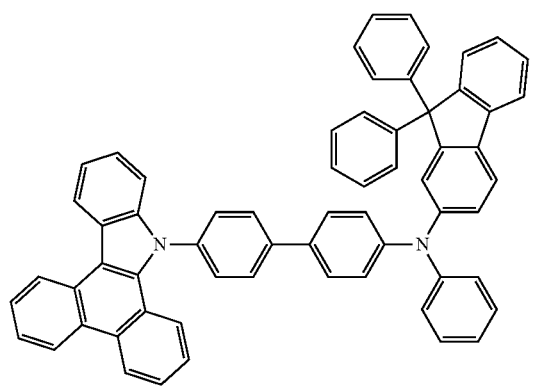
8-11
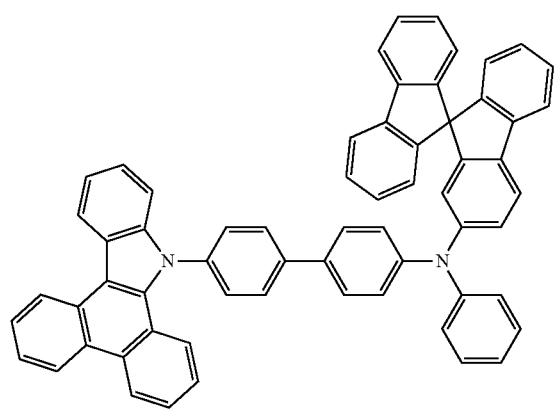
8-12
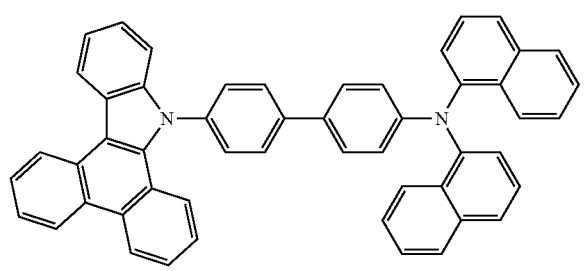
8-13
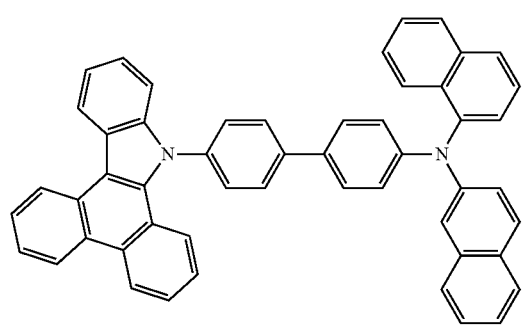
8-14
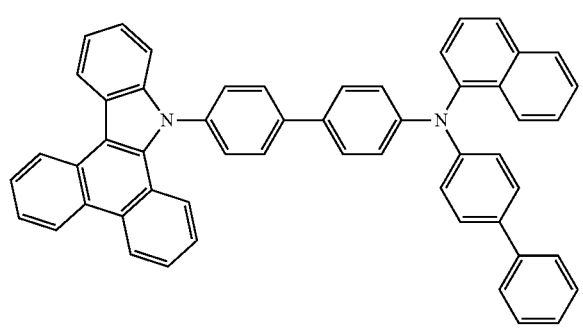

-continued
8-15
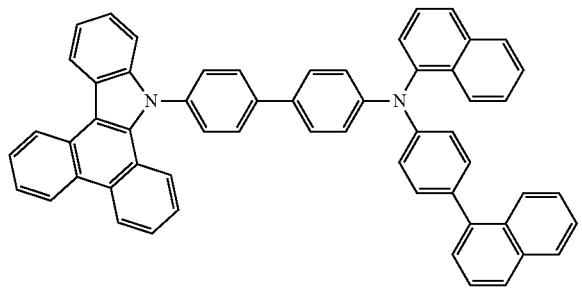
8-16
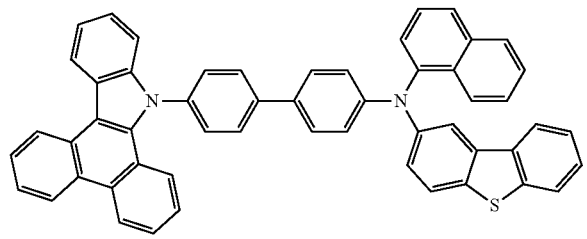
8-17
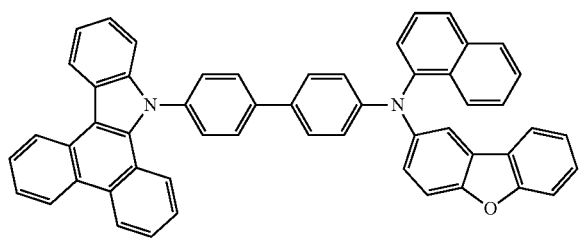
8-18
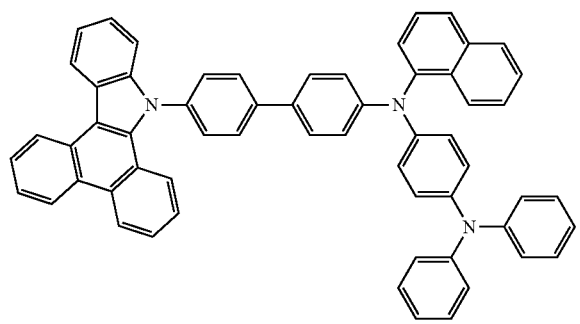
8-19
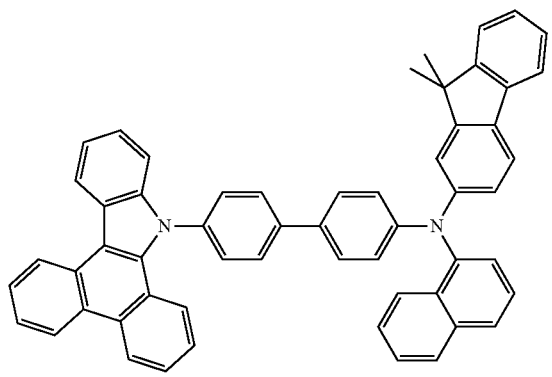
8-20
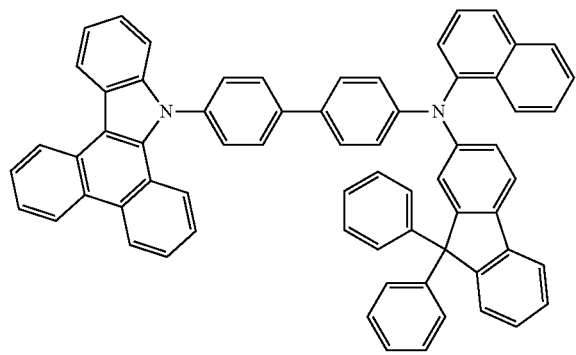
8-21
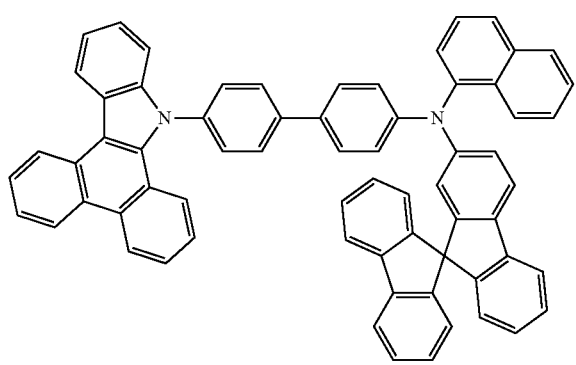
8-22
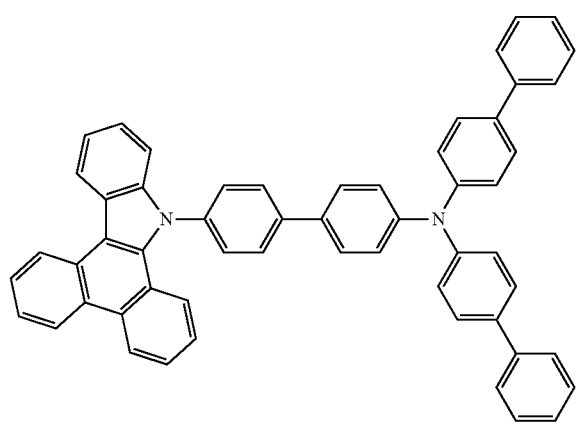

-continued
8-23
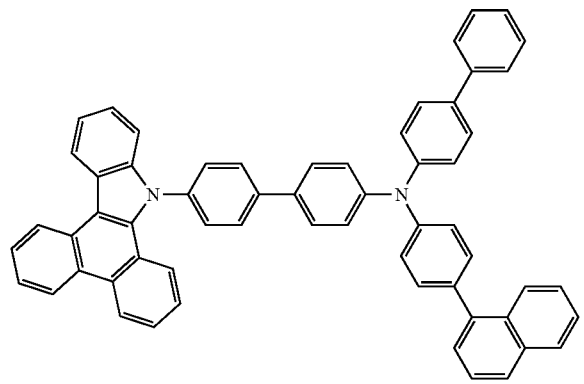
8-24
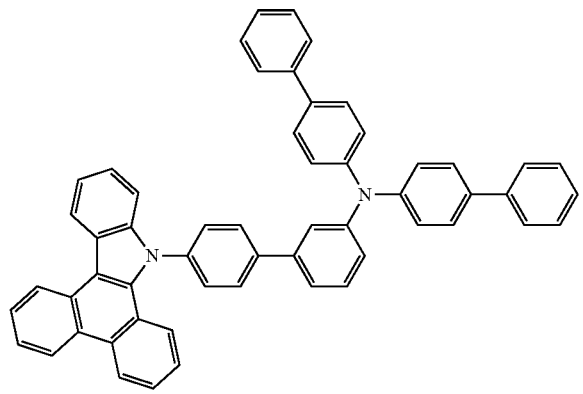
8-25
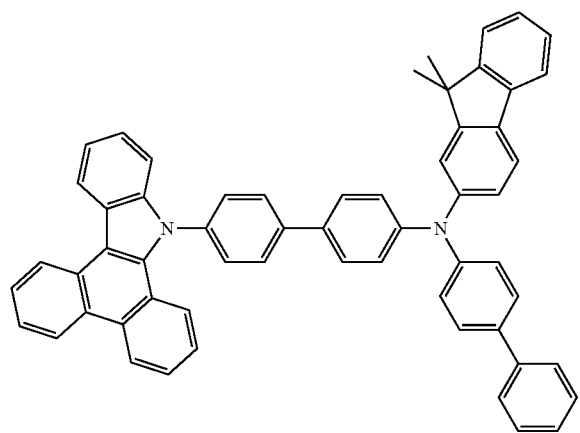
8-26
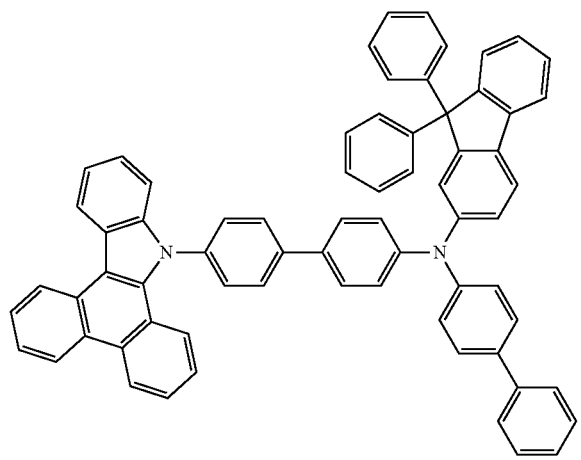
8-27
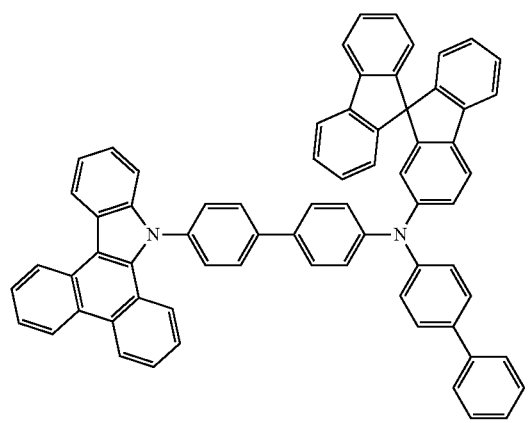
8-28
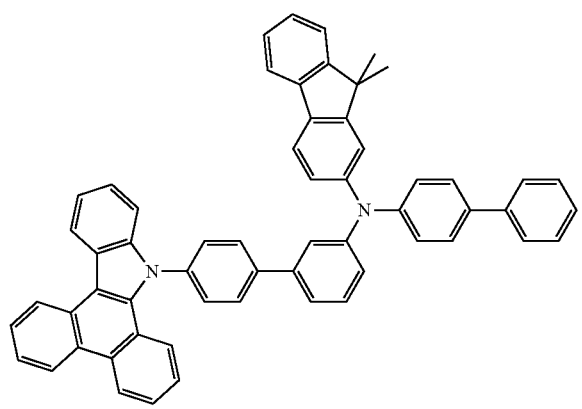

-continued
8-29
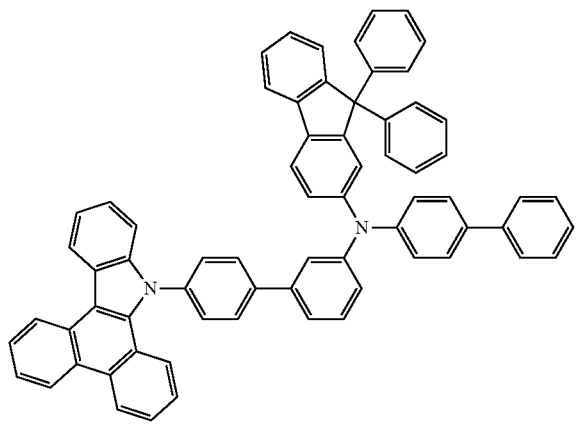
8-30
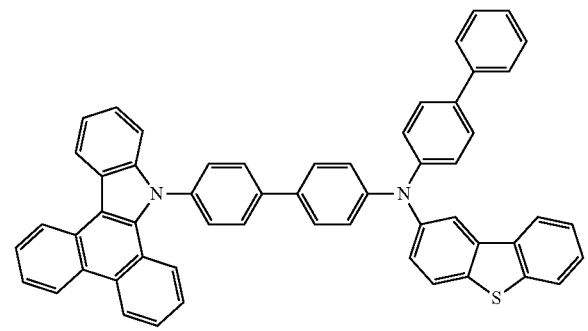
8-31
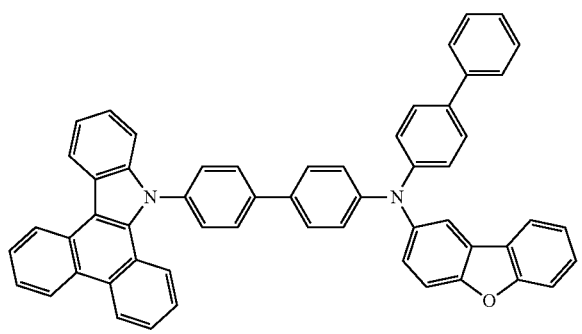
8-32
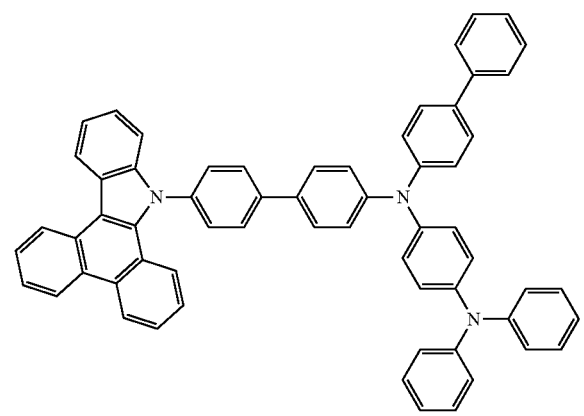
8-33
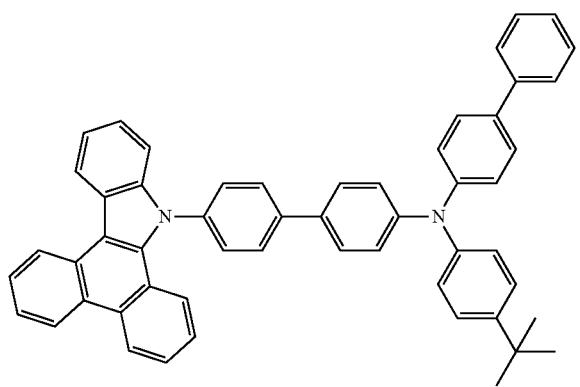
8-34
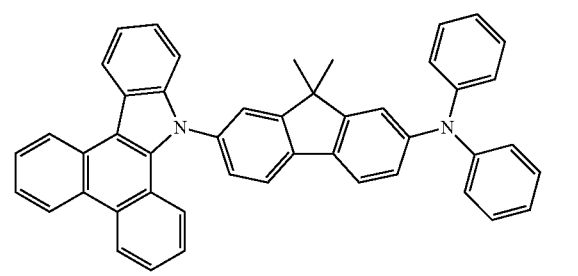
8-35
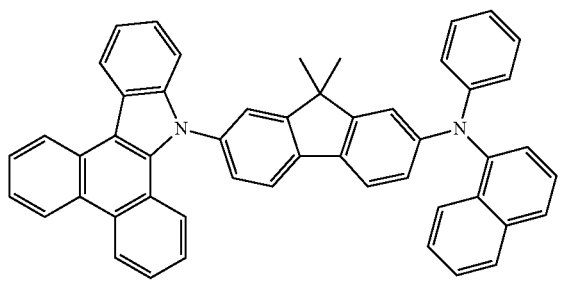
8-36
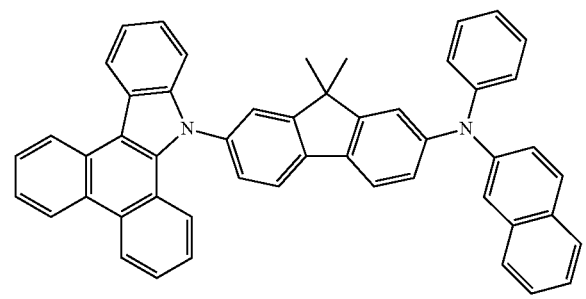

-continued
8-37
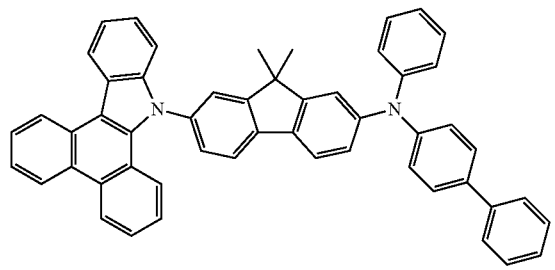
8-38
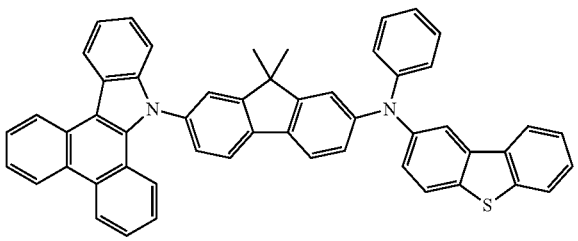
8-39
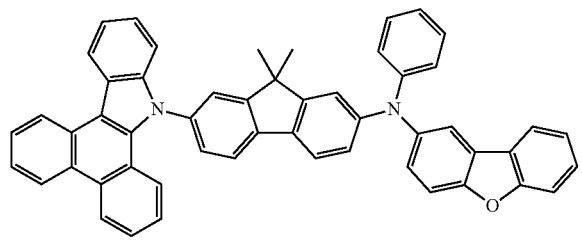
8-40
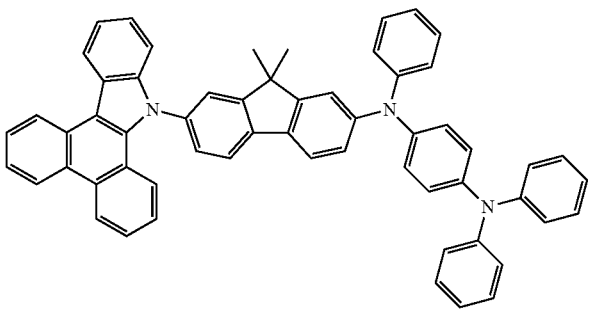
8-41
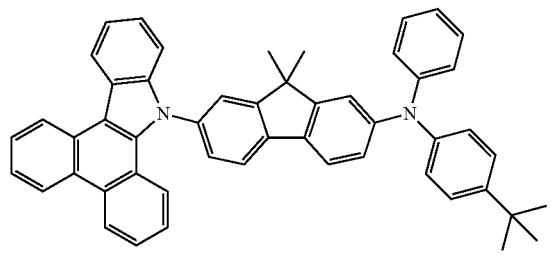
8-42
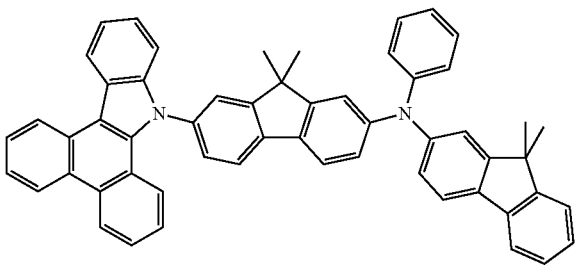
8-43
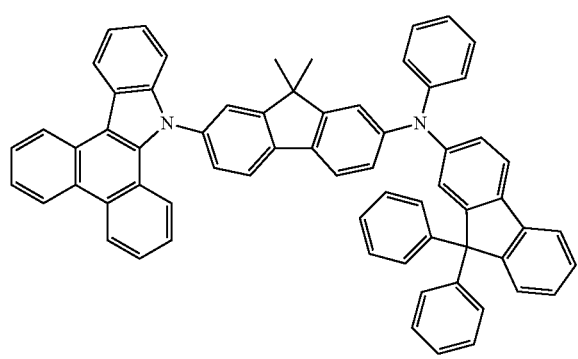
8-44
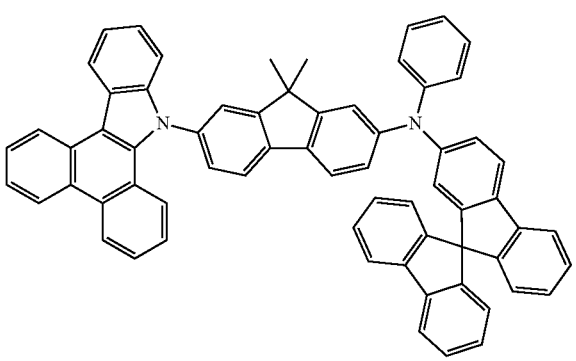
8-45
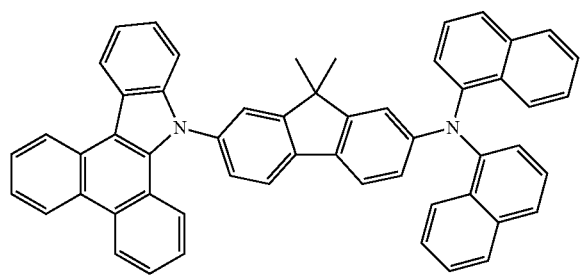
8-46
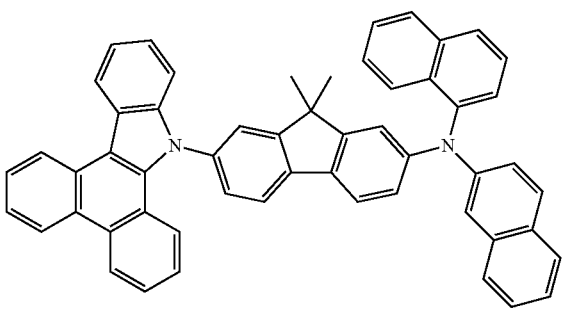

-continued
8-47
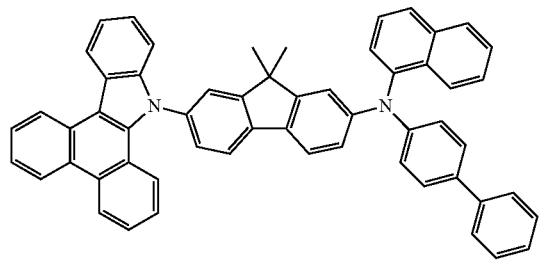
8-48
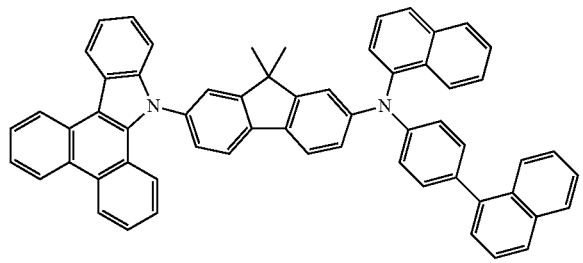
8-49
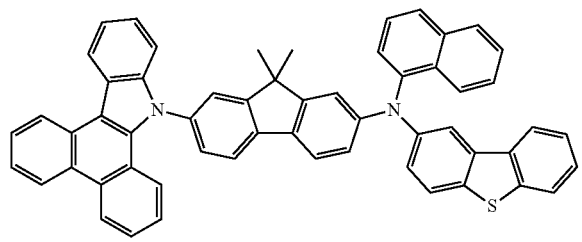
8-50
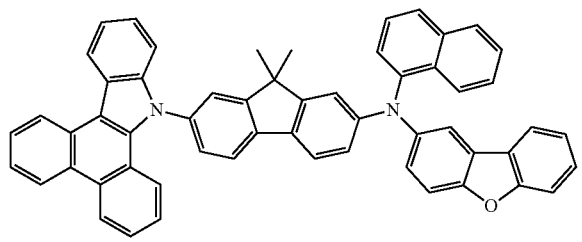
8-51
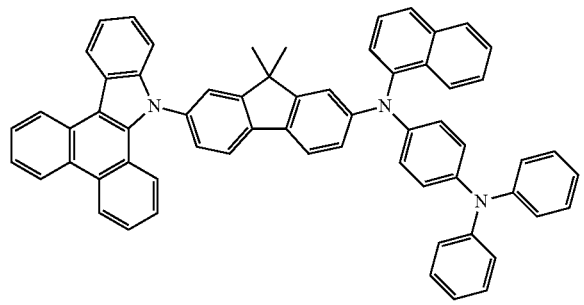
8-52
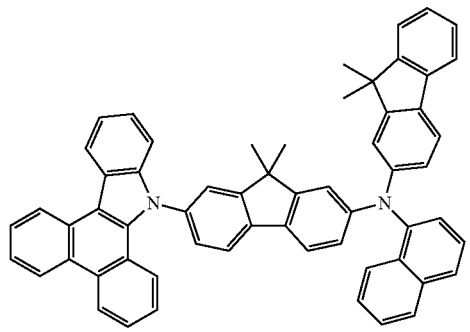
8-53
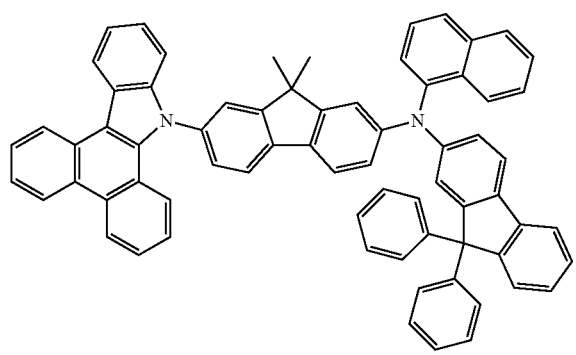
8-54
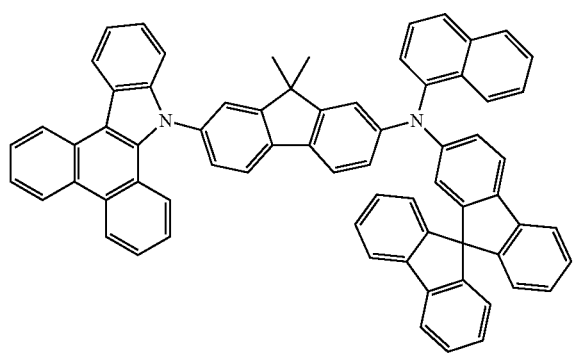

-continued
8-55
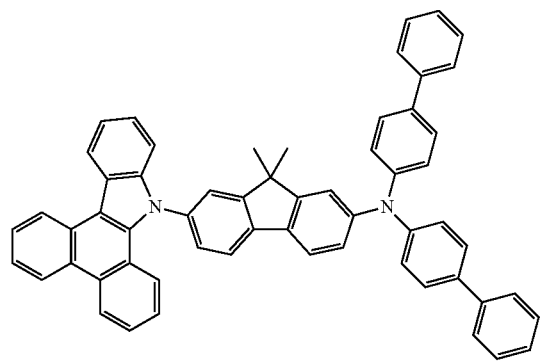
8-56
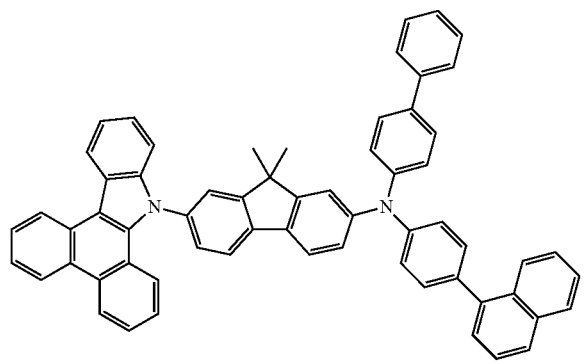
8-57
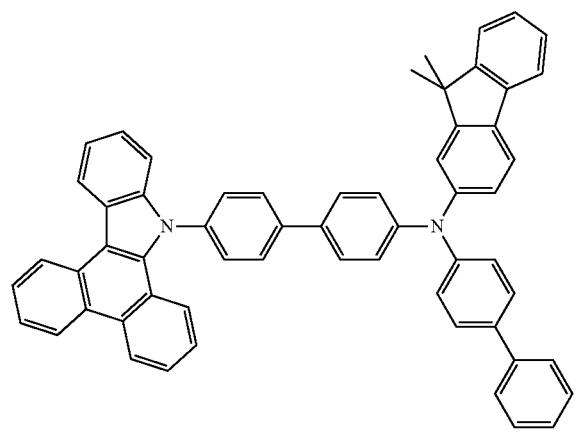
8-58
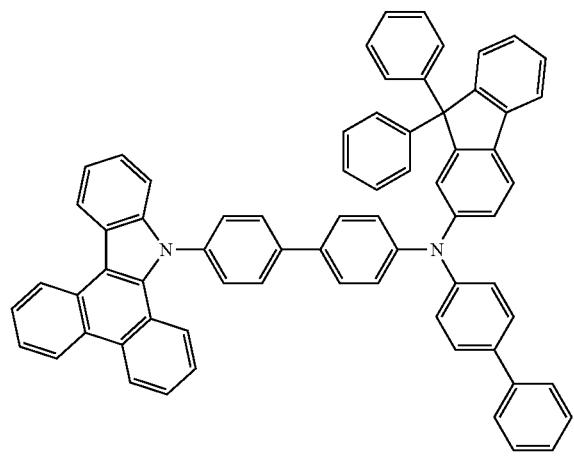
8-59
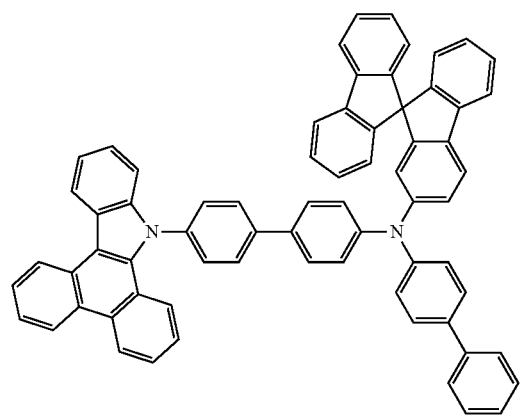
8-60
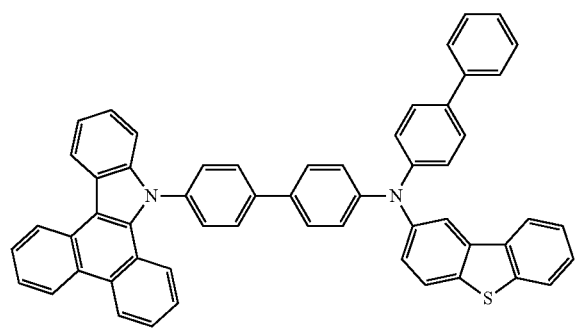

-continued
8-61
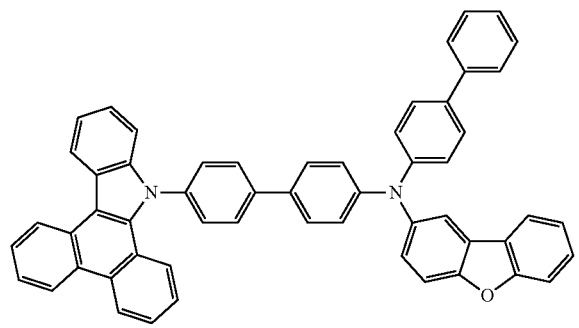
8-62
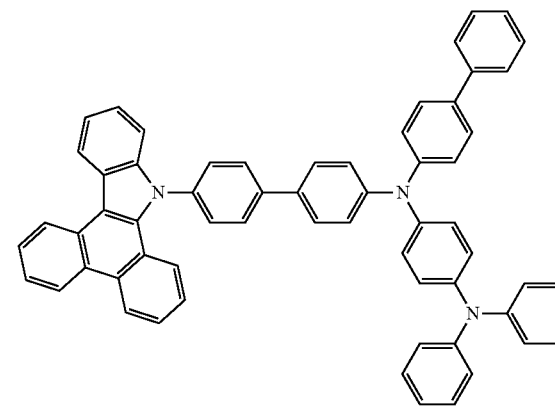
8-63
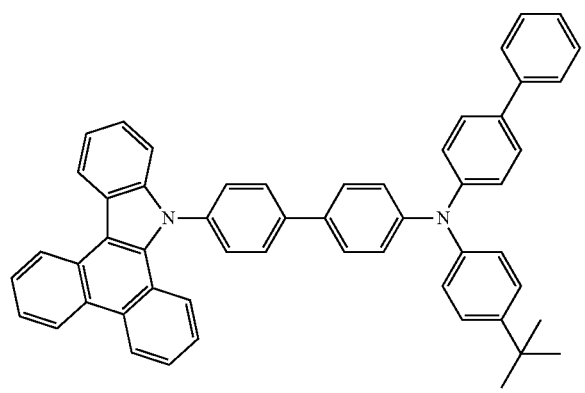
9-1
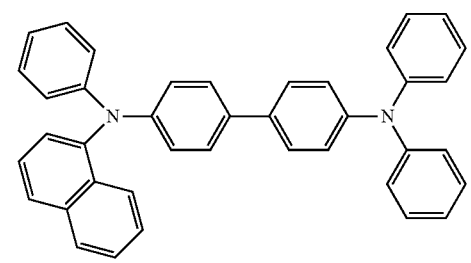
9-2
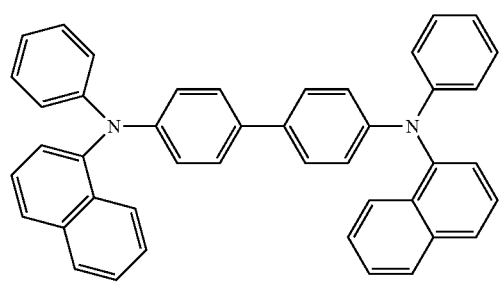
9-3
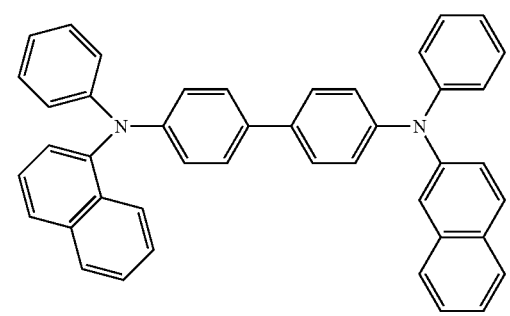
9-4
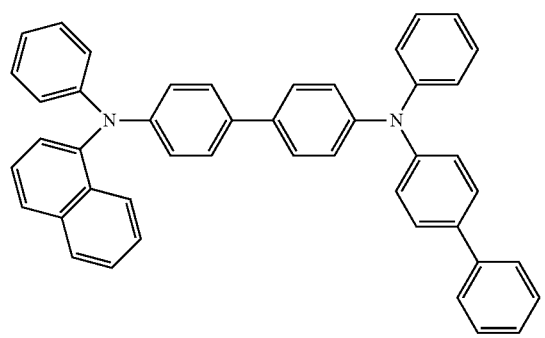
9-5
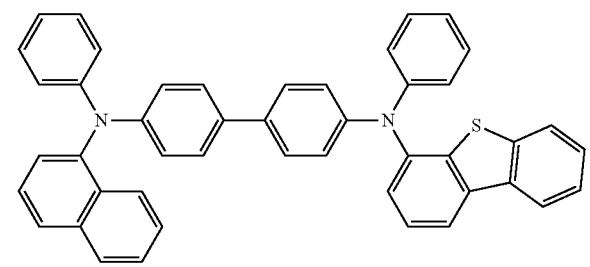

-continued
9-6
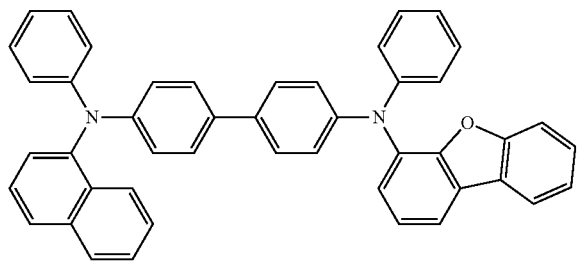
9-7
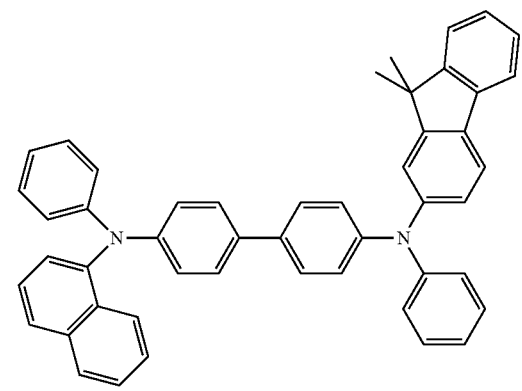
9-8
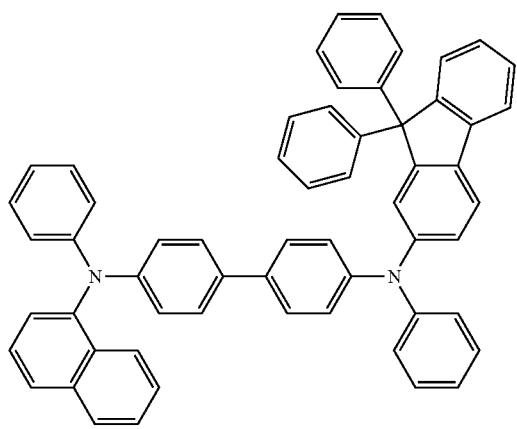
9-9
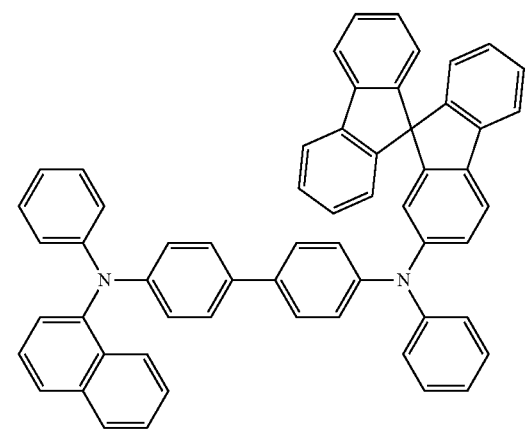
9-10
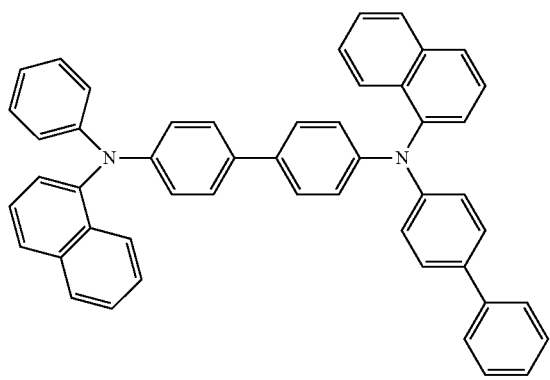
9-11
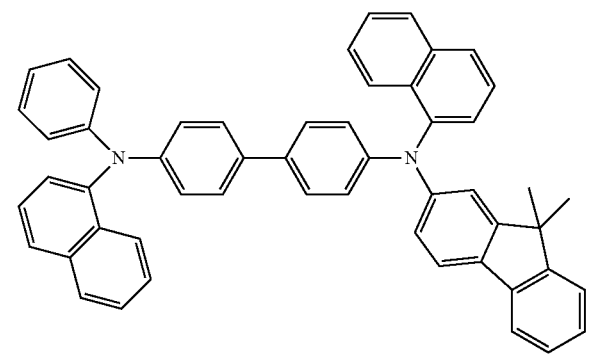
9-12
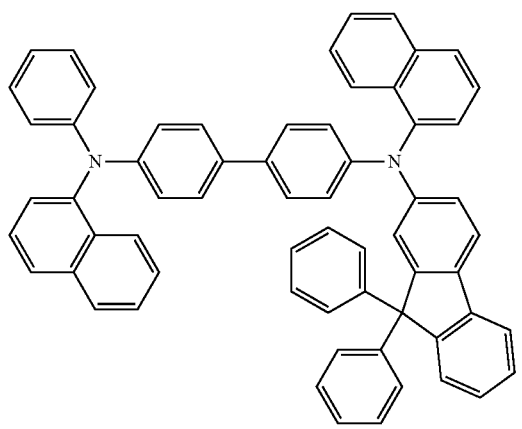
9-13
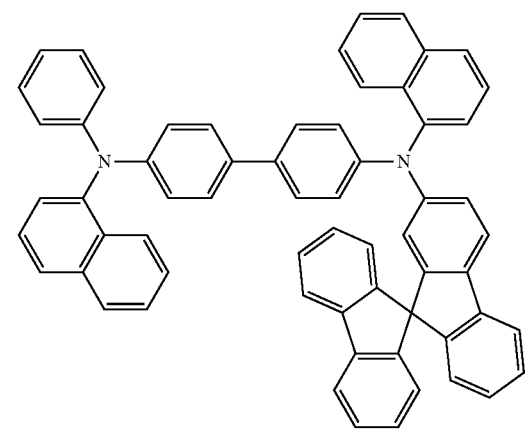

-continued
9-14
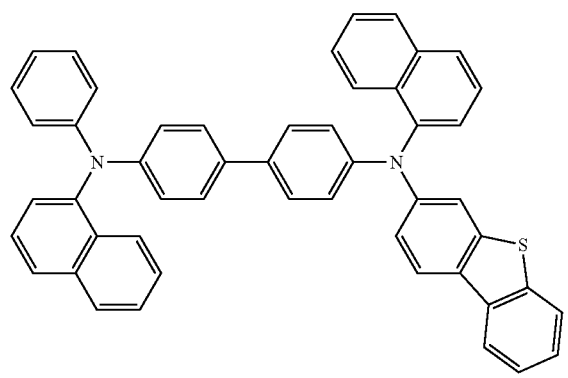
9-15
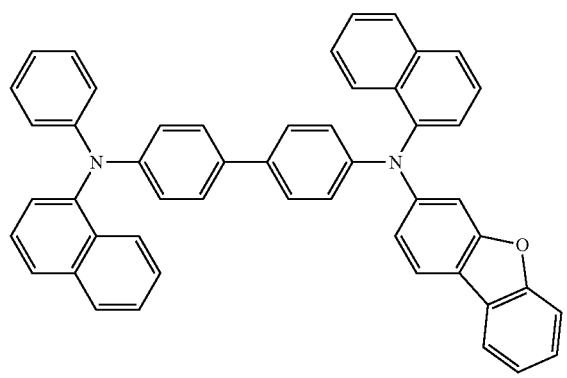
9-16
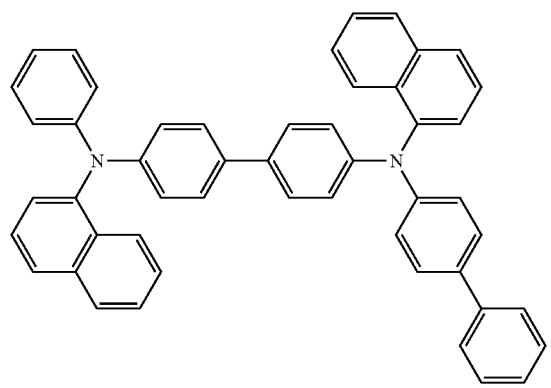
9-17
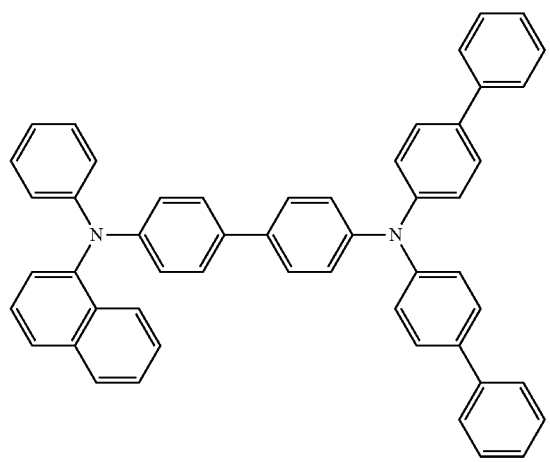
9-18
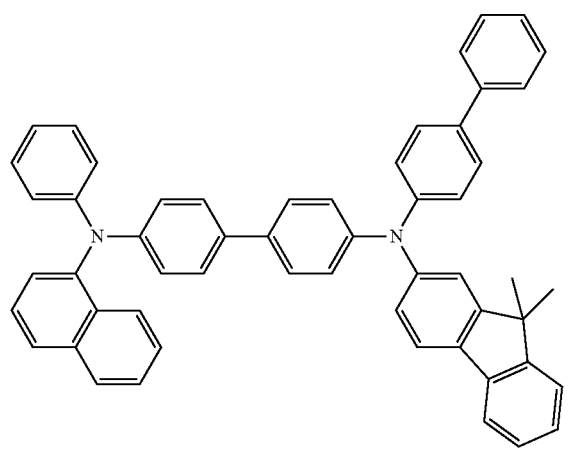
9-19
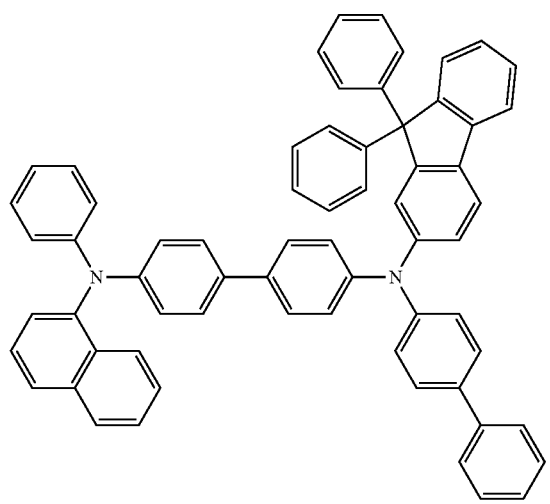

-continued
9-20
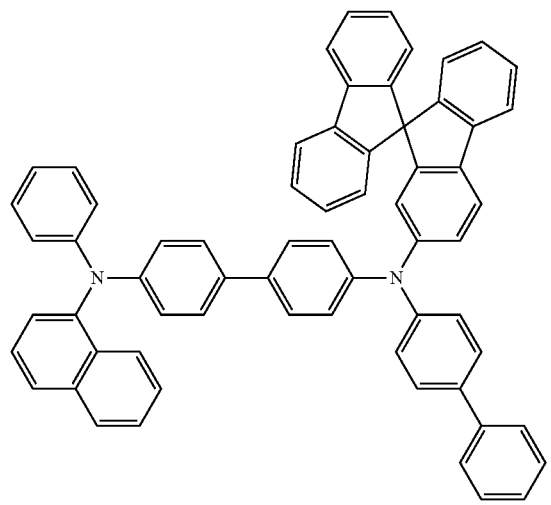
9-21
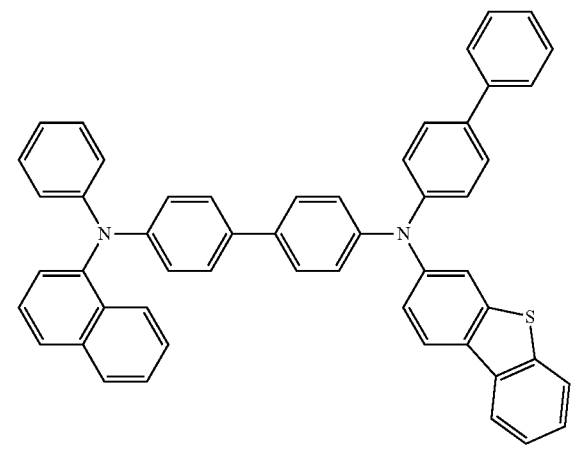
9-22
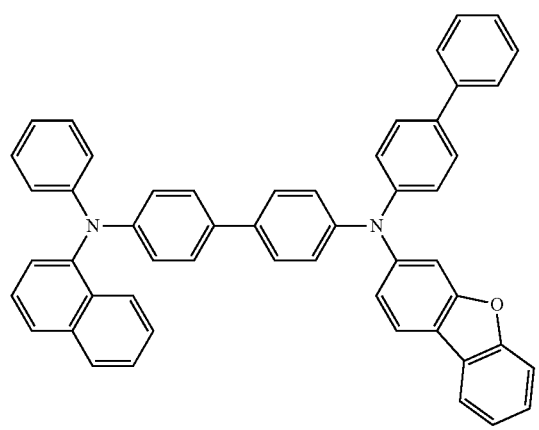
9-23
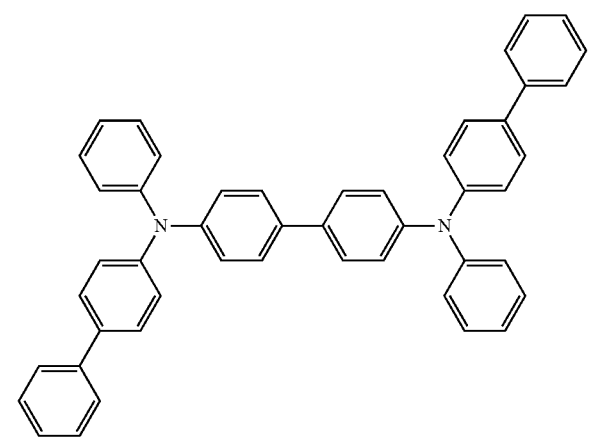
9-24
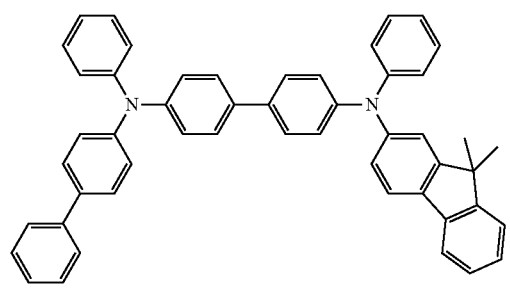
9-25
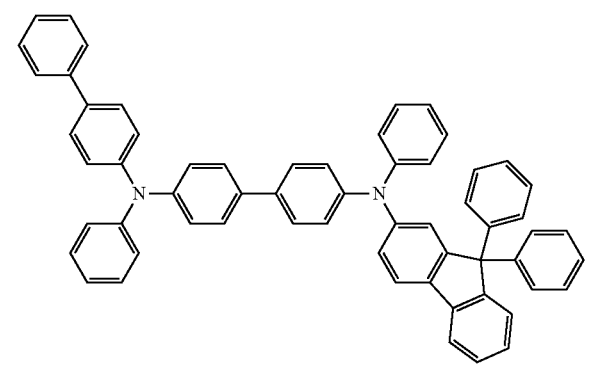

-continued
9-26
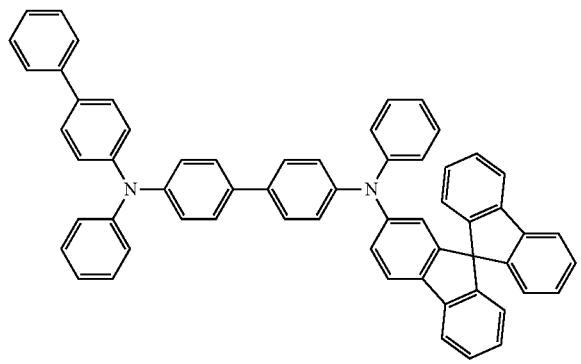
9-27
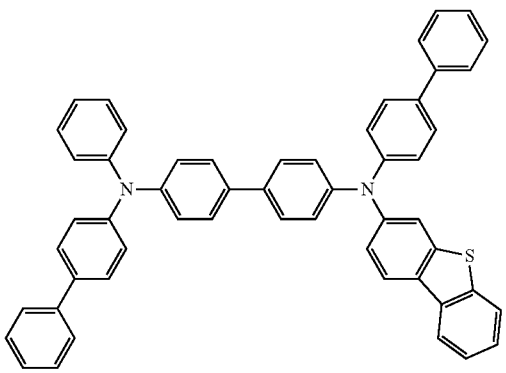
9-28
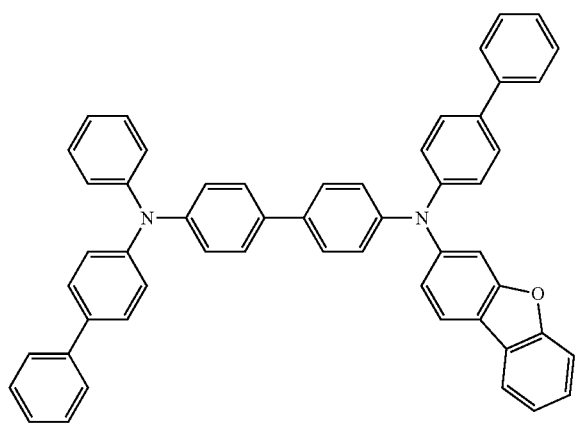
9-29
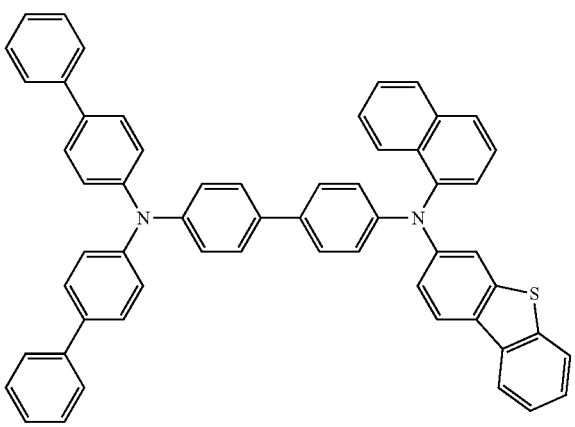
9-30
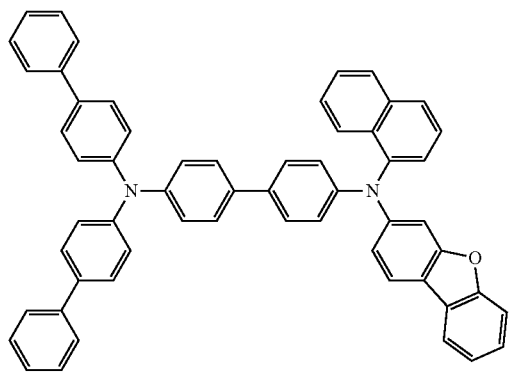
9-31
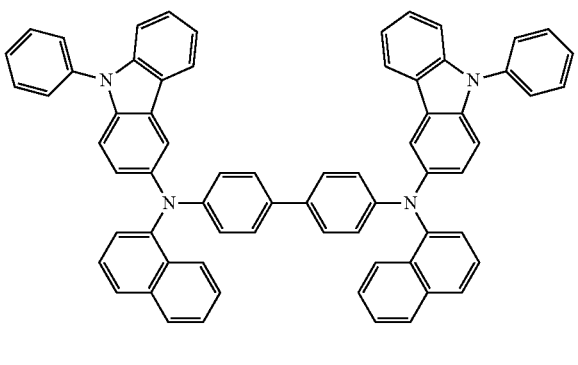
9-32
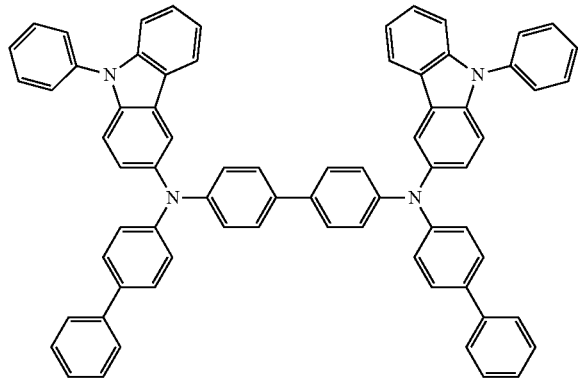
9-33
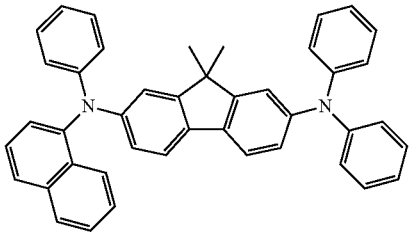

-continued
9-34
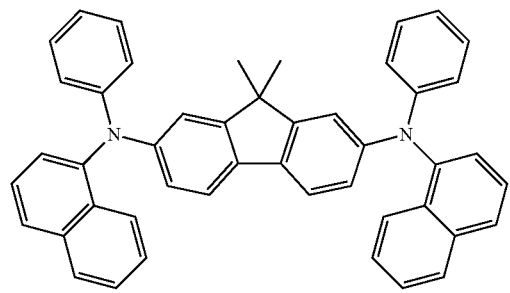
9-35
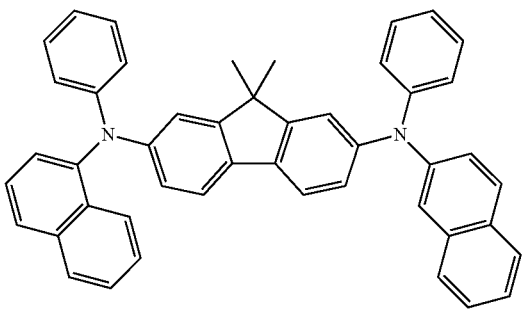
9-36
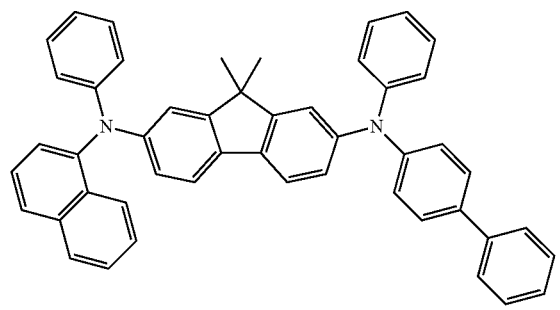
9-37
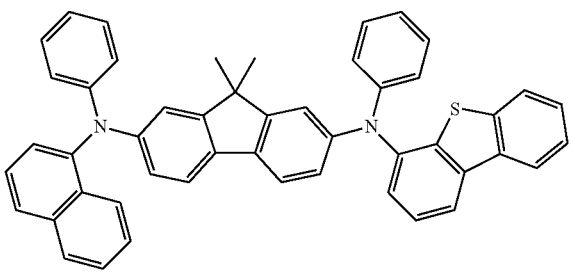
9-38
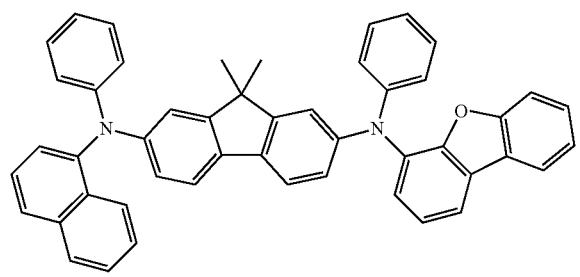
9-39
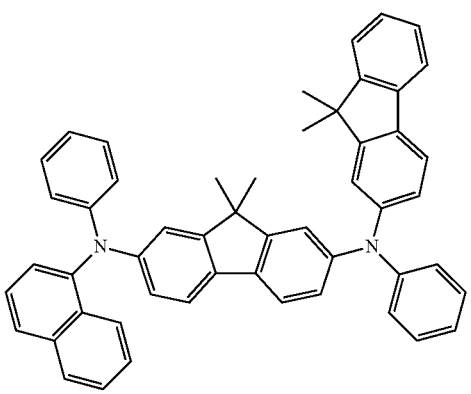
9-40
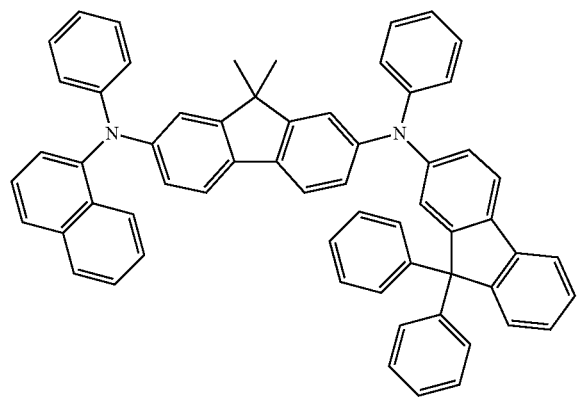
9-41
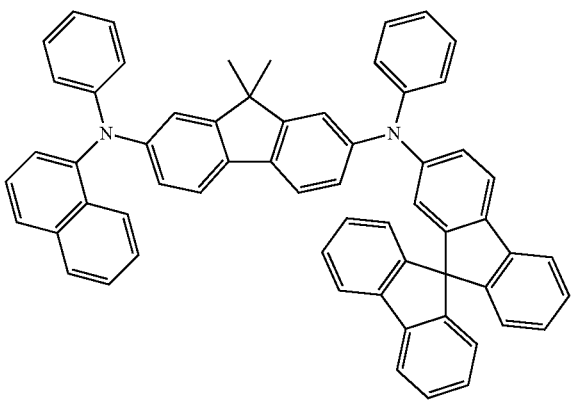

-continued
9-42
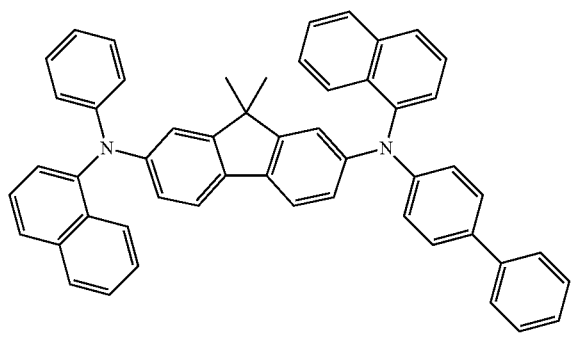
9-43
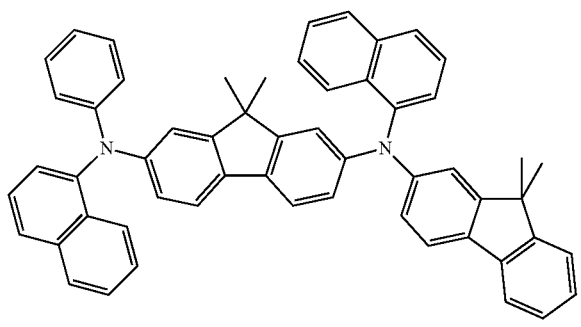
9-44
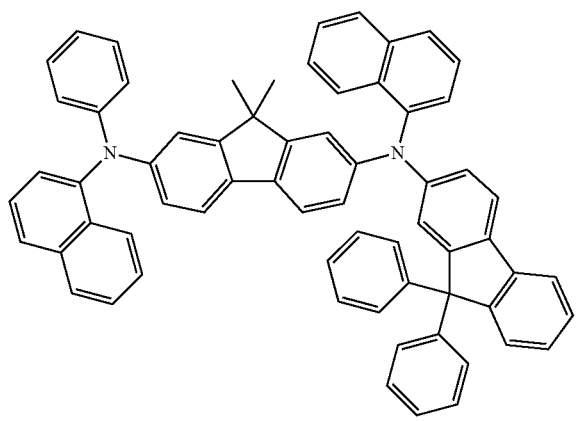
9-45
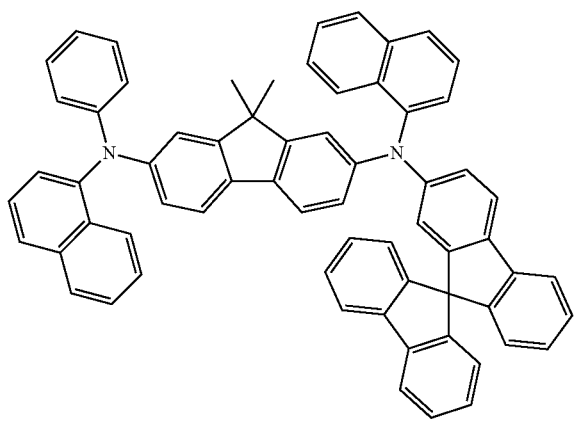
9-46
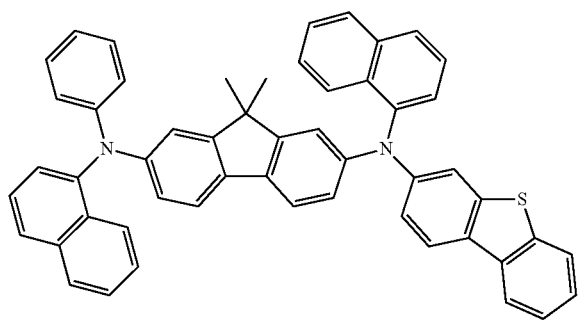
9-47
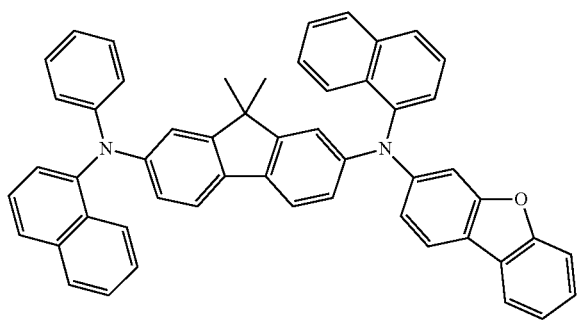
9-48
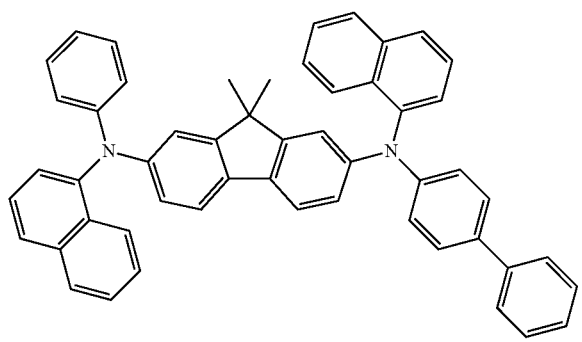
9-49
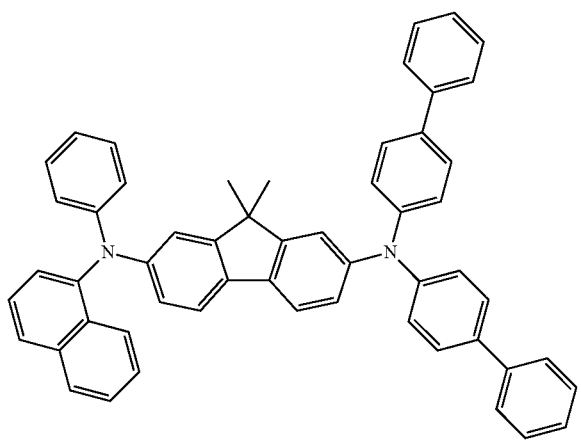

-continued
9-50
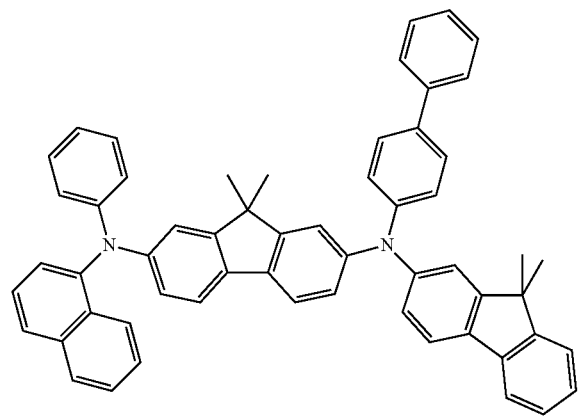
9-51
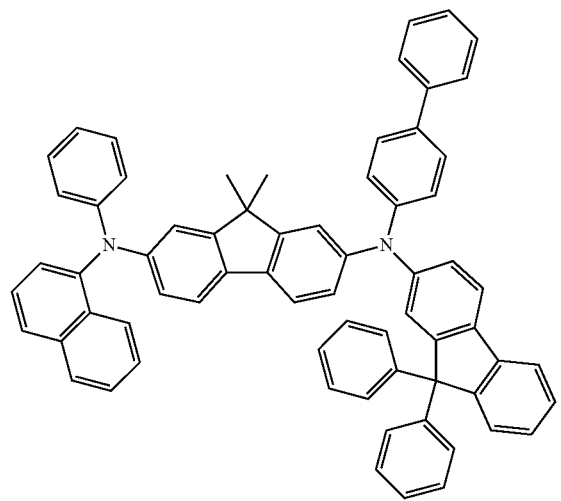
9-52
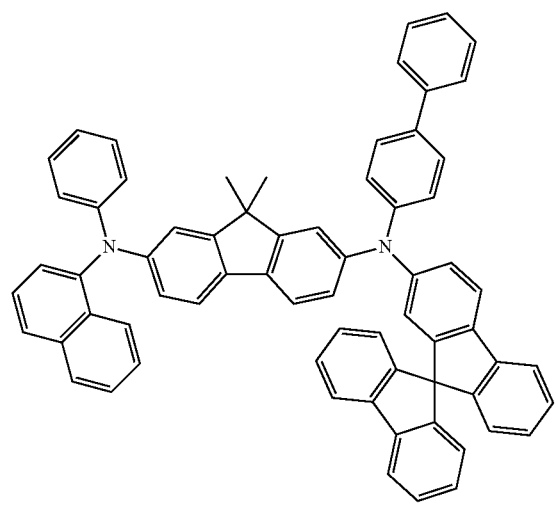
9-53
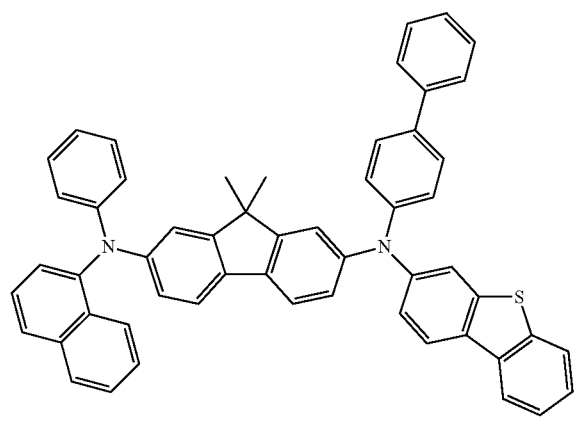
9-54
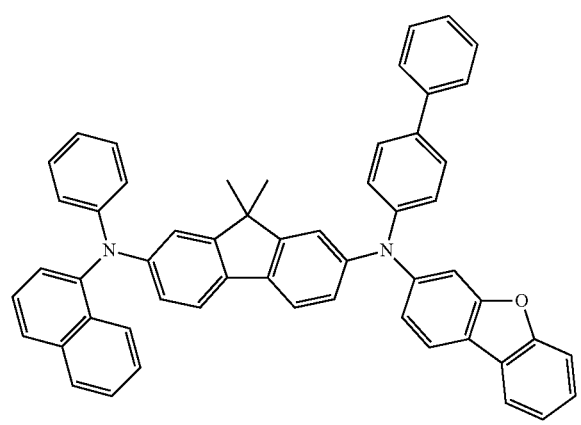
9-55
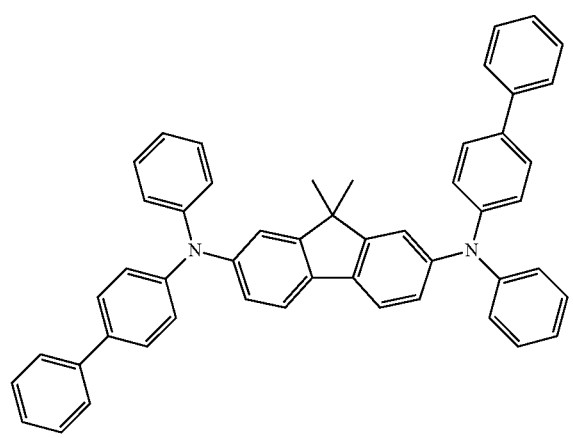

-continued
9-56
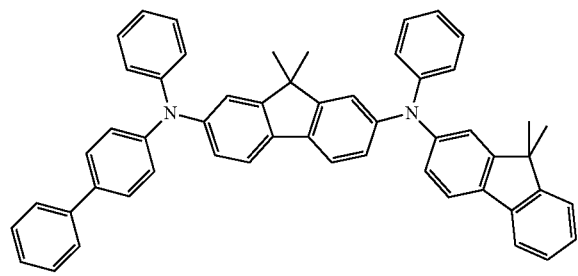
9-57
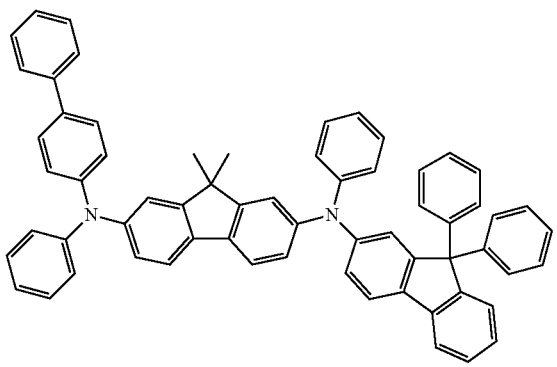
9-58
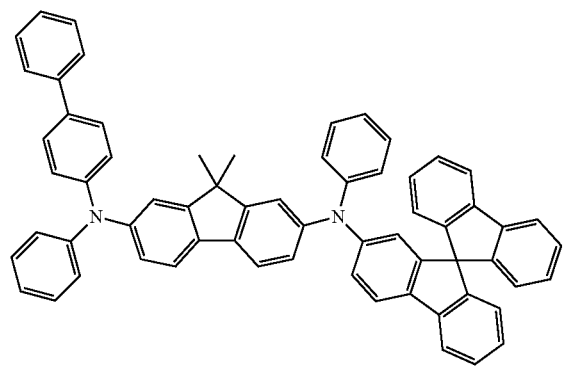
9-59
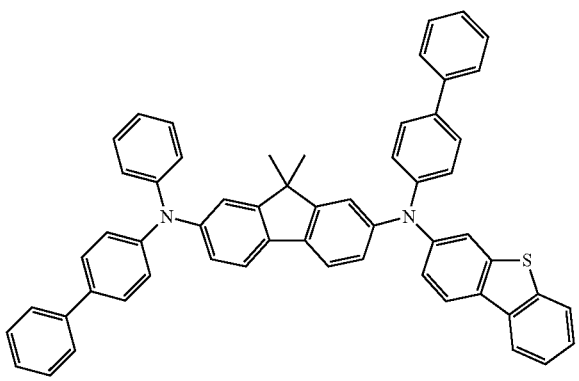
9-60
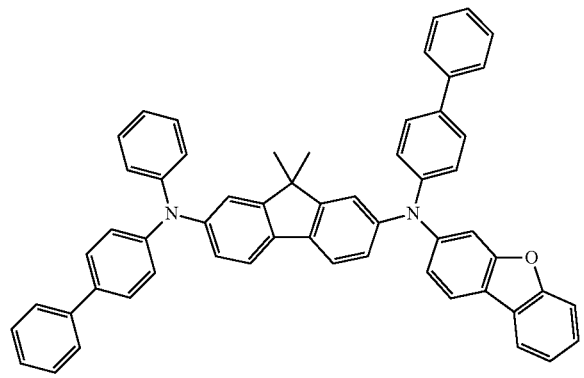
9-61
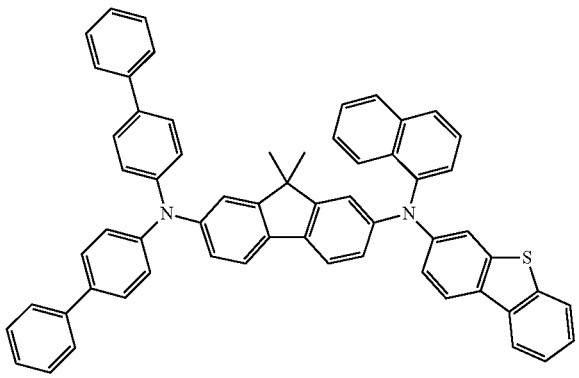
9-62
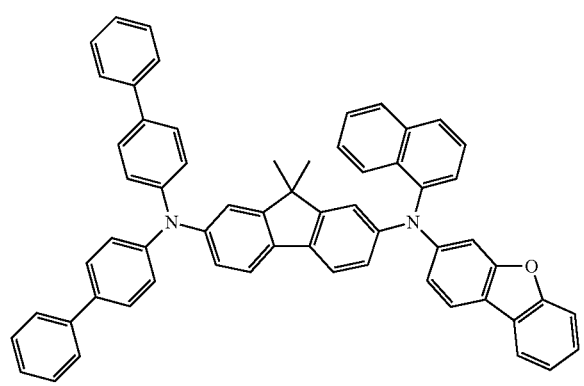
9-63
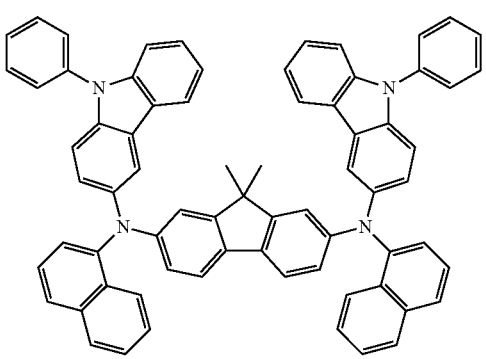

9-64
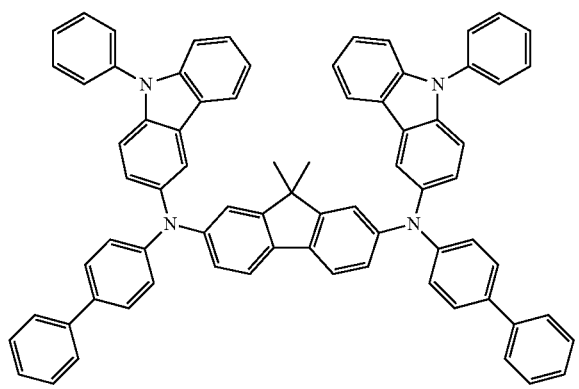
10-1
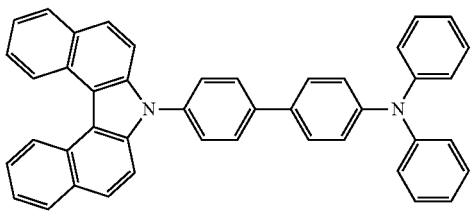
10-2
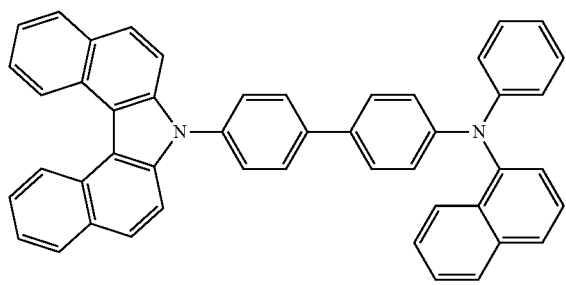
10-3
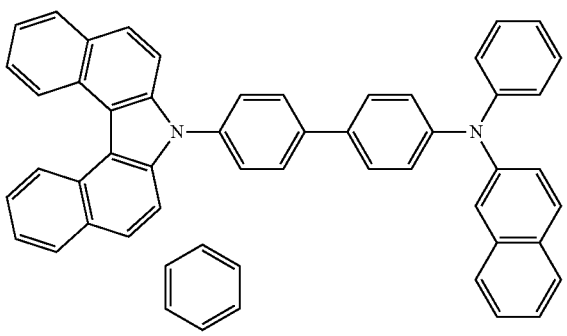
10-4
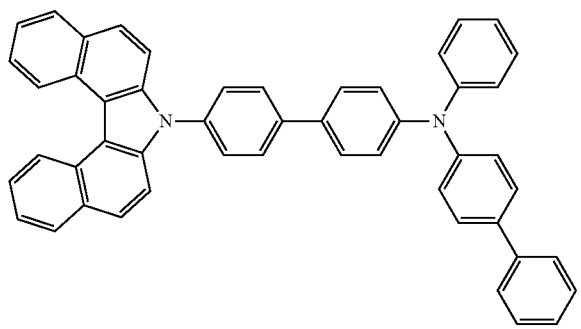
10-5
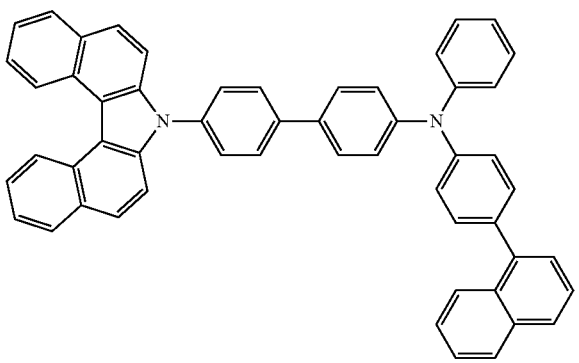
10-6
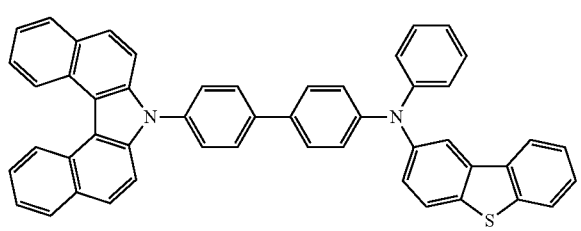
10-7
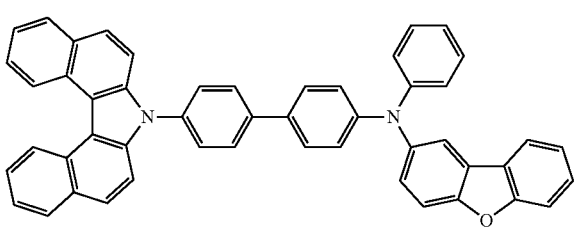

-continued
10-8
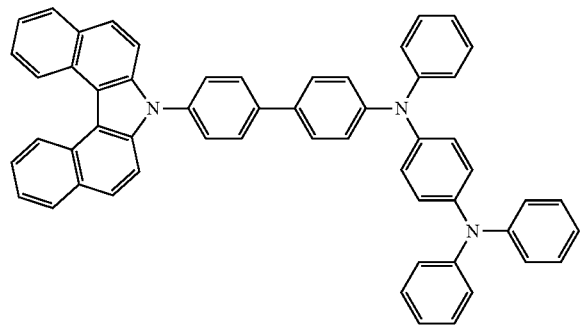
10-9
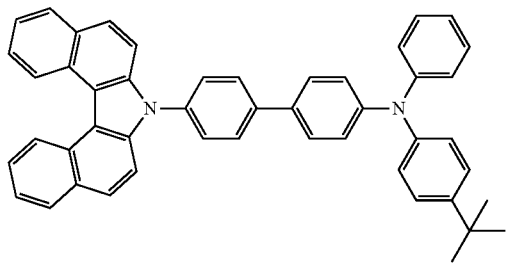
10-10
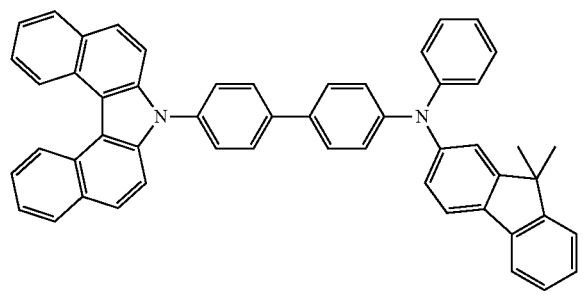
10-11
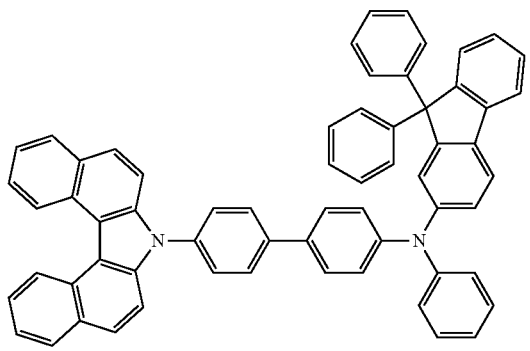
10-12
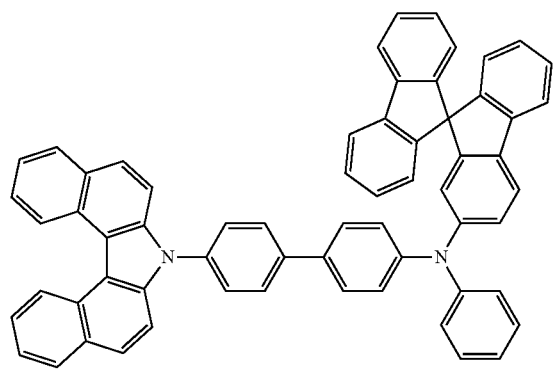
10-13
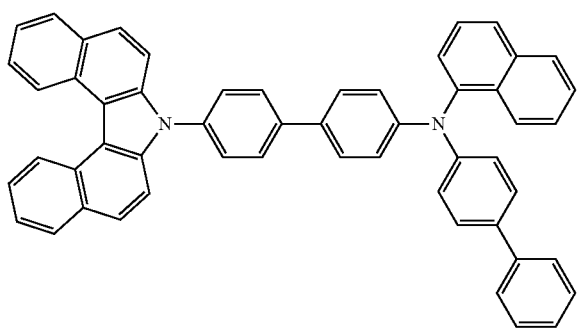
10-14
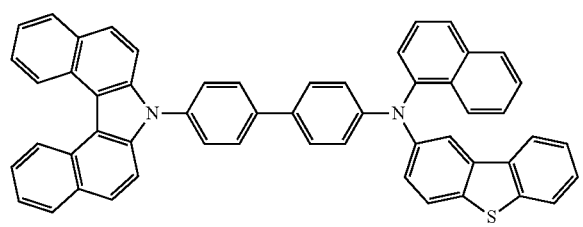
10-15
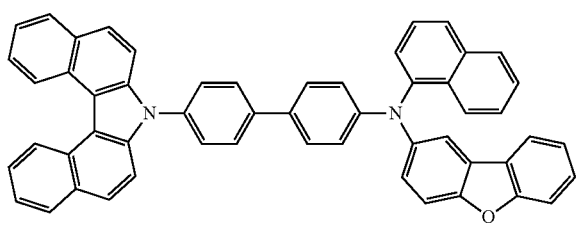

-continued
10-16
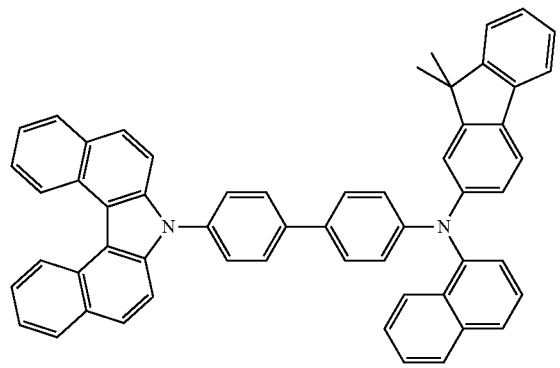
10-17
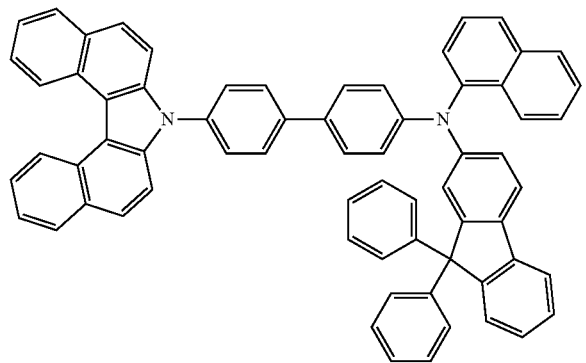
10-18
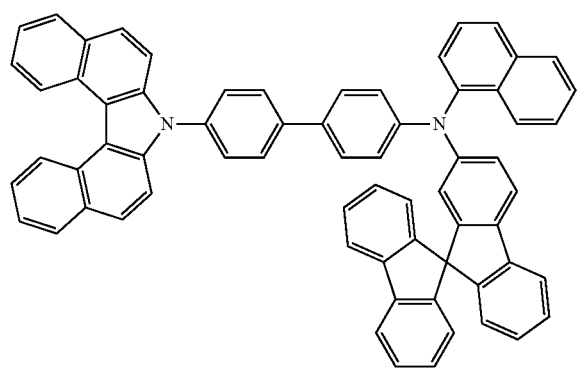
10-19
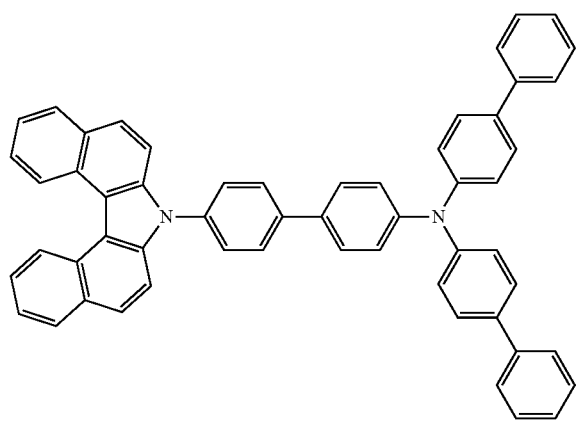
10-20
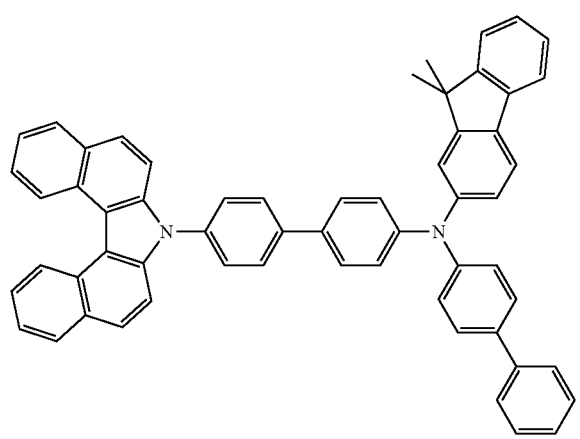
10-21
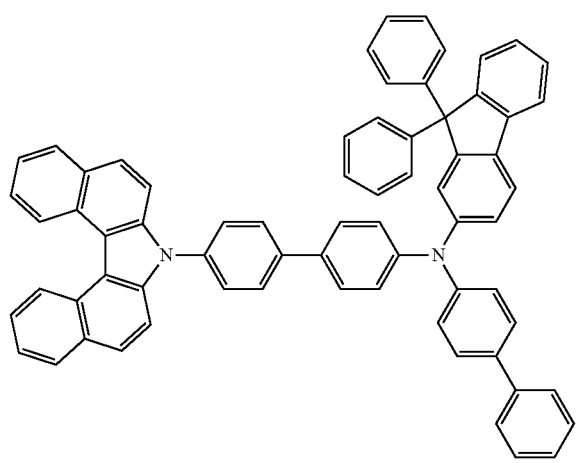

-continued
10-22
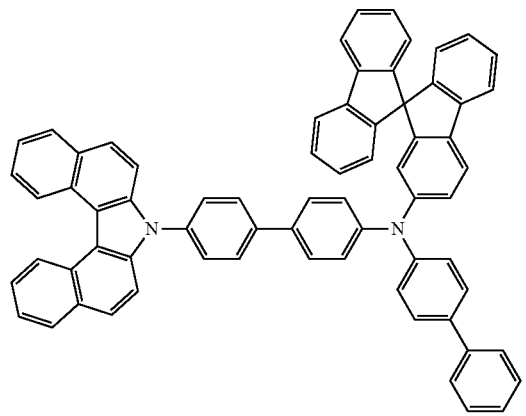
10-23
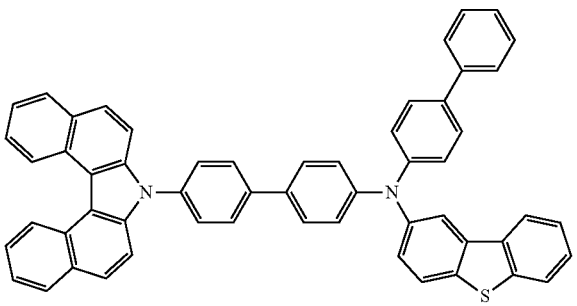
10-24
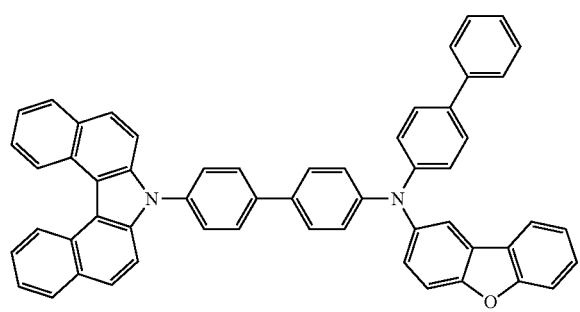
10-25
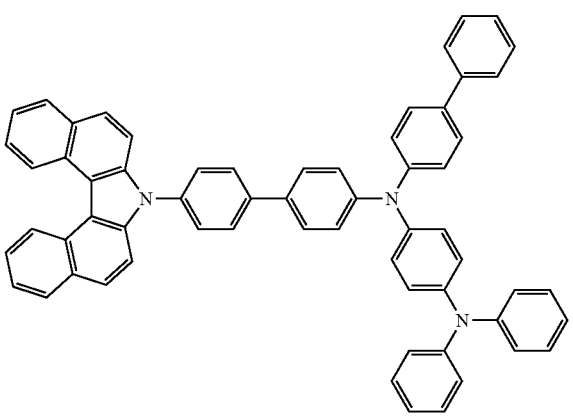
10-26
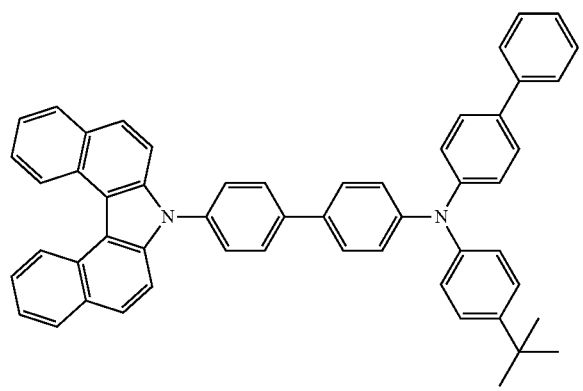
10-27
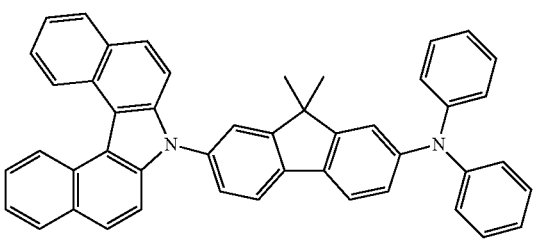
10-28
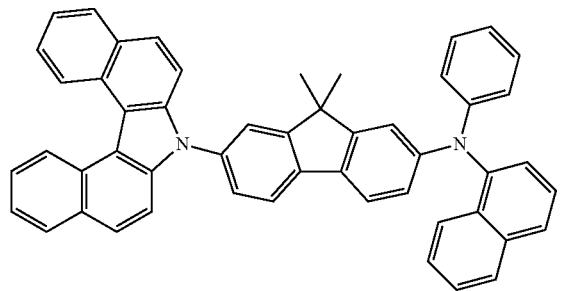
10-29
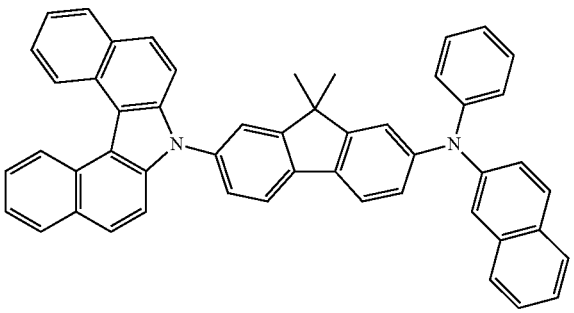

-continued
10-30
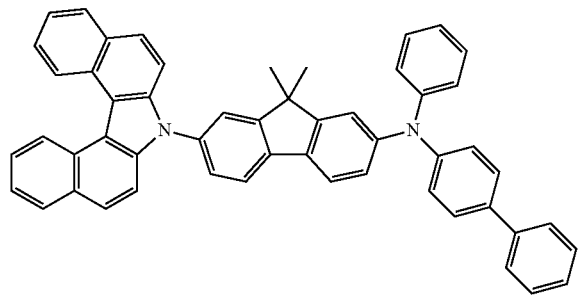
10-31
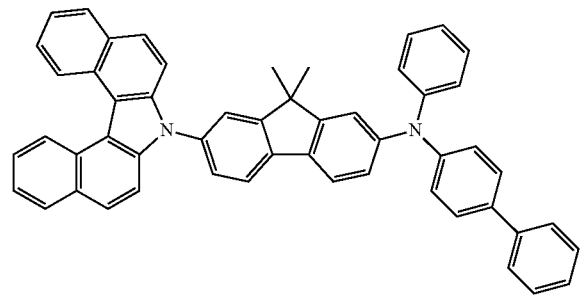
10-32
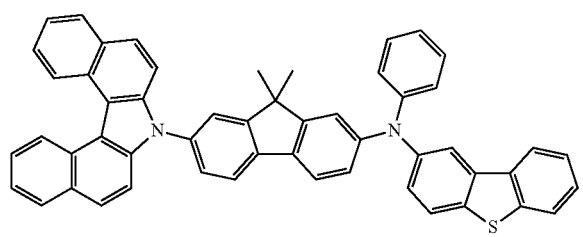
10-33
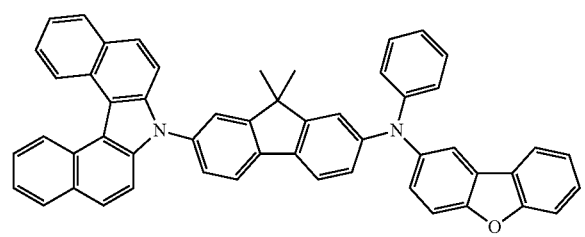
10-34
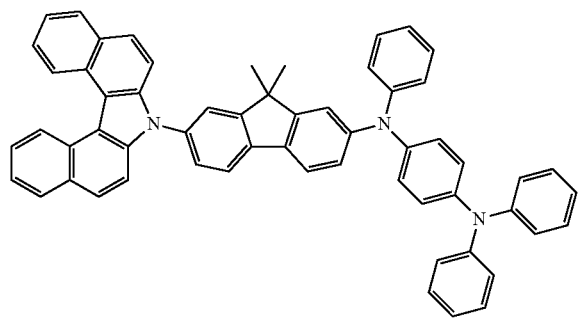
10-35
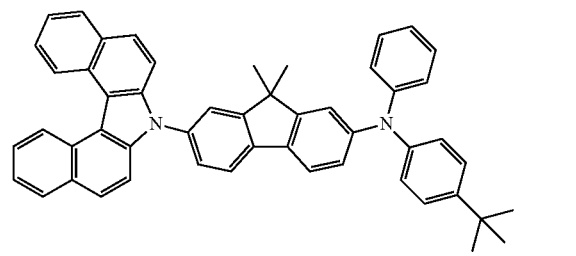
10-36
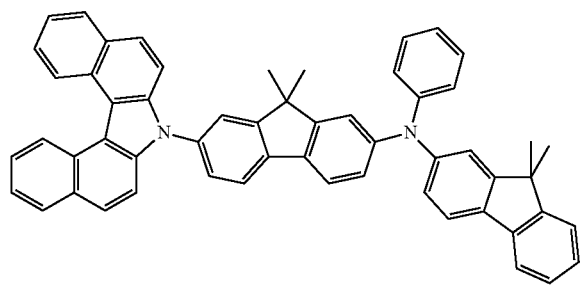
10-37
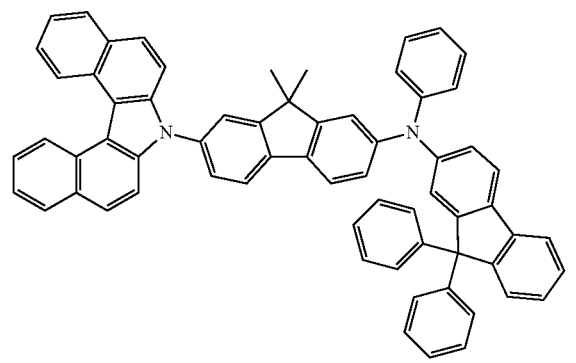

10-38
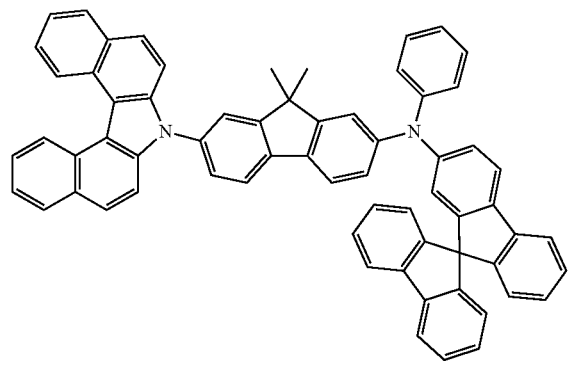
10-39
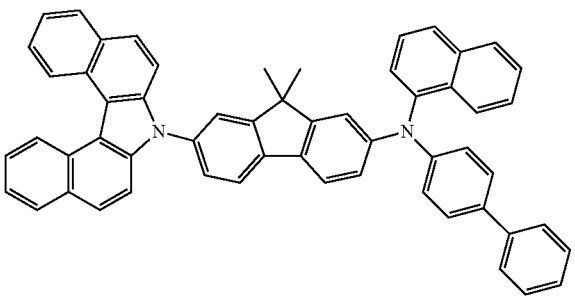
10-40
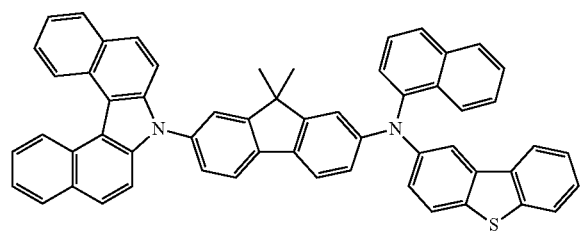
10-41
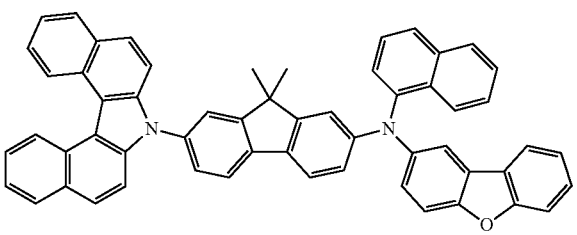
10-42
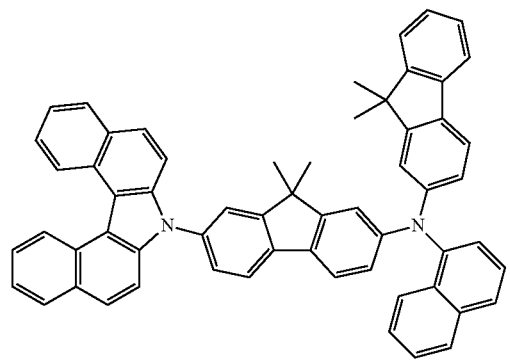
10-43
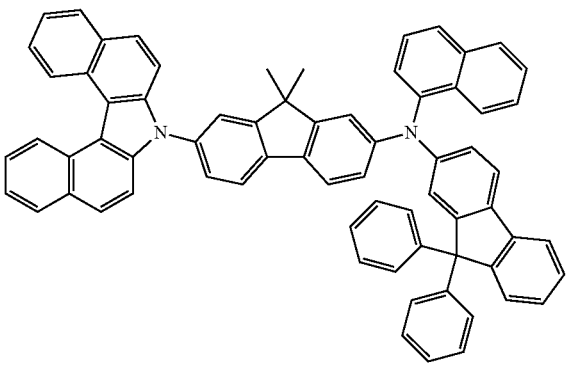
10-44
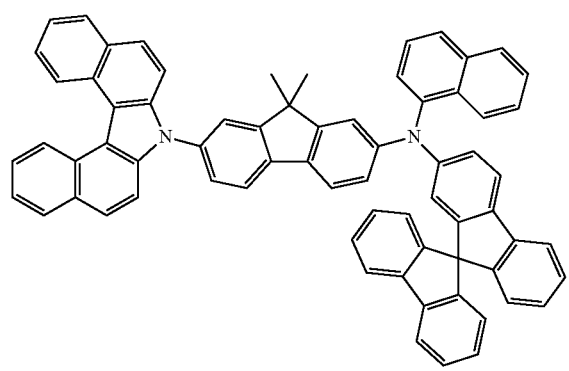
10-45
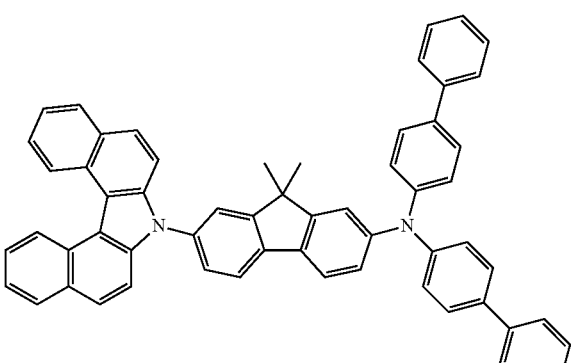

-continued
10-46
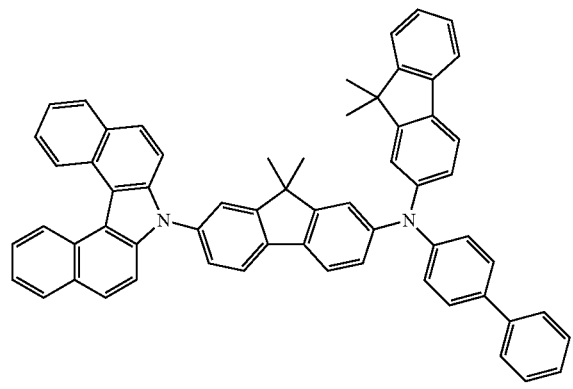
10-47
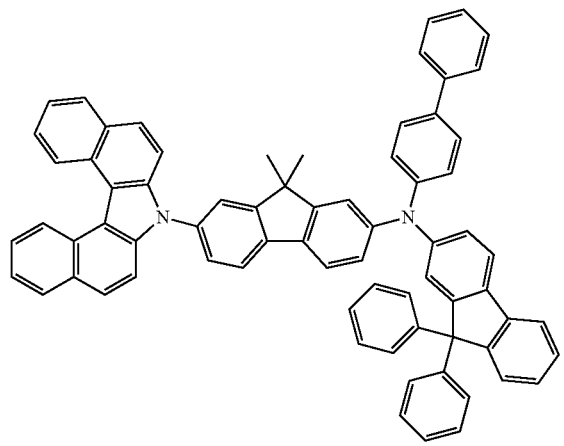
10-48
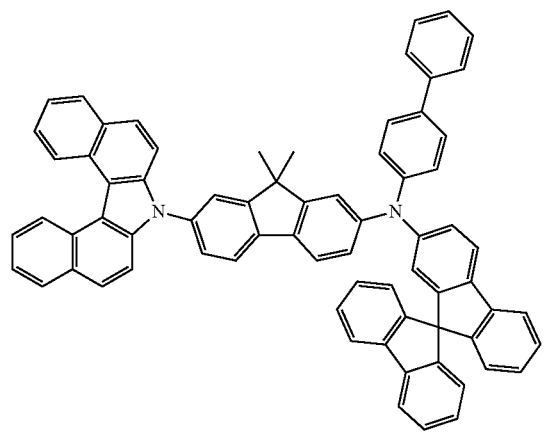
10-49
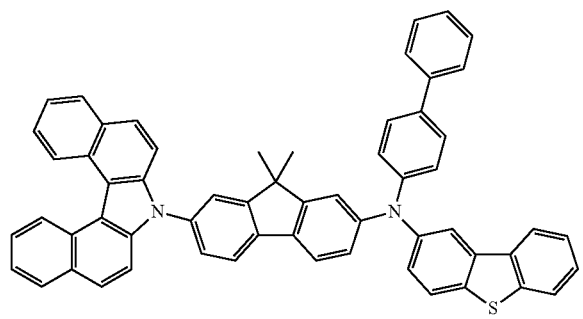
10-50
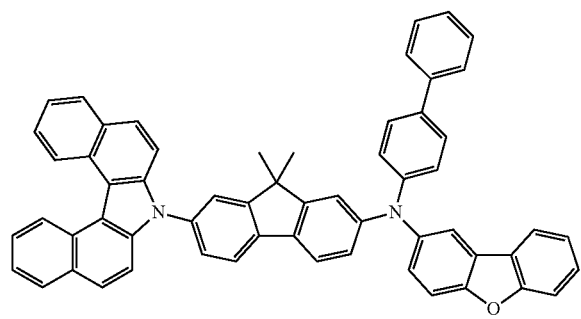
10-51
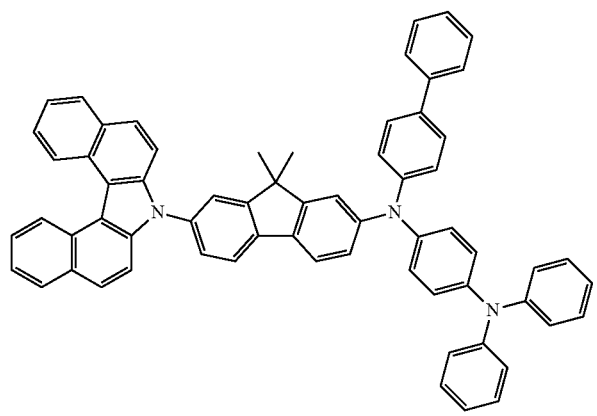

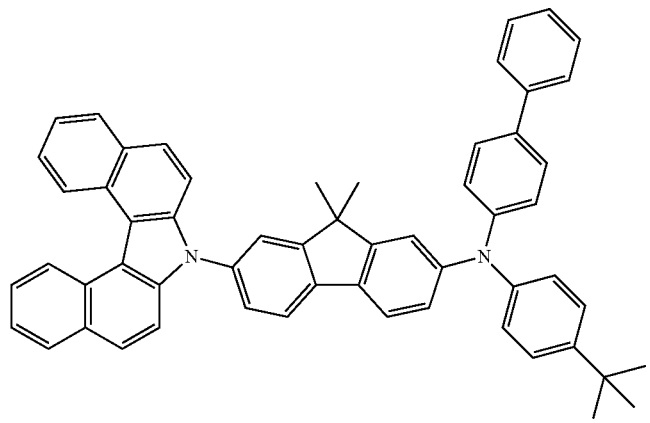

Hereinafter, Synthesis Examples of the inventive compound represented by Formula 1 or Formula 2 above and Preparation Examples of an organic electric element will be described in detail by way of example. However, the following examples are only for illustrative purposes and are not intended to limit the scope of the invention.

Synthesis Example 1: Synthesis of Formula 1

The inventive compound (final products; product 1-1 to product 1-150) is prepared by reacting Sub 1 with Sub 2, as represented in Reaction Scheme 1 below.

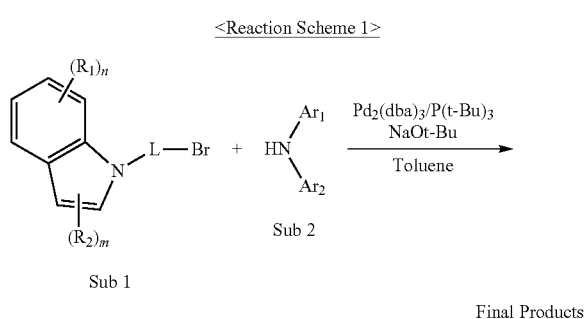

Example 1

Synthesis of Sub 1

Sub 1 in Reaction Scheme 1 above may be synthesized by the reaction pathway represented by Reaction Scheme 2 below.

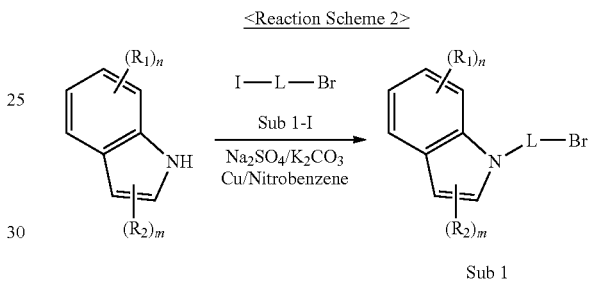

Examples of synthesizing specific compounds belonging to Sub 1 are as follows.

(1) Synthesis Method of Sub 1-1

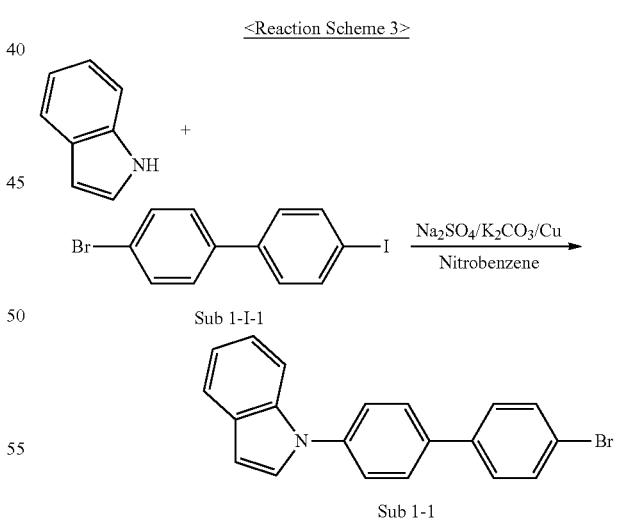

1H-indole (57.12 g, 487.6 mmol) as the starting material was dissolved in nitrobenzene in a round bottom flask, and Sub 1-I-1 (245.06 g, 682.6 mmol), $Na_2SO_4$ (69.24 g, 487.6 mmol), $K_2CO_3$ (67.29 g, 487.6 mmol), and Cu (9.3 g, 146.3 mmol) were added to the reaction solution, followed by stirring at 200° C. Upon completion of the reaction, nitrobenzene was removed by distillation, and the reaction product was extracted with $CH_2Cl_2$ and water. The extracted (2) Synthesis Method of Sub 1-3

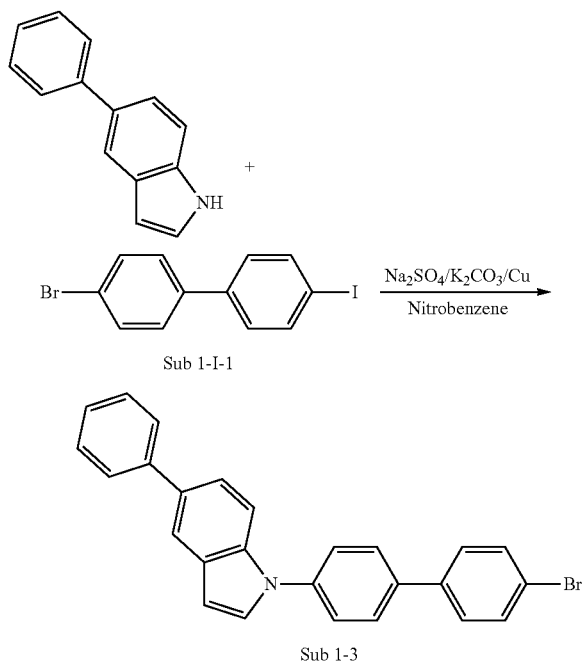

Sub 1-3

Using 5-phenyl-1H-indole (50.82 g, 263 mmol) as the starting material and using Sub 1-I-1 (132.18 g, 368.2 mmol), $Na_2SO_4$ (37.35 g, 263 mmol), $K_2CO_3$ (36.29 g, 263 mmol), Cu (5.01 g, 78.9 mmol), and nitrobenzene, the same procedure as described in the synthesis method of Sub 1-1 of Example 1 was carried out to obtain 75.89 g of product (yield: 68%).

(3) Synthesis Method of Sub 1-5

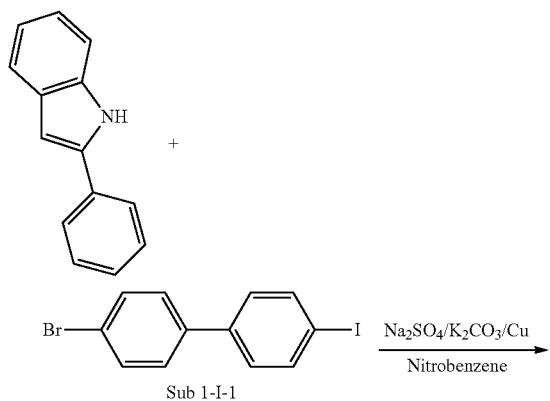

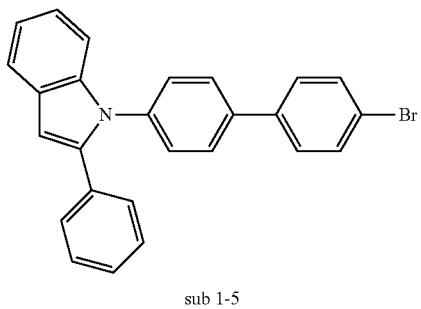

sub 1-5

Using 2-phenyl-1H-indole (51.97 g, 268.9 mmol) as the starting material and using Sub 1-I-1 (135.15 g, 376.5 mmol), $Na_2SO_4$ (38.18 g, 268.9 mmol), $K_2CO_3$ (37.11 g, 268.9 mmol), Cu (5.13 g, 80.7 mmol), and nitrobenzene, the same procedure as described in the synthesis method of Sub 1-1 of Example 1 was carried out to obtain 71.88 g of product (yield: 63%).

(4) Synthesis Method of Sub 1-7

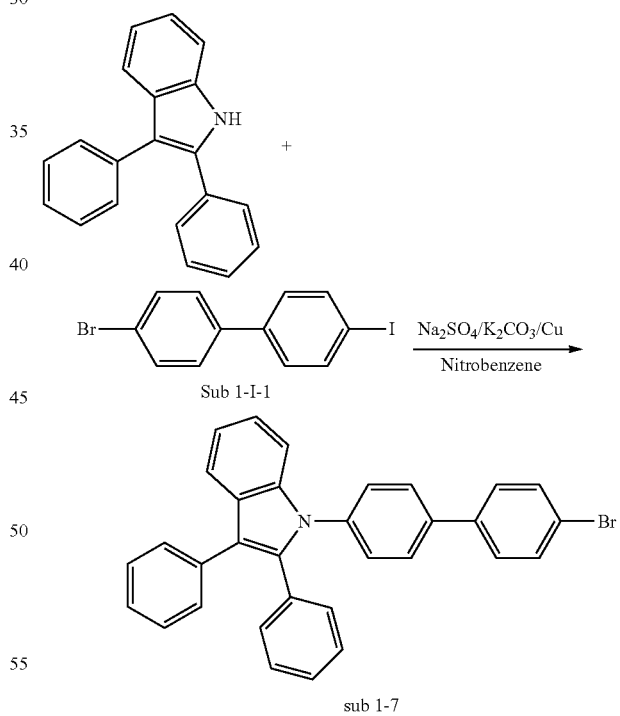

sub 1-7

Using 2,3-diphenyl-1H-indole (61.54 g, 228.5 mmol) as the starting material and using Sub 1-I-1 (114.83 g, 319.9 mmol), $Na_2SO_4$ (32.45 g, 228.5 mmol), $K_2CO_3$ (31.53 g, 228.5 mmol), Cu (4.36 g, 68.6 mmol), and nitrobenzene, the same procedure as described in the synthesis method of Sub 1-1 of Example 1 was carried out to obtain 67.47 g of product (yield: 59%).

(5) Synthesis Method of Sub 1-9

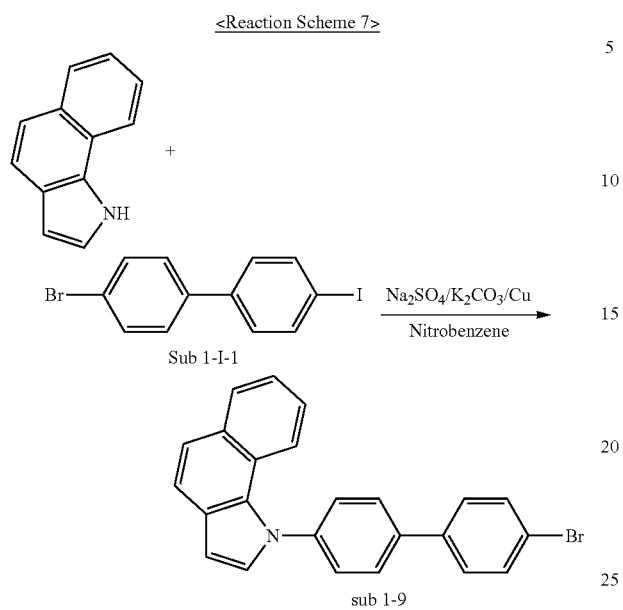

Using 1H-benzo[g]indole (55.36 g, 331.1 mmol) as the starting material and using Sub 1-I-1 (166.4 g, 463.5 mmol), Na₂SO₄ (47.02 g, 331.1 mmol), K₂CO₃ (45.69 g, 331.1 mmol), Cu (6.31 g, 99.3 mmol), and nitrobenzene, the same procedure as described in the synthesis method of Sub 1-1 of Example 1 was carried out to obtain 76.49 g of product (yield: 58%).

(6) Synthesis Method of Sub 1-10

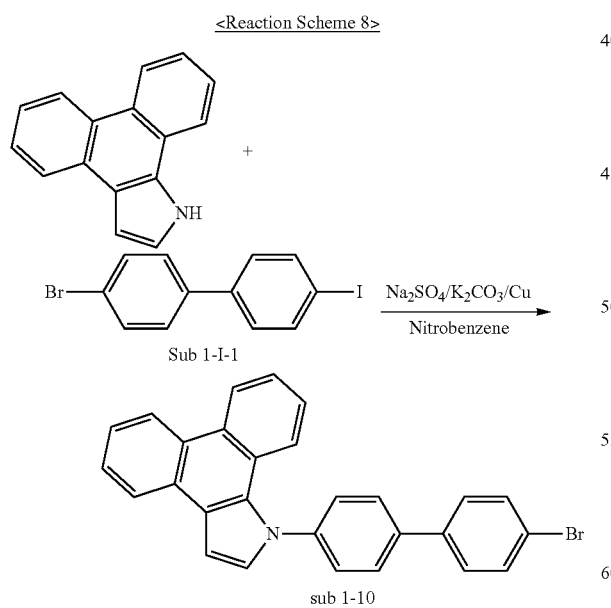

Using 1H-dibenzo[e,g]indole (58.77 g, 270.5 mmol) as the starting material and using Sub 1-I-1 (135.95 g, 378.7 mmol), Na₂SO₄ (38.41 g, 270.5 mmol), K₂CO₃ (37.33 g, 270.5 mmol), Cu (5.16 g, 81.2 mmol), and nitrobenzene, the same procedure as described in the synthesis method of Sub 1-1 of Example 1 was carried out to obtain 67.92 g of product (yield: 56%).

(7) Synthesis Method of Sub 1-11

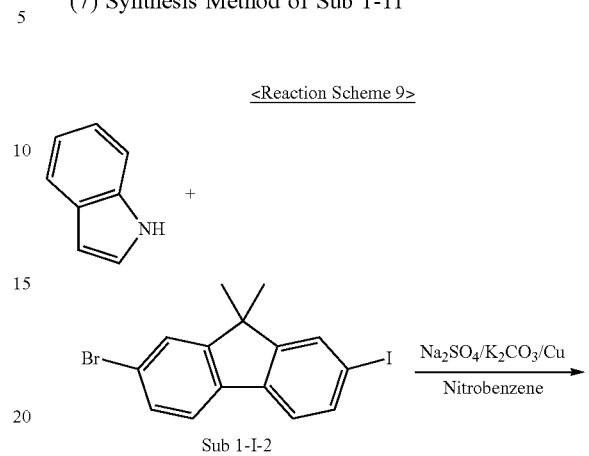

Using 1H-indole (40.17 g, 342.9 mmol) as the starting material and using Sub 1-I-2 (191.57 g, 480.1 mmol), Na₂SO₄ (48.69 g, 342.9 mmol), K₂CO₃ (47.32 g, 342.9 mmol), Cu (6.54 g, 102.9 mmol), and nitrobenzene, the same procedure as described in the synthesis method of Sub 1-1 of Example 1 was carried out to obtain 82.55 g of product (yield: 62%).

(8) Synthesis Method of Sub 1-12

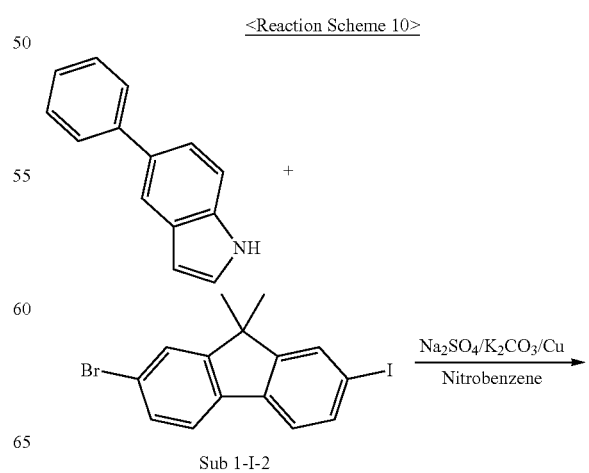

215
-continued

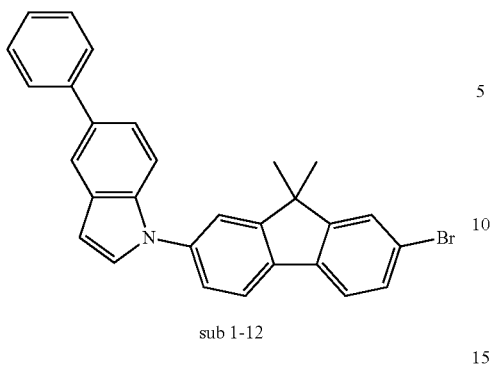

sub 1-12

Using 5-phenyl-1H-indole (46.23 g, 239.2 mmol) as the starting material and using Sub 1-I-2 (133.66 g, 334.9 mmol), Na$_2$SO$_4$ (33.97 g, 239.2 mmol), K$_2$CO$_3$ (33.01 g, 239.2 mmol), Cu (4.56 g, 71.8 mmol), and nitrobenzene, the same procedure as described in the synthesis method of Sub 1-1 of Example 1 was carried out to obtain 63.32 g of product (yield: 57%).

(9) Synthesis Method of Sub 1-13

<Reaction Scheme 11>

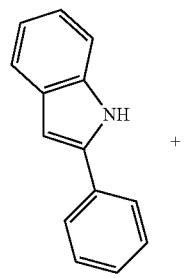

+

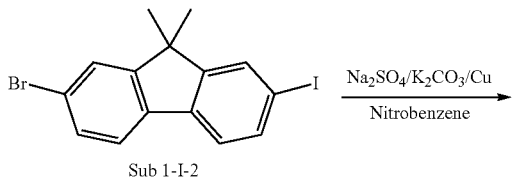

Sub 1-I-2

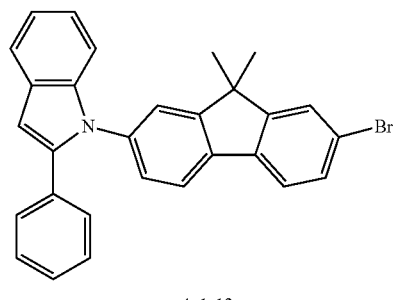

sub 1-13

Using 2-phenyl-1H-indole (49.92 g, 258.3 mmol) as the starting material and using Sub 1-I-2 (144.32 g, 361.7 mmol), Na$_2$SO$_4$ (36.68 g, 258.3 mmol), K$_2$CO$_3$ (35.65 g, 258.3 mmol), Cu (4.92 g, 77.5 mmol), and nitrobenzene, the same procedure as described in the synthesis method of Sub 1-1 of Example 1 was carried out to obtain 75.57 g of product (yield: 63%).

216
(10) Synthesis Method of Sub 1-14

<Reaction Scheme 12>

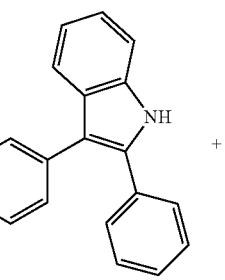

+

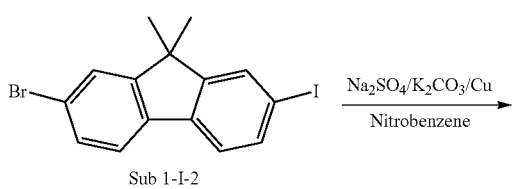

Sub 1-I-2

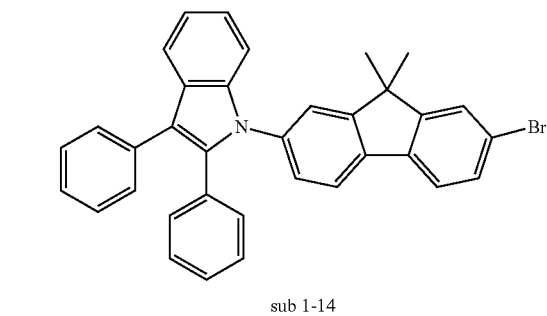

sub 1-14

Using 2,3-diphenyl-1H-indole (47.13 g, 175 mmol) as the starting material and using Sub 1-I-2 (97.72 g, 245 mmol), Na$_2$SO$_4$ (24.85 g, 175 mmol), K$_2$CO$_3$ (24.15 g, 175 mmol), Cu (3.34 g, 52.5 mmol), and nitrobenzene, the same procedure as described in the synthesis method of Sub 1-1 of Example 1 was carried out to obtain 49.18 g of product (yield: 52%).

(11) Synthesis Method of Sub 1-15

<Reaction Scheme 13>

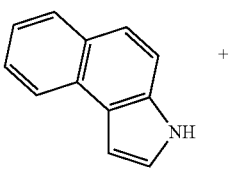

+

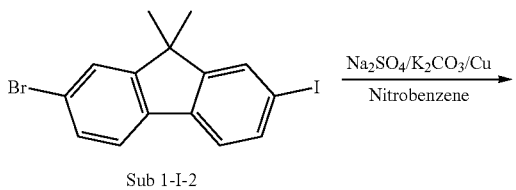

Sub 1-I-2

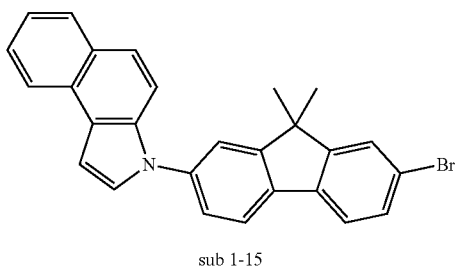

sub 1-15

Using 3H-benzo[e]indole (48.79 g, 291.8 mmol) as the starting material and using Sub 1-I-2 (163.02 g, 408.5 mmol), Na₂SO₄ (41.43 g, 291.8 mmol), K₂CO₃ (40.27 g, 291.8 mmol), Cu (5.56 g, 87.5 mmol), and nitrobenzene, the same procedure as described in the synthesis method of Sub 1-1 of Example 1 was carried out to obtain 60.11 g of product (yield: 47%).

(12) Synthesis Method of Sub 1-19

(13) Synthesis Method of Sub 1-25

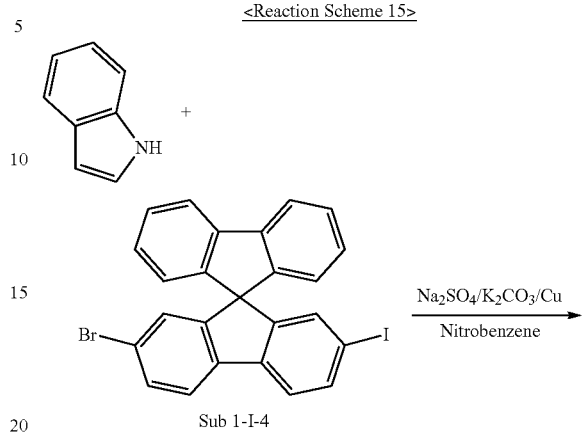

Using 1H-indole (39.94 g, 340.9 mmol) as the starting material and using Sub 1-I-4 (248.76 g, 477.3 mmol), Na₂SO₄ (48.41 g, 340.9 mmol), K₂CO₃ (47.04 g, 340.9 mmol), Cu (6.5 g, 102.3 mmol), and nitrobenzene, the same procedure as described in the synthesis method of Sub 1-1 of Example 1 was carried out to obtain 92.22 g of product (yield: 53%).

Examples of Sub 1-I include, but not limited to, compounds below.

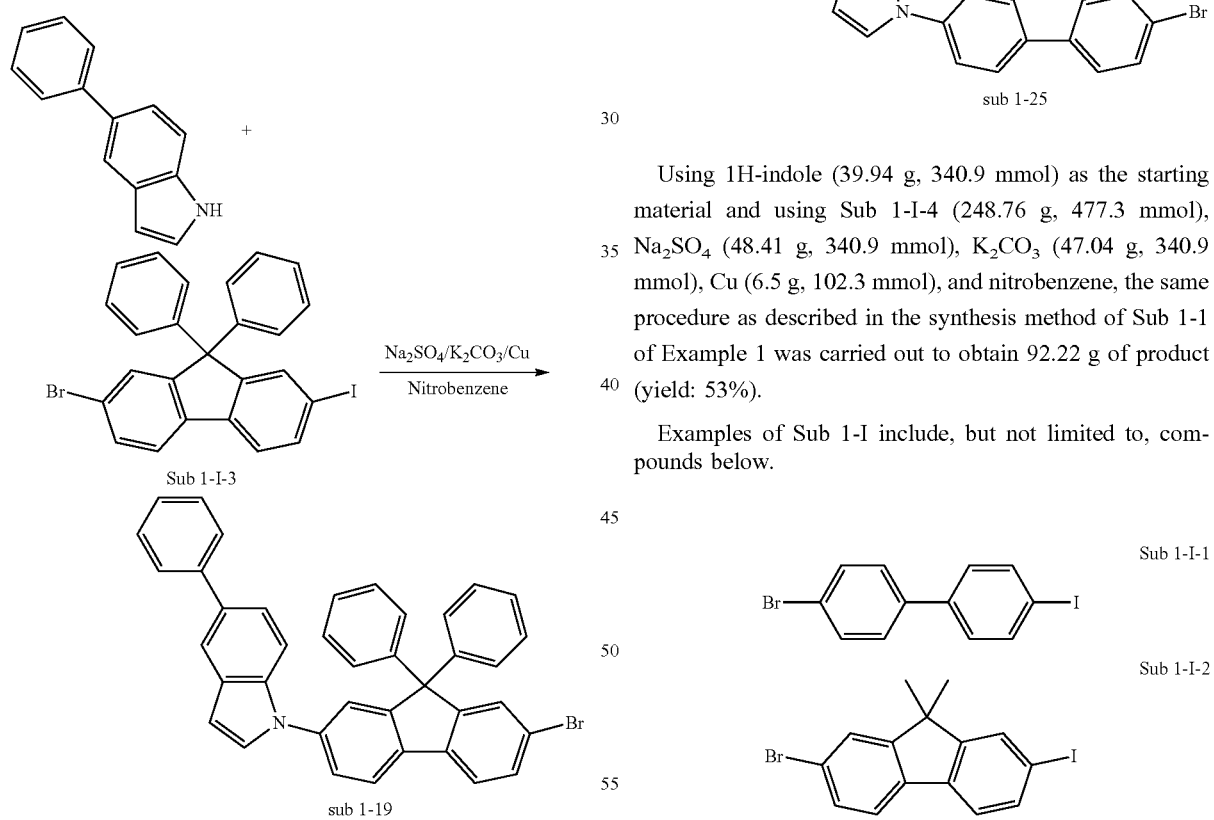

Using 5-phenyl-1H-indole (40.17 g, 208.3 mmol) as the starting material and using Sub 1-I-3 (152.61 g, 291.7 mmol), Na₂SO₄ (29.58 g, 208.3 mmol), K₂CO₃ (28.75 g, 208.3 mmol), Cu (3.97 g, 62.5 mmol), and nitrobenzene, the same procedure as described in the synthesis method of Sub 1-1 of Example 1 was carried out to obtain 74.78 g of product (yield: 61%).

Sub 1-I-4
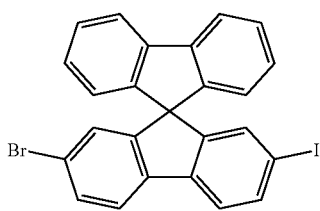
Examples of Sub 1 include, but not limited to, compounds below, and Field desorption mass spectrometry (FD-MS) values for the compounds of Sub 1 are given in Table 1 below.
sub 1-1
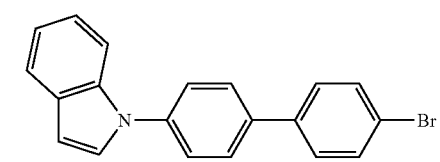
sub 1-2
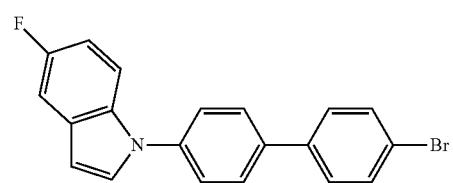
sub 1-3
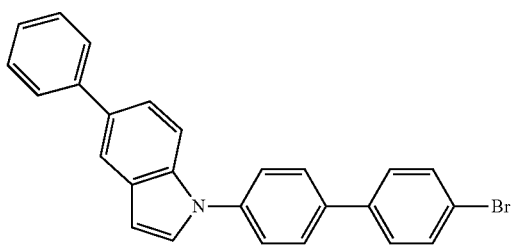
sub 1-4
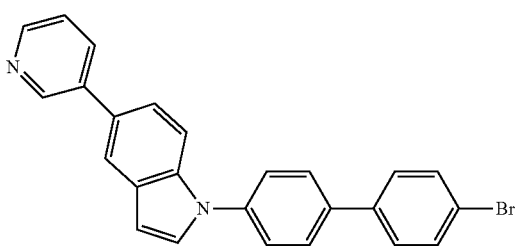
sub 1-5
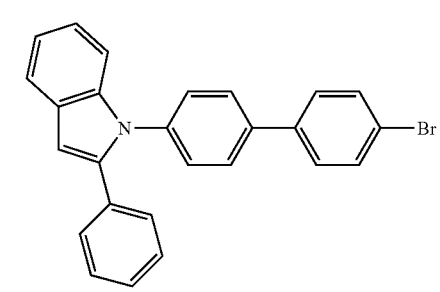
sub 1-6
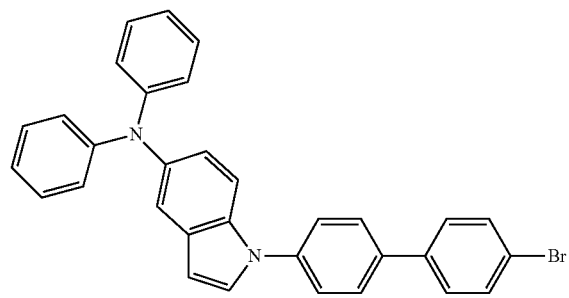
sub 1-7
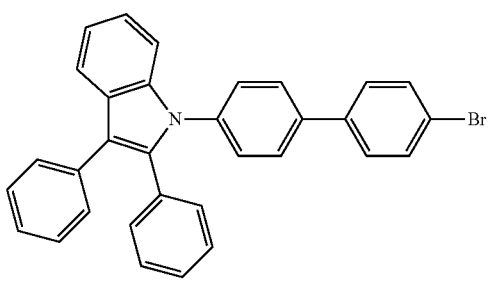
sub 1-8
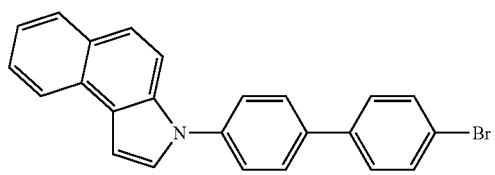
sub 1-9
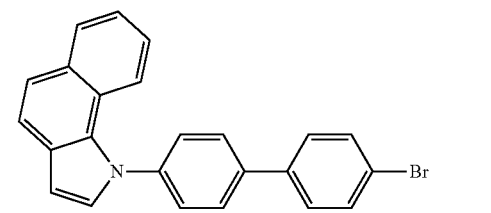
sub 1-10
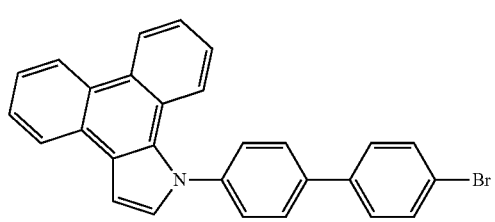
sub 1-11
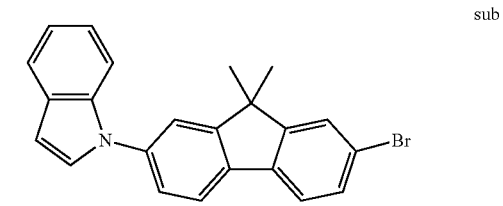

-continued
sub 1-12
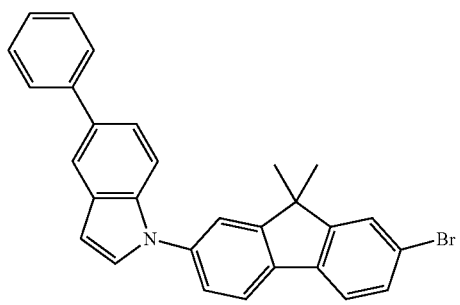
sub 1-17
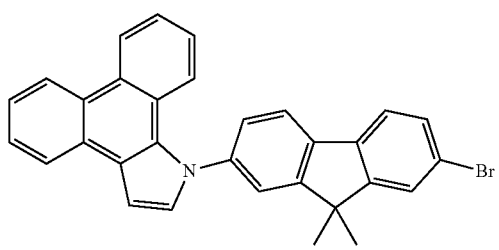
sub 1-13
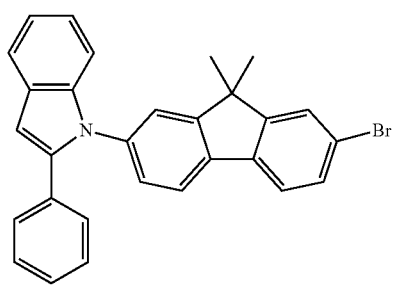
sub 1-18
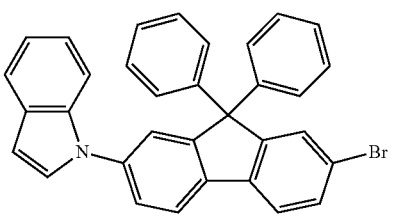
sub 1-14
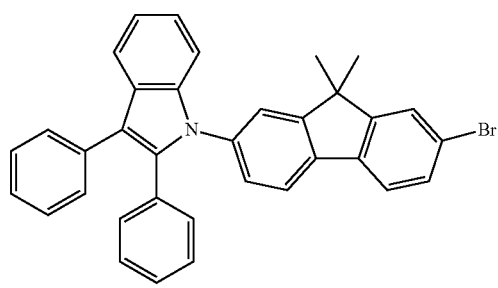
sub 1-19
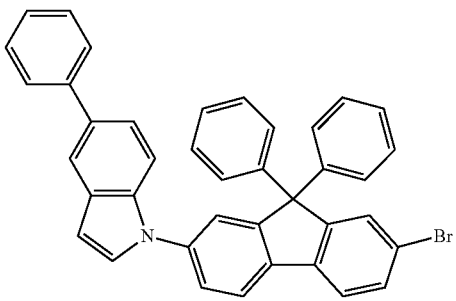
sub 1-15
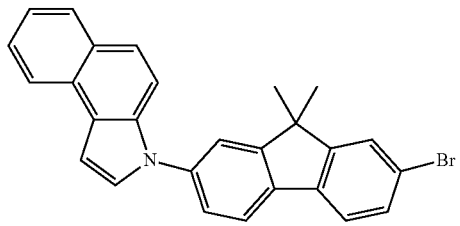
sub 1-20
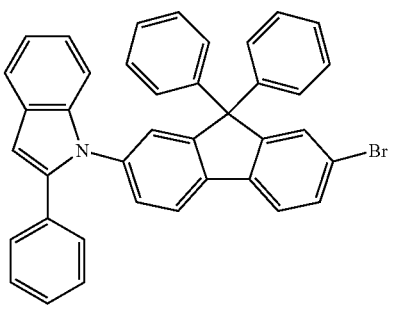
sub 1-16
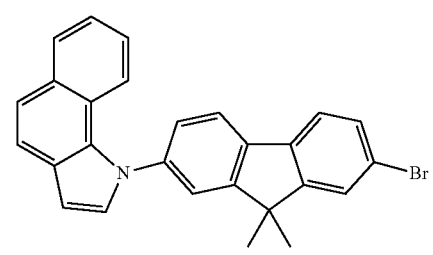
sub 1-21
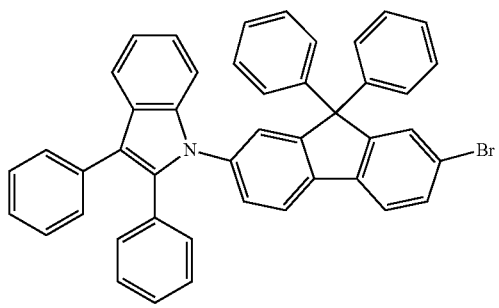

sub 1-22
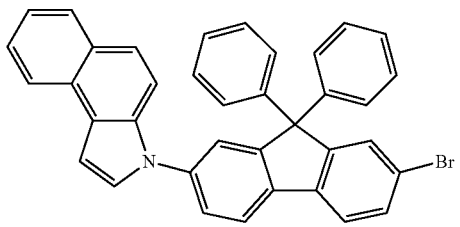

sub 1-23
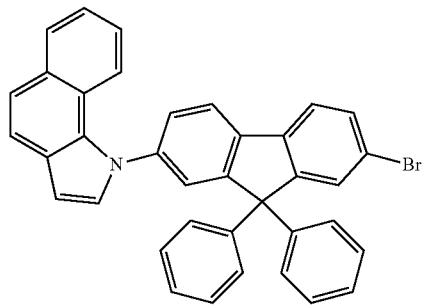

sub 1-24
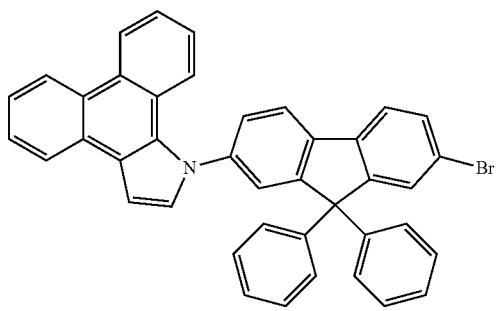

sub 1-25
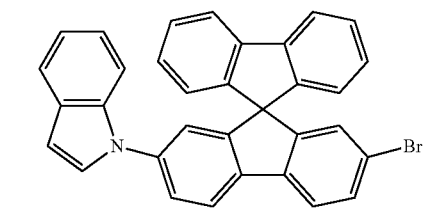

sub 1-26
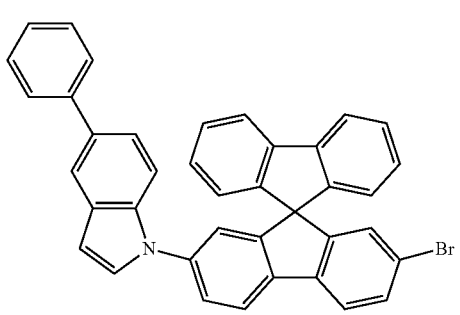

sub 1-27
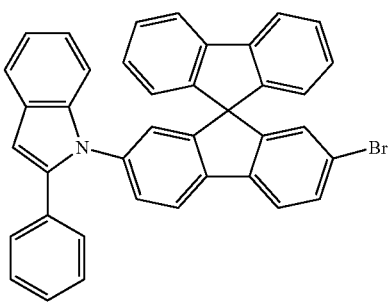

sub 1-28
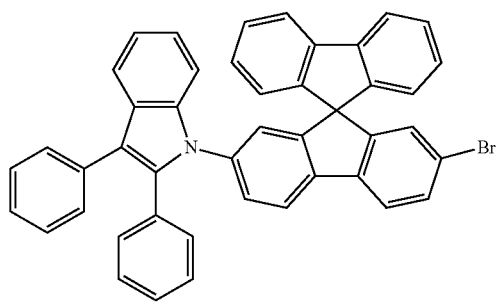

TABLE 1

| Compound | FD-MS | Compound | FD-MS |
|---|---|---|---|
| Sub 1-1 | m/z = 347.03($C_{20}H_{14}BrN$ = 348.24) | Sub 1-2 | m/z = 365.02($C_{20}H_{13}BrFN$ = 366.23) |
| Sub 1-3 | m/z = 423.06($C_{26}H_{18}BrN$ = 424.33) | Sub 1-4 | m/z = 424.06($C_{25}H_{17}BrN_2$ = 425.32) |
| Sub 1-5 | m/z = 423.06($C_{26}H_{18}BrN$ = 424.33) | Sub 1-6 | m/z = 514.10($C_{32}H_{23}BrN_2$ = 515.44) |
| Sub 1-7 | m/z = 499.09($C_{32}H_{22}BrN$ = 500.43) | Sub 1-8 | m/z = 397.05($C_{24}H_{16}BrN$ = 398.29) |
| Sub 1-9 | m/z = 397.05($C_{24}H_{16}BrN$ = 398.29) | Sub 1-10 | m/z = 447.06($C_{28}H_{18}BrN$ = 448.35) |
| Sub 1-11 | m/z = 387.06($C_{23}H_{18}BrN$ = 388.30) | Sub 1-12 | m/z = 463.09($C_{29}H_{22}BrN$ = 464.40) |
| Sub 1-13 | m/z = 463.09($C_{29}H_{22}BrN$ = 464.40) | Sub 1-14 | m/z = 539.12($C_{35}H_{26}BrN$ = 540.49) |
| Sub 1-15 | m/z = 437.08($C_{27}H_{20}BrN$ = 438.36) | Sub 1-16 | m/z = 437.08($C_{27}H_{20}BrN$ = 438.36) |
| Sub 1-17 | m/z = 487.09($C_{31}H_{22}BrN$ = 488.42) | Sub 1-18 | m/z = 511.09($C_{33}H_{22}BrN$ = 512.44) |
| Sub 1-19 | m/z = 587.12($C_{39}H_{26}BrN$ = 588.53) | Sub 1-20 | m/z = 587.12($C_{39}H_{26}BrN$ = 588.53) |
| Sub 1-21 | m/z = 663.16($C_{45}H_{30}BrN$ = 664.63) | Sub 1-22 | m/z = 561.11($C_{37}H_{24}BrN$ = 562.50) |
| Sub 1-23 | m/z = 561.11($C_{37}H_{24}BrN$ = 562.50) | Sub 1-24 | m/z = 611.12($C_{41}H_{26}BrN$ = 612.56) |
| Sub 1-25 | m/z = 509.08($C_{33}H_{20}BrN$ = 510.42) | Sub 1-26 | m/z = 585.11($C_{39}H_{24}BrN$ = 586.52) |

TABLE 1-continued

| Compound | FD-MS | Compound | FD-MS |
|---|---|---|---|
| Sub 1-27 | m/z = 585.11($C_{39}H_{24}BrN$ = 586.52) | Sub 1-28 | m/z = 661.14($C_{45}H_{28}BrN$ = 662.61) |

Example 2

Synthesis of Sub 2

Sub 2 in Reaction Scheme 2 above may be synthesized by the reaction pathway represented by Reaction Scheme 16 below.

<Reaction Scheme 16>

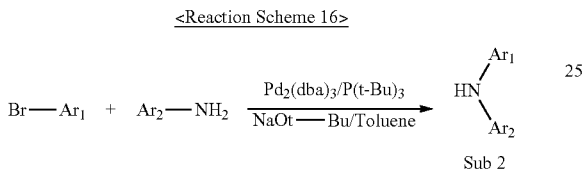

Examples of synthesizing specific compounds belonging to Sub 2 are as follows.

(1) Synthesis Method of Sub 2-11

<Reaction Scheme 17>

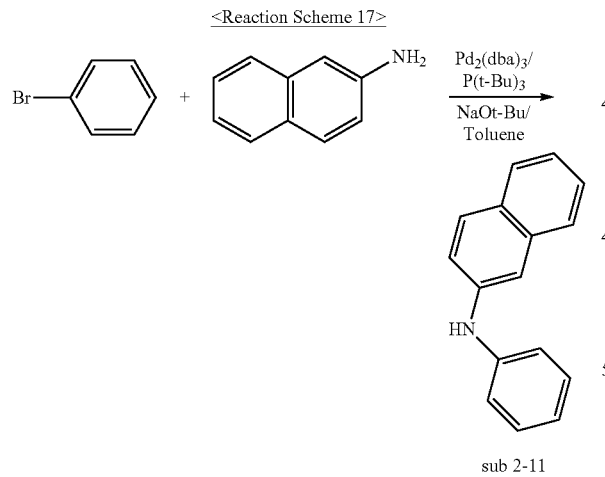

Bromobenzene (24.13 g, 154.3 mmol) as the starting material was dissolved in toluene in a round bottom flask, and naphthalen-2-amine (44.18 g, 308.6 mmol), $Pd_2(dba)_3$ (4.24 g, 4.63 mmol), 50% P(t-Bu)$_3$ (4.5 ml, 9.26 mmol), and NaOt-Bu (44.49 g, 462.9 mmol) were added to the reaction solution, followed by stirring at 40° C. Upon completion of the reaction, the reaction product was extracted with $CH_2Cl_2$ and water, the extracted organic layer was dried with $MgSO_4$ and concentrated, and then the produced organic material was separated by a silica gel column and recrystallized to obtain 27.69 g of product (yield: 82%).

(2) Synthesis Method of Sub 2-18

<Reaction Scheme 18>

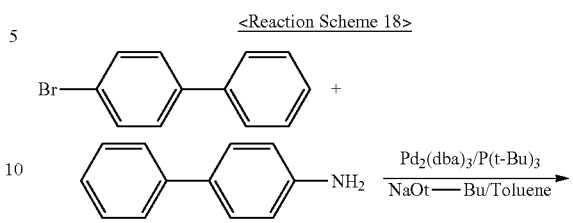

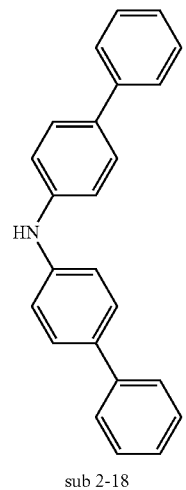

Using 4-bromo-1,1'-biphenyl (51.46 g, 220.7 mmol) obtained in the above synthesis, [1,1'-biphenyl]-4-amine (74.71 g, 441.5 mmol), $Pd_2(dba)_3$ (6.06 g, 6.6 mmol), 50% P(t-Bu)$_3$ (6.5 ml, 13.2 mmol), NaOt-Bu (63.63 g, 662 mmol), and toluene, the same procedure as described in the synthesis method of Sub 2-11 of Example 2 was carried out to obtain 56.75 g of product (yield: 80%).

(3) Synthesis Method of Sub 2-29

<Reaction Scheme 19>

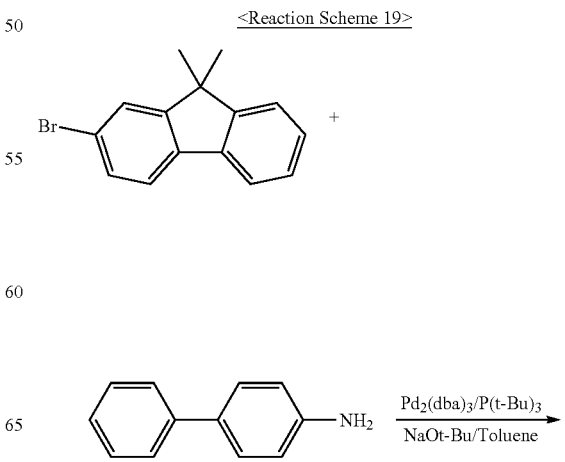

-continued

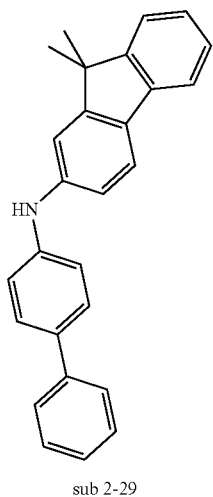

sub 2-29

Using 2-bromo-9,9'-dimethyl-9H-fluorene (40.24 g, 147 mmol) obtained in the above synthesis, [1,1'-biphenyl]-4-amine (49.86 g, 295 mmol), Pd₂(dba)₃ (4.04 g, 4.4 mmol), 50% P(t-Bu)₃ (4.3 ml, 8.8 mmol), NaOt-Bu (42.38 g, 441 mmol), and toluene, the same procedure as described in the synthesis method of Sub 2-11 of Example 2 was carried out to obtain 38.26 g of product (yield: 72%).

(4) Synthesis Method of Sub 2-33

<Reaction Scheme 20>

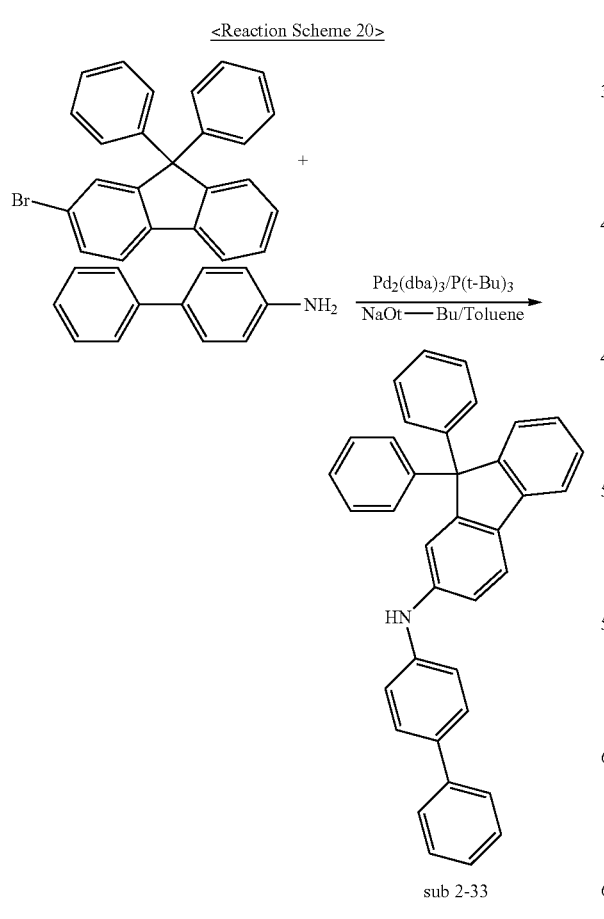

sub 2-33

Using 2-bromo-9,9'-diphenyl-9H-fluorene (38.93 g, 98 mmol) obtained in the above synthesis, [1,1'-biphenyl]-4-amine (33.16 g, 196 mmol), Pd₂(dba)₃ (2.66 g, 2.9 mmol), 50% P(t-Bu)₃ (2.9 ml, 5.9 mmol), NaOt-Bu (28.26 g, 294 mmol), and toluene, the same procedure as described in the synthesis method of Sub 2-11 of Example 2 was carried out to obtain 32.36 g of product (yield: 68%).

(5) Synthesis Method of Sub 2-43

<Reaction Scheme 21>

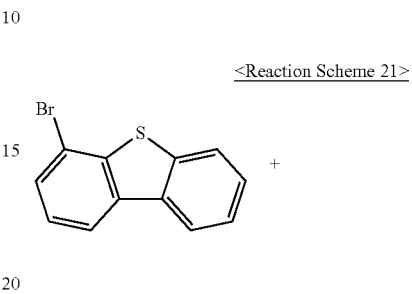

sub 2-43

Using 4-bromodibenzo[b,d]thiophene (41.56 g, 157.9 mmol) obtained in the above synthesis, [1,1'-biphenyl]-4-amine (53.45 g, 315.9 mmol), Pd₂(dba)₃ (4.34 g, 4.7 mmol), 50% P(t-Bu)₃ (4.6 ml, 9.5 mmol), NaOt-Bu (45.53 g, 473.7 mmol), and toluene, the same procedure as described in the synthesis method of Sub 2-11 of Example 2 was carried out to obtain 43.29 g of product (yield: 78%).

(6) Synthesis Method of Sub 2-47

<Reaction Scheme 22>

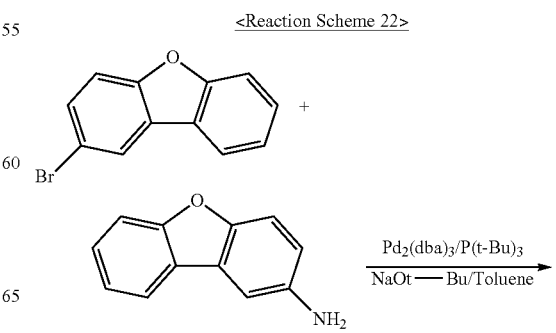

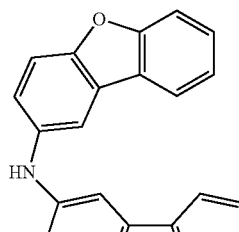
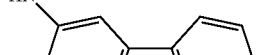

sub 2-47

Using 2-bromodibenzo[b,d]furan (32.41 g, 131.2 mmol) obtained in the above synthesis, dibenzo[b,d]furan-2-amine (48.06 g, 262 mmol), Pd$_2$(dba)$_3$ (3.6 g, 3.9 mmol), 50% P(t-Bu)$_3$ (3.8 ml, 7.9 mmol), NaOt-Bu (37.83 g, 393.6 mmol), and toluene, the same procedure as described in the synthesis method of Sub 2-11 of Example 2 was carried out to obtain 29.34 g of product (yield: 64%).

Examples of Sub 2 include, but not limited to, compounds below, and FD-MS values for the compounds of Sub 2 are given in Table 2 below.

sub 2-1

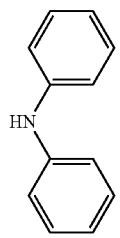

sub 2-2

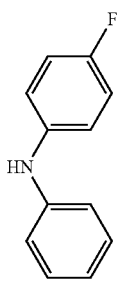

sub 2-3

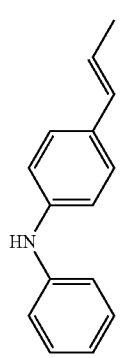

sub 2-4

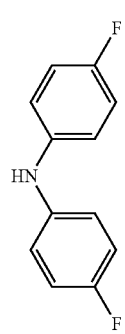

sub 2-5

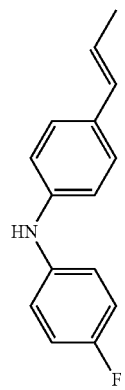

sub 2-6

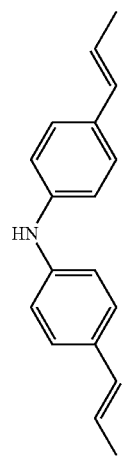

sub 2-7

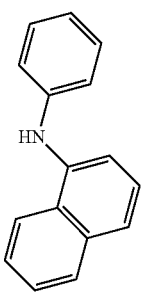

sub 2-8
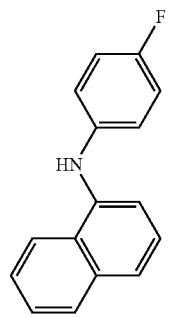
sub 2-9
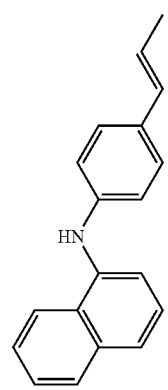
sub 2-10
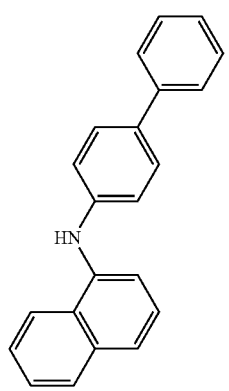
sub 2-11
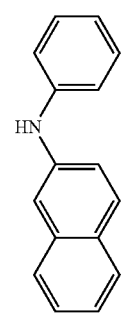
sub 2-12
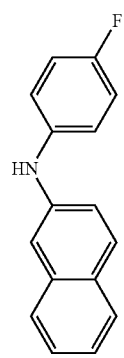
sub 2-13
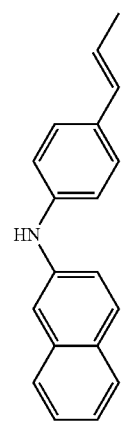
sub 2-14
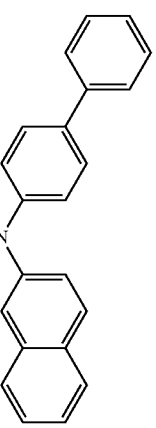
sub 2-15
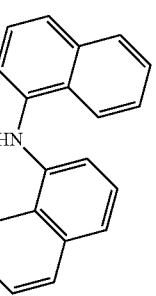

sub 2-16
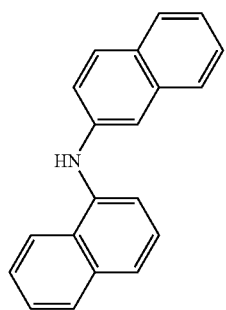
sub 2-17
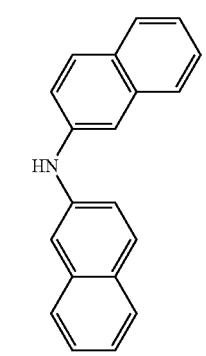
sub 2-18
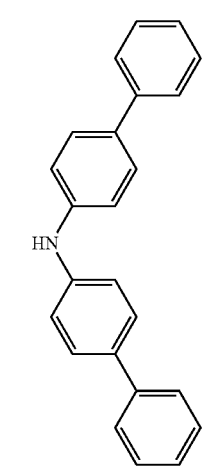
sub 2-19
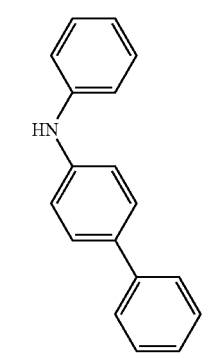
sub 2-20
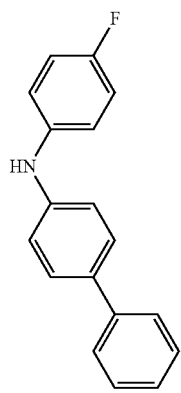
sub 2-21
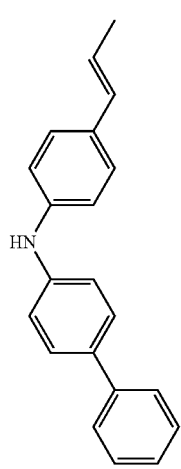
sub 2-22
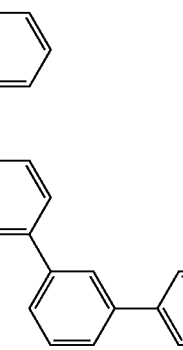
sub 2-23
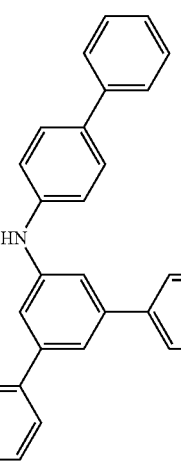

sub 2-24
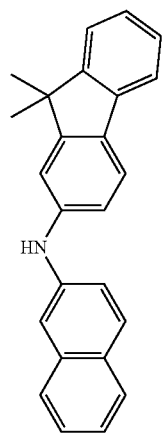
sub 2-25
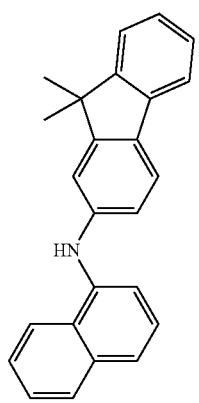
sub 2-26
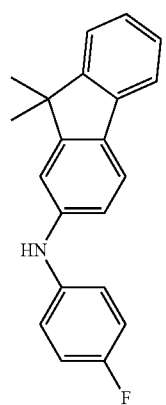
sub 2-27
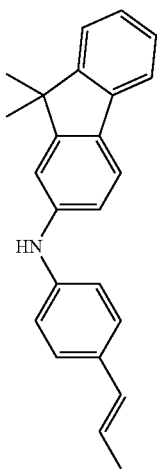
sub 2-28
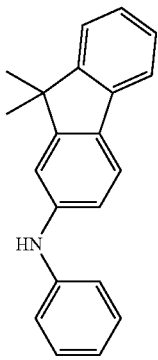
sub 2-29
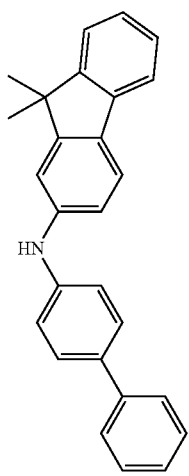

sub 2-30
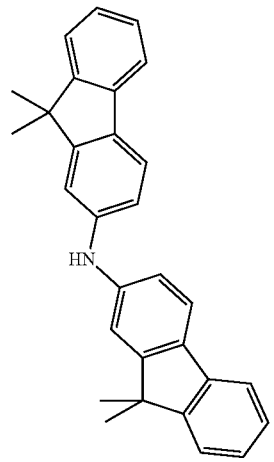
sub 2-31
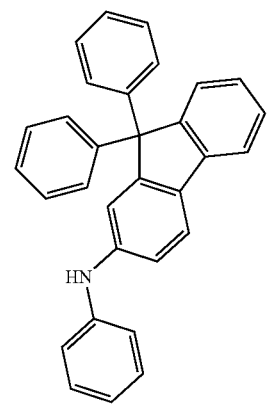
sub 3-32
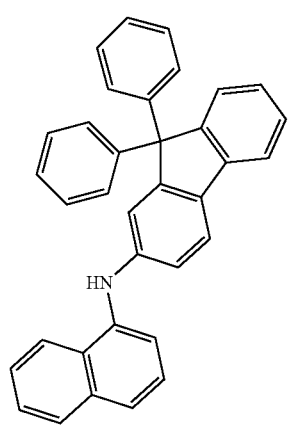
sub 2-33
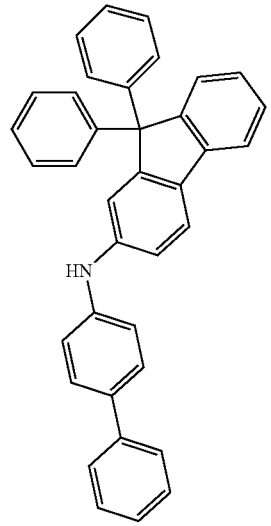
sub 2-34
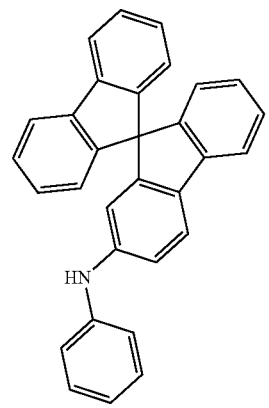
sub 2-35
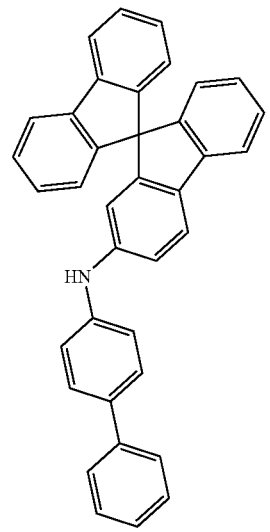

-continued
sub 2-36
sub 2-37
sub 2-38
sub 2-39
sub 2-40
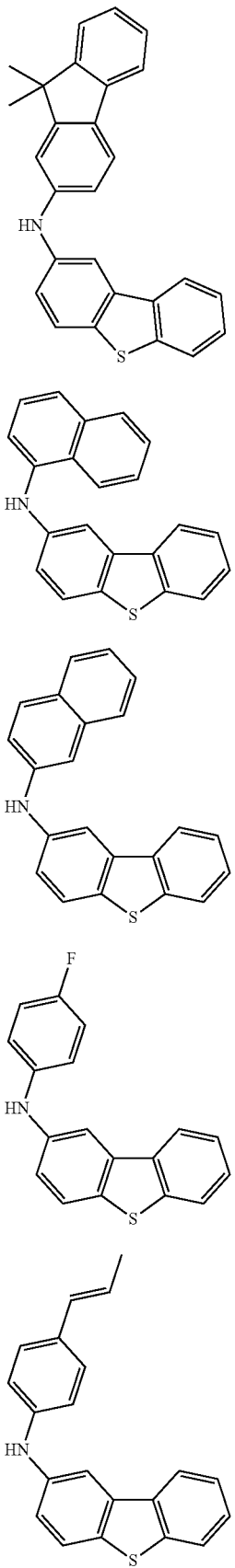
-continued
sub 2-41
sub 2-42
sub 2-43
sub 2-44
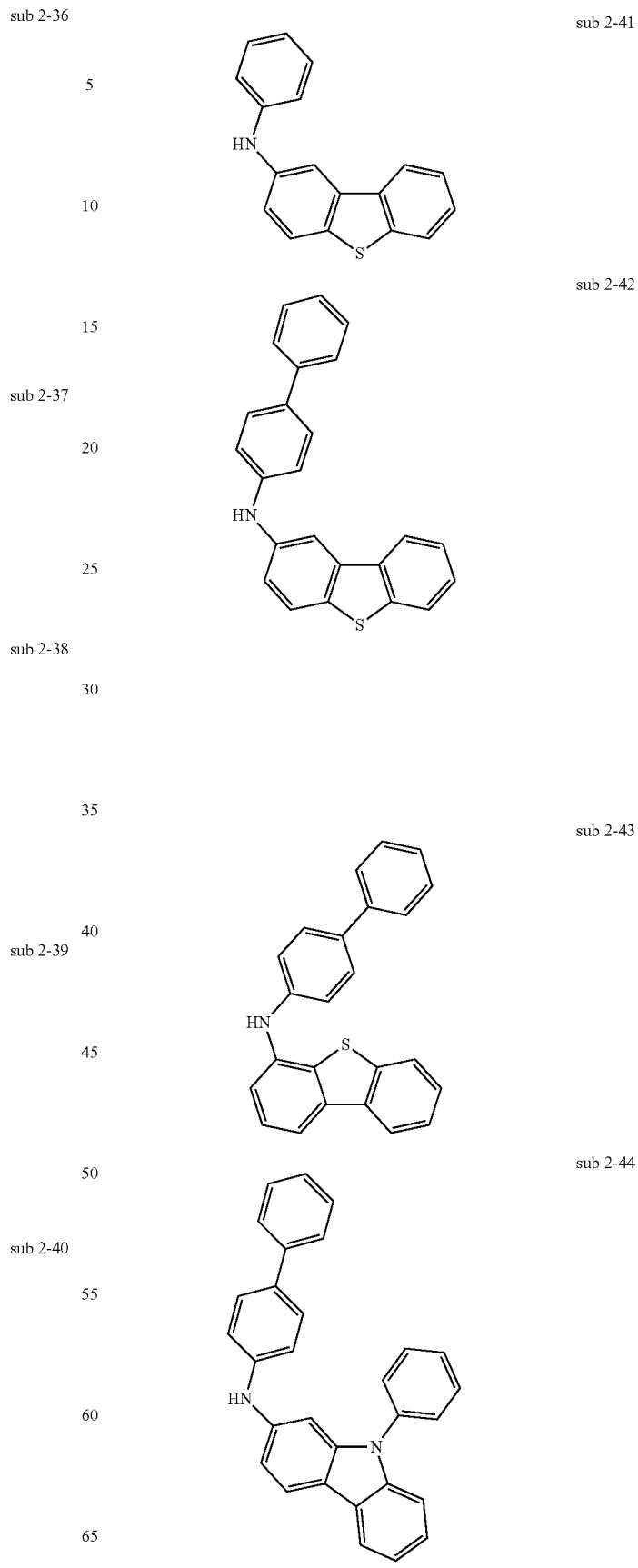

-continued sub 2-45 sub 2-46 sub 2-47

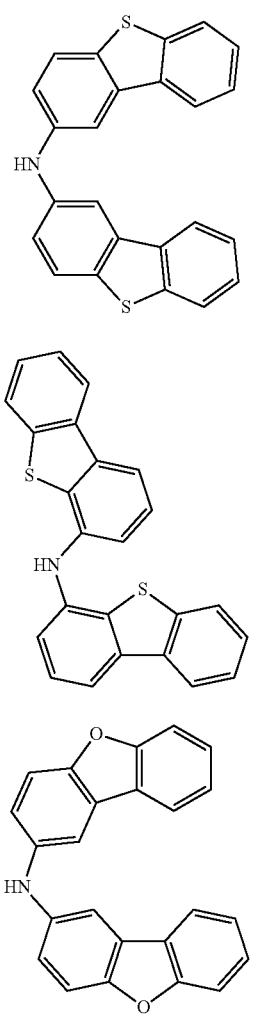

TABLE 2

| Compound | FD-MS | Compound | FD-MS |
|---|---|---|---|
| Sub 2-1 | m/z = 169.09($C_{12}H_{11}N$ = 169.22) | Sub 2-2 | m/z = 187.08($C_{12}H_{10}FN$ = 187.21) |
| Sub 2-3 | m/z = 209.12($C_{15}H_{15}N$ = 209.29) | Sub 2-4 | m/z = 205.07($C_{12}H_9F_2N$ = 205.20) |
| Sub 2-5 | m/z = 227.11($C_{15}H_{14}FN$ = 227.28) | Sub 2-6 | m/z = 249.15($C_{18}H_{19}N$ = 249.35) |
| Sub 2-7 | m/z = 219.10($C_{16}H_{13}N$ = 219.28) | Sub 2-8 | m/z = 237.10($C_{16}H_{12}FN$ = 237.27) |
| Sub 2-9 | m/z = 259.14($C_{19}H_{17}N$ = 259.34) | Sub 2-10 | m/z = 295.14($C_{22}H_{17}N$ = 295.38) |
| Sub 2-11 | m/z = 219.10($C_{16}H_{13}N$ = 219.28) | Sub 2-12 | m/z = 237.10($C_{16}H_{12}FN$ = 237.27) |
| Sub 2-13 | m/z = 259.14($C_{19}H_{17}N$ = 259.34) | Sub 2-14 | m/z = 295.14($C_{22}H_{17}N$ = 295.38) |
| Sub 2-15 | m/z = 269.12($C_{20}H_{15}N$ = 269.34) | Sub 2-16 | m/z = 269.12($C_{20}H_{15}N$ = 269.34) |
| Sub 2-17 | m/z = 269.12($C_{20}H_{15}N$ = 269.34) | Sub 2-18 | m/z = 321.15($C_{24}H_{19}N$ = 321.41) |
| Sub 2-19 | m/z = 245.12($C_{18}H_{15}N$ = 245.32) | Sub 2-20 | m/z = 263.11($C_{18}H_{14}FN$ = 263.31) |
| Sub 2-21 | m/z = 285.15($C_{21}H_{19}N$ = 285.38) | Sub 2-22 | m/z = 321.15($C_{24}H_{19}N$ = 321.41) |
| Sub 2-23 | m/z = 397.18($C_{30}H_{23}N$ = 397.51) | Sub 2-24 | m/z = 335.17($C_{25}H_{21}N$ = 335.44) |

TABLE 2-continued

| Compound | FD-MS | Compound | FD-MS |
|---|---|---|---|
| Sub 2-25 | m/z = 335.17($C_{25}H_{21}N$ = 335.44) | Sub 2-26 | m/z = 303.14($C_{21}H_{18}FN$ = 303.37) |
| Sub 2-27 | m/z = 325.18($C_{24}H_{23}N$ = 325.45) | Sub 2-28 | m/z = 285.15($C_{21}H_{19}N$ = 285.38) |
| Sub 2-29 | m/z = 361.18($C_{27}H_{23}N$ = 361.48) | Sub 2-30 | m/z = 401.21($C_{30}H_{27}N$ = 401.54) |
| Sub 2-31 | m/z = 409.18($C_{31}H_{23}N$ = 409.52) | Sub 2-32 | m/z = 459.20($C_{35}H_{25}N$ = 459.58) |
| Sub 2-33 | m/z = 485.21($C_{37}H_{27}N$ = 485.62) | Sub 2-34 | m/z = 407.17($C_{31}H_{21}N$ = 407.51) |
| Sub 2-35 | m/z = 483.20($C_{37}H_{25}N$ = 483.60) | Sub 2-36 | m/z = 391.14($C_{27}H_{21}NS$ = 391.53) |
| Sub 2-37 | m/z = 325.09($C_{22}H_{15}NS$ = 325.43) | Sub 2-38 | m/z = 325.09($C_{22}H_{15}NS$ = 325.43) |
| Sub 2-39 | m/z = 293.07($C_{18}H_{12}FNS$ = 293.36) | Sub 2-40 | m/z = 315.11($C_{21}H_{17}NS$ = 315.43) |
| Sub 2-41 | m/z = 275.08($C_{18}H_{13}NS$ = 275.37) | Sub 2-42 | m/z = 351.11($C_{24}H_{17}NS$ = 351.46) |
| Sub 2-43 | m/z = 351.11($C_{24}H_{17}NS$ = 351.46) | Sub 2-44 | m/z = 410.18($C_{30}H_{22}N_2$ = 410.51) |
| Sub 2-45 | m/z = 381.06($C_{24}H_{15}NS_2$ = 381.51) | Sub 2-46 | m/z = 381.06($C_{24}H_{15}NS_2$ = 381.51) |
| Sub 2-47 | m/z = 349.11($C_{24}H_{15}NO_2$ = 349.38) | | |

Example 3

Synthesis of Product

Sub 2 (1 equivalent weight) was dissolved in toluene in a round bottom flask, and Sub 1 (1.2 equivalent weight), $Pd_2(dba)_3$ (0.03 equivalent weight), $P(t-Bu)_3$ (0.08 equivalent weight), and NaOt-Bu (3 equivalent weight) were added to the reaction solution, followed by stirring at 100° C. Upon completion of the reaction, the reaction product was extracted with $CH_2Cl_2$ and water, the extracted organic layer was dried with $MgSO_4$ and concentrated, and then the produced organic material was separated by a silica gel column and recrystallized to obtain final products.

(1) Synthesis Method of Product 1-1

<Reaction Scheme 23>

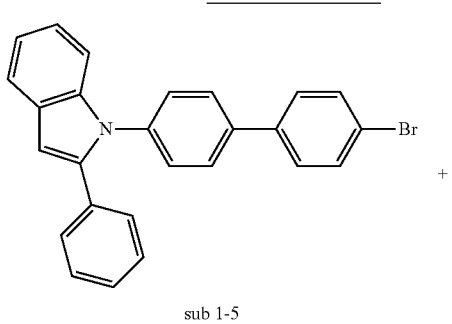

sub 1-5

+

-continued

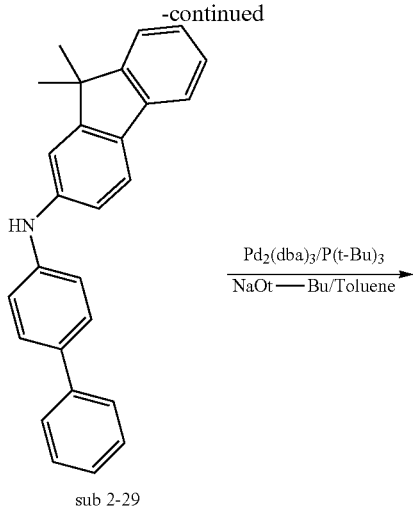

sub 2-29

(2) Synthesis Method of Product 1-2

<Reaction Scheme 24>

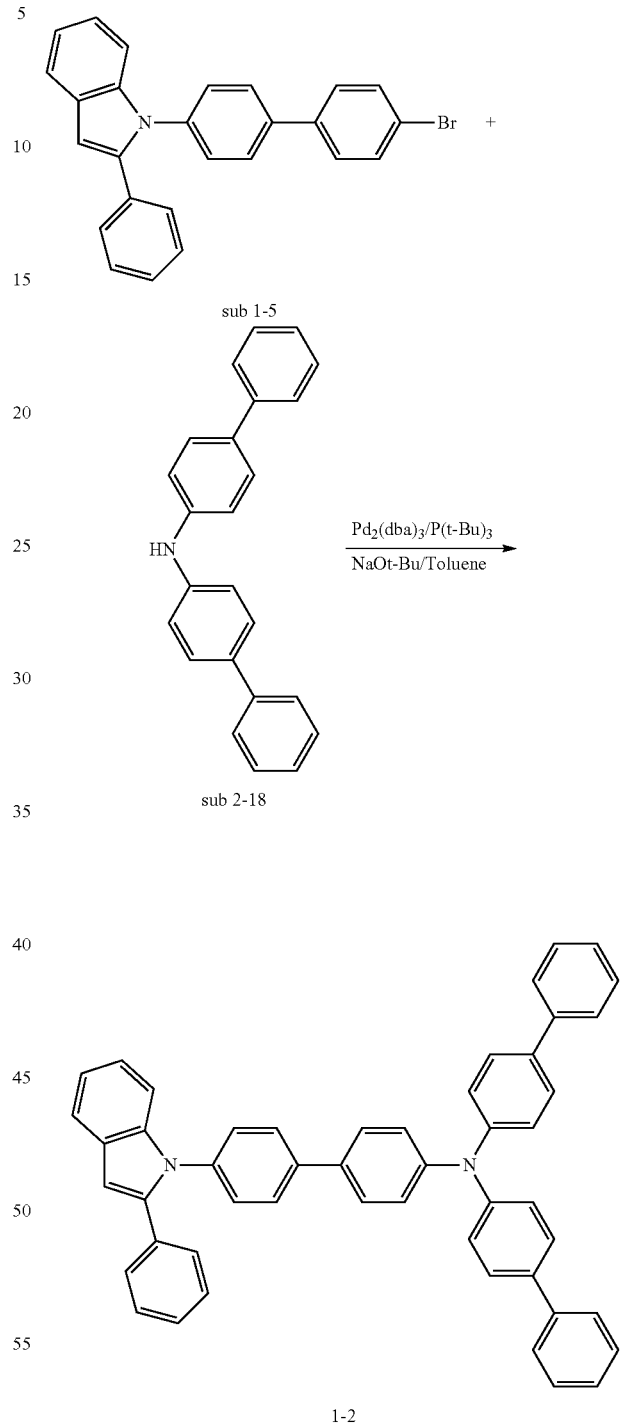

Sub 2-29 (7.5 g, 20.8 mmol) obtained in the above synthesis was dissolved in toluene in a round bottom flask, and Sub 1-5 (10.57 g, 24.9 mmol) obtained above synthesis, Pd$_2$(dba)$_3$ (0.57 g, 0.6 mmol), 50% P(t-Bu)$_3$ (0.8 ml, 1.7 mmol), and NaOt-Bu (6 g, 62.4 mmol) were added to the reaction solution, followed by stirring at 100° C. Upon completion of the reaction, the reaction product was extracted with CH$_2$Cl$_2$ and water, the extracted organic layer was dried with MgSO$_4$ and concentrated, and then the produced organic material was separated by a silica gel column and recrystallized to obtain 11.88 g of product (yield: 81%).

Using Sub 2-18 (7.71 g, 24 mmol) obtained in the above synthesis, Sub 1-5 (12.22 g, 28.8 mmol) obtained in the above synthesis, Pd$_2$(dba)$_3$ (0.64 g, 0.7 mmol), 50% P(t-Bu)$_3$ (0.9 ml, 1.9 mmol), NaOt-Bu (6.92 g, 72 mmol), and toluene, the same procedure as described in the synthesis method of Product 1-1 of Example 3 was carried out to obtain 11.81 g of product (yield: 74%).

(3) Synthesis Method of Product 1-4

(4) Synthesis Method of Product 1-5

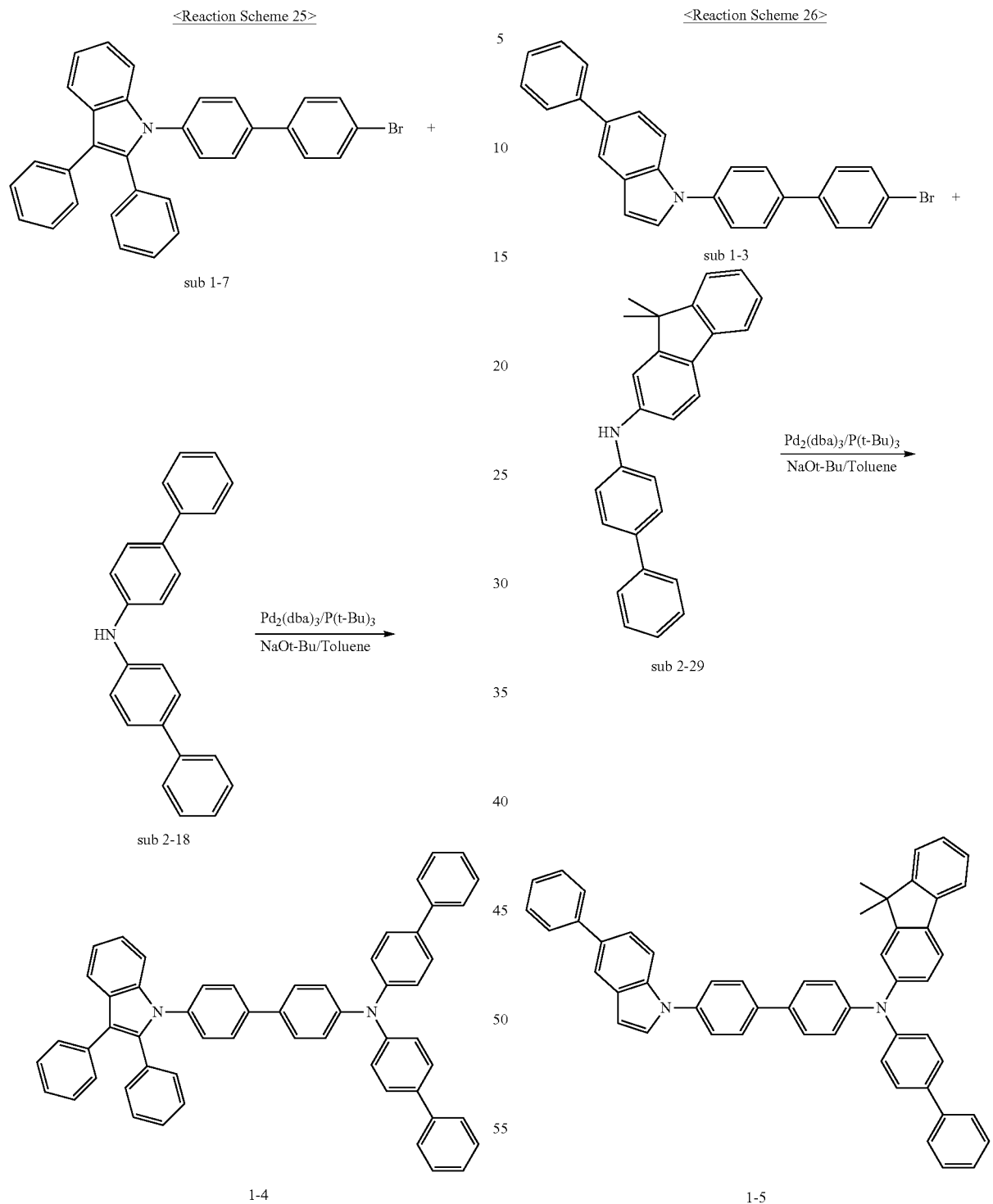

Using Sub 2-18 (7.29 g, 22.7 mmol) obtained in the above synthesis, Sub 1-7 (13.62 g, 27.2 mmol) obtained in the above synthesis, $Pd_2(dba)_3$ (0.62 g, 0.7 mmol), 50% P(t-Bu)$_3$ (0.9 ml, 1.8 mmol), NaOt-Bu (6.55 g, 68.1 mmol), and toluene, the same procedure as described in the synthesis method of Product 1-1 of Example 3 was carried out to obtain 12.11 g of product (yield: 72%).

Using Sub 2-29 (8.21 g, 22.7 mmol) obtained in the above synthesis, Sub 1-3 (11.58 g, 27.3 mmol) obtained in the above synthesis, $Pd_2(dba)_3$ (0.62 g, 0.7 mmol), 50% P(t-Bu)$_3$ (0.9 ml, 1.8 mmol), NaOt-Bu (6.55 g, 68.1 mmol), and toluene, the same procedure as described in the synthesis method of Product 1-1 of Example 3 was carried out to obtain 12 g of product (yield: 75%).

(5) Synthesis Method of Product 1-6

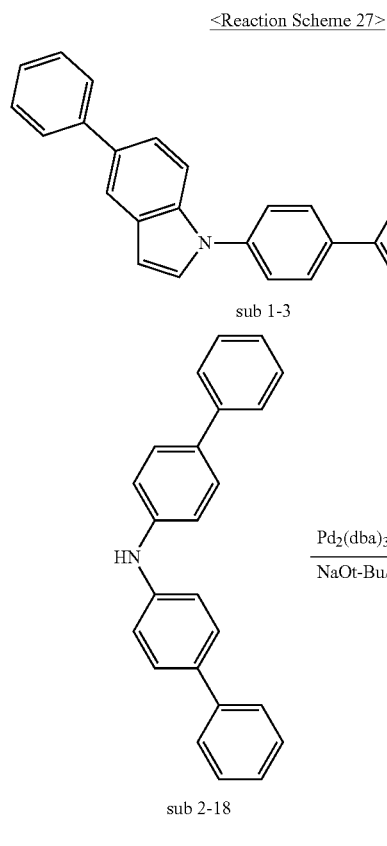

<Reaction Scheme 27> sub 1-3 sub 2-18

1-6

(6) Synthesis Method of Product 1-13

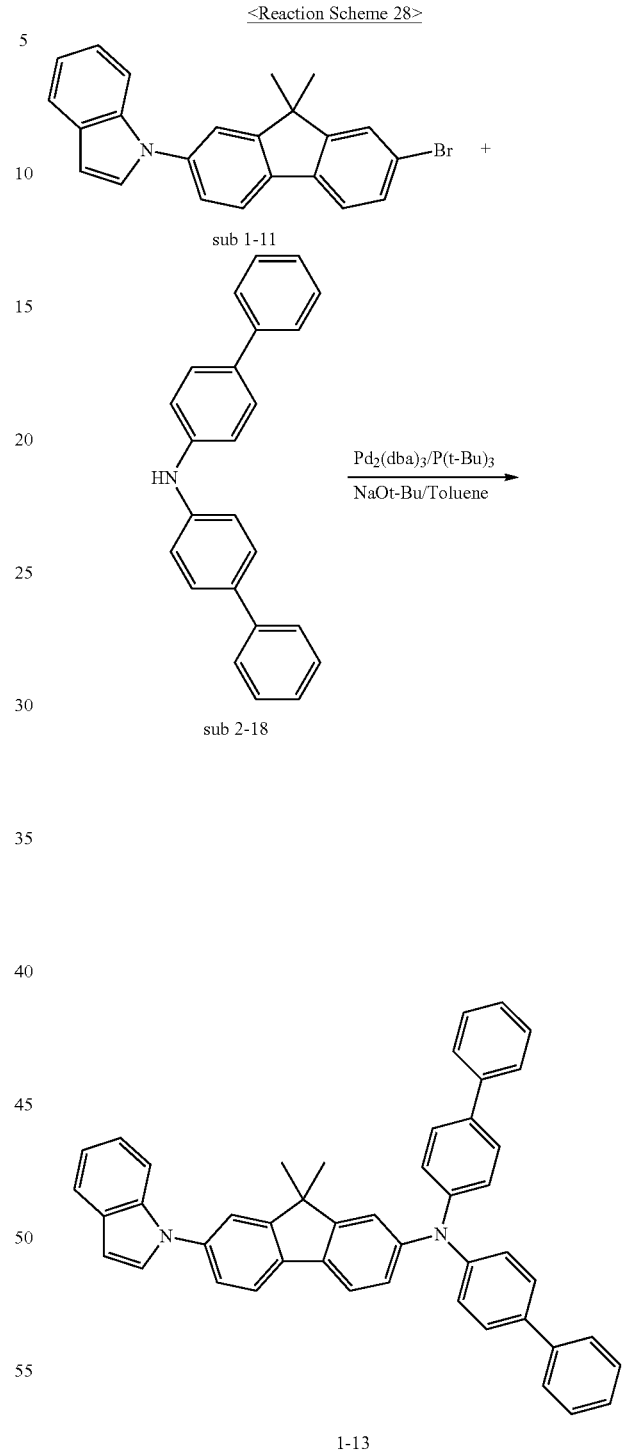

<Reaction Scheme 28> sub 1-11 sub 2-18

1-13

Using Sub 2-18 (10.37 g, 32.3 mmol) obtained in the above synthesis, Sub 1-3 (16.43 g, 38.7 mmol) obtained in the above synthesis, $Pd_2(dba)_3$ (0.89 g, 1 mmol), 50% $P(t\text{-}Bu)_3$ (1.3 ml, 2.6 mmol), NaOt-Bu (9.31 g, 96.3 mmol), and toluene, the same procedure as described in the synthesis method of Product 1-1 of Example 3 was carried out to obtain 17.6 g of product (yield: 82%).

Using Sub 2-18 (8.46 g, 26.3 mmol) obtained in the above synthesis, Sub 1-11 (12.26 g, 31.6 mmol) obtained in the above synthesis, $Pd_2(dba)_3$ (0.72 g, 0.8 mmol), 50% $P(t\text{-}Bu)_3$ (1 ml, 2.1 mmol), NaOt-Bu (7.58 g, 78.9 mmol), and toluene, the same procedure as described in the synthesis method of Product 1-1 of Example 3 was carried out to obtain 13.06 g of product (yield: 79%).

(7) Synthesis Method of Product 1-14

<Reaction Scheme 29>

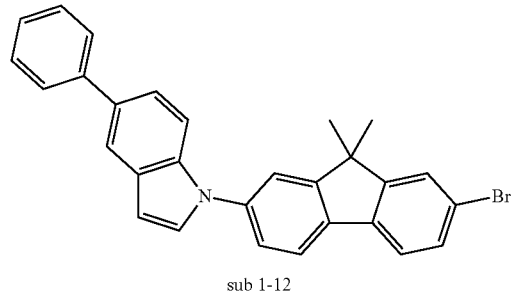

sub 1-12

+

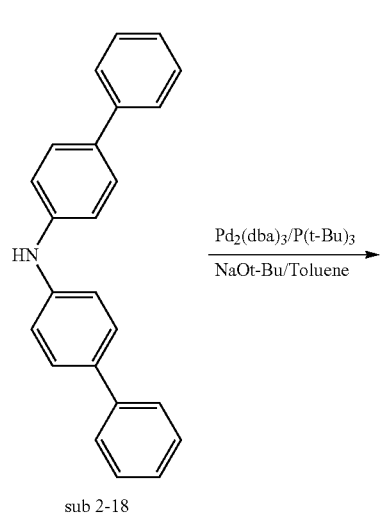

sub 2-18

→ (Pd$_2$(dba)$_3$/P(t-Bu)$_3$, NaOt-Bu/Toluene)

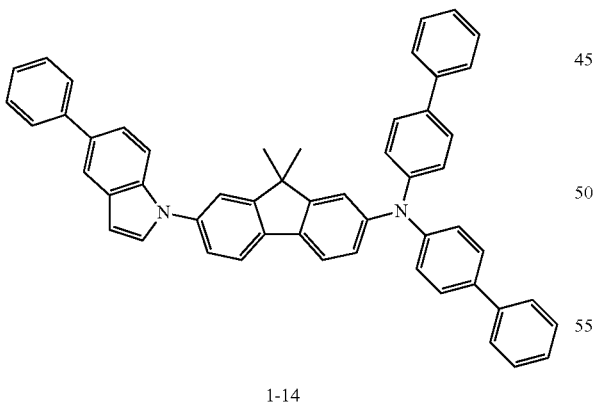

1-14

Using Sub 2-18 (8.46 g, 26.3 mmol) obtained in the above synthesis, Sub 1-12 (14.67 g, 31.6 mmol) obtained in the above synthesis, Pd$_2$(dba)$_3$ (0.72 g, 0.8 mmol), 50% P(t-Bu)$_3$ (1 ml, 2.1 mmol), NaOt-Bu (7.58 g, 78.9 mmol), and toluene, the same procedure as described in the synthesis method of Product 1-1 of Example 3 was carried out to obtain 14.27 g of product (yield: 77%).

(8) Synthesis Method of Product 1-15

<Reaction Scheme 30>

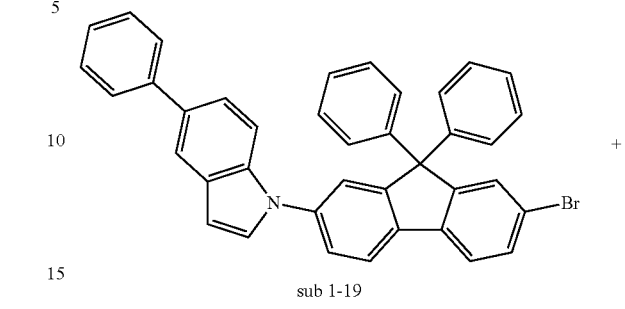

sub 1-19

+

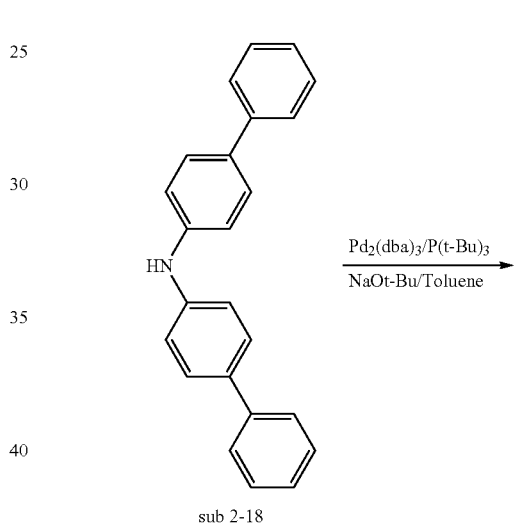

sub 2-18

→ (Pd$_2$(dba)$_3$/P(t-Bu)$_3$, NaOt-Bu/Toluene)

1-15

Using Sub 2-18 (11.84 g, 36.8 mmol) obtained in the above synthesis, Sub 1-19 (26.02 g, 44.2 mmol) obtained in the above synthesis, Pd$_2$(dba)$_3$ (1.01 g, 1.1 mmol), 50% P(t-Bu)$_3$ (1.4 ml, 2.9 mmol), NaOt-Bu (10.61 g, 110.4 mmol), and toluene, the same procedure as described in the synthesis method of Product 1-1 of Example 3 was carried out to obtain 20.44 g of product (yield: 67%).

(9) Synthesis Method of Product 1-17

<Reaction Scheme 31>

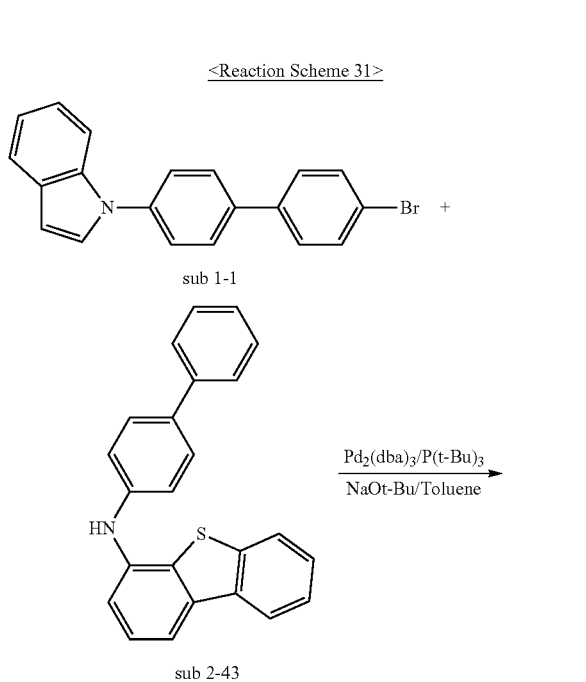

1-17

Using Sub 2-43 (8.33 g, 23.7 mmol) obtained in the above synthesis, Sub 1-1 (9.9 g, 28.4 mmol) obtained in the above synthesis, Pd$_2$(dba)$_3$ (0.65 g, 0.7 mmol), 50% P(t-Bu)$_3$ (0.9 ml, 1.9 mmol), NaOt-Bu (6.83 g, 71.1 mmol), and toluene, the same procedure as described in the synthesis method of Product 1-1 of Example 3 was carried out to obtain 11.29 g of product (yield: 77%).

(10) Synthesis Method of Product 1-20

<Reaction Scheme 32>

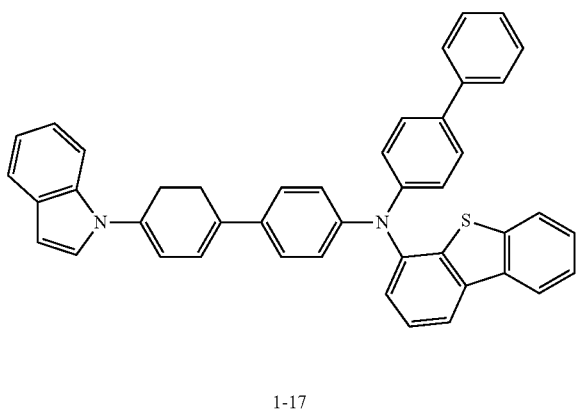

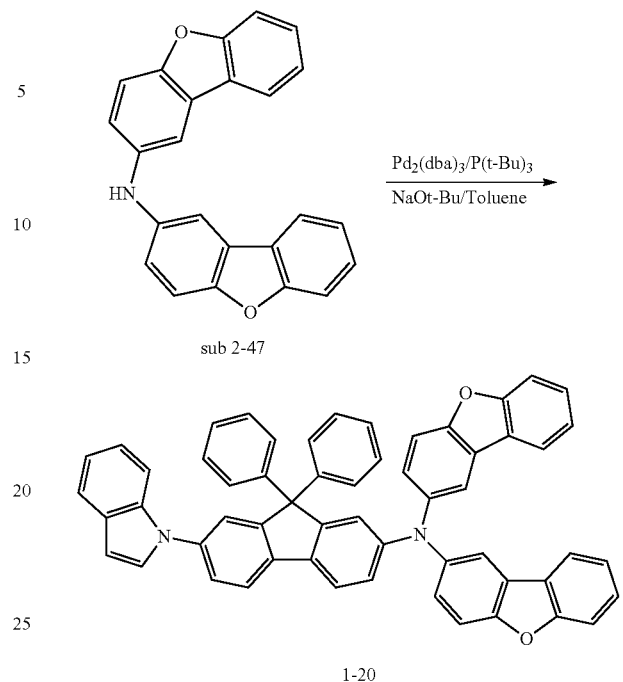

1-20

Using Sub 2-47 (9.81 g, 28.1 mmol) obtained in the above synthesis, Sub 1-25 (17.2 g, 33.7 mmol) obtained in the above synthesis, Pd$_2$(dba)$_3$ (0.77 g, 0.8 mmol), 50% P(t-Bu)$_3$ (1.1 ml, 2.3 mmol), NaOt-Bu (8.1 g, 84.3 mmol), and toluene, the same procedure as described in the synthesis method of Product 1-1 of Example 3 was carried out to obtain 18.17 g of product (yield: 83%).

(11) Synthesis Method of Product 1-96

<Reaction Scheme 33>

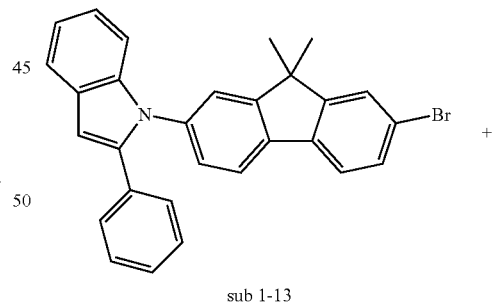

sub 1-13

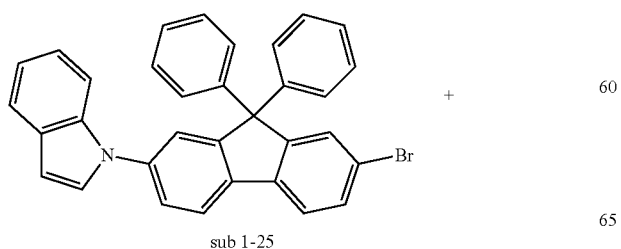

sub 2-11

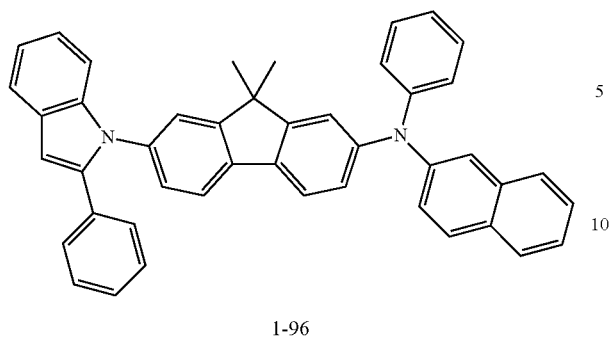

1-96

Using Sub 2-11 (7.02 g, 32 mmol) obtained in the above synthesis, Sub 1-13 (17.84 g, 38.4 mmol) obtained in the above synthesis, Pd$_2$(dba)$_3$ (0.88 g, 1 mmol), 50% P(t-Bu)$_3$ (1.3 ml, 2.6 mmol), NaOt-Bu (9.23 g, 96 mmol), and toluene, the same procedure as described in the synthesis method of Product 1-1 of Example 3 was carried out to obtain 13.31 g of product (yield: 69%).

(12) Synthesis Method of Product 1-112

<Reaction Scheme 34>

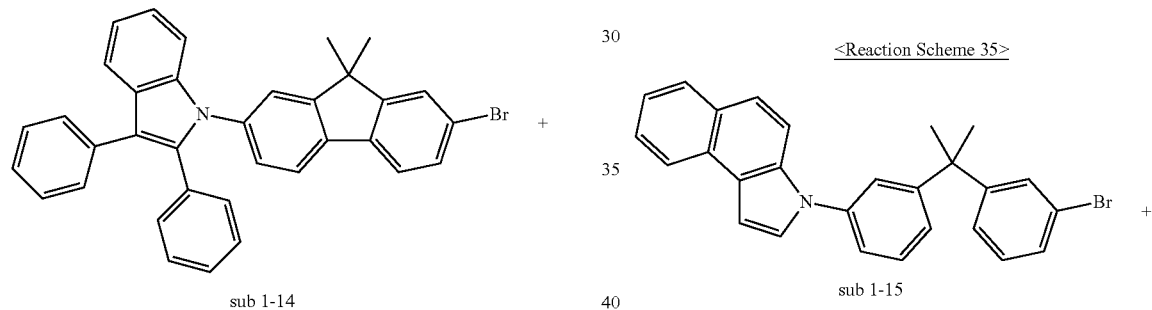

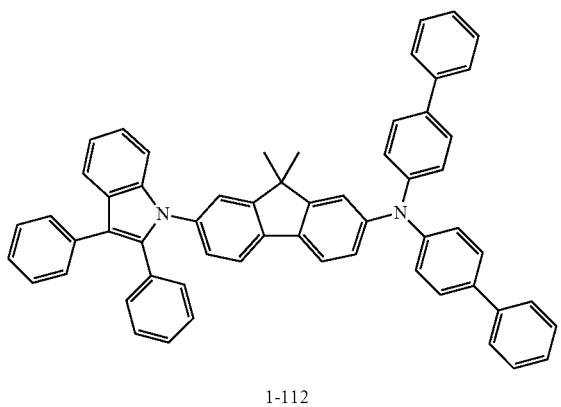

1-112

Using Sub 2-18 (7.17 g, 22.3 mmol) obtained in the above synthesis, Sub 1-14 (14.47 g, 26.8 mmol) obtained in the above synthesis, Pd$_2$(dba)$_3$ (0.61 g, 0.7 mmol), 50% P(t-Bu)$_3$ (0.9 ml, 1.8 mmol), NaOt-Bu (6.43 g, 66.9 mmol), and toluene, the same procedure as described in the synthesis method of Product 1-1 of Example 3 was carried out to obtain 11.15 g of product (yield: 64%).

(13) Synthesis Method of Product 1-127

<Reaction Scheme 35>

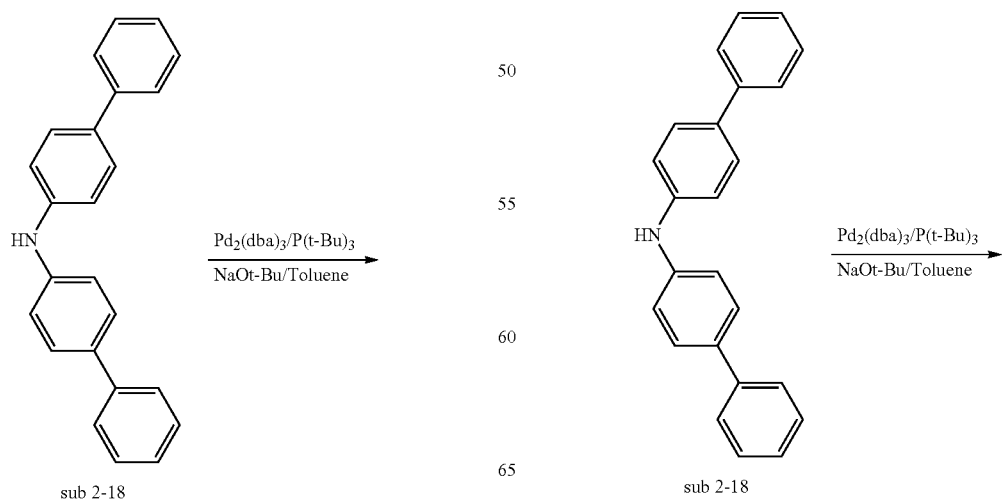

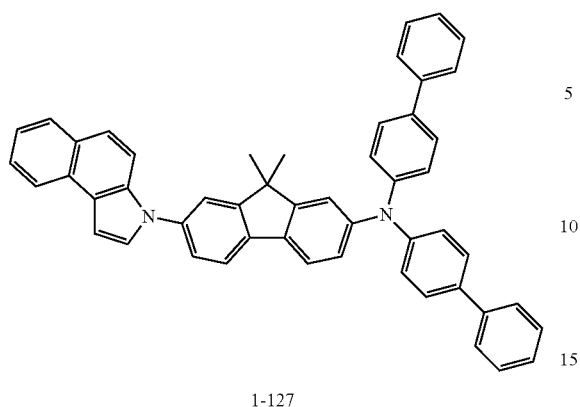

1-127

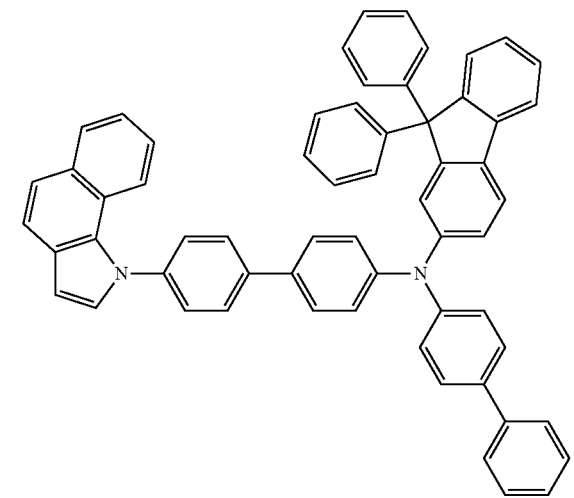

1-135

Using Sub 2-18 (7.05 g, 21.9 mmol) obtained in the above synthesis, Sub 1-15 (11.54 g, 26.3 mmol) obtained in the above synthesis, Pd$_2$(dba)$_3$ (0.6 g, 0.7 mmol), 50% P(t-Bu)$_3$ (0.9 ml, 1.8 mmol), NaOt-Bu (6.31 g, 65.7 mmol), and toluene, the same procedure as described in the synthesis method of Product 1-1 of Example 3 was carried out to obtain 10.56 g of product (yield: 71%).

(14) Synthesis Method of Product 1-135

Using Sub 2-33 (7.22 g, 14.9 mmol) obtained in the above synthesis, Sub 1-9 (7.11 g, 17.8 mmol) obtained in the above synthesis, Pd$_2$(dba)$_3$ (0.41 g, 0.5 mmol), 50% P(t-Bu)$_3$ (0.6 ml, 1.2 mmol), NaOt-Bu (4.3 g, 44.7 mmol), and toluene, the same procedure as described in the synthesis method of Product 1-1 of Example 3 was carried out to obtain 9.93 g of product (yield: 83%).

(15) Synthesis Method of Product 1-142

<Reaction Scheme 36>

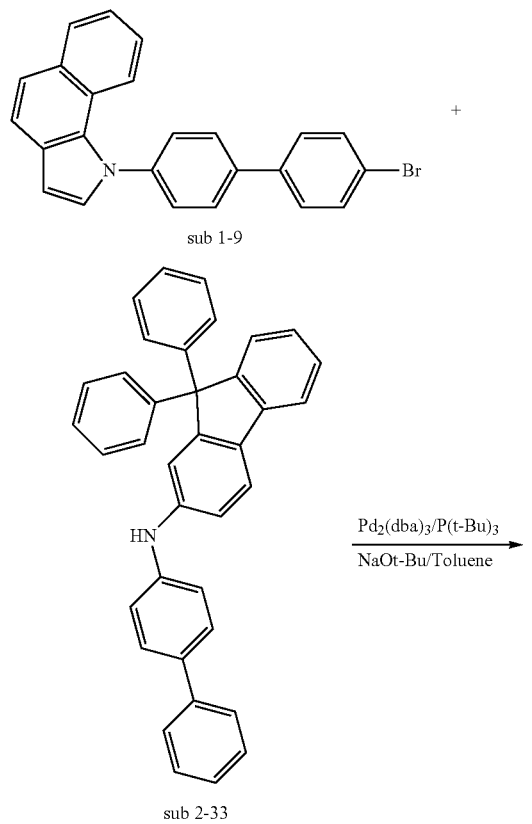

<Reaction Scheme 37>

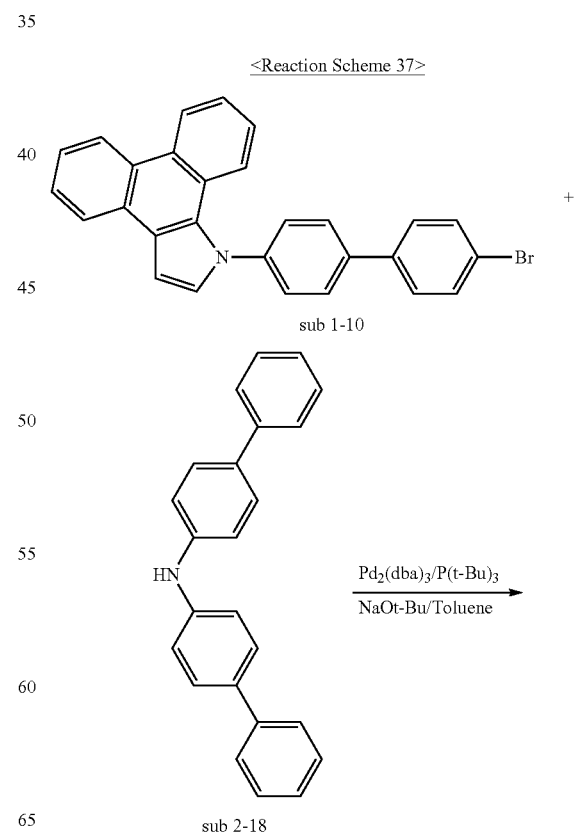

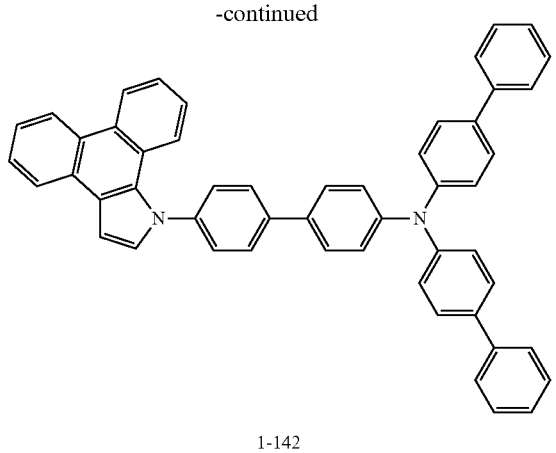

1-142

Using Sub 2-18 (8.24 g, 25.6 mmol) obtained in the above synthesis, Sub 1-10 (13.8 g, 30.8 mmol) obtained in the above synthesis, $Pd_2(dba)_3$ (0.71 g, 0.8 mmol), 50% $P(t\text{-}Bu)_3$ (1 ml, 2.1 mmol), NaOt-Bu (7.38 g, 76.8 mmol), and toluene, the same procedure as described in the synthesis method of Product 1-1 of Example 3 was carried out to obtain 13.4 g of product (yield: 76%).

FD-MS values for the inventive compounds 1-1 to 1-150 prepared according to Synthesis Methods above are given in Table 3 below.

TABLE 3

| Compound | FD-MS | Compound | FD-MS |
| --- | --- | --- | --- |
| 1-1 | m/z = 704.32($C_{53}H_{40}N_2$ = 704.90) | 1-2 | m/z = 664.29($C_{50}H_{36}N_2$ = 664.83) |
| 1-3 | m/z = 740.32($C_{56}H_{40}N_2$ = 740.93) | 1-4 | m/z = 740.32($C_{56}H_{40}N_2$ = 740.93) |
| 1-5 | m/z = 704.32($C_{53}H_{40}N_2$ = 704.90) | 1-6 | m/z = 664.29($C_{50}H_{36}N_2$ = 664.83) |
| 1-7 | m/z = 588.26($C_{44}H_{32}N_2$ = 588.74) | 1-8 | m/z = 664.29($C_{50}H_{36}N_2$ = 664.83) |
| 1-9 | m/z = 752.32($C_{57}H_{40}N_2$ = 752.94) | 1-10 | m/z = 750.30($C_{57}H_{38}N_2$ = 750.93) |
| 1-11 | m/z = 676.29($C_{51}H_{36}N_2$ = 676.84) | 1-12 | m/z = 674.27($C_{51}H_{34}N_2$ = 674.83) |
| 1-13 | m/z = 628.29($C_{47}H_{36}N_2$ = 628.80) | 1-14 | m/z = 704.32($C_{53}H_{40}N_2$ = 704.90) |
| 1-15 | m/z = 828.35($C_{63}H_{44}N_2$ = 829.04) | 1-16 | m/z = 752.32($C_{57}H_{40}N_2$ = 752.94) |
| 1-17 | m/z = 618.21($C_{44}H_{30}N_2S$ = 618.79) | 1-18 | m/z = 648.17($C_{44}H_{28}N_2S_2$ = 648.84) |
| 1-19 | m/z = 793.35($C_{59}H_{43}N_3$ = 793.99) | 1-20 | m/z = 778.26($C_{57}H_{34}N_2O_2$ = 778.89) |
| 1-21 | m/z = 436.19($C_{32}H_{24}N_2$ = 436.55) | 1-22 | m/z = 486.21($C_{36}H_{26}N_2$ = 486.61) |
| 1-23 | m/z = 486.21($C_{36}H_{26}N_2$ = 486.61) | 1-24 | m/z = 512.23$C_{38}H_{28}N_2$ = 512.64) |
| 1-25 | m/z = 542.18($C_{38}H_{26}N_2S$ = 542.69) | 1-26 | m/z = 552.26($C_{41}H_{32}N_2$ = 552.71) |
| 1-27 | m/z = 454.18($C_{32}H_{23}FN_2$ = 454.54) | 1-28 | m/z = 476.23($C_{35}H_{28}N_2$ = 476.61) |
| 1-29 | m/z = 536.23($C_{40}H_{28}N_2$ = 536.66) | 1-30 | m/z = 536.23($C_{40}H_{28}N_2$ = 536.66) |
| 1-31 | m/z = 562.24($C_{42}H_{30}N_2$ = 562.70) | 1-32 | m/z = 592.20($C_{42}H_{28}N_2S$ = 592.75) |
| 1-33 | m/z = 602.27($C_{45}H_{34}N_2$ = 602.76) | 1-34 | m/z = 504.20($C_{36}H_{25}FN_2$ = 504.60) |
| 1-35 | m/z = 526.24($C_{39}H_{30}N_2$ = 526.67) | 1-36 | m/z = 536.23($C_{40}H_{28}N_2$ = 536.66) |
| 1-37 | m/z = 562.24($C_{42}H_{30}N_2$ = 562.70) | 1-38 | m/z = 592.20($C_{42}H_{28}N_2S$ = 592.75) |
| 1-39 | m/z = 602.27($C_{45}H_{34}N_2$ = 602.76) | 1-40 | m/z = 504.20($C_{36}H_{25}FN_2$ = 504.60) |
| 1-41 | m/z = 526.24($C_{39}H_{30}N_2$ = 526.67) | 1-42 | m/z = 588.26($C_{44}H_{32}N_2$ = 588.74) |
| 1-43 | m/z = 618.21($C_{44}H_{30}N_2S$ = 618.79) | 1-44 | m/z = 628.29($C_{47}H_{36}N_2$ = 628.80) |
| 1-45 | m/z = 530.22($C_{38}H_{27}FN_2$ = 530.63) | 1-46 | m/z = 552.26($C_{41}H_{32}N_2$ = 552.71) |
| 1-47 | m/z = 648.17($C_{44}H_{28}N_2S_2$ = 648.84) | 1-48 | m/z = 658.24($C_{47}H_{34}N_2S$ = 658.85) |
| 1-49 | m/z = 560.17($C_{38}H_{25}FN_2S$ = 560.68) | 1-50 | m/z = 582.21($C_{41}H_{30}N_2S$ = 582.76) |
| 1-51 | m/z = 668.32($C_{50}H_{40}N_2$ = 668.87) | 1-52 | m/z = 570.25($C_{41}H_{31}FN_2$ = 570.70) |
| 1-53 | m/z = 592.29($C_{44}H_{36}N_2$ = 592.77) | 1-54 | m/z = 472.18($C_{32}H_{22}F_2N_2$ = 472.53) |
| 1-55 | m/z = 494.22($C_{35}H_{27}FN_2$ = 494.60) | 1-56 | m/z = 516.26($C_{38}H_{32}N_2$ = 516.67) |
| 1-57 | m/z = 454.18($C_{32}H_{23}FN_2$ = 454.54) | 1-58 | m/z = 512.23($C_{38}H_{28}N_2$ = 512.64) |
| 1-59 | m/z = 513.22($C_{37}H_{27}N_3$ = 513.63) | 1-60 | m/z = 603.27($C_{44}H_{33}N_3$ = 603.75) |
| 1-61 | m/z = 726.30($C_{55}H_{38}N_2$ = 726.90) | 1-62 | m/z = 552.26($C_{41}H_{32}N_2$ = 552.71) |
| 1-63 | m/z = 602.27($C_{45}H_{34}N_2$ = 602.76) | 1-64 | m/z = 526.24($C_{39}H_{30}N_2$ = 526.67) |
| 1-65 | m/z = 676.29($C_{51}H_{36}N_2$ = 676.84) | 1-66 | m/z = 726.30($C_{55}H_{38}N_2$ = 726.90) |
| 1-67 | m/z = 650.27($C_{49}H_{34}N_2$ = 650.81) | 1-68 | m/z = 750.30($C_{57}H_{38}N_2$ = 750.93) |
| 1-69 | m/z = 674.27($C_{51}H_{34}N_2$ = 674.83) | 1-70 | m/z = 724.29($C_{55}H_{36}N_2$ = 724.89) |
| 1-71 | m/z = 648.26($C_{49}H_{32}N_2$ = 648.79) | 1-72 | m/z = 828.35($C_{63}H_{44}N_2$ = 829.04) |
| 1-73 | m/z = 638.27($C_{48}H_{34}N_2$ = 638.80) | 1-74 | m/z = 562.24($C_{42}H_{30}N_2$ = 562.70) |
| 1-75 | m/z = 802.33($C_{61}H_{42}N_2$ = 803.00) | 1-76 | m/z = 678.30($C_{51}H_{38}N_2$ = 678.86) |
| 1-77 | m/z = 628.29($C_{47}H_{36}N_2$ = 628.80) | 1-78 | m/z = 678.30($C_{51}H_{38}N_2$ = 678.86) |
| 1-79 | m/z = 602.27($C_{45}H_{34}N_2$ = 602.76) | 1-80 | m/z = 726.30($C_{55}H_{38}N_2$ = 726.90) |
| 1-81 | m/z = 752.32($C_{57}H_{40}N_2$ = 752.94) | 1-82 | m/z = 802.33($C_{61}H_{42}N_2$ = 803.00) |
| 1-83 | m/z = 826.33($C_{63}H_{42}N_2$ = 827.02) | 1-84 | m/z = 750.30($C_{57}H_{38}N_2$ = 750.93) |
| 1-85 | m/z = 800.32($C_{61}H_{40}N_2$ = 800.98) | 1-86 | m/z = 724.29($C_{55}H_{36}N_2$ = 724.89) |
| 1-87 | m/z = 588.26($C_{44}H_{32}N_2$ = 588.74) | 1-88 | m/z = 828.35($C_{63}H_{44}N_2$ = 829.04) |
| 1-89 | m/z = 638.27($C_{48}H_{34}N_2$ = 638.80) | 1-90 | m/z = 562.24($C_{42}H_{30}N_2$ = 562.70) |
| 1-91 | m/z = 802.33($C_{61}H_{42}N_2$ = 803.00) | 1-92 | m/z = 678.30($C_{51}H_{38}N_2$ = 678.86) |
| 1-93 | m/z = 704.32($C_{53}H_{40}N_2$ = 704.90) | 1-94 | m/z = 628.29($C_{47}H_{36}N_2$ = 628.80) |
| 1-95 | m/z = 678.30($C_{51}H_{38}N_2$ = 678.86) | 1-96 | m/z = 602.27($C_{45}H_{34}N_2$ = 602.76) |
| 1-97 | m/z = 828.35($C_{63}H_{44}N_2$ = 829.04) | 1-98 | m/z = 752.32($C_{57}H_{40}N_2$ = 752.94) |
| 1-99 | m/z = 802.33($C_{61}H_{42}N_2$ = 803.00) | 1-100 | m/z = 726.30($C_{55}H_{38}N_2$ = 726.90) |
| 1-101 | m/z = 826.33($C_{63}H_{42}N_2$ = 827.02) | 1-102 | m/z = 750.30($C_{57}H_{38}N_2$ = 750.93) |
| 1-103 | m/z = 800.32($C_{61}H_{40}N_2$ = 800.98) | 1-104 | m/z = 724.29($C_{55}H_{36}N_2$ = 724.89) |
| 1-105 | m/z = 714.30($C_{54}H_{38}N_2$ = 714.89) | 1-106 | m/z = 664.29($C_{50}H_{36}N_2$ = 664.83) |
| 1-107 | m/z = 780.35($C_{59}H_{44}N_2$ = 780.99) | 1-108 | m/z = 904.38($C_{69}H_{48}N_2$ = 905.13) |
| 1-109 | m/z = 638.27($C_{48}H_{34}N_2$ = 638.80) | 1-110 | m/z = 878.37($C_{67}H_{46}N_2$ = 879.10) |
| 1-111 | m/z = 754.33($C_{57}H_{42}N_2$ = 754.96) | 1-112 | m/z = 780.35($C_{59}H_{44}N_2$ = 780.99) |
| 1-113 | m/z = 828.35($C_{63}H_{44}N_2$ = 829.04) | 1-114 | m/z = 704.32($C_{53}H_{40}N_2$ = 704.90) |
| 1-115 | m/z = 754.33($C_{57}H_{42}N_2$ = 754.96) | 1-116 | m/z = 678.30($C_{51}H_{38}N_2$ = 678.86) |

TABLE 3-continued

| Compound | FD-MS | Compound | FD-MS |
|---|---|---|---|
| 1-117 | m/z = 904.38($C_{69}H_{48}N_2$ = 905.13) | 1-118 | m/z = 826.33($C_{63}H_{42}N_2$ = 827.02) |
| 1-119 | m/z = 878.37($C_{67}H_{46}N_2$ = 879.10) | 1-120 | m/z = 802.33($C_{61}H_{42}N_2$ = 803.00) |
| 1-121 | m/z = 902.37($C_{69}H_{46}N_2$ = 903.12) | 1-122 | m/z = 876.35($C_{67}H_{44}N_2$ = 877.08) |
| 1-123 | m/z = 800.32($C_{61}H_{40}N_2$ = 800.98) | 1-124 | m/z = 638.27($C_{48}H_{34}N_2$ = 638.80) |
| 1-125 | m/z = 678.30($C_{51}H_{38}N_2$ = 678.86) | 1-126 | m/z = 802.33($C_{61}H_{42}N_2$ = 803.00) |
| 1-127 | m/z = 678.30($C_{51}H_{38}N_2$ = 678.86) | 1-128 | m/z = 718.33($C_{54}H_{42}N_2$ = 718.92) |
| 1-129 | m/z = 842.37($C_{64}H_{46}N_2$ = 843.06) | 1-130 | m/z = 802.33($C_{61}H_{42}N_2$ = 803.00) |
| 1-131 | m/z = 842.37($C_{64}H_{46}N_2$ = 843.06) | 1-132 | m/z = 966.40($C_{74}H_{50}N_2$ = 967.20) |
| 1-133 | m/z = 638.27($C_{48}H_{34}N_2$ = 638.80) | 1-134 | m/z = 678.30($C_{51}H_{38}N_2$ = 678.86) |
| 1-135 | m/z = 802.33($C_{61}H_{42}N_2$ = 803.00) | 1-136 | m/z = 678.30($C_{51}H_{38}N_2$ = 678.86) |
| 1-137 | m/z = 718.33($C_{54}H_{42}N_2$ = 718.92) | 1-138 | m/z = 842.37($C_{64}H_{46}N_2$ = 843.06) |
| 1-139 | m/z = 802.33($C_{61}H_{42}N_2$ = 803.00) | 1-140 | m/z = 842.37($C_{64}H_{46}N_2$ = 843.06) |
| 1-141 | m/z = 966.40($C_{74}H_{50}N_2$ = 967.20) | 1-142 | m/z = 688.29($C_{52}H_{36}N_2$ = 688.86) |
| 1-143 | m/z = 728.32($C_{55}H_{40}N_2$ = 728.92) | 1-144 | m/z = 852.35($C_{65}H_{44}N_2$ = 853.06) |
| 1-145 | m/z = 728.32($C_{55}H_{40}N_2$ = 728.92) | 1-146 | m/z = 768.35($C_{58}H_{44}N_2$ = 768.98) |
| 1-147 | m/z = 892.38($C_{68}H_{48}N_2$ = 893.12) | 1-148 | m/z = 852.35($C_{65}H_{44}N_2$ = 853.06) |
| 1-149 | m/z = 892.38($C_{68}H_{48}N_2$ = 893.12) | 1-150 | m/z = 1016.41($C_{78}H_{52}N_2$ = 1017.26) |

Synthesis Example 2: Synthesis of Formula 2

<Reaction Scheme 38>

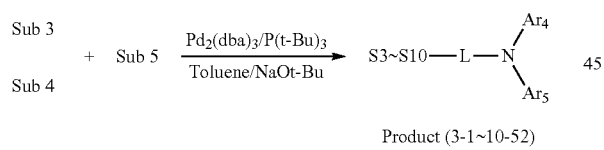

Product (3-1~10-52)

Example 4

1. Synthesis of Sub 3 (Same Experimental Method as Example 1 and Example 2 Above)

<Reaction Scheme 39> - Method 1

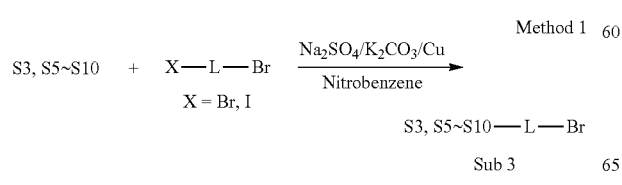

<Reaction Scheme 40> - Method 2

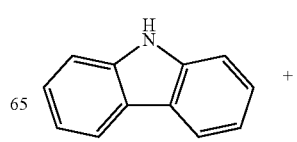

S3

S5

S6

S7

S8

S9

S10

(1) Synthesis Method of Sub 3-3-1 (L=biphenyl)

<Reaction Scheme 41>

261

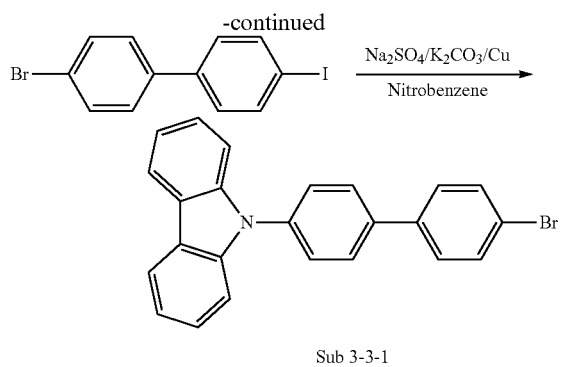

Sub 3-3-1

Using 9H-carbazole (50.16 g, 300 mmol) as the starting material and using 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-1 of Example 1 was carried out to obtain 80.05 g of product (yield: 67%).

(2) Synthesis Method of Sub 3-3-2 (L=9,9-dimethyl-9H-fluorene)

<Reaction Scheme 42>

Sub 3-3-2

Using 9H-carbazole (50.16 g, 300 mmol) as the starting material and using 2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-11 of Example 1 was carried out to obtain 88.11 g of product (yield: 67%).

262

(3) Synthesis Method of Sub 3-5-1 (L=9,9-dimethyl-9H-fluorene)

<Reaction Scheme 43>

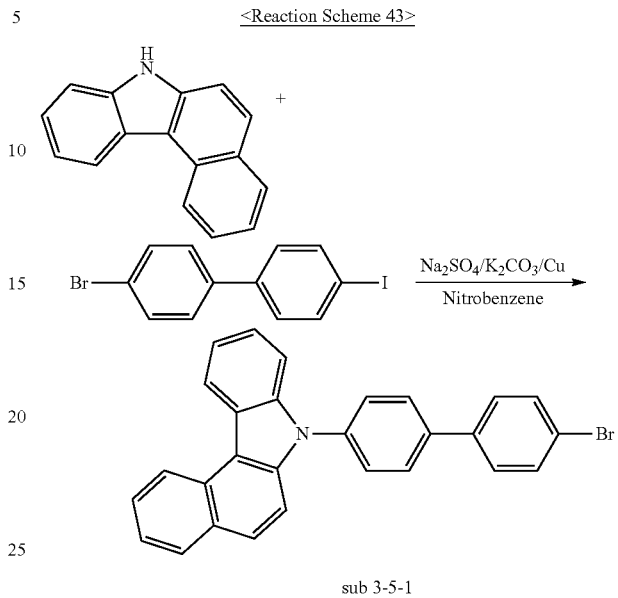

sub 3-5-1

Using 7H-benzo[c]carbazole (65.18 g, 300 mmol) as the starting material and using 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-1 of Example 1 was carried out to obtain 92.8 g of product (yield: 69%).

(4) Synthesis Method of Sub 3-5-2 (L=9,9-dimethyl-9H-fluorene)

<Reaction Scheme 44>

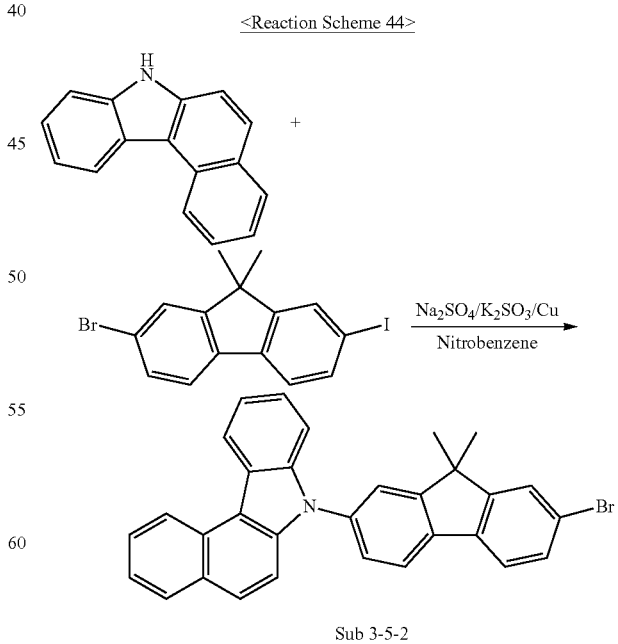

Sub 3-5-2

Using 7H-benzo[c]carbazole (65.18 g, 300 mmol) as the starting material and using 2-bromo-7-iodo-9,9-dimethyl- 9H-fluorene (143.7 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-11 of Example 1 was carried out to obtain 95.24 g of product (yield: 65%).

(5) Synthesis Method of Sub 3-6-1 (L=biphenyl)

<Reaction Scheme 45>

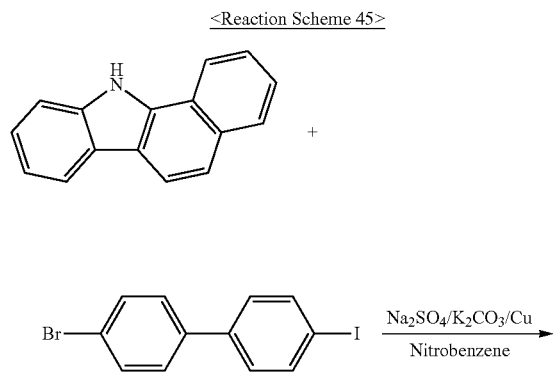

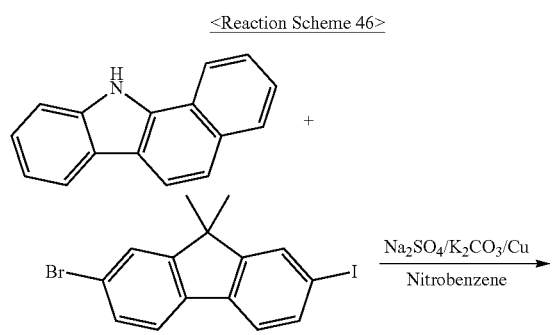

Sub 3-6-1

Using 11H-benzo[a]carbazole (65.18 g, 300 mmol) as the starting material and using 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-1 of Example 1 was carried out to obtain 80.05 g of product (yield: 62%).

(6) Synthesis Method of Sub 3-6-2 (L=9,9-dimethyl-9H-fluorene)

<Reaction Scheme 46>

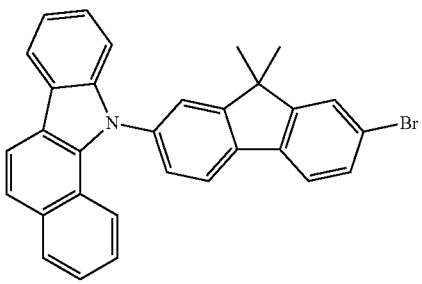

sub 3-6-2

Using 11H-benzo[a]carbazole (65.18 g, 300 mmol) as the starting material and using 2-bromo-7-iodo-9,9-dimethyl-9H-fluorene (143.7 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-11 of Example 1 was carried out to obtain 90.85 g of product (yield: 62%).

(7) Synthesis Method of Sub 3-7-1 (L=biphenyl)

<Reaction Scheme 47>

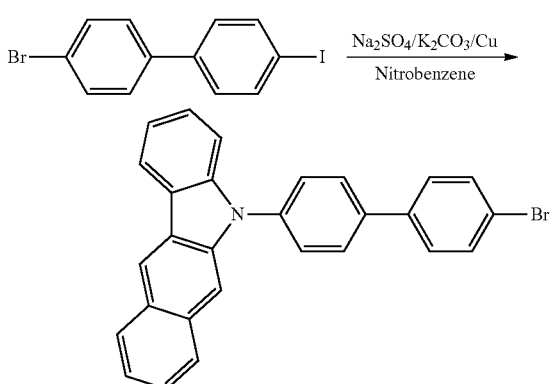

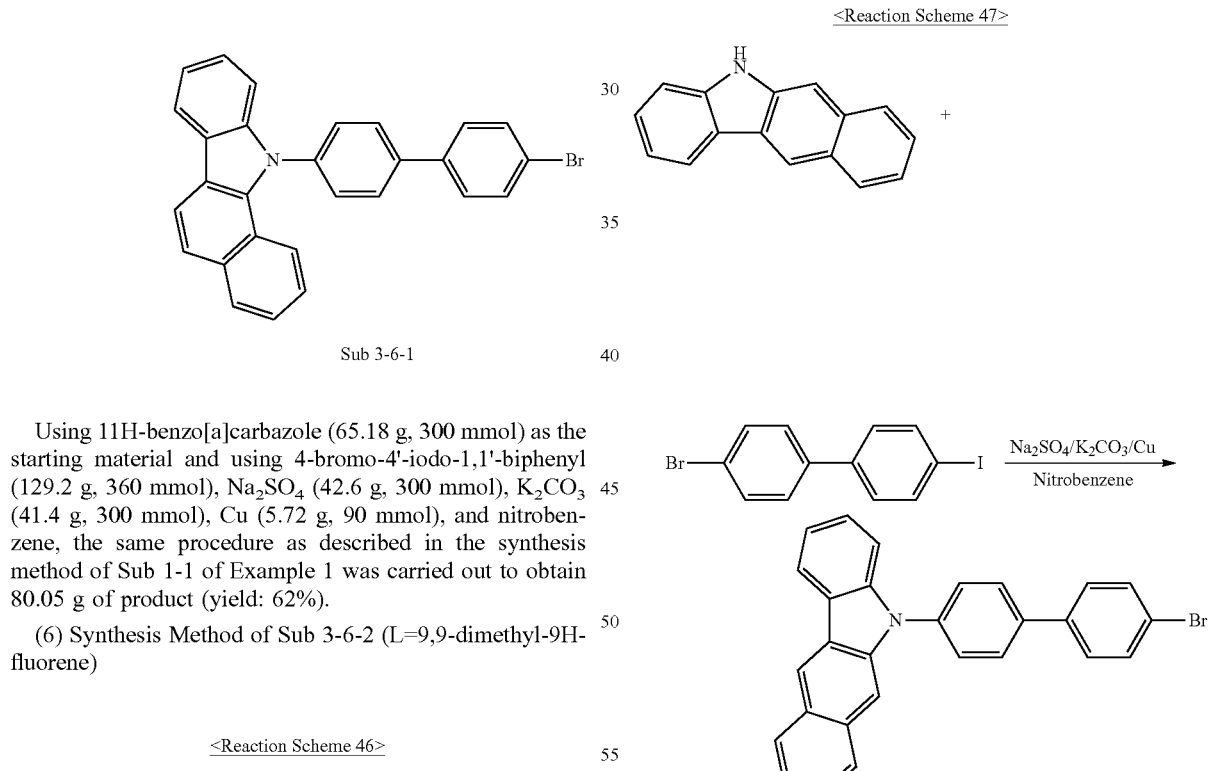

Sub 3-7-1

Using 5H-benzo[b]carbazole (65.18 g, 300 mmol) as the starting material and using 4-bromo-4'-iodo-1,1'-biphenyl (129.2 g, 360 mmol), Na₂SO₄ (42.6 g, 300 mmol), K₂CO₃ (41.4 g, 300 mmol), Cu (5.72 g, 90 mmol), and nitrobenzene, the same procedure as described in the synthesis method of Sub 1-1 of Example 1 was carried out to obtain 80.7 g of product (yield: 60%).

(8) Synthesis Method of Sub 3-7-2 (L=9,9-dimethyl-9H-fluorene)

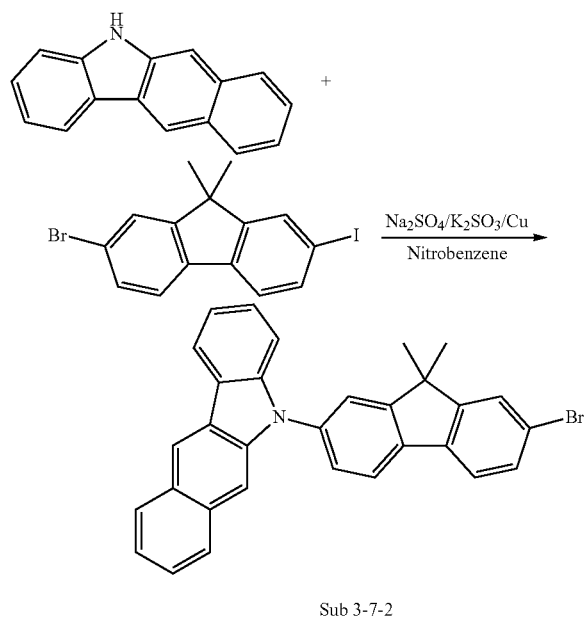

Sub 3-7-2

Using 5H-benzo[b]carbazole (65.18 g, 300 mmol) as the starting material and using 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), and nitrobenzene, the same procedure as described in the synthesis method of Sub 1-11 of Example 1 was carried out to obtain 93.78 g of product (yield: 64%).

(9) Synthesis Method of Sub 3-8-1 (L=biphenyl)

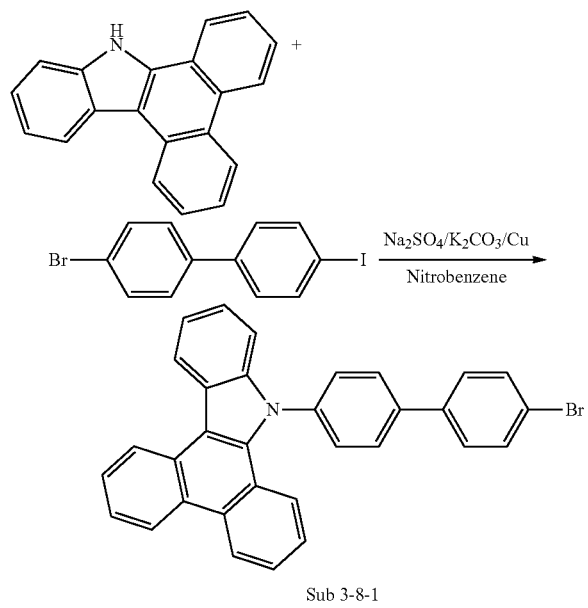

Sub 3-8-1

Using 9H-dibenzo[a,c]carbazole (80.2 g, 300 mmol) as the starting material and using 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), and nitrobenzene, the same procedure as described in the synthesis method of Sub 1-1 of Example 1 was carried out to obtain 98.7 g of product (yield: 66%).

(10) Synthesis Method of Sub 3-8-2 (L=9,9-dimethyl-9H-fluorene)

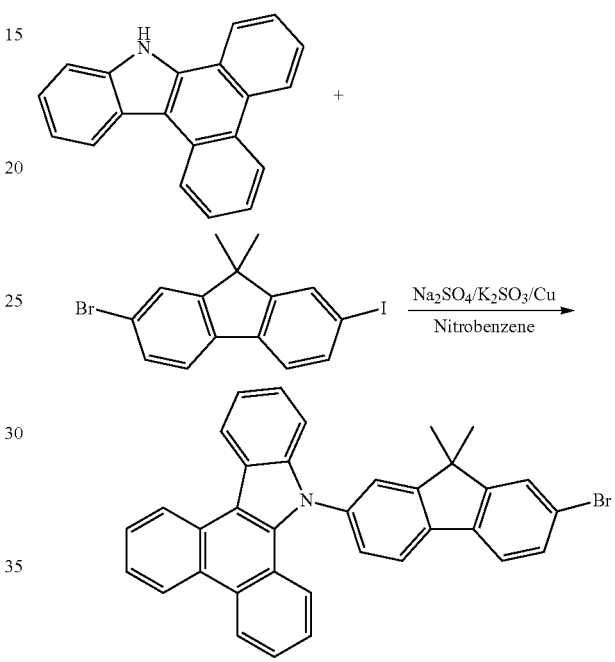

Sub 3-8-2

Using 9H-dibenzo[a,c]carbazole (80.2 g, 300 mmol) as the starting material and using 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), and nitrobenzene, the same procedure as described in the synthesis method of Sub 1-11 of Example 1 was carried out to obtain 109.8 g of product (yield: 68%).

(11) Synthesis Method of Sub 3-9-1 (L=biphenyl)

<Reaction Scheme 51>

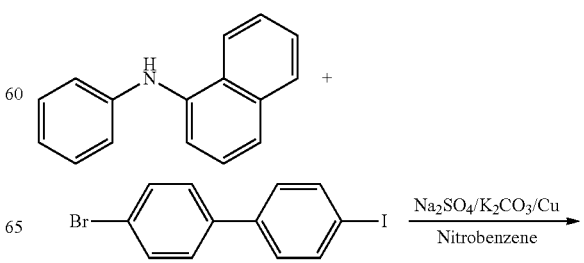

(13) Synthesis Method of Sub 3-10-1 (L=biphenyl)

<Reaction Scheme 53>

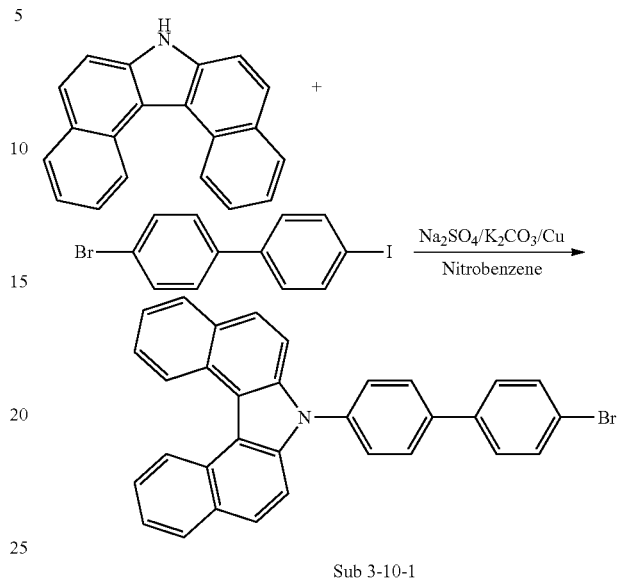

Sub 3-10-1

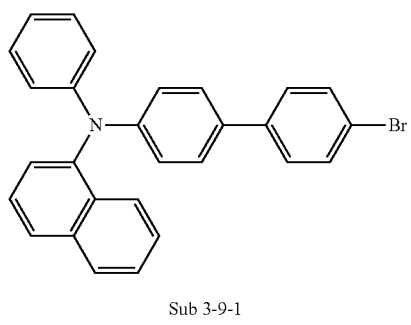

Sub 3-9-1

Using N-phenylnaphthalen-1-amine (65.8 g, 300 mmol) as the starting material and using 4-bromo-4'-iodo-1,1'-biphenyl (129.2 g, 360 mmol), $Na_2SO_4$ (42.6 g, 300 mmol), $K_2CO_3$ (41.4 g, 300 mmol), Cu (5.72 g, 90 mmol), and nitrobenzene, the same procedure as described in the synthesis method of Sub 1-1 of Example 1 was carried out to obtain 89.2 g of product (yield: 66%).

(12) Synthesis Method of Sub 3-9-2 (L=9,9-dimethyl-9H-fluorene)

<Reaction Scheme 52>

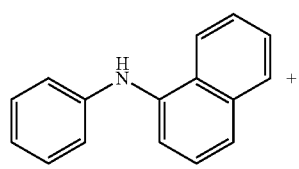

Using 7H-dibenzo[c,g]carbazole (80.2 g, 300 mmol) as the starting material and using 4-bromo-4'-iodo-1,1'-biphenyl (129.2 g, 360 mmol), $Na_2SO_4$ (42.6 g, 300 mmol), $K_2CO_3$ (41.4 g, 300 mmol), Cu (5.72 g, 90 mmol), and nitrobenzene, the same procedure as described in the synthesis method of Sub 1-1 of Example 1 was carried out to obtain 97.2 g of product (yield: 65%).

(14) Synthesis Method of Sub 3-10-2 (L=9,9-dimethyl-9H-fluorene)

<Reaction Scheme 54>

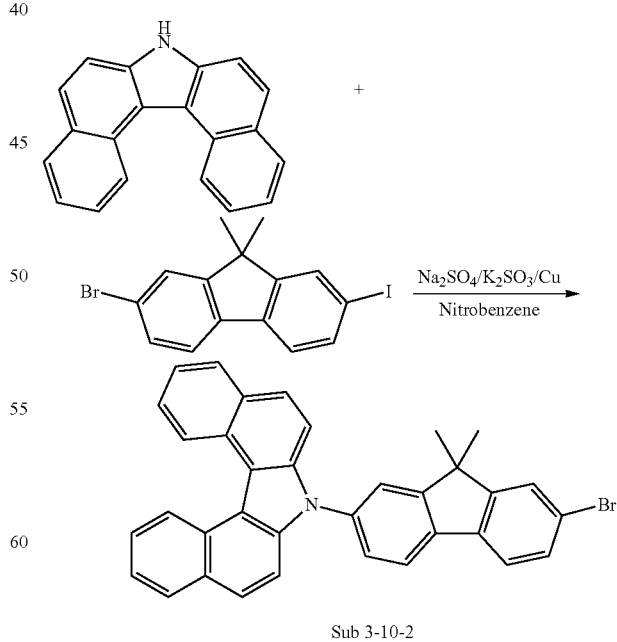

Sub 3-10-2

Sub 3-9-2

Using N-phenylnaphthalen-1-amine (65.8 g, 300 mmol) as the starting material and using 2-bromo-7-iodo-9,9-dimethyl-9H-fluorene (143.7 g, 360 mmol), $Na_2SO_4$ (42.6 g, 300 mmol), $K_2CO_3$ (41.4 g, 300 mmol), Cu (5.72 g, 90 mmol), and nitrobenzene, the same procedure as described in the synthesis method of Sub 1-11 of Example 1 was carried out to obtain 97.1 g of product (yield: 66%).

Using 7H-dibenzo[c,g]carbazole (80.2 g, 300 mmol) as the starting material and using 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), and nitrobenzene, the same procedure as described in the synthesis method of Sub 1-11 of Example 1 was carried out to obtain 98.5 g of product (yield: 61%).

2. Synthesis of Sub 4

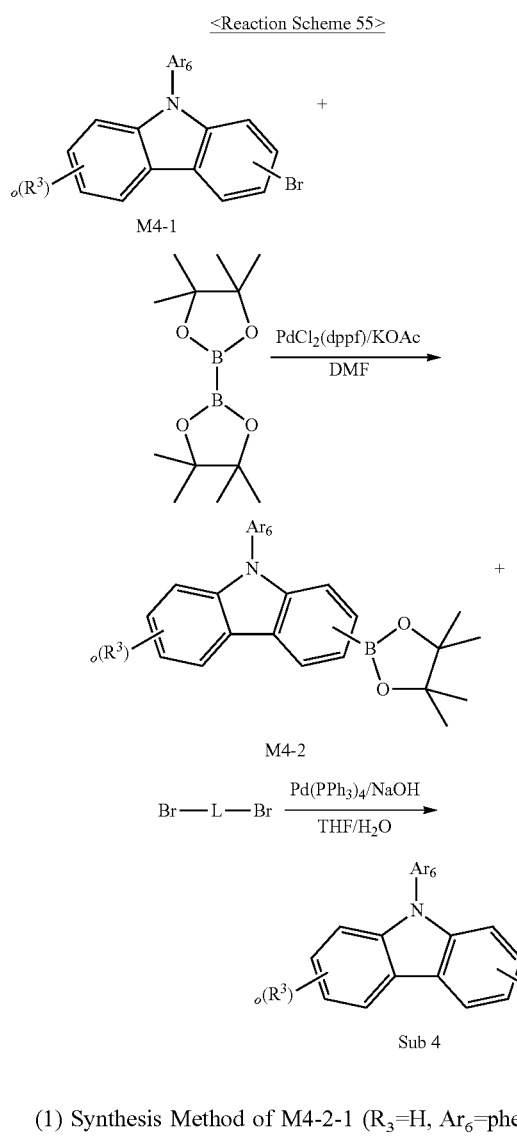

(1) Synthesis Method of M4-2-1 (R$_3$=H, Ar$_6$=phenyl)

<Reaction Scheme 56>

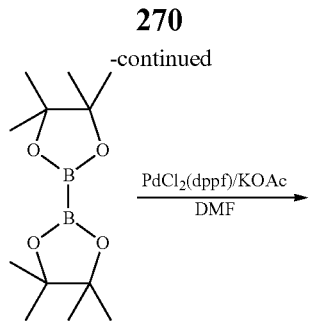

3-bromo-9-phenyl-9H-carbazole (45.1 g, 140 mmol) was dissolved in 980 mL of DMF, bispinacolborate (39.1 g, 154 mmol), a PdCl$_2$ (dppf) catalyst (3.43 g, 4.2 mmol), and KOAc (41.3 g, 420 mmol) were sequentially added to the reaction solution, and then the mixture was stirred for 24 hours to synthesize a borate compound. Subsequently, the produced compound was separated by a silica gel column and recrystallized to obtain 35.2 g of borate compound (yield: 68%).

(2) Synthesis Method of M4-2-2 (R$_3$=H, Ar$_6$=biphenyl)

<Reaction Scheme 57>

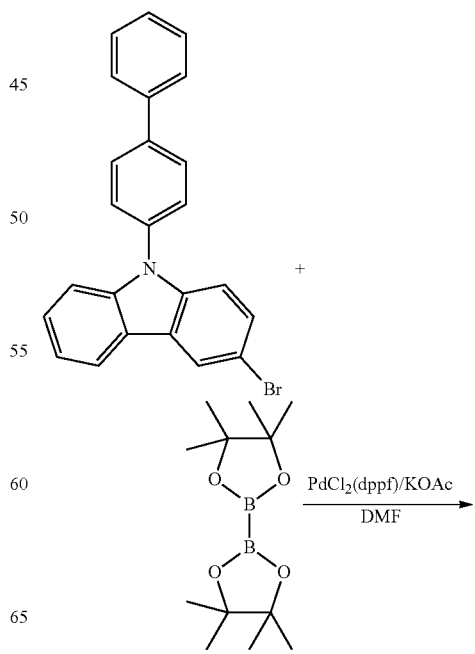

-continued

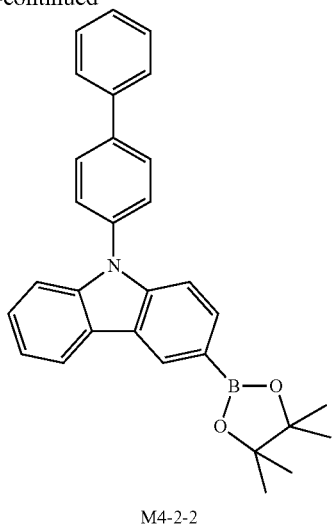

M4-2-2

The same experimental method as the synthesis method of M4-2-1 was carried out to obtain 40 g of product (yield: 64%).

(3) Synthesis Method of Sub 4-1-1 [$R_3$=H, $Ar_6$=phenyl, L=biphenyl (linear)]

<Reaction Scheme 58>

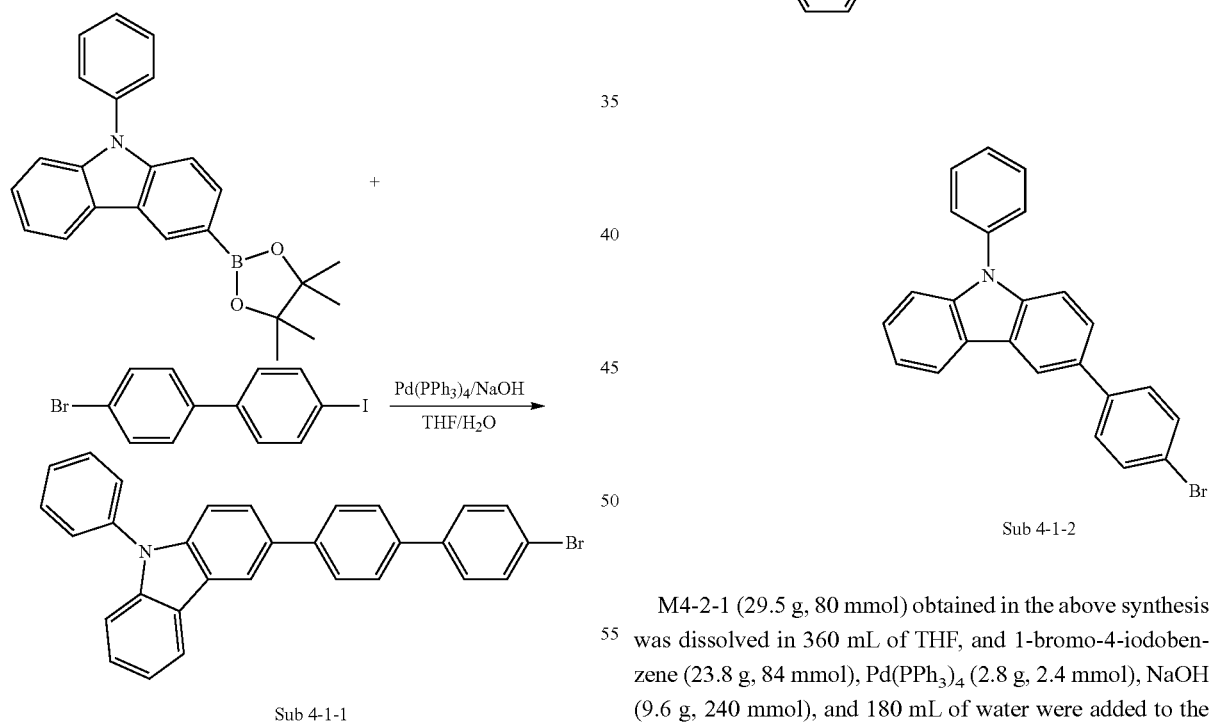

Sub 4-1-1

M4-2-1 (29.5 g, 80 mmol) obtained in the above synthesis was dissolved in 360 mL of THF, and 4-bromo-4'-iodo-1,1'-biphenyl (30.16 g, 84 mmol), Pd(PPh$_3$)$_4$ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO$_4$ and concentrated, and then the produced organic material was separated by a silica gel column and recrystallized to obtain 26.56 g of product (yield: 70%).

(4) Synthesis Method of Sub 4-1-2 [$R_3$=H, $Ar_6$=phenyl, L=phenyl]

<Reaction Scheme 59>

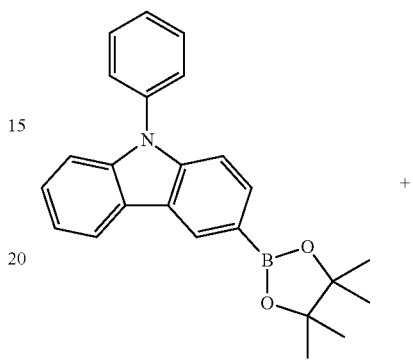

Sub 4-1-2

M4-2-1 (29.5 g, 80 mmol) obtained in the above synthesis was dissolved in 360 mL of THF, and 1-bromo-4-iodobenzene (23.8 g, 84 mmol), Pd(PPh$_3$)$_4$ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO$_4$ and concentrated, and then the produced organic material was separated by a silica gel column and recrystallized to obtain 22.9 g of product (yield: 72%).

(5) Synthesis Method of Sub 4-1-3 [R₃=H, Ar₆=phenyl, L=biphenyl (non-linear)]

<Reaction Scheme 60>

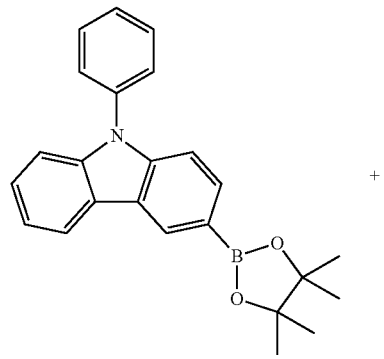

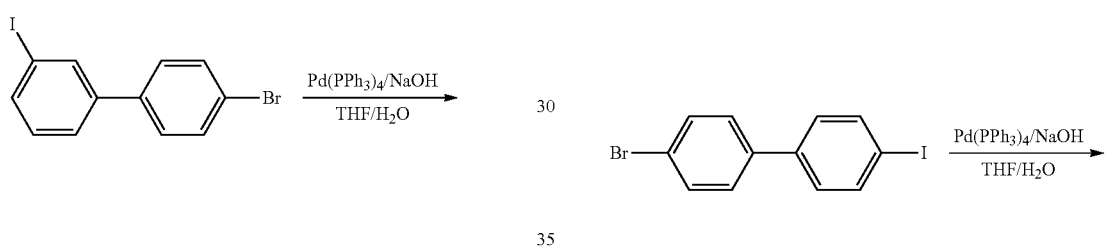

Sub 4-1-3

M4-2-1 (29.5 g, 80 mmol) obtained in the above synthesis was dissolved in 360 mL of THF, and 4'-bromo-3-iodo-1,1'-biphenyl (30.16 g, 84 mmol), Pd(PPh₃)₄ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO₄ and concentrated, and then the produced organic material was separated by a silica gel column and recrystallized to obtain 24.7 g of product (yield: 65%).

(6) Synthesis Method of Sub 4-2-1 [R₃=H, Ar₆=biphenyl, L=biphenyl (linear)]

<Reaction Scheme 61>

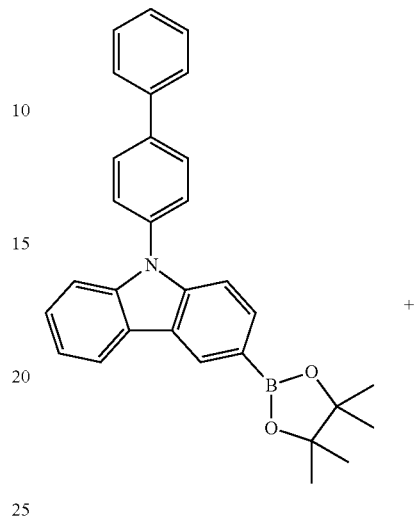

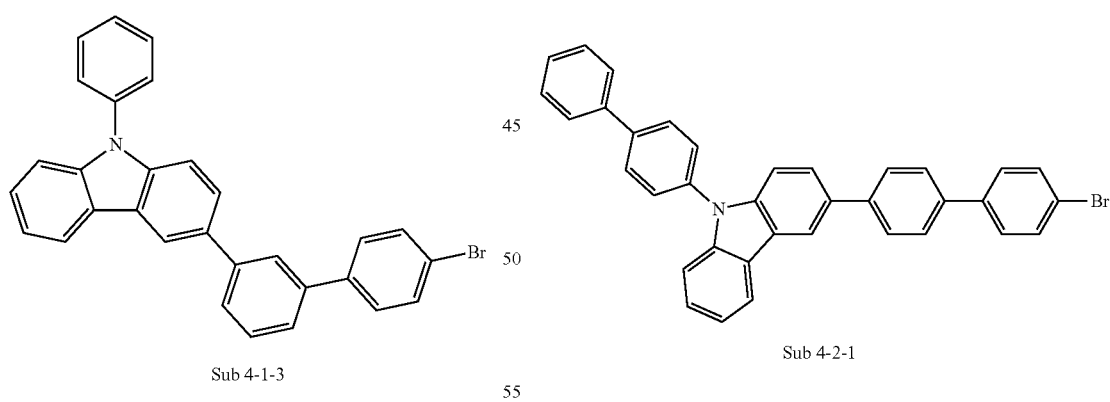

Sub 4-2-1

M4-2-2 (35.63 g, 80 mmol) obtained in the above synthesis was dissolved in 360 mL of THF, and 4-bromo-4'-iodo-1,1'-biphenyl (30.16 g, 84 mmol), Pd(PPh₃)₄ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO₄ and concentrated, and then the produced organic material was separated by a silica gel column and recrystallized to obtain 29.51 g of product (yield: 67%).

(7) Synthesis Method of Sub 4-2-2 [R₃=H, Ar₆=biphenyl, L=phenyl]

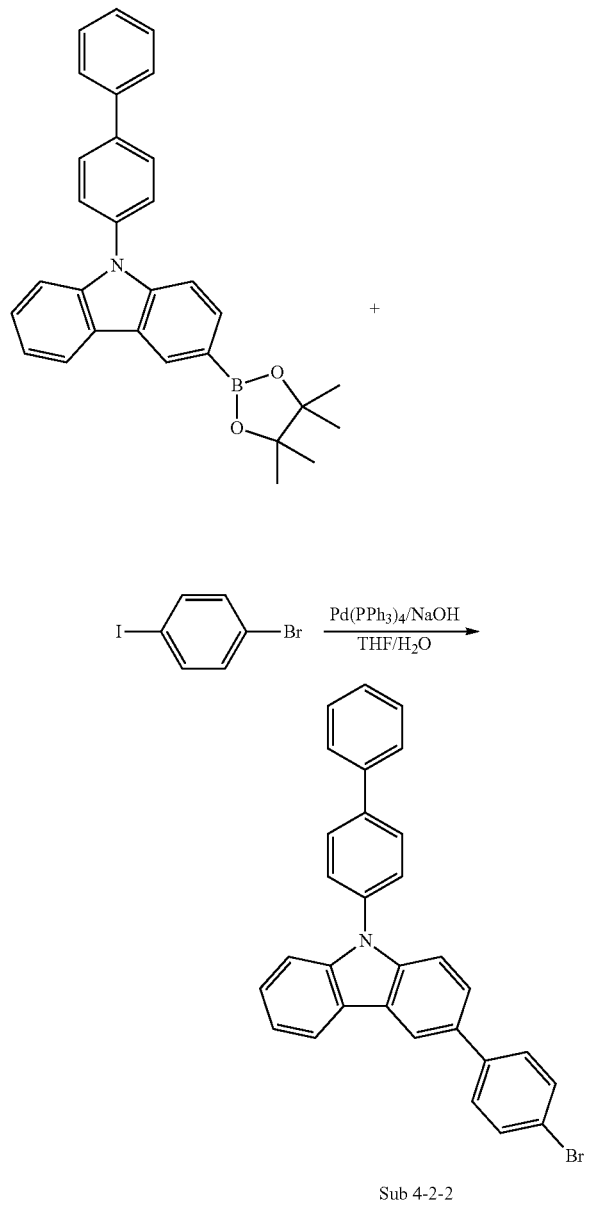

Sub 4-2-2

M4-2 (35.63 g, 80 mmol) was dissolved in 360 mL of THF, and 1-bromo-4-iodobenzene (23.8 g, 84 mmol), Pd(PPh₃)₄ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO₄ and concentrated, and then the produced organic material was separated by a silica gel column and recrystallized to obtain 25.05 g of product (yield: 66%).

(8) Synthesis Method of Sub 4-2-3 [R₃=H, Ar₆=biphenyl, L=biphenyl (Non-Linear)]

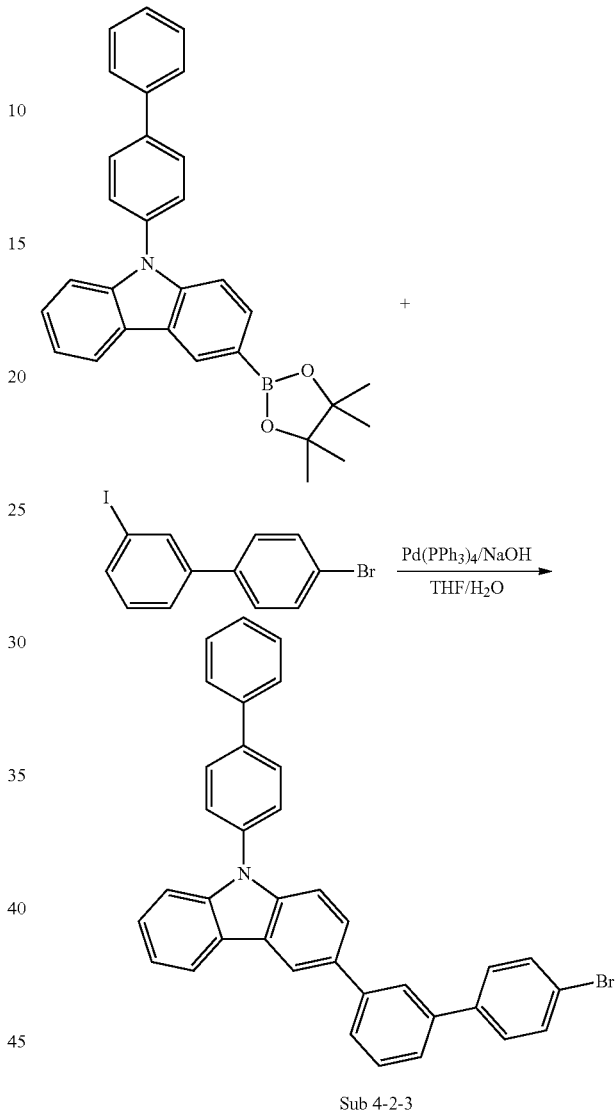

Sub 4-2-3

M4-2 (35.63 g, 80 mmol) was dissolved in 360 mL of THF, and 4'-bromo-3-iodo-1,1'-biphenyl (30.16 g, 84 mmol), Pd(PPh₃)₄ (2.8 g, 2.4 mmol), NaOH (9.6 g, 240 mmol), and 180 mL of water were added to the reaction solution, followed by reflux under stirring. Upon completion of the reaction, the reaction product was extracted with ether and water, the extracted organic layer was dried with MgSO₄ and concentrated, and then the produced organic material was separated by a silica gel column and recrystallized to obtain 29.95 g of product (yield: 68%).

3. Synthesis of Sub 5

The synthesis method of Sub 5 is the same as that of Sub 2, and uses the same and similar compounds.

Example 5

Synthesis of Product (3-1 to 10-52) (Same Experimental Method as Example 3 Above)

Sub 3 or Sub 4 (1 equivalent weight) was dissolved in toluene in a round bottom flask, and Sub 5 (1.2 equivalent weight), $Pd_2(dba)_3$ (0.03 equivalent weight), $P(t-Bu)_3$ (0.08 equivalent weight), and NaOt-Bu (3 equivalent weight) were added to the reaction solution, followed by stirring at 100° C. Upon completion of the reaction, the reaction product was extracted with $CH_2Cl_2$ and water, the extracted organic layer was dried with $MgSO_4$ and concentrated, and then the produced organic material was separated by a silica gel column and recrystallized to obtain final products (3-1 to 10-52).

FD-MS values for some of the products obtained above are given in Table 4 below.

TABLE 4

| Compound | FD-MS | Compound | FD-MS |
|---|---|---|---|
| 3-26 | m/z = 638.27 ($C_{48}H_{34}N_2$ = 638.80) | 3-29 | m/z = 678.30 ($C_{51}H_{38}N_2$ = 678.86) |
| 3-30 | m/z = 802.33 ($C_{61}H_{42}N_2$ = 803.00) | 3-31 | m/z = 800.32 ($C_{61}H_{40}N_2$ = 800.98) |
| 3-34 | m/z = 668.23 ($C_{48}H_{32}N_2S$ = 668.85) | 3-35 | m/z = 652.25 ($C_{48}H_{32}N_2O$ = 652.78) |
| 3-36 | m/z = 729.31 ($C_{54}H_{39}N_3$ = 729.91) | 3-66 | m/z = 678.30 ($C_{51}H_{38}N_2$ = 678.86) |
| 3-68 | m/z = 718.33 ($C_{54}H_{42}N_2$ = 718.92) | 3-69 | m/z = 842.37 ($C_{64}H_{46}N_2$ = 843.06) |
| 3-70 | m/z = 840.35 ($C_{64}H_{44}N_2$ = 841.05) | 3-71 | m/z = 708.26 ($C_{51}H_{36}N_2S$ = 708.91) |
| 3-72 | m/z = 692.28 ($C_{51}H_{36}N_2O$ = 692.84) | 3-73 | m/z = 769.35 ($C_{57}H_{43}N_3$ = 769.97) |
| 4-4 | m/z = 638.27 ($C_{48}H_{34}N_2$ = 638.80) | 4-7 | m/z = 652.25 ($C_{48}H_{32}N_2O$ = 652.78) |
| 4-8 | m/z = 668.23 ($C_{48}H_{32}N_2S$ = 668.85) | 4-9 | m/z = 678.30 ($C_{51}H_{38}N_2$ = 678.86) |
| 4-10 | m/z = 802.33 ($C_{61}H_{42}N_2$ = 803.00) | 4-11 | m/z = 800.32 ($C_{61}H_{40}N_2$ = 800.98) |
| 4-27 | m/z = 714.30 ($C_{54}H_{38}N_2$ = 714.89) | 4-30 | m/z = 728.28 ($C_{54}H_{36}N_2O$ = 728.88) |
| 4-31 | m/z = 744.26 ($C_{54}H_{36}N_2S$ = 744.94) | 4-32 | m/z = 754.33 ($C_{57}H_{42}N_2$ = 754.96) |
| 4-33 | m/z = 878.37 ($C_{67}H_{46}N_2$ = 879.10) | 4-34 | m/z = 876.35 ($C_{67}H_{44}N_2$ = 877.08) |
| 4-35 | m/z = 678.30 ($C_{51}H_{38}N_2$ = 678.86) | 4-43 | m/z = 714.30 ($C_{54}H_{38}N_2$ = 714.89) |
| 4-44 | m/z = 754.33 ($C_{57}H_{42}N_2$ = 754.96) | 4-45 | m/z = 878.37 ($C_{67}H_{46}N_2$ = 879.10) |
| 4-46 | m/z = 876.35 ($C_{67}H_{44}N_2$ = 877.08) | 4-47 | m/z = 744.26 ($C_{54}H_{36}N_2S$ = 744.94) |
| 4-49 | m/z = 678.30 ($C_{51}H_{38}N_2$ = 678.86) | 4-50 | m/z = 802.33 ($C_{61}H_{42}N_2$ = 803.00) |
| 4-51 | m/z = 800.32 ($C_{61}H_{40}N_2$ = 800.98) | 4-55 | m/z = 638.27 ($C_{48}H_{34}N_2$ = 638.80) |
| 4-56 | m/z = 688.29 ($C_{52}H_{36}N_2$ = 688.86) | 4-58 | m/z = 714.30 ($C_{54}H_{38}N_2$ = 714.89) |
| 4-61 | m/z = 728.28 ($C_{54}H_{36}N_2O$ = 728.88) | 4-62 | m/z = 744.26 ($C_{54}H_{36}N_2S$ = 744.94) |
| 4-63 | m/z = 754.33 ($C_{57}H_{42}N_2$ = 754.96) | 4-64 | m/z = 878.37 ($C_{67}H_{46}N_2$ = 879.10) |
| 4-65 | m/z = 876.35 ($C_{67}H_{44}N_2$ = 877.08) | 4-66 | m/z = 678.30 ($C_{51}H_{38}N_2$ = 678.86) |
| 4-67 | m/z = 802.33 ($C_{61}H_{42}N_2$ = 803.00) | 4-68 | m/z = 800.32 ($C_{61}H_{40}N_2$ = 800.98) |
| 4-103 | m/z = 754.33 ($C_{57}H_{42}N_2$ = 754.96) | 4-104 | m/z = 878.37 ($C_{67}H_{46}N_2$ = 879.10) |
| 4-105 | m/z = 876.35 ($C_{67}H_{44}N_2$ = 877.08) | 4-106 | m/z = 804.35 ($C_{61}H_{44}N_2$ = 805.02) |
| 4-107 | m/z = 928.38 ($C_{71}H_{48}N_2$ = 929.15) | 4-108 | m/z = 926.37 ($C_{71}H_{46}N_2$ = 927.14) |
| 5-2 | m/z = 586.24 ($C_{44}H_{30}N_2$ = 586.72) | 5-4 | m/z = 612.26 ($C_{46}H_{32}N_2$ = 612.76) |
| 5-6 | m/z = 642.21 ($C_{46}H_{30}N_2S$ = 642.81) | 5-7 | m/z = 626.24 ($C_{46}H_{32}N_2O$ = 626.74) |
| 5-8 | m/z = 703.30 ($C_{52}H_{37}N_3$ = 703.87) | 5-10 | m/z = 652.29 ($C_{49}H_{36}N_2$ = 652.82) |
| 5-11 | m/z = 776.32 ($C_{59}H_{40}N_2$ = 776.96) | 5-12 | m/z = 774.30 ($C_{59}H_{38}N_2$ = 774.95) |
| 5-13 | m/z = 662.27 ($C_{50}H_{34}N_2$ = 662.82) | 5-16 | m/z = 702.30 ($C_{53}H_{38}N_2$ = 702.88) |
| 5-17 | m/z = 826.33 ($C_{63}H_{42}N_2$ = 827.02) | 5-18 | m/z = 824.32 ($C_{63}H_{40}N_2$ = 825.01) |
| 5-19 | m/z = 688.29 ($C_{52}H_{36}N_2$ = 688.86) | 5-20 | m/z = 728.32 ($C_{55}H_{40}N_2$ = 728.92) |
| 5-21 | m/z = 852.35 ($C_{65}H_{44}N_2$ = 853.06) | 5-22 | m/z = 850.33 ($C_{65}H_{42}N_2$ = 851.04) |
| 5-23 | m/z = 718.24 ($C_{52}H_{34}N_2S$ = 718.90) | 5-24 | m/z = 702.27 ($C_{52}H_{34}N_2O$ = 702.84) |
| 5-36 | m/z = 692.32 ($C_{52}H_{40}N_2$ = 692.89) | 5-37 | m/z = 816.35 ($C_{62}H_{44}N_2$ = 817.03) |
| 5-38 | m/z = 814.33 ($C_{62}H_{42}N_2$ = 815.01) | 5-39 | m/z = 702.30 ($C_{53}H_{38}N_2$ = 702.88) |
| 5-42 | m/z = 742.33 ($C_{56}H_{42}N_2$ = 742.95) | 5-43 | m/z = 866.37 ($C_{66}H_{46}N_2$ = 867.08) |
| 5-44 | m/z = 864.35 ($C_{66}H_{44}N_2$ = 865.07) | 5-45 | m/z = 728.32 ($C_{55}H_{40}N_2$ = 728.92) |
| 5-46 | m/z = 768.35 ($C_{58}H_{44}N_2$ = 768.98) | 5-47 | m/z = 892.38 ($C_{68}H_{48}N_2$ = 893.12) |
| 5-48 | m/z = 890.37 ($C_{68}H_{46}N_2$ = 891.11) | 5-49 | m/z = 758.28 ($C_{55}H_{38}N_2S$ = 758.97) |
| 5-50 | m/z = 742.30 ($C_{55}H_{38}N_2O$ = 742.90) | 6-2 | m/z = 586.24 ($C_{44}H_{30}N_2$ = 586.72) |
| 6-4 | m/z = 612.26 ($C_{46}H_{32}N_2$ = 612.76) | 6-6 | m/z = 642.21 ($C_{46}H_{30}N_2S$ = 642.81) |
| 6-7 | m/z = 626.24 ($C_{46}H_{30}N_2O$ = 626.74) | 6-8 | m/z = 703.30 ($C_{52}H_{37}N_3$ = 703.87) |
| 6-10 | m/z = 652.29 ($C_{49}H_{36}N_2$ = 652.82) | 6-11 | m/z = 776.32 ($C_{59}H_{40}N_2$ = 776.96) |
| 6-12 | m/z = 774.30 ($C_{59}H_{38}N_2$ = 774.95) | 6-13 | m/z = 662.27 ($C_{50}H_{34}N_2$ = 662.82) |
| 6-16 | m/z = 702.30 ($C_{53}H_{38}N_2$ = 702.88) | 6-17 | m/z = 826.33 ($C_{63}H_{42}N_2$ = 827.02) |
| 6-18 | m/z = 824.32 ($C_{63}H_{40}N_2$ = 825.01) | 6-19 | m/z = 688.29 ($C_{52}H_{36}N_2$ = 688.86) |
| 6-20 | m/z = 728.32 ($C_{55}H_{40}N_2$ = 728.92) | 6-21 | m/z = 852.35 ($C_{65}H_{44}N_2$ = 853.06) |
| 6-22 | m/z = 850.33 ($C_{65}H_{42}N_2$ = 851.04) | 6-23 | m/z = 718.24 ($C_{52}H_{34}N_2S$ = 718.90) |
| 6-24 | m/z = 702.27 ($C_{52}H_{34}N_2O$ = 702.84) | 6-36 | m/z = 692.32 ($C_{52}H_{40}N_2$ = 692.89) |
| 6-37 | m/z = 816.35 ($C_{62}H_{44}N_2$ = 817.03) | 6-38 | m/z = 814.33 ($C_{62}H_{42}N_2$ = 815.01) |
| 6-39 | m/z = 702.30 ($C_{53}H_{38}N_2$ = 702.88) | 6-40 | m/z = 732.26 ($C_{53}H_{36}N_2S$ = 732.93) |
| 6-41 | m/z = 716.28 ($C_{53}H_{36}N_2O$ = 716.87) | 6-42 | m/z = 742.33 ($C_{56}H_{42}N_2$ = 742.95) |
| 6-43 | m/z = 866.37 ($C_{66}H_{46}N_2$ = 867.08) | 6-44 | m/z = 864.35 ($C_{66}H_{44}N_2$ = 865.07) |
| 6-45 | m/z = 728.32 ($C_{55}H_{40}N_2$ = 728.92) | 6-46 | m/z = 768.35 ($C_{58}H_{44}N_2$ = 768.98) |
| 6-47 | m/z = 892.38 ($C_{68}H_{48}N_2$ = 893.12) | 6-48 | m/z = 890.37 ($C_{68}H_{46}N_2$ = 891.11) |
| 6-49 | m/z = 758.28 ($C_{55}H_{38}N_2S$ = 758.97) | 6-50 | m/z = 742.30 ($C_{55}H_{38}N_2O$ = 742.90) |
| 7-2 | m/z = 586.24 ($C_{44}H_{30}N_2$ = 586.72) | 7-4 | m/z = 612.26 ($C_{46}H_{32}N_2$ = 612.76) |
| 7-5 | m/z = 642.21 ($C_{46}H_{30}N_2S$ = 642.81) | 7-6 | m/z = 626.24 ($C_{46}H_{30}N_2O$ = 626.74) |
| 7-7 | m/z = 703.30 ($C_{52}H_{37}N_3$ = 703.87) | 7-9 | m/z = 652.29 ($C_{49}H_{36}N_2$ = 652.82) |
| 7-10 | m/z = 776.32 ($C_{59}H_{40}N_2$ = 776.96) | 7-11 | m/z = 774.30 ($C_{59}H_{38}N_2$ = 774.95) |
| 7-12 | m/z = 636.26 ($C_{48}H_{32}N_2$ = 636.78) | 7-14 | m/z = 662.27 ($C_{50}H_{34}N_2$ = 662.82) |
| 7-16 | m/z = 692.23 ($C_{50}H_{32}N_2S$ = 692.87) | 7-17 | m/z = 676.25 ($C_{50}H_{32}N_2O$ = 676.80) |
| 7-18 | m/z = 753.31 ($C_{56}H_{39}N_3$ = 753.93) | 7-19 | m/z = 702.30 ($C_{53}H_{38}N_2$ = 702.88) |
| 7-20 | m/z = 826.33 ($C_{63}H_{42}N_2$ = 827.02) | 7-21 | m/z = 824.32 ($C_{63}H_{40}N_2$ = 825.01) |

TABLE 4-continued

| Compound | FD-MS | Compound | FD-MS |
|---|---|---|---|
| 7-22 | m/z = 688.29 ($C_{52}H_{36}N_2$ = 688.86) | 7-25 | m/z = 728.32 ($C_{55}H_{40}N_2$ = 728.92) |
| 7-26 | m/z = 852.35 ($C_{65}H_{44}N_2$ = 853.06) | 7-27 | m/z = 850.33 ($C_{65}H_{42}N_2$ = 851.04) |
| 7-30 | m/z = 718.24 ($C_{52}H_{34}N_2S$ = 718.90) | 7-31 | m/z = 702.27 ($C_{52}H_{34}N_2O$ = 702.84) |
| 7-38 | m/z = 652.29 ($C_{49}H_{36}N_2$ = 652.82) | 7-39 | m/z = 682.24 ($C_{49}H_{34}N_2S$ = 682.87) |
| 7-40 | m/z = 666.27 ($C_{49}H_{34}N_2O$ = 666.81) | 7-41 | m/z = 743.33 ($C_{55}H_{41}N_3$ = 743.93) |
| 7-43 | m/z = 692.32 ($C_{52}H_{40}N_2$ = 692.89) | 7-44 | m/z = 816.35 ($C_{62}H_{44}N_2$ = 817.03) |
| 7-45 | m/z = 814.33 ($C_{62}H_{42}N_2$ = 815.01) | 7-46 | m/z = 676.29 ($C_{51}H_{36}N_2$ = 676.84) |
| 7-48 | m/z = 702.30 ($C_{53}H_{38}N_2$ = 702.88) | 7-50 | m/z = 732.26 ($C_{53}H_{36}N_2S$ = 732.93) |
| 7-51 | m/z = 716.28 ($C_{53}H_{36}N_2O$ = 716.87) | 7-52 | m/z = 793.35 ($C_{59}H_{43}N_3$ = 793.99) |
| 7-53 | m/z = 742.33 ($C_{56}H_{42}N_2$ = 742.95) | 7-54 | m/z = 866.37 ($C_{66}H_{46}N_2$ = 867.08) |
| 7-55 | m/z = 864.35 ($C_{66}H_{44}N_2$ = 865.07) | 7-56 | m/z = 728.32 ($C_{55}H_{40}N_2$ = 728.92) |
| 7-58 | m/z = 768.35 ($C_{58}H_{44}N_2$ = 768.98) | 7-59 | m/z = 892.38 ($C_{68}H_{48}N_2$ = 893.12) |
| 7-60 | m/z = 890.37 ($C_{68}H_{46}N_2$ = 891.11) | 7-61 | m/z = 758.28 ($C_{55}H_{38}N_2S$ = 758.97) |
| 7-62 | m/z = 742.30 ($C_{55}H_{38}N_2O$ = 742.90) | 7-63 | m/z = 819.36 ($C_{61}H_{45}N_3$ = 820.03) |
| 8-2 | m/z = 636.26 ($C_{48}H_{32}N_2$ = 636.78) | 8-4 | m/z = 662.27 ($C_{50}H_{34}N_2$ = 662.82) |
| 8-5 | m/z = 692.23 ($C_{50}H_{32}N_2S$ = 692.87) | 8-6 | m/z = 676.25 ($C_{50}H_{32}N_2O$ = 676.80) |
| 8-7 | m/z = 753.31 ($C_{56}H_{39}N_3$ = 753.93) | 8-9 | m/z = 702.30 ($C_{53}H_{38}N_2$ = 702.88) |
| 8-10 | m/z = 826.33 ($C_{63}H_{42}N_2$ = 827.02) | 8-11 | m/z = 824.32 ($C_{63}H_{40}N_2$ = 825.01) |
| 8-12 | m/z = 686.27 ($C_{52}H_{34}N_2$ = 686.84) | 8-14 | m/z = 712.29 ($C_{54}H_{36}N_2$ = 712.88) |
| 8-16 | m/z = 742.24 ($C_{54}H_{34}N_2S$ = 742.93) | 8-17 | m/z = 726.27 ($C_{54}H_{34}N_2O$ = 726.86) |
| 8-18 | m/z = 803.33 ($C_{60}H_{41}N_3$ = 803.99) | 8-19 | m/z = 752.32 ($C_{57}H_{40}N_2$ = 752.94) |
| 8-20 | m/z = 876.35 ($C_{67}H_{44}N_2$ = 877.08) | 8-21 | m/z = 874.33 ($C_{67}H_{42}N_2$ = 875.06) |
| 8-22 | m/z = 738.30 ($C_{56}H_{38}N_2$ = 738.91) | 8-23 | m/z = 788.32 ($C_{60}H_{40}N_2$ = 788.97) |
| 8-25 | m/z = 778.33 ($C_{59}H_{42}N_2$ = 778.98) | 8-26 | m/z = 902.37 ($C_{69}H_{46}N_2$ = 903.12) |
| 8-27 | m/z = 900.35 ($C_{69}H_{44}N_2$ = 901.10) | 8-30 | m/z = 768.26 ($C_{56}H_{36}N_2S$ = 768.96) |
| 8-31 | m/z = 752.28 ($C_{56}H_{36}N_2O$ = 752.90) | 8-32 | m/z = 829.35 ($C_{62}H_{43}N_3$ = 830.02) |
| 8-34 | m/z = 626.27 ($C_{47}H_{34}N_2$ = 626.79) | 8-35 | m/z = 676.29 ($C_{51}H_{36}N_2$ = 676.84) |
| 8-36 | m/z = 676.29 ($C_{51}H_{36}N_2$ = 676.84) | 8-37 | m/z = 702.30 ($C_{53}H_{38}N_2$ = 702.88) |
| 8-38 | m/z = 732.26 ($C_{53}H_{36}N_2S$ = 732.93) | 8-39 | m/z = 716.28 ($C_{53}H_{36}N_2O$ = 716.87) |
| 8-40 | m/z = 793.35 ($C_{59}H_{43}N_3$ = 793.99) | 8-42 | m/z = 742.33 ($C_{56}H_{42}N_2$ = 742.95) |
| 8-43 | m/z = 866.37 ($C_{66}H_{46}N_2$ = 867.08) | 8-44 | m/z = 864.35 ($C_{66}H_{44}N_2$ = 865.07) |
| 8-45 | m/z = 726.30 ($C_{55}H_{38}N_2$ = 726.90) | 8-47 | m/z = 752.32 ($C_{57}H_{40}N_2$ = 752.94) |
| 8-49 | m/z = 782.28 ($C_{57}H_{38}N_2S$ = 782.99) | 8-50 | m/z = 766.30 ($C_{57}H_{38}N_2O$ = 766.92) |
| 8-51 | m/z = 843.36 ($C_{63}H_{45}N_3$ = 844.05) | 8-52 | m/z = 792.35 ($C_{60}H_{44}N_2$ = 793.00) |
| 8-53 | m/z = 916.38 ($C_{70}H_{48}N_2$ = 917.14) | 8-54 | m/z = 914.37 ($C_{70}H_{46}N_2$ = 915.13) |
| 8-55 | m/z = 778.33 ($C_{59}H_{42}N_2$ = 778.98) | 8-57 | m/z = 818.37 ($C_{62}H_{46}N_2$ = 819.04) |
| 8-58 | m/z = 942.40 ($C_{72}H_{50}N_2$ = 943.18) | 8-59 | m/z = 940.38 ($C_{72}H_{48}N_2$ = 941.16) |
| 8-60 | m/z = 808.29 ($C_{59}H_{40}N_2S$ = 809.03) | 8-61 | m/z = 792.31 ($C_{59}H_{40}N_2O$ = 792.96) |
| 8-62 | m/z = 869.38 ($C_{65}H_{47}N_3$ = 870.09) | 9-1 | m/z = 538.24 ($C_{40}H_{30}N_2$ = 538.68) |
| 9-2 | m/z = 588.26 ($C_{44}H_{32}N_2$ = 588.74) | 9-3 | m/z = 588.26 ($C_{44}H_{32}N_2$ = 588.74) |
| 9-4 | m/z = 614.27 ($C_{46}H_{34}N_2$ = 614.78) | 9-5 | m/z = 644.23 ($C_{46}H_{32}N_2S$ = 644.82) |
| 9-6 | m/z = 628.25 ($C_{46}H_{32}N_2O$ = 628.76) | 9-7 | m/z = 654.30 ($C_{49}H_{38}N_2$ = 654.84) |
| 9-8 | m/z = 778.33 ($C_{59}H_{42}N_2$ = 778.98) | 9-9 | m/z = 776.32 ($C_{59}H_{40}N_2$ = 776.96) |
| 9-10 | m/z = 664.29 ($C_{50}H_{36}N_2$ = 664.83) | 9-11 | m/z = 704.32 ($C_{53}H_{40}N_2$ = 704.90) |
| 9-12 | m/z = 828.35 ($C_{63}H_{44}N_2$ = 829.04) | 9-13 | m/z = 826.33 ($C_{63}H_{42}N_2$ = 827.02) |
| 9-14 | m/z = 694.24 ($C_{50}H_{34}N_2S$ = 694.88) | 9-15 | m/z = 678.27 ($C_{50}H_{34}N_2O$ = 678.82) |
| 9-16 | m/z = 664.29 ($C_{50}H_{36}N_2$ = 664.83) | 9-17 | m/z = 690.30 ($C_{52}H_{38}N_2$ = 690.87) |
| 9-18 | m/z = 730.33 ($C_{55}H_{42}N_2$ = 730.94) | 9-19 | m/z = 854.37 ($C_{65}H_{46}N_2$ = 855.07) |
| 9-20 | m/z = 852.35 ($C_{65}H_{44}N_2$ = 853.06) | 9-21 | m/z = 720.26 ($C_{52}H_{36}N_2S$ = 720.92) |
| 9-22 | m/z = 704.28 ($C_{52}H_{36}N_2O$ = 704.86) | 9-23 | m/z = 640.29 ($C_{48}H_{36}N_2$ = 640.81) |
| 9-24 | m/z = 680.32 ($C_{51}H_{40}N_2$ = 680.88) | 9-25 | m/z = 804.35 ($C_{61}H_{44}N_2$ = 805.02) |
| 9-26 | m/z = 802.33 ($C_{61}H_{42}N_2$ = 803.00) | 9-27 | m/z = 746.28 ($C_{54}H_{38}N_2S$ = 746.96) |
| 9-28 | m/z = 730.30 ($C_{54}H_{38}N_2O$ = 730.89) | 9-29 | m/z = 796.29 ($C_{58}H_{40}N_2S$ = 797.02) |
| 9-30 | m/z = 780.31 ($C_{58}H_{40}N_2O$ = 780.95) | 9-31 | m/z = 918.37 ($C_{68}H_{46}N_4$ = 919.12) |
| 9-32 | m/z = 970.40 ($C_{72}H_{50}N_4$ = 971.19) | 9-33 | m/z = 578.27 ($C_{43}H_{34}N_2$ = 578.74) |
| 9-34 | m/z = 628.29 ($C_{47}H_{36}N_2$ = 628.80) | 9-35 | m/z = 628.29 ($C_{47}H_{36}N_2$ = 628.80) |
| 9-36 | m/z = 654.30 ($C_{49}H_{38}N_2$ = 654.84) | 9-37 | m/z = 684.26 ($C_{49}H_{36}N_2S$ = 684.89) |
| 9-38 | m/z = 668.28 ($C_{49}H_{36}N_2O$ = 668.82) | 9-39 | m/z = 694.33 ($C_{52}H_{42}N_2$ = 694.90) |
| 9-40 | m/z = 818.37 ($C_{62}H_{46}N_2$ = 819.04) | 9-41 | m/z = 816.35 ($C_{62}H_{44}N_2$ = 817.03) |
| 9-42 | m/z = 704.32 ($C_{53}H_{40}N_2$ = 704.90) | 9-43 | m/z = 744.35 ($C_{56}H_{44}N_2$ = 744.96) |
| 9-44 | m/z = 868.38 ($C_{66}H_{48}N_2$ = 869.10) | 9-45 | m/z = 866.37($C_{66}H_{46}N_2$ = 867.08) |
| 9-46 | m/z = 734.28 ($C_{53}H_{38}N_2S$ = 734.95) | 9-47 | m/z = 718.30 ($C_{53}H_{38}N_2O$ = 718.88) |
| 9-48 | m/z = 704.32 ($C_{53}H_{40}N_2$ = 704.90) | 9-49 | m/z = 730.33 ($C_{55}H_{42}N_2$ = 730.94) |
| 9-50 | m/z = 770.37 ($C_{58}H_{46}N_2$ = 771.00) | 9-51 | m/z = 894.40 ($C_{68}H_{50}N_2$ = 895.14) |
| 9-52 | m/z = 892.38 ($C_{68}H_{48}N_2$ = 893.12) | 9-53 | m/z = 760.29 ($C_{55}H_{40}N_2S$ = 760.98) |
| 9-54 | m/z = 744.31 ($C_{55}H_{40}N_2O$ = 744.92) | 9-55 | m/z = 680.32 ($C_{51}H_{40}N_2$ = 680.88) |
| 9-56 | m/z = 720.35 ($C_{54}H_{44}N_2$ = 720.94) | 9-57 | m/z = 844.38 ($C_{64}H_{48}N_2$ = 845.08) |
| 9-58 | m/z = 842.37 ($C_{64}H_{46}N_2$ = 843.06) | 9-59 | m/z = 786.31 ($C_{52}H_{42}N_2S$ = 787.02) |
| 9-60 | m/z = 770.33 ($C_{57}H_{42}N_2O$ = 770.96) | 9-61 | m/z = 836.32 ($C_{61}H_{44}N_2S$ = 837.08) |
| 9-62 | m/z = 820.35 ($C_{61}H_{44}N_2O$ = 821.01) | 9-63 | m/z = 958.40 ($C_{71}H_{50}N_4$ = 959.18) |
| 10-2 | m/z = 636.26 ($C_{48}H_{32}N_2$ = 636.78) | 10-4 | m/z = 662.27 ($C_{50}H_{34}N_2$ = 662.82) |
| 10-6 | m/z = 692.23 ($C_{50}H_{32}N_2S$ = 692.87) | 10-7 | m/z = 676.25 ($C_{50}H_{32}N_2O$ = 676.80) |
| 10-10 | m/z = 702.30 ($C_{53}H_{38}N_2$ = 702.88) | 10-11 | m/z = 826.33 ($C_{63}H_{42}N_2$ = 827.02) |
| 10-12 | m/z = 824.32 ($C_{63}H_{40}N_2$ = 825.01) | 10-13 | m/z = 712.29 ($C_{54}H_{36}N_2$ = 712.88) |
| 10-14 | m/z = 742.24 ($C_{54}H_{34}N_2S$ = 742.93) | 10-15 | m/z = 726.27 ($C_{54}H_{34}N_2O$ = 726.86) |
| 10-16 | m/z = 752.32 ($C_{57}H_{40}N_2$ = 752.94) | 10-17 | m/z = 876.35 ($C_{67}H_{44}N_2$ = 877.08) |
| 10-18 | m/z = 874.33 ($C_{62}H_{42}N_2$ = 875.06) | 10-19 | m/z = 738.30 ($C_{56}H_{38}N_2$ = 738.91) |
| 10-20 | m/z = 778.33 ($C_{59}H_{42}N_2$ = 778.98) | 10-21 | m/z = 902.37 ($C_{69}H_{46}N_2$ = 903.12) |

TABLE 4-continued

| Compound | FD-MS | Compound | FD-MS |
|---|---|---|---|
| 10-22 | m/z = 900.35 ($C_{69}H_{44}N_2$ = 901.10) | 10-23 | m/z = 768.26 ($C_{56}H_{36}N_2S$ = 768.96) |
| 10-24 | m/z = 752.28 ($C_{56}H_{36}N_2O$ = 752.90) | 10-27 | m/z = 626.27 ($C_{47}H_{34}N_2$ = 626.79) |
| 10-28 | m/z = 676.29 ($C_{51}H_{36}N_2$ = 676.84) | 10-30 | m/z = 702.30 ($C_{53}H_{38}N_2$ = 702.88) |
| 10-31 | m/z = 702.30 ($C_{53}H_{38}N_2$ = 702.88) | 10-32 | m/z = 732.26 ($C_{53}H_{36}N_2S$ = 732.93) |
| 10-33 | m/z = 716.28 ($C_{53}H_{36}N_2O$ = 716.87) | 10-34 | m/z = 793.3 ($C_{59}H_{43}N_3$ = 793.99) |
| 10-36 | m/z = 742.33 ($C_{56}H_{42}N_2$ = 742.95) | 10-37 | m/z = 866.37 ($C_{66}H_{46}N_2$ = 867.08) |
| 10-38 | m/z = 864.35 ($C_{66}H_{44}N_2$ = 865.07) | 10-39 | m/z = 752.32 ($C_{57}H_{40}N_2$ = 752.94) |
| 10-40 | m/z = 782.28 ($C_{57}H_{38}N_2S$ = 782.99) | 10-41 | m/z = 766.30 ($C_{57}H_{38}N_2O$ = 766.92) |
| 10-45 | m/z = 778.33 ($C_{59}H_{42}N_2$ = 778.98) | 10-49 | m/z = 808.29 ($C_{59}H_{40}N_2S$ = 809.03) |
| 10-50 | m/z = 792.31 ($C_{59}H_{40}N_2O$ = 792.96) | | |

Although the synthesis examples of the inventive compounds represented by Formula 1 and Formula 2 have been described above by way of example, those skilled in the art will readily appreciate that they are all based on the Ullmann reaction and the Buchwald-Hartwig cross coupling reaction, and these reactions can proceed even when substituents ($R_1$, $R_2$, L, $Ar_1$, $Ar_2$, and the like) other than the substituents specified in the above concrete synthesis examples are linked. For example, the synthesis reactions of Sub 1 and Sub 3 are based on the Ullmann reaction, and the synthesis reactions of Sub 2, Sub 5, and the products are based on the Buchwald-Hartwig cross coupling reaction. Even when substituents not specified in the above concrete synthesis examples are linked, the synthesis reactions proceed in the same manner.

Fabrication and Evaluation of Organic Electric Element

[Example 6] Hole Transport Layer

First, an ITO layer (anode) was formed on a glass substrate, and then a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, the inventive compound was vacuum-deposited with a thickness of 20 nm on the hole injection layer to form a hole transport layer. Also, a light emitting layer with a thickness of 30 nm was deposited on the hole transport layer by doping the hole transport layer with CBP[4,4'-N,N'-dicarbazole-biphenyl] as a host material and Ir(ppy)$_3$[tris(2-phenylpyridine)-iridium] as a dopant material in a weight ratio of 90:10. Next, (1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and then a film of tris(8-quinolinolato)aluminum (hereinafter abbreviated as "Alq$_3$") was formed with a thickness of 40 nm on the hole blocking layer to form an electron transport layer. Thereafter, LiF as halogenated alkali metal was deposited with a thickness of 0.2 nm on the electron transport layer to form an electron injection layer, and then Al was deposited with a thickness of 150 nm thereon to form a cathode. In this way, an organic light emitting diode (OLED) was completed.

Comparative Example 1

An OLED was manufactured in the same manner as described in Example 6, except that Comparative Compound 1 represented below was used to form the hole transport layer, instead of the inventive compound.

<Comparative Compound 1>

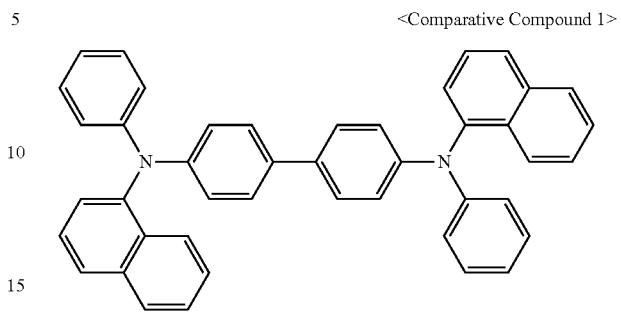

A forward bias DC voltage was applied to each of the OLEDs manufactured in Example 6 and Comparative Example 1, and electro-luminescence (EL) characteristics of the OLED were measured by PR-650 (Photoresearch). Also, T95 life span was measured by life span measuring equipment (Mcscience) at a reference brightness of 300 cd/m².

Table 5 below shows the fabrication and evaluation results for the OLEDs according to the examples employing the inventive compounds and the comparative example. In Tables 5 and 6 below, "Ex." indicates "Example", "Comp. Ex." indicates "Comparative Example", "Comp. Com." indicates "Comparative Compound", and "Com." indicates "Compound".

TABLE 5

| | Compound | Driving Voltage | Current Density (mA/cm2) | Brightness (cd/m2) | Efficiency (cd/A) | T(90) |
|---|---|---|---|---|---|---|
| Comp.Ex(1) | Comp.Com 1 | 6.2 | 7.9 | 300.0 | 3.8 | 78 |
| Ex.(1) | Com.(1-1) | 5.3 | 5.7 | 300.0 | 5.3 | 126.7 |
| Ex.(2) | Com.(1-2) | 5.3 | 5.5 | 300.0 | 5.4 | 104.1 |
| Ex.(3) | Com.(1-3) | 5.6 | 6.7 | 300.0 | 4.5 | 122.3 |
| Ex.(4) | Com.(1-4) | 5.1 | 5.6 | 300.0 | 5.3 | 126.5 |
| Ex.(5) | Com.(1-5) | 4.8 | 5.1 | 300.0 | 5.8 | 130.9 |
| Ex.(6) | Com.(1-6) | 4.8 | 5.1 | 300.0 | 5.9 | 142.0 |
| Ex.(7) | Com.(1-7) | 5.3 | 5.3 | 300.0 | 5.6 | 119.5 |
| Ex.(8) | Com.(1-8) | 5.3 | 5.9 | 300.0 | 5.1 | 96.8 |
| Ex.(9) | Com.(1-9) | 5.2 | 5.4 | 300.0 | 5.5 | 99.0 |
| Ex.(10) | Com.(1-10) | 5.4 | 6.2 | 300.0 | 4.8 | 129.4 |
| Ex.(11) | Com.(1-11) | 5.4 | 8.0 | 300.0 | 3.7 | 95.8 |
| Ex.(12) | Com.(1-12) | 5.0 | 5.8 | 300.0 | 5.2 | 96.5 |
| Ex.(13) | Com.(1-13) | 5.7 | 7.1 | 300.0 | 4.2 | 122.0 |
| Ex.(14) | Com.(1-14) | 4.8 | 5.0 | 300.0 | 6.0 | 124.6 |
| Ex.(15) | Com.(1-15) | 5.1 | 5.2 | 300.0 | 5.8 | 107.2 |
| Ex.(16) | Com.(1-16) | 5.2 | 6.8 | 300.0 | 4.4 | 128.4 |
| Ex.(17) | Com.(1-17) | 5.7 | 7.9 | 300.0 | 3.8 | 125.9 |
| Ex.(18) | Com.(1-18) | 5.2 | 10.0 | 300.0 | 3.0 | 108.2 |
| Ex.(19) | Com.(1-19) | 5.0 | 5.1 | 300.0 | 5.9 | 111.9 |
| Ex.(20) | Com.(1-20) | 5.2 | 9.7 | 300.0 | 3.1 | 97.1 |
| Ex.(21) | Com.(1-21) | 5.7 | 5.7 | 300.0 | 5.3 | 118.0 |
| Ex.(22) | Com.(1-22) | 5.6 | 5.2 | 300.0 | 5.7 | 122.3 |
| Ex.(23) | Com.(1-23) | 5.1 | 9.2 | 300.0 | 3.3 | 121.0 |
| Ex.(24) | Com.(1-24) | 5.6 | 6.4 | 300.0 | 4.7 | 107.1 |
| Ex.(25) | Com.(1-25) | 5.1 | 9.3 | 300.0 | 3.2 | 113.3 |
| Ex.(26) | Com.(1-26) | 5.3 | 8.3 | 300.0 | 3.6 | 119.4 |
| Ex.(27) | Com.(1-27) | 5.8 | 9.8 | 300.0 | 3.1 | 97.1 |
| Ex.(28) | Com.(1-28) | 5.9 | 6.3 | 300.0 | 4.7 | 99.9 |
| Ex.(29) | Com.(1-29) | 5.7 | 7.8 | 300.0 | 3.9 | 106.4 |
| Ex.(30) | Com.(1-30) | 5.1 | 9.0 | 300.0 | 3.3 | 96.0 |
| Ex.(31) | Com.(1-31) | 5.7 | 9.3 | 300.0 | 3.2 | 115.0 |
| Ex.(32) | Com.(1-32) | 5.3 | 7.0 | 300.0 | 4.3 | 122.3 |
| Ex.(33) | Com.(1-33) | 5.5 | 8.4 | 300.0 | 3.6 | 103.8 |
| Ex.(34) | Com.(1-34) | 5.3 | 6.8 | 300.0 | 4.4 | 112.5 |
| Ex.(35) | Com.(1-35) | 5.6 | 7.2 | 300.0 | 4.1 | 110.2 |

TABLE 5-continued

| | Compound | Driving Voltage | Current Density (mA/cm2) | Brightness (cd/m2) | Efficiency (cd/A) | T(90) |
|---|---|---|---|---|---|---|
| Ex.(36) | Com.(1-36) | 5.0 | 5.4 | 300.0 | 5.6 | 98.2 |
| Ex.(37) | Com.(1-37) | 5.7 | 6.1 | 300.0 | 4.9 | 92.1 |
| Ex.(38) | Com.(1-38) | 5.7 | 6.5 | 300.0 | 4.6 | 117.1 |
| Ex.(39) | Com.(1-39) | 5.1 | 7.3 | 300.0 | 4.1 | 114.3 |
| Ex.(40) | Com.(1-40) | 5.5 | 6.1 | 300.0 | 4.9 | 108.0 |
| Ex.(41) | Com.(1-41) | 5.3 | 6.2 | 300.0 | 4.9 | 98.5 |
| Ex.(42) | Com.(1-42) | 5.1 | 5.8 | 300.0 | 5.2 | 108.8 |
| Ex.(43) | Com.(1-43) | 5.3 | 5.9 | 300.0 | 5.1 | 116.8 |
| Ex.(44) | Com.(1-44) | 5.4 | 6.0 | 300.0 | 5.0 | 110.8 |
| Ex.(45) | Com.(1-45) | 5.8 | 5.3 | 300.0 | 5.7 | 128.7 |
| Ex.(46) | Com.(1-46) | 5.6 | 6.4 | 300.0 | 4.7 | 108.6 |
| Ex.(47) | Com.(1-47) | 5.0 | 8.5 | 300.0 | 3.5 | 94.7 |
| Ex.(48) | Com.(1-48) | 5.2 | 5.9 | 300.0 | 5.1 | 91.7 |
| Ex.(49) | Com.(1-49) | 5.5 | 6.9 | 300.0 | 4.3 | 121.1 |
| Ex.(50) | Com.(1-50) | 5.5 | 8.8 | 300.0 | 3.4 | 90.2 |
| Ex.(51) | Com.(1-51) | 5.0 | 8.4 | 300.0 | 3.6 | 118.5 |
| Ex.(52) | Com.(1-52) | 5.8 | 6.4 | 300.0 | 4.7 | 123.4 |
| Ex.(53) | Com.(1-53) | 5.4 | 6.9 | 300.0 | 4.4 | 114.8 |
| Ex.(54) | Com.(1-54) | 5.7 | 5.2 | 300.0 | 5.7 | 109.9 |
| Ex.(55) | Com.(1-55) | 5.8 | 6.7 | 300.0 | 4.5 | 115.6 |
| Ex.(56) | Com.(1-56) | 5.6 | 5.4 | 300.0 | 5.5 | 126.8 |
| Ex.(57) | Com.(1-57) | 5.8 | 9.5 | 300.0 | 3.2 | 97.1 |
| Ex.(58) | Com.(1-58) | 5.8 | 7.2 | 300.0 | 4.2 | 99.4 |
| Ex.(59) | Com.(1-59) | 5.5 | 7.7 | 300.0 | 3.9 | 113.2 |
| Ex.(60) | Com.(1-60) | 5.8 | 5.4 | 300.0 | 5.5 | 111.5 |
| Ex.(61) | Com.(1-61) | 5.0 | 6.5 | 300.0 | 4.6 | 126.2 |
| Ex.(62) | Com.(1-62) | 5.4 | 7.4 | 300.0 | 4.0 | 123.4 |
| Ex.(63) | Com.(1-63) | 5.7 | 9.5 | 300.0 | 3.2 | 103.7 |
| Ex.(64) | Com.(1-64) | 5.1 | 6.2 | 300.0 | 4.9 | 104.5 |
| Ex.(65) | Com.(1-65) | 5.3 | 6.1 | 300.0 | 5.0 | 114.7 |
| Ex.(66) | Com.(1-66) | 5.0 | 9.2 | 300.0 | 3.3 | 128.3 |
| Ex.(67) | Com.(1-67) | 5.7 | 6.6 | 300.0 | 4.6 | 121.3 |
| Ex.(68) | Com.(1-68) | 5.2 | 5.3 | 300.0 | 5.7 | 119.2 |
| Ex.(69) | Com.(1-69) | 5.4 | 7.3 | 300.0 | 4.1 | 109.5 |
| Ex.(70) | Com.(1-70) | 5.4 | 6.6 | 300.0 | 4.5 | 110.7 |
| Ex.(71) | Com.(1-71) | 5.8 | 5.6 | 300.0 | 5.3 | 92.0 |
| Ex.(72) | Com.(1-72) | 4.9 | 5.1 | 300.0 | 5.9 | 104.3 |
| Ex.(73) | Com.(1-73) | 5.1 | 9.3 | 300.0 | 3.2 | 92.4 |
| Ex.(74) | Com.(1-74) | 5.0 | 6.4 | 300.0 | 4.7 | 93.6 |
| Ex.(75) | Com.(1-75) | 5.0 | 8.7 | 300.0 | 3.5 | 98.7 |
| Ex.(76) | Com.(1-76) | 5.1 | 5.5 | 300.0 | 5.5 | 118.2 |
| Ex.(77) | Com.(1-77) | 5.0 | 8.7 | 300.0 | 3.4 | 94.5 |
| Ex.(78) | Com.(1-78) | 5.1 | 7.8 | 300.0 | 3.8 | 105.1 |
| Ex.(79) | Com.(1-79) | 5.0 | 5.2 | 300.0 | 5.7 | 123.3 |
| Ex.(80) | Com.(1-80) | 5.0 | 5.9 | 300.0 | 5.1 | 100.9 |
| Ex.(81) | Com.(1-81) | 5.1 | 8.4 | 300.0 | 3.6 | 118.3 |
| Ex.(82) | Com.(1-82) | 5.1 | 6.7 | 300.0 | 4.5 | 113.7 |
| Ex.(83) | Com.(1-83) | 5.0 | 9.9 | 300.0 | 3.0 | 97.1 |
| Ex.(84) | Com.(1-84) | 5.3 | 8.5 | 300.0 | 3.5 | 114.9 |
| Ex.(85) | Com.(1-85) | 5.1 | 7.2 | 300.0 | 4.2 | 111.3 |
| Ex.(86) | Com.(1-86) | 5.2 | 8.8 | 300.0 | 3.4 | 91.7 |
| Ex.(87) | Com.(1-87) | 5.5 | 6.8 | 300.0 | 4.4 | 96.5 |
| Ex.(88) | Com.(1-88) | 5.3 | 5.7 | 300.0 | 5.3 | 104.9 |
| Ex.(89) | Com.(1-89) | 5.3 | 7.0 | 300.0 | 4.3 | 123.1 |
| Ex.(90) | Com.(1-90) | 5.3 | 5.8 | 300.0 | 5.2 | 103.3 |
| Ex.(91) | Com.(1-91) | 5.8 | 8.1 | 300.0 | 3.7 | 91.0 |
| Ex.(92) | Com.(1-92) | 5.6 | 9.0 | 300.0 | 3.3 | 109.1 |
| Ex.(93) | Com.(1-93) | 5.3 | 5.5 | 300.0 | 5.4 | 119.6 |
| Ex.(94) | Com.(1-94) | 5.8 | 7.5 | 300.0 | 4.0 | 95.4 |
| Ex.(95) | Com.(1-95) | 5.5 | 7.2 | 300.0 | 4.2 | 90.2 |
| Ex.(96) | Com.(1-96) | 5.8 | 8.5 | 300.0 | 3.5 | 96.5 |
| Ex.(97) | Com.(1-97) | 5.2 | 5.4 | 300.0 | 5.5 | 103.3 |
| Ex.(98) | Com.(1-98) | 5.5 | 5.8 | 300.0 | 5.1 | 96.5 |
| Ex.(99) | Com.(1-99) | 5.8 | 5.7 | 300.0 | 5.2 | 115.7 |
| Ex.(100) | Com.(1-100) | 5.1 | 9.1 | 300.0 | 3.3 | 109.7 |
| Ex.(101) | Com.(1-101) | 5.4 | 9.7 | 300.0 | 3.1 | 117.8 |
| Ex.(102) | Com.(1-102) | 5.5 | 8.7 | 300.0 | 3.4 | 97.0 |
| Ex.(103) | Com.(1-103) | 5.5 | 7.1 | 300.0 | 4.2 | 124.3 |
| Ex.(104) | Com.(1-104) | 5.3 | 9.9 | 300.0 | 3.0 | 119.0 |
| Ex.(105) | Com.(1-105) | 5.3 | 5.5 | 300.0 | 5.5 | 91.2 |
| Ex.(106) | Com.(1-106) | 5.3 | 7.4 | 300.0 | 4.0 | 96.9 |
| Ex.(107) | Com.(1-107) | 5.1 | 5.8 | 300.0 | 5.1 | 91.3 |
| Ex.(108) | Com.(1-108) | 5.0 | 5.6 | 300.0 | 5.3 | 111.6 |
| Ex.(109) | Com.(1-109) | 5.4 | 7.7 | 300.0 | 3.9 | 98.8 |
| Ex.(110) | Com.(1-110) | 5.3 | 9.2 | 300.0 | 3.2 | 114.4 |
| Ex.(111) | Com.(1-111) | 5.3 | 9.1 | 300.0 | 3.3 | 92.5 |
| Ex.(112) | Com.(1-112) | 5.1 | 5.6 | 300.0 | 5.3 | 95.0 |
| Ex.(113) | Com.(1-113) | 5.2 | 8.8 | 300.0 | 3.4 | 128.2 |
| Ex.(114) | Com.(1-114) | 5.3 | 8.0 | 300.0 | 3.7 | 127.9 |
| Ex.(115) | Com.(1-115) | 5.3 | 7.0 | 300.0 | 4.3 | 122.0 |
| Ex.(116) | Com.(1-116) | 5.2 | 8.0 | 300.0 | 3.7 | 112.8 |
| Ex.(117) | Com.(1-117) | 5.4 | 6.3 | 300.0 | 4.8 | 130.0 |
| Ex.(118) | Com.(1-118) | 5.4 | 7.8 | 300.0 | 3.9 | 112.6 |
| Ex.(119) | Com.(1-119) | 5.4 | 9.8 | 300.0 | 3.0 | 91.1 |
| Ex.(120) | Com.(1-120) | 5.3 | 9.2 | 300.0 | 3.3 | 97.5 |
| Ex.(121) | Com.(1-121) | 5.2 | 5.3 | 300.0 | 5.6 | 99.2 |
| Ex.(122) | Com.(1-122) | 5.2 | 5.5 | 300.0 | 5.4 | 124.6 |
| Ex.(123) | Com.(1-123) | 5.3 | 5.7 | 300.0 | 5.3 | 110.3 |
| Ex.(124) | Com.(1-124) | 5.5 | 6.1 | 300.0 | 4.9 | 129.0 |
| Ex.(125) | Com.(1-125) | 5.8 | 6.2 | 300.0 | 4.8 | 115.2 |
| Ex.(126) | Com.(1-126) | 5.3 | 6.1 | 300.0 | 4.9 | 99.6 |
| Ex.(127) | Com.(1-127) | 5.4 | 6.5 | 300.0 | 4.6 | 124.7 |
| Ex.(128) | Com.(1-128) | 5.1 | 6.5 | 300.0 | 4.6 | 104.3 |
| Ex.(129) | Com.(1-129) | 5.7 | 5.3 | 300.0 | 5.6 | 118.2 |
| Ex.(130) | Com.(1-130) | 5.1 | 6.9 | 300.0 | 4.4 | 104.7 |
| Ex.(131) | Com.(1-131) | 5.2 | 7.0 | 300.0 | 4.3 | 124.2 |
| Ex.(132) | Com.(1-132) | 5.1 | 8.3 | 300.0 | 3.6 | 103.1 |
| Ex.(133) | Com.(1-133) | 5.8 | 9.6 | 300.0 | 3.1 | 122.8 |
| Ex.(134) | Com.(1-134) | 5.2 | 5.7 | 300.0 | 5.3 | 123.6 |
| Ex.(135) | Com.(1-135) | 5.5 | 5.3 | 300.0 | 5.7 | 117.5 |
| Ex.(136) | Com.(1-136) | 5.1 | 8.2 | 300.0 | 3.6 | 109.7 |
| Ex.(137) | Com.(1-137) | 5.6 | 6.9 | 300.0 | 4.4 | 108.4 |
| Ex.(138) | Com.(1-138) | 5.2 | 6.3 | 300.0 | 4.8 | 123.5 |
| Ex.(139) | Com.(1-139) | 5.6 | 9.2 | 300.0 | 3.2 | 91.5 |
| Ex.(140) | Com.(1-140) | 5.8 | 7.3 | 300.0 | 4.1 | 123.8 |
| Ex.(141) | Com.(1-141) | 5.9 | 8.1 | 300.0 | 3.7 | 123.3 |
| Ex.(142) | Com.(1-142) | 5.2 | 8.5 | 300.0 | 3.5 | 111.7 |
| Ex.(143) | Com.(1-143) | 5.4 | 6.1 | 300.0 | 4.9 | 93.5 |
| Ex.(144) | Com.(1-144) | 5.0 | 5.8 | 300.0 | 5.2 | 111.7 |
| Ex.(145) | Com.(1-145) | 5.8 | 5.9 | 300.0 | 5.1 | 113.6 |
| Ex.(146) | Com.(1-146) | 5.5 | 5.9 | 300.0 | 5.1 | 97.4 |
| Ex.(147) | Com.(1-147) | 5.6 | 6.2 | 300.0 | 4.8 | 112.4 |
| Ex.(148) | Com.(1-148) | 5.8 | 9.4 | 300.0 | 3.2 | 90.0 |
| Ex.(149) | Com.(1-149) | 5.1 | 6.2 | 300.0 | 4.9 | 99.7 |
| Ex.(150) | Com.(1-150) | 5.8 | 5.4 | 300.0 | 5.5 | 96.8 |
| Ex.(151) | Com.(3-1) | 5.0 | 6.6 | 300.0 | 4.5 | 100.1 |
| Ex.(152) | Com.(3-2) | 5.4 | 9.6 | 300.0 | 3.1 | 116.4 |
| Ex.(153) | Com.(3-4) | 5.6 | 5.8 | 300.0 | 5.2 | 118.2 |
| Ex.(154) | Com.(3-4) | 5.1 | 9.1 | 300.0 | 3.3 | 94.5 |
| Ex.(155) | Com.(3-9) | 5.3 | 5.7 | 300.0 | 5.3 | 97.2 |
| Ex.(156) | Com.(3-10) | 5.5 | 9.0 | 300.0 | 3.3 | 94.7 |
| Ex.(157) | Com.(3-11) | 5.4 | 8.2 | 300.0 | 3.7 | 102.4 |
| Ex.(158) | Com.(3-13) | 5.0 | 8.7 | 300.0 | 3.4 | 94.4 |
| Ex.(159) | Com.(3-14) | 5.4 | 7.3 | 300.0 | 4.1 | 91.3 |
| Ex.(160) | Com.(3-15) | 4.9 | 7.7 | 300.0 | 3.9 | 100.0 |
| Ex.(161) | Com.(3-16) | 5.6 | 9.4 | 300.0 | 3.2 | 117.1 |
| Ex.(162) | Com.(3-20) | 5.3 | 6.6 | 300.0 | 4.6 | 117.6 |
| Ex.(163) | Com.(3-21) | 5.1 | 6.2 | 300.0 | 4.8 | 90.1 |
| Ex.(164) | Com.(3-23) | 5.1 | 7.5 | 300.0 | 4.0 | 110.7 |
| Ex.(165) | Com.(3-24) | 5.3 | 9.6 | 300.0 | 3.1 | 100.2 |
| Ex.(166) | Com.(3-25) | 5.1 | 9.4 | 300.0 | 3.2 | 95.1 |
| Ex.(167) | Com.(3-26) | 5.1 | 6.6 | 300.0 | 4.5 | 114.6 |
| Ex.(168) | Com.(3-29) | 4.9 | 5.9 | 300.0 | 5.1 | 115.6 |
| Ex.(169) | Com.(3-30) | 5.4 | 7.3 | 300.0 | 4.1 | 104.7 |
| Ex.(170) | Com.(3-31) | 5.5 | 9.1 | 300.0 | 3.3 | 110.9 |
| Ex.(171) | Com.(3-34) | 5.0 | 9.4 | 300.0 | 3.2 | 103.8 |
| Ex.(172) | Com.(3-35) | 5.1 | 6.9 | 300.0 | 4.4 | 110.2 |
| Ex.(173) | Com.(3-49) | 5.5 | 6.6 | 300.0 | 4.6 | 103.3 |
| Ex.(174) | Com.(3-50) | 4.9 | 9.0 | 300.0 | 3.3 | 115.1 |
| Ex.(175) | Com.(3-58) | 5.6 | 6.0 | 300.0 | 5.0 | 93.2 |
| Ex.(176) | Com.(3-60) | 5.0 | 6.2 | 300.0 | 4.9 | 118.4 |
| Ex.(177) | Com.(3-61) | 5.5 | 7.6 | 300.0 | 3.9 | 92.6 |
| Ex.(178) | Com.(3-66) | 5.5 | 7.3 | 300.0 | 4.1 | 105.5 |
| Ex.(179) | Com.(3-68) | 5.4 | 8.0 | 300.0 | 3.7 | 99.1 |
| Ex.(180) | Com.(3-69) | 5.4 | 7.5 | 300.0 | 4.0 | 91.9 |
| Ex.(181) | Com.(3-70) | 5.3 | 6.8 | 300.0 | 4.4 | 92.5 |
| Ex.(182) | Com.(3-71) | 5.1 | 6.7 | 300.0 | 4.5 | 104.8 |
| Ex.(183) | Com.(3-72) | 5.1 | 6.3 | 300.0 | 4.8 | 111.4 |
| Ex.(184) | Com.(4-4) | 4.9 | 6.7 | 300.0 | 4.5 | 94.2 |
| Ex.(185) | Com.(4-7) | 5.2 | 8.0 | 300.0 | 3.8 | 102.0 |

TABLE 5-continued

| | Compound | Driving Voltage | Current Density (mA/cm2) | Brightness (cd/m2) | Efficiency (cd/A) | T(90) |
|---|---|---|---|---|---|---|
| Ex.(186) | Com.(4-8) | 4.9 | 7.3 | 300.0 | 4.1 | 105.4 |
| Ex.(187) | Com.(4-9) | 4.7 | 7.0 | 300.0 | 4.3 | 105.3 |
| Ex.(188) | Com.(4-10) | 4.6 | 6.7 | 300.0 | 4.5 | 94.0 |
| Ex.(189) | Com.(4-11) | 5.2 | 9.2 | 300.0 | 3.2 | 93.4 |
| Ex.(190) | Com.(4-24) | 4.8 | 6.3 | 300.0 | 4.7 | 99.9 |
| Ex.(191) | Com.(4-25) | 5.0 | 8.9 | 300.0 | 3.4 | 98.4 |
| Ex.(192) | Com.(4-27) | 5.0 | 6.6 | 300.0 | 4.5 | 99.4 |
| Ex.(193) | Com.(4-32) | 5.0 | 5.8 | 300.0 | 5.2 | 91.4 |
| Ex.(194) | Com.(4-33) | 4.6 | 6.0 | 300.0 | 5.0 | 95.3 |
| Ex.(195) | Com.(4-36) | 4.6 | 6.1 | 300.0 | 4.9 | 105.1 |
| Ex.(196) | Com.(4-43) | 4.8 | 5.8 | 300.0 | 5.2 | 96.0 |
| Ex.(197) | Com.(4-44) | 4.5 | 6.3 | 300.0 | 4.8 | 90.2 |
| Ex.(198) | Com.(4-45) | 4.3 | 6.5 | 300.0 | 4.6 | 103.4 |
| Ex.(199) | Com.(4-47) | 5.1 | 7.0 | 300.0 | 4.3 | 92.5 |
| Ex.(200) | Com.(4-48) | 4.9 | 6.7 | 300.0 | 4.5 | 96.4 |
| Ex.(201) | Com.(4-55) | 5.1 | 6.9 | 300.0 | 4.3 | 98.5 |
| Ex.(202) | Com.(4-58) | 4.8 | 6.2 | 300.0 | 4.8 | 105.0 |
| Ex.(203) | Com.(4-61) | 4.9 | 7.7 | 300.0 | 3.9 | 105.8 |
| Ex.(204) | Com.(4-62) | 5.0 | 8.8 | 300.0 | 3.4 | 102.7 |
| Ex.(205) | Com.(4-63) | 4.9 | 7.5 | 300.0 | 4.0 | 97.3 |
| Ex.(206) | Com.(4-64) | 5.2 | 6.7 | 300.0 | 4.5 | 108.4 |
| Ex.(207) | Com.(4-65) | 4.9 | 5.7 | 300.0 | 5.3 | 100.4 |
| Ex.(208) | Com.(4-66) | 5.1 | 7.0 | 300.0 | 4.3 | 105.8 |
| Ex.(209) | Com.(4-67) | 5.3 | 7.7 | 300.0 | 3.9 | 101.3 |
| Ex.(210) | Com.(4-68) | 4.9 | 6.4 | 300.0 | 4.7 | 102.2 |
| Ex.(211) | Com.(4-69) | 4.8 | 8.2 | 300.0 | 3.6 | 93.2 |
| Ex.(212) | Com.(4-70) | 5.2 | 6.2 | 300.0 | 4.8 | 106.1 |
| Ex.(213) | Com.(4-71) | 4.8 | 8.8 | 300.0 | 3.4 | 95.2 |
| Ex.(214) | Com.(4-104) | 5.3 | 7.6 | 300.0 | 3.9 | 108.3 |
| Ex.(215) | Com.(4-105) | 5.1 | 7.9 | 300.0 | 3.8 | 103.7 |
| Ex.(216) | Com.(4-106) | 5.0 | 8.5 | 300.0 | 3.5 | 108.6 |
| Ex.(217) | Com.(4-107) | 5.1 | 6.7 | 300.0 | 4.4 | 103.3 |
| Ex.(218) | Com.(4-108) | 5.2 | 9.7 | 300.0 | 3.1 | 92.2 |
| Ex.(219) | Com.(5-2) | 5.3 | 8.7 | 300.0 | 3.5 | 90.8 |
| Ex.(220) | Com.(5-4) | 5.3 | 5.8 | 300.0 | 5.2 | 101.7 |
| Ex.(221) | Com.(5-6) | 5.3 | 9.5 | 300.0 | 3.2 | 98.9 |
| Ex.(222) | Com.(5-7) | 5.4 | 5.7 | 300.0 | 5.3 | 93.0 |
| Ex.(223) | Com.(5-10) | 5.5 | 6.1 | 300.0 | 4.9 | 106.5 |
| Ex.(224) | Com.(5-11) | 5.4 | 8.9 | 300.0 | 3.4 | 92.8 |
| Ex.(225) | Com.(5-12) | 5.3 | 6.7 | 300.0 | 4.5 | 97.9 |
| Ex.(226) | Com.(5-16) | 5.1 | 6.9 | 300.0 | 4.3 | 101.9 |
| Ex.(227) | Com.(5-17) | 5.0 | 8.3 | 300.0 | 3.6 | 103.7 |
| Ex.(228) | Com.(5-18) | 5.2 | 7.6 | 300.0 | 4.0 | 104.7 |
| Ex.(229) | Com.(5-19) | 4.8 | 5.9 | 300.0 | 5.1 | 96.9 |
| Ex.(230) | Com.(5-20) | 4.7 | 6.6 | 300.0 | 4.6 | 98.1 |
| Ex.(231) | Com.(5-21) | 4.8 | 6.5 | 300.0 | 4.6 | 102.4 |
| Ex.(232) | Com.(5-22) | 5.0 | 6.2 | 300.0 | 4.9 | 103.7 |
| Ex.(233) | Com.(5-23) | 5.2 | 7.2 | 300.0 | 4.2 | 109.3 |
| Ex.(234) | Com.(5-24) | 4.9 | 5.9 | 300.0 | 5.0 | 96.7 |
| Ex.(235) | Com.(5-27) | 5.5 | 9.0 | 300.0 | 3.3 | 91.3 |
| Ex.(236) | Com.(5-28) | 5.6 | 9.0 | 300.0 | 3.3 | 92.3 |
| Ex.(237) | Com.(5-30) | 5.4 | 5.8 | 300.0 | 5.2 | 98.6 |
| Ex.(238) | Com.(5-32) | 5.5 | 7.6 | 300.0 | 4.0 | 98.2 |
| Ex.(239) | Com.(5-33) | 5.4 | 8.1 | 300.0 | 3.7 | 104.1 |
| Ex.(240) | Com.(5-34) | 4.9 | 6.1 | 300.0 | 4.9 | 105.0 |
| Ex.(241) | Com.(5-36) | 5.4 | 7.0 | 300.0 | 4.3 | 102.2 |
| Ex.(242) | Com.(5-37) | 5.1 | 6.0 | 300.0 | 5.0 | 96.6 |
| Ex.(243) | Com.(5-38) | 4.9 | 7.6 | 300.0 | 4.0 | 90.6 |
| Ex.(244) | Com.(5-40) | 5.4 | 6.4 | 300.0 | 4.7 | 105.2 |
| Ex.(245) | Com.(5-41) | 4.9 | 6.7 | 300.0 | 4.5 | 93.9 |
| Ex.(246) | Com.(5-42) | 5.4 | 7.4 | 300.0 | 4.1 | 101.1 |
| Ex.(247) | Com.(5-43) | 5.5 | 8.0 | 300.0 | 3.7 | 102.9 |
| Ex.(248) | Com.(5-44) | 5.6 | 5.7 | 300.0 | 5.3 | 94.0 |
| Ex.(249) | Com.(5-45) | 4.8 | 9.4 | 300.0 | 3.2 | 99.3 |
| Ex.(250) | Com.(5-47) | 5.3 | 8.3 | 300.0 | 3.6 | 109.2 |
| Ex.(251) | Com.(5-49) | 5.2 | 6.5 | 300.0 | 4.6 | 103.3 |
| Ex.(252) | Com.(5-50) | 5.0 | 6.2 | 300.0 | 4.8 | 106.2 |
| Ex.(253) | Com.(5-51) | 5.3 | 6.2 | 300.0 | 4.8 | 98.8 |
| Ex.(254) | Com.(6-10) | 5.4 | 9.6 | 300.0 | 3.1 | 91.4 |
| Ex.(255) | Com.(6-11) | 5.2 | 7.4 | 300.0 | 4.1 | 104.4 |
| Ex.(256) | Com.(6-12) | 5.3 | 6.2 | 300.0 | 4.8 | 90.2 |
| Ex.(257) | Com.(6-13) | 5.7 | 6.8 | 300.0 | 4.4 | 105.9 |
| Ex.(258) | Com.(6-14) | 5.4 | 6.3 | 300.0 | 4.8 | 103.5 |
| Ex.(259) | Com.(6-15) | 5.4 | 6.5 | 300.0 | 4.6 | 111.5 |
| Ex.(260) | Com.(6-16) | 5.2 | 6.7 | 300.0 | 4.4 | 109.9 |
| Ex.(261) | Com.(6-17) | 5.4 | 9.4 | 300.0 | 3.2 | 101.4 |
| Ex.(262) | Com.(6-18) | 5.5 | 5.7 | 300.0 | 5.3 | 110.0 |
| Ex.(263) | Com.(6-19) | 5.5 | 6.1 | 300.0 | 4.9 | 111.3 |
| Ex.(264) | Com.(6-20) | 5.3 | 9.2 | 300.0 | 3.3 | 110.0 |
| Ex.(265) | Com.(6-21) | 5.2 | 7.2 | 300.0 | 4.2 | 98.8 |
| Ex.(266) | Com.(6-22) | 5.7 | 6.3 | 300.0 | 4.7 | 97.0 |
| Ex.(267) | Com.(6-23) | 5.6 | 6.8 | 300.0 | 4.4 | 96.2 |
| Ex.(268) | Com.(6-24) | 5.6 | 6.6 | 300.0 | 4.6 | 90.9 |
| Ex.(269) | Com.(6-28) | 5.6 | 7.1 | 300.0 | 4.2 | 116.5 |
| Ex.(270) | Com.(6-32) | 5.8 | 9.9 | 300.0 | 3.0 | 90.2 |
| Ex.(271) | Com.(6-33) | 5.4 | 6.4 | 300.0 | 4.7 | 99.7 |
| Ex.(272) | Com.(6-39) | 5.3 | 7.0 | 300.0 | 4.3 | 95.8 |
| Ex.(273) | Com.(6-40) | 5.6 | 7.3 | 300.0 | 4.1 | 111.7 |
| Ex.(274) | Com.(6-41) | 5.7 | 8.5 | 300.0 | 3.5 | 96.2 |
| Ex.(275) | Com.(6-43) | 5.6 | 6.7 | 300.0 | 4.5 | 92.2 |
| Ex.(276) | Com.(6-47) | 5.5 | 5.7 | 300.0 | 5.3 | 95.6 |
| Ex.(277) | Com.(6-49) | 5.5 | 6.8 | 300.0 | 4.4 | 119.5 |
| Ex.(278) | Com.(6-50) | 5.2 | 7.1 | 300.0 | 4.2 | 101.8 |
| Ex.(279) | Com.(7-9) | 5.7 | 9.1 | 300.0 | 3.3 | 114.6 |
| Ex.(280) | Com.(7-10) | 5.8 | 10.0 | 300.0 | 3.0 | 110.4 |
| Ex.(281) | Com.(7-11) | 5.6 | 6.7 | 300.0 | 4.5 | 100.4 |
| Ex.(282) | Com.(7-12) | 5.6 | 6.0 | 300.0 | 5.0 | 94.9 |
| Ex.(283) | Com.(7-14) | 5.8 | 6.8 | 300.0 | 4.4 | 94.9 |
| Ex.(284) | Com.(7-16) | 5.5 | 7.4 | 300.0 | 4.1 | 94.1 |
| Ex.(285) | Com.(7-17) | 5.7 | 9.4 | 300.0 | 3.2 | 91.5 |
| Ex.(286) | Com.(7-19) | 5.7 | 6.0 | 300.0 | 5.0 | 105.0 |
| Ex.(287) | Com.(7-20) | 5.5 | 9.9 | 300.0 | 3.0 | 104.1 |
| Ex.(288) | Com.(7-21) | 5.9 | 7.4 | 300.0 | 4.0 | 104.4 |
| Ex.(289) | Com.(7-22) | 5.6 | 8.0 | 300.0 | 3.8 | 118.1 |
| Ex.(290) | Com.(7-25) | 5.8 | 9.6 | 300.0 | 3.1 | 108.0 |
| Ex.(291) | Com.(7-26) | 5.8 | 6.7 | 300.0 | 4.5 | 98.5 |
| Ex.(292) | Com.(7-27) | 5.7 | 7.8 | 300.0 | 3.8 | 111.9 |
| Ex.(293) | Com.(7-30) | 5.6 | 6.4 | 300.0 | 4.7 | 92.4 |
| Ex.(294) | Com.(7-31) | 5.8 | 5.7 | 300.0 | 5.3 | 114.6 |
| Ex.(295) | Com.(7-36) | 5.8 | 8.9 | 300.0 | 3.4 | 113.0 |
| Ex.(296) | Com.(7-46) | 5.5 | 8.5 | 300.0 | 3.5 | 116.9 |
| Ex.(297) | Com.(7-50) | 5.8 | 6.4 | 300.0 | 4.7 | 103.7 |
| Ex.(298) | Com.(7-51) | 5.8 | 6.2 | 300.0 | 4.8 | 112.2 |
| Ex.(299) | Com.(7-52) | 5.6 | 8.3 | 300.0 | 3.6 | 94.2 |
| Ex.(300) | Com.(7-56) | 5.6 | 7.8 | 300.0 | 3.8 | 94.0 |
| Ex.(301) | Com.(7-61) | 5.6 | 8.8 | 300.0 | 3.4 | 94.3 |
| Ex.(302) | Com.(7-62) | 5.9 | 6.6 | 300.0 | 4.5 | 103.1 |
| Ex.(303) | Com.(7-63) | 5.6 | 8.3 | 300.0 | 3.6 | 108.8 |
| Ex.(304) | Com.(8-1) | 5.2 | 9.5 | 300.0 | 3.2 | 98.5 |
| Ex.(305) | Com.(8-2) | 5.5 | 6.2 | 300.0 | 4.9 | 110.8 |
| Ex.(306) | Com.(8-5) | 5.6 | 7.8 | 300.0 | 3.8 | 103.2 |
| Ex.(307) | Com.(8-6) | 5.4 | 7.2 | 300.0 | 4.2 | 90.7 |
| Ex.(308) | Com.(8-7) | 5.4 | 7.3 | 300.0 | 4.1 | 103.1 |
| Ex.(309) | Com.(8-9) | 5.6 | 7.3 | 300.0 | 4.1 | 119.3 |
| Ex.(310) | Com.(8-10) | 5.3 | 5.9 | 300.0 | 5.1 | 107.6 |
| Ex.(311) | Com.(8-11) | 5.6 | 5.8 | 300.0 | 5.1 | 95.9 |
| Ex.(312) | Com.(8-12) | 5.3 | 6.4 | 300.0 | 4.7 | 109.5 |
| Ex.(313) | Com.(8-16) | 5.2 | 10.0 | 300.0 | 3.0 | 118.9 |
| Ex.(314) | Com.(8-17) | 5.7 | 8.2 | 300.0 | 3.6 | 118.3 |
| Ex.(315) | Com.(8-18) | 5.3 | 9.4 | 300.0 | 3.2 | 99.1 |
| Ex.(316) | Com.(8-20) | 5.2 | 9.8 | 300.0 | 3.1 | 115.4 |
| Ex.(317) | Com.(8-22) | 5.6 | 7.3 | 300.0 | 4.1 | 103.3 |
| Ex.(318) | Com.(8-25) | 5.8 | 8.2 | 300.0 | 3.6 | 100.3 |
| Ex.(319) | Com.(8-26) | 5.6 | 7.0 | 300.0 | 4.3 | 115.9 |
| Ex.(320) | Com.(8-27) | 5.8 | 7.1 | 300.0 | 4.2 | 108.4 |
| Ex.(321) | Com.(8-30) | 5.3 | 6.3 | 300.0 | 4.8 | 101.6 |
| Ex.(322) | Com.(8-31) | 5.6 | 9.9 | 300.0 | 3.0 | 114.0 |
| Ex.(323) | Com.(8-35) | 5.7 | 6.7 | 300.0 | 4.5 | 106.4 |
| Ex.(324) | Com.(8-40) | 5.2 | 9.8 | 300.0 | 3.1 | 118.0 |
| Ex.(325) | Com.(8-47) | 5.4 | 5.7 | 300.0 | 5.2 | 97.0 |
| Ex.(326) | Com.(8-49) | 5.4 | 5.9 | 300.0 | 5.1 | 104.3 |
| Ex.(327) | Com.(8-50) | 5.4 | 9.9 | 300.0 | 3.0 | 112.9 |
| Ex.(328) | Com.(8-51) | 5.3 | 7.0 | 300.0 | 4.3 | 109.0 |
| Ex.(329) | Com.(8-55) | 5.2 | 7.9 | 300.0 | 3.8 | 90.5 |
| Ex.(330) | Com.(8-57) | 5.2 | 8.6 | 300.0 | 3.5 | 112.6 |
| Ex.(331) | Com.(8-58) | 5.7 | 9.8 | 300.0 | 3.1 | 109.1 |
| Ex.(332) | Com.(8-59) | 5.5 | 7.2 | 300.0 | 4.1 | 101.5 |
| Ex.(333) | Com.(8-60) | 5.4 | 6.4 | 300.0 | 4.7 | 99.1 |
| Ex.(334) | Com.(8-61) | 5.6 | 6.9 | 300.0 | 4.4 | 118.6 |
| Ex.(335) | Com.(9-2) | 5.6 | 6.1 | 300.0 | 4.9 | 98.5 |

TABLE 5-continued

| Compound | Driving Voltage | Current Density (mA/cm2) | Brightness (cd/m2) | Efficiency (cd/A) | T(90) |
|---|---|---|---|---|---|
| Ex.(336) Com.(9-8) | 5.4 | 5.8 | 300.0 | 5.1 | 116.6 |
| Ex.(337) Com.(9-11) | 5.5 | 9.4 | 300.0 | 3.2 | 113.9 |
| Ex.(338) Com.(9-12) | 5.8 | 6.5 | 300.0 | 4.6 | 95.5 |
| Ex.(339) Com.(9-13) | 5.8 | 6.7 | 300.0 | 4.5 | 115.5 |
| Ex.(340) Com.(9-14) | 5.5 | 9.2 | 300.0 | 3.3 | 106.5 |
| Ex.(341) Com.(9-15) | 5.3 | 6.7 | 300.0 | 4.5 | 116.2 |
| Ex.(342) Com.(9-17) | 5.5 | 6.2 | 300.0 | 4.9 | 95.4 |
| Ex.(343) Com.(9-18) | 5.8 | 6.0 | 300.0 | 5.0 | 102.5 |
| Ex.(344) Com.(9-19) | 5.3 | 5.7 | 300.0 | 5.3 | 118.7 |
| Ex.(345) Com.(9-20) | 5.5 | 7.7 | 300.0 | 3.9 | 102.6 |
| Ex.(346) Com.(9-21) | 5.3 | 6.8 | 300.0 | 4.4 | 102.3 |
| Ex.(347) Com.(9-22) | 5.3 | 8.0 | 300.0 | 3.7 | 91.2 |
| Ex.(348) Com.(9-25) | 5.8 | 6.6 | 300.0 | 4.6 | 106.8 |
| Ex.(349) Com.(9-27) | 5.7 | 6.6 | 300.0 | 4.6 | 116.0 |
| Ex.(350) Com.(9-28) | 5.4 | 5.9 | 300.0 | 5.1 | 94.8 |
| Ex.(351) Com.(9-29) | 5.8 | 8.7 | 300.0 | 3.4 | 93.2 |
| Ex.(352) Com.(9-30) | 5.3 | 9.9 | 300.0 | 3.0 | 103.9 |
| Ex.(353) Com.(9-36) | 5.4 | 9.6 | 300.0 | 3.1 | 108.1 |
| Ex.(354) Com.(9-37) | 5.2 | 6.3 | 300.0 | 4.8 | 102.0 |
| Ex.(355) Com.(9-38) | 5.4 | 9.1 | 300.0 | 3.3 | 109.1 |
| Ex.(356) Com.(9-46) | 5.5 | 6.0 | 300.0 | 5.0 | 92.8 |
| Ex.(357) Com.(9-47) | 5.7 | 9.4 | 300.0 | 3.2 | 103.0 |
| Ex.(358) Com.(9-49) | 5.5 | 9.4 | 300.0 | 3.2 | 93.4 |
| Ex.(359) Com.(9-50) | 5.5 | 6.5 | 300.0 | 4.6 | 98.8 |
| Ex.(360) Com.(9-51) | 5.8 | 6.7 | 300.0 | 4.5 | 101.6 |
| Ex.(361) Com.(9-53) | 5.2 | 6.6 | 300.0 | 4.5 | 91.6 |
| Ex.(362) Com.(9-54) | 5.4 | 6.5 | 300.0 | 4.6 | 109.9 |
| Ex.(363) Com.(9-57) | 5.8 | 8.1 | 300.0 | 3.7 | 108.3 |
| Ex.(364) Com.(9-58) | 5.4 | 8.6 | 300.0 | 3.5 | 99.3 |
| Ex.(365) Com.(10-1) | 5.6 | 6.2 | 300.0 | 4.9 | 100.4 |
| Ex.(366) Com.(10-2) | 5.9 | 6.2 | 300.0 | 4.9 | 116.7 |
| Ex.(367) Com.(10-4) | 5.7 | 6.2 | 300.0 | 4.8 | 110.5 |
| Ex.(368) Com.(10-6) | 5.8 | 7.6 | 300.0 | 4.0 | 113.3 |
| Ex.(369) Com.(10-7) | 5.6 | 6.2 | 300.0 | 4.8 | 109.6 |
| Ex.(370) Com.(10-8) | 5.7 | 9.4 | 300.0 | 3.2 | 111.8 |
| Ex.(371) Com.(10-10) | 5.7 | 6.2 | 300.0 | 4.8 | 97.9 |
| Ex.(372) Com.(10-11) | 5.8 | 6.3 | 300.0 | 4.8 | 105.9 |
| Ex.(373) Com.(10-12) | 5.5 | 8.1 | 300.0 | 3.7 | 111.5 |
| Ex.(374) Com.(10-14) | 5.9 | 5.8 | 300.0 | 5.2 | 94.4 |
| Ex.(375) Com.(10-15) | 5.7 | 7.2 | 300.0 | 4.2 | 105.9 |
| Ex.(376) Com.(10-16) | 5.8 | 9.0 | 300.0 | 3.3 | 94.0 |
| Ex.(377) Com.(10-17) | 5.7 | 7.1 | 300.0 | 4.3 | 116.7 |
| Ex.(378) Com.(10-18) | 5.6 | 7.0 | 300.0 | 4.3 | 110.8 |
| Ex.(379) Com.(10-19) | 5.7 | 5.9 | 301.0 | 5.1 | 109.0 |
| Ex.(380) Com.(10-20) | 5.8 | 7.1 | 302.0 | 4.2 | 90.3 |
| Ex.(381) Com.(10-21) | 5.8 | 7.3 | 303.0 | 4.2 | 97.2 |
| Ex.(382) Com.(10-22) | 5.6 | 8.8 | 304.0 | 3.5 | 95.4 |
| Ex.(383) Com.(10-23) | 5.8 | 8.7 | 305.0 | 3.5 | 93.2 |
| Ex.(384) Com.(10-24) | 5.8 | 6.2 | 306.0 | 4.9 | 108.5 |
| Ex.(385) Com.(10-45) | 5.7 | 9.4 | 307.0 | 3.3 | 107.9 |
| Ex.(386) Com.(10-46) | 5.6 | 6.9 | 308.0 | 4.4 | 119.1 |
| Ex.(387) Com.(10-47) | 5.6 | 7.5 | 309.0 | 4.1 | 118.6 |
| Ex.(388) Com.(10-48) | 5.8 | 8.1 | 310.0 | 3.8 | 97.6 |
| Ex.(389) Com.(10-49) | 5.8 | 10.1 | 311.0 | 3.1 | 92.2 |
| Ex.(390) Com.(10-50) | 5.7 | 6.1 | 312.0 | 5.1 | 118.8 |

It can be seen from Table 5 above that as a result of using the compounds of Formula 1 and Formula 2 as the hole transport layer, the compounds of Formula 2 (corresponding to the case where Ar₃ is

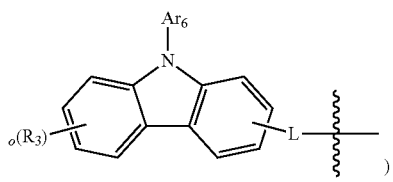

showed low driving voltage, and Compound 1-5 and Compound 1-6 also showed relatively low driving voltage.

In particular, it can be noted that the indole compounds showed relatively higher efficiency and longer life span than the compounds of Formula 2.

Accordingly, OLEDs in which Compound 4-45 showing low driving voltage and the indole compounds having high efficiency and long life span are used as the hole transport layer and the emission-auxiliary layer, respectively, were manufactured as follows.

[Example 7] Emission-Auxiliary Layer

First, an ITO layer (anode) was formed on a glass substrate, and then 2-TNATA was vacuum-deposited on the ITO layer to form a hole injection layer with a thickness of 60 nm. Subsequently, Compound 4-45 as a hole transport compound was vacuum-deposited with a thickness of 20 nm on the hole injection layer to form a hole transport layer. Next, the inventive compound as an emission-auxiliary material was vacuum-deposited with a thickness of 20 nm on the hole transport layer to from an emission-auxiliary layer. Thereafter, a light emitting layer with a thickness of 30 nm was deposited on the emission-auxiliary layer by doping the emission-auxiliary layer with CBP[4,4'-N,N'-dicarbazole-biphenyl] as a host material and (piq)₂Ir(acac)[bis-(1-phenylisoquinolyl)iridium(III)acetylacetonate] as a dopant material in a weight ratio of 95:5. Next, BAlq was vacuum-deposited with a thickness of 10 nm on the light emitting layer to form a hole blocking layer, and then a film of Alq₃ was formed with a thickness of 40 nm on the hole blocking layer to form an electron transport layer. Subsequently, LiF as halogenated alkali metal was deposited with a thickness of 0.2 nm on the electron transport layer to form an electron injection layer, and then Al was deposited with a thickness of 150 nm thereon to form a cathode. In this way, an OLED was completed.

Comparative Example 2

An OLED was manufactured in the same manner as described in Example 7, except that Comparative Compound 2 represented below was used to form the emission-auxiliary layer, instead of the inventive compound.

<Comparative Compound 2>

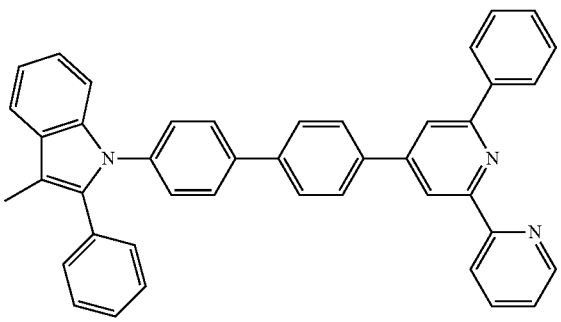

Comparative Example 3

An OLED was manufactured in the same manner as described in Example 7, except that Comparative Compound 3 represented below was used to form the emission-auxiliary layer, instead of the inventive compound.

<Comparative Compound 3>

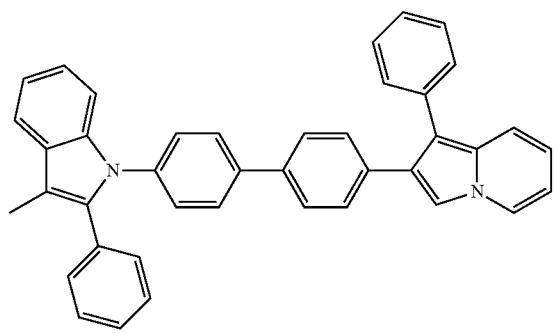

Comparative Example 4

An OLED was manufactured in the same manner as described in Example 7, except that Comparative Compound 4 represented below was used to form the emission-auxiliary layer, instead of the inventive compound.

<Comparative Compound 4>

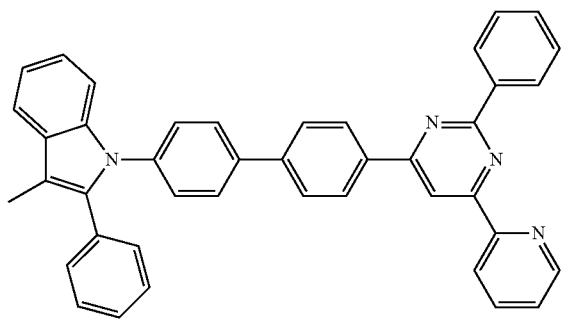

Comparative Example 5

An OLED was manufactured in the same manner as described in Example 7, except that Comparative Compound 5 represented below was used to form the emission-auxiliary layer, instead of the inventive compound.

<Comparative Compound 5>

Comparative Example 6

An OLED was manufactured in the same manner as described in Example 7, except that the emission-auxiliary layer was not used, and only Compound 4-45 was used as the hole transport layer.

A forward bias DC voltage was applied to each of the OLEDs manufactured in Example 7 and Comparative Examples 2 to 6, and electro-luminescence (EL) characteristics of the OLED were measured by PR-650 (Photoresearch). Also, T95 life span was measured by life span measuring equipment (Mcscience) at a reference brightness of 300 cd/m$^2$.

Table 6 below shows the fabrication and evaluation results for the OLEDs according to the examples employing the inventive compounds and the comparative examples.

TABLE 6

| | Compound | Driving Voltage | Current Density (mA/cm$^2$) | Brightness (cd/m$^2$) | Efficiency (cd/A) | T(90) | CIE x | y |
|---|---|---|---|---|---|---|---|---|
| Comp.Ex(2) | Comp.Com 2 | 5.7 | 7.2 | 300.0 | 4.2 | 99.1 | 0.66 | 0.32 |
| Comp.Ex(3) | Comp.Com 3 | 5.6 | 7.5 | 300.0 | 4.0 | 95.1 | 0.66 | 0.32 |
| Comp.Ex(4) | Comp.Com 4 | 5.7 | 8.5 | 300.0 | 3.5 | 108.7 | 0.66 | 0.32 |
| Comp.Ex(5) | Comp.Com 5 | 5.6 | 8.2 | 300.0 | 3.7 | 91.8 | 0.66 | 0.32 |
| Comp.Ex(6) | Not Used | 4.5 | 6.5 | 300.0 | 4.6 | 91.6 | 0.66 | 0.32 |
| Ex.(1) | Com.(1-1) | 5.0 | 5.3 | 300.0 | 5.7 | 158.9 | 0.66 | 0.33 |
| Ex.(2) | Com.(1-2) | 4.9 | 5.3 | 300.0 | 5.7 | 162.6 | 0.66 | 0.32 |
| Ex.(3) | Com.(1-3) | 4.9 | 5.6 | 300.0 | 5.3 | 122.0 | 0.66 | 0.33 |
| Ex.(4) | Com.(1-4) | 4.5 | 5.4 | 300.0 | 5.6 | 157.7 | 0.66 | 0.32 |
| Ex.(5) | Com.(1-5) | 4.3 | 4.4 | 300.0 | 6.8 | 180.9 | 0.66 | 0.32 |
| Ex.(6) | Com.(1-6) | 4.3 | 4.5 | 300.0 | 6.7 | 191.0 | 0.66 | 0.32 |
| Ex.(7) | Com.(1-7) | 4.7 | 5.6 | 300.0 | 5.4 | 131.5 | 0.66 | 0.33 |
| Ex.(8) | Com.(1-8) | 4.8 | 5.3 | 300.0 | 5.7 | 119.8 | 0.66 | 0.32 |
| Ex.(9) | Com.(1-9) | 5.2 | 5.3 | 300.0 | 5.7 | 147.5 | 0.66 | 0.32 |
| Ex.(10) | Com.(1-10) | 4.9 | 5.5 | 300.0 | 5.4 | 138.4 | 0.66 | 0.32 |
| Ex.(11) | Com.(1-11) | 4.8 | 5.5 | 300.0 | 5.5 | 146.1 | 0.66 | 0.32 |
| Ex.(12) | Com.(1-12) | 4.7 | 5.5 | 300.0 | 5.4 | 140.8 | 0.66 | 0.33 |
| Ex.(13) | Com.(1-13) | 4.8 | 5.4 | 300.0 | 5.5 | 138.7 | 0.66 | 0.32 |
| Ex.(14) | Com.(1-14) | 4.4 | 5.4 | 300.0 | 5.6 | 178.9 | 0.66 | 0.33 |
| Ex.(15) | Com.(1-15) | 5.0 | 5.5 | 300.0 | 5.5 | 116.1 | 0.66 | 0.33 |
| Ex.(16) | Com.(1-16) | 5.1 | 5.6 | 300.0 | 5.4 | 147.9 | 0.66 | 0.33 |
| Ex.(17) | Com.(1-17) | 4.8 | 5.5 | 300.0 | 5.4 | 127.1 | 0.66 | 0.32 |
| Ex.(18) | Com.(1-18) | 4.9 | 5.3 | 300.0 | 5.7 | 121.1 | 0.66 | 0.32 |
| Ex.(19) | Com.(1-19) | 5.1 | 5.4 | 300.0 | 5.6 | 134.3 | 0.66 | 0.32 |

TABLE 6-continued

| | Compound | Driving Voltage | Current Density (mA/cm$^2$) | Brightness (cd/m$^2$) | Efficiency (cd/A) | T(90) | CIE x | y |
|---|---|---|---|---|---|---|---|---|
| Ex.(20) | Com.(1-20) | 4.9 | 5.4 | 300.0 | 5.6 | 119.7 | 0.66 | 0.33 |
| Ex.(21) | Com.(1-21) | 5.0 | 5.6 | 300.0 | 5.4 | 140.7 | 0.66 | 0.32 |
| Ex.(22) | Com.(1-22) | 4.9 | 5.6 | 300.0 | 5.3 | 144.9 | 0.66 | 0.32 |
| Ex.(23) | Com.(1-23) | 5.2 | 5.7 | 300.0 | 5.3 | 146.8 | 0.66 | 0.32 |
| Ex.(24) | Com.(1-24) | 5.1 | 5.3 | 300.0 | 5.6 | 129.1 | 0.66 | 0.33 |
| Ex.(25) | Com.(1-25) | 5.2 | 5.6 | 300.0 | 5.4 | 125.4 | 0.66 | 0.33 |
| Ex.(26) | Com.(1-26) | 5.2 | 5.4 | 300.0 | 5.6 | 138.2 | 0.66 | 0.33 |
| Ex.(27) | Com.(1-27) | 5.0 | 5.6 | 300.0 | 5.3 | 142.6 | 0.66 | 0.32 |
| Ex.(28) | Com.(1-28) | 5.0 | 5.3 | 300.0 | 5.7 | 145.4 | 0.66 | 0.33 |
| Ex.(29) | Com.(1-29) | 5.0 | 5.5 | 300.0 | 5.4 | 132.4 | 0.66 | 0.33 |
| Ex.(30) | Com.(1-30) | 4.8 | 5.6 | 300.0 | 5.3 | 131.6 | 0.66 | 0.33 |
| Ex.(31) | Com.(1-31) | 5.0 | 5.4 | 300.0 | 5.5 | 145.3 | 0.66 | 0.32 |
| Ex.(32) | Com.(1-32) | 5.1 | 5.4 | 300.0 | 5.6 | 144.8 | 0.66 | 0.32 |
| Ex.(33) | Com.(1-33) | 5.1 | 5.6 | 300.0 | 5.3 | 125.7 | 0.66 | 0.33 |
| Ex.(34) | Com.(1-34) | 4.7 | 5.4 | 300.0 | 5.6 | 129.3 | 0.66 | 0.33 |
| Ex.(35) | Com.(1-35) | 4.7 | 5.6 | 300.0 | 5.3 | 124.4 | 0.66 | 0.32 |
| Ex.(36) | Com.(1-36) | 4.9 | 5.4 | 300.0 | 5.6 | 143.1 | 0.66 | 0.33 |
| Ex.(37) | Com.(1-37) | 4.9 | 5.6 | 300.0 | 5.3 | 117.6 | 0.66 | 0.32 |
| Ex.(38) | Com.(1-38) | 4.9 | 5.5 | 300.0 | 5.5 | 123.7 | 0.66 | 0.32 |
| Ex.(39) | Com.(1-39) | 4.8 | 5.5 | 300.0 | 5.5 | 137.3 | 0.66 | 0.32 |
| Ex.(40) | Com.(1-40) | 5.2 | 5.3 | 300.0 | 5.7 | 126.0 | 0.66 | 0.33 |
| Ex.(41) | Com.(1-41) | 4.8 | 5.2 | 300.0 | 5.7 | 129.0 | 0.66 | 0.33 |
| Ex.(42) | Com.(1-42) | 4.9 | 5.3 | 300.0 | 5.7 | 132.1 | 0.66 | 0.32 |
| Ex.(43) | Com.(1-43) | 5.0 | 5.5 | 300.0 | 5.5 | 126.7 | 0.66 | 0.32 |
| Ex.(44) | Com.(1-44) | 5.1 | 5.3 | 300.0 | 5.6 | 141.1 | 0.66 | 0.32 |
| Ex.(45) | Com.(1-45) | 4.8 | 5.6 | 300.0 | 5.4 | 132.2 | 0.66 | 0.32 |
| Ex.(46) | Com.(1-46) | 5.2 | 5.3 | 300.0 | 5.6 | 129.0 | 0.66 | 0.33 |
| Ex.(47) | Com.(1-47) | 5.0 | 5.5 | 300.0 | 5.5 | 149.0 | 0.66 | 0.33 |
| Ex.(48) | Com.(1-48) | 5.2 | 5.2 | 300.0 | 5.7 | 120.6 | 0.66 | 0.33 |
| Ex.(49) | Com.(1-49) | 4.9 | 5.3 | 300.0 | 5.7 | 140.5 | 0.66 | 0.32 |
| Ex.(50) | Com.(1-50) | 5.0 | 5.6 | 300.0 | 5.4 | 138.1 | 0.66 | 0.33 |
| Ex.(51) | Com.(1-51) | 4.8 | 5.4 | 300.0 | 5.5 | 119.2 | 0.66 | 0.32 |
| Ex.(52) | Com.(1-52) | 5.2 | 5.6 | 300.0 | 5.4 | 141.4 | 0.66 | 0.32 |
| Ex.(53) | Com.(1-53) | 5.1 | 5.4 | 300.0 | 5.6 | 139.8 | 0.66 | 0.33 |
| Ex.(54) | Com.(1-54) | 4.9 | 5.5 | 300.0 | 5.4 | 133.0 | 0.66 | 0.32 |
| Ex.(55) | Com.(1-55) | 5.0 | 5.3 | 300.0 | 5.7 | 146.3 | 0.66 | 0.32 |
| Ex.(56) | Com.(1-56) | 4.9 | 5.5 | 300.0 | 5.5 | 138.2 | 0.66 | 0.32 |
| Ex.(57) | Com.(1-57) | 4.8 | 5.4 | 300.0 | 5.6 | 121.7 | 0.66 | 0.33 |
| Ex.(58) | Com.(1-58) | 4.8 | 5.6 | 300.0 | 5.3 | 133.5 | 0.66 | 0.32 |
| Ex.(59) | Com.(1-59) | 5.1 | 5.6 | 300.0 | 5.4 | 133.1 | 0.66 | 0.33 |
| Ex.(60) | Com.(1-60) | 5.0 | 5.4 | 300.0 | 5.5 | 132.9 | 0.66 | 0.32 |
| Ex.(61) | Com.(1-61) | 4.9 | 5.4 | 300.0 | 5.5 | 120.5 | 0.66 | 0.32 |
| Ex.(62) | Com.(1-62) | 5.1 | 5.6 | 300.0 | 5.4 | 116.4 | 0.66 | 0.32 |
| Ex.(63) | Com.(1-63) | 5.1 | 5.2 | 300.0 | 5.7 | 121.4 | 0.66 | 0.32 |
| Ex.(64) | Com.(1-64) | 4.8 | 5.4 | 300.0 | 5.5 | 126.4 | 0.66 | 0.32 |
| Ex.(65) | Com.(1-65) | 4.9 | 5.2 | 300.0 | 5.7 | 134.9 | 0.66 | 0.32 |
| Ex.(66) | Com.(1-66) | 5.0 | 5.4 | 300.0 | 5.6 | 139.2 | 0.66 | 0.32 |
| Ex.(67) | Com.(1-67) | 4.8 | 5.3 | 300.0 | 5.7 | 133.7 | 0.66 | 0.32 |
| Ex.(68) | Com.(1-68) | 5.1 | 5.3 | 300.0 | 5.7 | 120.4 | 0.66 | 0.33 |
| Ex.(69) | Com.(1-69) | 4.8 | 5.4 | 300.0 | 5.5 | 148.3 | 0.66 | 0.32 |
| Ex.(70) | Com.(1-70) | 5.1 | 5.6 | 300.0 | 5.3 | 115.3 | 0.66 | 0.32 |
| Ex.(71) | Com.(1-71) | 5.0 | 5.2 | 300.0 | 5.7 | 116.2 | 0.66 | 0.32 |
| Ex.(72) | Com.(1-72) | 4.4 | 5.6 | 300.0 | 5.4 | 183.5 | 0.66 | 0.33 |
| Ex.(73) | Com.(1-73) | 4.9 | 5.6 | 300.0 | 5.4 | 129.4 | 0.66 | 0.33 |
| Ex.(74) | Com.(1-74) | 4.9 | 5.3 | 300.0 | 5.6 | 137.6 | 0.66 | 0.32 |
| Ex.(75) | Com.(1-75) | 4.7 | 5.7 | 300.0 | 5.3 | 140.7 | 0.66 | 0.33 |
| Ex.(76) | Com.(1-76) | 5.2 | 5.3 | 300.0 | 5.7 | 120.1 | 0.66 | 0.33 |
| Ex.(77) | Com.(1-77) | 4.8 | 5.3 | 300.0 | 5.6 | 136.0 | 0.66 | 0.32 |
| Ex.(78) | Com.(1-78) | 5.0 | 5.5 | 300.0 | 5.5 | 119.2 | 0.66 | 0.33 |
| Ex.(79) | Com.(1-79) | 5.1 | 5.2 | 300.0 | 5.7 | 143.0 | 0.66 | 0.32 |
| Ex.(80) | Com.(1-80) | 4.8 | 5.3 | 300.0 | 5.7 | 123.5 | 0.66 | 0.33 |
| Ex.(81) | Com.(1-81) | 4.8 | 5.4 | 300.0 | 5.5 | 143.2 | 0.66 | 0.32 |
| Ex.(82) | Com.(1-82) | 5.1 | 5.4 | 300.0 | 5.6 | 144.5 | 0.66 | 0.33 |
| Ex.(83) | Com.(1-83) | 5.1 | 5.5 | 300.0 | 5.4 | 142.5 | 0.66 | 0.32 |
| Ex.(84) | Com.(1-84) | 5.0 | 5.6 | 300.0 | 5.3 | 148.8 | 0.66 | 0.33 |
| Ex.(85) | Com.(1-85) | 5.2 | 5.5 | 300.0 | 5.4 | 121.7 | 0.66 | 0.32 |
| Ex.(86) | Com.(1-86) | 5.1 | 5.6 | 300.0 | 5.3 | 117.3 | 0.66 | 0.33 |
| Ex.(87) | Com.(1-87) | 4.9 | 5.5 | 300.0 | 5.4 | 148.2 | 0.66 | 0.32 |
| Ex.(88) | Com.(1-88) | 4.8 | 5.5 | 300.0 | 5.5 | 118.3 | 0.66 | 0.32 |
| Ex.(89) | Com.(1-89) | 5.1 | 5.4 | 300.0 | 5.6 | 132.3 | 0.66 | 0.33 |
| Ex.(90) | Com.(1-90) | 4.8 | 5.3 | 300.0 | 5.7 | 133.3 | 0.66 | 0.33 |
| Ex.(91) | Com.(1-91) | 5.0 | 5.6 | 300.0 | 5.3 | 132.9 | 0.66 | 0.32 |
| Ex.(92) | Com.(1-92) | 5.0 | 5.4 | 300.0 | 5.5 | 121.7 | 0.66 | 0.33 |
| Ex.(93) | Com.(1-93) | 4.9 | 5.3 | 300.0 | 5.6 | 137.8 | 0.66 | 0.33 |
| Ex.(94) | Com.(1-94) | 4.9 | 5.5 | 300.0 | 5.5 | 141.2 | 0.66 | 0.33 |

TABLE 6-continued

| | Compound | Driving Voltage | Current Density (mA/cm²) | Brightness (cd/m²) | Efficiency (cd/A) | T(90) | CIE x | CIE y |
|---|---|---|---|---|---|---|---|---|
| Ex.(95) | Com.(1-95) | 5.0 | 5.6 | 300.0 | 5.3 | 141.7 | 0.66 | 0.32 |
| Ex.(96) | Com.(1-96) | 5.0 | 5.2 | 300.0 | 5.7 | 149.8 | 0.66 | 0.32 |
| Ex.(97) | Com.(1-97) | 4.9 | 5.6 | 300.0 | 5.4 | 134.3 | 0.66 | 0.32 |
| Ex.(98) | Com.(1-98) | 5.1 | 5.6 | 300.0 | 5.3 | 117.6 | 0.66 | 0.33 |
| Ex.(99) | Com.(1-99) | 4.9 | 5.3 | 300.0 | 5.6 | 133.9 | 0.66 | 0.33 |
| Ex.(100) | Com.(1-100) | 4.9 | 5.4 | 300.0 | 5.6 | 143.9 | 0.66 | 0.33 |
| Ex.(101) | Com.(1-101) | 5.1 | 5.5 | 300.0 | 5.4 | 148.9 | 0.66 | 0.32 |
| Ex.(102) | Com.(1-102) | 5.2 | 5.4 | 300.0 | 5.6 | 126.8 | 0.66 | 0.32 |
| Ex.(103) | Com.(1-103) | 4.9 | 5.2 | 300.0 | 5.7 | 129.5 | 0.66 | 0.32 |
| Ex.(104) | Com.(1-104) | 5.0 | 5.4 | 300.0 | 5.6 | 132.6 | 0.66 | 0.33 |
| Ex.(105) | Com.(1-105) | 5.0 | 5.3 | 300.0 | 5.6 | 140.5 | 0.66 | 0.33 |
| Ex.(106) | Com.(1-106) | 4.9 | 5.2 | 300.0 | 5.7 | 117.6 | 0.66 | 0.33 |
| Ex.(107) | Com.(1-107) | 5.1 | 5.5 | 300.0 | 5.4 | 162.3 | 0.66 | 0.33 |
| Ex.(108) | Com.(1-108) | 5.0 | 5.5 | 300.0 | 5.4 | 169.4 | 0.66 | 0.32 |
| Ex.(109) | Com.(1-109) | 5.0 | 5.3 | 300.0 | 5.7 | 133.2 | 0.66 | 0.32 |
| Ex.(110) | Com.(1-110) | 4.8 | 5.6 | 300.0 | 5.3 | 129.1 | 0.66 | 0.33 |
| Ex.(111) | Com.(1-111) | 4.9 | 5.6 | 300.0 | 5.3 | 139.0 | 0.66 | 0.32 |
| Ex.(112) | Com.(1-112) | 5.0 | 5.2 | 300.0 | 5.7 | 124.4 | 0.66 | 0.33 |
| Ex.(113) | Com.(1-113) | 4.9 | 5.4 | 300.0 | 5.6 | 145.9 | 0.66 | 0.33 |
| Ex.(114) | Com.(1-114) | 4.8 | 5.5 | 300.0 | 5.4 | 148.8 | 0.66 | 0.32 |
| Ex.(115) | Com.(1-115) | 5.0 | 5.7 | 300.0 | 5.3 | 117.8 | 0.66 | 0.32 |
| Ex.(116) | Com.(1-116) | 4.8 | 5.6 | 300.0 | 5.4 | 116.0 | 0.66 | 0.32 |
| Ex.(117) | Com.(1-117) | 5.1 | 5.4 | 300.0 | 5.5 | 128.8 | 0.66 | 0.32 |
| Ex.(118) | Com.(1-118) | 5.0 | 5.3 | 300.0 | 5.7 | 122.4 | 0.66 | 0.32 |
| Ex.(119) | Com.(1-119) | 4.9 | 5.2 | 300.0 | 5.7 | 149.4 | 0.66 | 0.33 |
| Ex.(120) | Com.(1-120) | 4.8 | 5.5 | 300.0 | 5.5 | 122.3 | 0.66 | 0.33 |
| Ex.(121) | Com.(1-121) | 4.7 | 5.6 | 300.0 | 5.4 | 128.7 | 0.66 | 0.32 |
| Ex.(122) | Com.(1-122) | 4.8 | 5.4 | 300.0 | 5.6 | 121.9 | 0.66 | 0.32 |
| Ex.(123) | Com.(1-123) | 4.9 | 5.6 | 300.0 | 5.4 | 121.6 | 0.66 | 0.33 |
| Ex.(124) | Com.(1-124) | 5.0 | 5.2 | 300.0 | 5.7 | 135.0 | 0.66 | 0.33 |
| Ex.(125) | Com.(1-125) | 4.7 | 5.3 | 300.0 | 5.7 | 135.9 | 0.66 | 0.32 |
| Ex.(126) | Com.(1-126) | 4.8 | 5.6 | 300.0 | 5.3 | 116.7 | 0.66 | 0.32 |
| Ex.(127) | Com.(1-127) | 4.9 | 5.6 | 300.0 | 5.4 | 148.5 | 0.66 | 0.32 |
| Ex.(128) | Com.(1-128) | 5.0 | 5.6 | 300.0 | 5.3 | 133.9 | 0.66 | 0.33 |
| Ex.(129) | Com.(1-129) | 4.7 | 5.4 | 300.0 | 5.6 | 119.1 | 0.66 | 0.33 |
| Ex.(130) | Com.(1-130) | 4.8 | 5.5 | 300.0 | 5.4 | 141.0 | 0.66 | 0.32 |
| Ex.(131) | Com.(1-131) | 4.7 | 5.5 | 300.0 | 5.5 | 124.9 | 0.66 | 0.33 |
| Ex.(132) | Com.(1-132) | 5.0 | 5.5 | 300.0 | 5.4 | 136.5 | 0.66 | 0.32 |
| Ex.(133) | Com.(1-133) | 5.1 | 5.5 | 300.0 | 5.4 | 149.6 | 0.66 | 0.33 |
| Ex.(134) | Com.(1-134) | 5.1 | 5.2 | 300.0 | 5.7 | 121.8 | 0.66 | 0.32 |
| Ex.(135) | Com.(1-135) | 4.9 | 5.6 | 300.0 | 5.4 | 116.6 | 0.66 | 0.32 |
| Ex.(136) | Com.(1-136) | 4.8 | 5.5 | 300.0 | 5.5 | 144.3 | 0.66 | 0.33 |
| Ex.(137) | Com.(1-137) | 5.2 | 5.5 | 300.0 | 5.5 | 142.0 | 0.66 | 0.32 |
| Ex.(138) | Com.(1-138) | 5.2 | 5.5 | 300.0 | 5.5 | 144.8 | 0.66 | 0.33 |
| Ex.(139) | Com.(1-139) | 4.7 | 5.6 | 300.0 | 5.4 | 118.2 | 0.66 | 0.32 |
| Ex.(140) | Com.(1-140) | 4.9 | 5.6 | 300.0 | 5.4 | 142.0 | 0.66 | 0.32 |
| Ex.(141) | Com.(1-141) | 4.9 | 5.5 | 300.0 | 5.5 | 117.2 | 0.66 | 0.32 |
| Ex.(142) | Com.(1-142) | 4.9 | 5.3 | 300.0 | 5.7 | 135.8 | 0.66 | 0.32 |
| Ex.(143) | Com.(1-143) | 4.8 | 5.7 | 300.0 | 5.3 | 142.3 | 0.66 | 0.33 |
| Ex.(144) | Com.(1-144) | 5.1 | 5.4 | 300.0 | 5.6 | 120.7 | 0.66 | 0.32 |
| Ex.(145) | Com.(1-145) | 4.8 | 5.5 | 300.0 | 5.5 | 117.3 | 0.66 | 0.33 |
| Ex.(146) | Com.(1-146) | 4.7 | 5.3 | 300.0 | 5.6 | 123.9 | 0.66 | 0.33 |
| Ex.(147) | Com.(1-147) | 4.8 | 5.2 | 300.0 | 5.7 | 123.4 | 0.66 | 0.33 |
| Ex.(148) | Com.(1-148) | 4.7 | 5.4 | 300.0 | 5.6 | 123.3 | 0.66 | 0.33 |
| Ex.(149) | Com.(1-149) | 4.8 | 5.4 | 300.0 | 5.6 | 132.2 | 0.66 | 0.32 |
| Ex.(150) | Com.(1-150) | 5.1 | 5.3 | 300.0 | 5.7 | 130.5 | 0.66 | 0.33 |

As a result of using the indole core, which had showed relatively high efficiency and relatively long life span in Table 6 above, as the red phosphorescent emission-auxiliary layer material, the following results were shown in Table 6 above.

It can be seen from Table 6 that in spite of having the same indole core, the compounds in which an arylamine group is present as the main substituent (the inventive compounds) showed significant improvements in both efficiency and life span, as compared to the compounds in which a heterocyclic group containing N is present as the main substituent (Comparative Example 2 to Comparative Example 5). This is believed because the inventive compounds maintain charge balance and have high T1 values, thereby lowering driving voltage and efficiently blocking the exciton so that the exciton is kept within the light emitting layer. Also, it can be noted that efficiency and life span were very greatly increased (twice or more), as compared to Comparative Example 6 where the emission-auxiliary layer was not used.

This is because the inventive compounds with high T1 energy levels and deep HOMO energy levels serve to prevent light emission leakage by more smoothly transporting the hole from the hole transport layer to the light emitting layer and keeping the exciton within the light emitting layer, which makes it possible to achieve superior OLEDs.

Finally, considering the indole core, it can be noted that the indole core substituted by a phenyl group was improved in efficiency and life span, as compared to the unsubstituted indole core, and particularly the inventive Compound 1-5, Compound 1-6, and the like corresponding to the indole core substituted by a phenyl group at position 5 showed low driving voltage, high efficiency, and long life span.

This implies that depending on the type and position of a substituent to be attached, a band gap, electrical properties, interfacial properties, and the like may greatly vary even in the same indole core. In particular, even when a similar core is used, it is very difficult for even those skilled in the art to infer the characteristics of an emission-auxiliary layer where the inventive compound is used because the correlation between the emission-auxiliary layer and a hole transport layer and the correlation between the emission-auxiliary layer and a light emitting layer (host) must be discovered.

As described above, since when the inventive compounds are applied to an organic electric element, the organic electric element shows excellent properties, the inventive compounds may be used for not only an organic light emitting diode (OLED), but also a display device, an organic solar cell, an organic photo conductor (OPC), an organic transistor (organic TFT), an element for monochromatic or white illumination, and the like. Also, it is obvious that even when the inventive compounds are used in organic material layers other than a hole transport layer or emission-auxiliary layer, for example, a hole injection layer, a light emitting layer, a buffer layer, an electron injection layer, and an electron transport layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:
1. An organic electric element, comprising:
a first electrode;
a second electrode; and
an organic material layer formed between the first electrode and the second electrode, the organic material layer comprising a light emitting layer, a hole transport layer between the light emitting layer and the first electrode, and an emission-auxiliary layer formed between the light emitting layer and the hole transport layer, the emission-auxiliary layer comprising a compound represented by Formula 1 below, the hole transport layer comprising a compound represented by Formula 2 below:

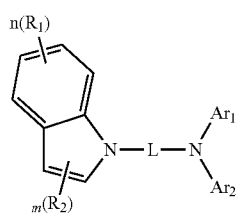

(1)

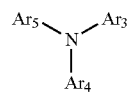

(2)

wherein Formula 2 above,

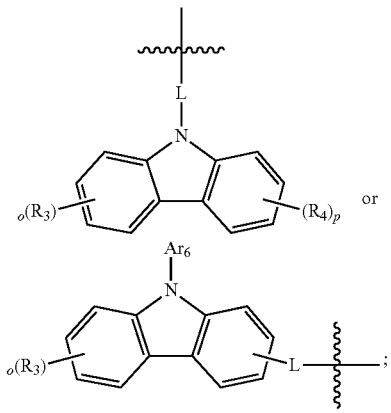

in Formulas 1 and 2 above,
n, o, and p are each an integer from 1 to 4;
m is an integer of 1 or 2;
when m, n, o, and p are each 2 or greater, a plurality of $R_1$s, $R_2$s, $R_3$s, or $R_4$s are the same as or different from each other;
$R_1$, $R_2$, $R_3$, and $R_4$ are each independently selected from the group consisting of hydrogen, deuterium, tritium, a halogen group, a $C_6$ to $C_{60}$ aryl group, a $C_1$ to $C_{50}$ alkyl group, a $C_2$ to $C_{40}$ alkenyl group, a $C_6$ to $C_{60}$ arylamine group, a $C_2$ to $C_{60}$ heterocyclic group containing at least one heteroatom selected from the group consisting of O, N, S, Si, and P, a fused ring group of a $C_6$ to $C_{60}$ aromatic ring and a $C_4$ to $C_{60}$ aliphatic ring, an amine group, a nitro group, a nitrile group, an amide group, and a silane group, and at least one pair of two adjacent $R_1$s, two adjacent $R_2$s, two adjacent $R_3$s, and two adjacent $R_4$s are optionally linked together to form a fused ring;
L is selected from the group consisting of a single bond, a $C_6$ to $C_{60}$ arylene group, a fluorenyl group, a $C_3$ to $C_{60}$ heteroarylene group, and a bivalent aliphatic hydrocarbon group wherein the arylene group, the fluorenyl group, the heteroarylene group, and the aliphatic hydrocarbon group each are optionally substituted by one or more substituents selected from the group consisting of hydrogen, deuterium, tritium, nitro group, nitrile group, halogen, an acetylene group, a $C_7$ to $C_{20}$ arylalkyl group, a $C_8$ to $C_{20}$ arylalkenyl group, a $C_1$ to $C_{50}$ alkyl group, a $C_2$ to $C_{20}$ alkenyl group, a $C_1$ to $C_{20}$ alkoxy group, a $C_6$ to $C_{20}$ aryl group, a $C_2$ to $C_{20}$ heterocyclic group, and an amino group; and
$Ar_1$ to $Ar_6$ are each independently selected from the group consisting of a $C_6$ to $C_{60}$ aryl group, a $C_2$ to $C_{60}$ heteroaryl group containing at least one heteroatom selected from the group consisting of O, N, S, Si, and P, a $C_2$ to $C_{20}$ alkenyl group, a fluorenyl group, a $C_1$ to $C_{30}$ alkoxy group, a $C_6$ to $C_{30}$ aryloxy group, a $C_6$ to $C_{60}$ arylamine group, and a $C_1$ to $C_{50}$ alkyl group;

when R₁ to R₄ and Ar₁ to Ar₆ are an aryl group, R₁ to R₄ and Ar₁ to Ar₆ each are optionally substituted by one or more substituents selected from the group consisting of hydrogen, deuterium, tritium, a halogen group, a $C_1$ to $C_{60}$ alkyl group, a $C_1$ to $C_{60}$ alkoxy group, a $C_1$ to $C_{60}$ alkylamine group, a $C_6$ to $C_{60}$ arylamine group, a $C_1$ to $C_{60}$ alkylthiophene group, a $C_6$ to $C_{60}$ arylthiophene group, a $C_2$ to $C_{60}$ alkenyl group, a $C_2$ to $C_{60}$ alkynyl group, a $C_3$ to $C_{60}$ cycloalkyl group, a $C_6$ to $C_{60}$ aryl group, a $C_6$ to $C_{60}$ aryl group substituted by deuterium, a $C_8$ to $C_{60}$ arylalkenyl group, a substituted or unsubstituted silane group, a substituted or unsubstituted boron group, a substituted or unsubstituted germanium group, and a substituted or unsubstituted $C_2$ to $C_{60}$ heterocyclic group (with the proviso that when Ar₁ and Ar₂ are an aryl group, the group from which the substituents are selected may further include deuterium, an amino group, a nitrile group, a nitro group, and a phosphineoxide group);

when R₁ to R₄ and Ar₁ to Ar₆ are a heterocyclic group, R₁ to R₄ and Ar₁ to Ar₆ each are optionally substituted by one or more substituents selected from the group consisting of hydrogen, deuterium, tritium, a halogen group, a $C_1$ to $C_{60}$ alkyl group, a $C_2$ to $C_{60}$ alkenyl group, a $C_1$ to $C_{60}$ alkoxy group, a $C_1$ to $C_{60}$ alkylamine group, a $C_6$ to $C_{60}$ arylamine group, a $C_1$ to $C_{60}$ alkylthio group, a $C_6$ to $C_{60}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{60}$ heterocyclic group, a $C_2$ to $C_{60}$ alkynyl group, a substituted or unsubstituted silane group, a substituted or unsubstituted boron group, a substituted or unsubstituted germanium group, a nitrile group, and an acetylene group;

when R₁ to R₄ and Ar₁ to Ar₆ are an alkyl group, R₁ to R₄ and Ar₁ to Ar₆ each are optionally substituted by one or more substituents selected from the group consisting of hydrogen, deuterium, tritium, a halogen group, a $C_1$ to $C_{20}$ alkyl group, a $C_2$ to $C_{20}$ alkenyl group, a $C_1$ to $C_{20}$ alkoxy group, a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{20}$ heterocyclic group, a nitrile group, and an acetylene group;

when R₁ to R₄ and Ar₁ to Ar₆ are an alkenyl group, R₁ to R₄ and Ar₁ to Ar₆ each are optionally substituted by one or more substituents selected from the group consisting of hydrogen, deuterium, tritium, a halogen group, a $C_1$ to $C_{20}$ alkyl group, a $C_2$ to $C_{20}$ alkenyl group, a $C_1$ to $C_{20}$ alkoxy group, a $C_6$ to $C_{20}$ arylamine group, a $C_6$ to $C_{60}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{20}$ heterocyclic group, a nitrile group, and an acetylene group;

when R₁ to R₄ are an amine group, R₁ to R₄ each are optionally substituted by one or more substituents selected from the group consisting of a $C_1$ to $C_{60}$ alkyl group, a $C_2$ to $C_{60}$ alkenyl group, a $C_6$ to $C_{60}$ aryl group, and a $C_8$ to $C_{60}$ arylalkenyl group;

when R₁ to R₄ and Ar₁ to Ar₆ are an alkoxy group, R₁ to R₄ and Ar₁ to Ar₆ each may be substituted by one or more substituents selected from the group consisting of hydrogen, deuterium, a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocloalkyl group, a $C_6$ to $C_{60}$ aryl group, a $C_6$ to $C_{60}$ aryl group substituted by deuterium, and a $C_2$ to $C_{60}$ heteroaryl group;

when Ar₁ is a fluorenyl group, Ar₁ may be substituted by one or more substituents selected from the group consisting of hydrogen, deuterium, tritium, a halogen group, a $C_2$ to $C_{20}$ alkenyl group, a $C_1$ to $C_{20}$ alkoxy group, a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_1$ to $C_{50}$ alkyl group, a $C_2$ to $C_{20}$ heterocyclic group, a nitrile group, and an acetylene group;

when Ar₁ to Ar₆ are an aryloxy group, Ar₁ to Ar₆ each may be substituted by one or more substituents selected from the group consisting of hydrogen, deuterium, a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocycloalkyl group, a $C_2$ to $C_{30}$ heterocyclic group, a $C_6$ to $C_{60}$ aryl group, a $C_6$ to $C_{60}$ aryl group substituted by deuterium, and a $C_2$ to $C_{60}$ heteroaryl group; and when R₁ to R₄ and Ar₁ to Ar₆ are an arylamine group, R₁ to R₄ and Ar₁ to Ar₆ each may be substituted by one or more substituents selected from the group consisting of a halogen group, an amino group, a nitrile group, a nitro group, a $C_1$ to $C_{20}$ alkyl group, a $C_2$ to $C_{20}$ alkenyl group, a $C_1$ to $C_{20}$ alkoxy group, a $C_3$ to $C_{30}$ cycloalkyl group, a $C_2$ to $C_{30}$ heterocycloalkyl group, a $C_6$ to $C_{60}$ aryl group, a $C_6$ to $C_{20}$ aryl group substituted by deuterium, and a $C_2$ to $C_{60}$ heteroaryl group.

2. The organic electric element as claimed in claim 1, wherein Ar₁ and Ar₂ in Formula 1 are each independently selected from the group consisting of compounds below:

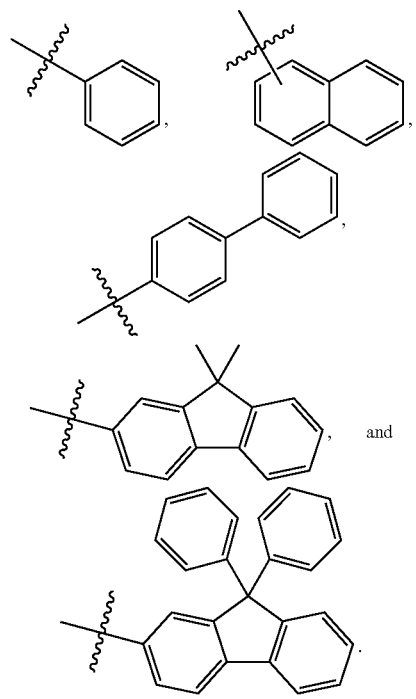

3. The organic electric element as claimed in claim 1, wherein L in Formulas 1 and 2 is selected from the group consisting of compounds below:

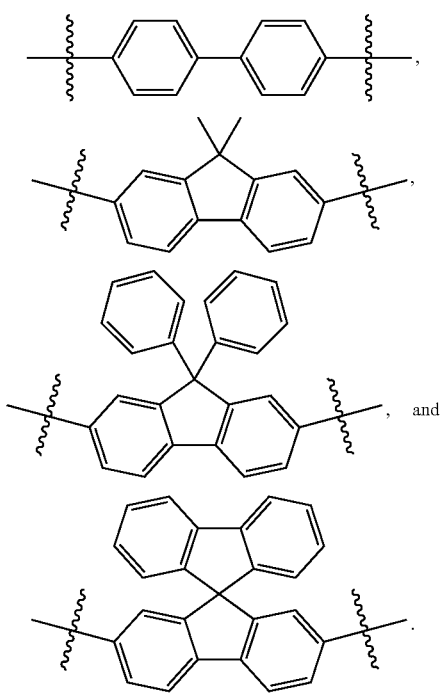
4. The organic electric element as claimed in claim 1, wherein Formula 1 is represented by any one of Formulas below:
(3)
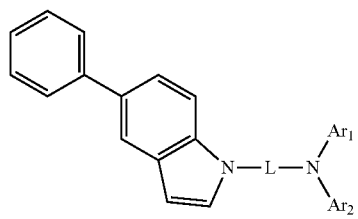
(4)
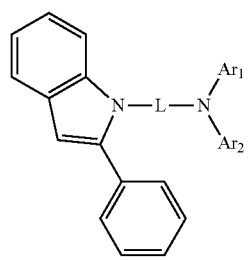
(5)
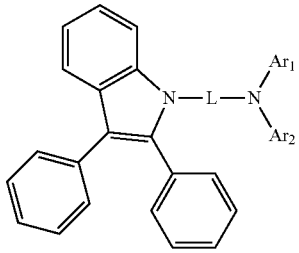
-continued
(6)
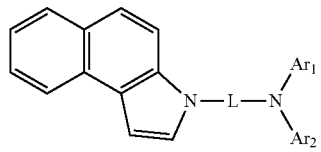
(7)
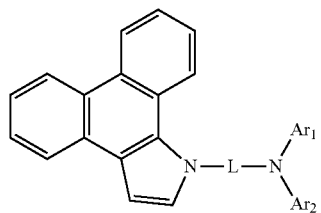
(8)
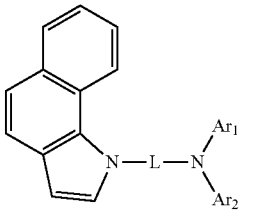
(9)
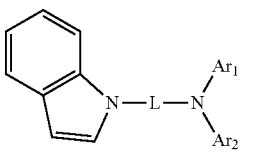
(15)
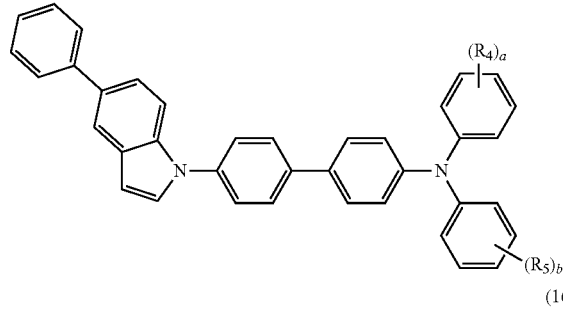
(16)
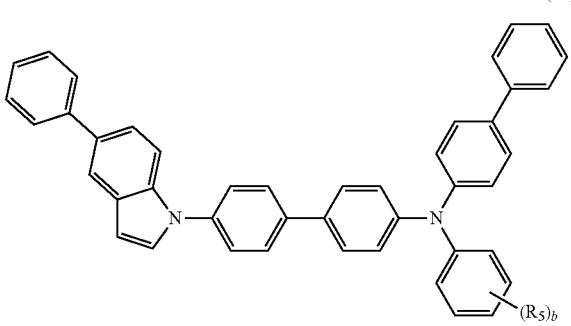

301
-continued (17)

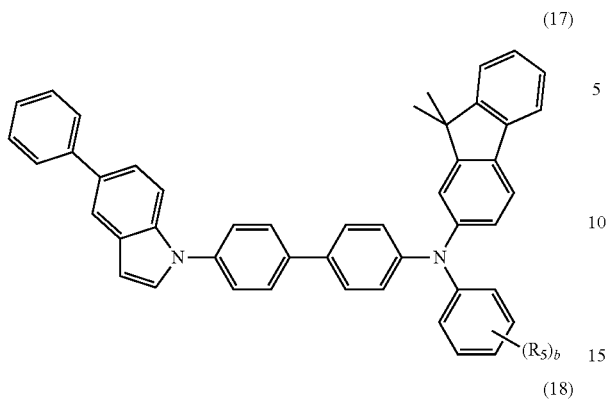

(18)

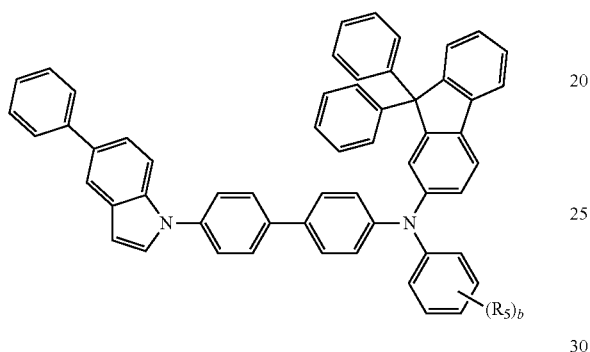

wherein Formulas 3 to 9 and 15 to 18 above, L, Ar$_1$, and Ar$_2$ are as defined in Formula 1 above;

a and b are each an integer from 1 to 5;

when a and/or b are/is 2 or greater, a plurality of R$_4$s or R$_5$s are the same as or different from each other;

R$_4$ and R$_5$ are each independently selected from the group consisting of a C$_6$ to C$_{25}$ aryl group and a C$_2$ to C$_{20}$ alkenyl group, and two adjacent R$_4$s and/or two adjacent R$_5$s are each optionally linked together to form a fused ring; and when R$_4$ and R$_5$ are an aryl group or an alkenyl group, R$_4$ and R$_5$ each are optionally substituted by one or more substituents selected from the group consisting of a C$_1$ to C$_4$ alkyl group, a C$_2$ to C$_6$ alkenyl group, and a C$_6$ to C$_{20}$ aryl group.

5. The organic electric element as claimed in claim 1, wherein Formula 2 is represented by any one of the Formulas below:

[Formula 10]

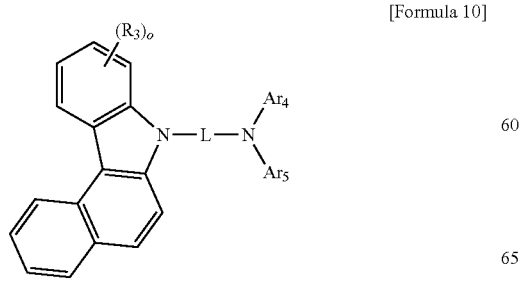

302
-continued

[Formula 11]

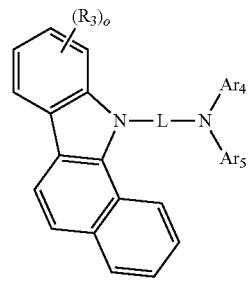

[Formula 12]

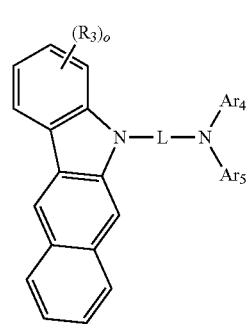

[Formula 13]

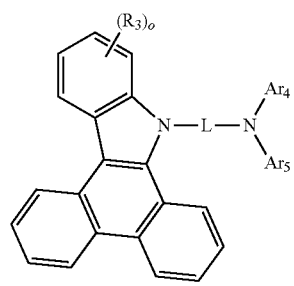

[Formula 14]

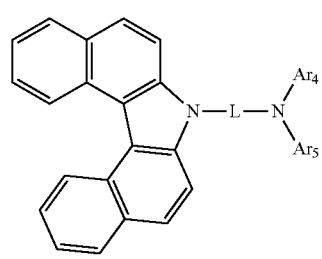

wherein, in Formulas 10 to 14 above, L, Ar$_4$, Ar$_5$, R$_3$ and o are the same as defined in Formula 2 of claim 1.

6. The organic electric element as claimed in claim 1, wherein Formula 1 comprises any one of the compounds below:

303
1-1
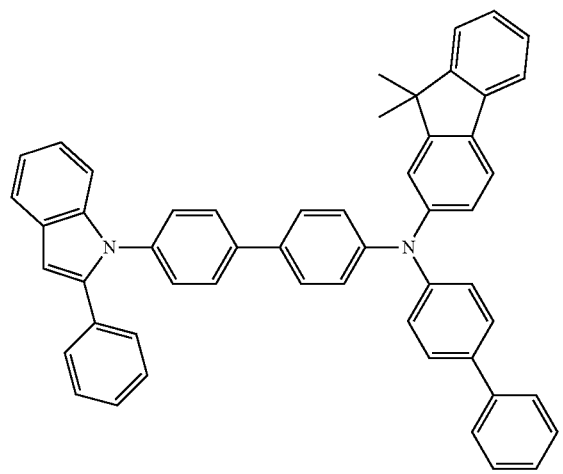
304
1-2
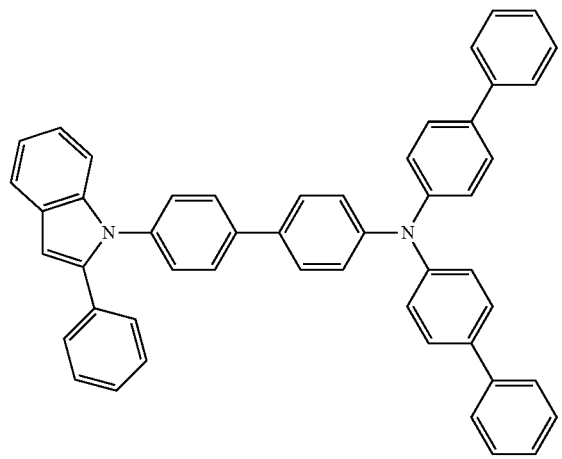
1-3
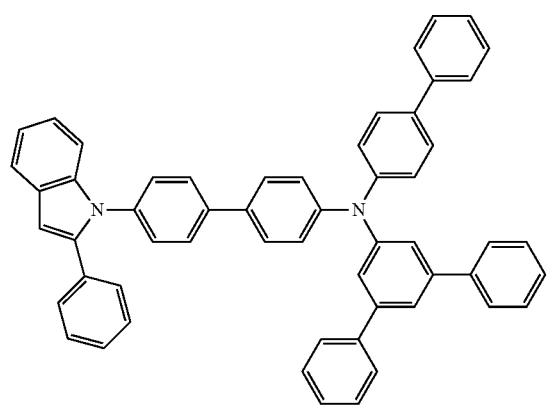
1-4
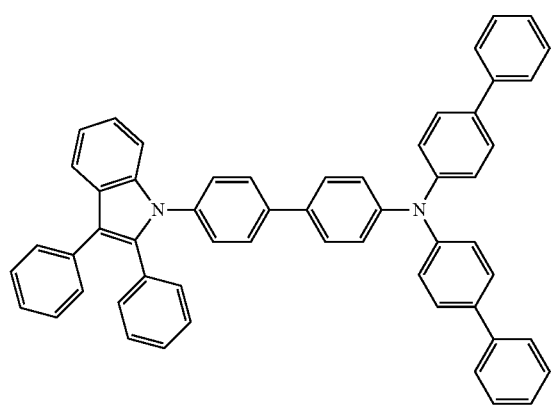
1-5
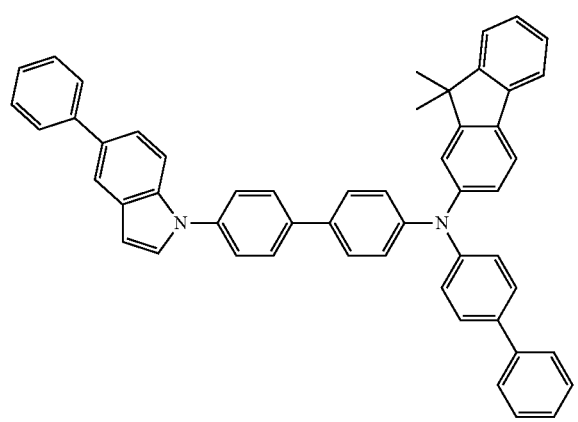
1-6
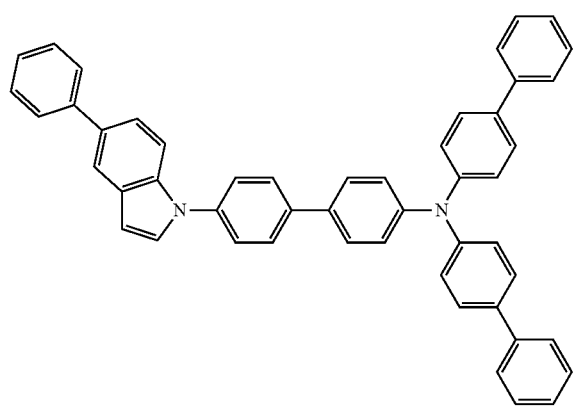

-continued
1-7
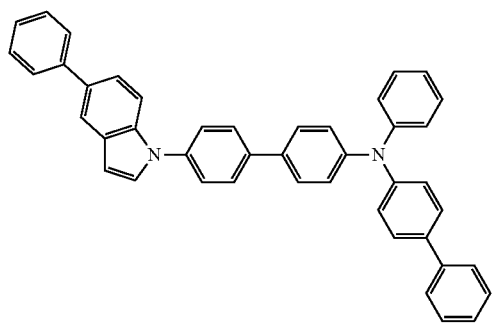
1-8
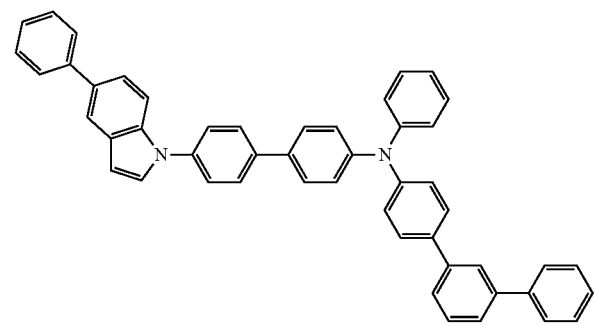
1-9
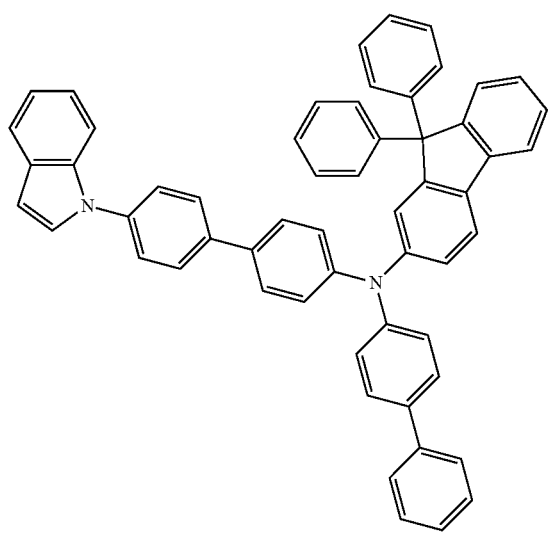
1-10
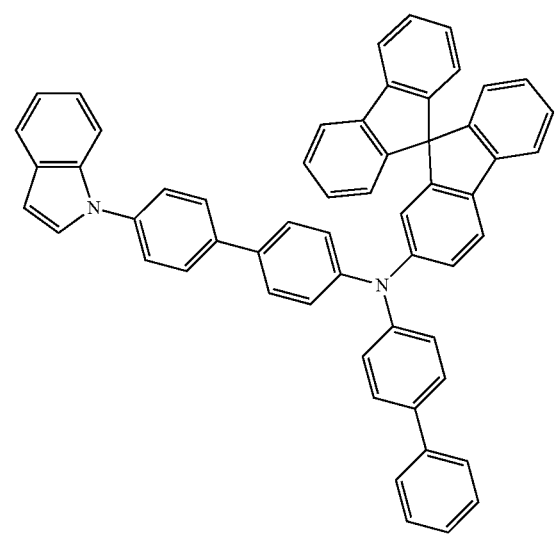
1-11
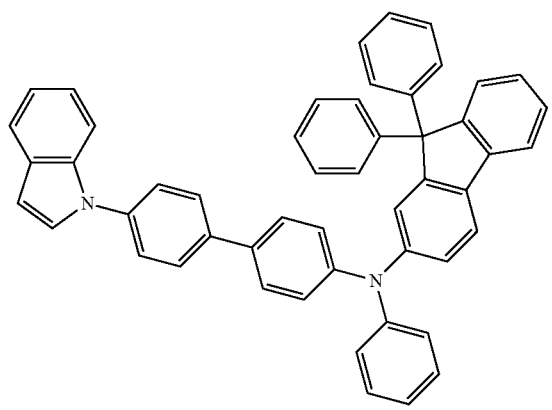
1-12
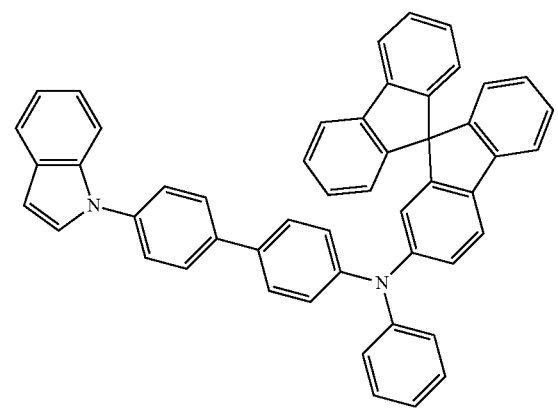

1-13
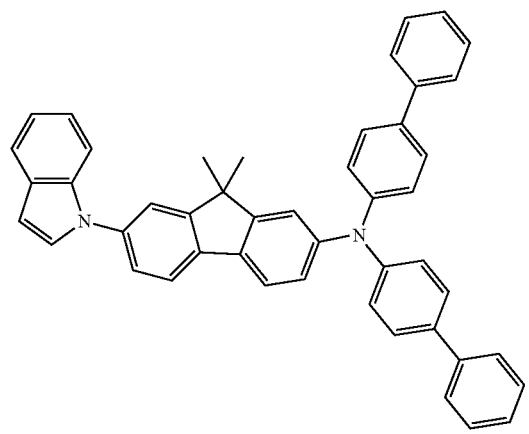
1-14
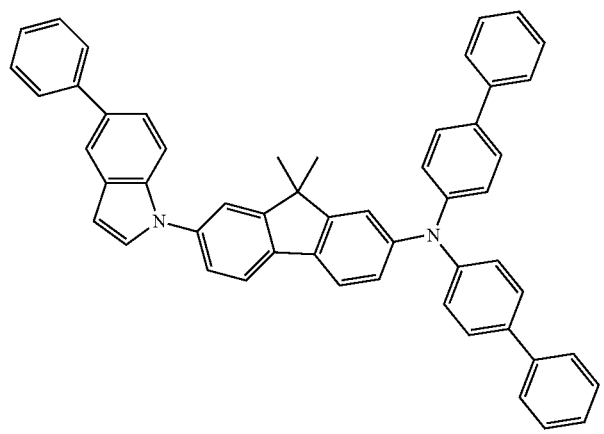
1-15
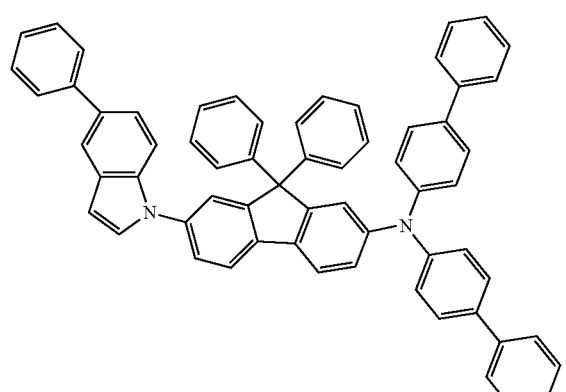
1-16
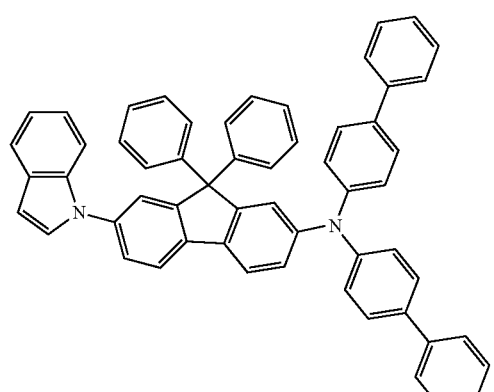
1-17
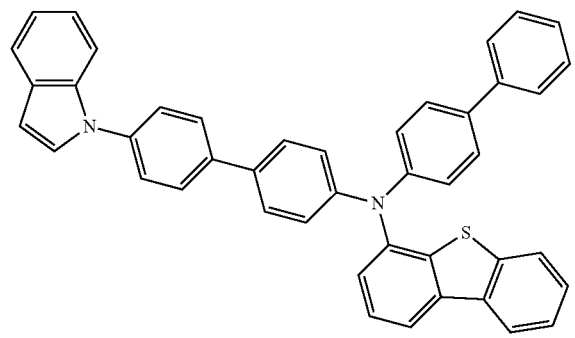
1-18
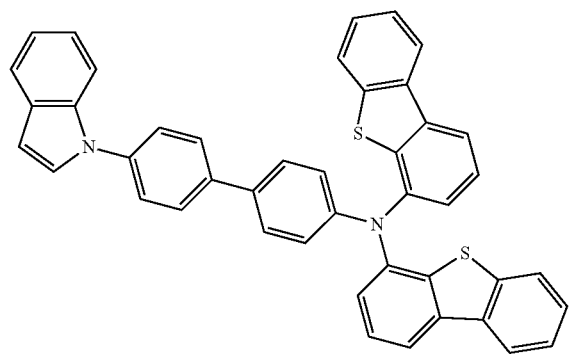
1-19
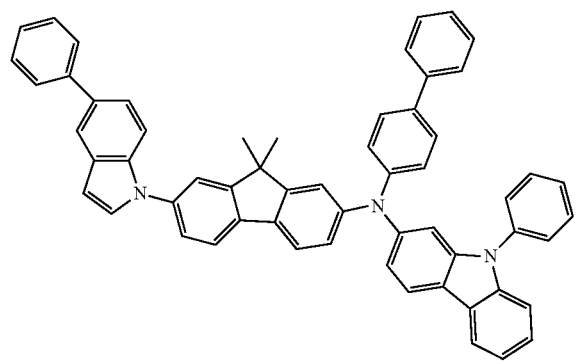
1-20
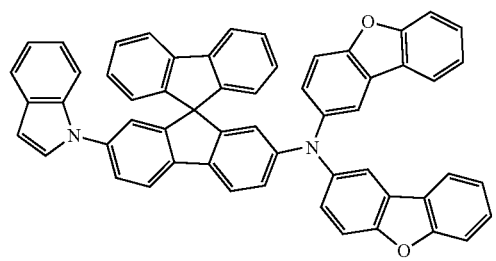

-continued
1-21
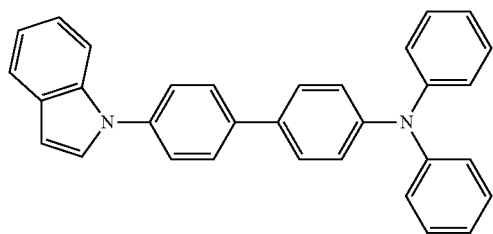
1-22
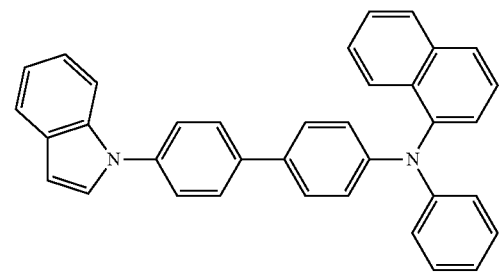
1-23
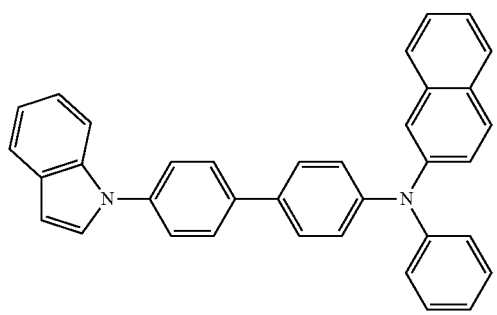
1-24
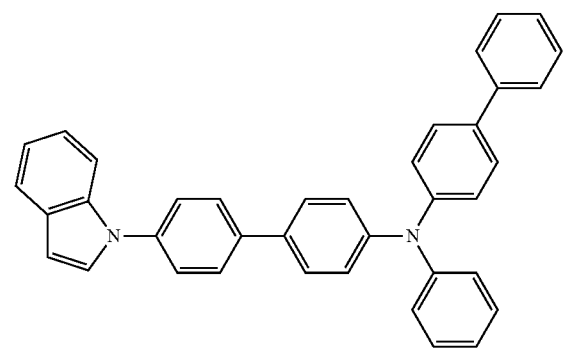
1-25
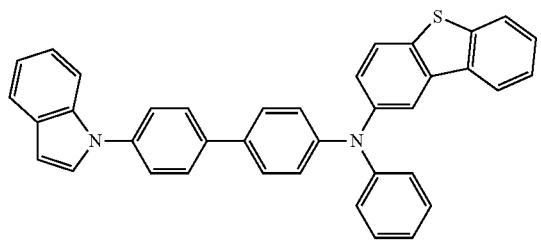
1-26
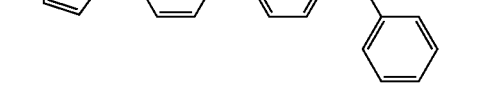
1-27
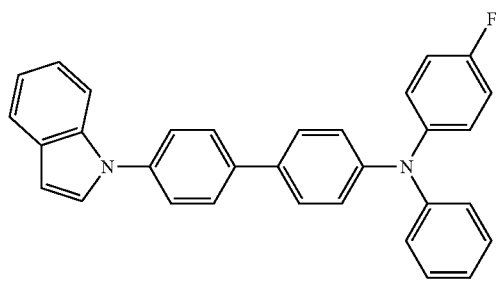
1-28
1-29
1-30
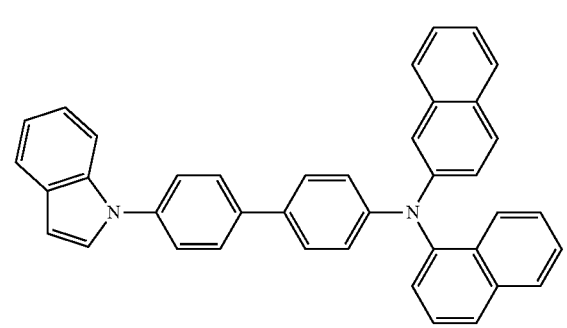

-continued
1-31
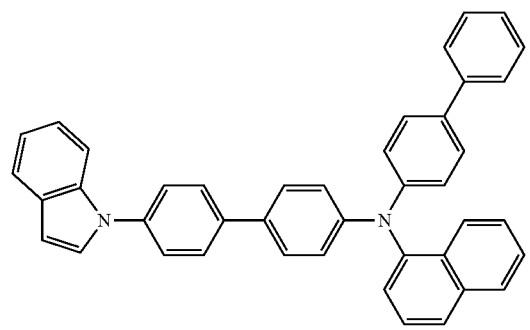
1-32
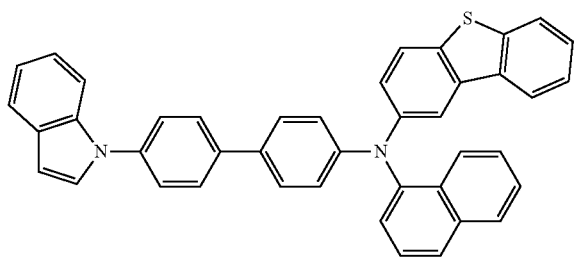
1-33
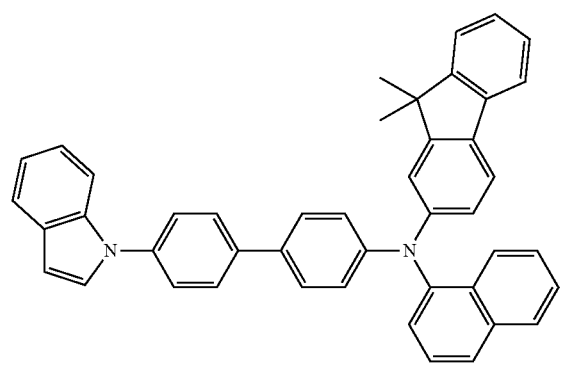
1-34
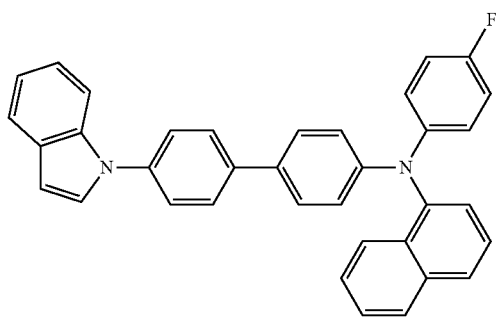
1-35
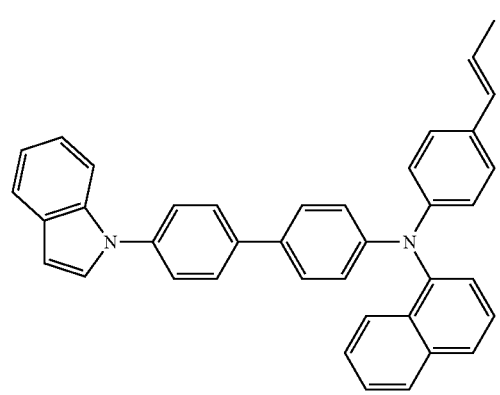
1-36
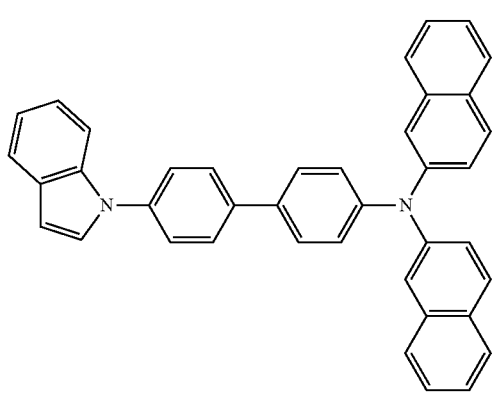
1-37
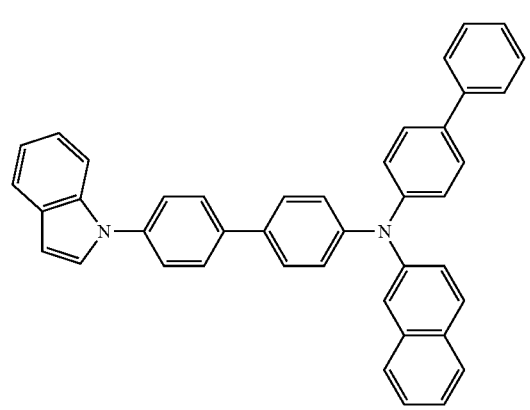
1-38
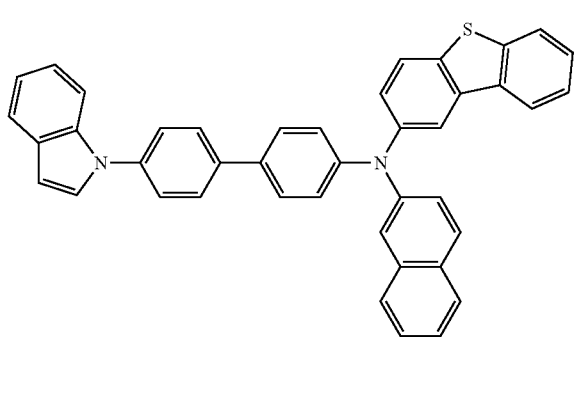

-continued
1-39
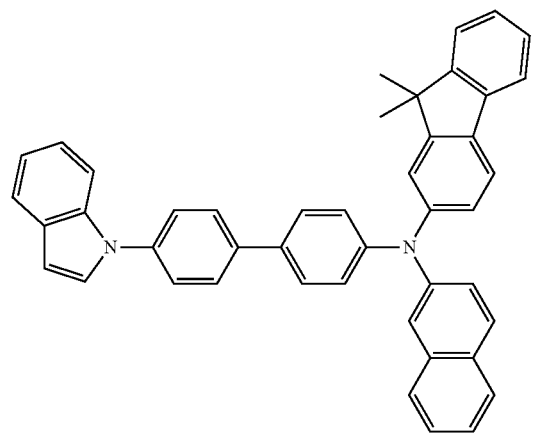
1-40
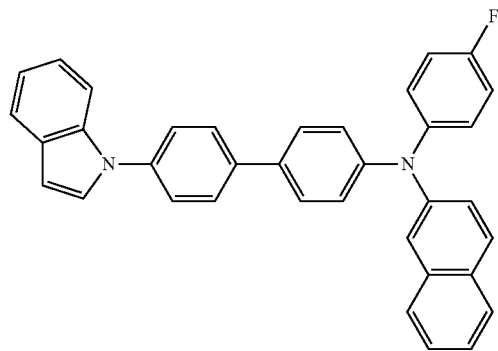
1-41
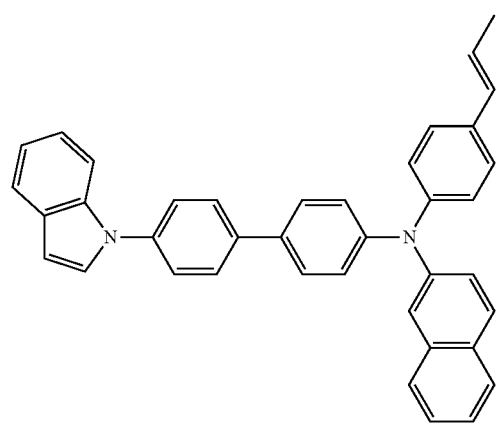
1-42
1-43
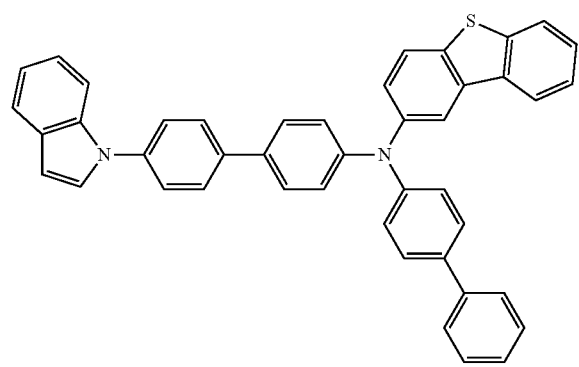
1-44
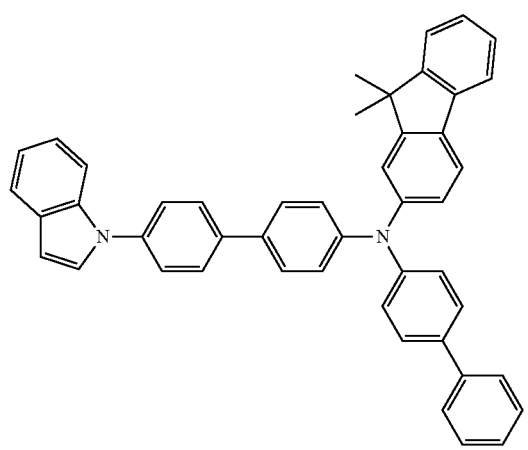

-continued
1-45
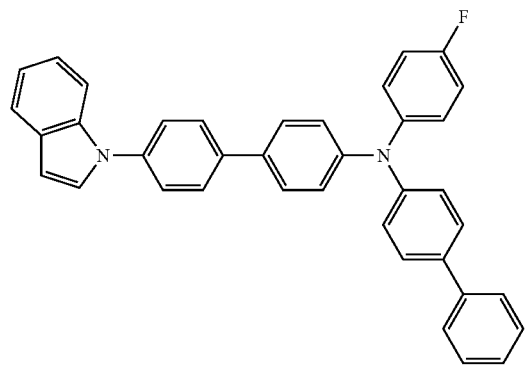
1-46
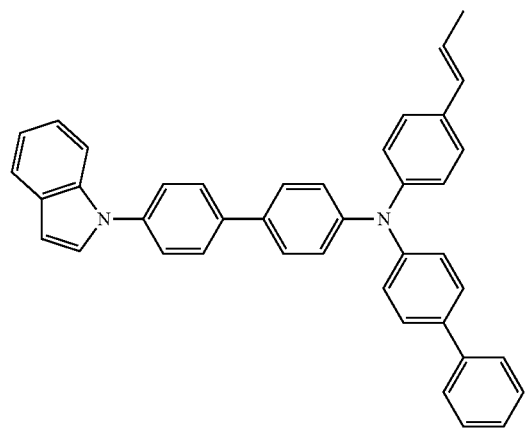
1-47
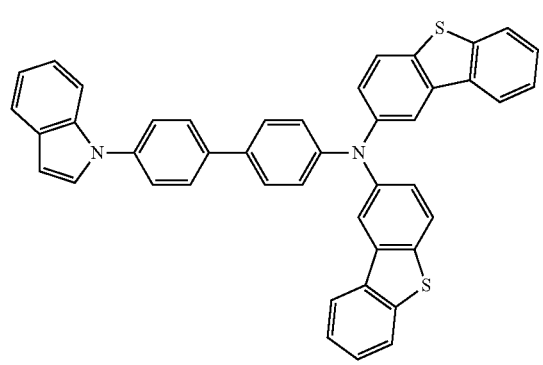
1-48
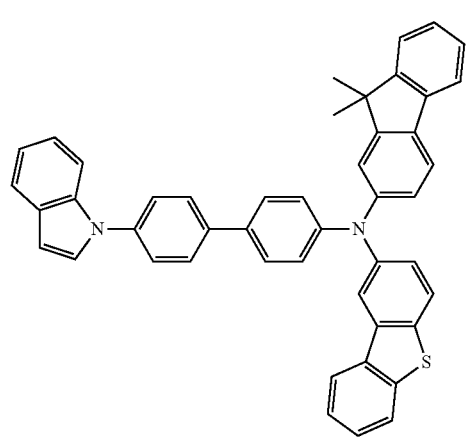
1-49
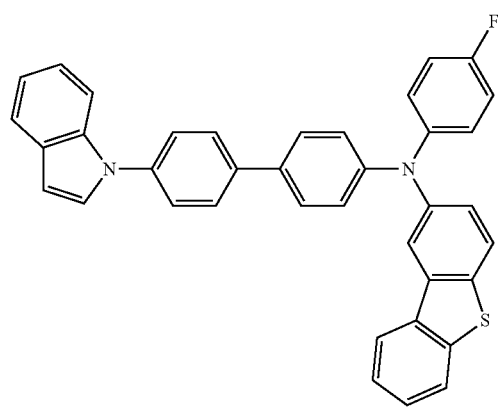
1-50
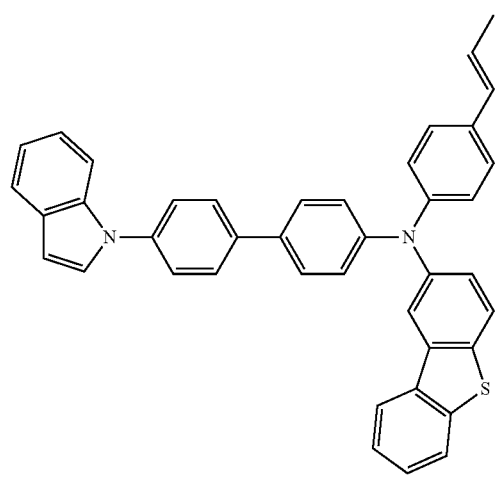

-continued
1-51
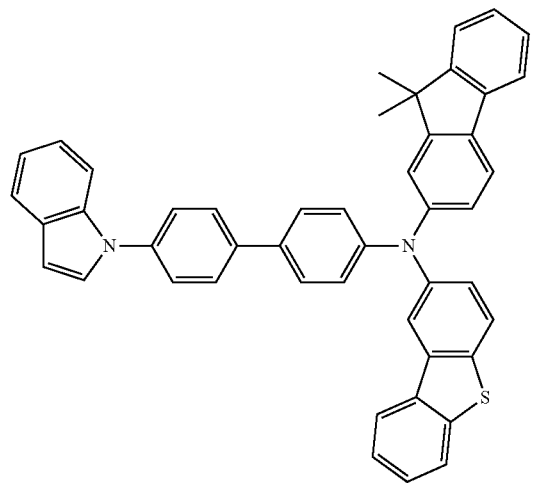
1-52
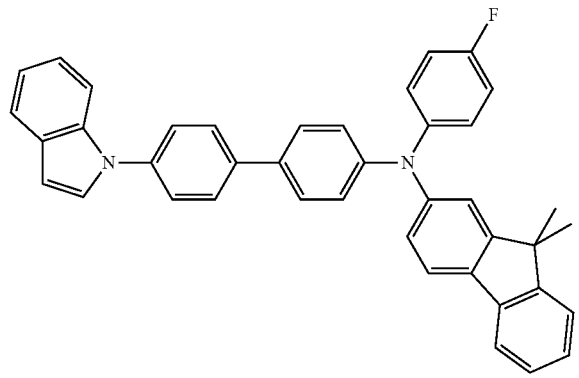
1-53
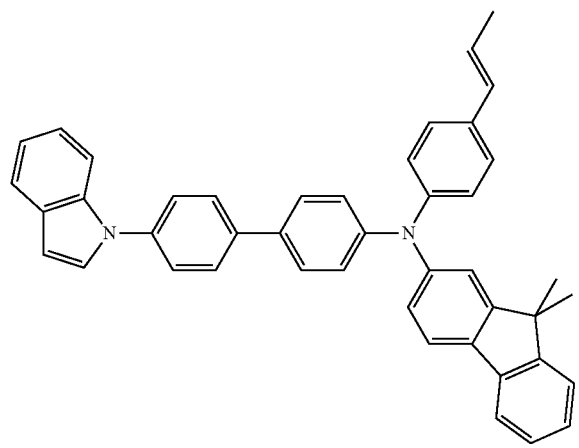
1-54
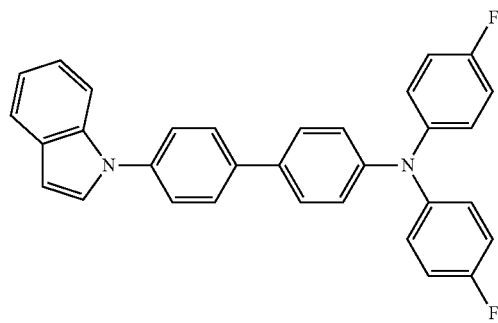
1-55
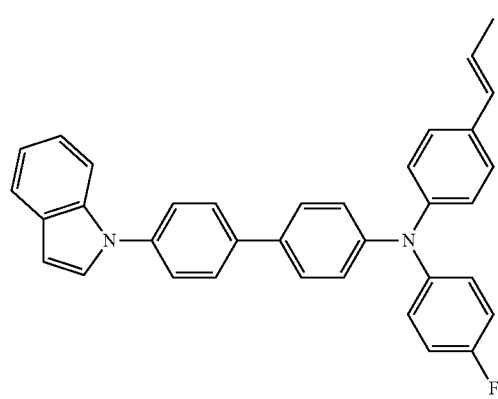
1-56
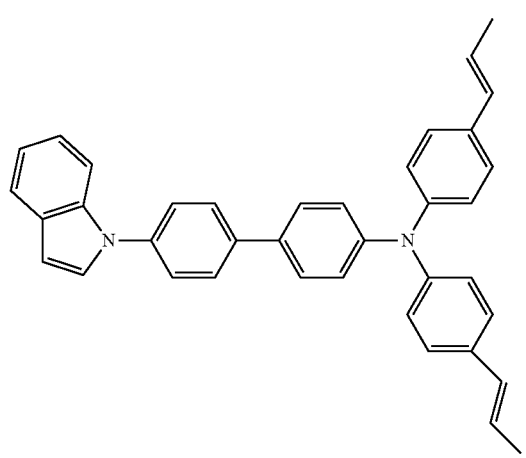

-continued
1-57
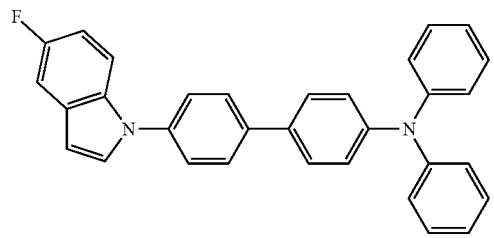
1-58
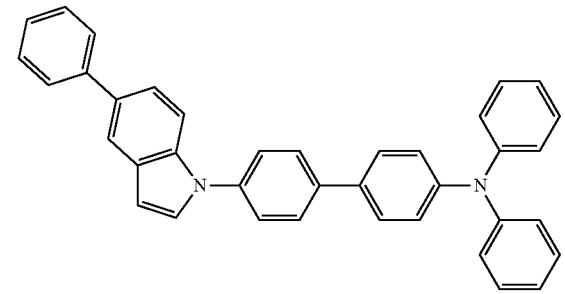
1-59
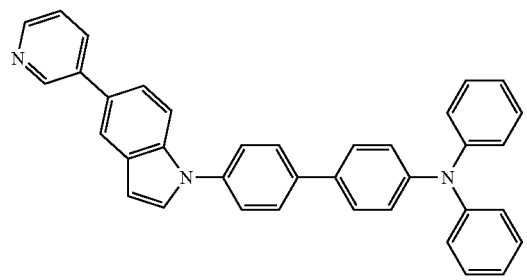
1-60
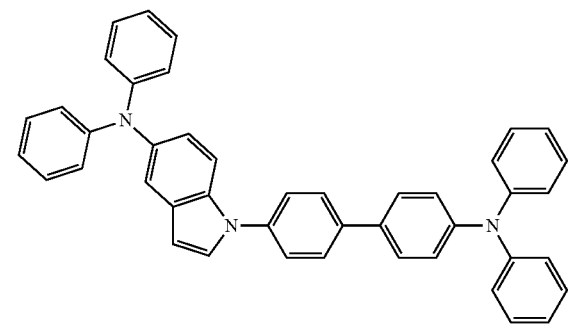
1-61
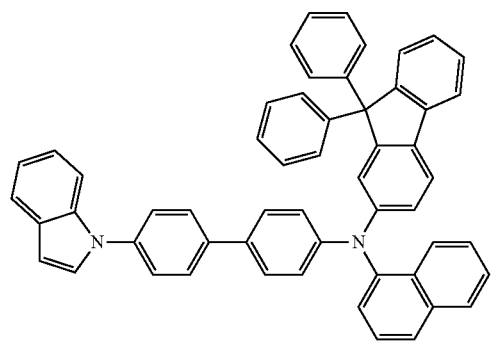
1-62
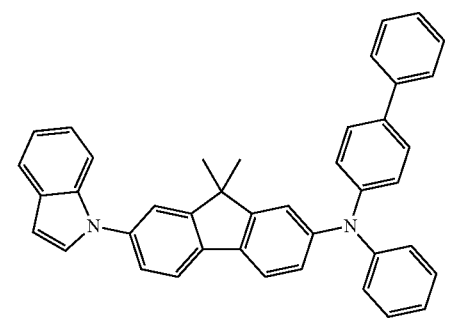
1-63
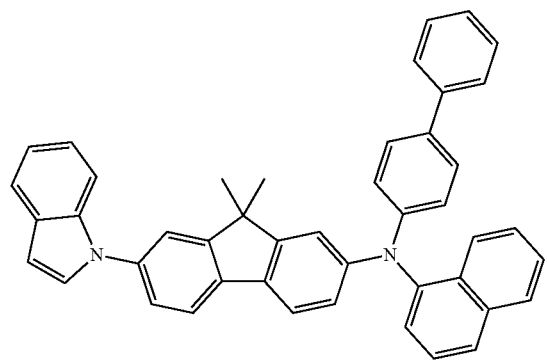
1-64
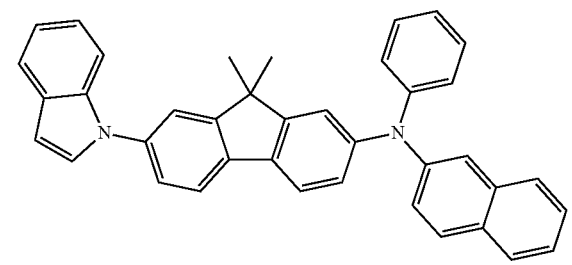

1-65
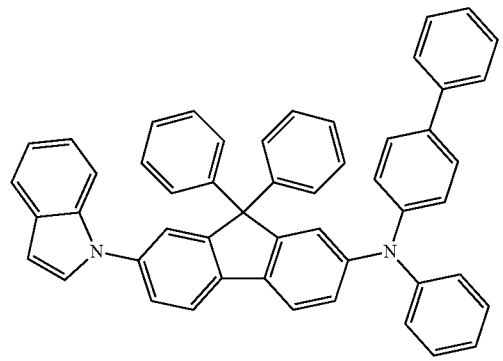
1-66
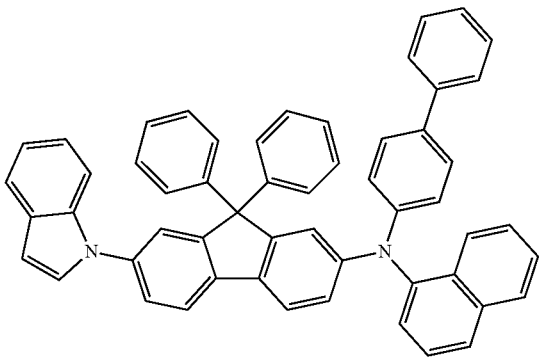
1-67
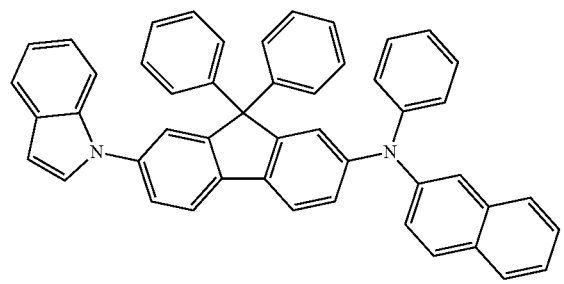
1-68
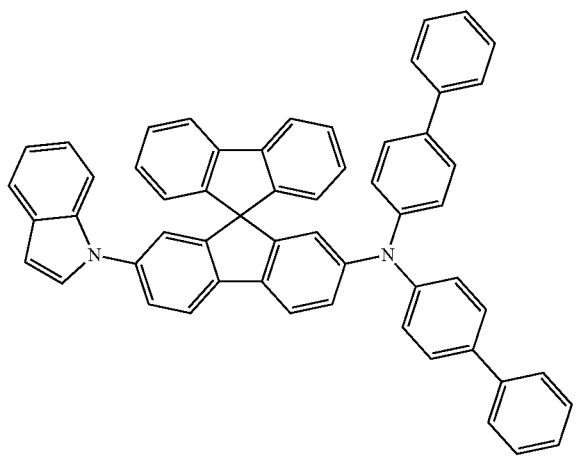
1-69
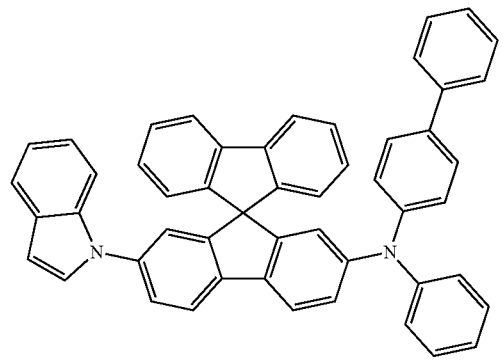
1-70
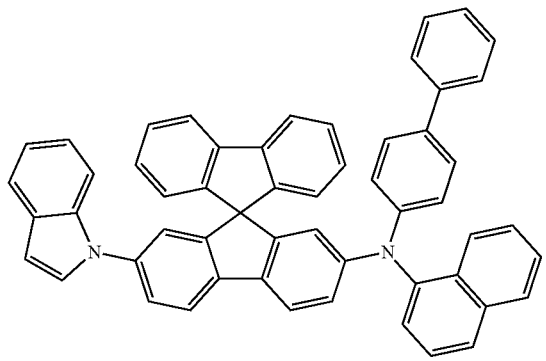
1-71
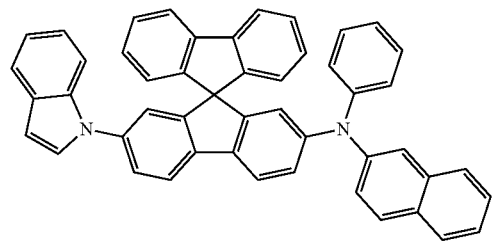
1-72
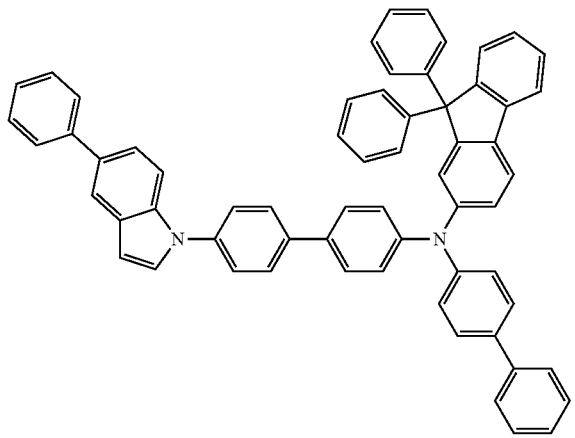

-continued
1-73
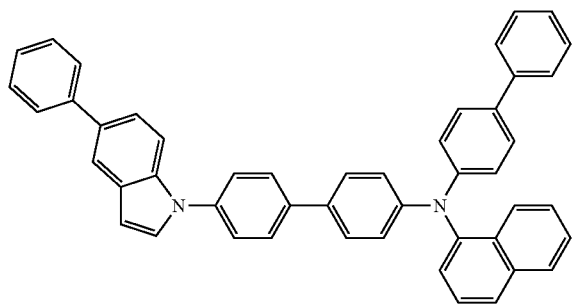
1-74
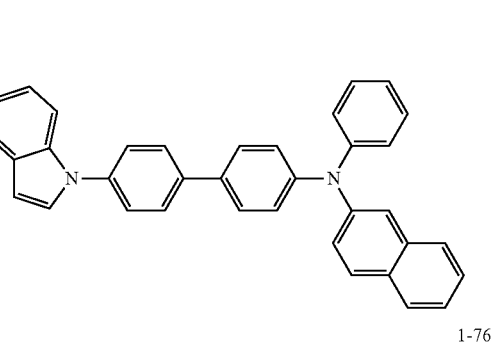
1-75
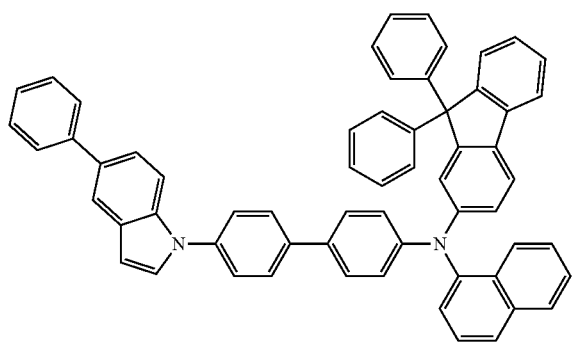
1-76
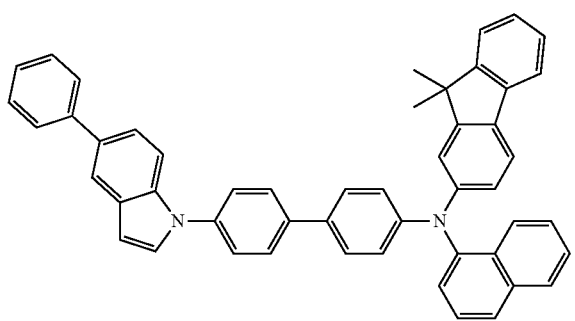
1-77
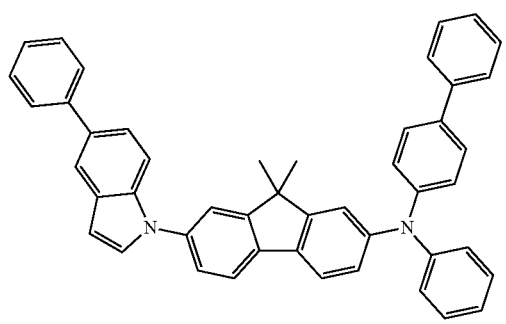
1-78
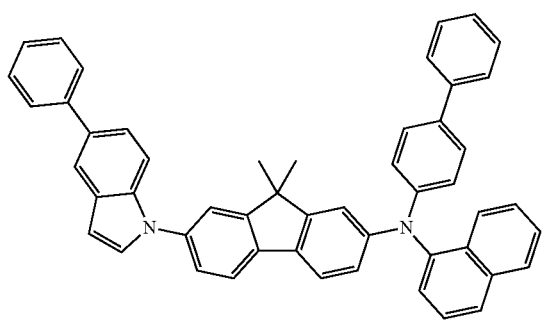
1-79
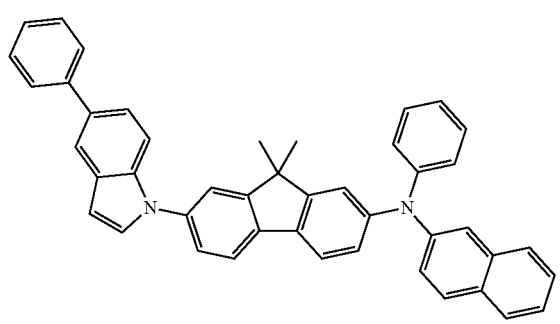
1-80
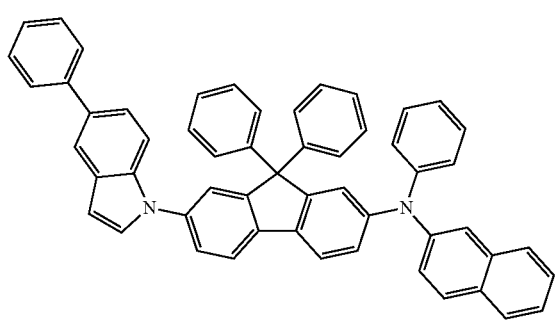

-continued
1-81
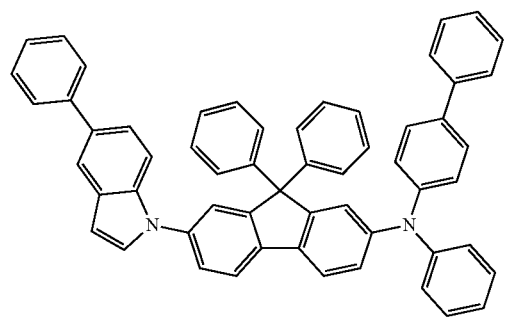
1-82
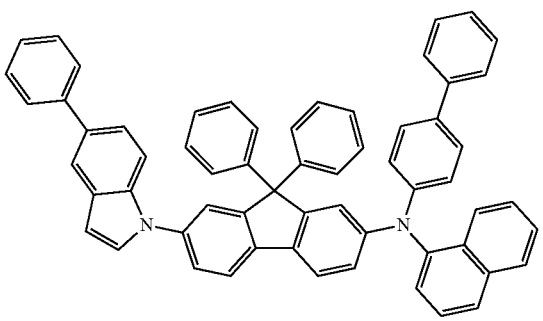
1-83
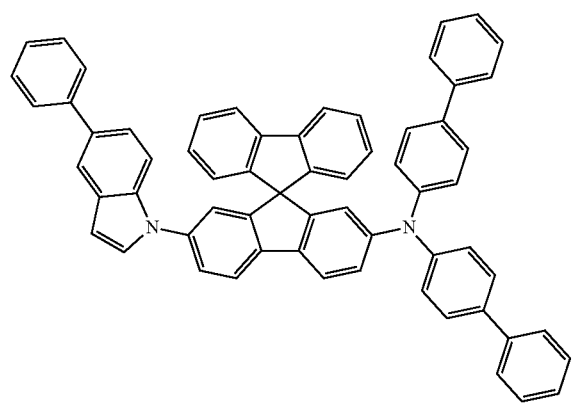
1-84
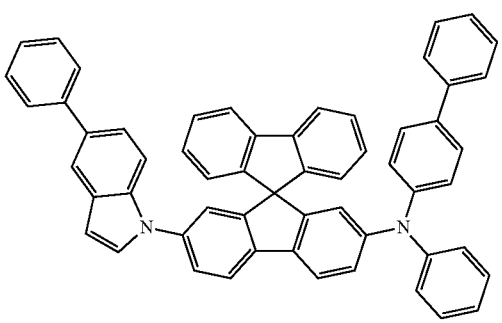
1-85
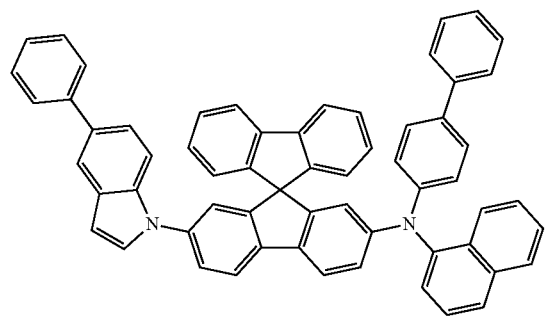
1-86
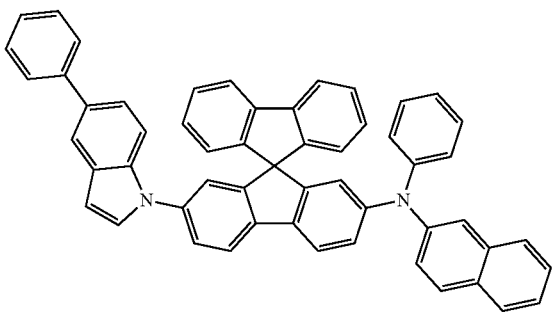
1-87
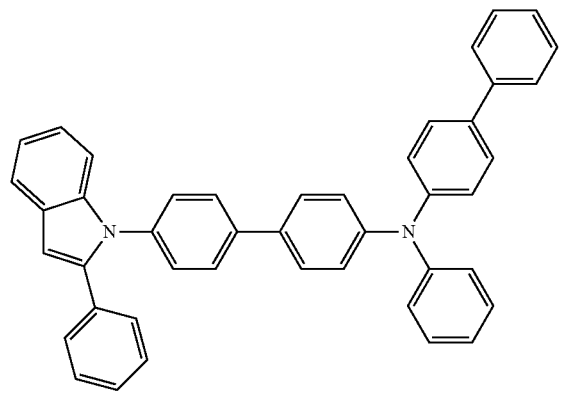
1-88
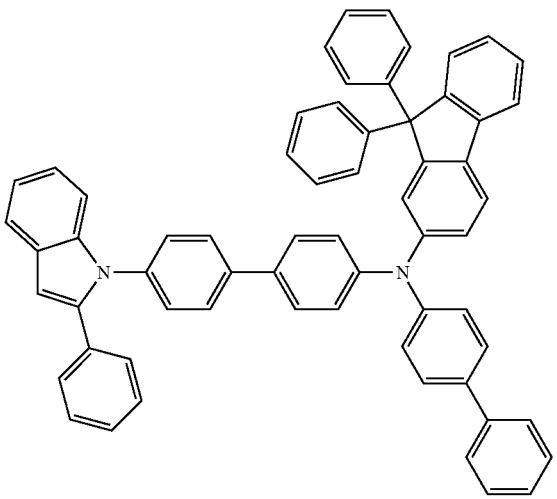

-continued
1-89
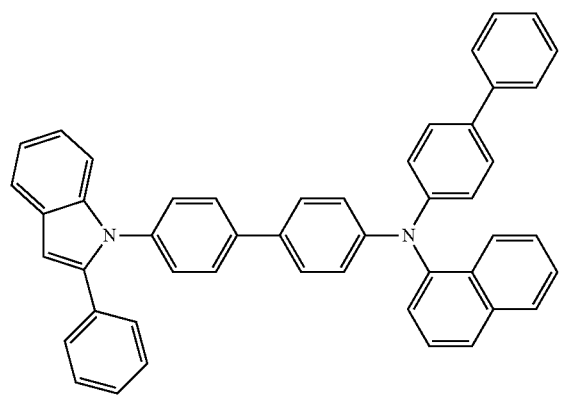
1-90
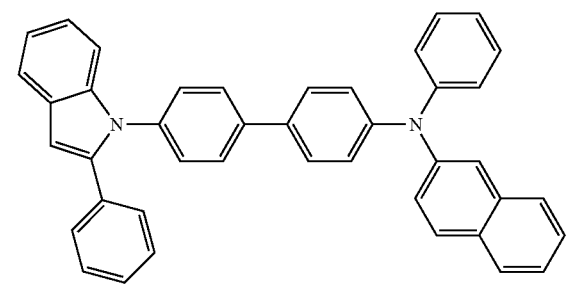
1-91
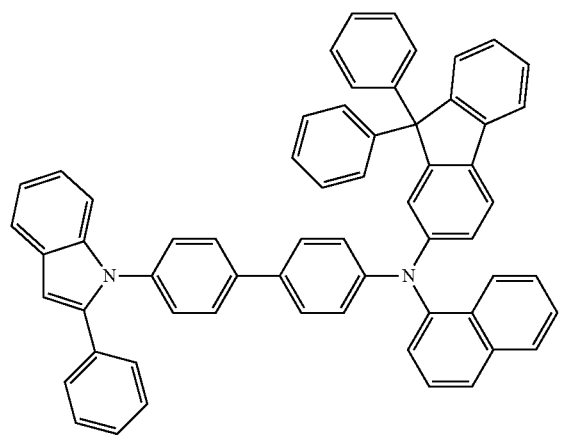
1-92
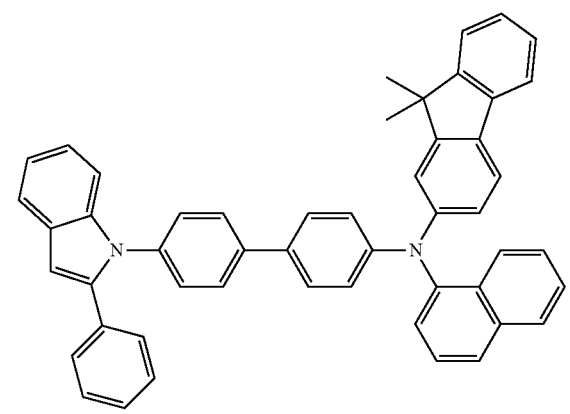
1-93
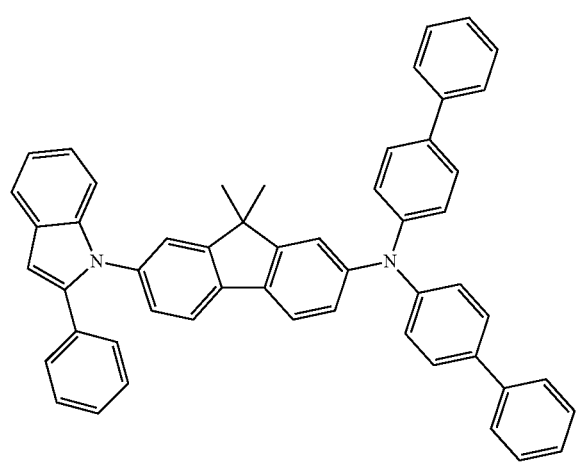
1-94
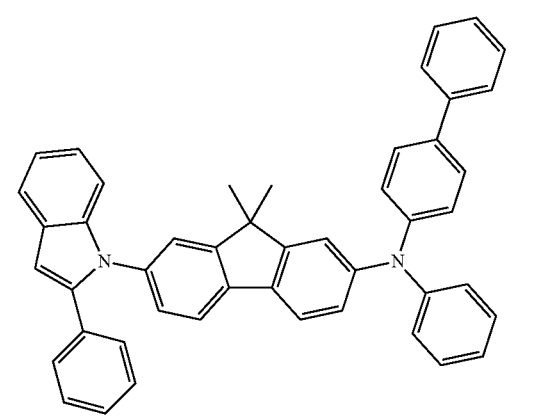

-continued
1-95
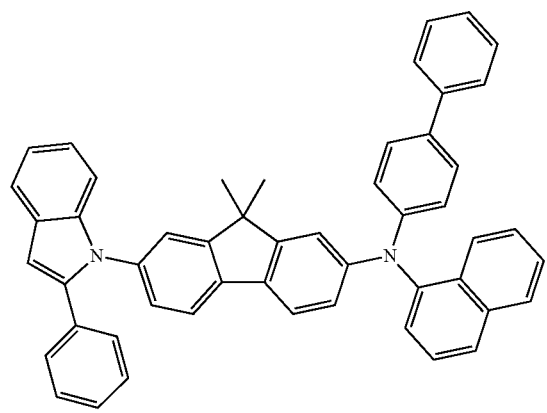
1-96
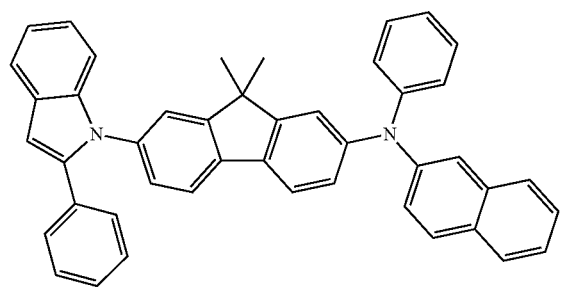
1-97
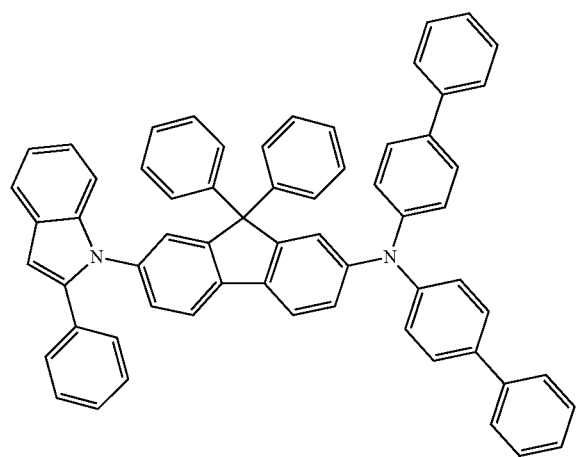
1-98
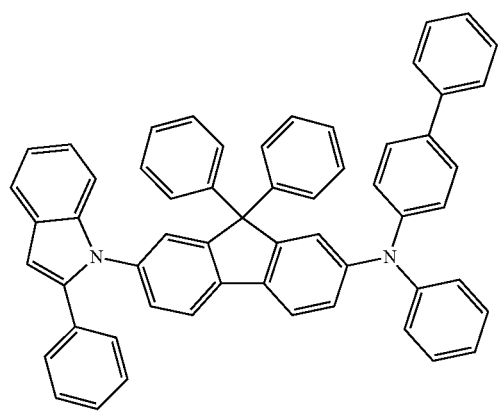
1-99
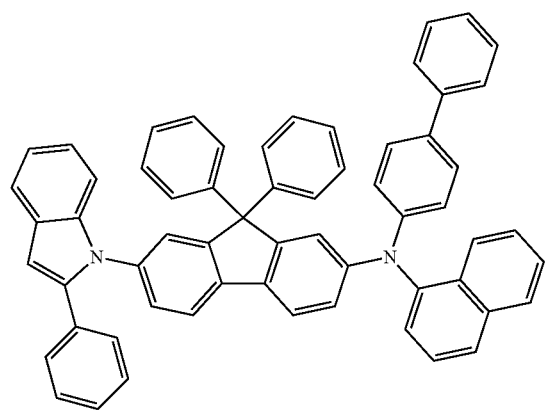
1-100
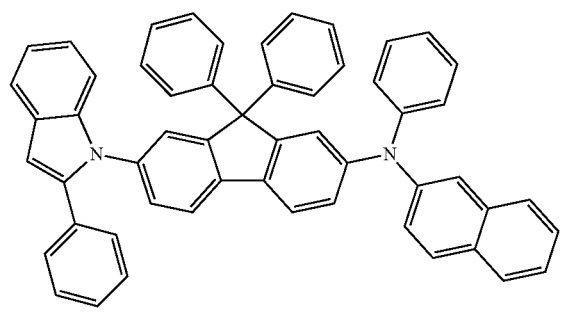

-continued
1-101
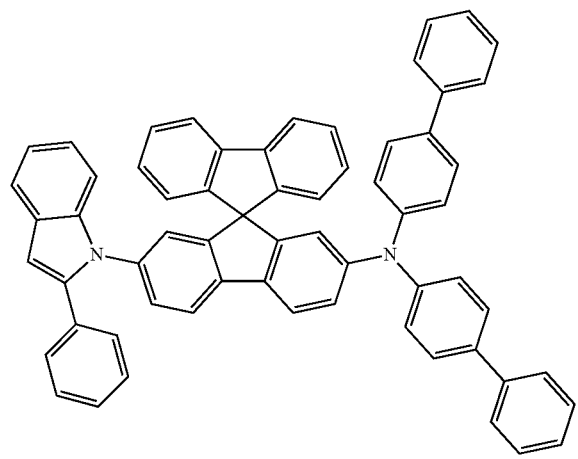
1-102
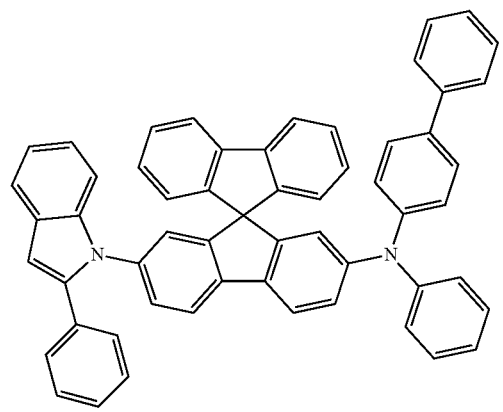
1-103
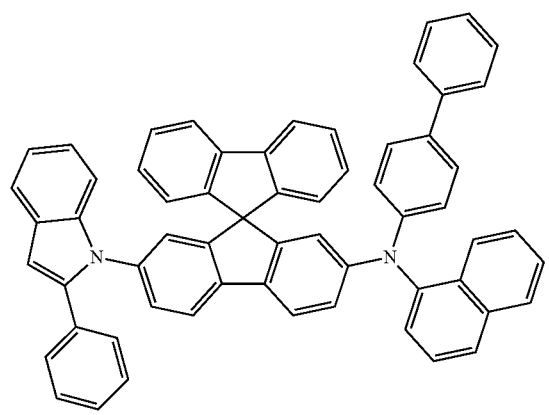
1-104
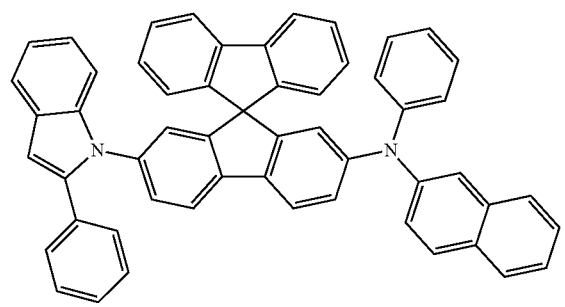
1-105
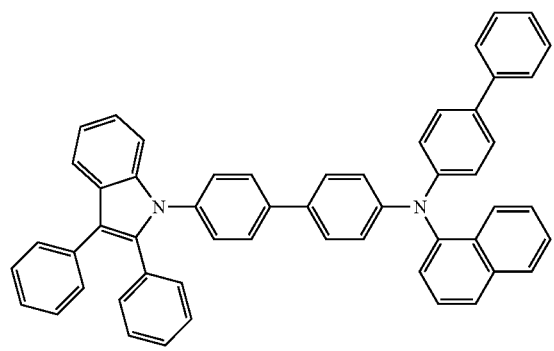
1-106
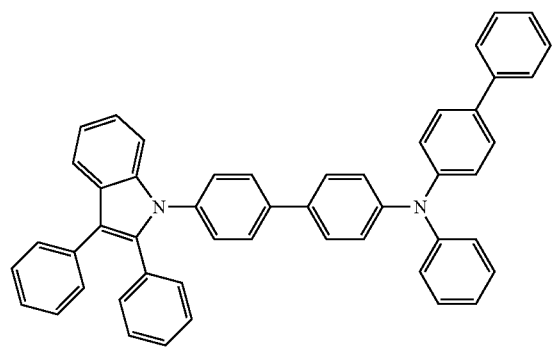

-continued
1-107
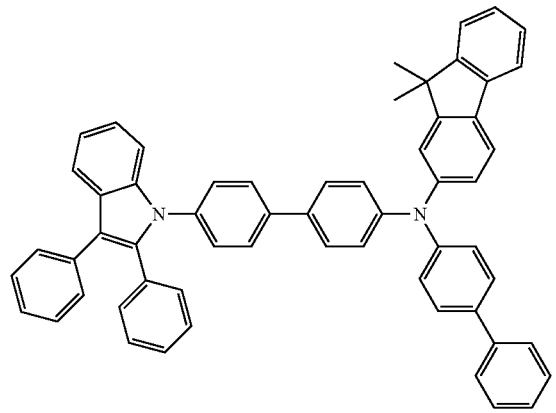
1-108
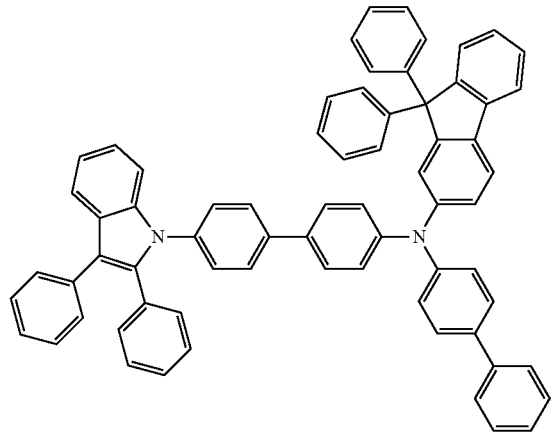
1-109
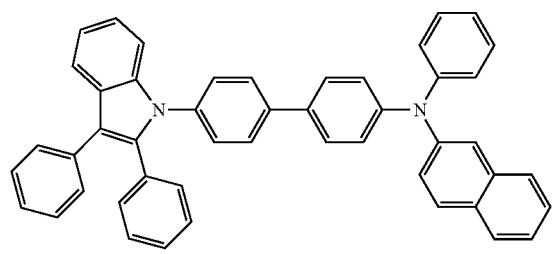
1-110
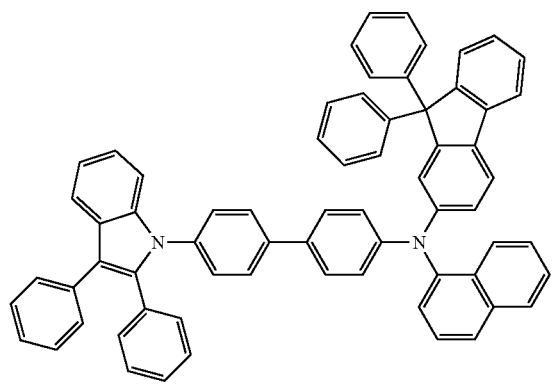
1-111
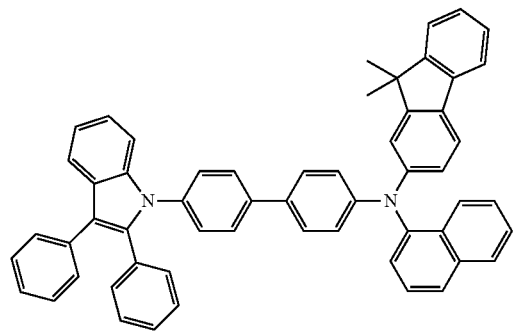
1-112
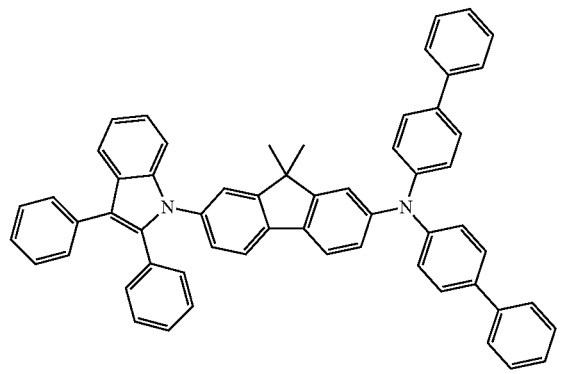
1-113
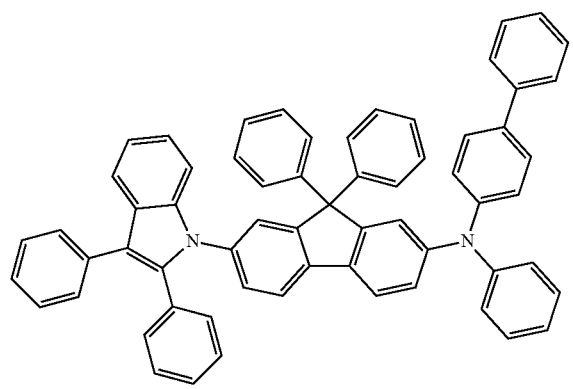
1-114
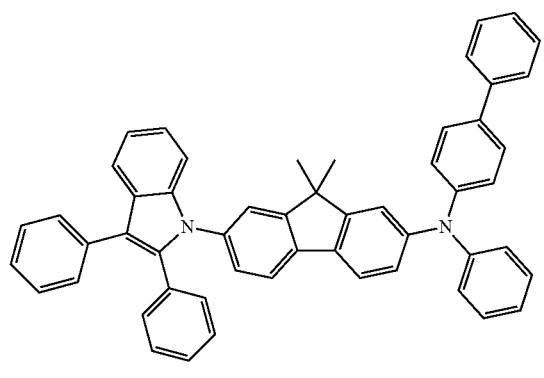

-continued
1-115
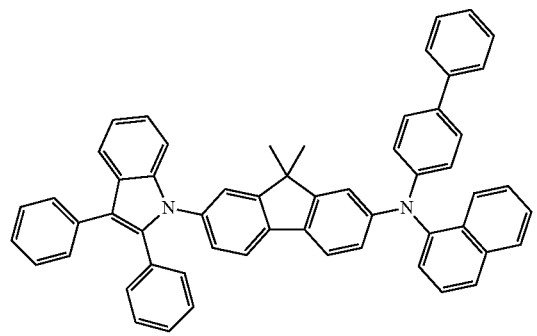
1-116
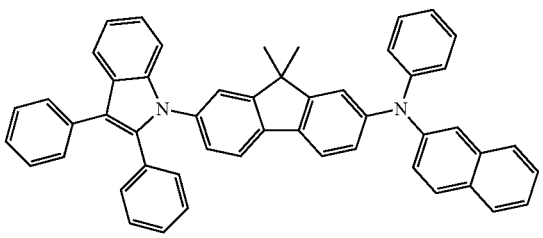
1-117
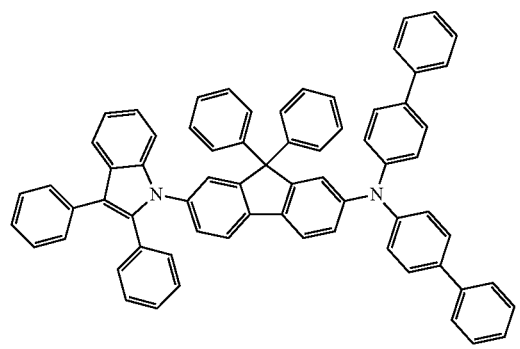
1-118
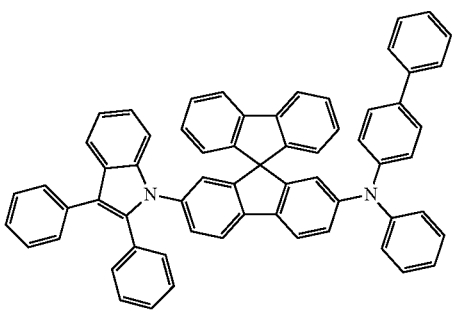
1-119
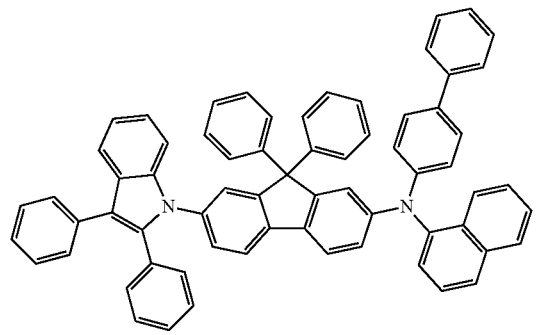
1-120
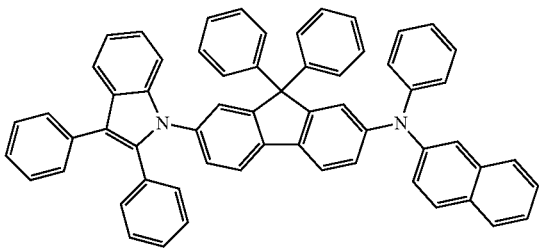
1-121
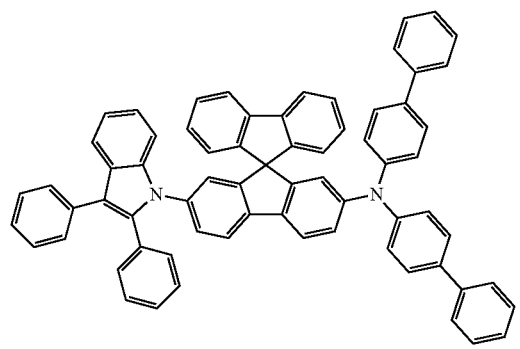
1-122
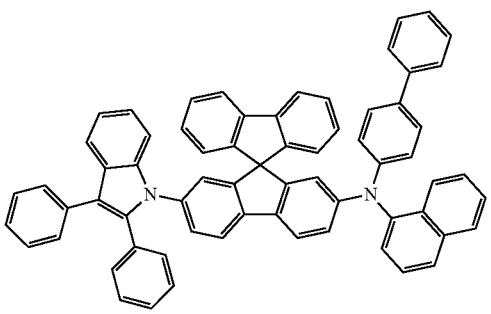

-continued
1-123
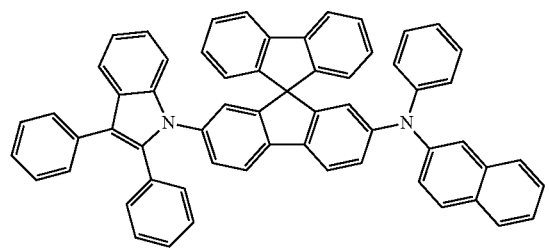
1-124
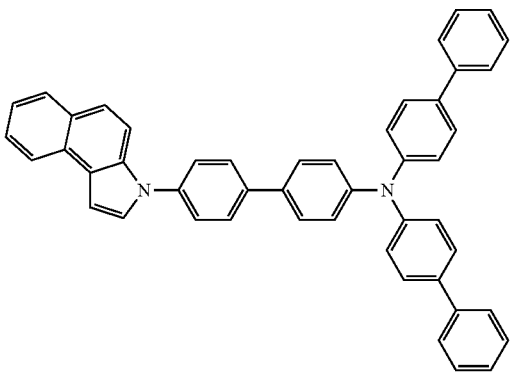
1-125
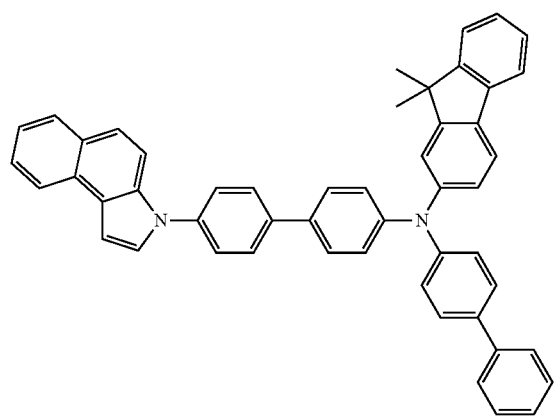
1-126
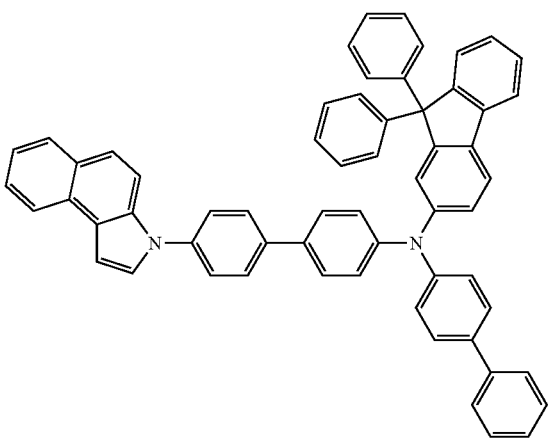
1-127
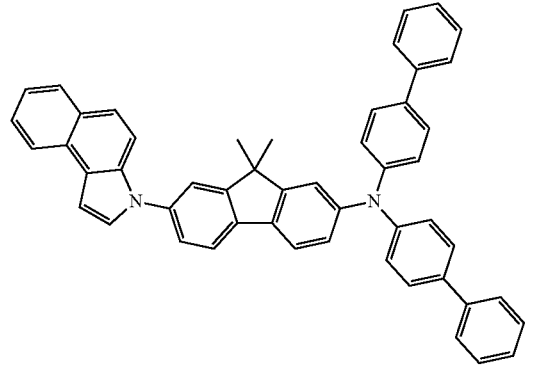
1-128
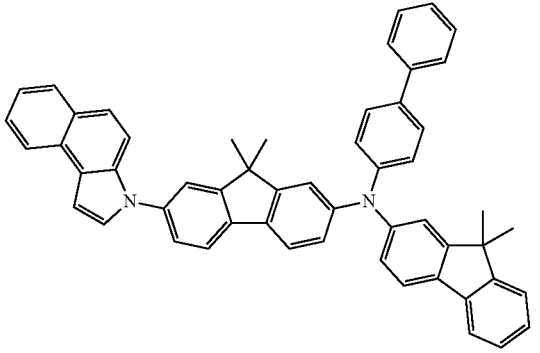
1-129
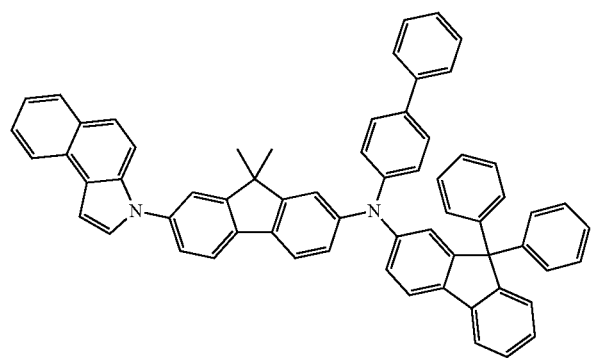
1-130
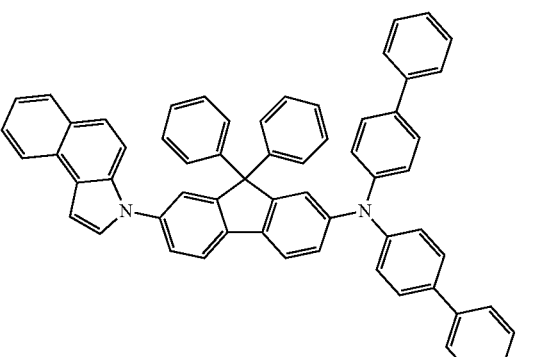

-continued
1-131
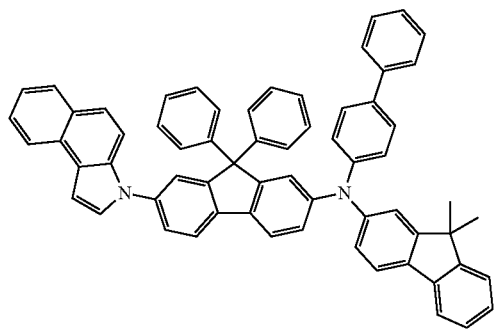
1-132
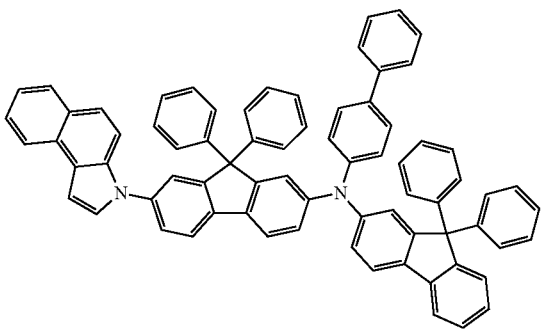
1-133
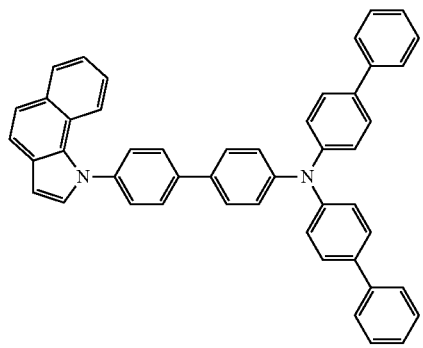
1-134
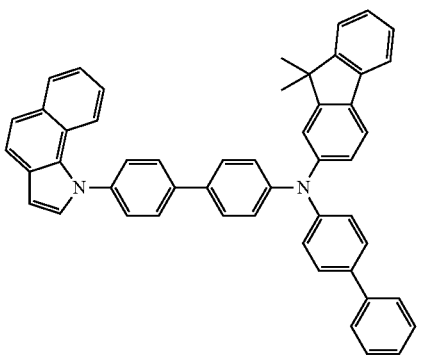
1-135
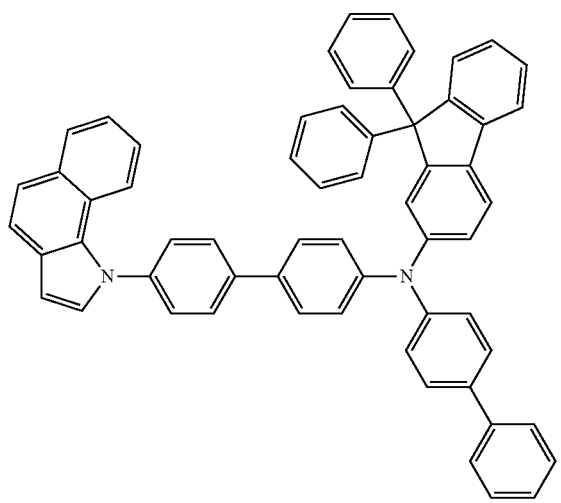
1-136
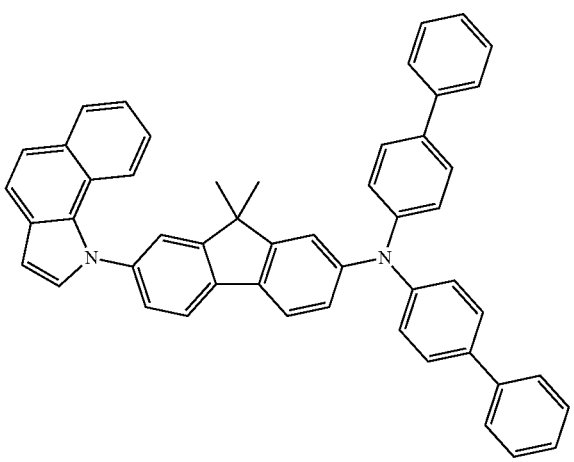
1-137
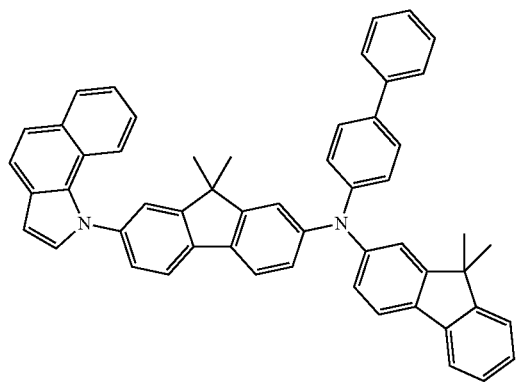
1-138
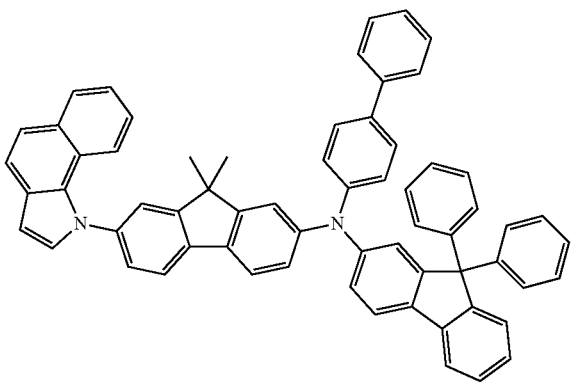

-continued
1-139
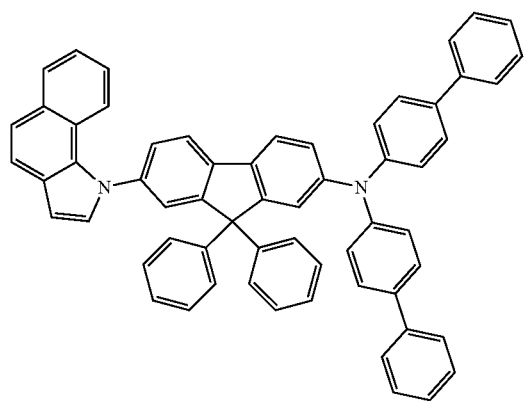
1-140
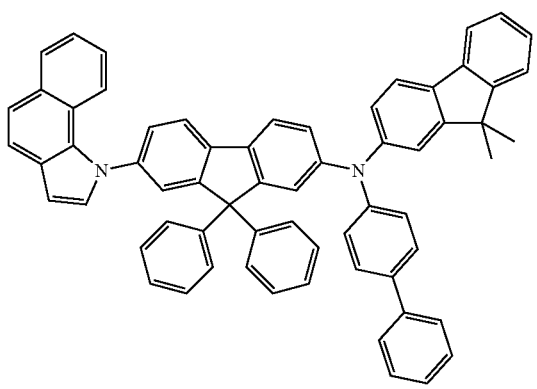
1-141
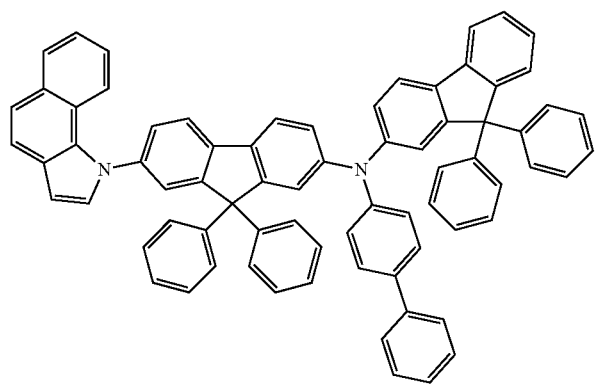
1-142
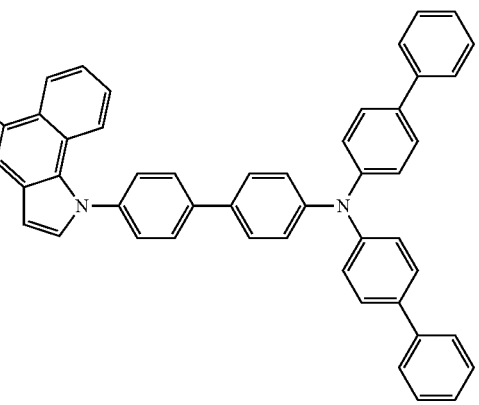
1-143
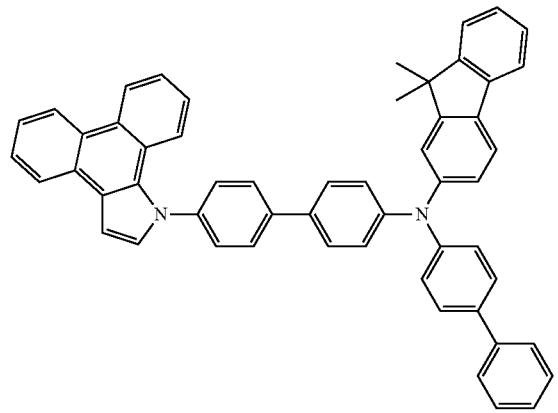
1-144
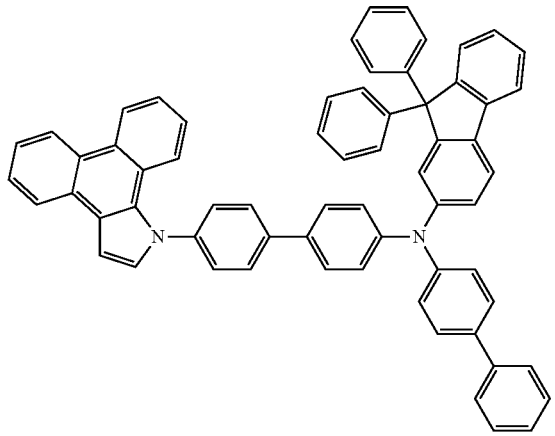
1-145
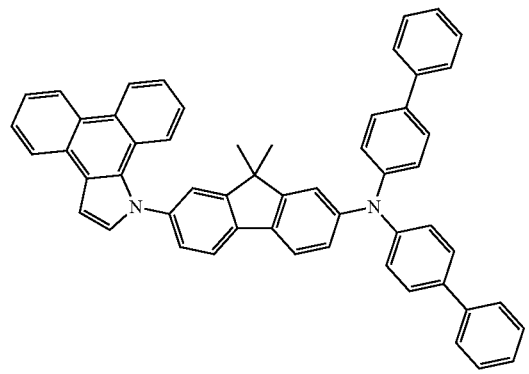
1-146
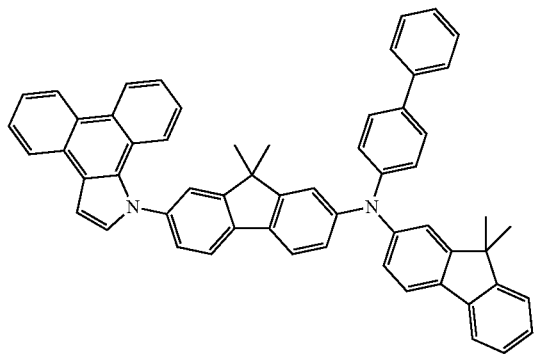

-continued
1-147
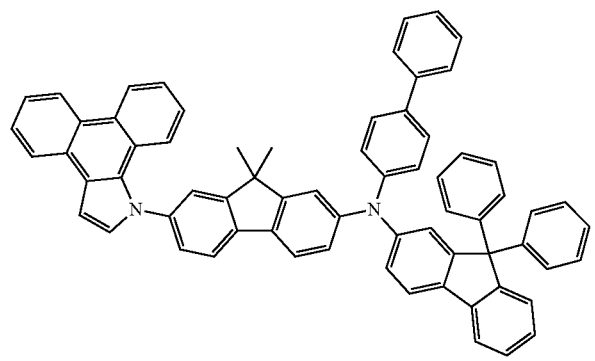
1-148
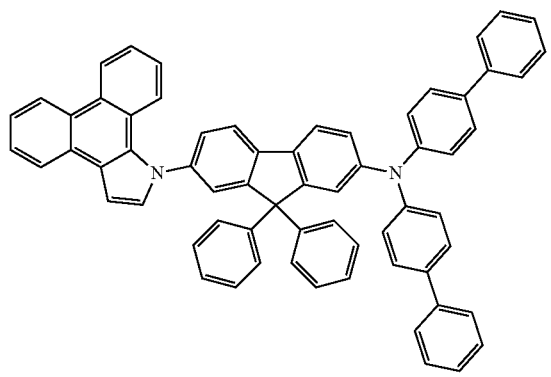
1-149
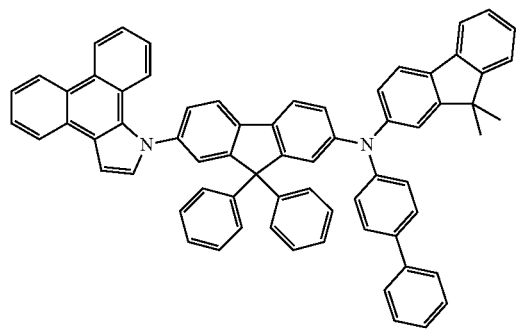
1-150
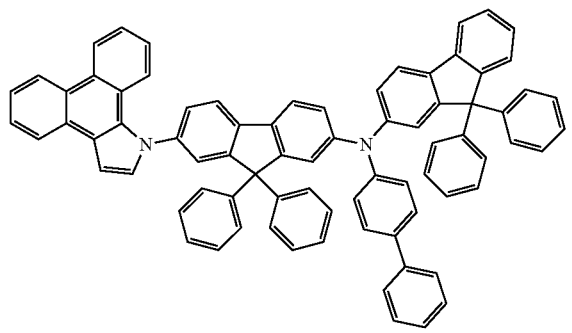
7. The organic electric element as claimed in claim 1, wherein Formula 2 comprises any one of the compounds below:
3-1
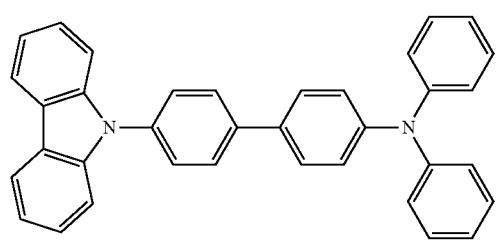
3-2
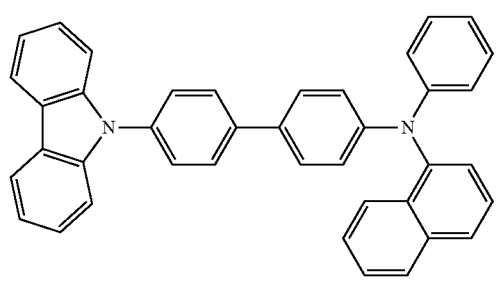
3-3
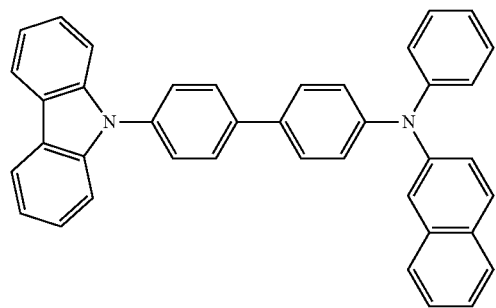
3-4
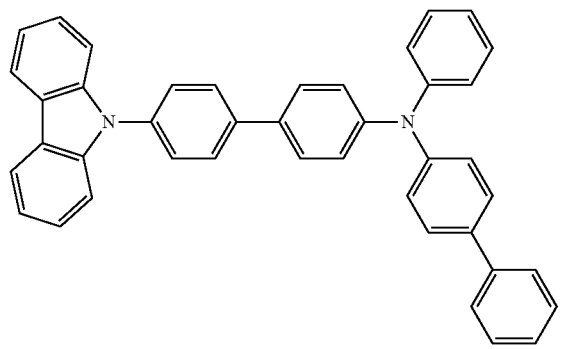

345
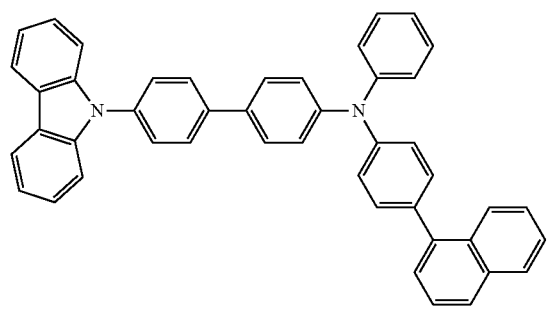
3-5
346
-continued
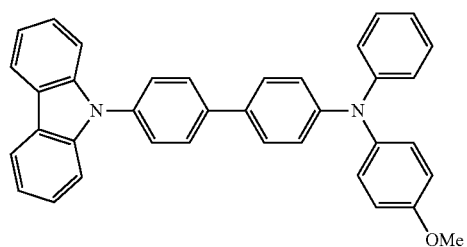
3-6
3-7
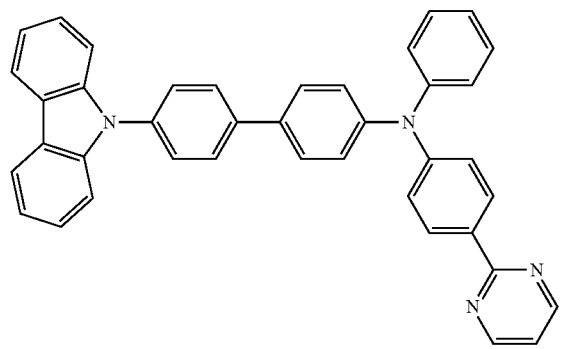
3-8
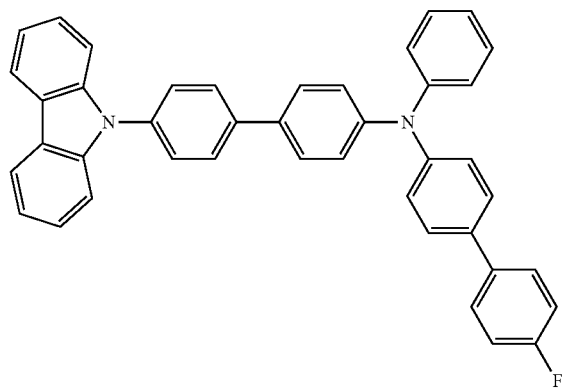
3-9
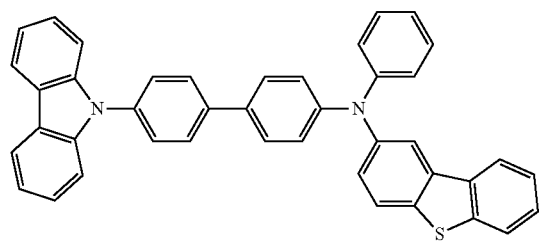
3-10
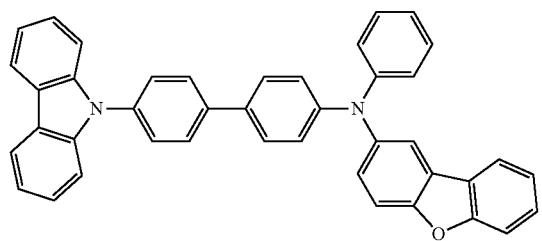
3-11
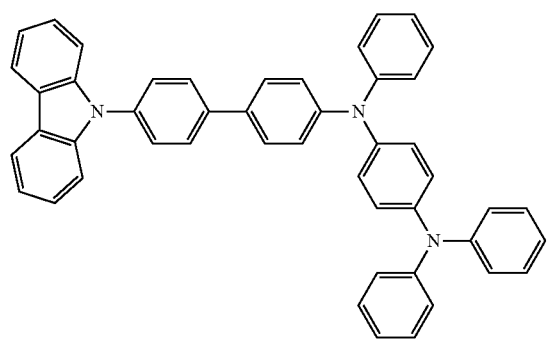
3-12
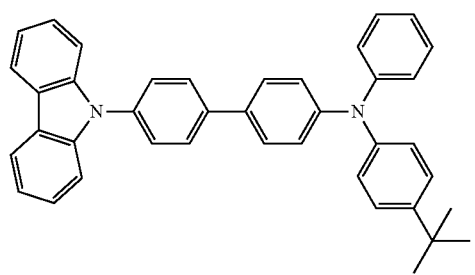

3-13
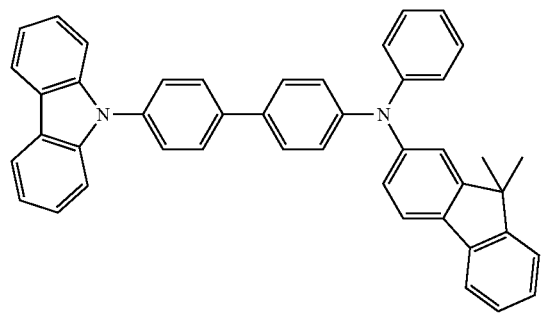
3-14
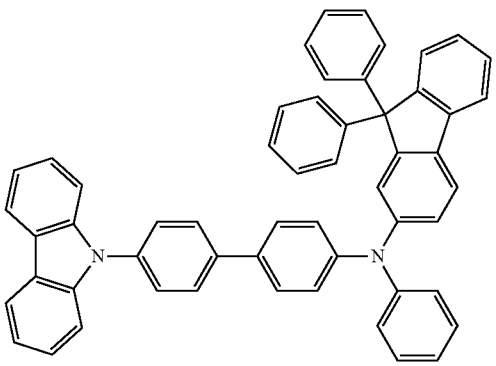
3-15
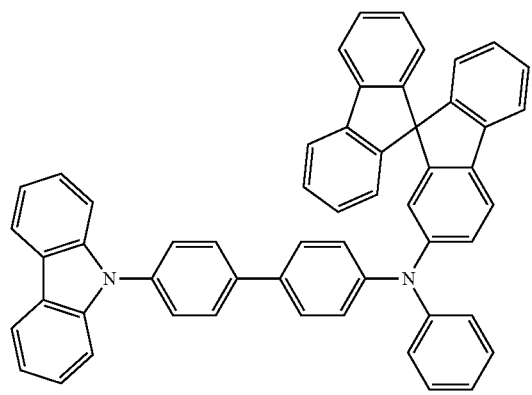
3-16
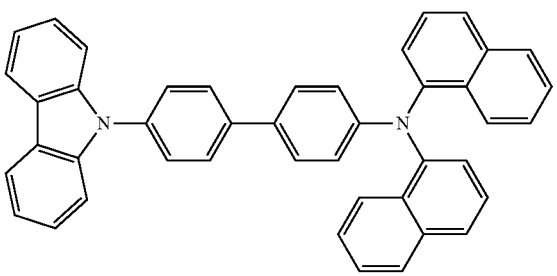
3-17
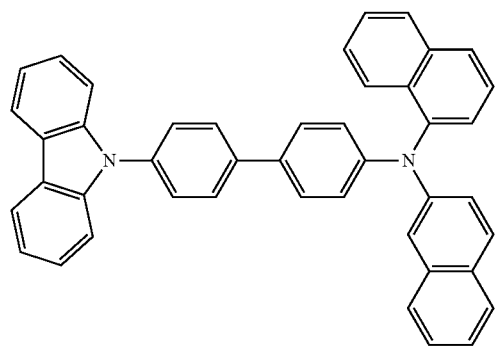
3-18
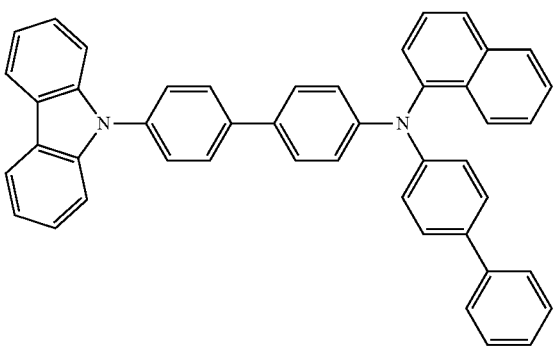
3-19
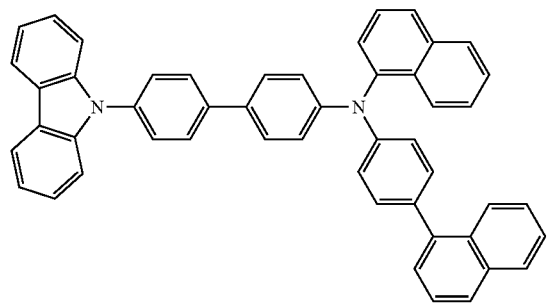
3-20
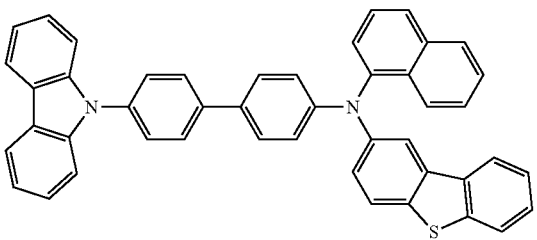

-continued
3-21
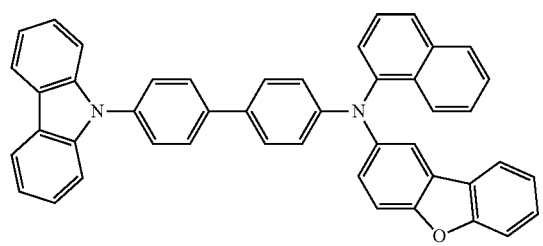
3-22
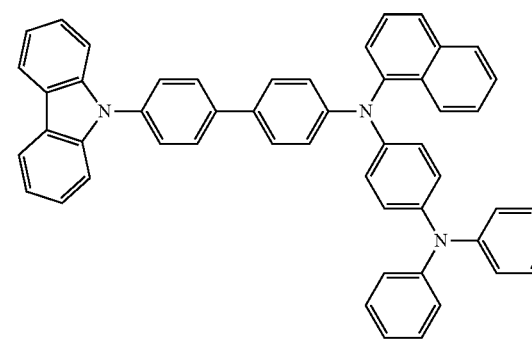
3-23
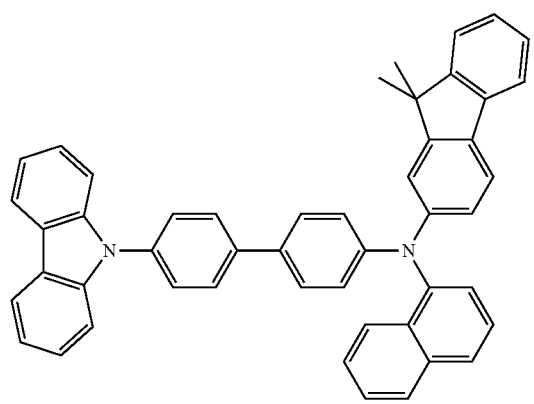
3-24
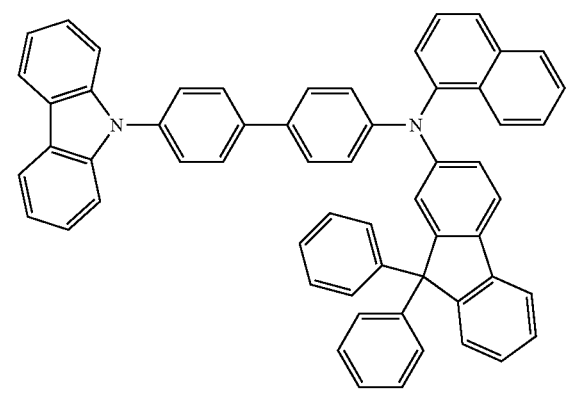
3-25
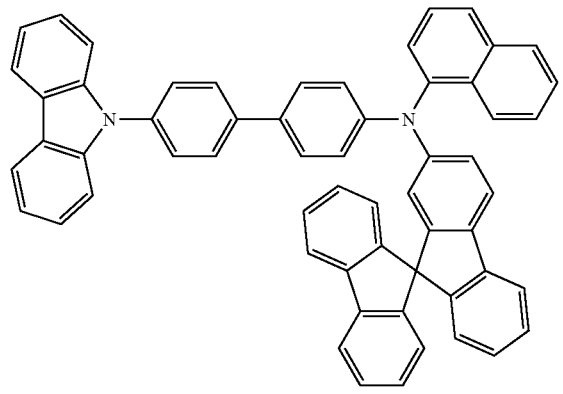
3-26
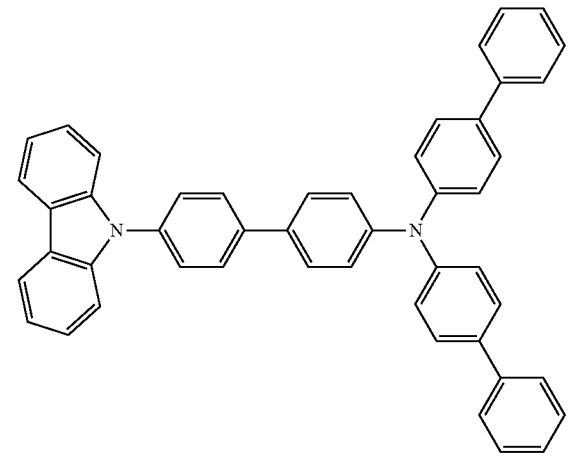
3-27
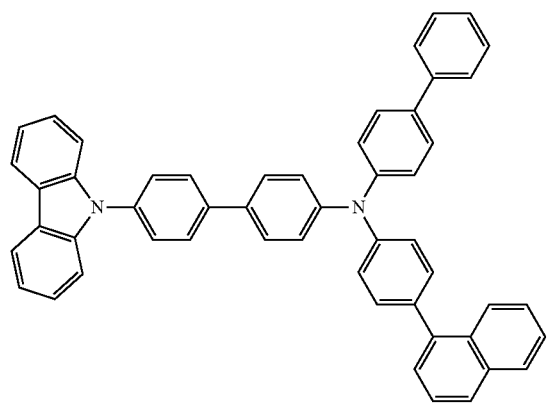
3-28
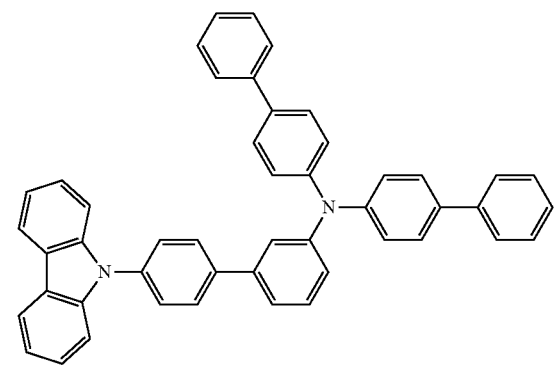

-continued
3-29
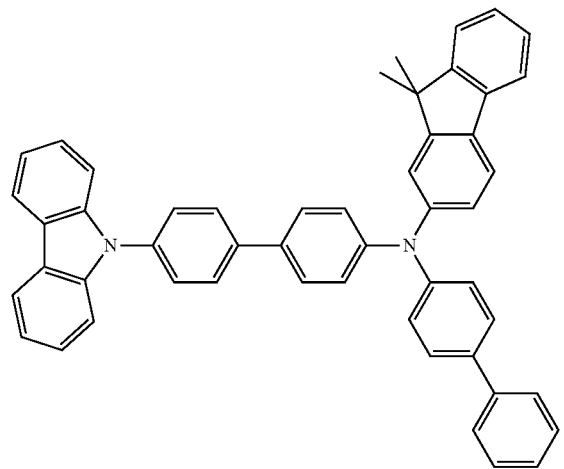
3-30
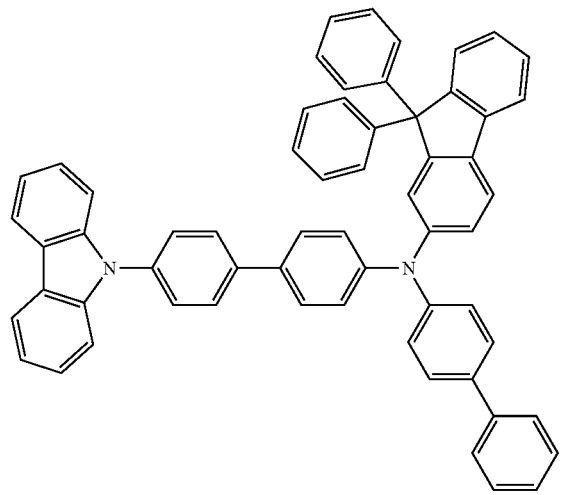
3-31
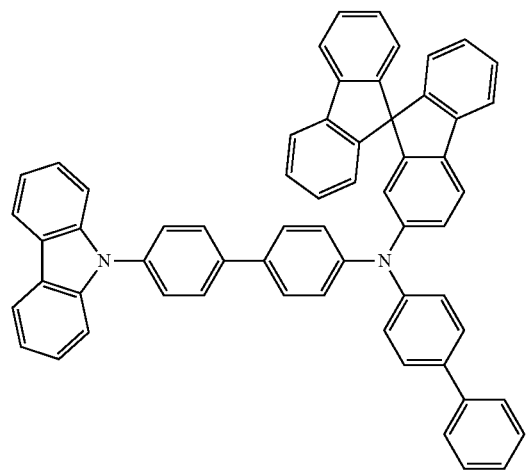
3-32
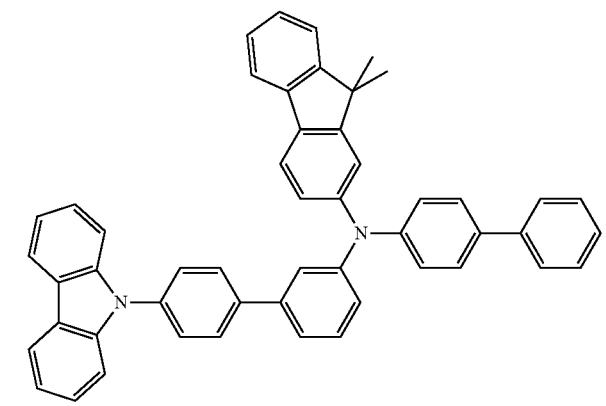
3-33
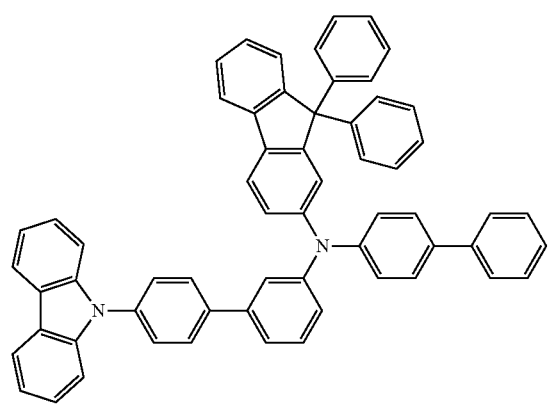
3-34
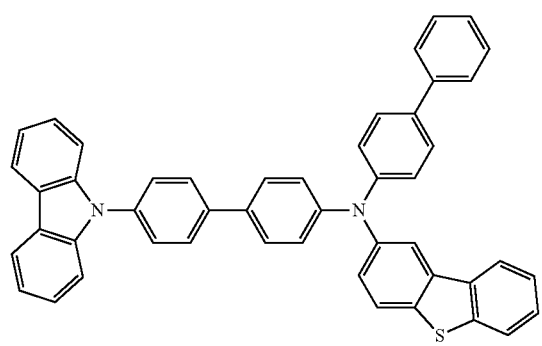

-continued
3-35
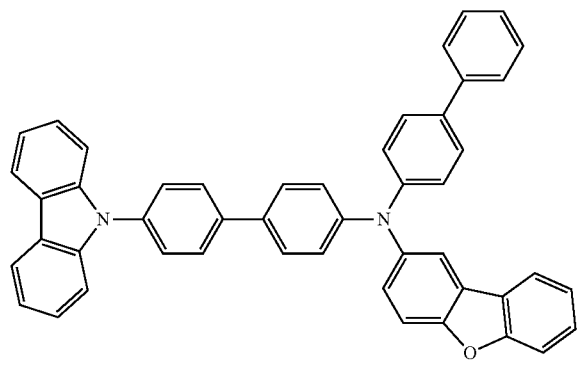
3-36
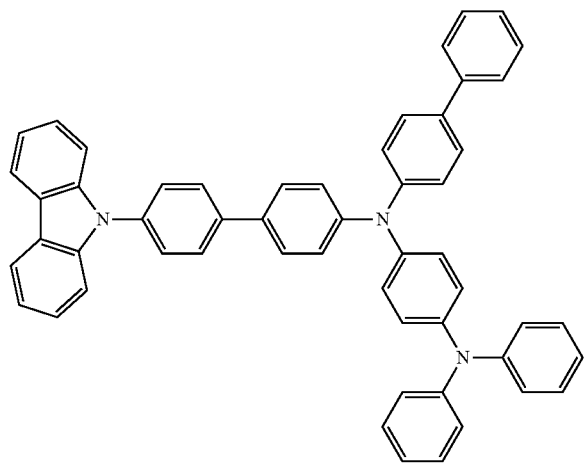
3-37
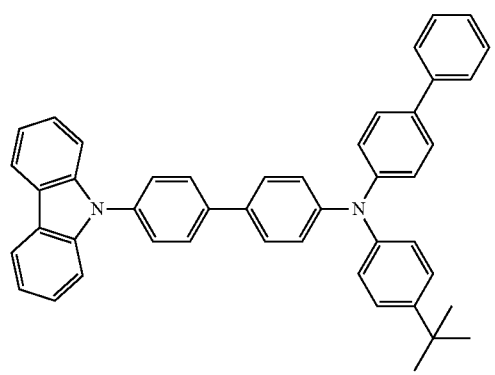
3-38
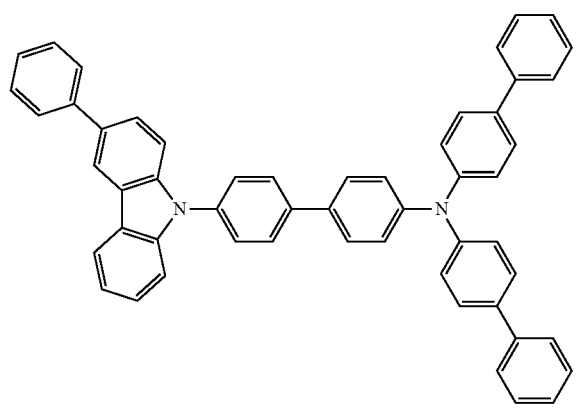
3-39
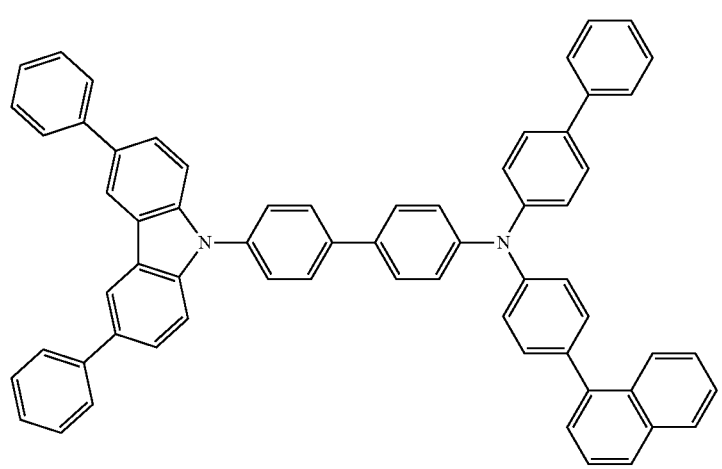

3-40
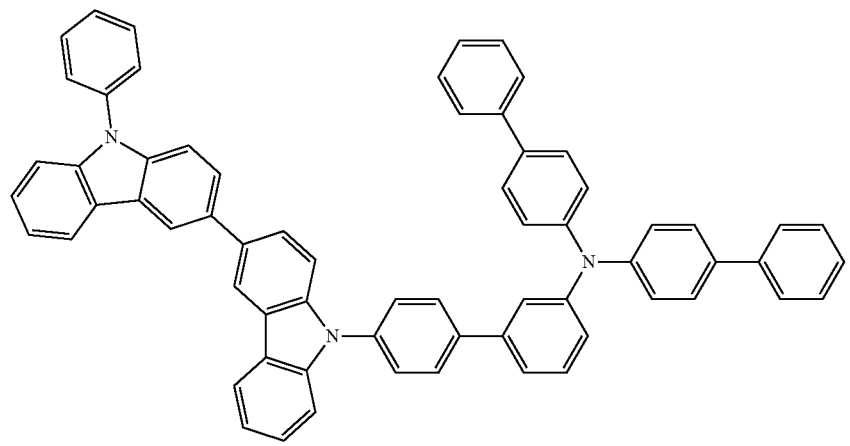
3-41
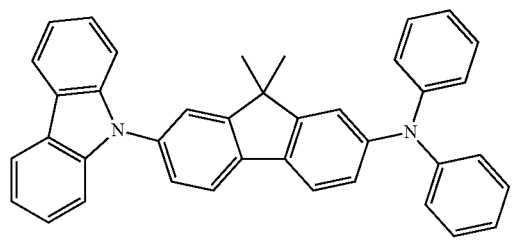
3-42
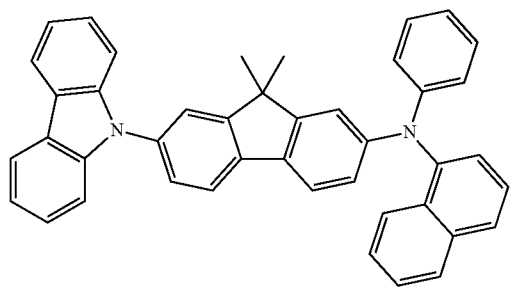
3-43
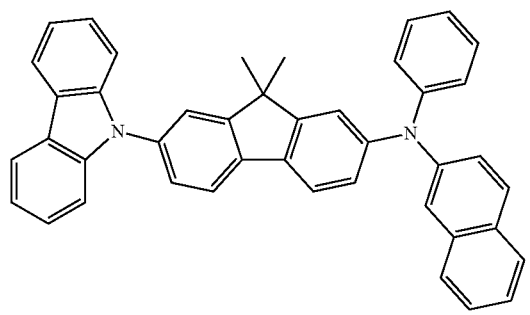
3-44
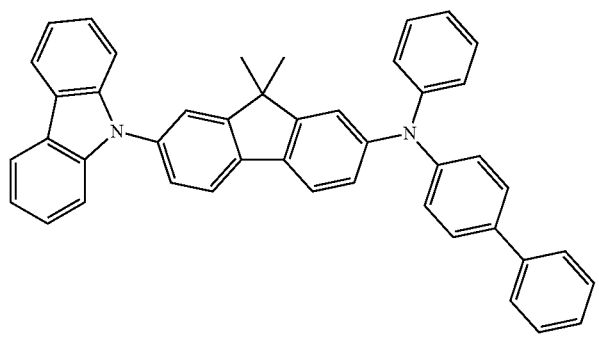
3-45
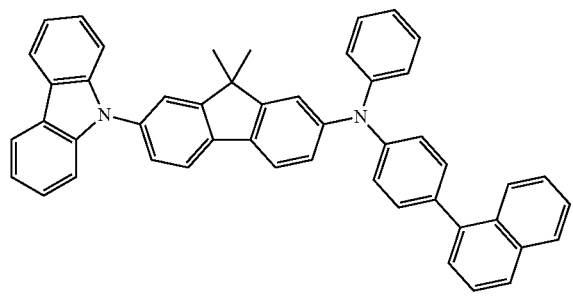
3-46
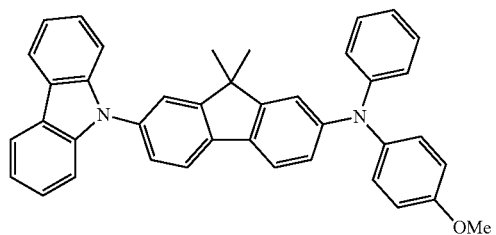

-continued
3-47
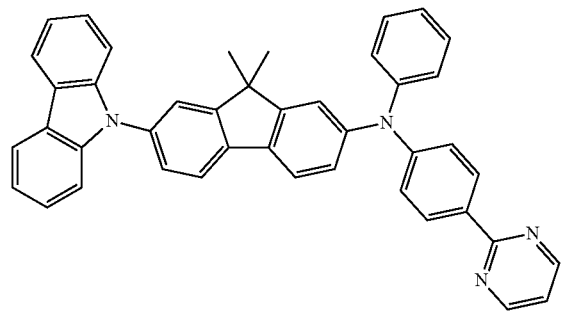
3-48
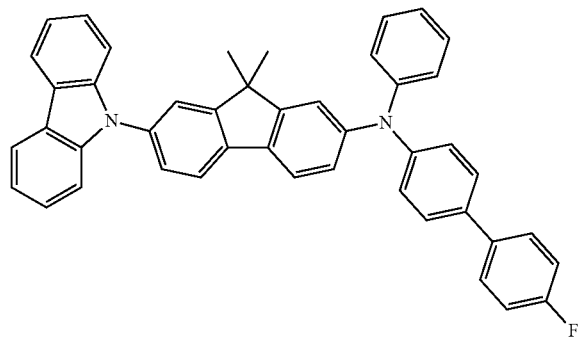
3-49
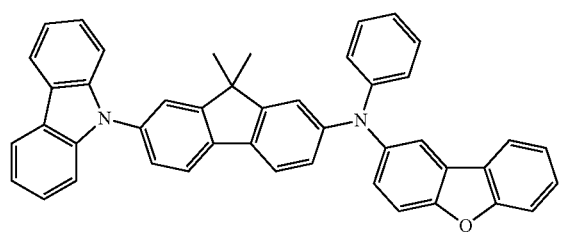
3-50
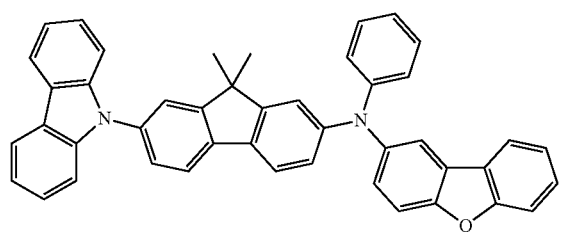
3-51
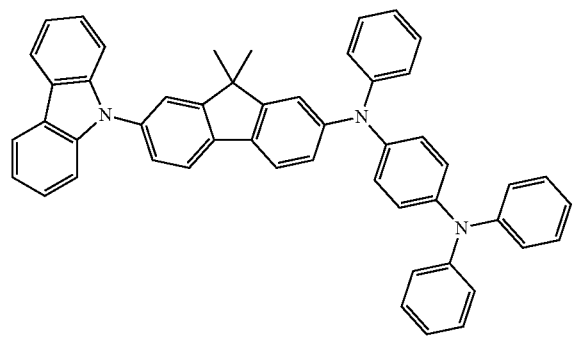
3-52
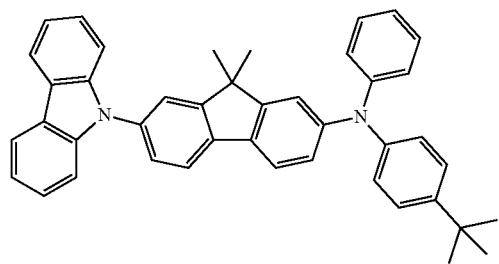
3-53
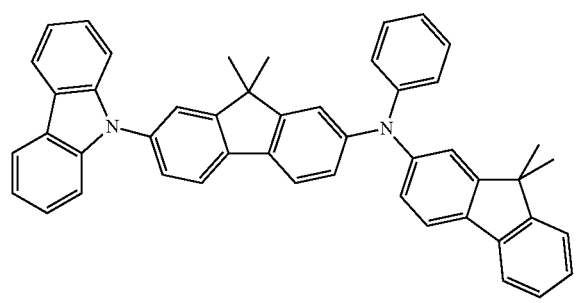
3-54
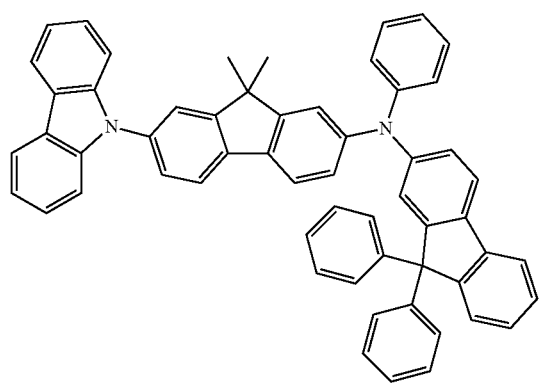

-continued
3-55
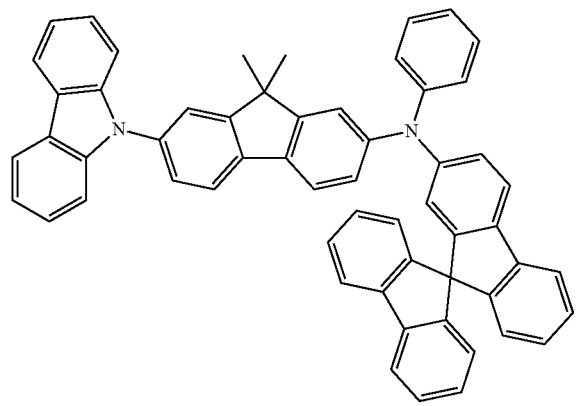
3-56
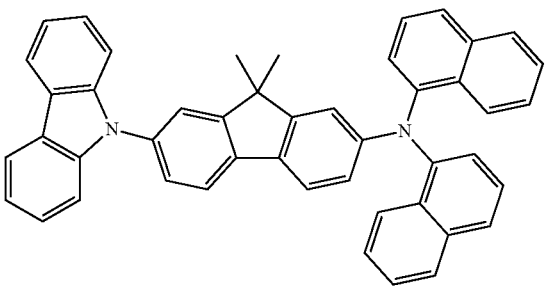
3-57
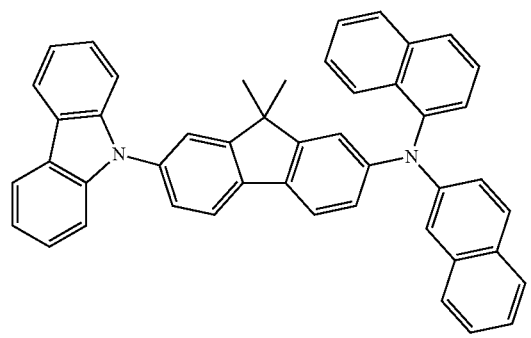
3-58
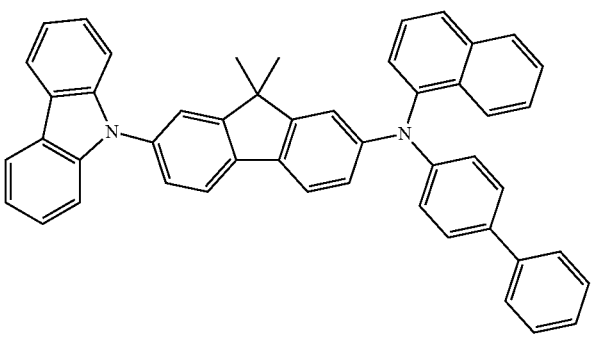
3-59
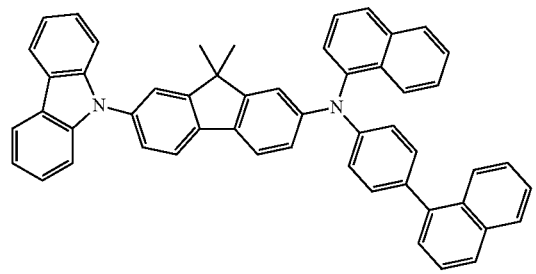
3-60
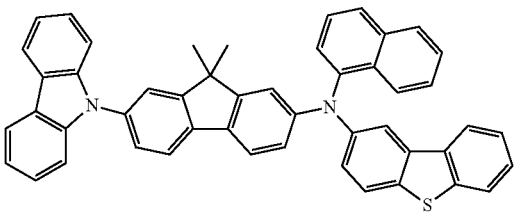
3-61
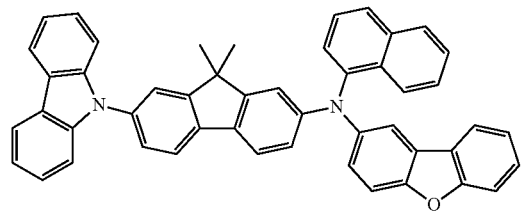
3-62
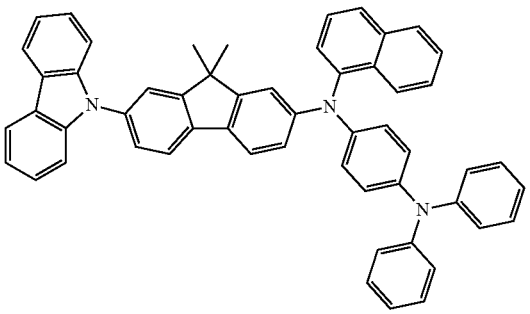

-continued
3-63
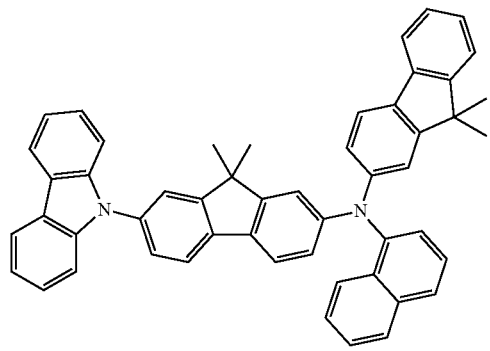
3-64
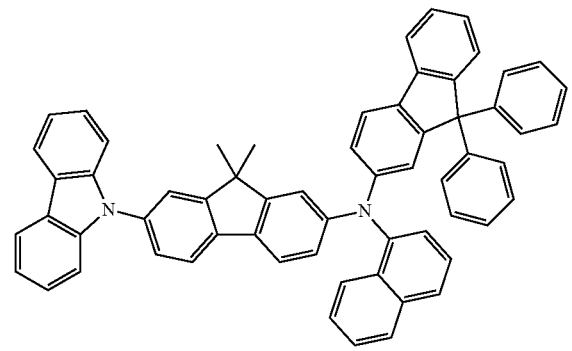
3-65
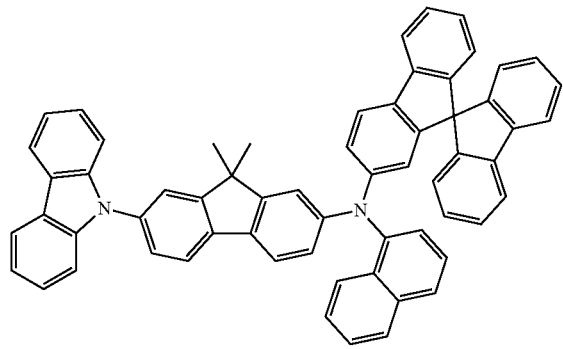
3-66
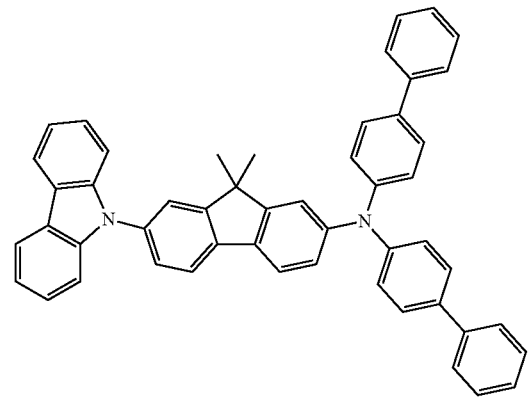
3-67
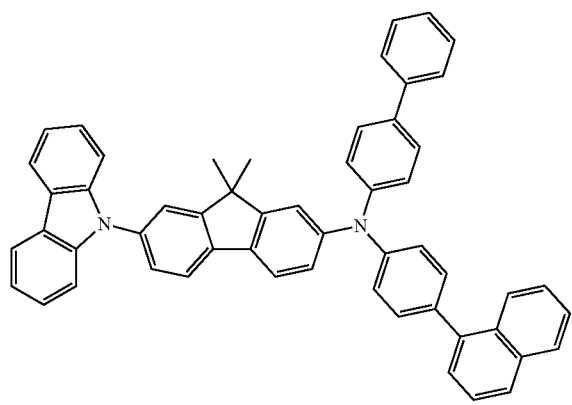
3-68
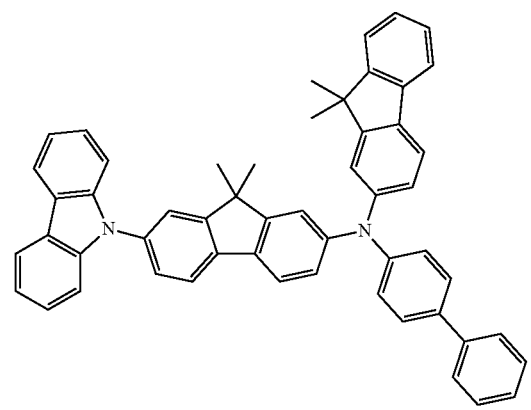

-continued
3-69
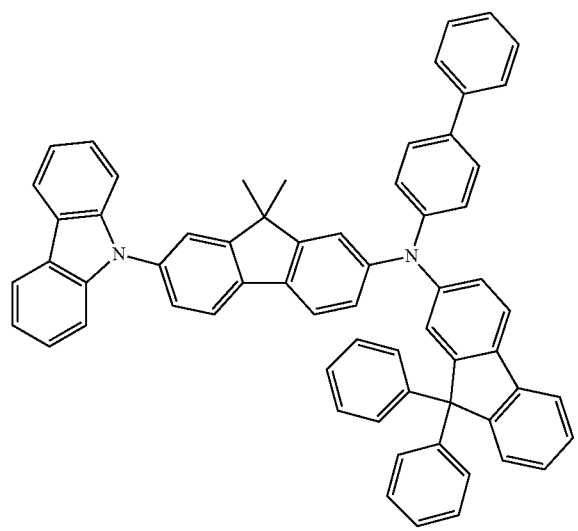
3-70
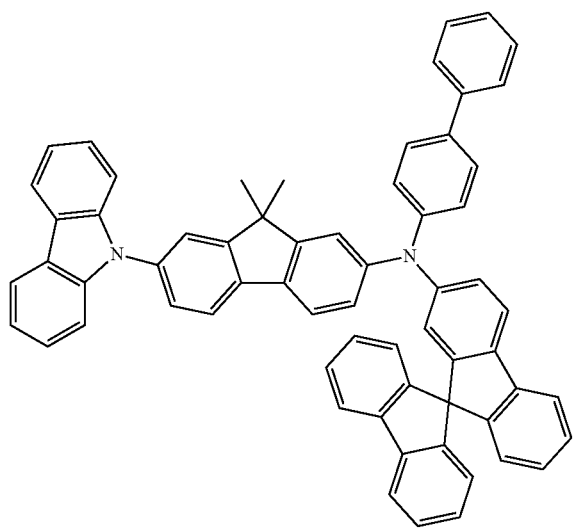
3-71
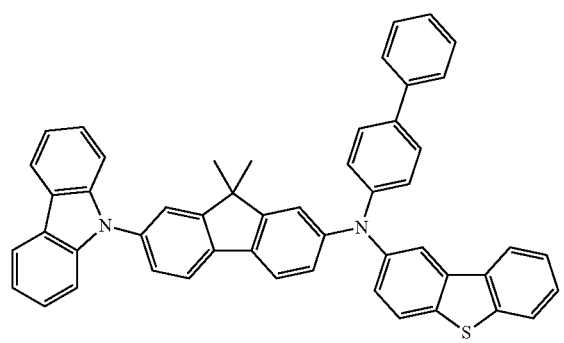
3-72
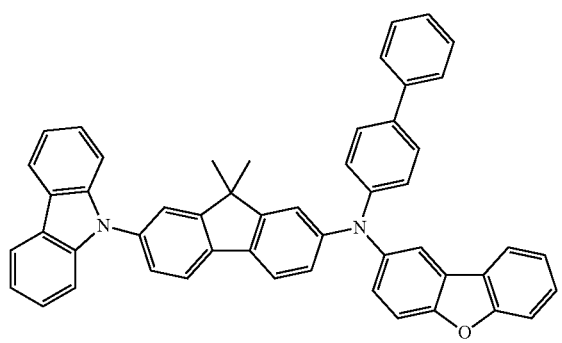
3-73
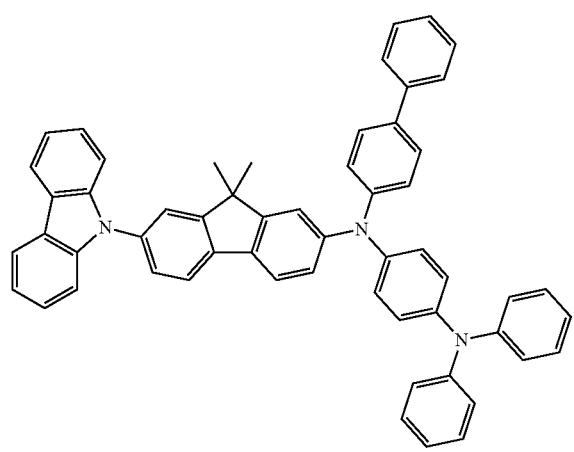
3-74
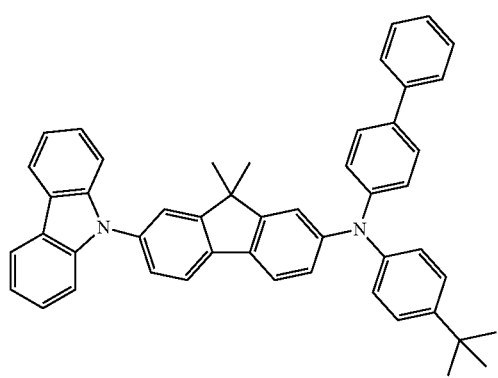

3-75
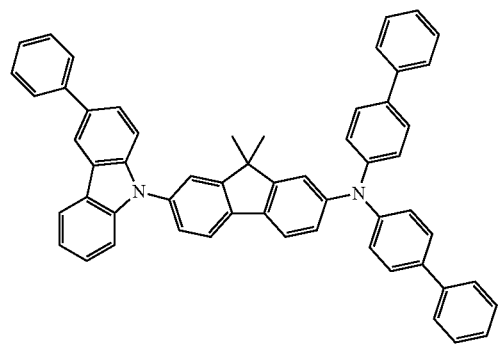
3-76
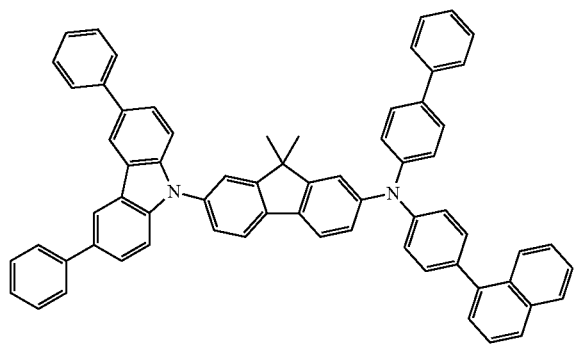
4-1
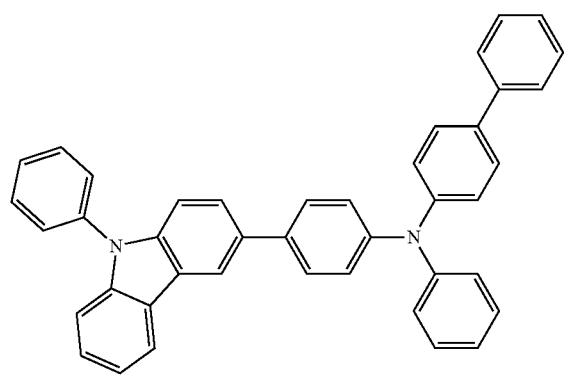
4-2
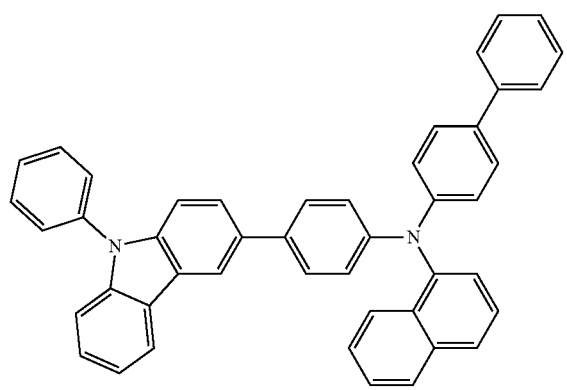
4-3
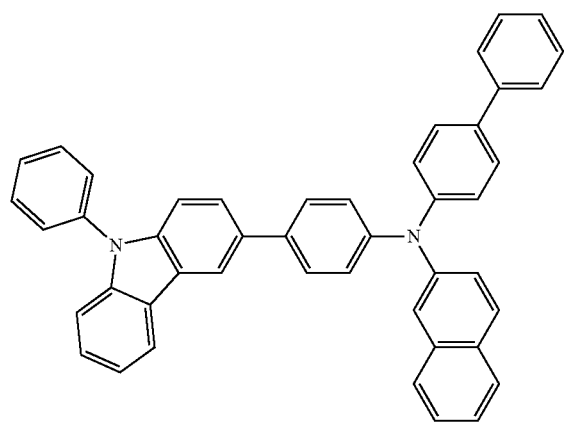
4-4
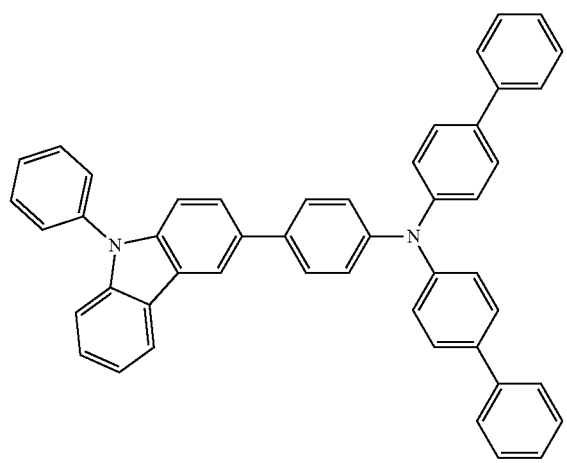

-continued
4-5
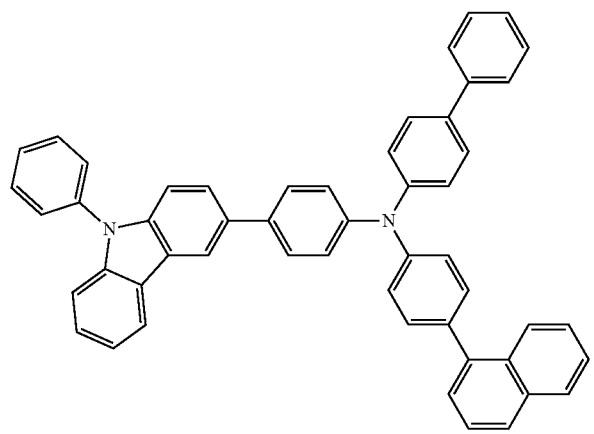
4-6
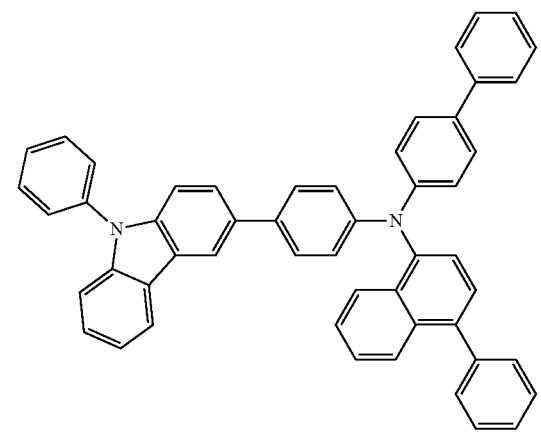
4-7
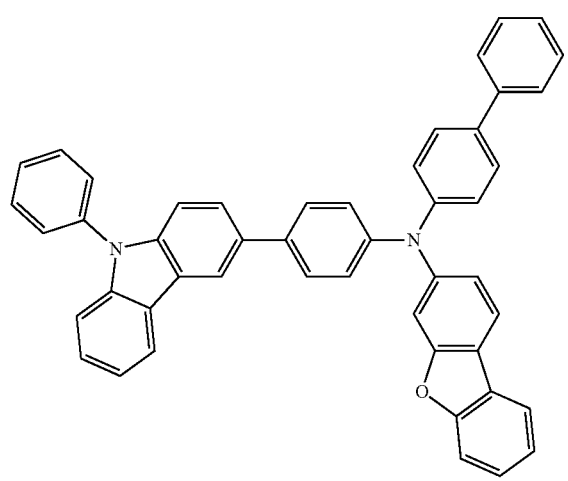
4-8
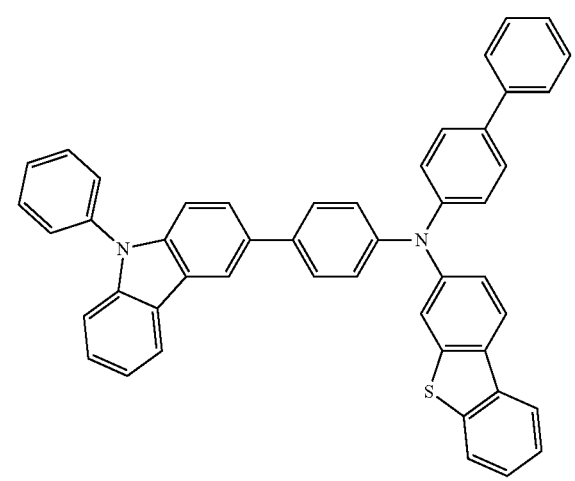
4-9
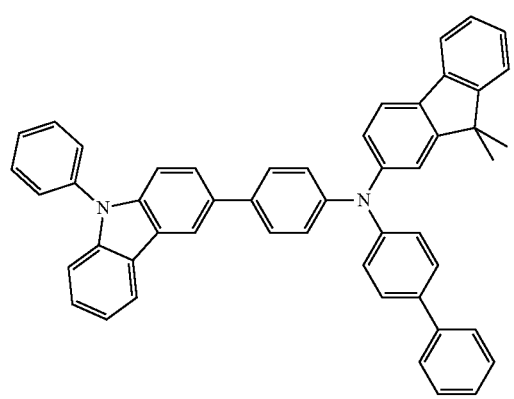
4-10
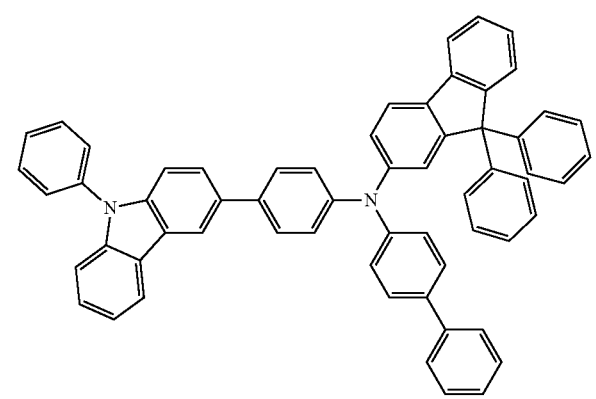

-continued
4-11
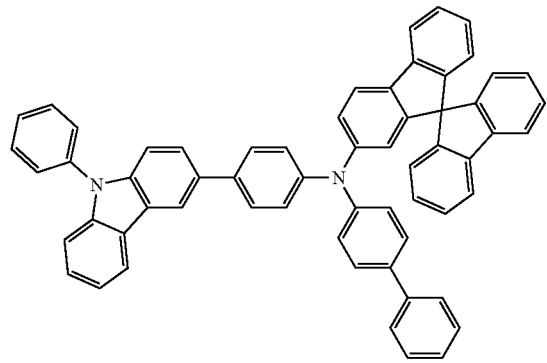
4-12
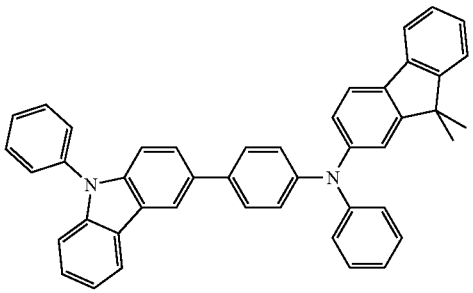
4-13
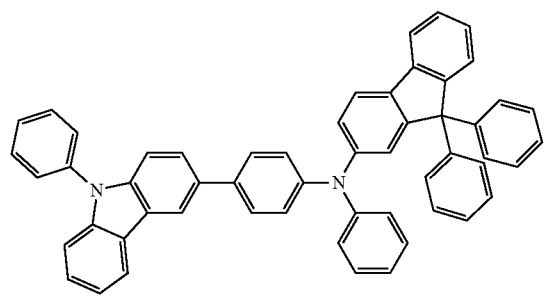
4-14
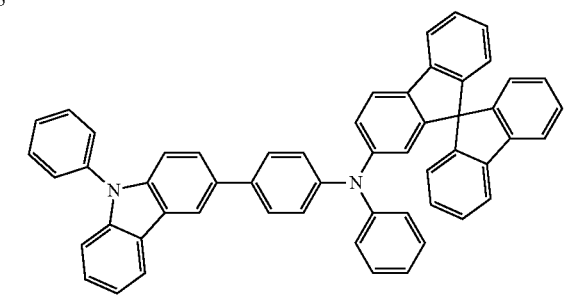
4-15
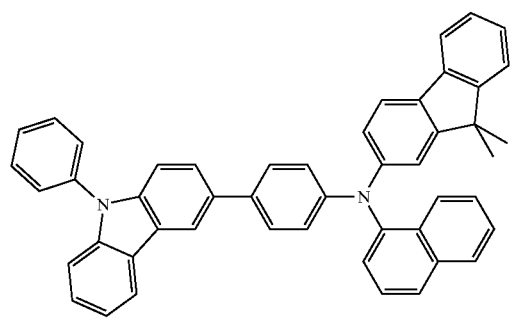
4-16
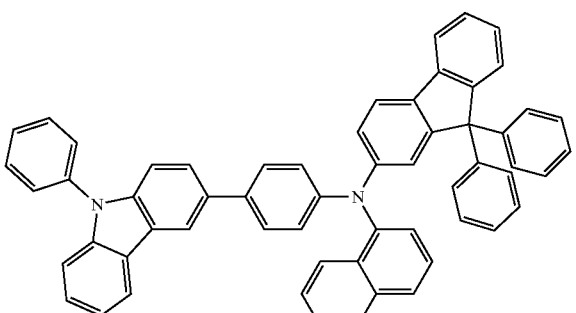
4-17
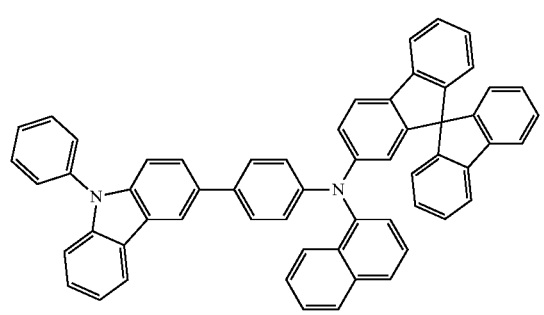
4-18
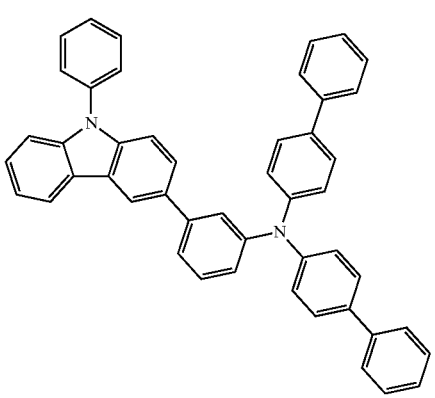

4-19
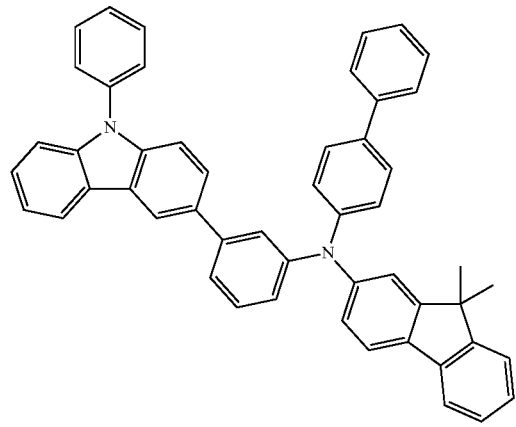
4-20
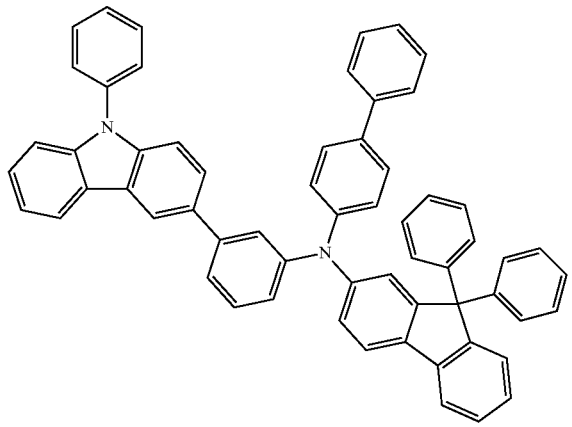
4-21
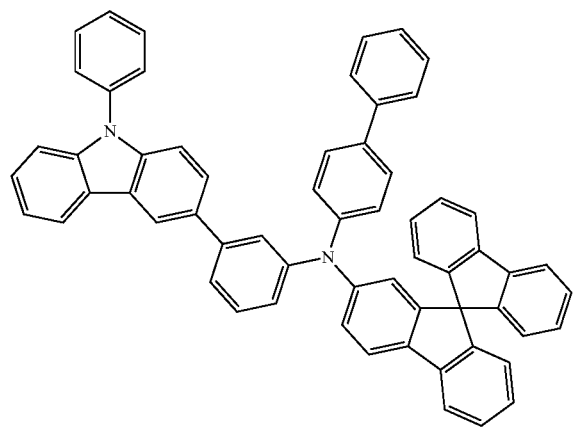
4-22
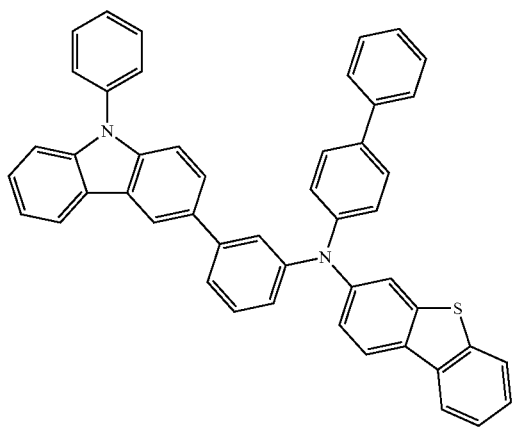
4-23
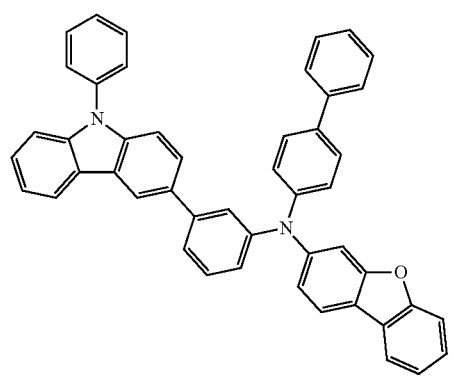
4-24
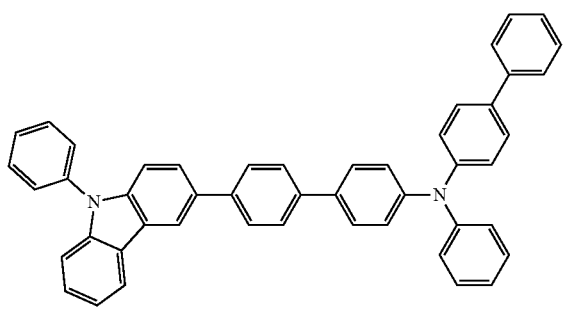
4-25
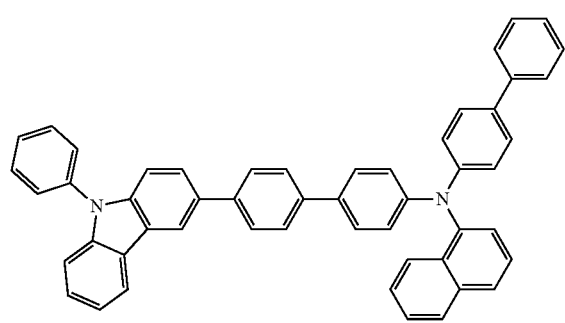
4-26
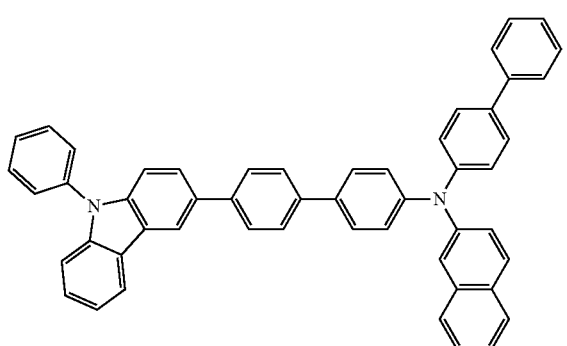

-continued
4-27
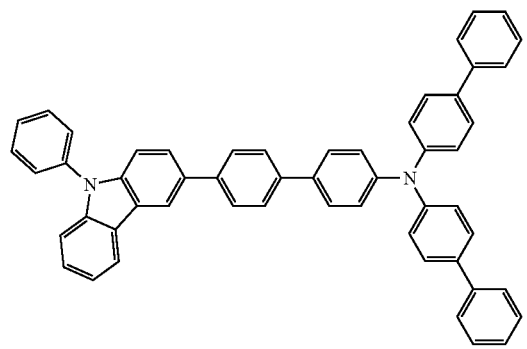
4-28
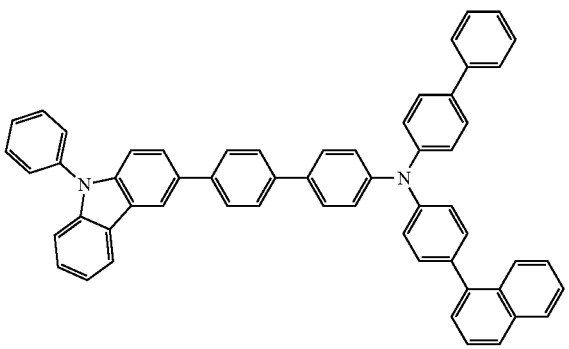
4-29
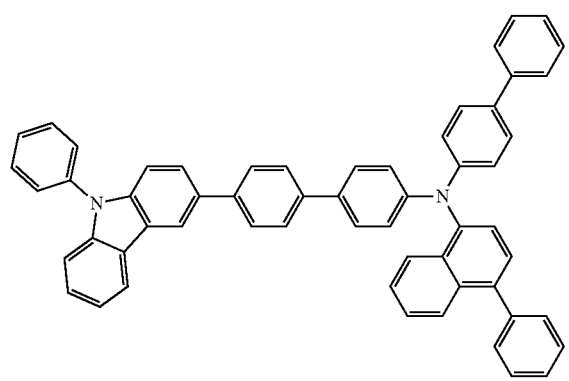
4-30
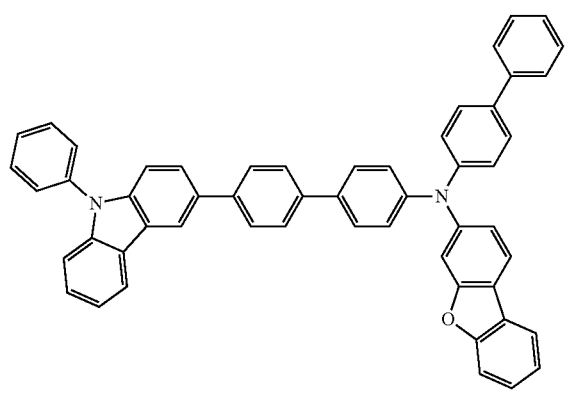
4-31
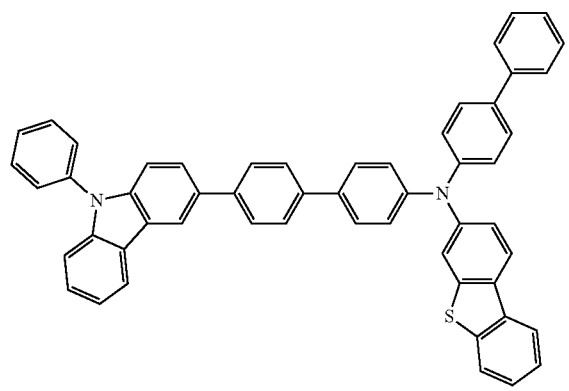
4-32
4-33
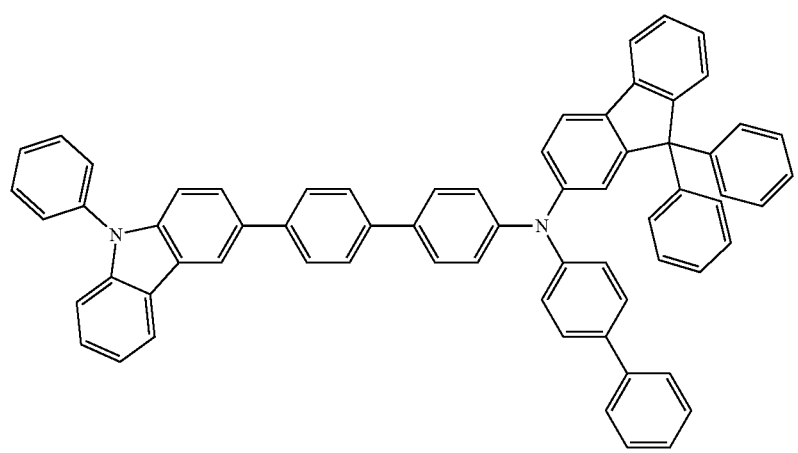

4-34
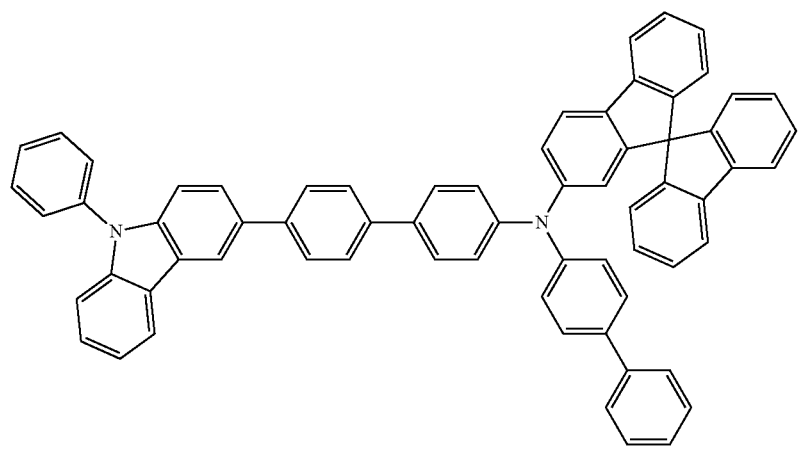
4-35
4-36
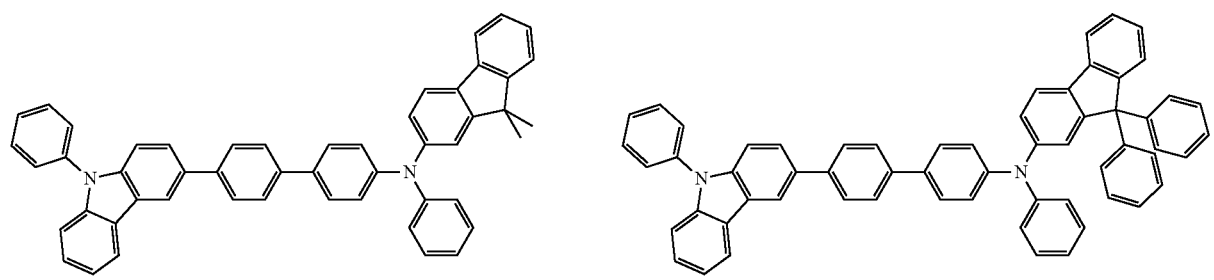
4-37
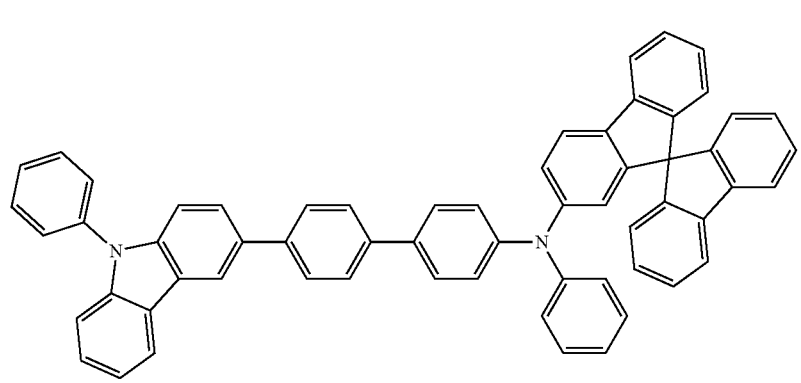
4-38
4-39
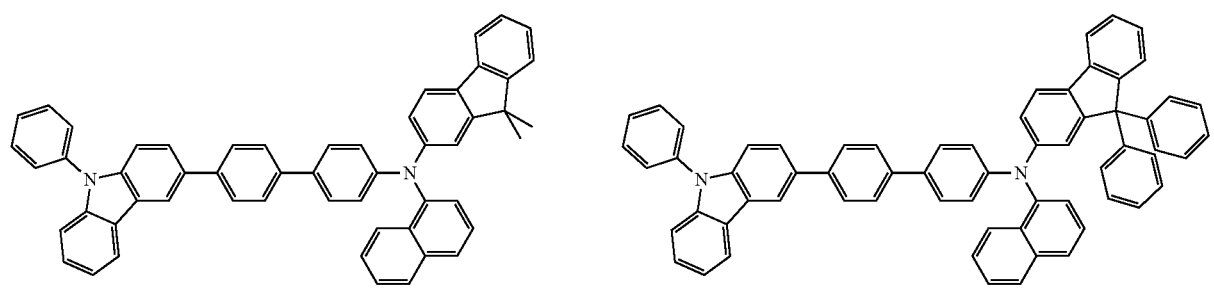

-continued
4-40
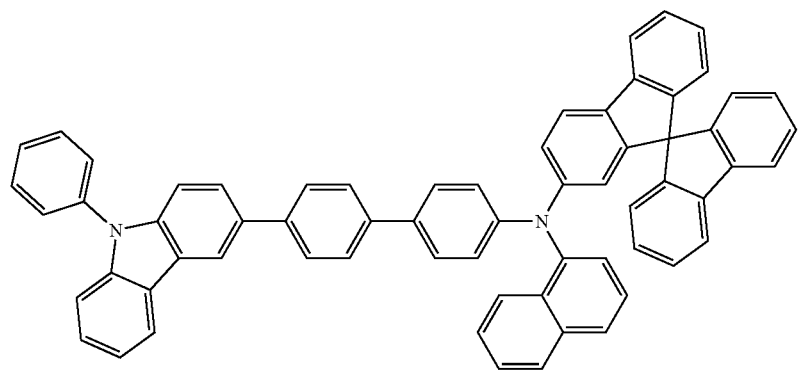
4-41 4-42
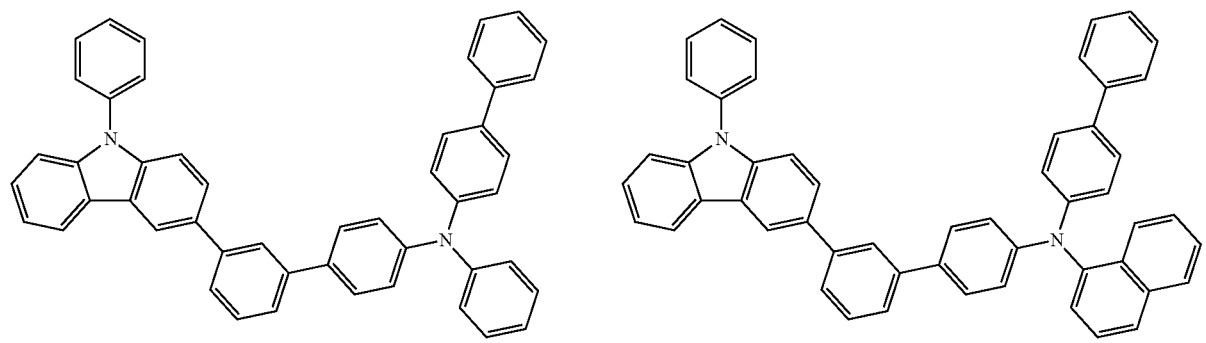
4-43 4-44
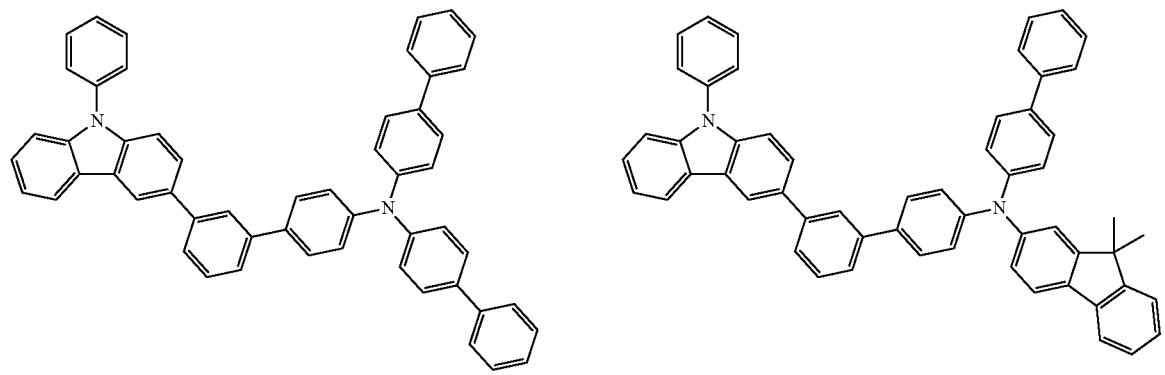
4-45 4-46
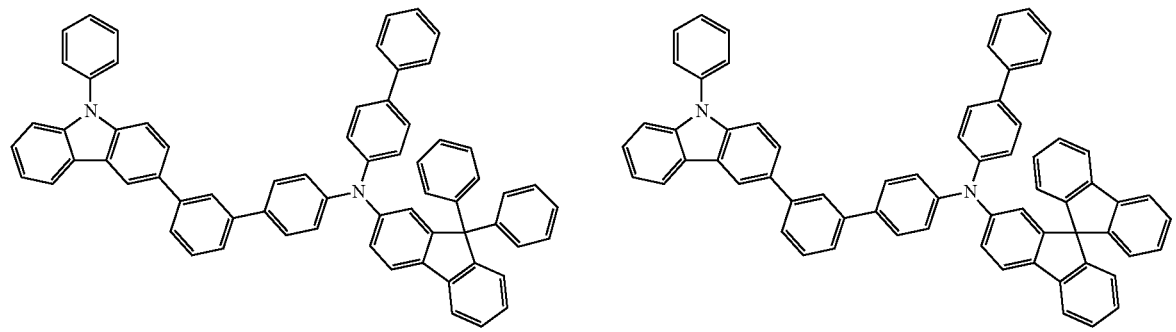

-continued
4-47
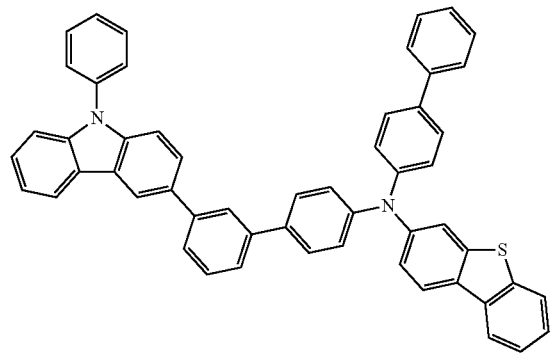
4-48
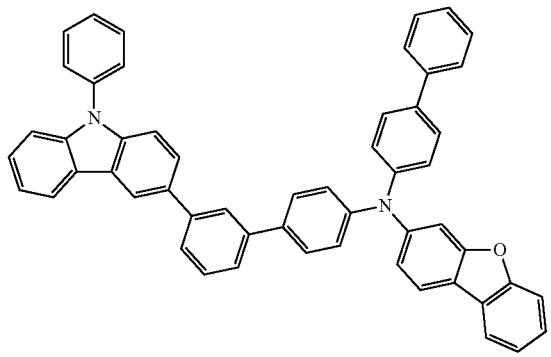
4-49
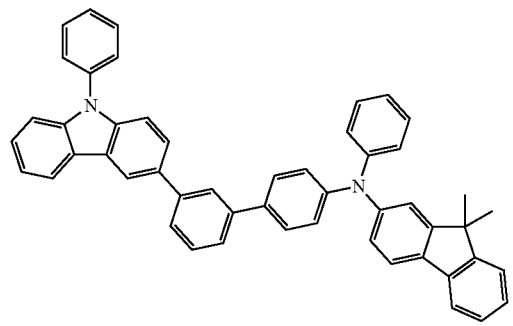
4-50
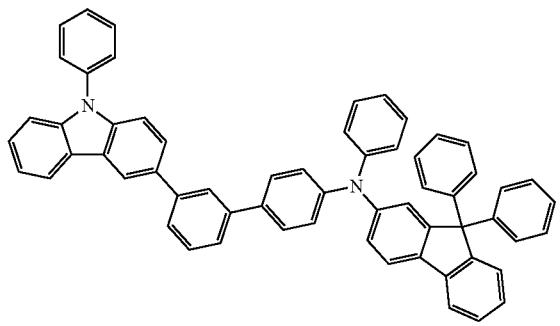
4-51
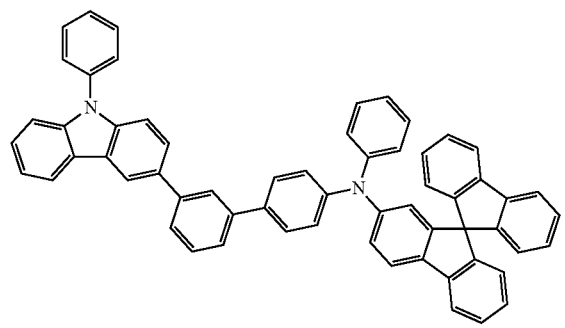
4-52
4-53
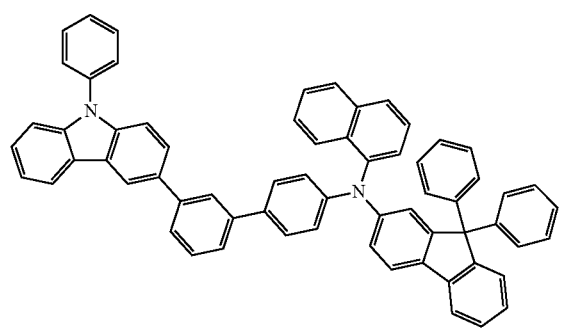
4-54
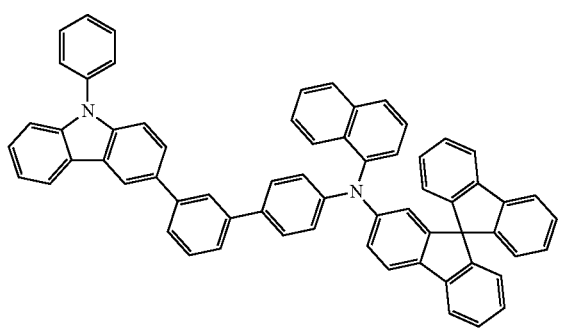

-continued
4-55
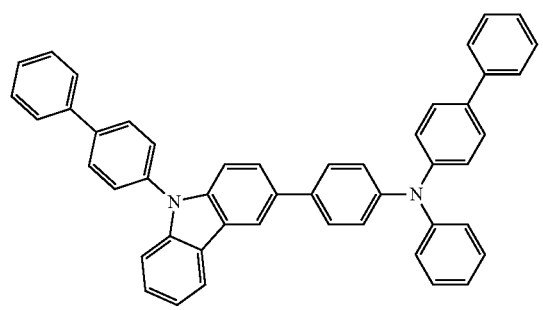
4-56
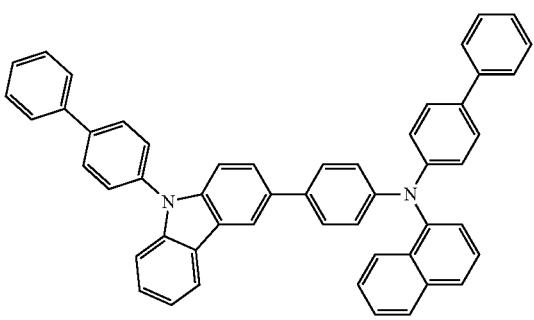
4-57
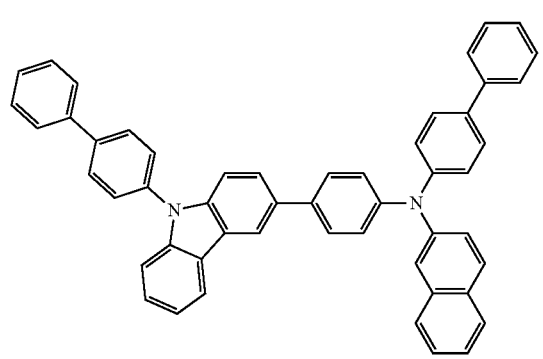
4-58
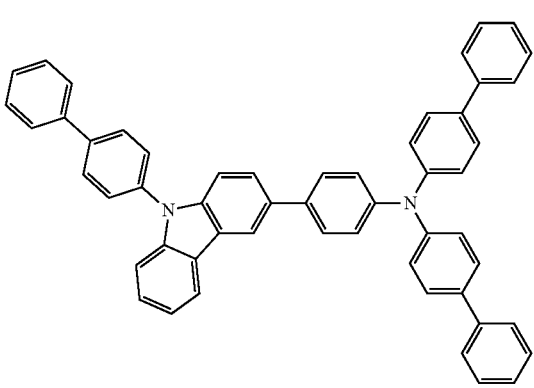
4-59
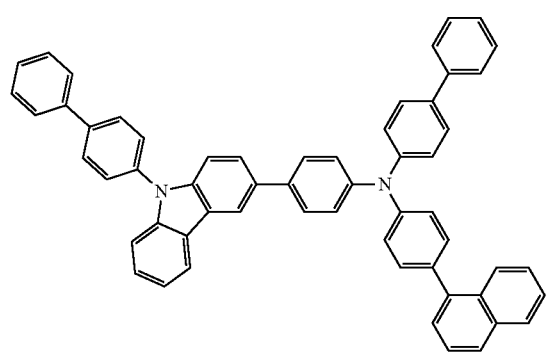
4-60
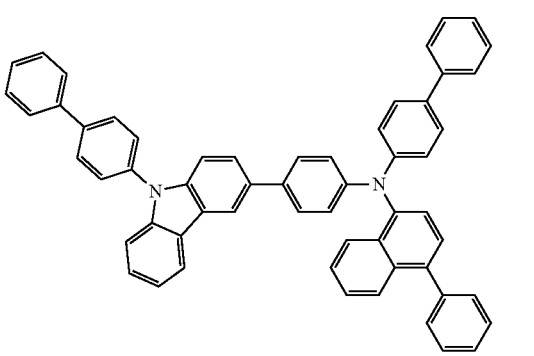
4-61
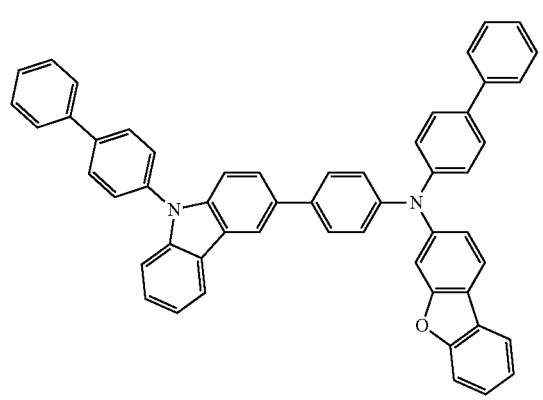
4-62
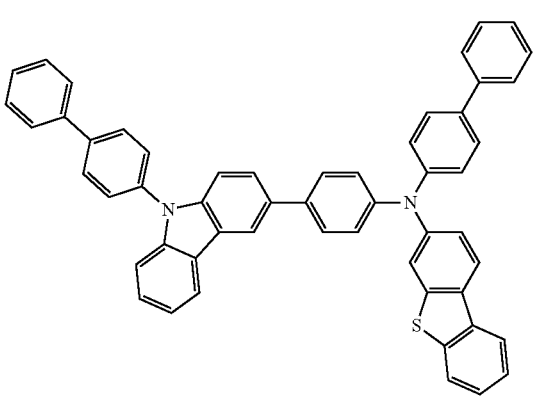

-continued
4-63
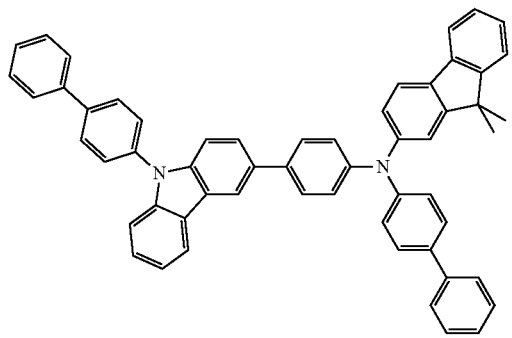
4-64
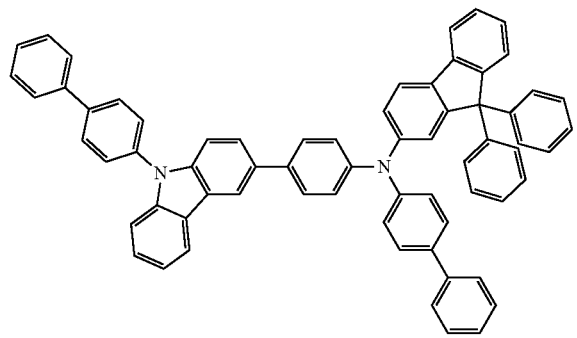
4-65
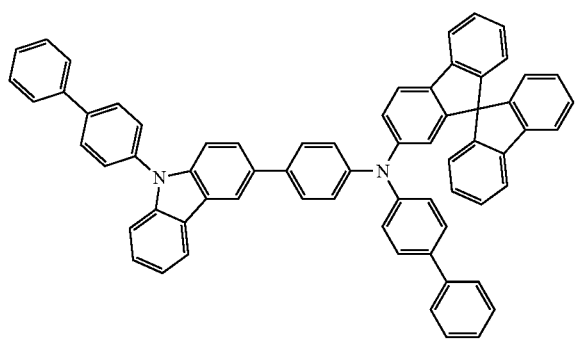
4-66
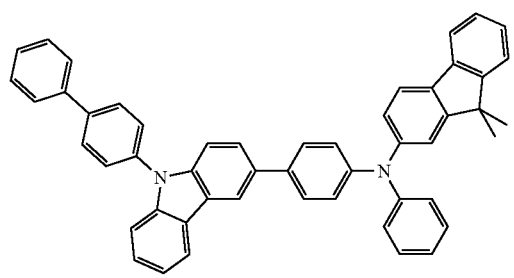
4-67
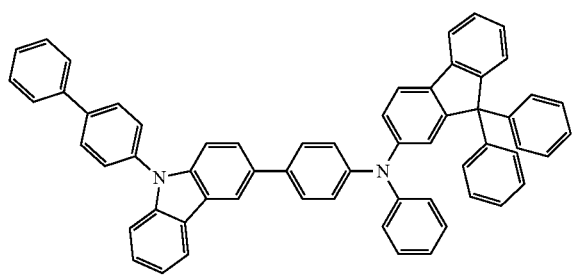
4-68
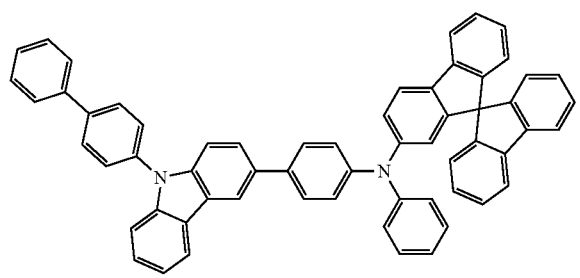
4-69
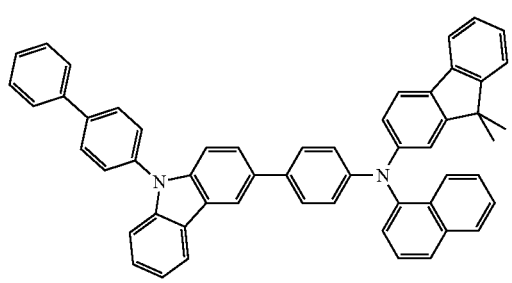
4-70
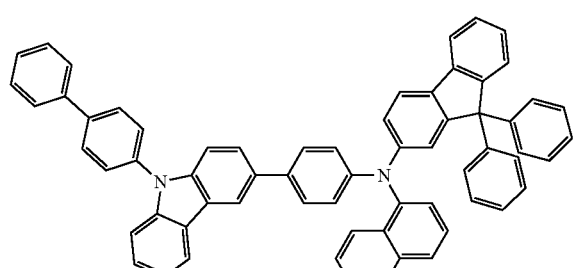

-continued
4-71
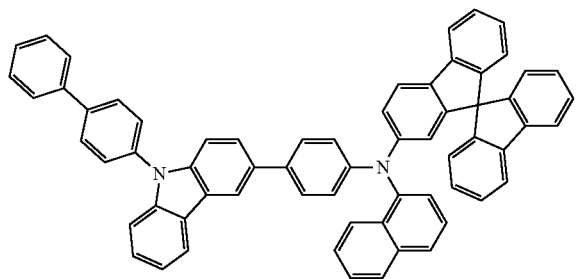
4-72
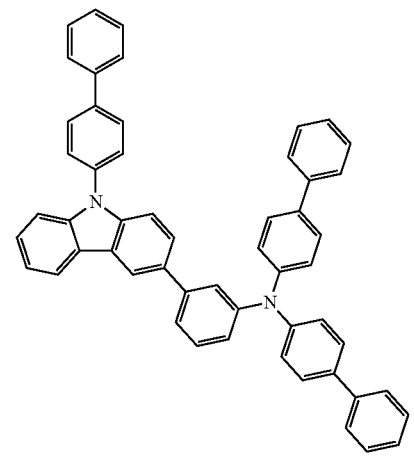
4-73
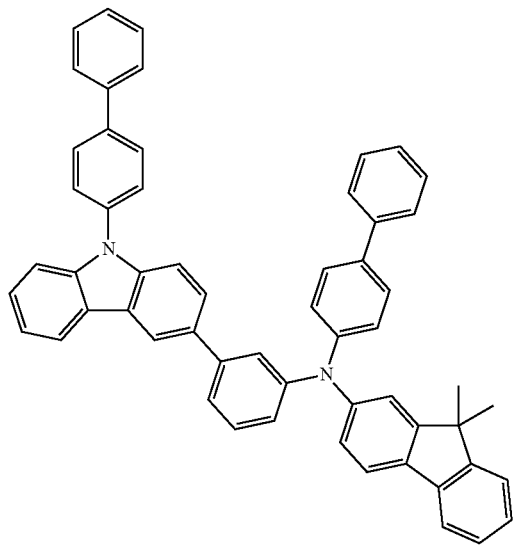
4-74
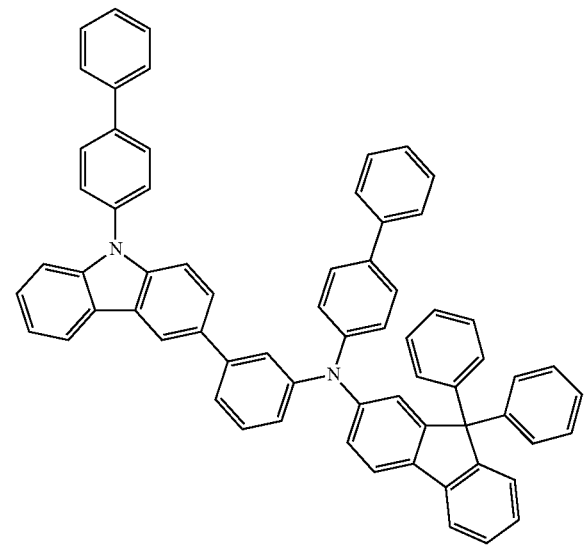
4-75
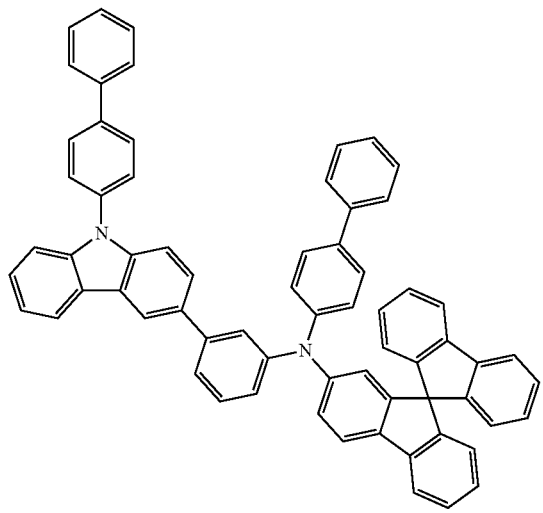
4-76
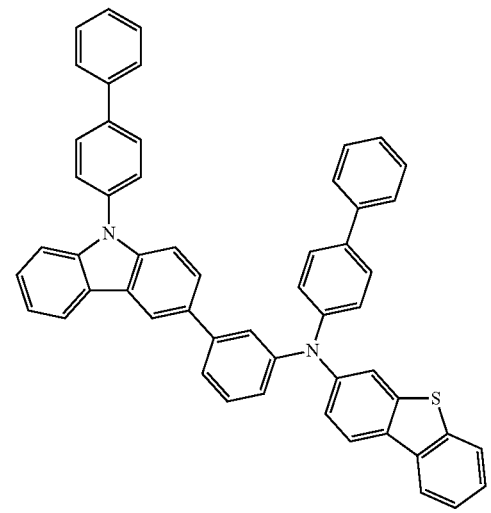

-continued
4-77
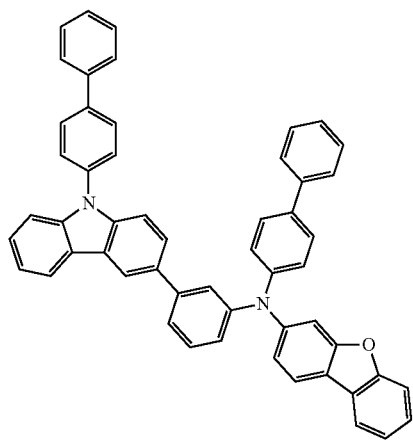
4-78
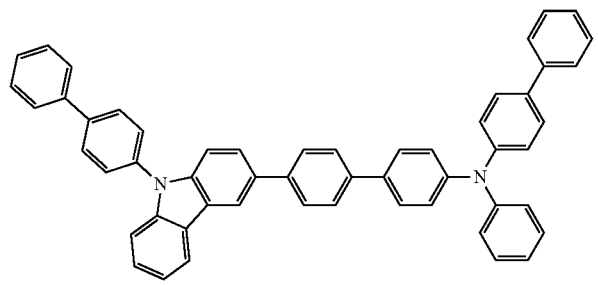
4-79
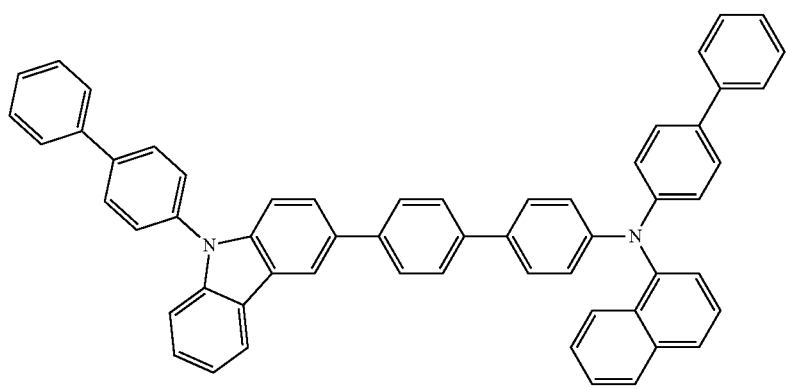
4-80
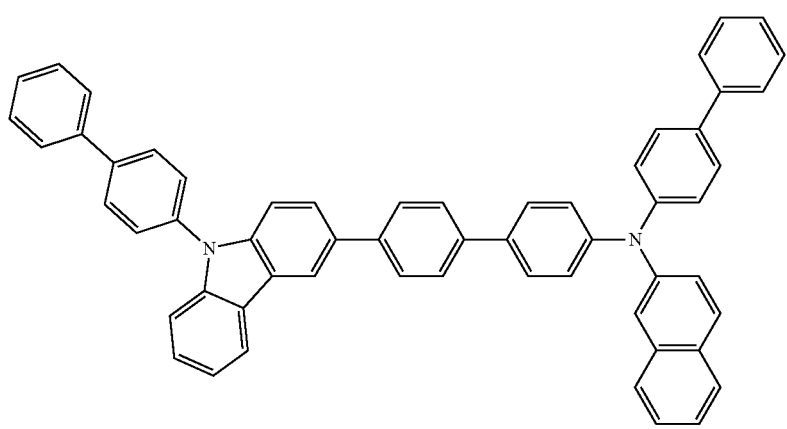

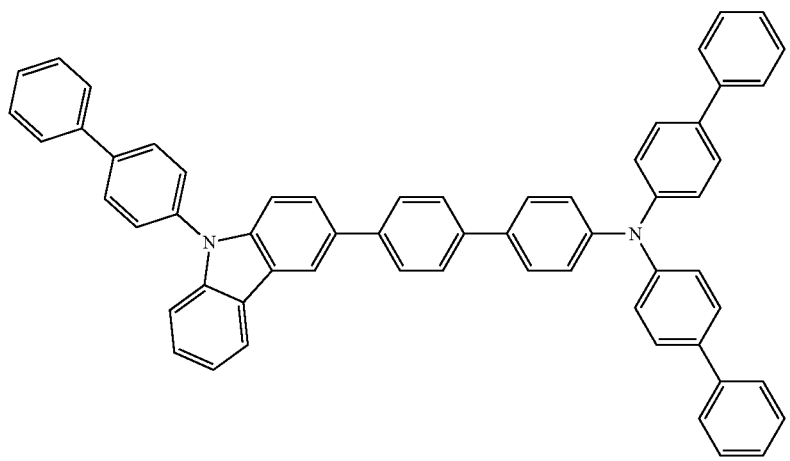
4-81
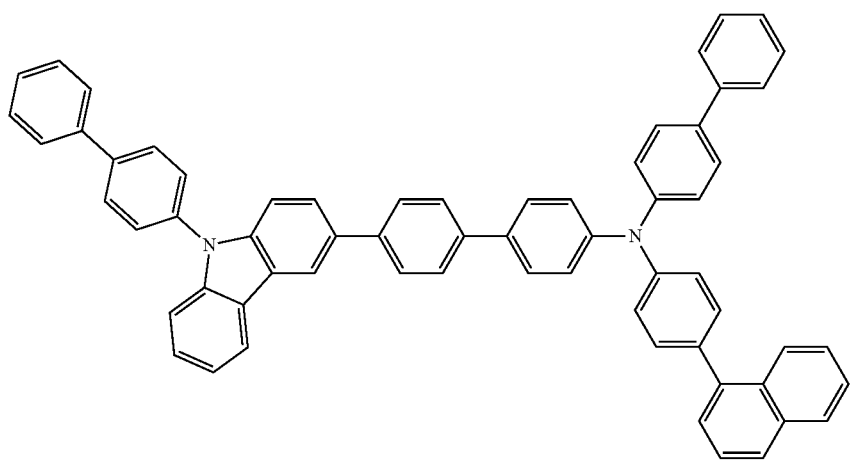
4-82
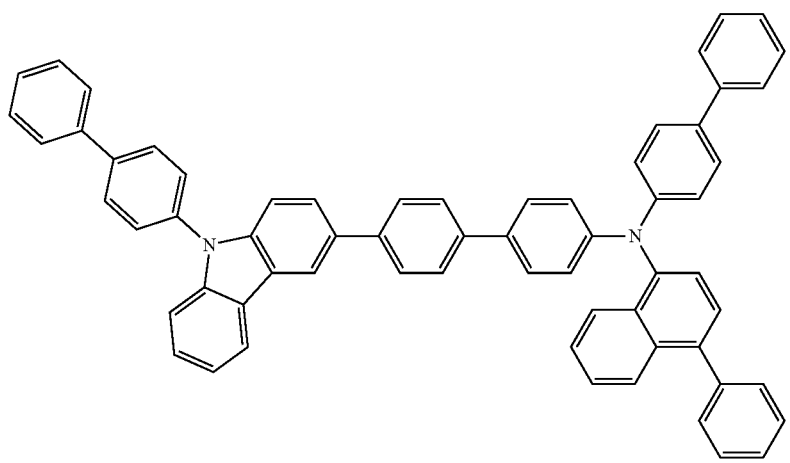
4-83

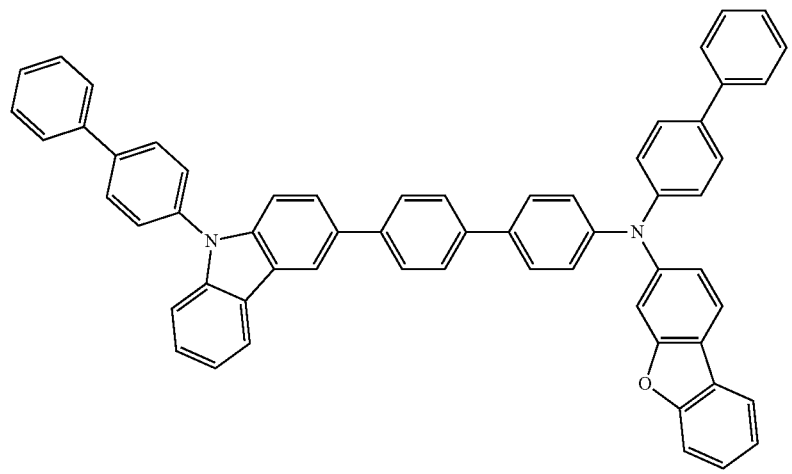
4-84
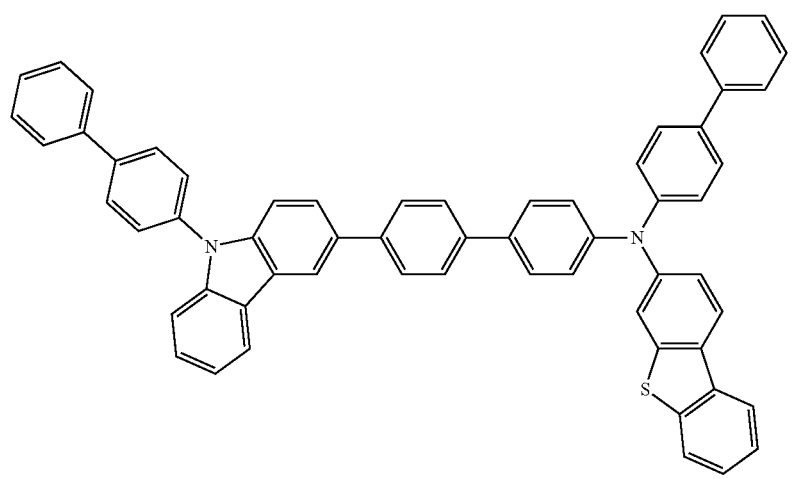
4-85
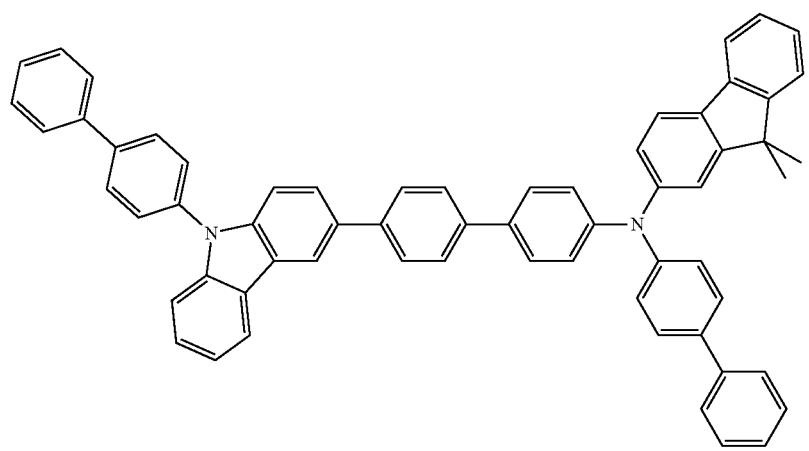
4-86

-continued
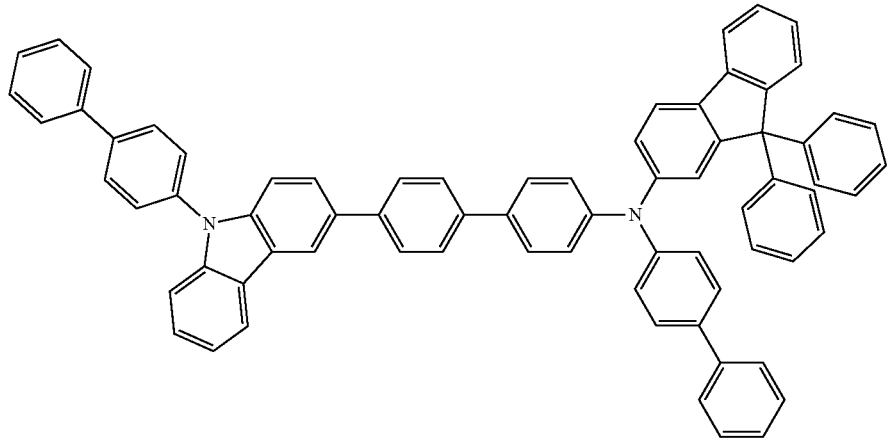
4-87
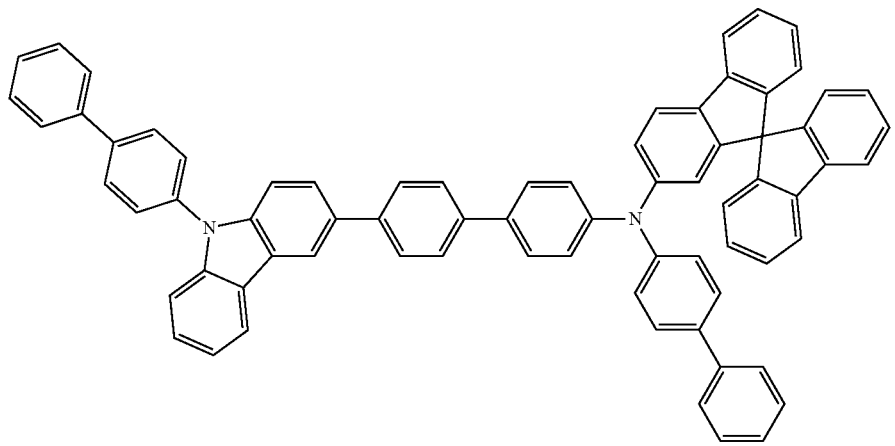
4-88
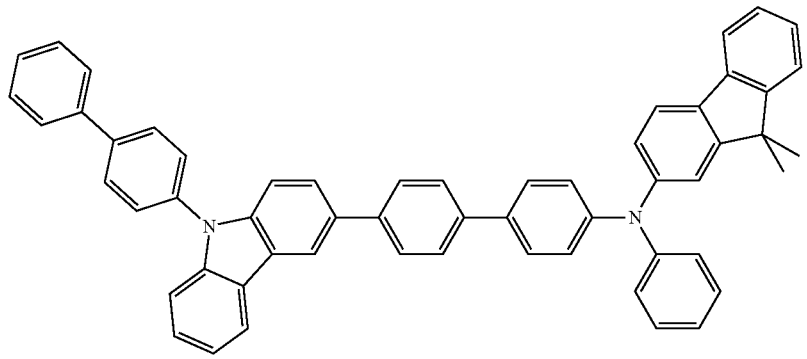
4-89
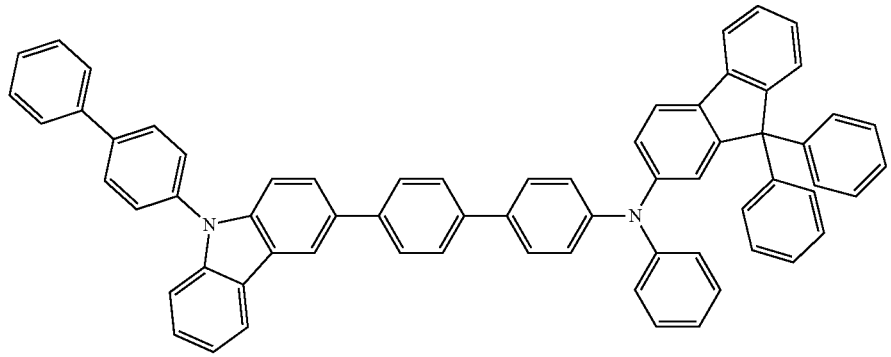
4-90

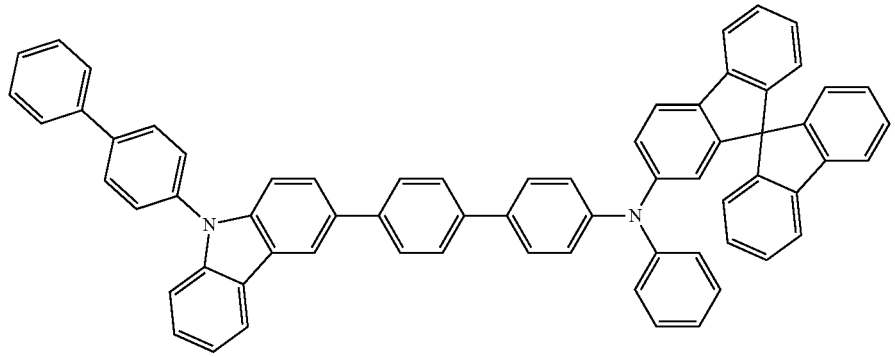
4-91
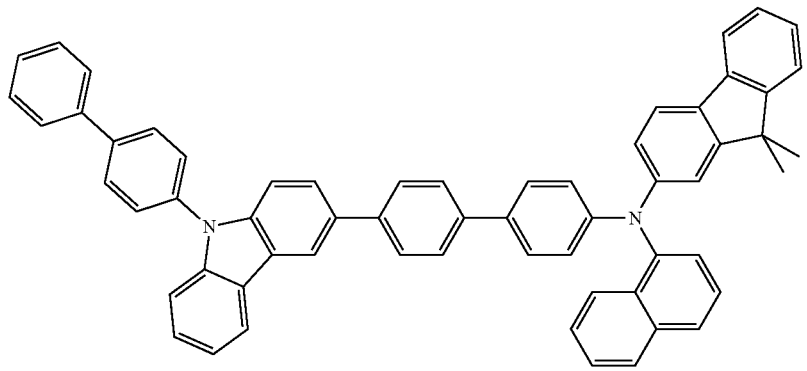
4-92
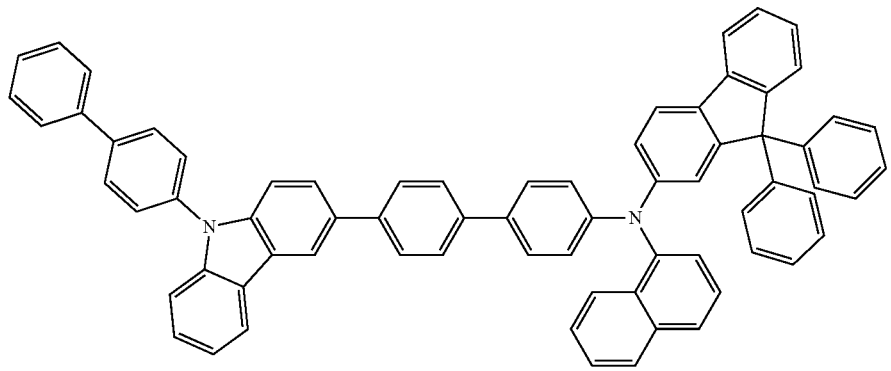
4-93
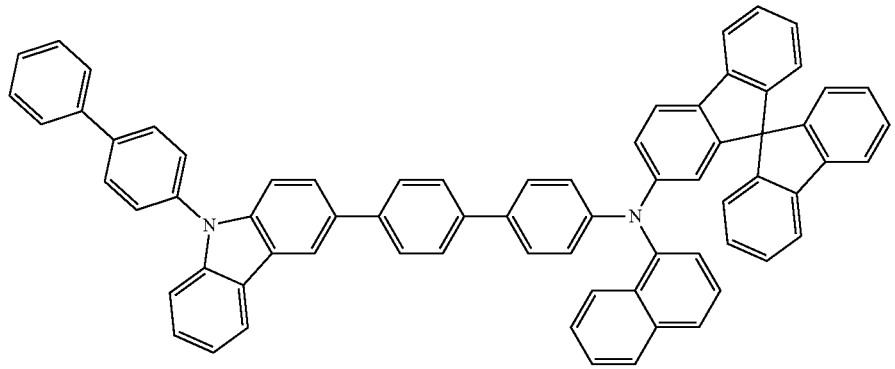
4-94

-continued
4-95
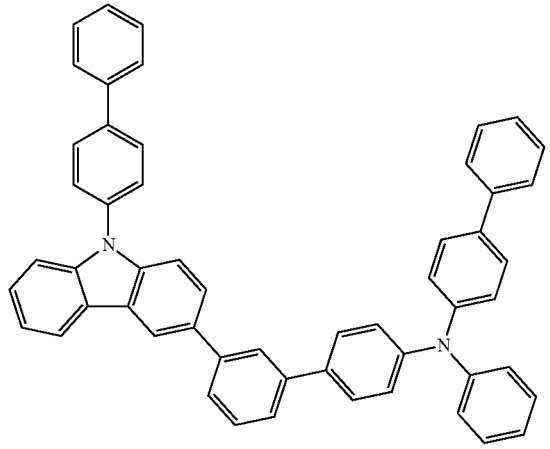
4-96
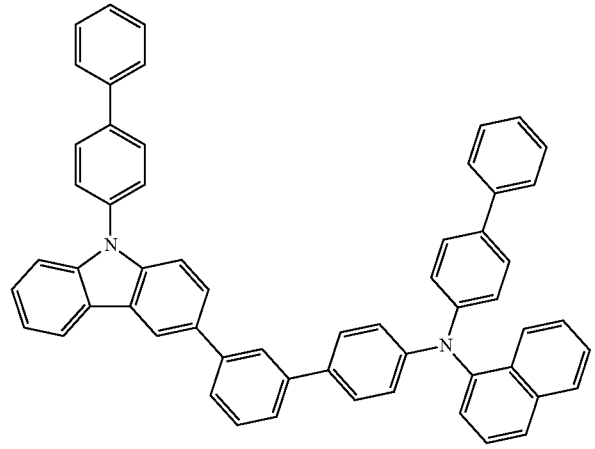
4-97
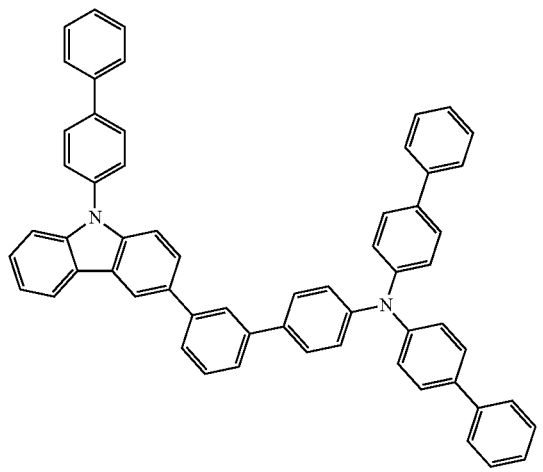
4-98
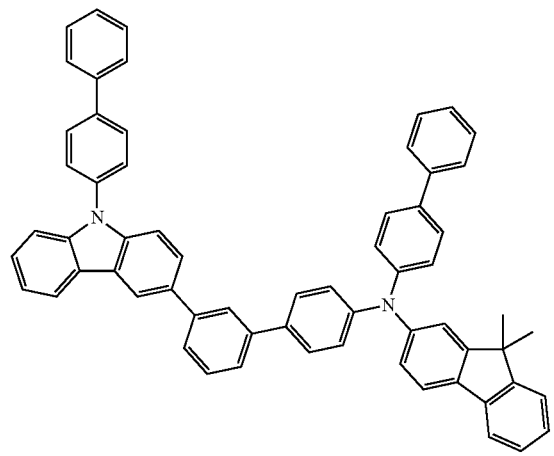
4-99
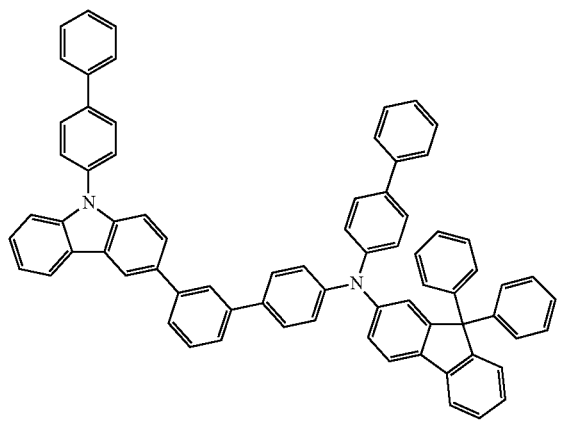
4-100
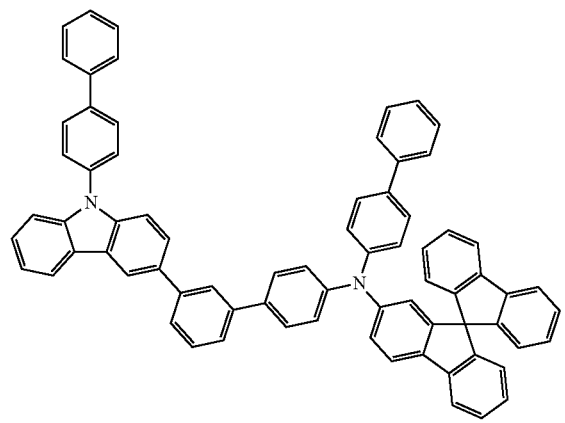

-continued
4-101
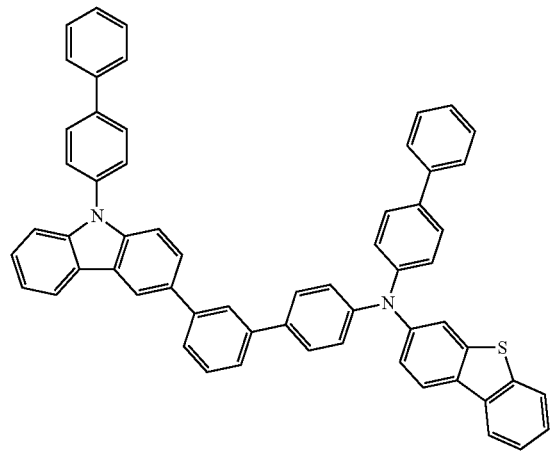
4-102
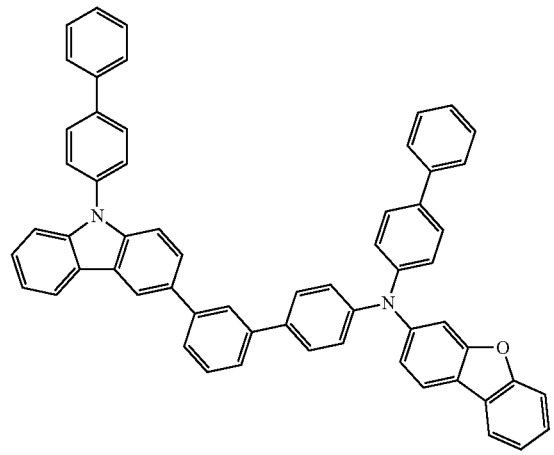
4-103
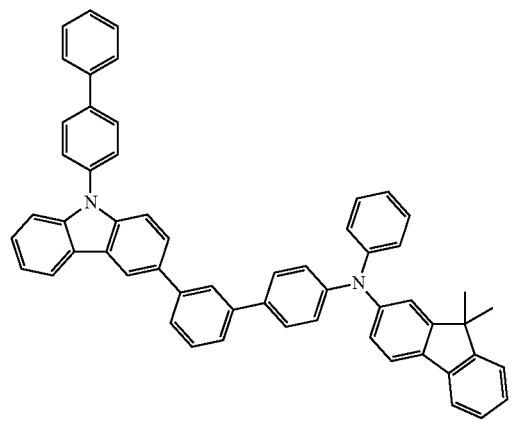
4-104
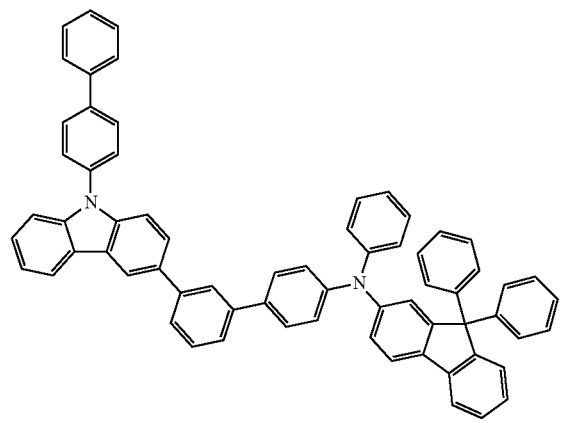
4-105
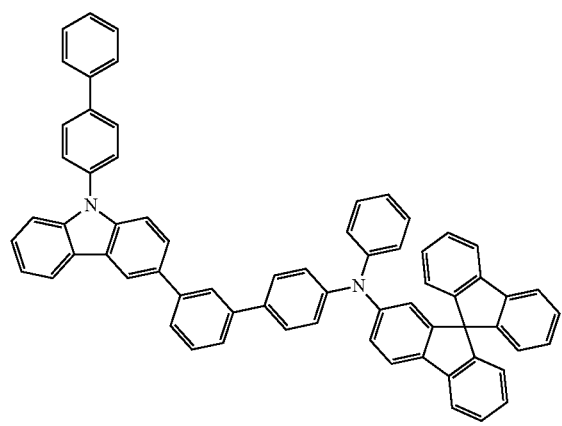
4-106
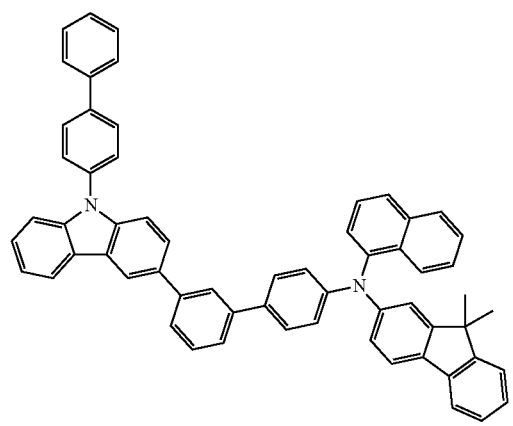

-continued
4-107
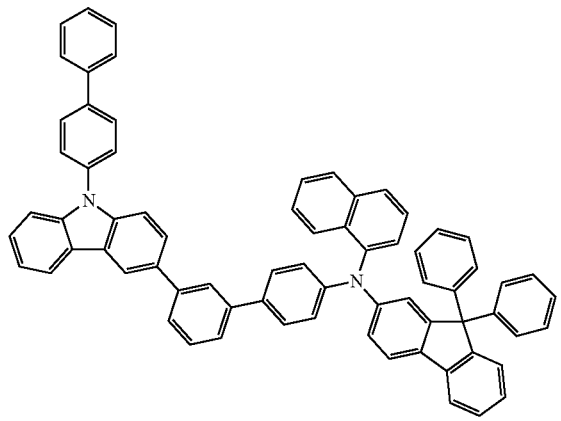
4-108
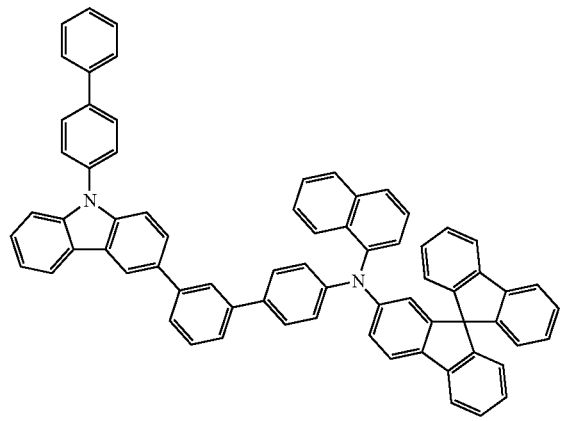
5-1
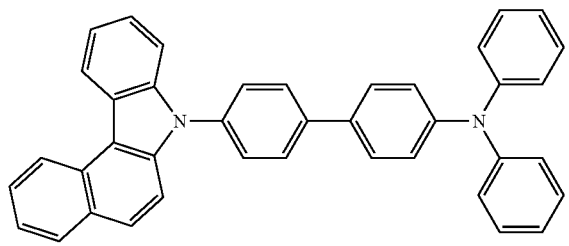
5-2
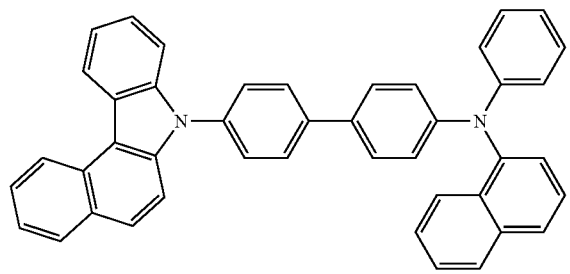
5-3
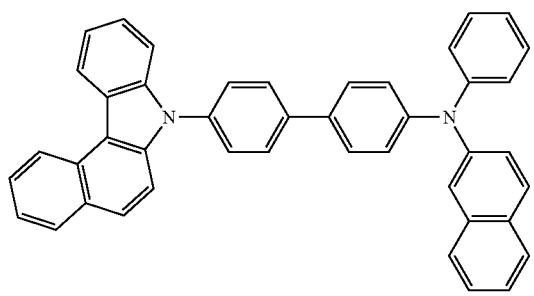
5-4
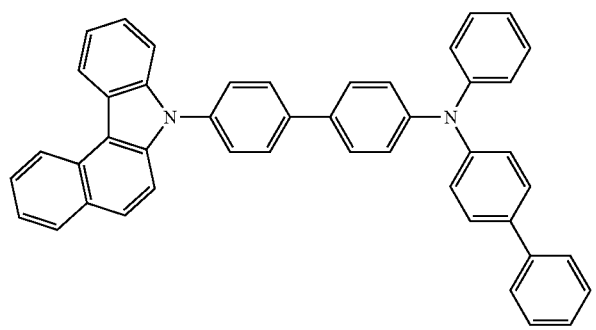
5-5
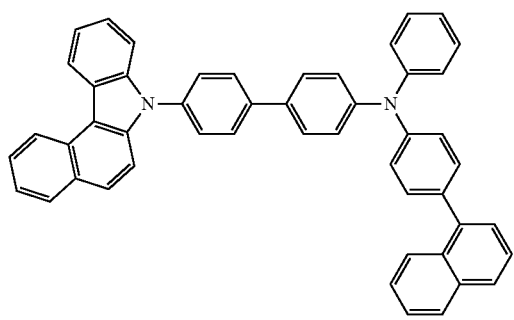
5-6
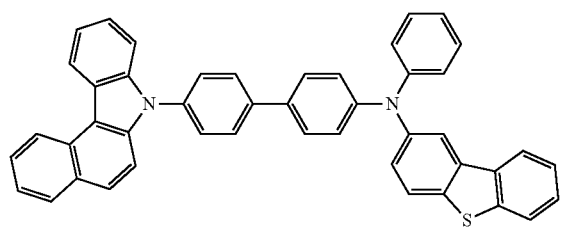

-continued
5-7
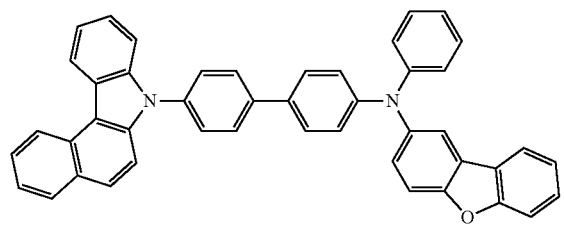
5-8
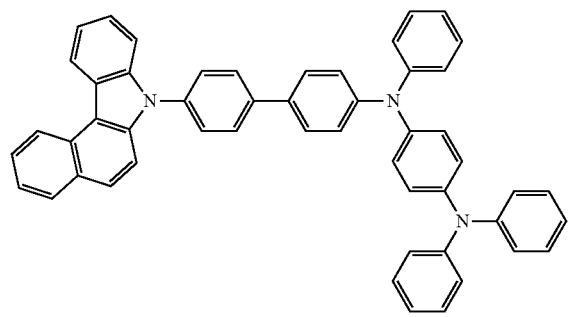
5-9
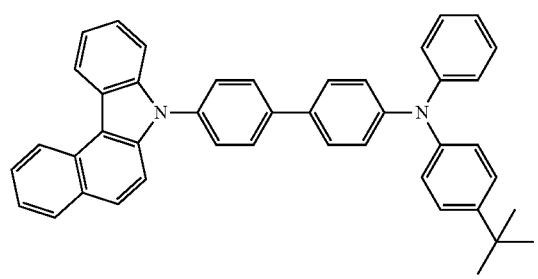
5-10
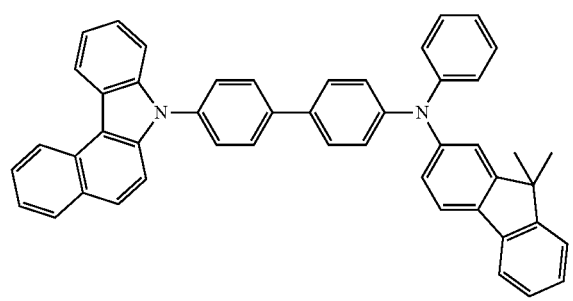
5-11
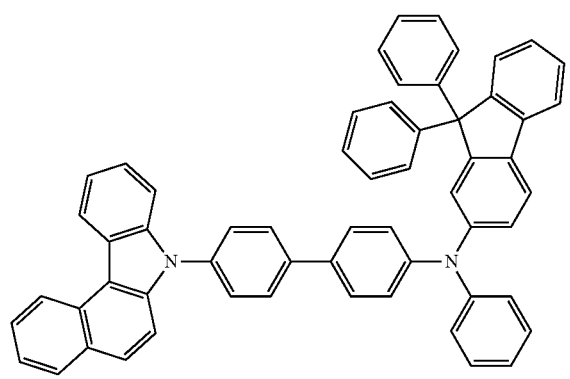
5-12
5-13
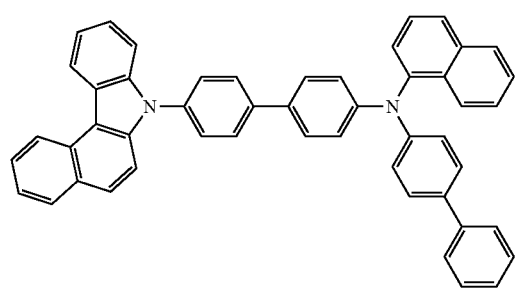
5-14
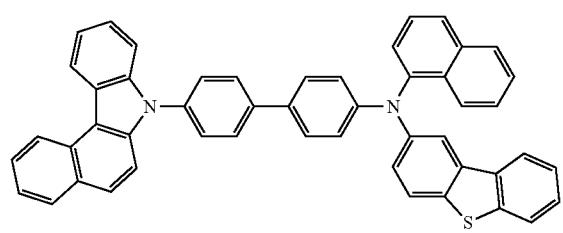

-continued
5-15
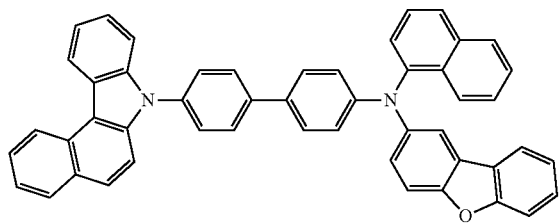
5-16
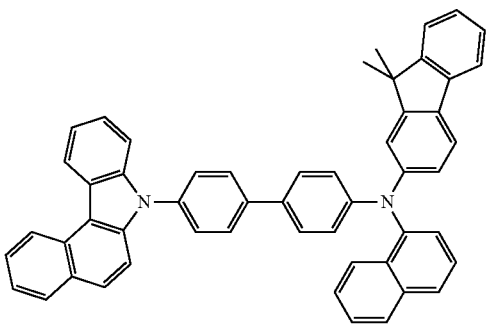
5-17
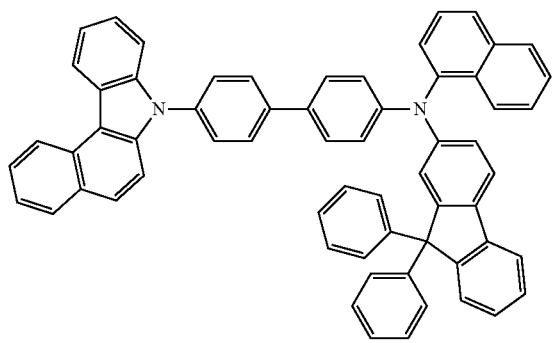
5-18
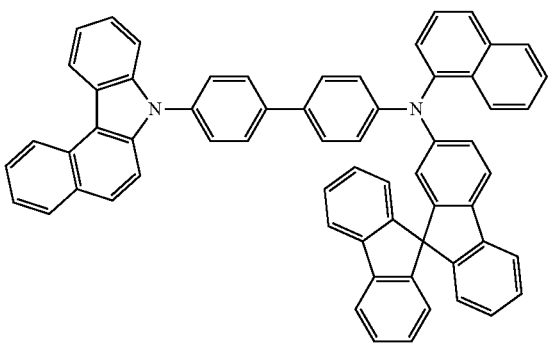
5-19
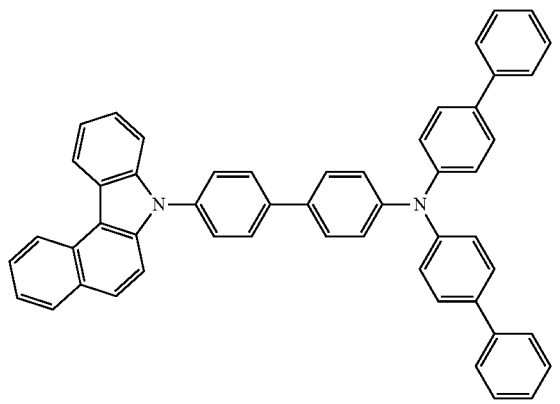
5-20
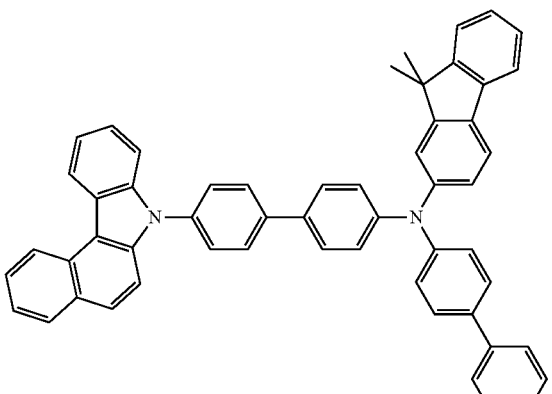
5-21
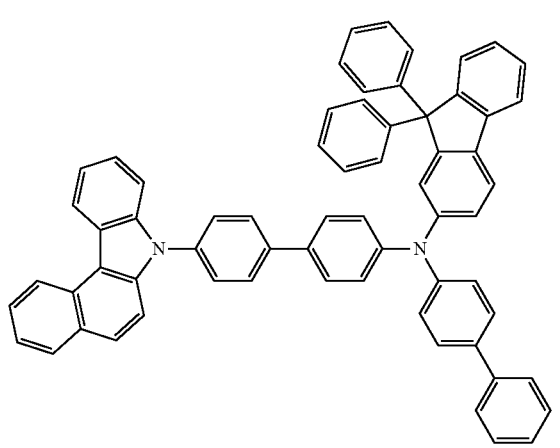
5-22
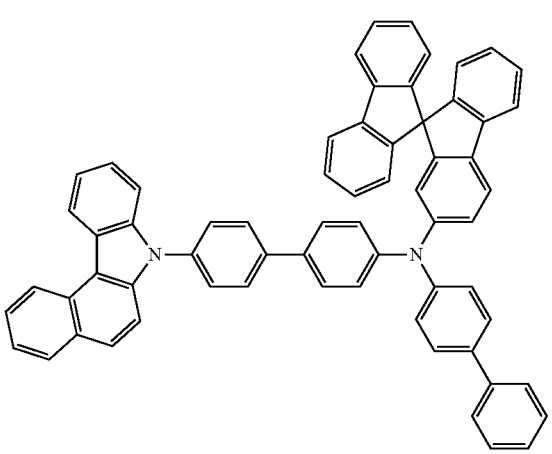

-continued
| 5-23 | 5-24 |
|---|---|
| 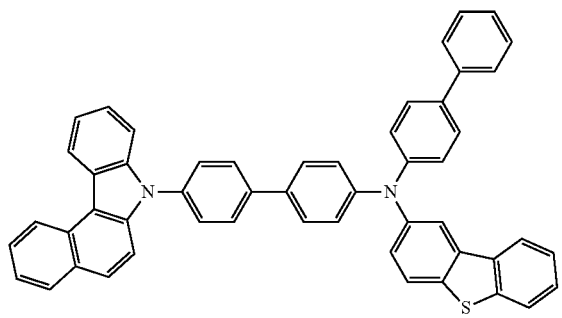 | 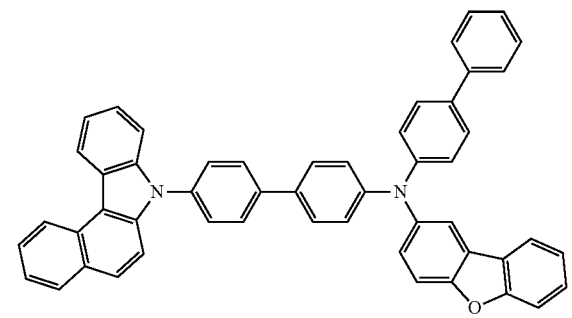 |
| 5-25 | 5-26 |
| 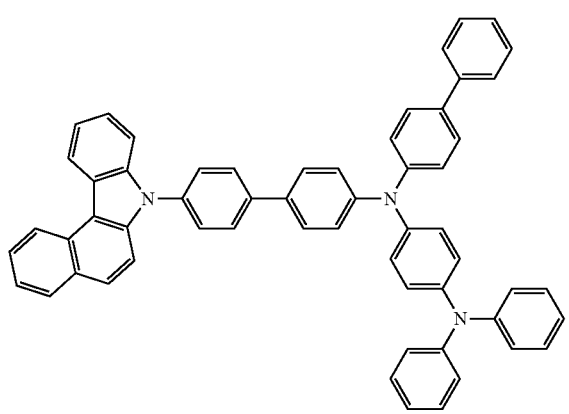 | 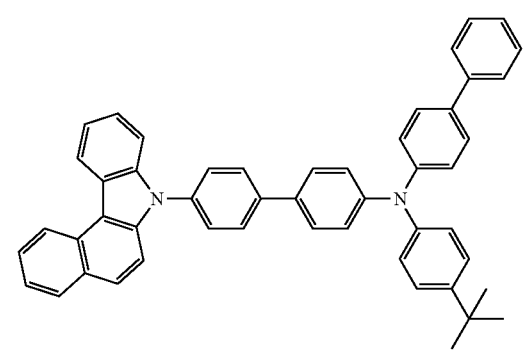 |
| 5-27 | 5-28 |
| 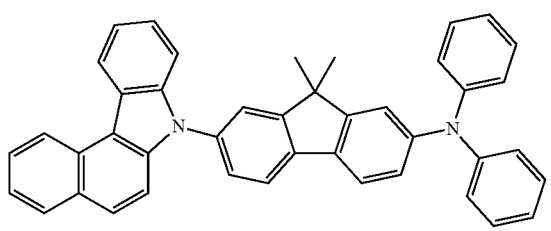 | 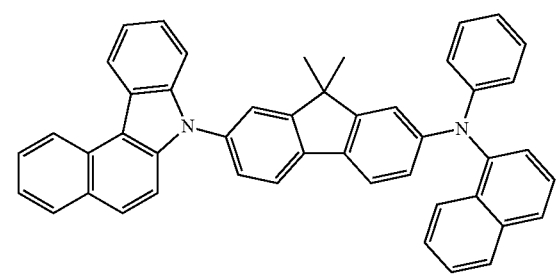 |
| 5-29 | 5-30 |
| 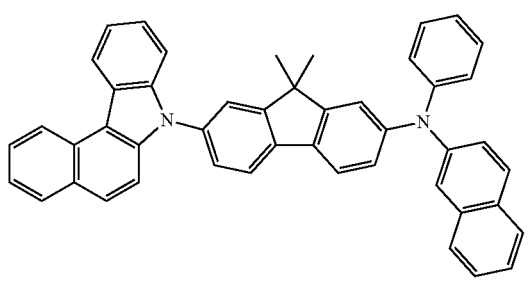 | 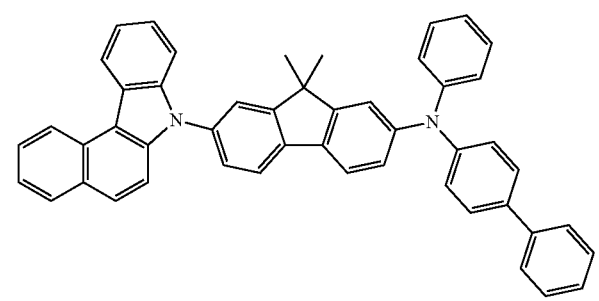 |

5-31
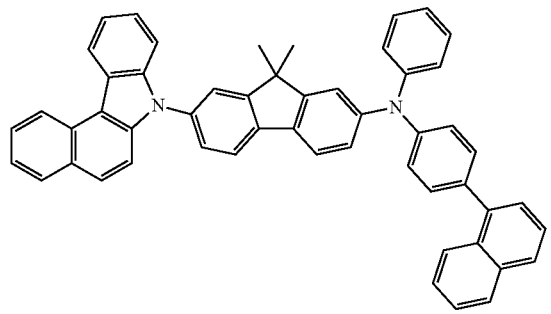
5-32
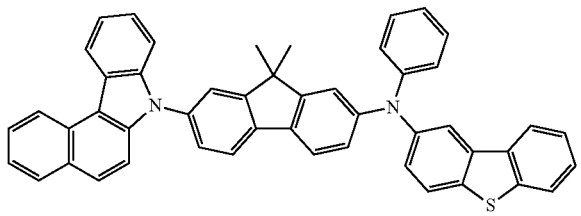
5-33
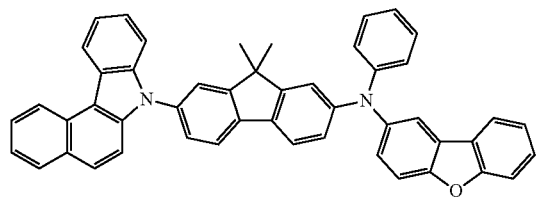
5-34
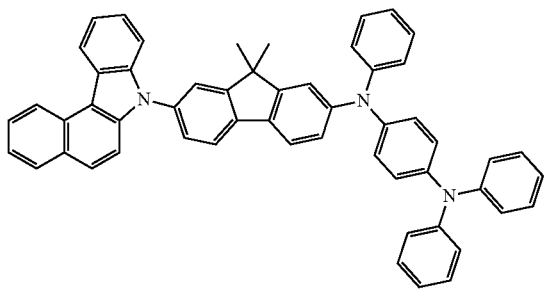
5-35
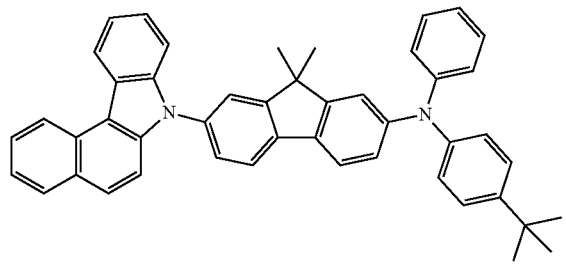
5-36
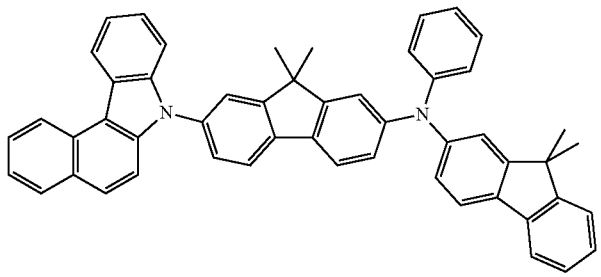
5-37
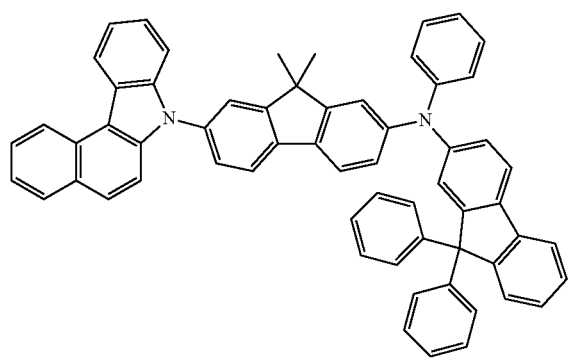
5-38
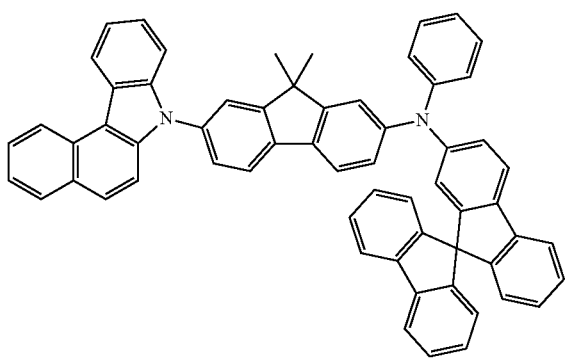
5-39
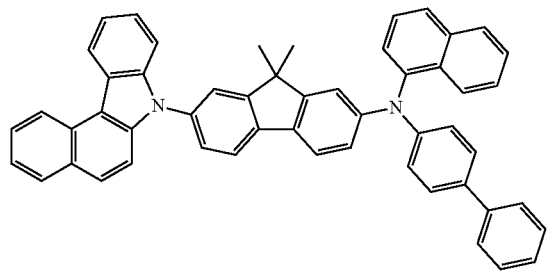
5-40
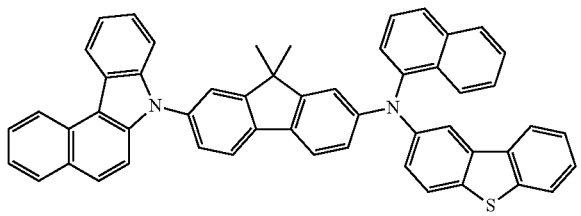

-continued
| 5-41 | 5-42 |
|---|---|
| 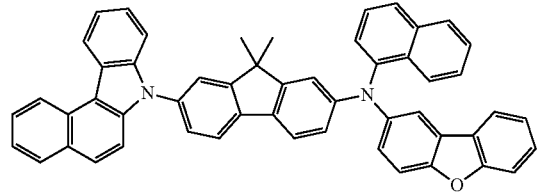 | 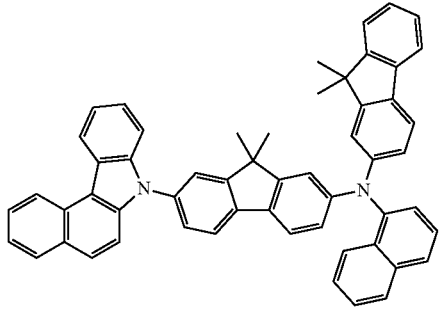 |
| 5-43 | 5-44 |
| 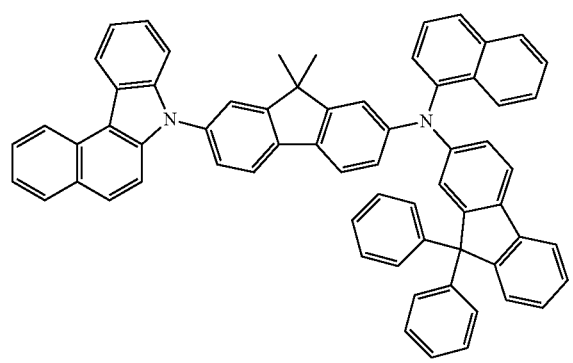 | 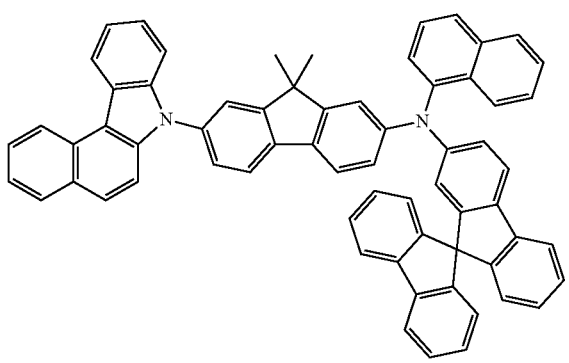 |
| 5-45 | 5-46 |
| 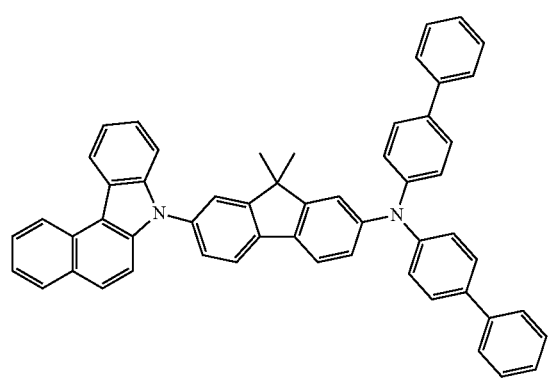 | 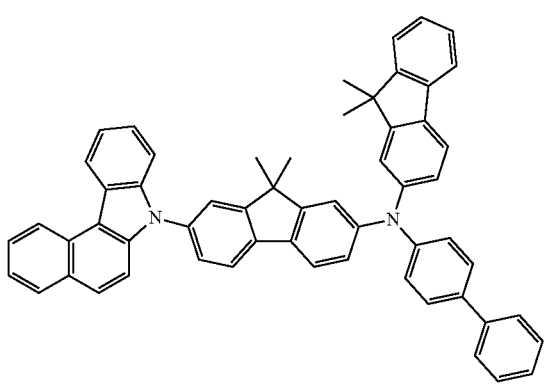 |
| 5-47 | 5-48 |
| 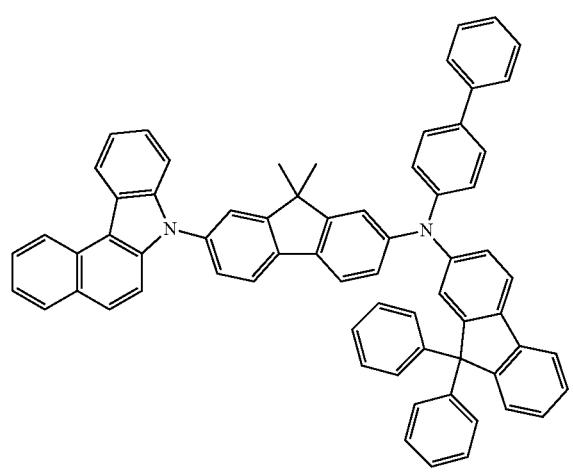 | 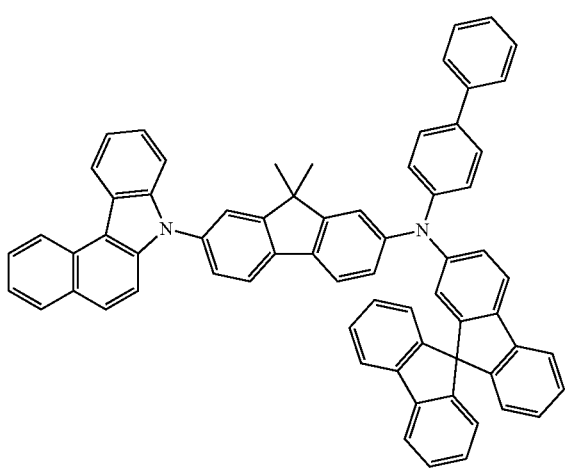 |

-continued
5-49
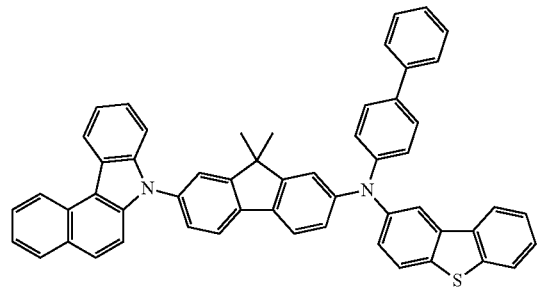
5-50
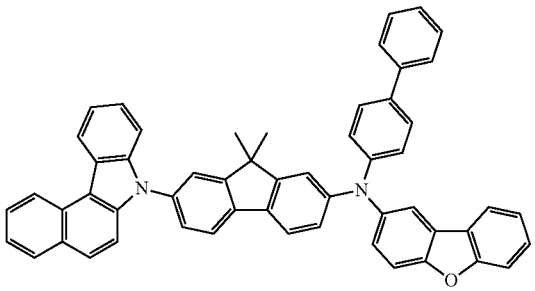
5-51
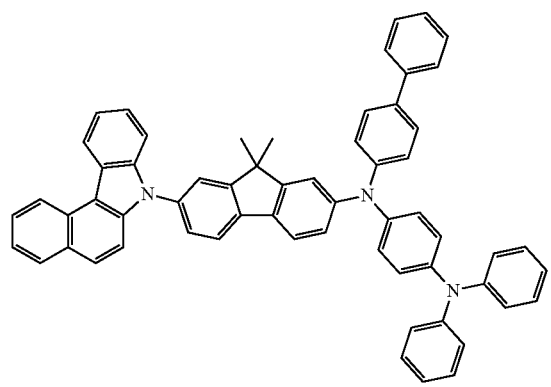
5-52
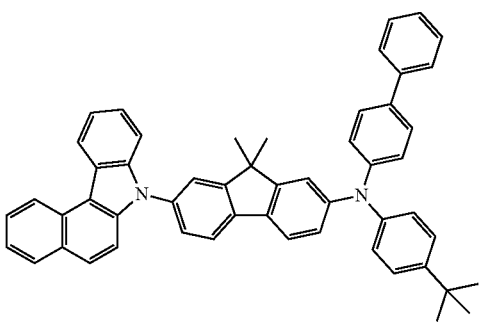
6-1
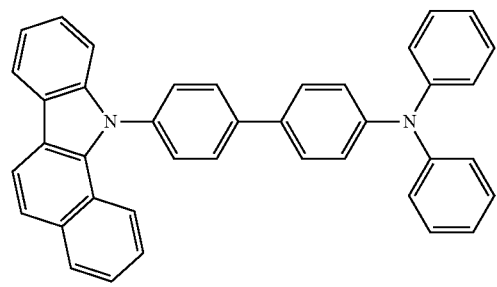
6-2
6-3
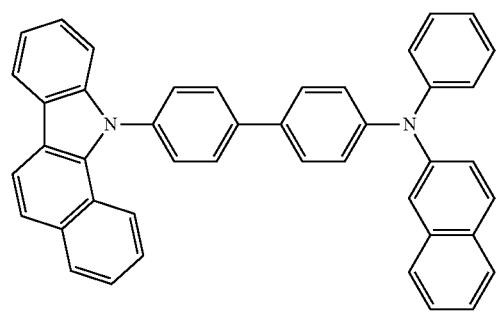
6-4
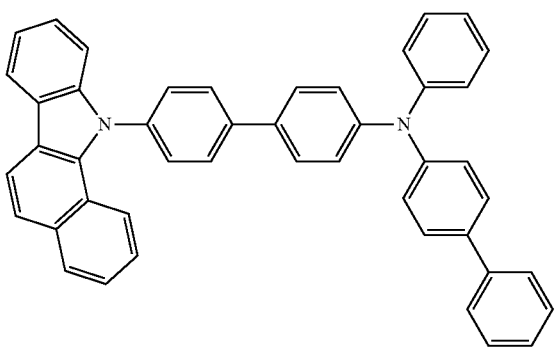

-continued
| 6-5 | 6-6 |
|---|---|
| 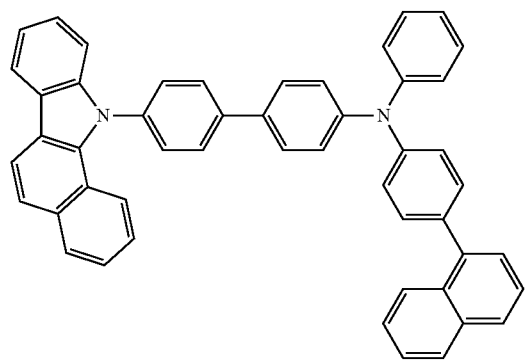 | 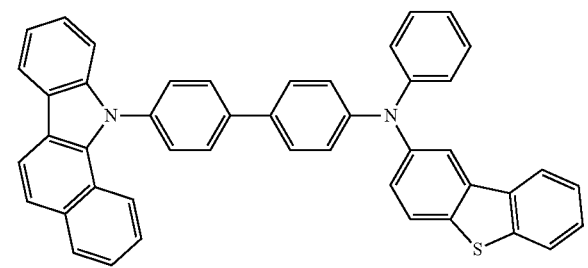 |
| 6-7 | 6-8 |
| 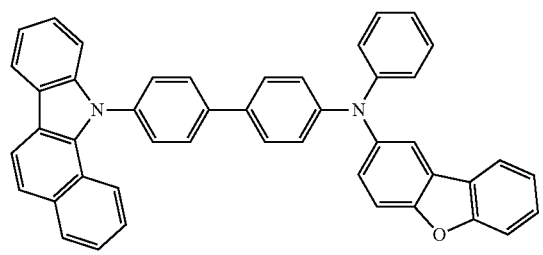 | 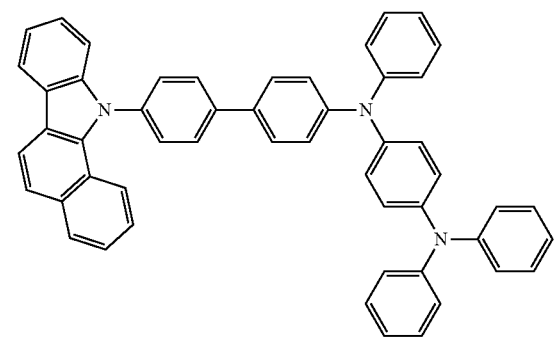 |
| 6-9 | 6-10 |
| 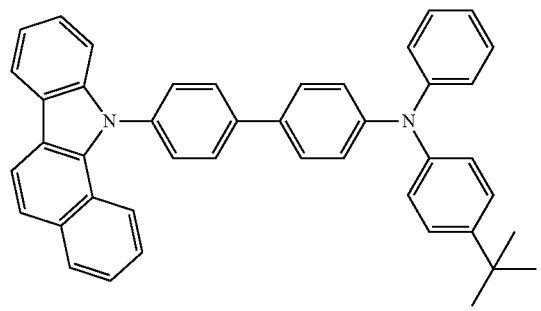 | 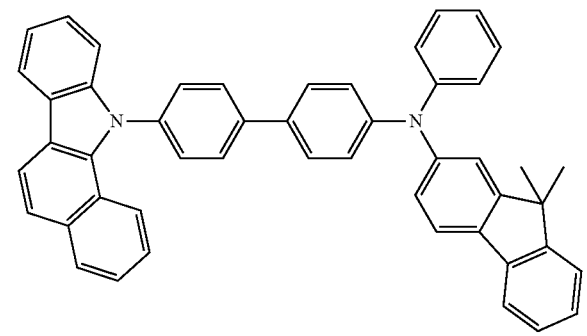 |
| 6-11 | 6-12 |
| 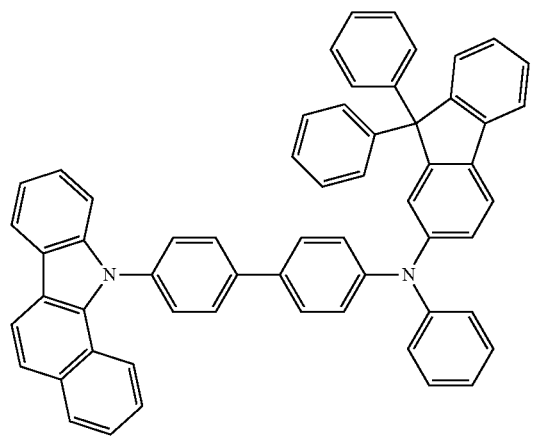 | 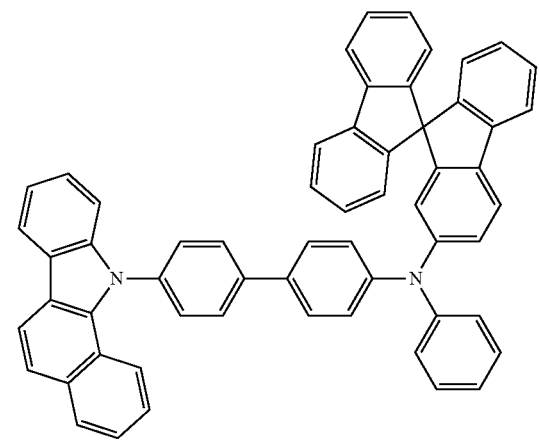 |

-continued
6-13
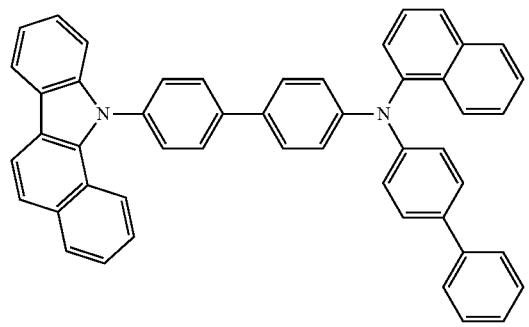
6-14
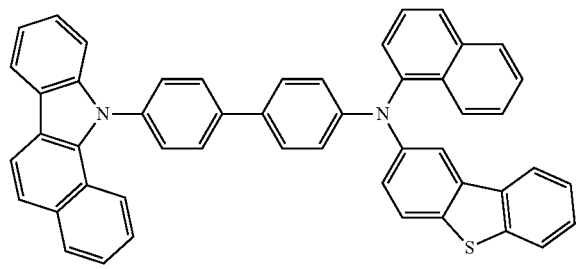
6-15
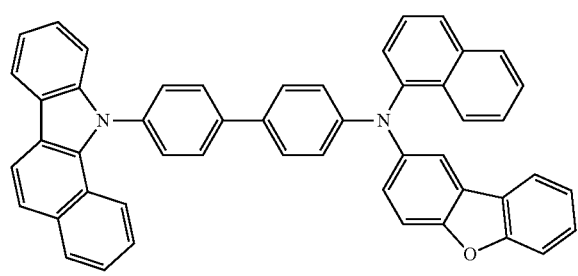
6-16
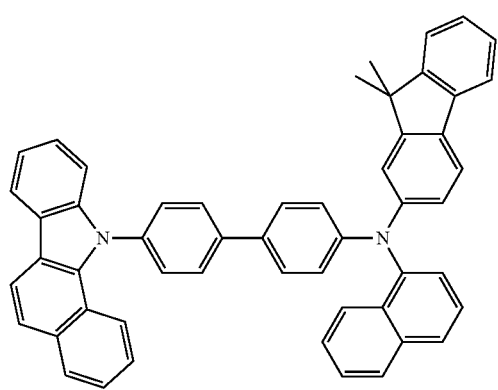
6-17
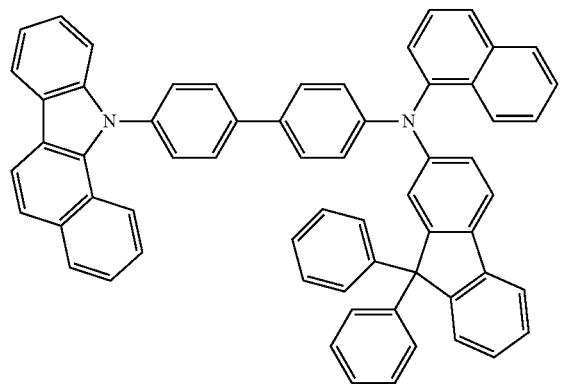
6-18
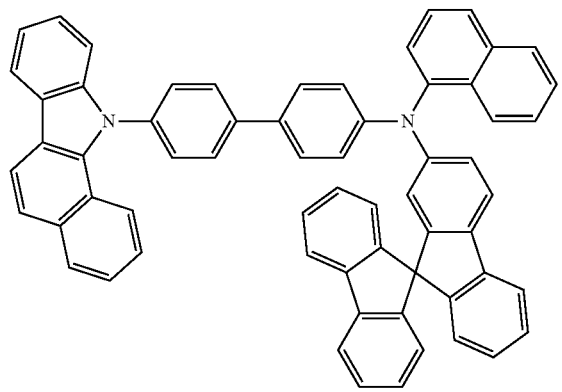
6-19
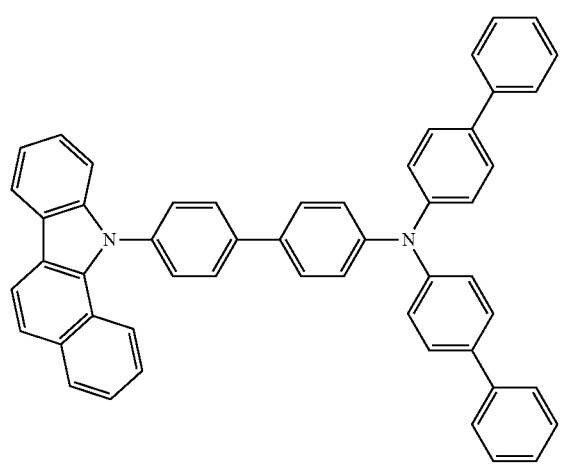
6-20
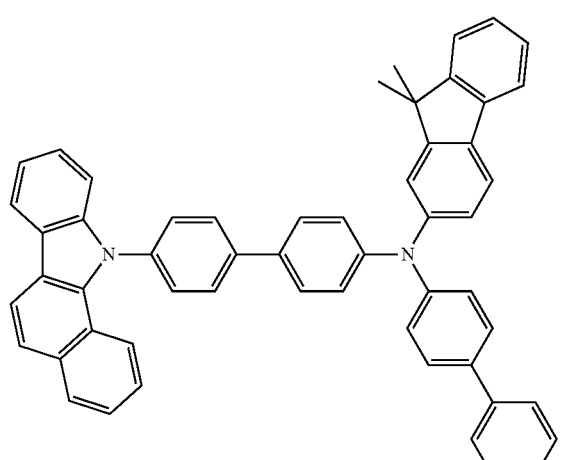

-continued
6-21
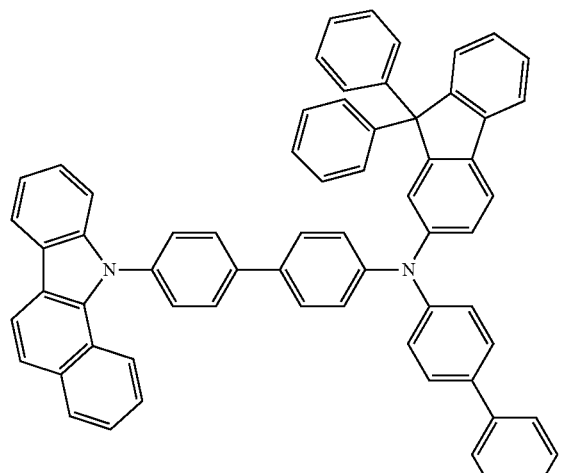
6-22
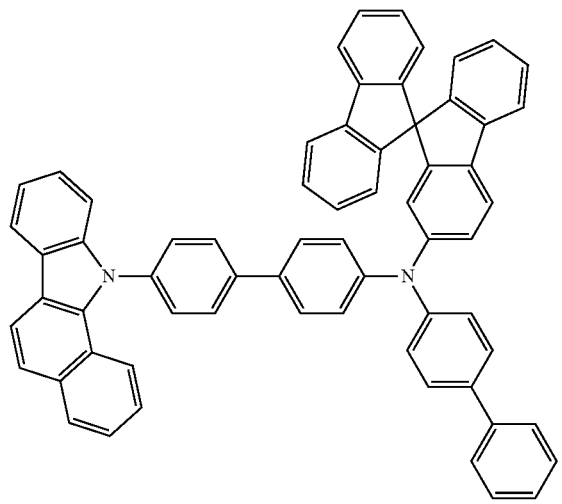
6-23
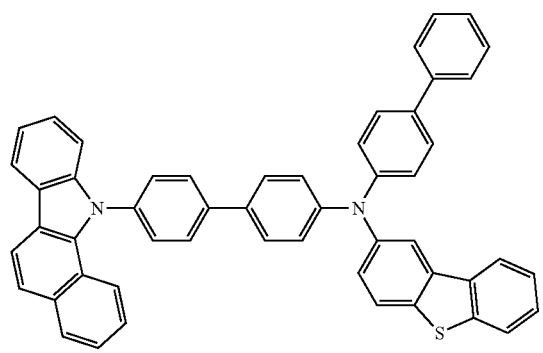
6-24
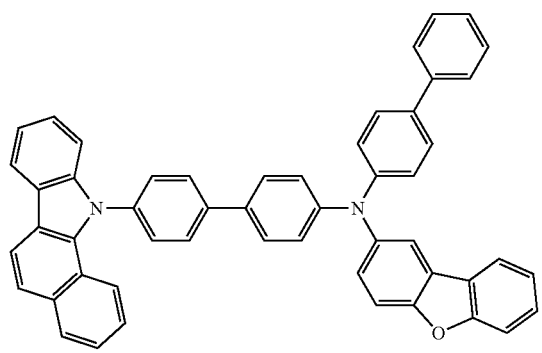
6-25
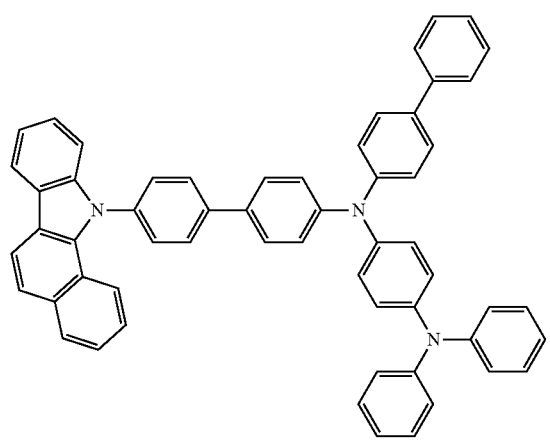
6-26
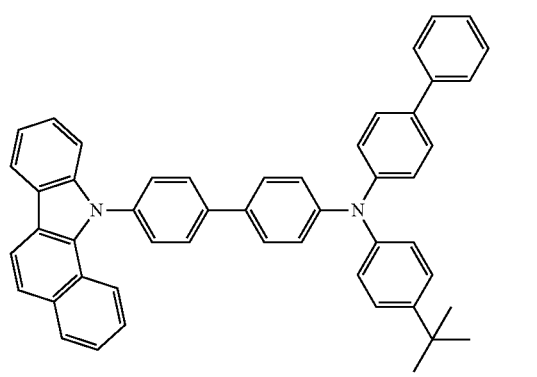
6-27
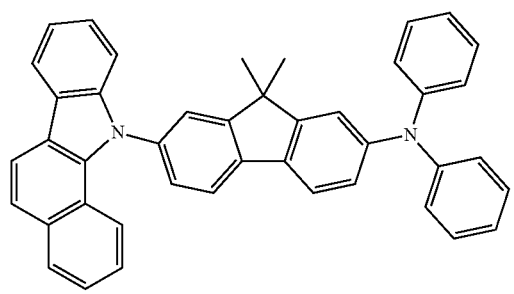
6-28
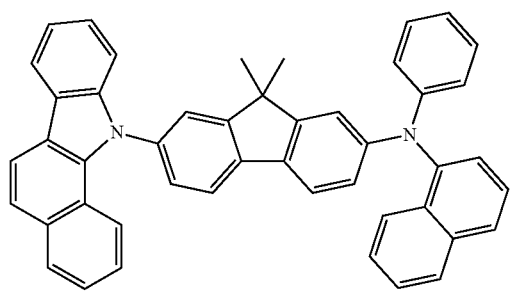

-continued
6-29
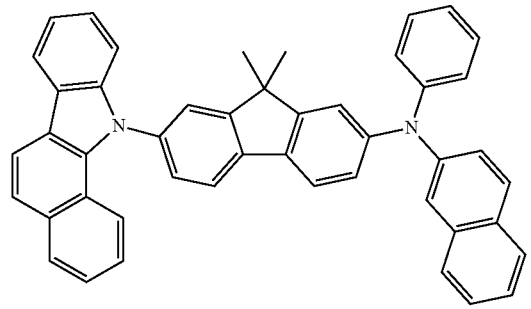
6-30
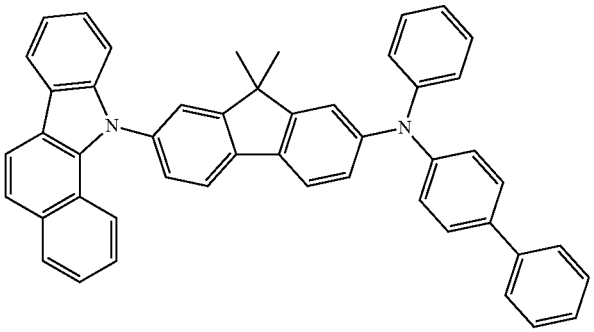
6-31
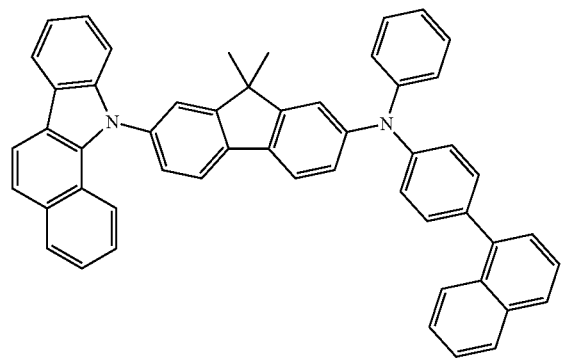
6-32
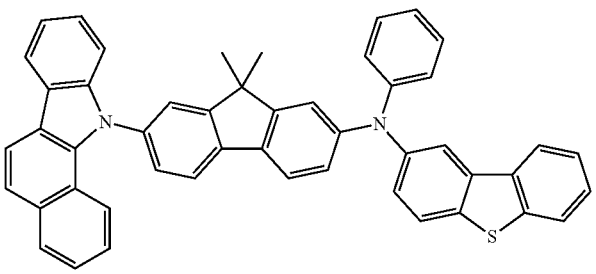
6-33
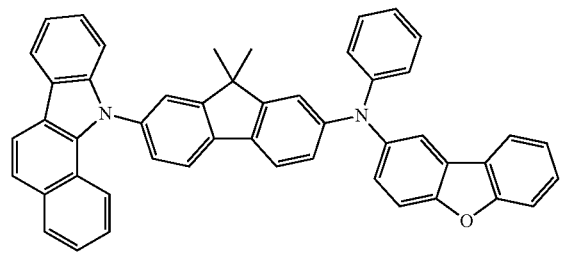
6-34
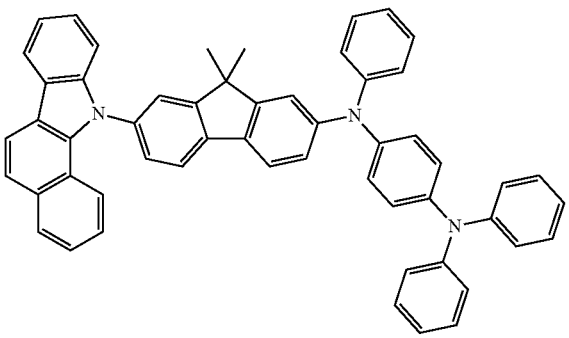
6-35
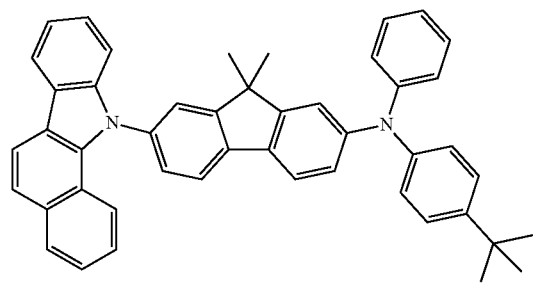
6-36
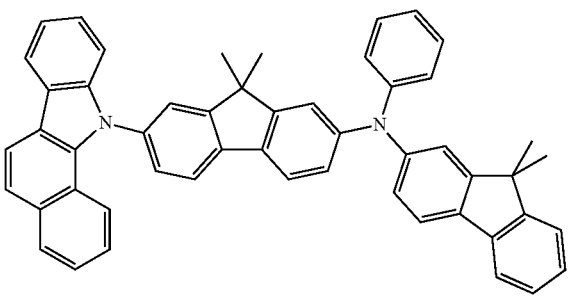

-continued
6-37
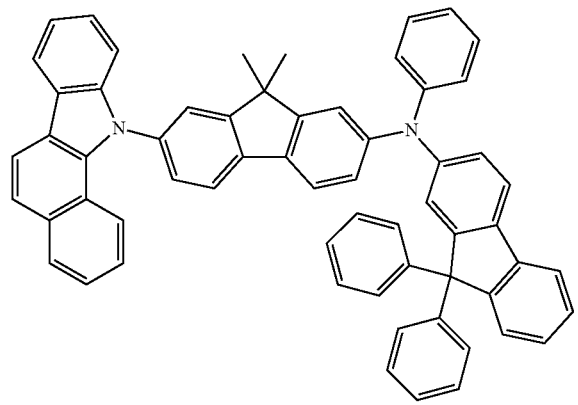
6-38
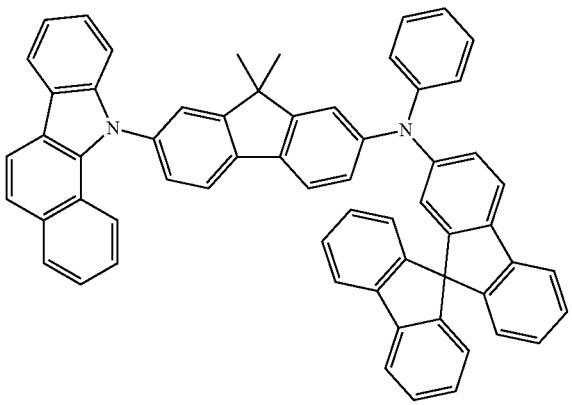
6-39
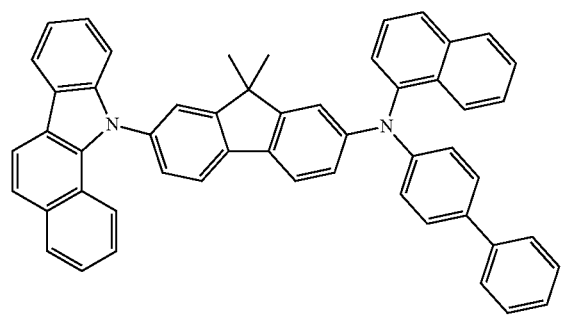
6-40
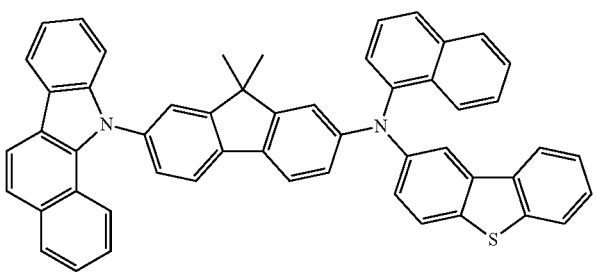
6-41
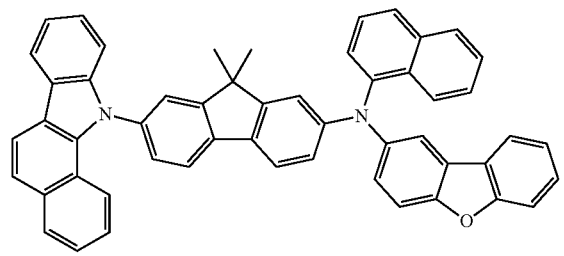
6-42
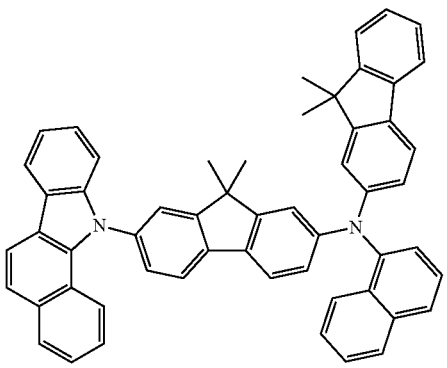
6-43
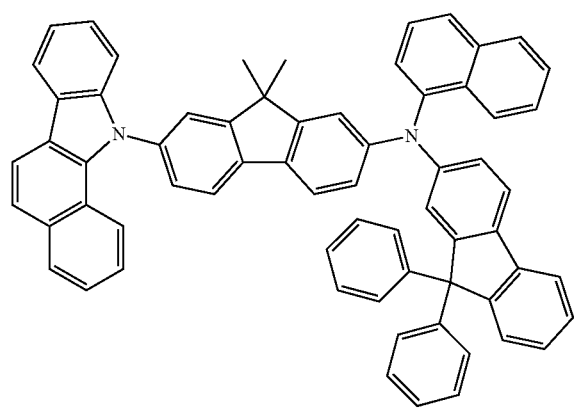
6-44
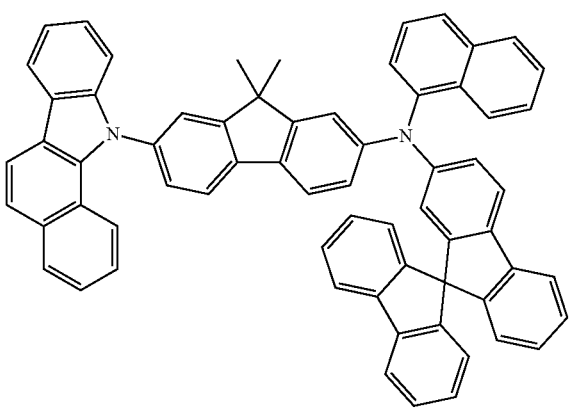

-continued
6-45
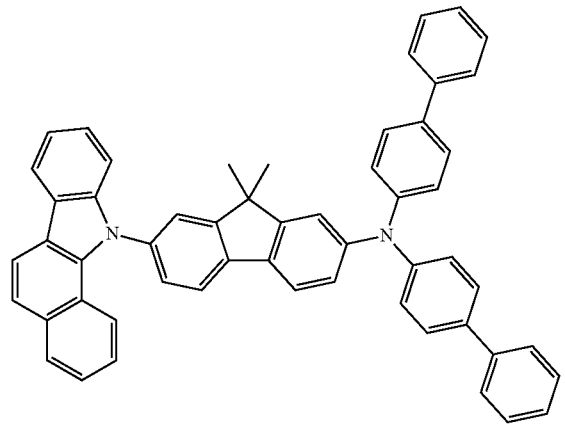
6-46
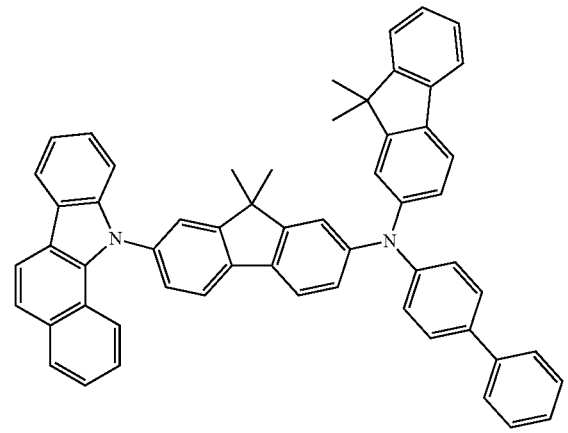
6-47
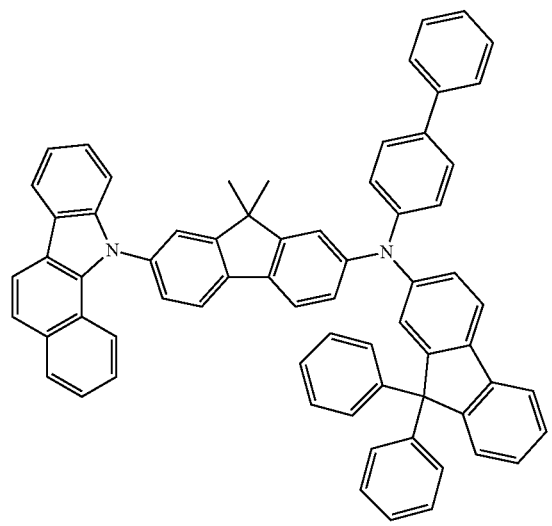
6-48
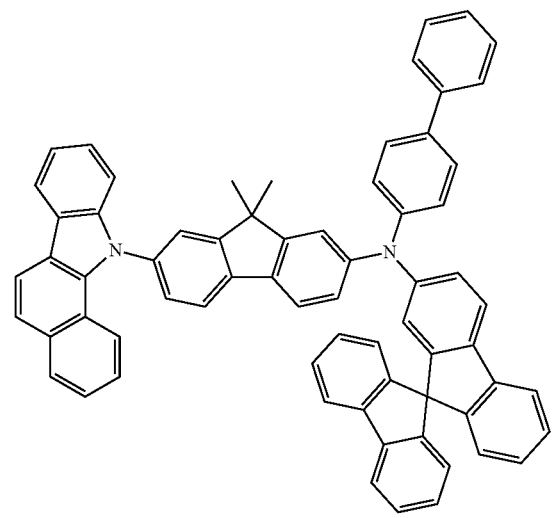
6-49
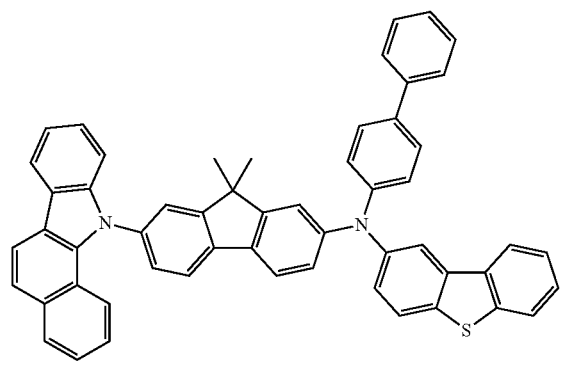
6-50
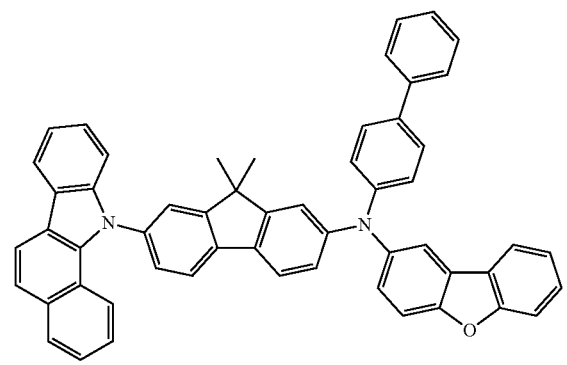

-continued
6-51
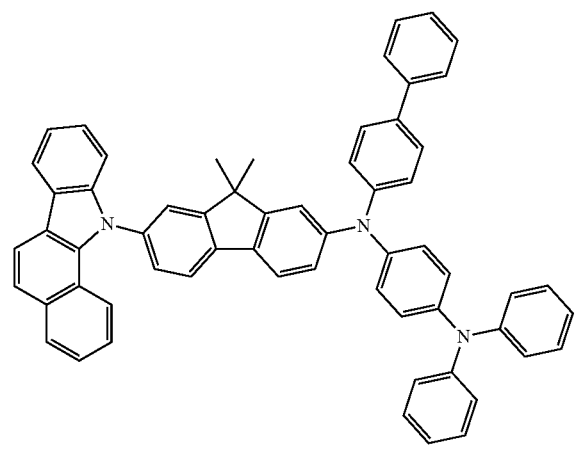
6-52
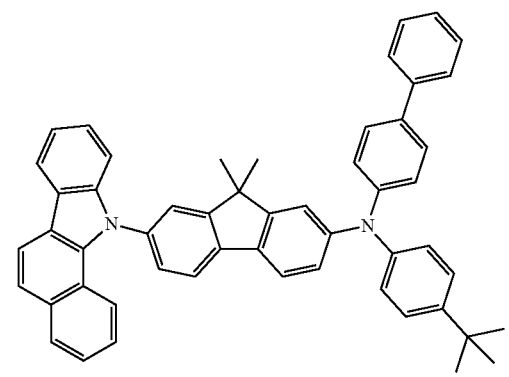
7-1
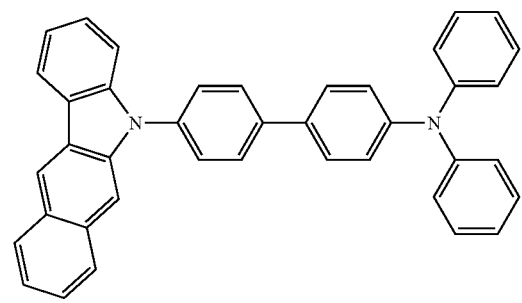
7-2
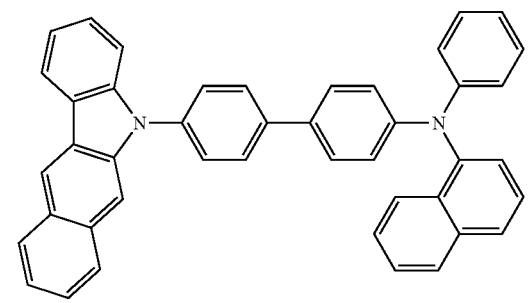
7-3
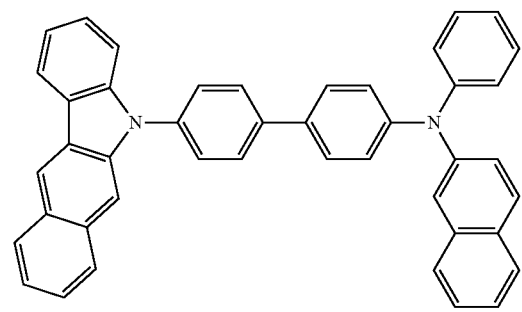
7-4
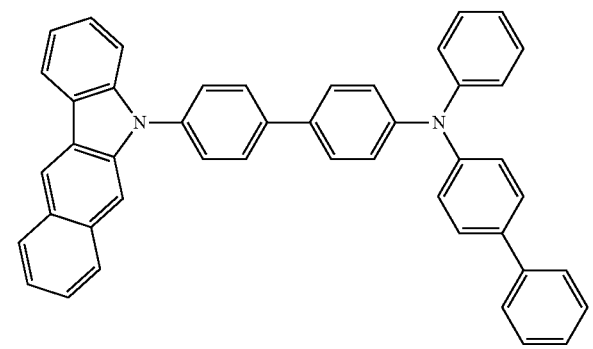
7-5
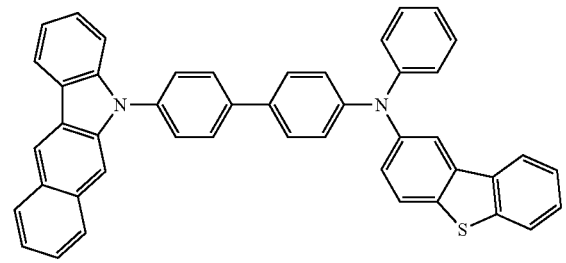
7-6
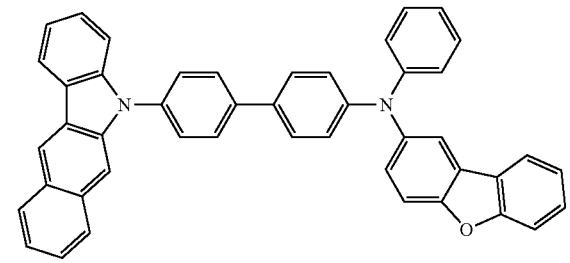

7-7
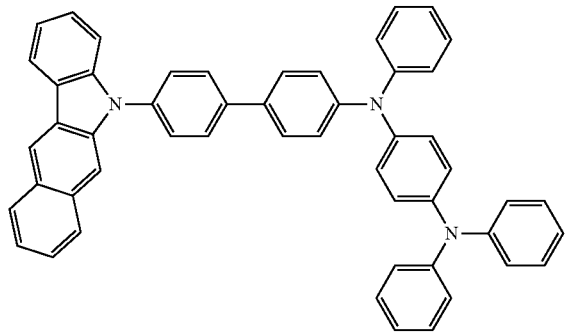
7-8
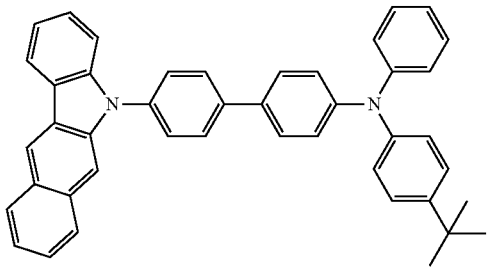
7-9
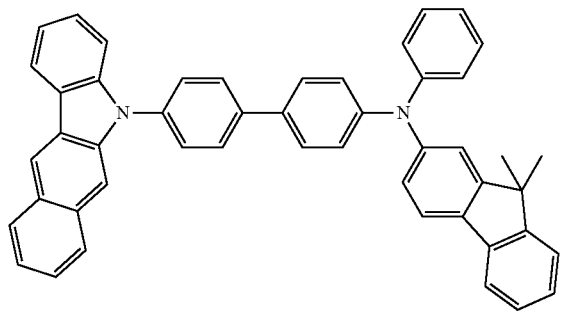
7-10
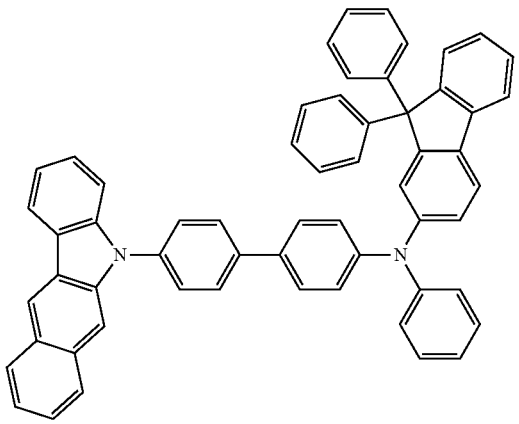
7-11
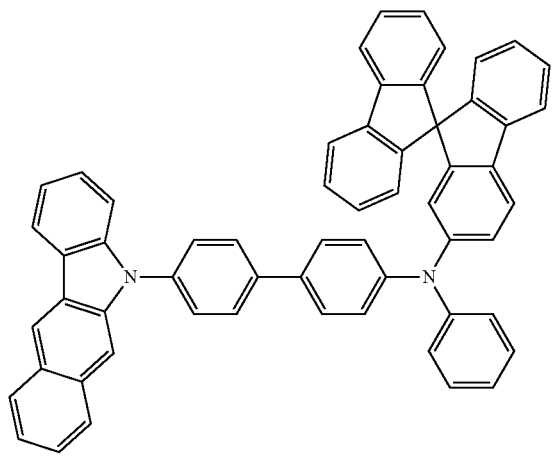
7-12
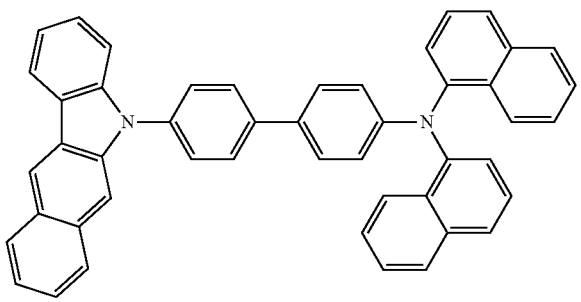
7-13
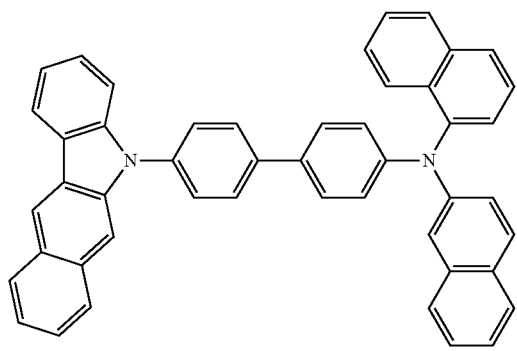
7-14
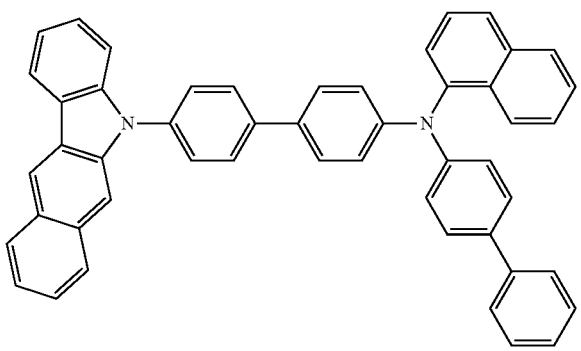

-continued
7-15
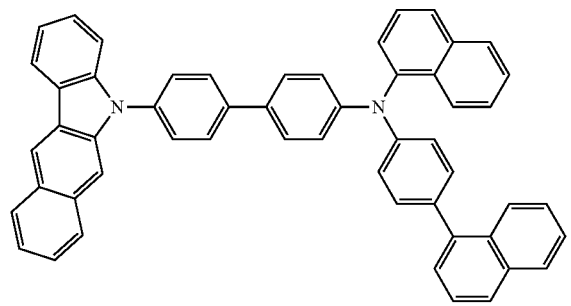
7-16
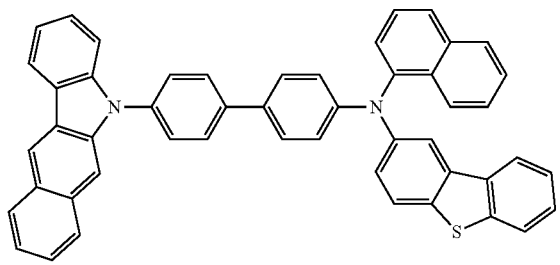
7-17
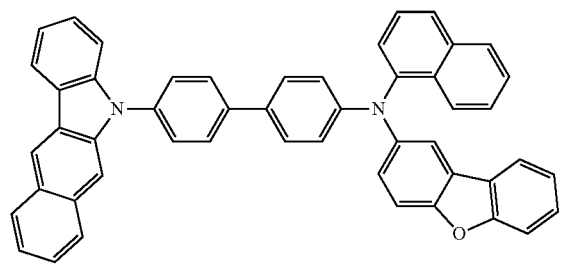
7-18
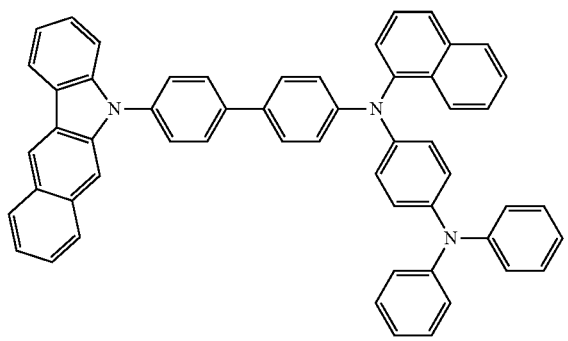
7-19
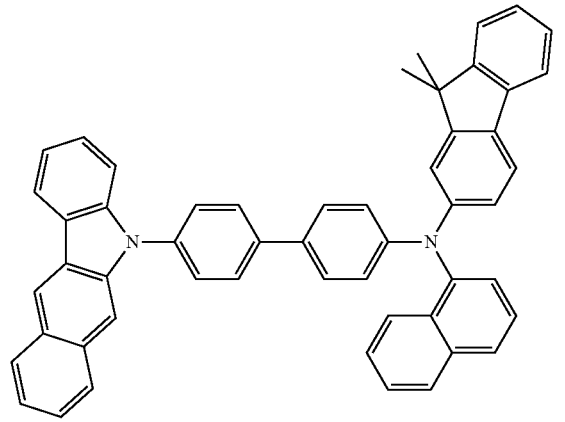
7-20
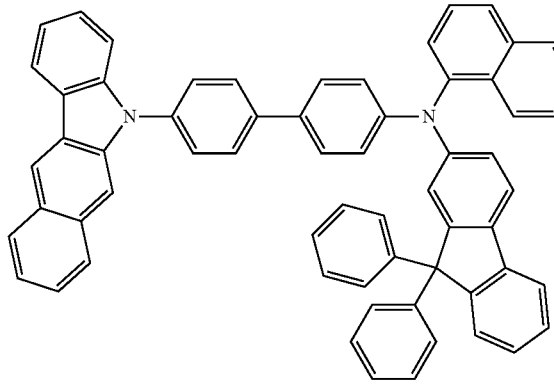
7-21
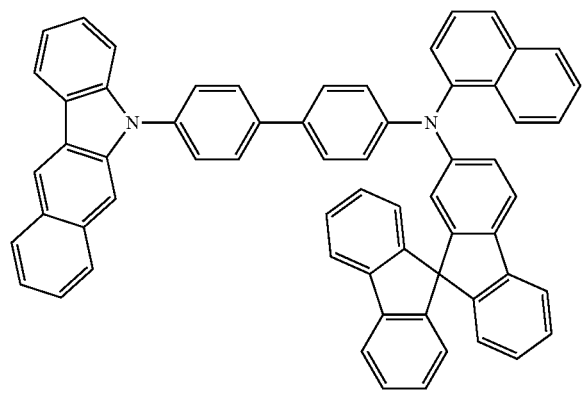
7-22
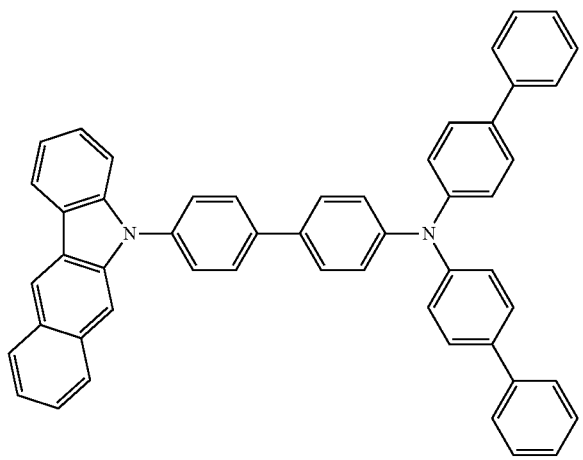

-continued
7-23
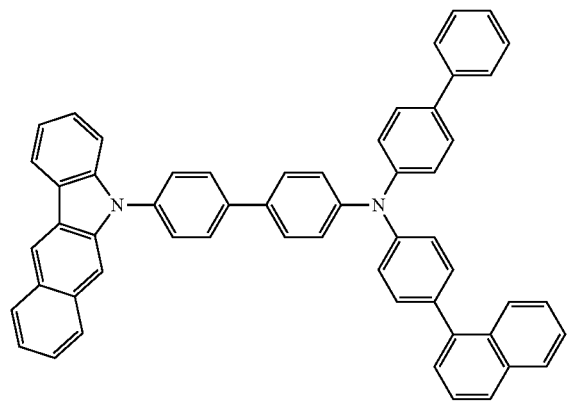
7-24
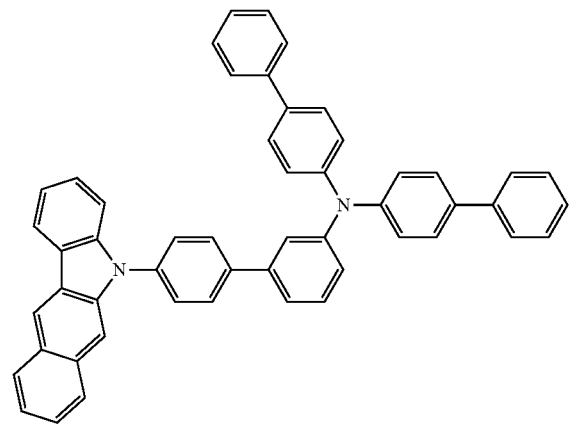
7-25
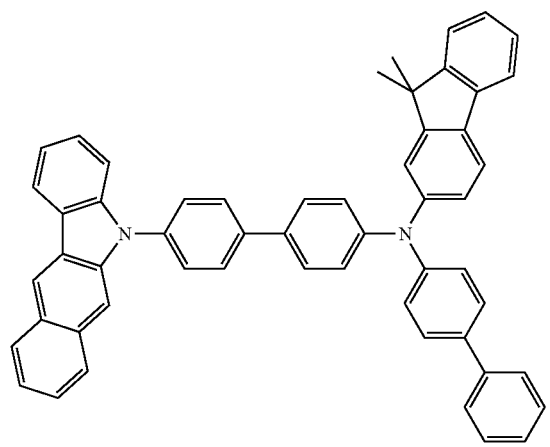
7-26
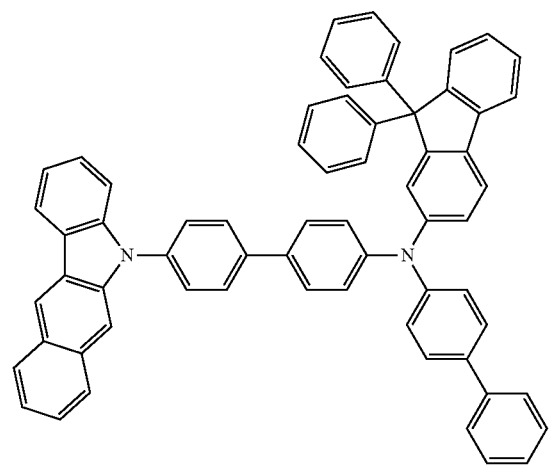
7-27
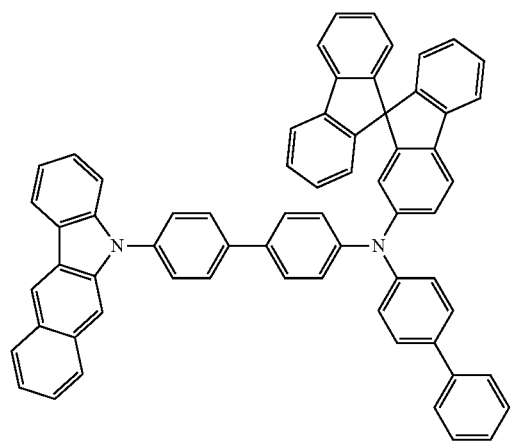
7-28
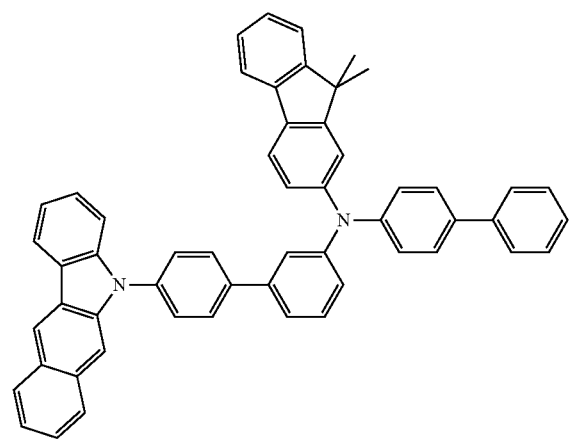

-continued
7-29
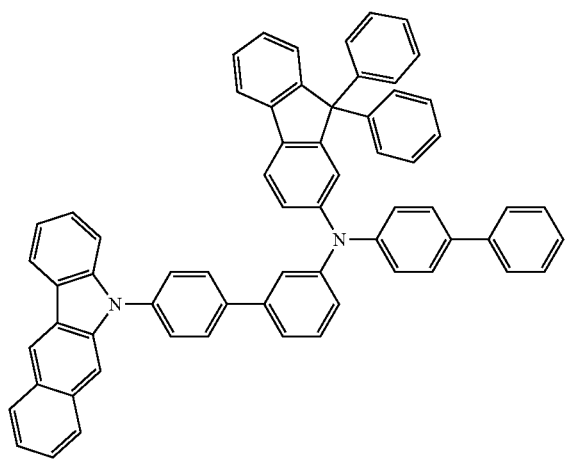
7-30
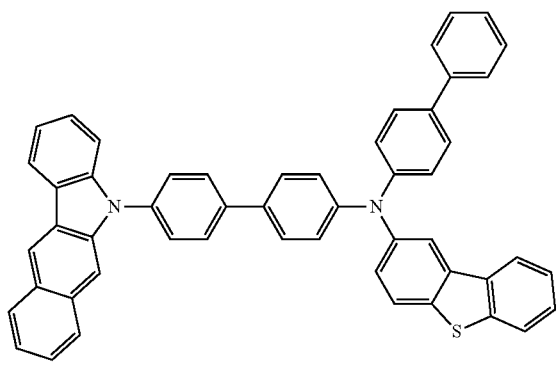
7-31
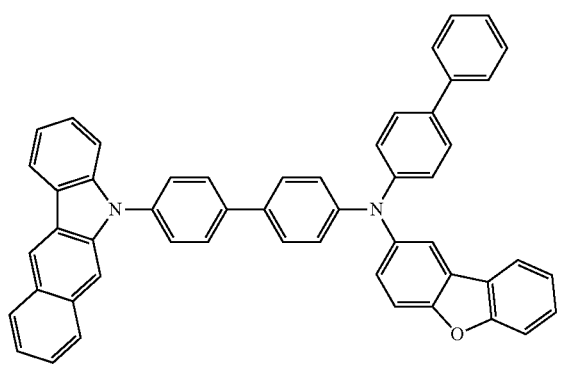
7-32
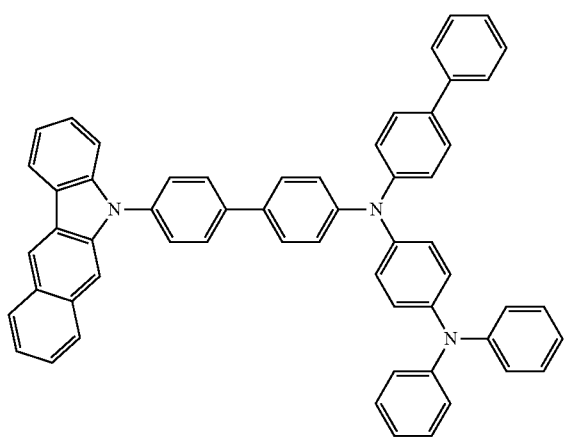
7-33
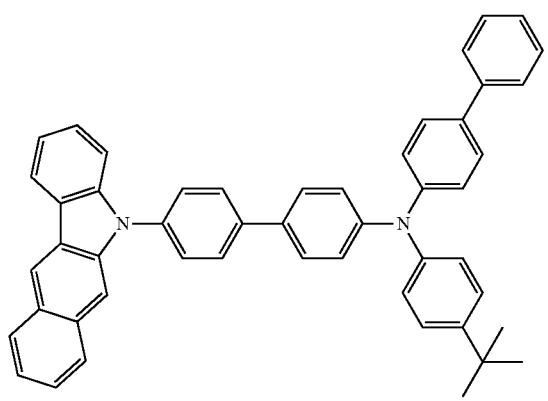

7-34
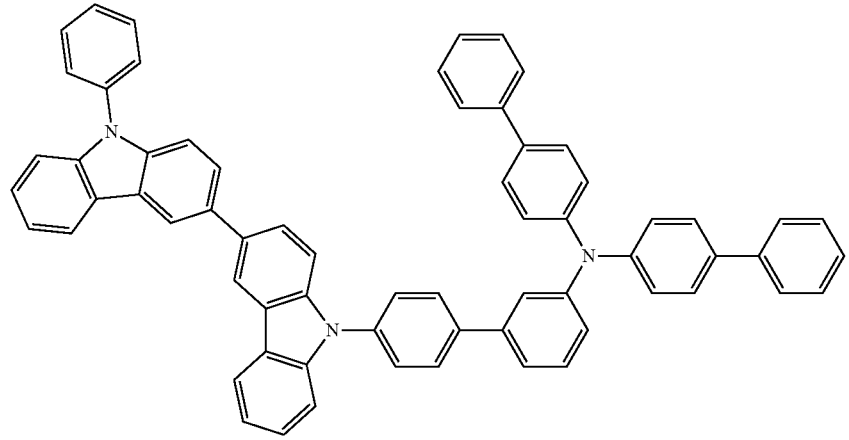
7-35
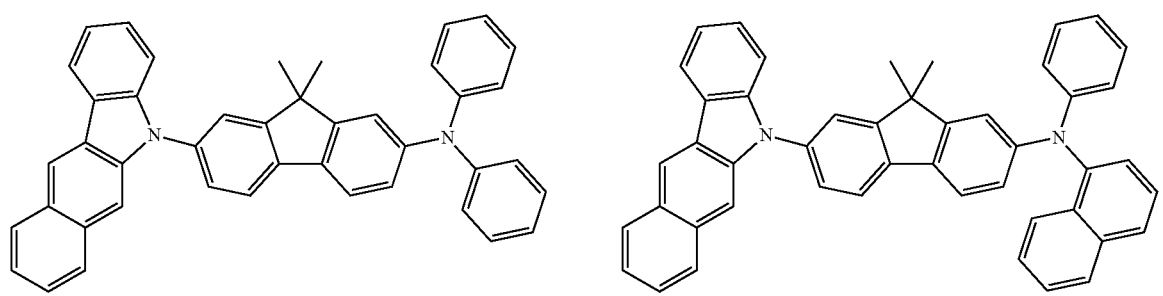
7-36
7-37
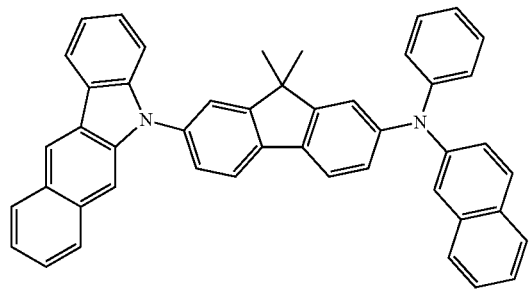
7-38
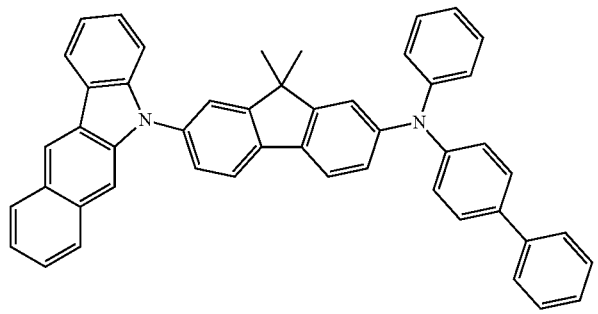
7-39
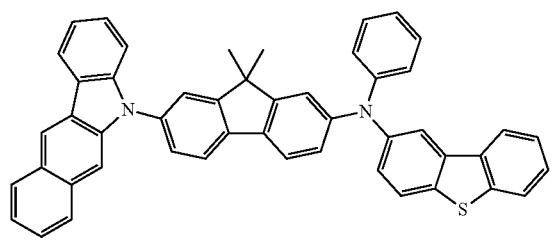
7-40
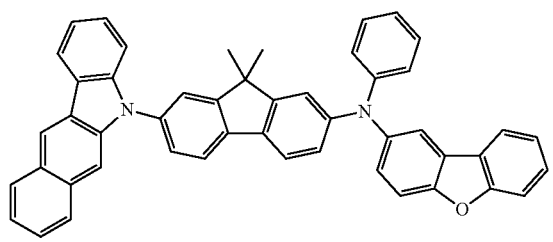

-continued
7-41
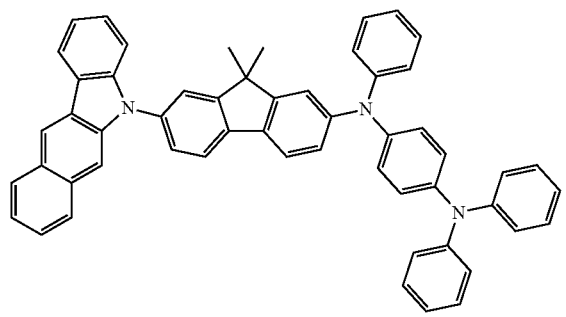
7-42
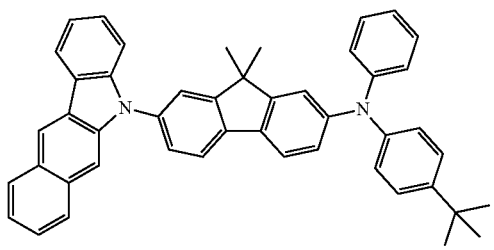
7-43
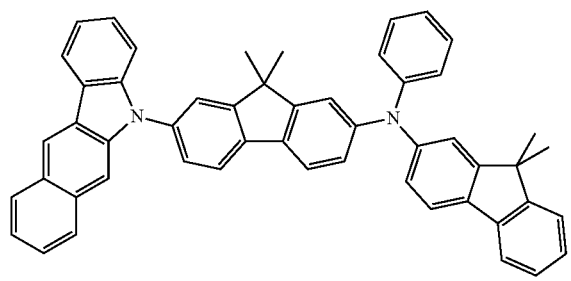
7-44
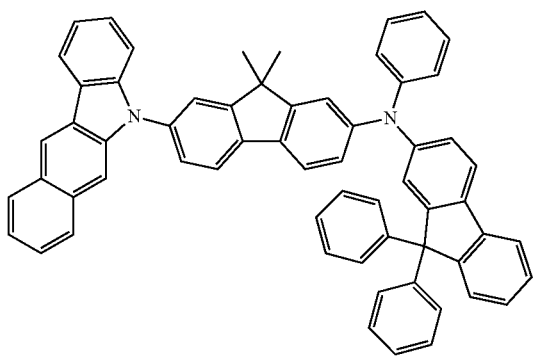
7-45
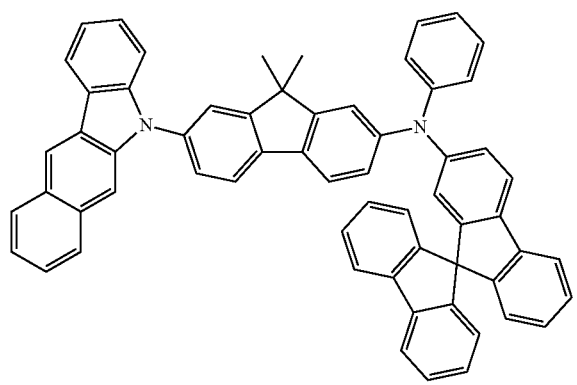
7-46
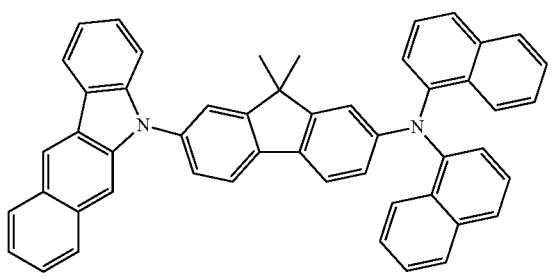
7-47
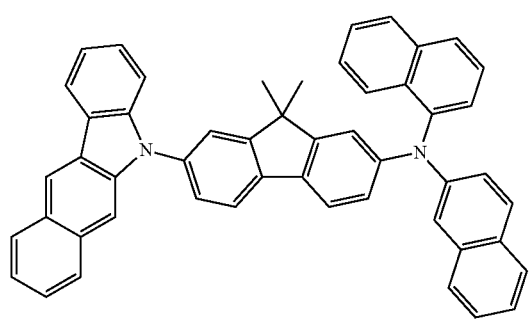
7-48
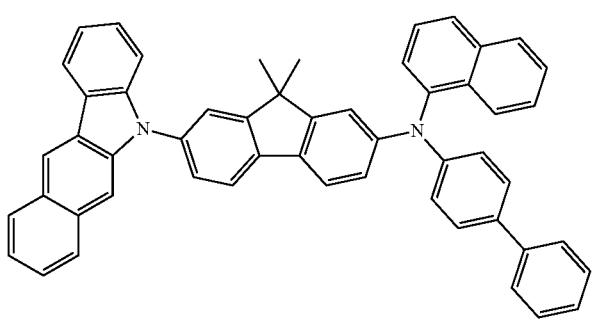

-continued
7-49
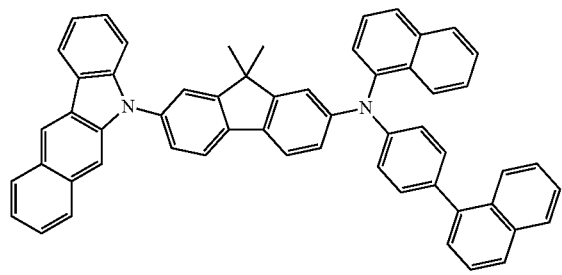
7-50
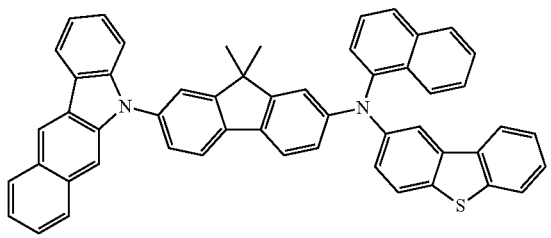
7-51
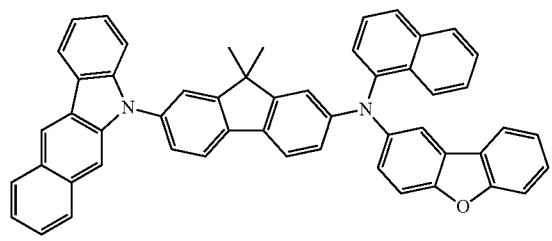
7-52
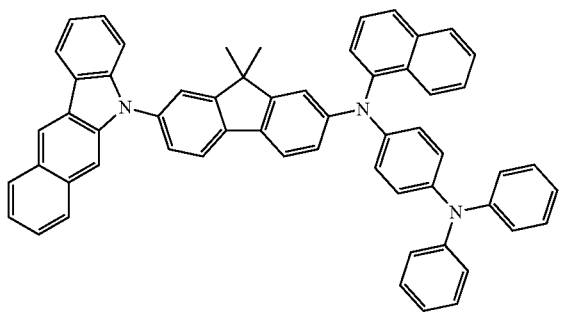
7-53
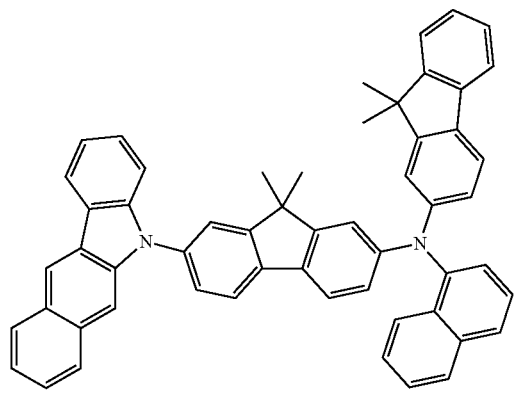
7-54
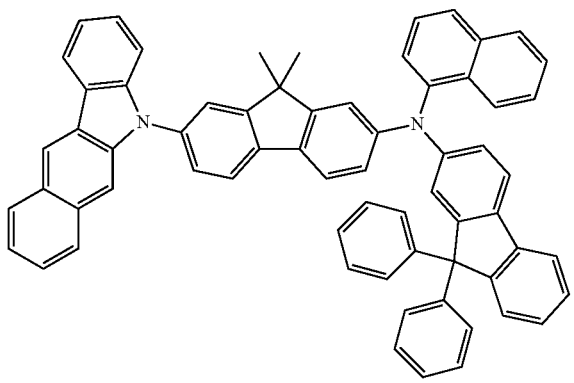
7-55
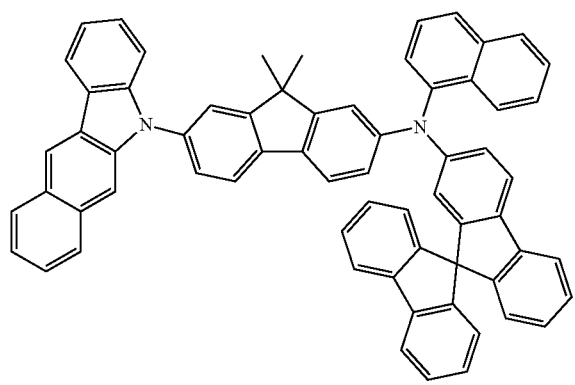
7-56
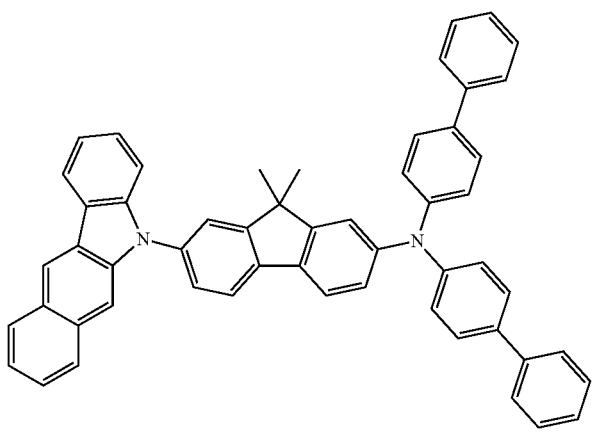

-continued
7-57
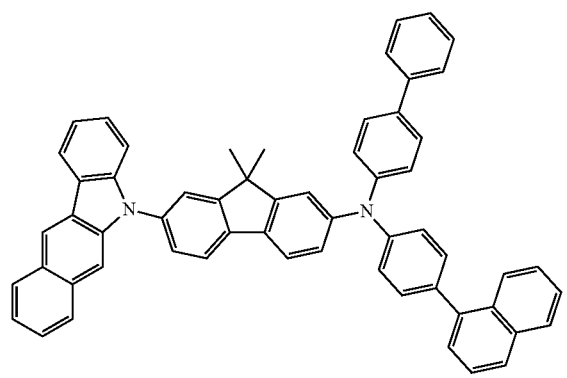
7-58
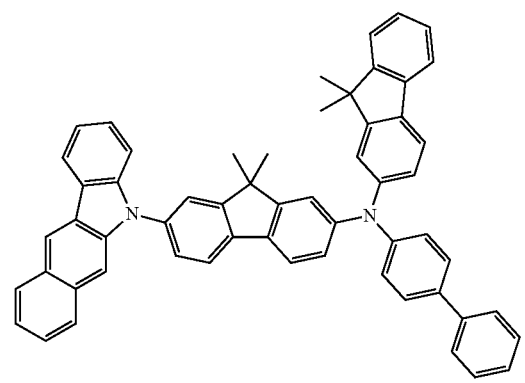
7-59
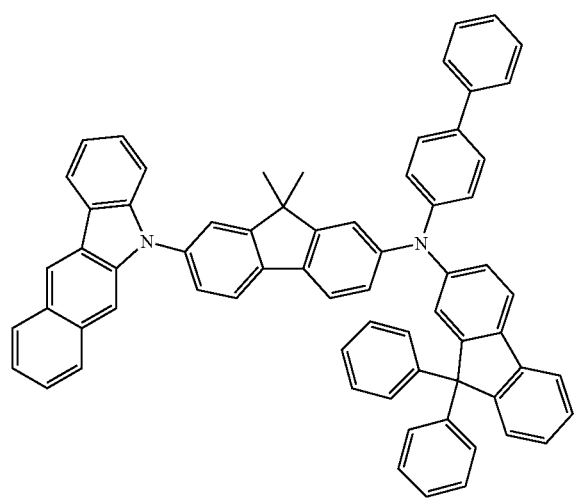
7-60
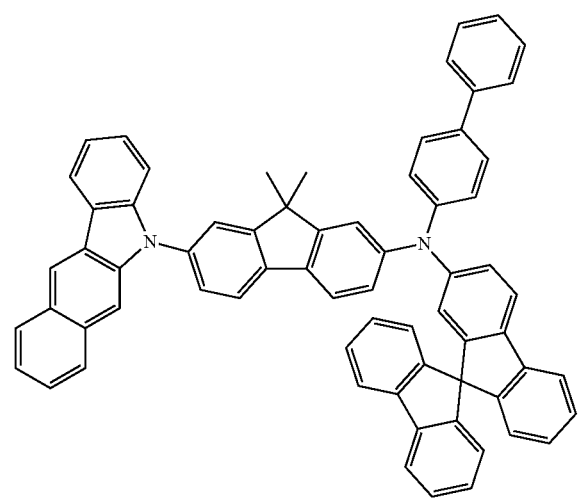
7-61
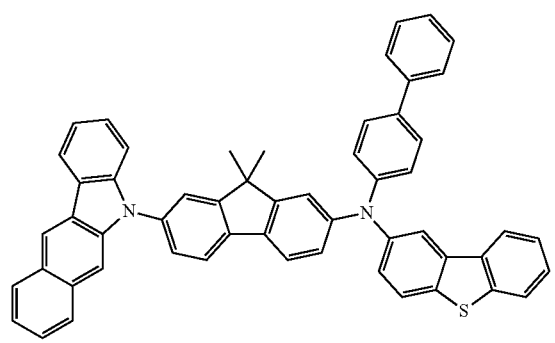
7-62
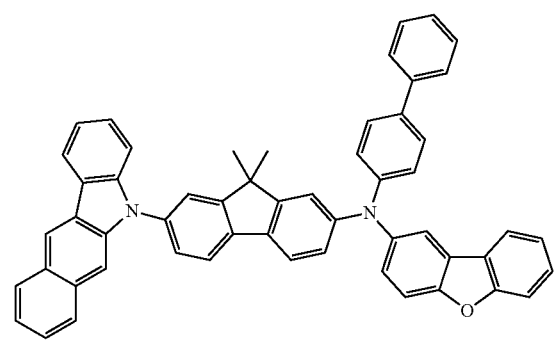

7-63
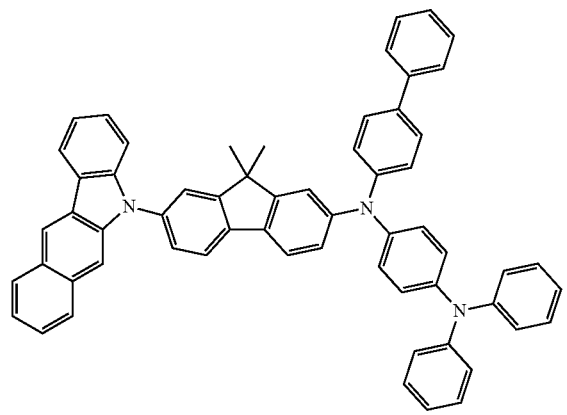
7-64
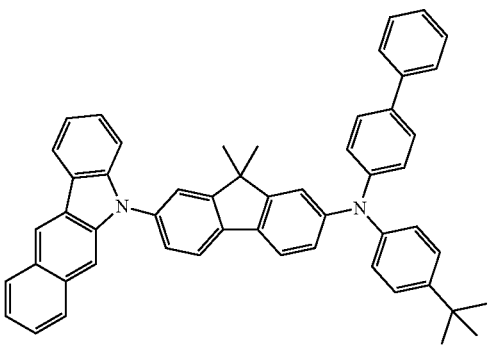
8-1
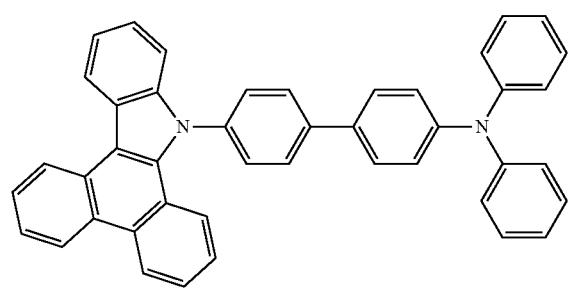
8-2
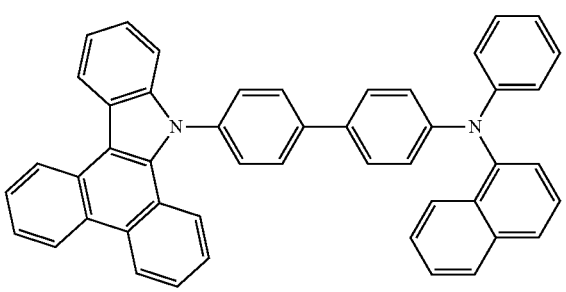
8-3
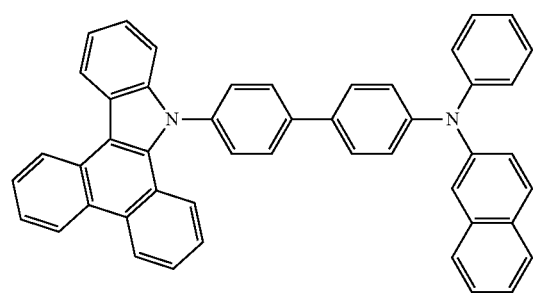
8-4
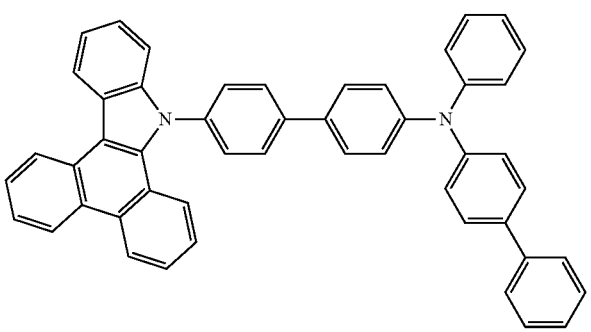
8-5
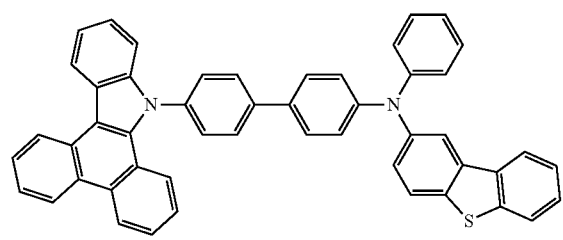
8-6
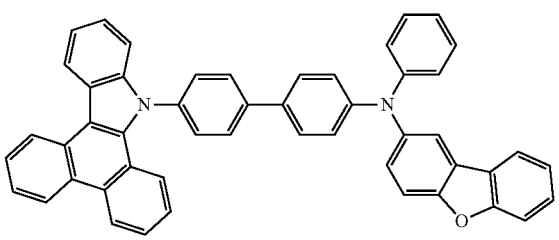

8-7
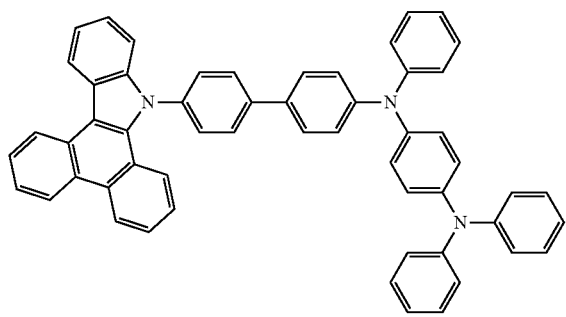
8-8
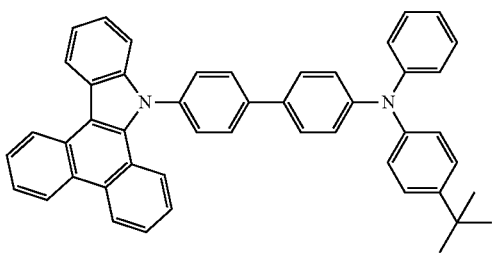
8-9
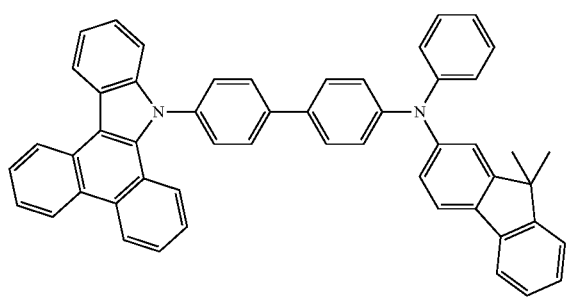
8-10
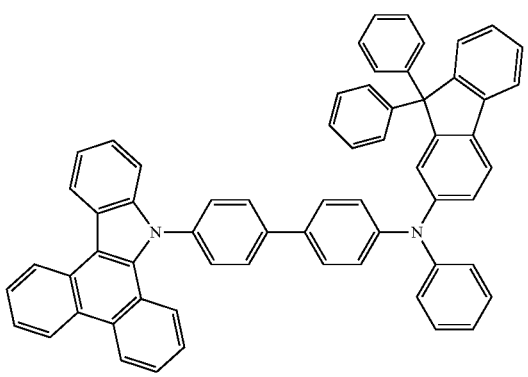
8-11
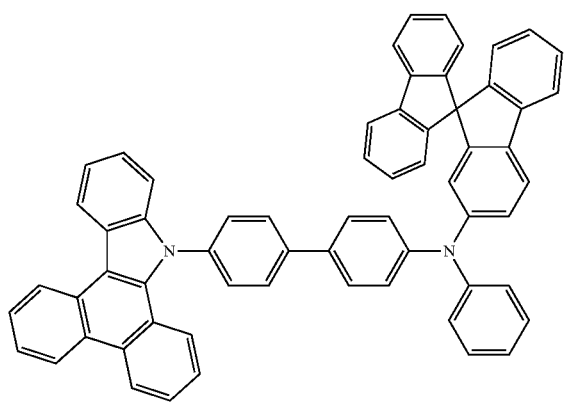
8-12
8-13
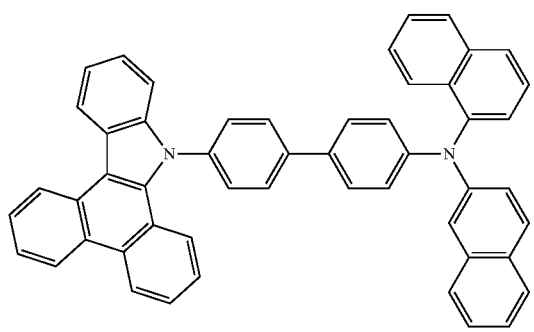
8-14
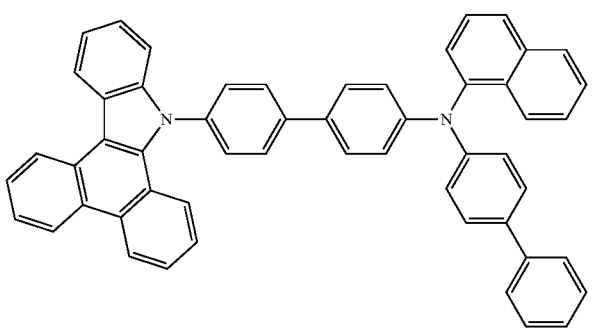

-continued
8-15
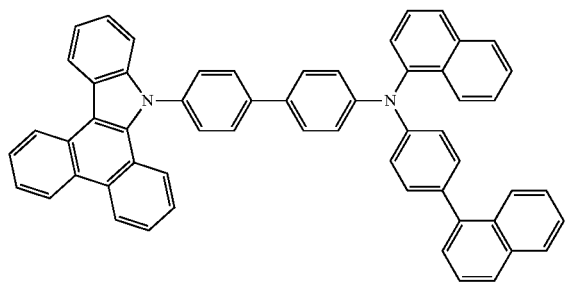
8-16
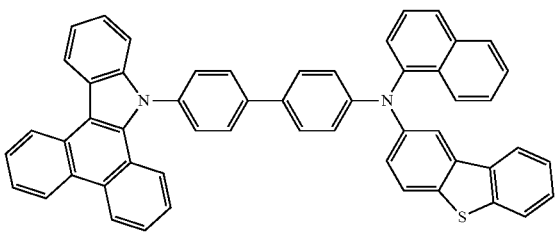
8-17
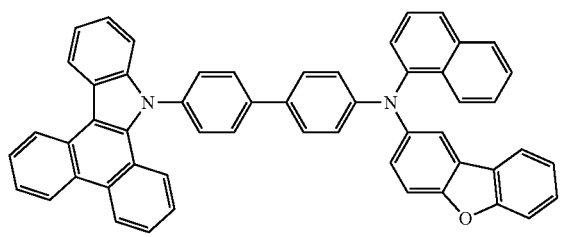
8-18
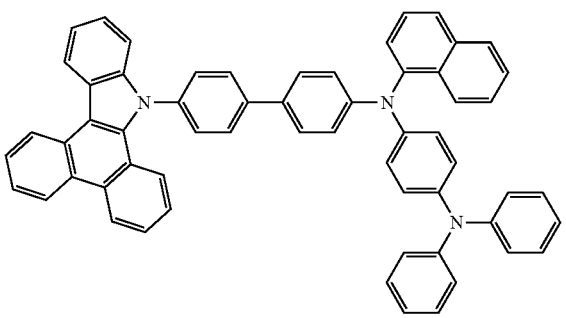
8-19
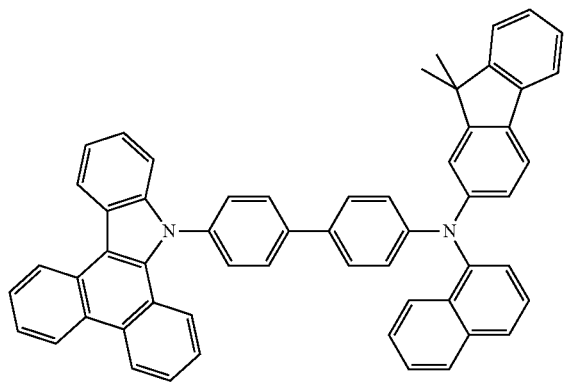
8-20
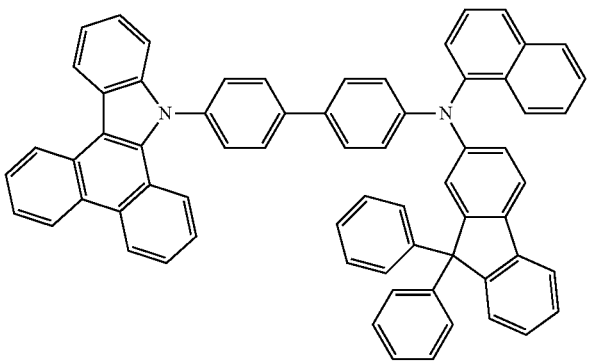
8-21
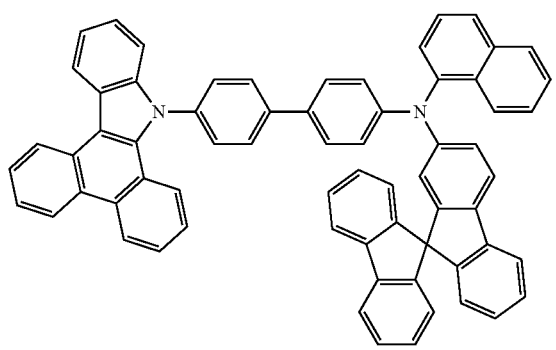
8-22
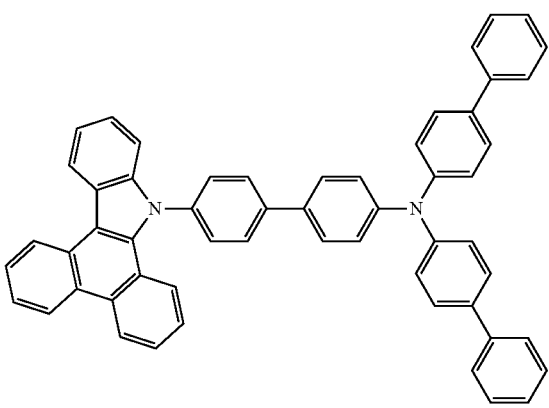

-continued
8-23
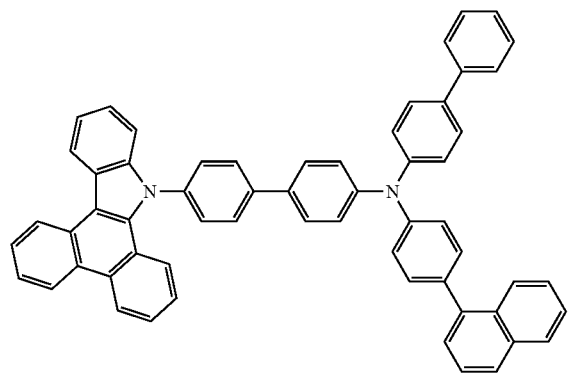
8-24
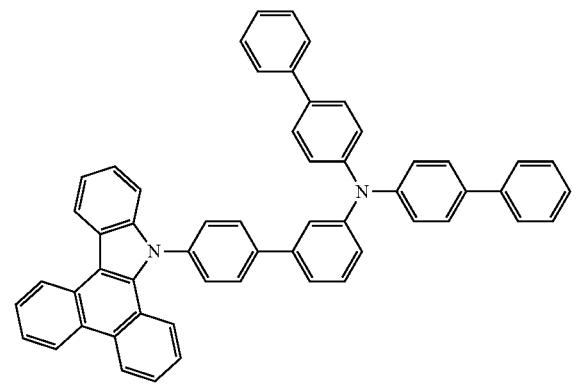
8-25
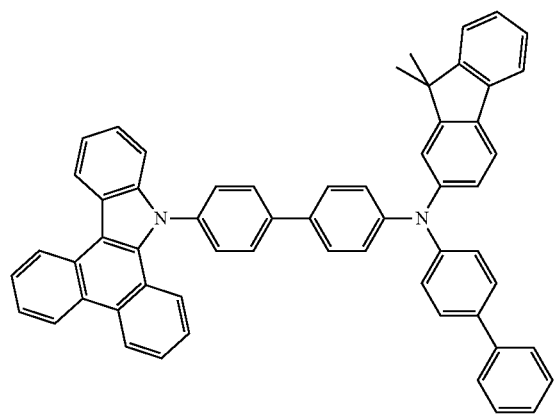
8-26
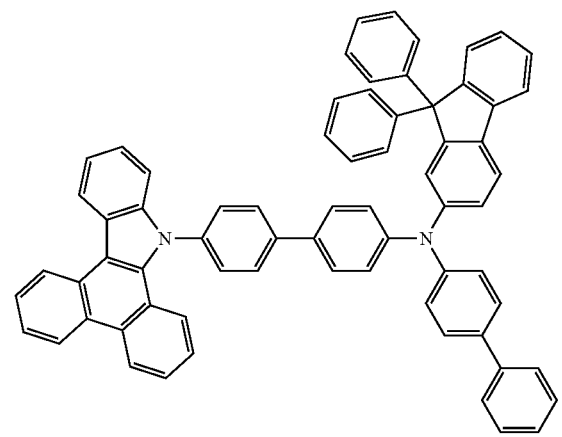
8-27
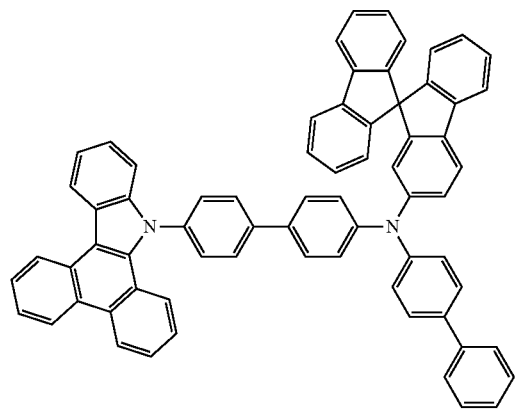
8-28
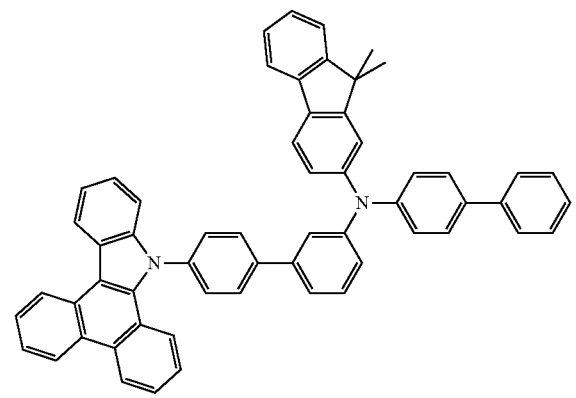

-continued
8-29
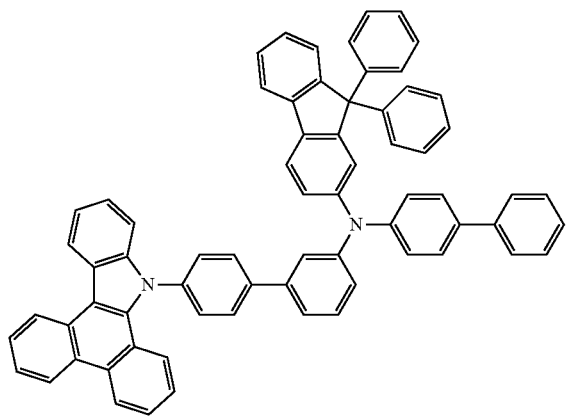
8-30
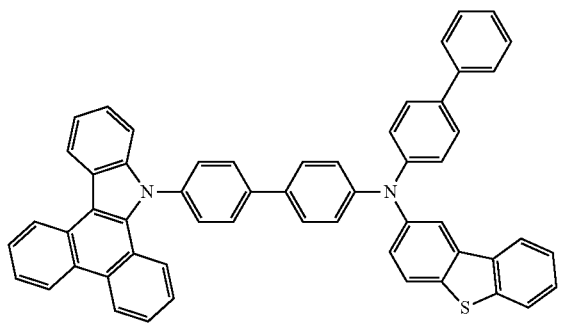
8-31
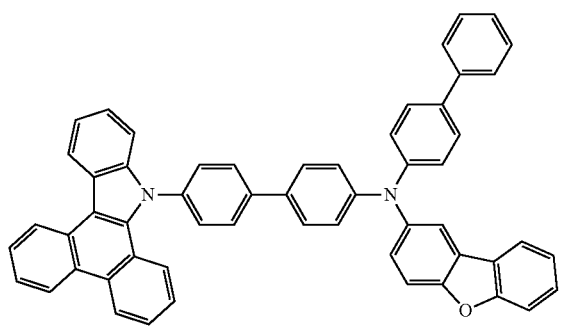
8-32
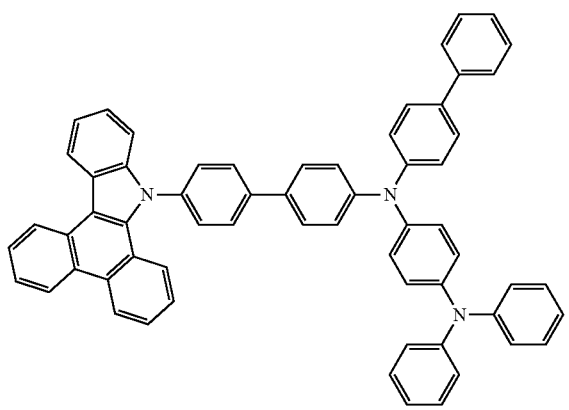
8-33
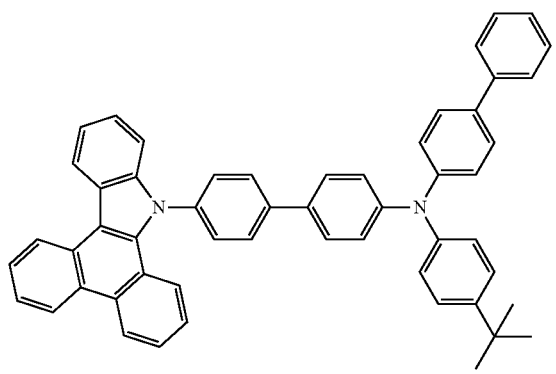
8-34
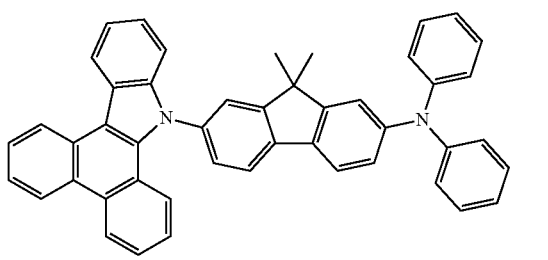
8-35
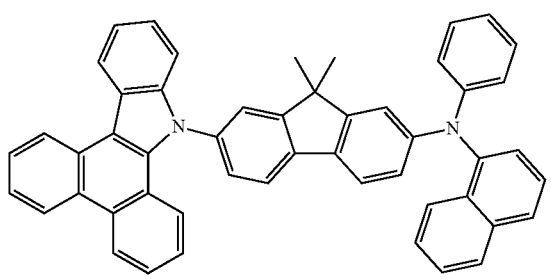
8-36
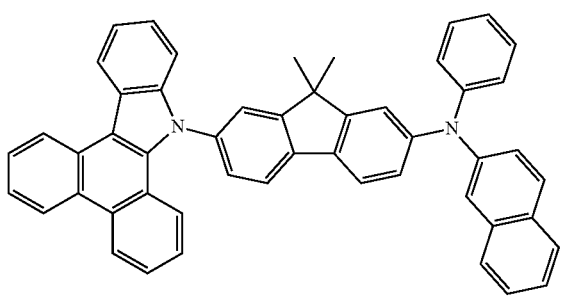

-continued
8-37
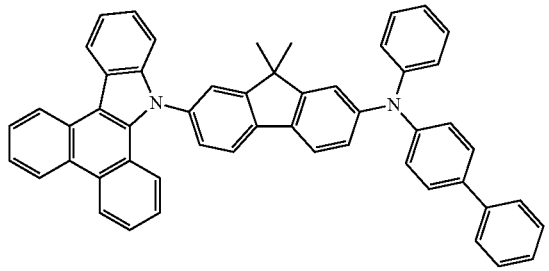
8-38
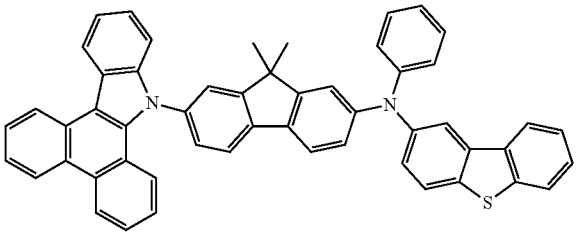
8-39
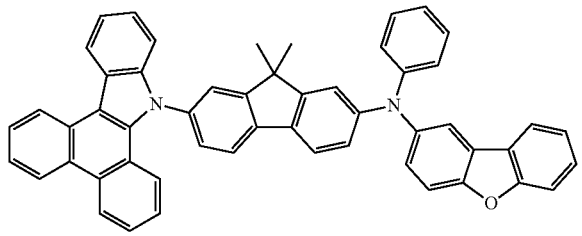
8-40
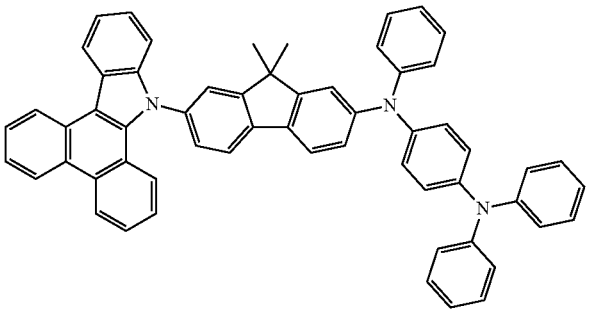
8-41
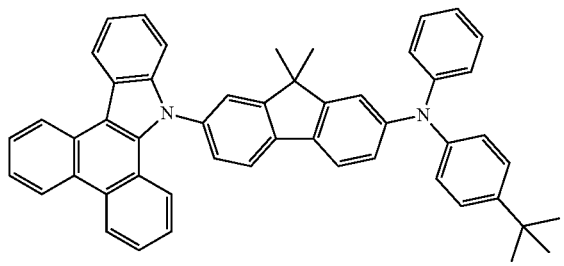
8-42
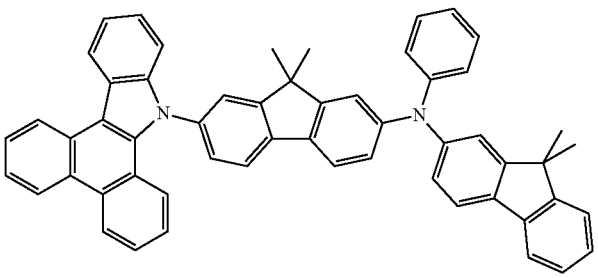
8-43
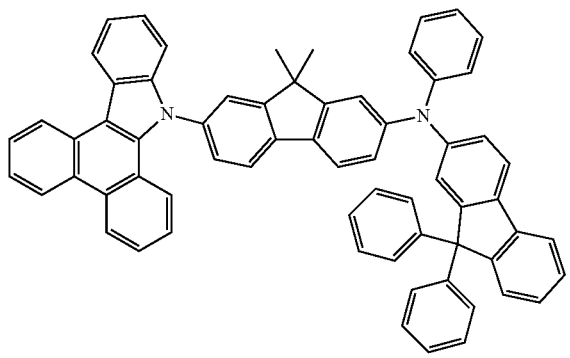
8-44
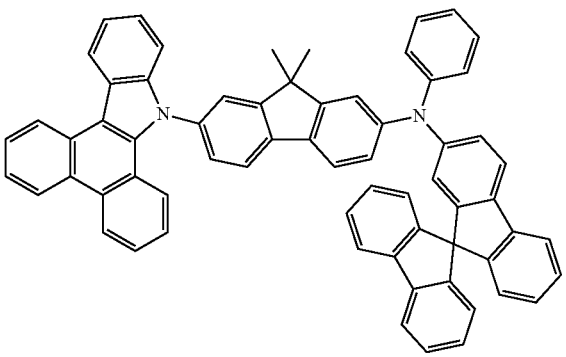
8-45
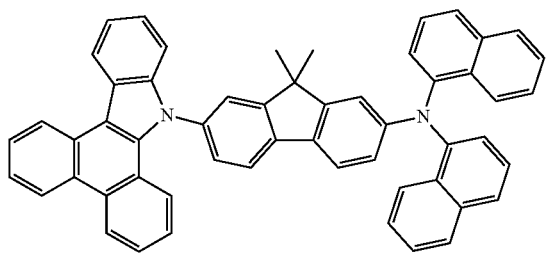
8-46
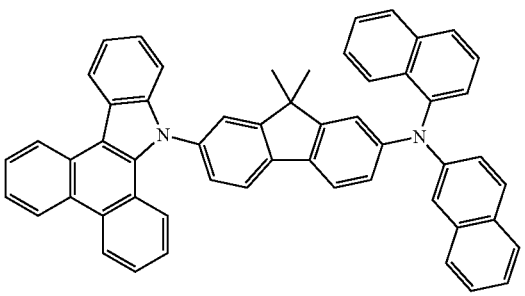

-continued
8-47
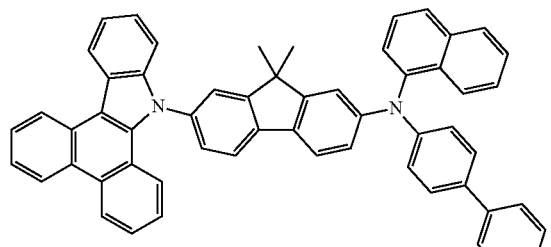
8-48
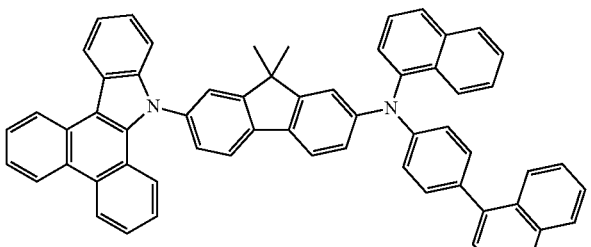
8-49
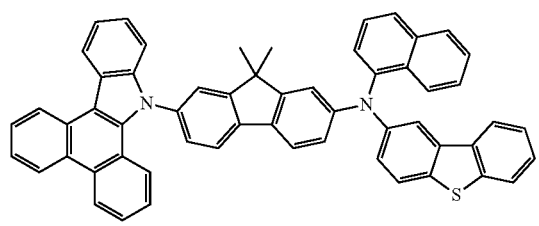
8-50
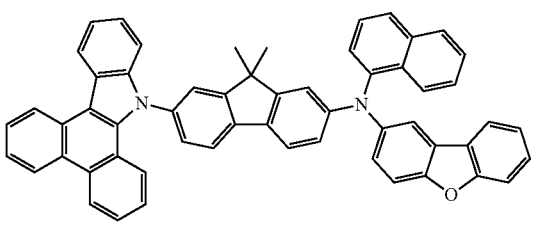
8-51
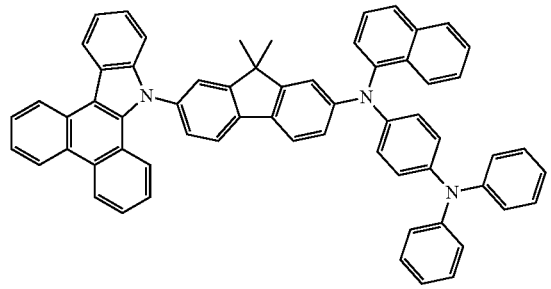
8-52
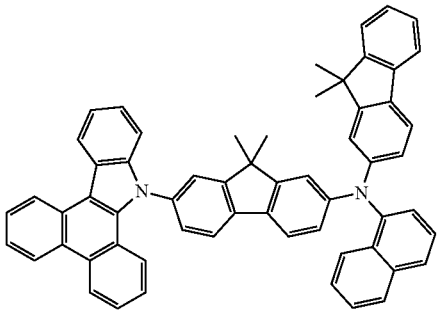
8-53
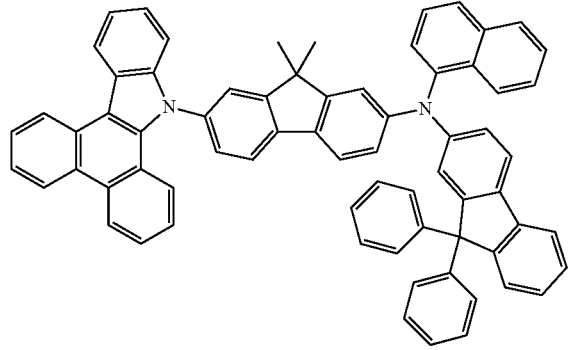
8-54
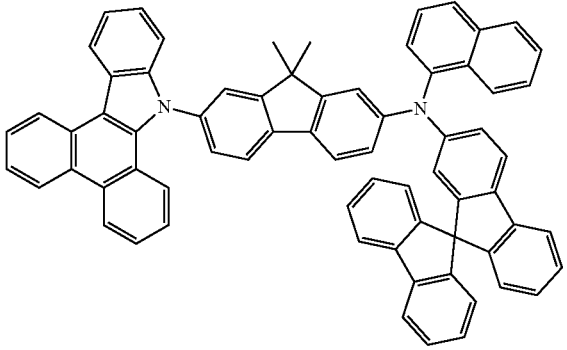
8-55
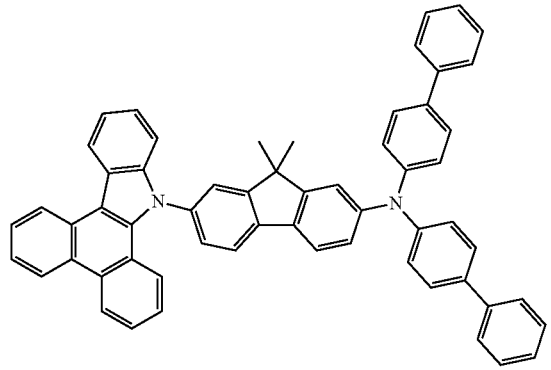
8-56
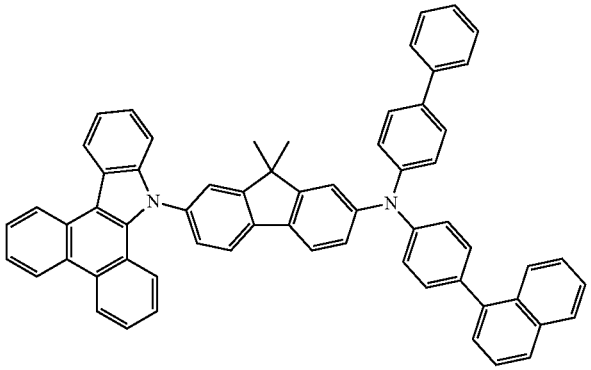

-continued
8-57
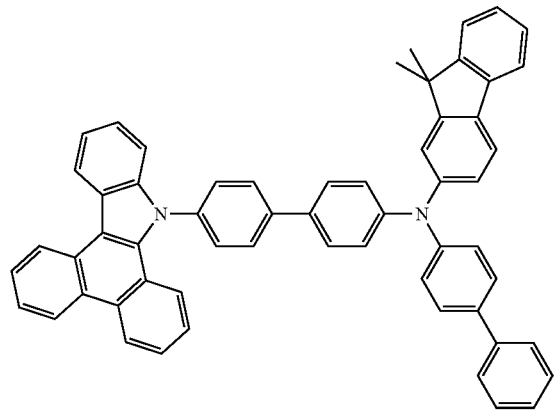
8-58
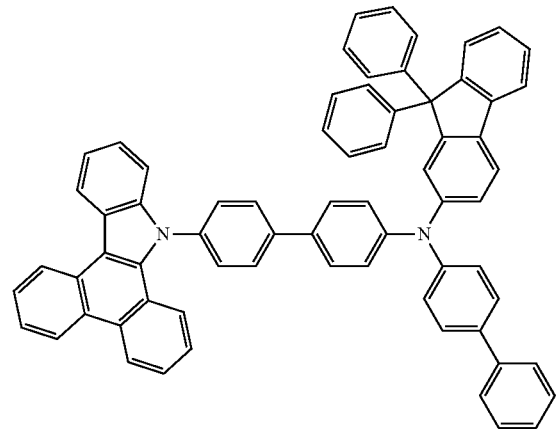
8-59
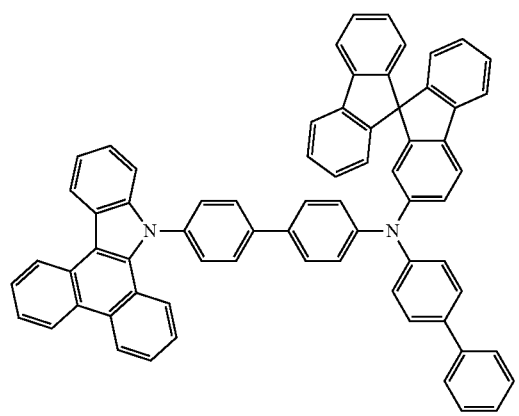
8-60
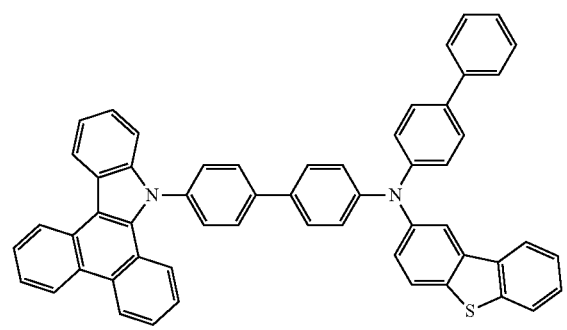
8-61
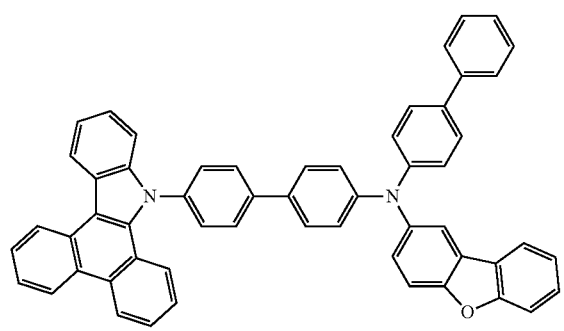
8-62
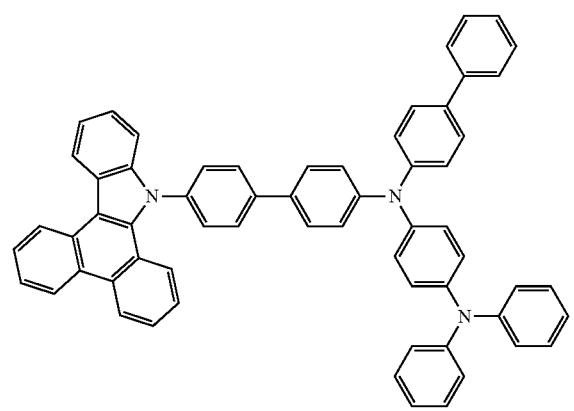

-continued
8-63
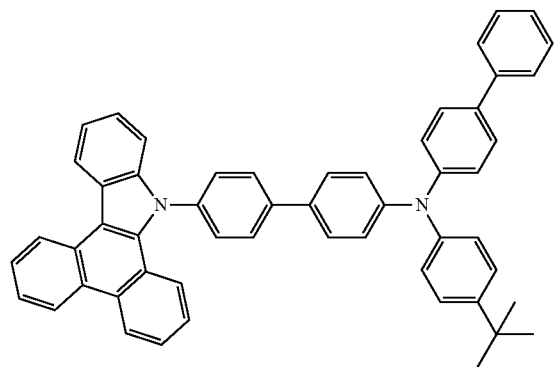
10-1
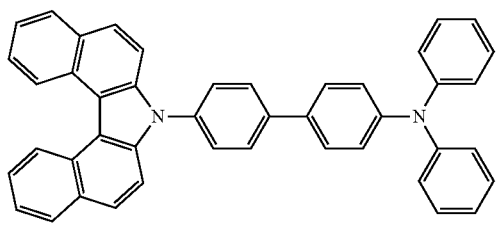
10-2
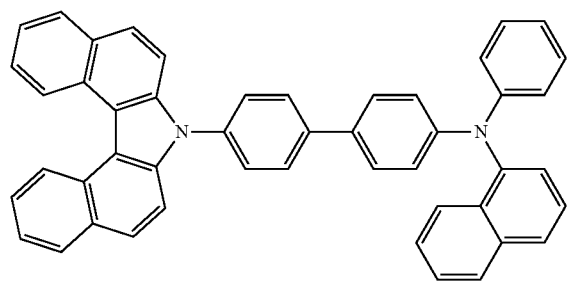
10-3
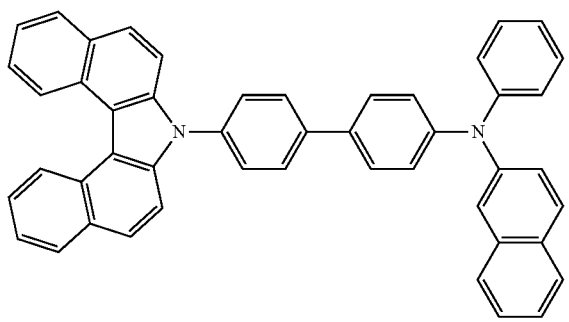
10-4
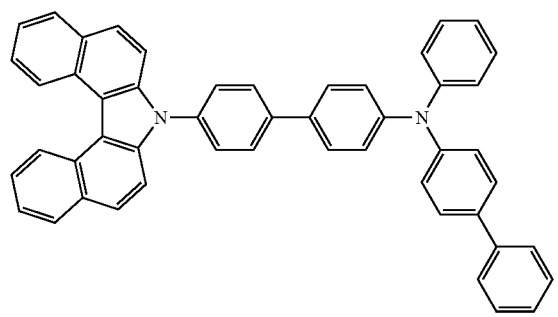
10-5
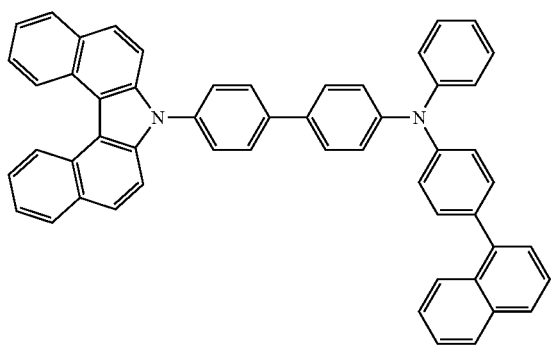
10-6
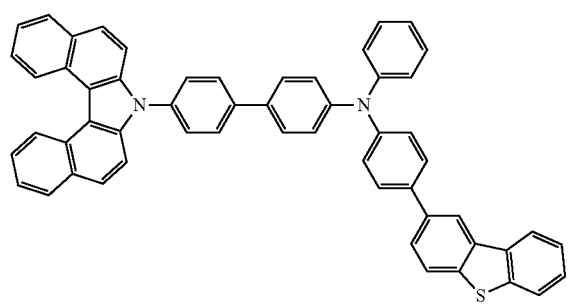
10-7
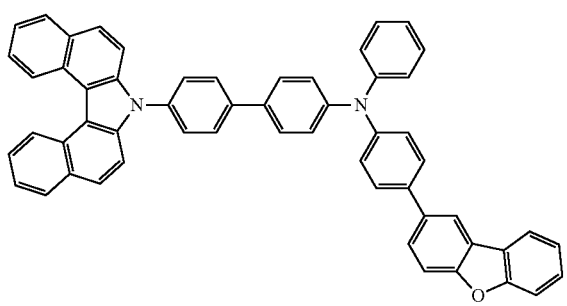

-continued
10-8
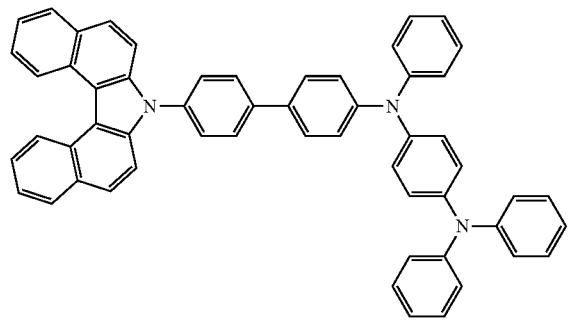
10-9
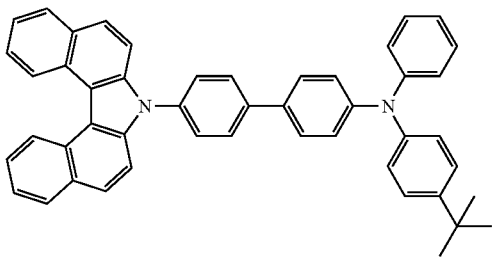
10-10
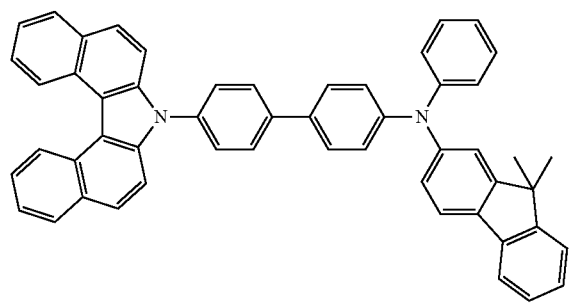
10-11
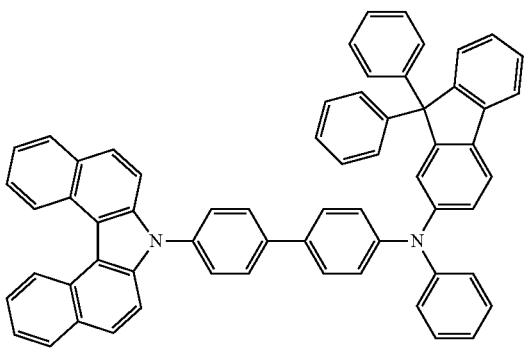
10-12
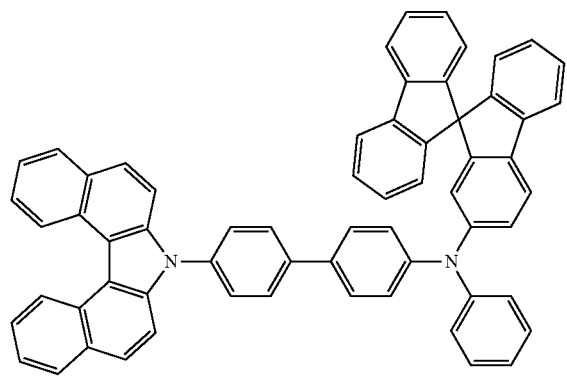
10-13
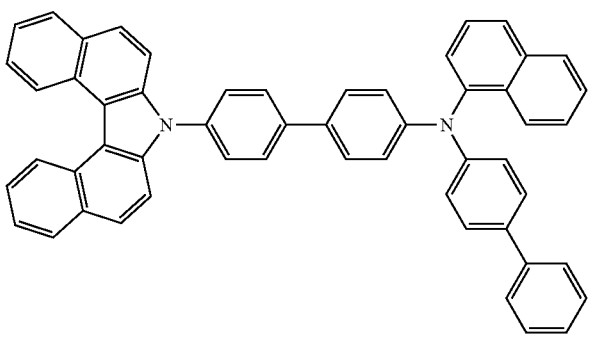
10-14
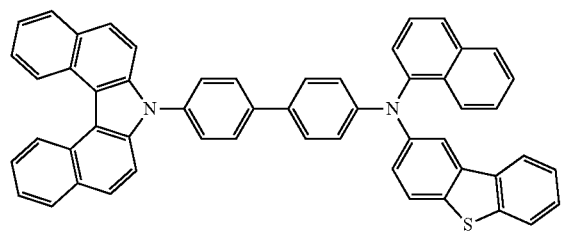
10-15
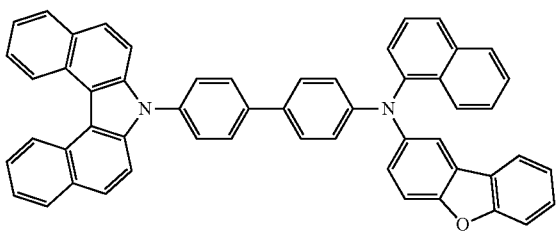

-continued
10-16
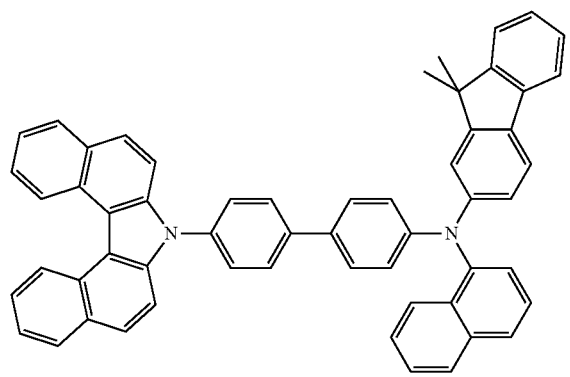
10-17
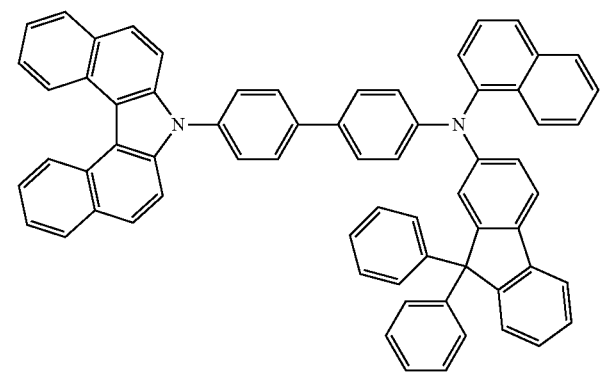
10-18
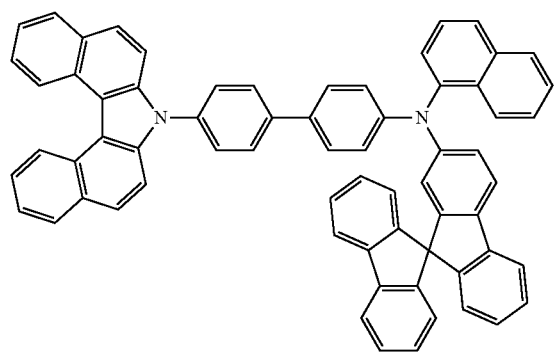
10-19
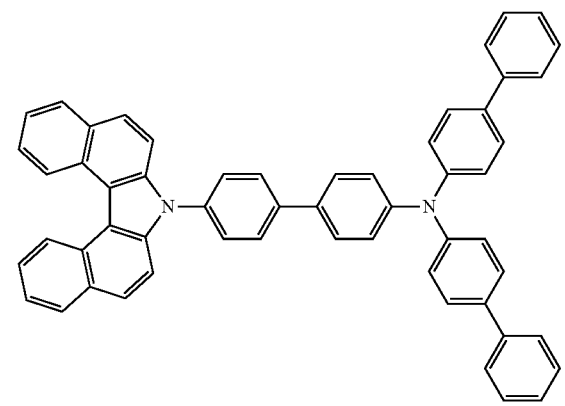
10-20
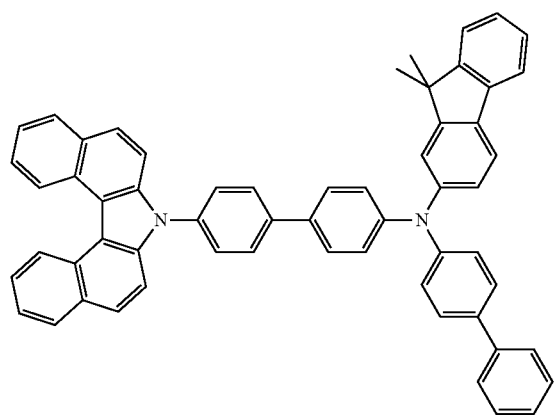
10-21
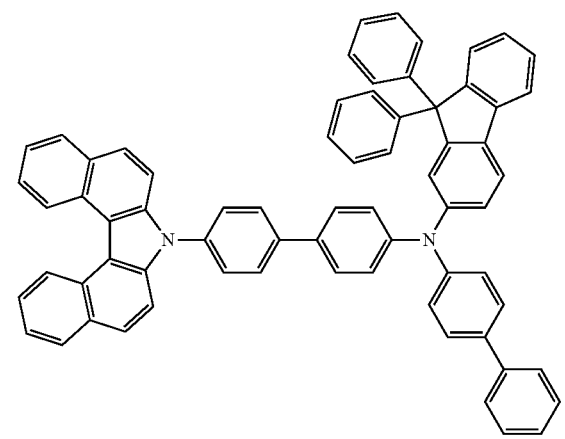

-continued
10-22
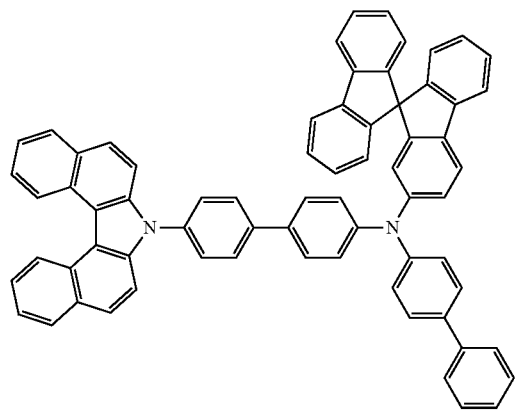
10-23
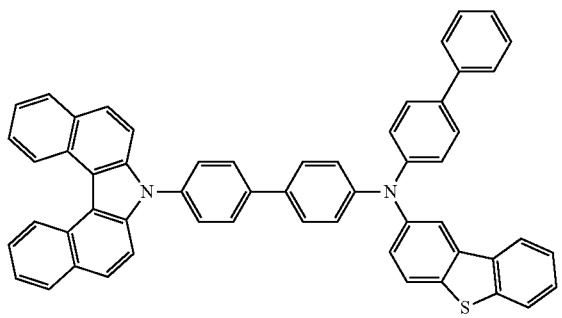
10-24
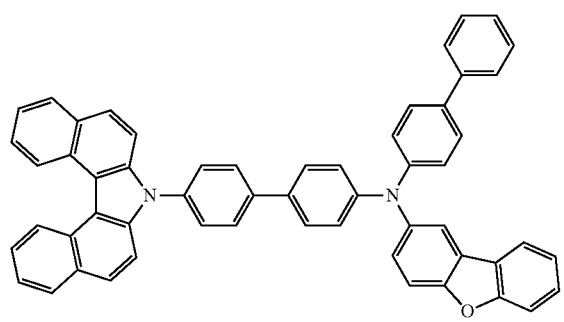
10-25
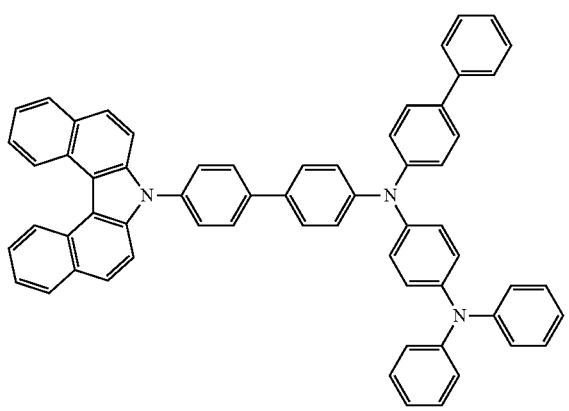
10-26
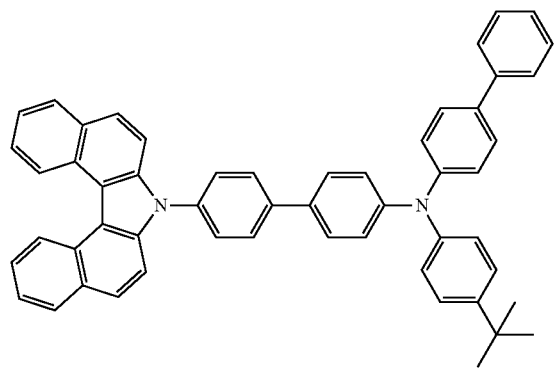
10-27
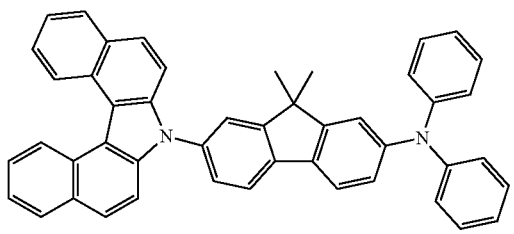
10-28
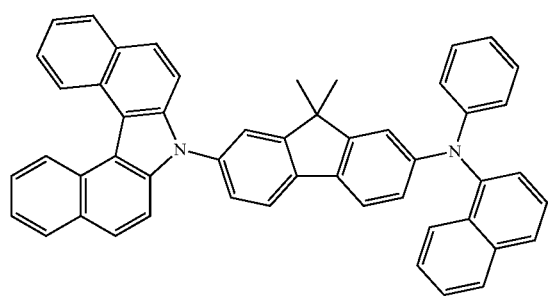
10-29
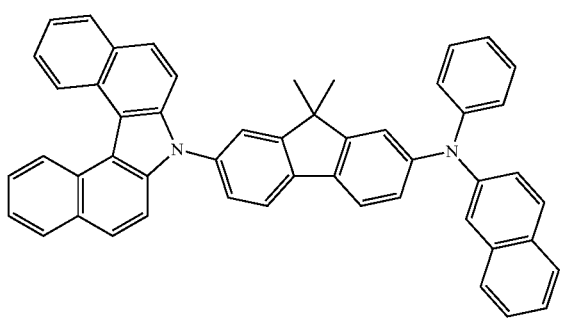

-continued
10-30
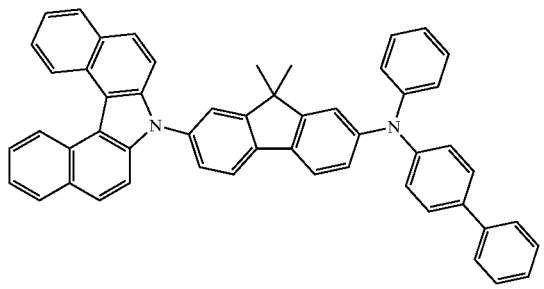
10-31
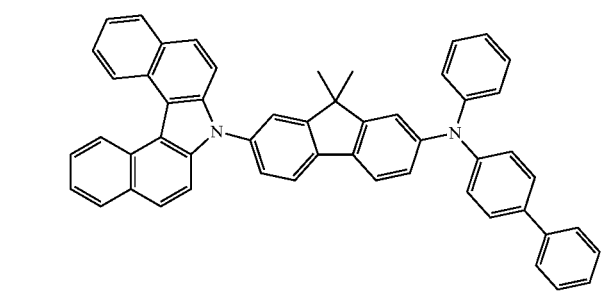
10-32
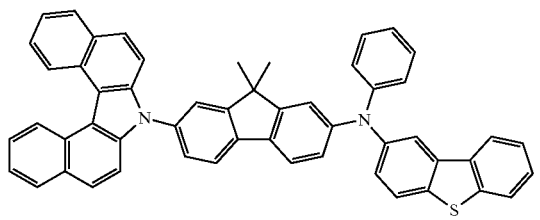
10-33
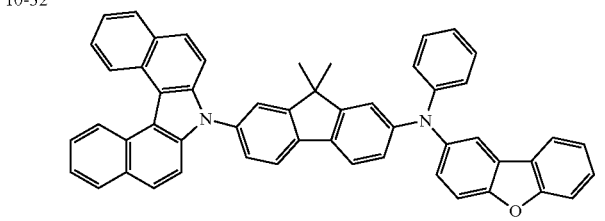
10-34
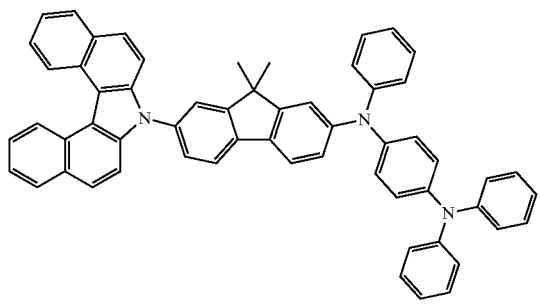
10-35
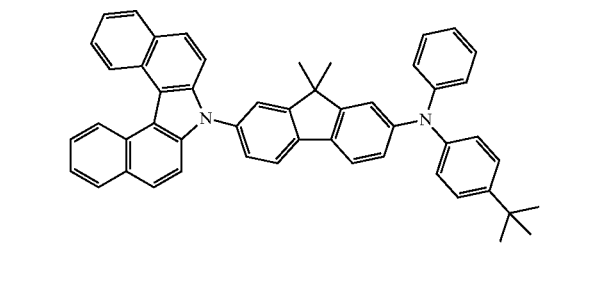
10-36
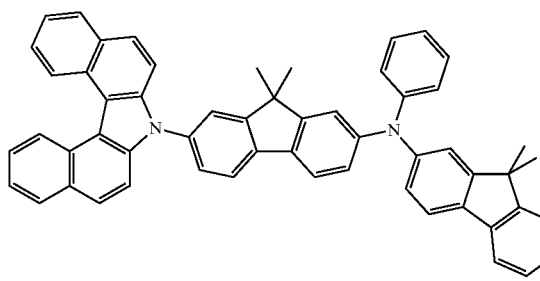
10-37
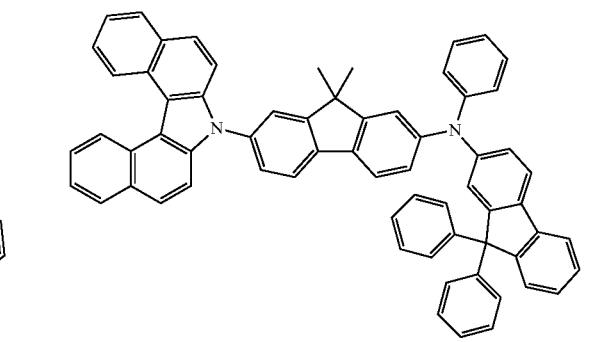
10-38
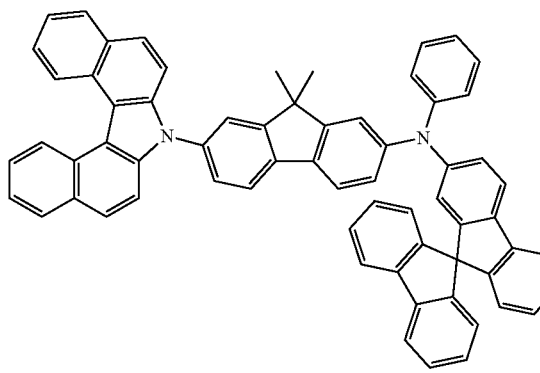
10-39
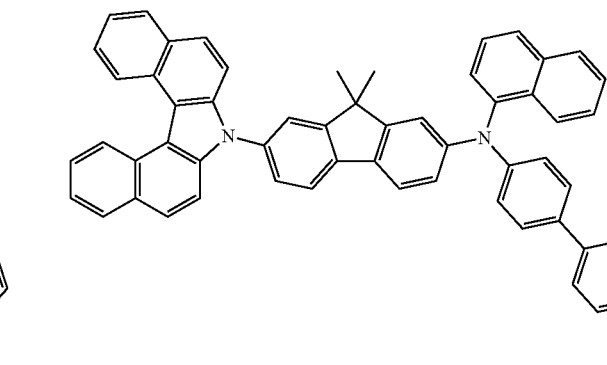

-continued
10-40
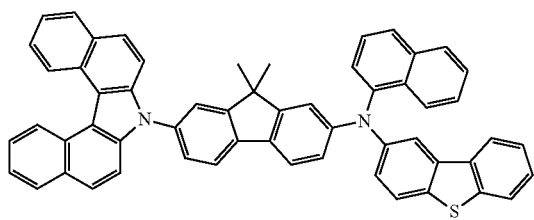
10-41
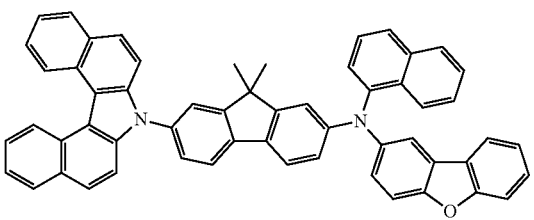
10-42
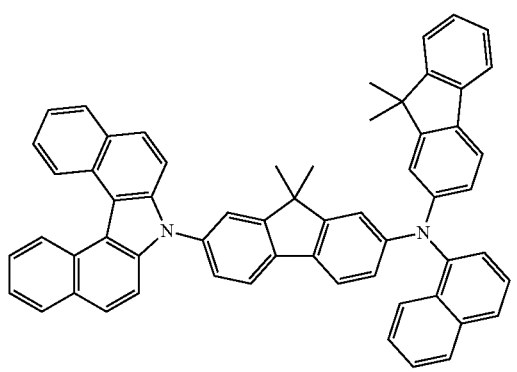
10-43
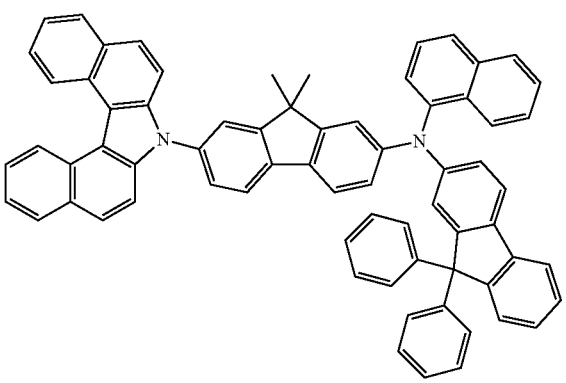
10-44
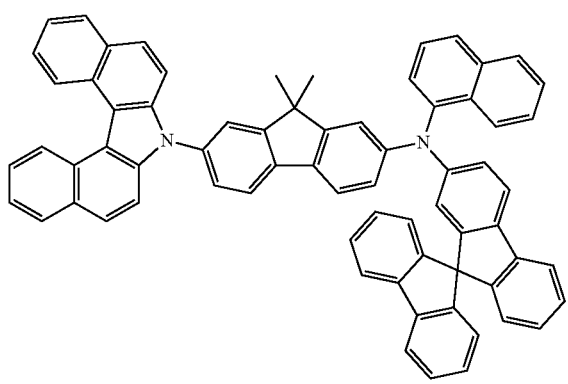
10-45
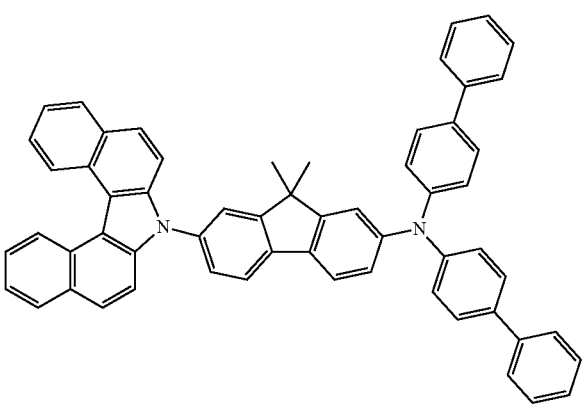
10-46
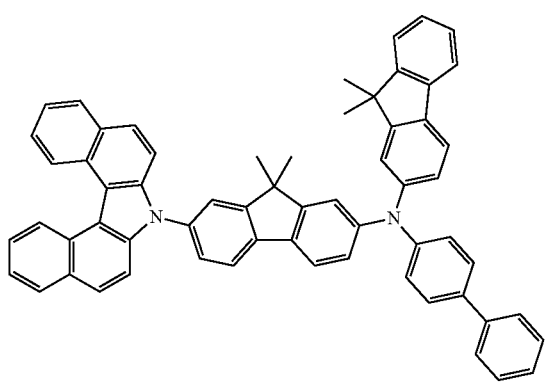
10-47
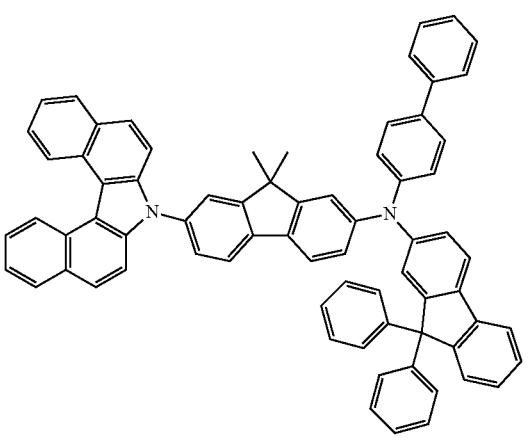

-continued
10-48
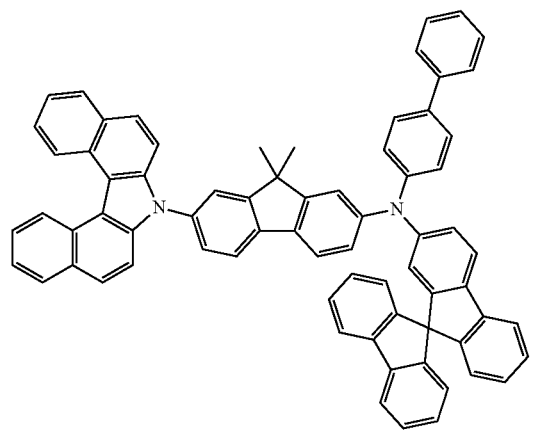
10-49
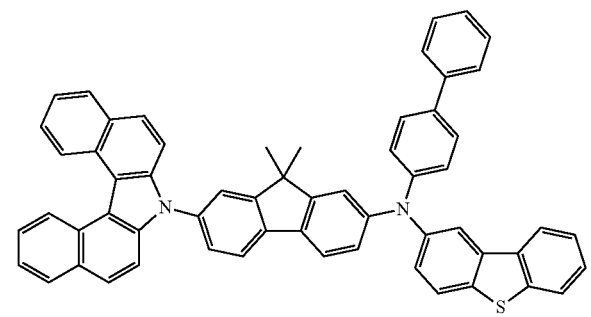
10-50
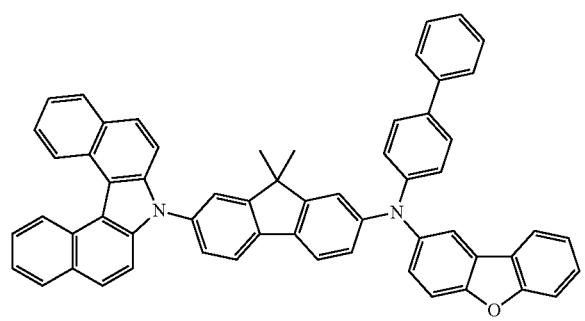
10-51
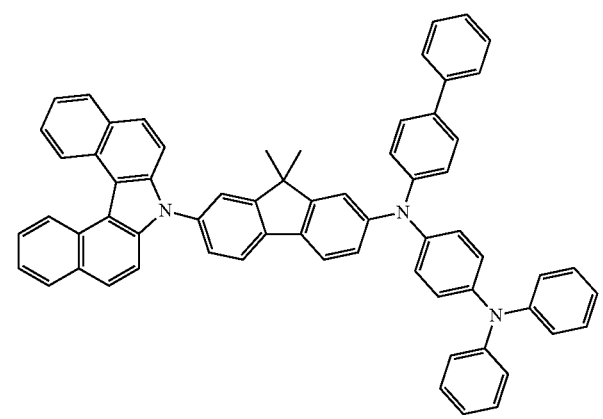
10-52
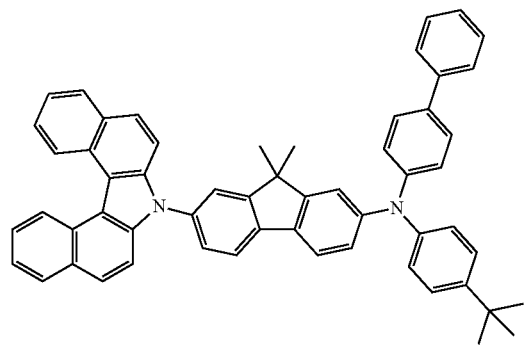

8. The organic electric element as claimed in claim 1, wherein the compound is formed into the organic material layer by a soluble process.

9. A compound for an organic electric element, represented by Formula 1 below:

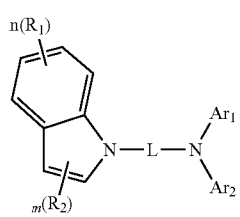

(1)

wherein, in Formula 1 above, m is an integer of 1 or 2; n is an integer from 1 to 4;
when m and/or n are/is 2 or greater, a plurality of $R_1$s or $R_2$s are the same as or different from each other;
$R_1$ and $R_2$ are each independently selected from the group consisting of hydrogen, deuterium, tritium, a halogen group, a $C_1$ to $C_{50}$ alkyl group, a $C_2$ to $C_{60}$ heterocyclic group containing at least one heteroatom selected from the group consisting of O, N, S, Si, and P, a $C_2$ to $C_{20}$ alkenyl group, a $C_6$ to $C_{60}$ aryl group, and a $C_6$ to $C_{60}$ arylamine group, and at least one pair of two adjacent $R_1$s and two adjacent $R_2$s are optionally linked together to form a fused ring;
L is a $C_6$ to $C_{60}$ arylene group, a fluorenyl group, a $C_3$ to $C_{60}$ heteroarylene group, or a bivalent aliphatic hydrocarbon group, where the arylene group, the fluorenyl group, the heteroarylene group, and the aliphatic hydrocarbon group each are optionally substituted by one or more substituents selected from the group consisting of nitro group, nitrile group, halogen, a $C_1$ to $C_{20}$ alkyl group, a $C_1$ to $C_{20}$ alkoxy group, a $C_6$ to $C_{20}$ aryl group, a $C_2$ to $C_{20}$ heterocyclic group, and an amino group; and
$Ar_1$ and $Ar_2$ are each independently selected from the group consisting of a $C_6$ to $C_{60}$ aryl group, a $C_2$ to $C_{60}$ heteroaryl group containing at least one heteroatom selected from the group consisting of O, N, S, Si, and P, a $C_2$ to $C_{20}$ alkenyl group, and a fluorenyl group;
when $R_1$, $R_2$, $Ar_1$, and $Ar_2$ are a heterocyclic group, $R_1$, $R_2$, $Ar_1$, and $Ar_2$ each are optionally substituted by one or more substituents selected from the group consisting of hydrogen, deuterium, tritium, a halogen group, a $C_1$ to $C_{20}$ alkyl group, a $C_2$ to $C_{20}$ alkenyl group, a $C_1$ to $C_{20}$ alkoxy group, a $C_6$ to $C_{20}$ arylamine group, a $C_6$ to $C_{60}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{60}$ heterocyclic group, a nitrile group, and an acetylene group;
when $R_1$, $R_2$, $Ar_1$, and $Ar_2$ are an alkenyl group, $R_1$, $R_2$, $Ar_1$, and $Ar_2$ each are optionally substituted by one or more substituents selected from the group consisting of hydrogen, deuterium, tritium, a halogen group, a $C_1$ to $C_{20}$ alkyl group, a $C_2$ to $C_{20}$ alkenyl group, a $C_1$ to $C_{20}$ alkoxy group, a $C_6$ to $C_{20}$ arylamine group, a $C_6$ to $C_{60}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{20}$ heterocyclic group, a nitrile group, and an acetylene group;
when $R_1$, $R_2$, $Ar_1$, and $Ar_2$ are an aryl group, $R_1$, $R_2$, $Ar_1$, and $Ar_2$ each are optionally substituted by one or more substituents selected from the group consisting of hydrogen, deuterium, tritium, a halogen group, a $C_1$ to $C_{20}$ alkyl group, a $C_1$ to $C_{20}$ alkoxy group, a $C_1$ to $C_{20}$ alkylamine group, a $C_1$ to $C_{20}$ alkylthiophene group, a $C_6$ to $C_{20}$ arylthiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group substituted by deuterium, a $C_6$ to $C_{20}$ arylamine group, a $C_8$ to $C_{20}$ arylalkenyl group, a silane group, a boron group, a germanium group, and a $C_2$ to $C_{20}$ heterocyclic group, with the proviso that when $Ar_1$ and $Ar_2$ are an aryl group, the group from which the substituents are selected further includes a phosphineoxide group;
when $R_1$ and $R_2$ are an alkyl group, $R_1$ and $R_2$ each are optionally substituted by one or more substituents selected from the group consisting of hydrogen, deuterium, tritium, a halogen group, a $C_2$ to $C_{20}$ alkenyl group, a $C_1$ to $C_{20}$ alkoxy group, a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{20}$ heterocyclic group, a nitrile group, and an acetylene group;
when $R_1$ and $R_2$ are an arylamine group, $R_1$ and $R_2$ each are optionally substituted by one or more substituents selected from the group consisting of a $C_6$ to $C_{20}$ aryl group, a $C_6$ to $C_{20}$ aryl group substituted by deuterium, and a $C_2$ to $C_{20}$ heterocyclic group; and
when $Ar_1$ and $Ar_2$ are a fluorenyl group, $Ar_1$ and $Ar_2$ each are optionally substituted by one or more substituents selected from the group consisting of hydrogen, deuterium, tritium, a halogen group, a $C_2$ to $C_{20}$ alkenyl group, a $C_1$ to $C_{20}$ alkoxy group, a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_1$ to $C_{50}$ alkyl group, a $C_2$ to $C_{20}$ heterocyclic group, a nitrile group, and an acetylene group.

10. The compound as claimed in claim 9, wherein the compound is represented by one of Formulas below:

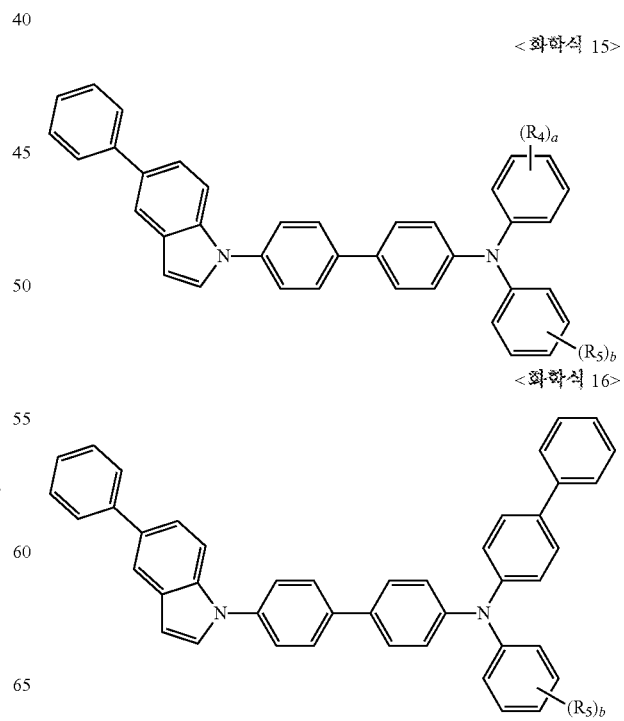

<화학식 17>

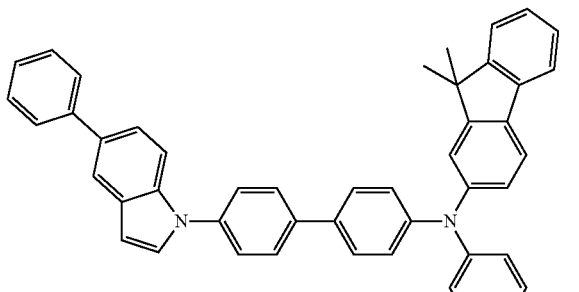

<화학식 18>

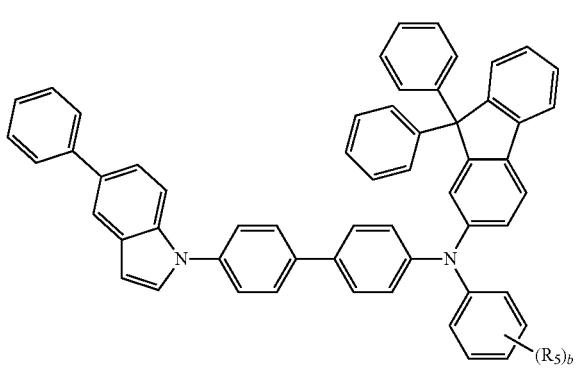

where, in Formulas 15 to 18 above, a and b are each an integer from 1 to 5;

when a and/or b are/is 2 or greater, a plurality of $R_4$s or $R_5$s are the same as or different from each other;

$R_4$ and $R_5$ are each independently selected from the group consisting of a $C_6$ to $C_{25}$ aryl group and a $C_2$ to $C_{20}$ alkenyl group, and two adjacent $R_4$s and/or two adjacent $R_5$s are each optionally linked together to form a fused ring; and when $R_4$ and $R_5$ are an aryl group or an alkenyl group, $R_4$ and $R_5$ each are optionally substituted by one or more substituents selected from the group consisting of a $C_1$ to $C_4$ alkyl group, a $C_2$ to $C_6$ alkenyl group, and a $C_6$ to $C_{20}$ aryl group.

11. An organic electric element comprising a first electrode, a second electrode, and an organic material layer disposed between the first electrode and the second electrode, wherein the organic material layer contains the compound as claimed in claim 9.

12. An electronic device comprising a display device, which comprises the organic electric element as claimed in claim 1, and a control unit for driving the display device.

13. The electronic device as claimed in claim 12, wherein the organic electric element comprises at least one of an organic light emitting diode (OLED), an organic solar cell, an organic photo conductor (OPC), an organic transistor (organic TFT), and an element for monochromatic or white illumination.

14. The organic electric element of claim 11, wherein the organic material layer comprises a light emitting layer and a hole transport layer between the light emitting layer and the first electrode, and the hole transport layer comprise the compound.

15. The organic electric element of claim 14, wherein the organic material layer further comprises a hole injection layer between the first electrode and the hole transport layer, an electron transport layer between the light emitting layer and the second electrode, an electron injection layer between the electron transport layer and the second electrode.

16. The organic electric element of claim 14, wherein the organic material layer further comprise an emission-auxiliary layer between the hole transport layer and the light emitting layer, the hole transport layer comprises a compound represented by

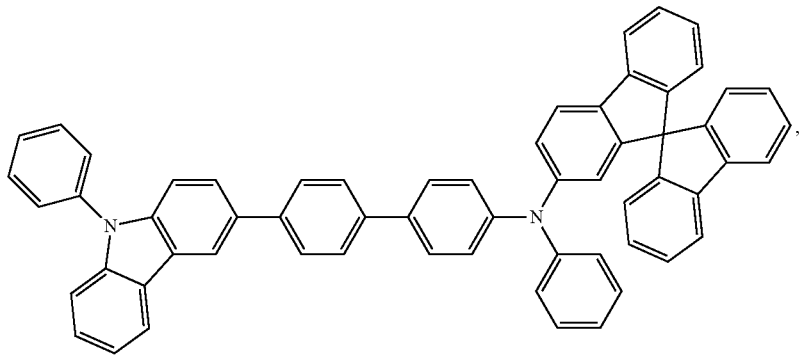 [SMILES: c1ccc(N(c2ccc(-c3ccc(-c4ccc5c(c4)c4ccccc4n5-c4ccccc4)cc3)cc2)c2ccc3c(c2)C2(c4ccccc4-c4ccccc42)c2ccccc2-3)cc1]

and the emission-auxiliary layer comprises the compound represented by Formula 1.

17. The compound of claim 9, wherein $Ar_1$ and $Ar_2$ are each independently selected from the group consisting of the compounds below:

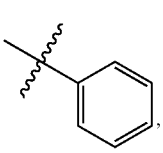 , 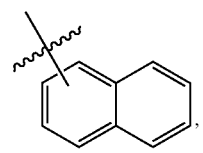 , and

-continued
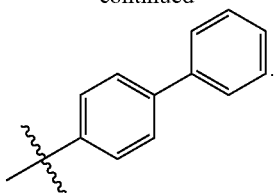
18. The compound of claim 9, wherein Ar$_1$ and Ar$_2$ are each independently selected from the group consisting of the compounds below:
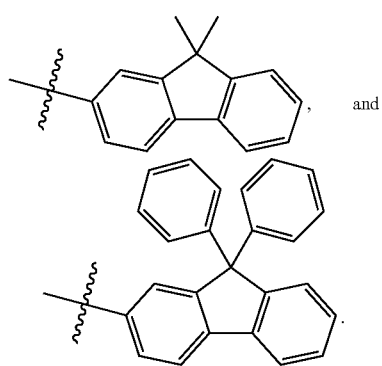
19. The compound of claim 9, wherein L is selected from the group consisting of the compounds below:
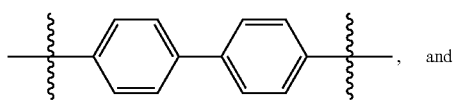, and
-continued
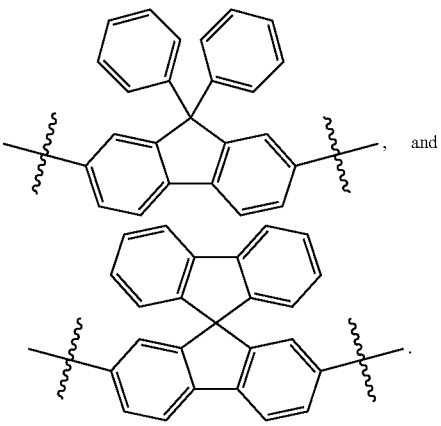
20. The compound of claim 9, wherein L is selected from the group consisting of the compounds below:
, and
.
* * * * *